(12) United States Patent
Kaslow et al.

(10) Patent No.: US 8,530,234 B2
(45) Date of Patent: Sep. 10, 2013

(54) HEPATITIS C VIRUS VACCINE

(75) Inventors: David C. Kaslow, Rancho Santa Fe, CA (US); Andrew J. Bett, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/633,104

(22) Filed: Dec. 8, 2009

(65) Prior Publication Data

US 2010/0129901 A1 May 27, 2010

Related U.S. Application Data

(62) Division of application No. 12/396,747, filed on Mar. 3, 2009, now Pat. No. 8,142,794, which is a division of application No. 10/492,178, filed as application No. PCT/US02/32512 on Oct. 10, 2002, now Pat. No. 7,598,362.

(60) Provisional application No. 60/363,774, filed on Mar. 13, 2002, provisional application No. 60/328,655, filed on Oct. 11, 2001.

(51) Int. Cl.
*C12N 15/63* (2006.01)
*C07H 21/04* (2006.01)
*A61K 48/00* (2006.01)

(52) U.S. Cl.
USPC ....... 435/320.1; 536/23.1; 514/44; 435/252.3

(58) Field of Classification Search
None
See application file for complete search history.

(56) References Cited

U.S. PATENT DOCUMENTS

| | | | | |
|---|---|---|---|---|
| 5,585,362 A | * | 12/1996 | Wilson et al. | 514/44 R |
| 5,792,462 A | | 8/1998 | Johnston et al. | |
| 6,033,908 A | | 3/2000 | Bout et al. | |
| 6,127,525 A | * | 10/2000 | Crystal et al. | 530/388.22 |
| 6,140,087 A | * | 10/2000 | Graham et al. | 435/91.42 |
| 6,156,558 A | | 12/2000 | Johnston et al. | |
| 6,221,646 B1 | * | 4/2001 | Dwarki et al. | 435/235.1 |
| 6,627,190 B2 | * | 9/2003 | Wold et al. | 424/93.2 |
| 6,787,351 B2 | * | 9/2004 | Chen et al. | 435/320.1 |
| 7,598,362 B2 | * | 10/2009 | Emini et al. | 536/23.1 |

FOREIGN PATENT DOCUMENTS

| | | |
|---|---|---|
| WO | 95/32733 | 12/1995 |
| WO | WO 98 51788 A3 | 11/1998 |
| WO | WO99/57296 | * 11/1999 |
| WO | WO 99 57296 A1 | 11/1999 |
| WO | WO 00 11202 A1 | 3/2000 |
| WO | WO00/42208 | 7/2000 |
| WO | 01/02607 | 1/2001 |
| WO | 02/22080 | 3/2002 |

OTHER PUBLICATIONS

Chroboczek et al. Virology, 1992, vol. 186, p. 280-285 discloses present SEQ ID No. 9.*
Tikoczenko et al. (Gene, 1981, vol. 4, p. 349-359).*
Anderson et al. (Gene Therapy, 2000, vol. 7, p. 1034-1038).*
Bett, A. et al. "Packaging Capacity and Stability of Human Adenovirus Type 5 Vectors", Journal of Virology, 1993, vol. 67, pp. 5911-5921.
Bett, A et al. "An efficient and flexible system for construction of adenovirus vectors with insertions or deletions in early regions 1 and 3", Proc. Natl. Acad. Sci. USA, 1994, vol. 91, pp. 8802-8806.
Bramson, J. et al. "The use of adenoviral vectors for the gene therapy and gene transfer in vivo", Current Opinion in Biotechnology, 1995, Vo. 6, pp. 590-595.
Brenner, M. "Gene Transfer by Adenovectors", Blood, 1999, vol. 94, pp. 3965-3967.
Capone et al., "A Novel Adenovirus Type 6 (Ad6)-Based Hepatitis C Virus Vector That Overcomes Preexisting Anti-Ad5 Immunity and Induces Potent and Broad Cellular Immune Responses in Rhesus Macaques", Journal of Virology, 2006, vol. 80, No. 4, pp. 1688-1699.
Chartier, C. et al. "Efficient Generation of Recombinant Adenovirus Vectors by Homologous Recombination in *Escherichia coli*", Journal of Virology, 1996, vol. 70, pp. 4805-4810.
Chroboczek, J. et al. "The Sequence of the Genome of Adenovirus Type 5 and Its Comparison with the Genome of Adenovirus Type 2", Virology, 1992, vol. 186, pp. 280-285.
Danthinne, X. et al. "Production of first generation adenovirus vectors: a review", Gene Therapy, 2000, vol. 7, pp. 1707-1714.
Fattori et al., "Efficient immunization of rhesus macaques with an HCV candidate vaccine by heterologous priming-boosting with novel adenoviral vectors based on different serotypes", Gene Therapy, 2006, vol. 13, pp. 1088-1096.
Fallaux, F. et al. "New Helper Cells and Matched Early Region 1-Deleted Adenovirus Vectors Prevent Generation of Replication-Competent Adenoviruses", Human Gene Therapy, 1998, vol. 9, pp. 1909-1917.
Gilbert, S et al. "Enhanced CD8 T cell immunogenicity and protective efficacy in a mouse malaria model usinga recombinant adenoviral vaccine in heterologous prime-boost immunisation regimes", Vaccine, 2002, vol. 20, pp. 1039-1045.
Graham, F. et al. "Characteristics of a Human Cell Line Transformed by DNA from Human Adenovirus Type 5", Journal General Virology, 1977, vol. 36, pp. 59-74.
Graham, F. "Covalently closed circles of human adenovirus DNA are infectious", The EMBO Journal, 1984, vol. 3, pp. 2917-2922.
Graham, F. "Adenovirus vectors for high-efficiency gene transfer into mammalian cells", Trends Immunology Today, 2000, vol. 21, pp. 426-428.
Hitt, M. et al. "Human Adenovirus Vectors for Gene Transfer into Mammalian Cells", Advances in Pharmacology, 1997, vol. 40, pp. 137-206.
Hitt, M. et al. "Techniques of Human Adenovirus Vector Construction and Characterization", Methods in Molecular Genetics, 1995, vol. 7, pp. 13-30.
Naroditsky et al., "Analysis of DNA From Human Adenovirus Type 6 With Restriction Endonucleases HindIII, BglIII and BamHI", Biochimica et Biophysica Acta, 1980, vol. 606, pp. 214-227.
Russell, W. "Update on adenovirus and its vectors", Journal of General Virology, 2000, vol. 81, pp. 2573-2604.
Schiedner, G. et al. "Efficient Transformation of Primary Human Amniocytes by E1 Functions of Ad5: Generation of New Cel Lines for Adenoviral Vector Production", Human Gene Therapy, 2000, vol. 11, pp. 2105-2116.

(Continued)

*Primary Examiner* — Agnieszka Boesen
(74) *Attorney, Agent, or Firm* — Alysia A. Finnegan; Sheldon O. Heber

(57) ABSTRACT

The present invention features Ad6 vectors and a nucleic acid encoding a Met-NS3-NS4A-NS4B-NS5A-NS5B polypeptide containing an inactive NS5B RNA-dependent RNA polymerase region. The nucleic acid is particularly useful as a component of an adenovector or DNA plasmid vaccine providing a broad range of antigens for generating an HCV specific cell mediated immune (CMI) response against HCV.

3 Claims, 92 Drawing Sheets

(56) References Cited

OTHER PUBLICATIONS

Stunnenberg, H. et al. "High expression of functional adenovirus DNA polymerase and precursor terminal protein using recombinant vaccine virus", Nucleic Acids Research, 1988, vol. 16, pp. 2431-2444.

Tikchonenko et al, "Biophysical Properties of Virions of Human Adenovirus of the Type 6 and Its DNA", Archives of Virology, 1979, vol. 62, pp. 117-130.

Pring-Akerblom et al., "The hexon genes of adenoviruses of subgenus C: comparison of the variable regions", Res. Virol., 144, p. 117-127, 1993.

Garaev et al, "Characteristics of the tetracycline operon of vector plasmids during the cloning of DNA fragments" Vestnik Akademii Medicinskih Nauk SSR, Medicina, 1981, No. 2, pp. 35-40, English Abstract, p. 40.

Neumann et al, "Determination of the nucleotide sequence for the penton-base gene of human adenovirus type 5", Gene, 1988, vol. 69, No. 1, pp. 153-157.

Grafsky, "pHelper for use in the AAV Helper-Free System", Database Accession No. AF369965 dated Jul. 22, 2001.

Borcherding et al, "Adenoviruses of subgenus c with different organ tropism" Database Accession No. AJ293916 dated Sep. 4, 2001.

Adrian et al, "Adenovirus 6 genome types: mapping of restriction site alterations on the genome." Research in Virology, 1989, vol. 140, pp. 545-550.

D'Ambrosio et al, "Neutralizing antibodies against 33 human adenoviruses in normal children in Rome", The Journal of Hygiene, 1982, vol. 89, No. 1, p. 155.

Bobkov et al. "Cloning of Inner Fragments of Adenovirus DNA", Vestnik Akademii Meditsinskikh Nauk SSSR, 1981, No. 2, pp. 32-35, English Abstract, p. 35.

\* cited by examiner

```
  1     MAPITAYSQQ  TRGLLGCIIT  SLTGRDKNQV  EGEVQVVSTA  TQSFLATCVN
 51     GVCWTVYHGA  GSKTLAGPKG  PITQMYTNVD  QDLVGWQAPP  GARSLTPCTC
101     GSSDLYLVTR  HADVIPVRRR  GDSRGSLLSP  RPVSYLKGSS  GGPLLCPSGH
151     AVGIFRAAVC  TRGVAKAVDF  VPVESMETTM  RSPVFTDNSS  PPAVPQSFQV
201     AHLHAPTGSG  KSTKVPAAYA  AQGYKVLVLN  PSVAATLGFG  AYMSKAHGID
251     PNIRTGVRTI  TTGAPVTYST  YGKFLADGGC  SGGAYDIIIC  DECHSTDSTT
301     ILGIGTVLDQ  AETAGARLVV  LATATPPGSV  TVPHPNIEEV  ALSNTGEIPF
351     YGKAIPIEAI  RGGRHLIFCH  SKKKCDELAA  KLSGLGINAV  AYYRGLDVSV
401     IPTIGDVVVV  ATDALMTGYT  GDFDSVIDCN  TCVTQTVDFS  LDPTFTIETT
451     TVPQDAVSRS  QRRGRTGRGR  RGIYRFVTPG  ERPSGMFDSS  VLCECYDAGC
501     AWYELTPAET  SVRLRAYLNT  PGLPVCQDHL  EFWESVFTGL  THIDAHFLSQ
551     TKQAGDNFPY  LVAYQATVCA  RAQAPPPSWD  QMWKCLIRLK  PTLHGPTPLL
601     YRLGAVQNEV  TLTHPITKYI  MACMSADLEV  VTSTWVLVGG  VLAALAAYCL
651     TTGSVVIVGR  IILSGRPAIV  PDREFLYQEF  DEMEECASHL  PYIEQGMQLA
701     EQFKQKALGL  LQTATKQAEA  AAPVVESKWR  ALETFWAKHM  WNFISGIQYL
751     AGLSTLPGNP  AIASLMAFTA  SITSPLTTQS  TLLFNILGGW  VAAQLAPPSA
801     ASAFVGAGIA  GAAVGSIGLG  KVLVDILAGY  GAGVAGALVA  FKVMSGEMPS
851     TEDLVNLLPA  ILSPGALVVG  VVCAAILRRH  VGPGEGAVQW  MNRLIAFASR
901     GNHVSPTHYV  PESDAAARVT  QILSSLTITQ  LLKRLHQWIN  EDCSTPCSGS
951     WLRDVWDWIC  TVLTDFKTWL  QSKLLPQLPG  VPFFSCQRGY  KGVWRGDGIM
1001    QTTCPCGAQI  TGHVKNGSMR  IVGPKTCSNT  WHGTFPINAY  TTGPCTPSPA
1051    PNYSRALWRV  AAEEYVEVTR  VGDFHYVTGM  TTDNVKCPCQ  VPAPEFFTEV
1101    DGVRLHRYAP  ACRPLLREEV  TFQVGLNQYL  VGSQLPCEPE  PDVAVLTSML
1151    TDPSHITAET  AKRRLARGSP  PSLASSSASQ  LSAPSLKATC  TTHHVSPDAD
1201    LIEANLLWRQ  EMGGNITRVE  SENKVVVLDS  FDPLRAEEDE  REVSVPAEIL
1251    RKSKKFPAAM  PIWARPDYNP  PLLESWKDPD  YVPPVHGCP   LPPIKAPPIP
1301    PPRRKRTVVL  TESSVSSALA  ELATKTFGSS  ESSAVDSGTA  TALPDQASDD
1351    GDKGSDVESY  SSMPPLEGEP  GDPDLSDGSW  STVSEEASED  VVCCSMSYTW
1401    TGALITPCAA  EESKLPINAL  SNSLLRHHNM  VYATTSRSAG  LRQKKVTFDR
1451    LQVLDDHYRD  VLKEMKAKAS  TVKAKLLSVE  EACKLTPPHS  AKSKFGYGAK
1501    DVRNLSSKAV  NHIHSVWKDL  LEDTVTPIDT  TIMAKNEVFC  VQPEKGGRKP
1551    ARLIVFPDLG  VRVCEKMALY  DVVSTLPQVV  MGSSYGFQYS  PGQRVEFLVN
1601    TWKSKKNPMG  FSYDTRCFDS  TVTENDIRVE  ESIYQCCDLA  PEARQAIKSL
1651    TERLYIGGPL  TNSKGQNCGY  RRCRASGVLT  TSCGNTLTCY  LKASAACRAA
```

FIG. 1A

```
1701    KLQDCTMLVN  AAGLVVICES  AGTQEDAASL  RVFTEAMTRY  SAPPGDPPQP
1751    EYDLELITSC  SSNVSVAHDA  SGKRVYYLTR  DPTTPLARAA  WETARHTPVN
1801    SWLGNIIMYA  PTLWARMILM  THFFSILLAQ  EQLEKALDCQ  IYGACYSIEP
1851    LDLPQIIERL  HGLSAFSLHS  YSPGEINRVA  SCLRKLGVPP  LRVWRHRARS
1901    VRARLLSQGG  RAATCGKYLF  NWAVKTKLKL  TPIPAASQLD  LSGWFVAGYS
1951    GGDIYHSLSR  ARPRWFMLCL  LLLSVGVGIY  LLPNR
```

FIG. 1B

| | | | | |
|---|---|---|---|---|
| 1 | GCCACCATGG | CGCCCATCAC | GGCCTACTCC | CAACAGACGC | GGGGCCTACT |
| 51 | TGGTTGCATC | ATCACTAGCC | TTACAGGCCG | GGACAAGAAC | CAGGTCGAGG |
| 101 | GAGAGGTTCA | GGTGGTTTCC | ACCGCAACAC | AATCCTTCCT | GGCGACCTGC |
| 151 | GTCAACGGCG | TGTGTTGGAC | CGTTTACCAT | GGTGCTGGCT | CAAAGACCTT |
| 201 | AGCCGGCCCA | AAGGGGCCAA | TCACCCAGAT | GTACACTAAT | GTGGACCAGG |
| 251 | ACCTCGTCGG | CTGGCAGGCG | CCCCCCGGGG | CGCGTTCCTT | GACACCATGC |
| 301 | ACCTGTGGCA | GCTCAGACCT | TTACTTGGTC | ACGAGACATG | CTGACGTCAT |
| 351 | TCCGGTGCGC | CGGCGGGGCG | ACAGTAGGGG | GAGCCTGCTC | TCCCCCAGGC |
| 401 | CTGTCTCCTA | CTTGAAGGGC | TCTTCGGGTG | GTCCACTGCT | CTGCCCTTCG |
| 451 | GGGCACGCTG | TGGGCATCTT | CCGGGCTGCC | GTATGCACCC | GGGGGGTTGC |
| 501 | GAAGGCGGTG | GACTTTGTGC | CCGTAGAGTC | CATGGAAACT | ACTATGCGGT |
| 551 | CTCCGGTCTT | CACGGACAAC | TCATCCCCCC | CGGCCGTACC | GCAGTCATTT |
| 601 | CAAGTGGCCC | ACCTACACGC | TCCCACTGGC | AGCGGCAAGA | GTACTAAAGT |
| 651 | GCCGGCTGCA | TATGCAGCCC | AAGGGTACAA | GGTGCTCGTC | CTCAATCCGT |
| 701 | CCGTTGCCGC | TACCTTAGGG | TTTGGGGCGT | ATATGTCTAA | GGCACACGGT |
| 751 | ATTGACCCCA | ACATCAGAAC | TGGGGTAAGG | ACCATTACCA | CAGGCGCCCC |
| 801 | CGTCACATAC | TCTACCTATG | GCAAGTTTCT | TGCCGATGGT | GGTTGCTCTG |
| 851 | GGGGCGCTTA | TGACATCATA | ATATGTGATG | AGTGCCATTC | AACTGACTCG |
| 901 | ACTACAATCT | TGGGCATCGG | CACAGTCCTG | GACCAAGCGG | AGACGGCTGG |
| 951 | AGCGCGGCTT | GTCGTGCTCG | CCACCGCTAC | GCCTCCGGGA | TCGGTCACCG |
| 1001 | TGCCACACCC | AAACATCGAG | GAGGTGGCCC | TGTCTAATAC | TGGAGAGATC |
| 1051 | CCCTTCTATG | CAAAGCCAT | CCCCATTGAA | GCCATCAGGG | GGGAAGGCA |
| 1101 | TCTCATTTTC | TGTCATTCCA | AGAAGAAGTG | CGACGAGCTC | GCCGCAAAGC |
| 1151 | TGTCAGGCCT | CGGAATCAAC | GCTGTGGCGT | ATTACCGGGG | GCTCGATGTG |
| 1201 | TCCGTCATAC | CAACTATCGG | AGACGTCGTT | GTCGTGGCAA | CAGACGCTCT |
| 1251 | GATGACGGGC | TATACGGGCG | ACTTTGACTC | AGTGATCGAC | TGTAACACAT |
| 1301 | GTGTCACCCA | GACAGTCGAC | TTCAGCTTGG | ATCCCACCTT | CACCATTGAG |
| 1351 | ACGACGACCG | TGCCTCAAGA | CGCAGTGTCG | CGCTCGCAGC | GGCGGGGTAG |
| 1401 | GACTGGCAGG | GGTAGGAGAG | GCATCTACAG | GTTTGTGACT | CCGGGAGAAC |
| 1451 | GGCCCTCGGG | CATGTTCGAT | TCCTCGGTCC | TGTGTGAGTG | CTATGACGCG |
| 1501 | GGCTGTGCTT | GGTACGAGCT | CACCCCCGCC | GAGACCTCGG | TTAGGTTGCG |
| 1551 | GGCCTACCTG | AACACACCAG | GGTTGCCCGT | TTGCCAGGAC | CACCTGGAGT |
| 1601 | TCTGGGAGAG | TGTCTTCACA | GGCCTCACCC | ACATAGATGC | ACACTTCTTG |
| 1651 | TCCCAGACCA | AGCAGGCAGG | AGACAACTTC | CCCTACCTGG | TAGCATACCA |

FIG. 2A

```
1701   AGCCACGGTG TGCGCCAGGG CTCAGGCCCC ACCTCCATCA TGGGATCAAA
1751   TGTGGAAGTG TCTCATACGG CTGAAACCTA CGCTGCACGG GCCAACACCC
1801   TTGCTGTACA GGCTGGGAGC CGTCCAAAAT GAGGTCACCC TCACCCACCC
1851   CATAACCAAA TACATCATGG CATGCATGTC GGCTGACCTG GAGGTCGTCA
1901   CTAGCACCTG GGTGCTGGTG GGCGGAGTCC TTGCAGCTCT GGCCGCGTAT
1951   TGCCTGACAA CAGGCAGTGT GGTCATTGTG GTAGGATTA TCTTGTCCGG
2001   GAGGCCGGCT ATTGTTCCCG ACAGGGAGTT TCTCTACCAG GAGTTCGATG
2051   AAATGGAAGA GTGCGCCTCG CACCTCCCTT ACATCGAGCA GGGAATGCAG
2101   CTCGCCGAGC AATTCAAGCA GAAAGCGCTC GGGTTACTGC AAACAGCCAC
2151   CAAACAAGCG GAGGCTGCTG CTCCCGTGGT GGAGTCCAAG TGGCGAGCCC
2201   TTGAGACATT CTGGGCGAAG CACATGTGGA ATTTCATCAG CGGGATACAG
2251   TACTTAGCAG GCTTATCCAC TCTGCCTGGG AACCCCGCAA TAGCATCATT
2301   GATGGCATTC ACAGCCTCTA TCACCAGCCC GCTCACCACC CAAAGTACCC
2351   TCCTGTTTAA CATCTTGGGG GGGTGGGTGG CTGCCCAACT CGCCCCCCCC
2401   AGCGCCGCTT CGGCTTTCGT GGGCGCCGGC ATCGCCGGTG CGGCTGTTGG
2451   CAGCATAGGC CTTGGGAAGG TGCTTGTGGA CATTCTGGCG GGTTATGGAG
2501   CAGGAGTGGC CGGCGCGCTC GTGGCCTTCA AGGTCATGAG CGGCGAGATG
2551   CCCTCCACCG AGGACCTGGT CAATCTACTT CCTGCCATCC TCTCTCCTGG
2601   CGCCCTGGTC GTCGGGGTCG TGTGTGCAGC AATACTGCGT CGACACGTGG
2651   GTCCGGGAGA GGGGGCTGTG CAGTGGATGA ACCGGCTGAT AGCGTTCGCC
2701   TCGCGGGGTA ATCATGTTTC CCCCACGCAC TATGTGCCTG AGAGCGACGC
2751   CGCAGCGCGT GTTACTCAGA TCCTCTCCAG CCTTACCATC ACTCAGCTGC
2801   TGAAAAGGCT CCACCAGTGG ATTAATGAAG ACTGCTCCAC ACCGTGTTCC
2851   GGCTCGTGGC TAAGGGATGT TTGGGACTGG ATATGCACGG TGTTGACTGA
2901   CTTCAAGACC TGGCTCCAGT CCAAGCTCCT GCCGCAGCTA CCGGGAGTCC
2951   CTTTTTTCTC GTGCCAACGC GGGTACAAGG GAGTCTGGCG GGGAGACGGC
3001   ATCATGCAAA CCACCTGCCC ATGTGGAGCA CAGATCACCG GACATGTCAA
3051   AAACGGTTCC ATGAGGATCG TCGGGCCTAA GACCTGCAGC AACACGTGGC
3101   ATGGAACATT CCCCATCAAC GCATACACCA CGGGCCCCTG CACACCCTCT
3151   CCAGCGCCAA ACTATTCTAG GGCGCTGTGG CGGGTGGCCG CTGAGGAGTA
3201   CGTGGAGGTC ACGCGGGTGG GGGATTTCCA CTACGTGACG GGCATGACCA
3251   CTGACAACGT AAAGTGCCCA TGCCAGGTTC CGGCTCCTGA ATTCTTCACG
3301   GAGGTGGACG GAGTGCGGTT GCACAGGTAC GCTCCGGCGT GCAGGCCTCT
3351   CCTACGGGAG GAGGTTACAT TCCAGGTCGG GCTCAACCAA TACCTGGTTG
```

FIG. 2B

```
3401  GGTCACAGCT ACCATGCGAG CCCGAACCGG ATGTAGCAGT GCTCACTTCC
3451  ATGCTCACCG ACCCCTCCCA CATCACAGCA GAAACGGCTA AGCGTAGGTT
3501  GGCCAGGGGG TCTCCCCCCT CCTTGGCCAG CTCTTCAGCT AGCCAGTTGT
3551  CTGCGCCTTC CTTGAAGGCG ACATGCACTA CCCACCATGT CTCTCCGGAC
3601  GCTGACCTCA TCGAGGCCAA CCTCCTGTGG CGGCAGGAGA TGGGCGGGAA
3651  CATCACCCGC GTGGAGTCGG AGAACAAGGT GGTAGTCCTG GACTCTTTCG
3701  ACCCGCTTCG AGCGGAGGAG GATGAGAGGG AAGTATCCGT TCCGGCGGAG
3751  ATCCTGCGGA AATCCAAGAA GTTCCCCGCA GCGATGCCCA TCTGGGCGCG
3801  CCCGGATTAC AACCCTCCAC TGTTAGAGTC CTGGAAGGAC CCGGACTACG
3851  TCCCTCCGGT GGTGCACGGG TGCCCGTTGC CACCTATCAA GGCCCCTCCA
3901  ATACCACCTC CACGGAGAAA GAGGACGGTT GTCCTAACAG AGTCCTCCGT
3951  GTCTTCTGCC TTAGCGGAGC TCGCTACTAA GACCTTCGGC AGCTCCGAAT
4001  CATCGGCCGT CGACAGCGGC ACGGCGACCG CCCTTCCTGA CCAGGCCTCC
4051  GACGACGGTG ACAAAGGATC CGACGTTGAG TCGTACTCCT CCATGCCCCC
4101  CCTTGAGGGG GAACCGGGGG ACCCCGATCT CAGTGACGGG TCTTGGTCTA
4151  CCGTGAGCGA GGAAGCTAGT GAGGATGTCG TCTGCTGCTC AATGTCCTAC
4201  ACATGGACAG GCGCCTTGAT CACGCCATGC GCTGCGGAGG AAAGCAAGCT
4251  GCCCATCAAC GCGTTGAGCA ACTCTTTGCT GCGCCACCAT AACATGGTTT
4301  ATGCCACAAC ATCTCGCAGC GCAGGCCTGC GGCAGAAGAA GGTCACCTTT
4351  GACAGACTGC AAGTCCTGGA CGACCACTAC CGGGACGTGC TCAAGGAGAT
4401  GAAGGCGAAG GCGTCCACAG TTAAGGCTAA ACTCCTATCC GTAGAGGAAG
4451  CCTGCAAGCT GACGCCCCCA CATTCGGCCA AATCCAAGTT TGGCTATGGG
4501  GCAAAGGACG TCCGGAACCT ATCCAGCAAG GCCGTTAACC ACATCCACTC
4551  CGTGTGGAAG GACTTGCTGG AAGACACTGT GACACCAATT GACACCACCA
4601  TCATGGCAAA AAATGAGGTT TTCTGTGTCC AACCAGAGAA AGGAGGCCGT
4651  AAGCCAGCCC GCCTTATCGT ATTCCCAGAT CTGGGAGTCC GTGTATGCGA
4701  GAAGATGGCC CTCTATGATG TGGTCTCCAC CCTTCCTCAG GTCGTGATGG
4751  GCTCCTCATA CGGATTCCAG TACTCTCCTG GGCAGCGAGT CGAGTTCCTG
4801  GTGAATACCT GGAAATCAAA GAAAAACCCC ATGGGCTTTT CATATGACAC
4851  TCGCTGTTTC GACTCAACGG TCACCGAGAA CGACATCCGT GTTGAGGAGT
4901  CAATTTACCA ATGTTGTGAC TTGGCCCCCG AAGCCAGACA GGCCATAAAA
4951  TCGCTCACAG AGCGGCTTTA TATCGGGGGT CCTCTGACTA ATTCAAAAGG
5001  GCAGAACTGC GGTTATCGCC GGTGCCGCGC GAGCGGCGTG CTGACGACTA
5051  GCTGCGGTAA CACCCTCACA TGTTACTTGA AGGCCTCTGC AGCCTGTCGA
```

FIG. 2C

```
5101  GCTGCGAAGC TCCAGGACTG CACGATGCTC GTGAACGCCG CCGGCCTTGT
5151  CGTTATCTGT GAAAGCGCGG GAACCCAAGA GGACGCGGCG AGCCTACGAG
5201  TCTTCACGGA GGCTATGACT AGGTACTCTG CCCCCCCCGG GGACCCGCCC
5251  CAACCAGAAT ACGACTTGGA GCTGATAACA TCATGTTCCT CCAATGTGTC
5301  GGTCGCCCAC GATGCATCAG GCAAAAGGGT GTACTACCTC ACCCGTGATC
5351  CCACCACCCC CCTCGCACGG GCTGCGTGGG AAACAGCTAG ACACACTCCA
5401  GTTAACTCCT GGCTAGGCAA CATTATCATG TATGCGCCCA CTTTGTGGGC
5451  AAGGATGATT CTGATGACTC ACTTCTTCTC CATCCTTCTA GCACAGGAGC
5501  AACTTGAAAA AGCCCTGGAC TGCCAGATCT ACGGGCCTG TTACTCCATT
5551  GAGCCACTTG ACCTACCTCA GATCATTGAA CGACTCCATG GCCTTAGCGC
5601  ATTTTCACTC CATAGTTACT CTCCAGGTGA GATCAATAGG GTGGCTTCAT
5651  GCCTCAGGAA ACTTGGGGTA CCACCCTTGC GAGTCTGGAG ACATCGGGCC
5701  AGGAGCGTCC GCGCTAGGCT ACTGTCCCAG GGGGGAGGG CCGCCACTTG
5751  TGGCAAGTAC CTCTTCAACT GGGCAGTGAA GACCAAACTC AAACTCACTC
5801  CAATCCCGGC TGCGTCCCAG CTGGACTTGT CCGGCTGGTT CGTTGCTGGT
5851  TACAGCGGGG GAGACATATA TCACAGCCTG TCTCGTGCCC GACCCGCTG
5901  GTTCATGCTG TGCCTACTCC TACTTTCTGT AGGGGTAGGC ATCTACCTGC
5951  TCCCCAACCG ATAAA
```

FIG. 2D

```
   1    GCCACCATGG CCCCCATCAC CGCCTACAGC CAGCAGACCC GCGGCCTGCT
  51    GGGCTGCATC ATCACCAGCC TGACCGGCCG CGACAAGAAC CAGGTGGAGG
 101    GCGAGGTGCA GGTGGTGAGC ACCGCCACCC AGAGCTTCCT GGCCACCTGC
 151    GTGAACGGCG TGTGCTGGAC CGTGTACCAC GGCGCCGGCA GCAAGACCCT
 201    GGCCGGCCCC AAGGGCCCCA TCACCCAGAT GTACACCAAC GTGGACCAGG
 251    ACCTGGTGGG CTGGCAGGCC CCCCCGGCG CCCGCAGCCT GACCCCCTGC
 301    ACCTGCGGCA GCAGCGACCT GTACCTGGTG ACCCGCCACG CCGACGTGAT
 351    CCCCGTGCGC CGCCGCGGCG ACAGCCGCGG CAGCCTGCTG AGCCCCCGCC
 401    CCGTGAGCTA CCTGAAGGGC AGCAGCGGCG CCCCCTGCT GTGCCCCAGC
 451    GGCCACGCCG TGGGCATCTT CCGCGCCGCC GTGTGCACCC GCGGCGTGGC
 501    CAAGGCCGTG GACTTCGTGC CGTGGAGAG CATGGAGACC ACCATGCGCA
 551    GCCCCGTGTT CACCGACAAC AGCAGCCCCC CGCCGTGCC CCAGAGCTTC
 601    CAGGTGGCCC ACCTGCACGC CCCCACCGGC AGCGGCAAGA GCACCAAGGT
 651    GCCCGCCGCC TACGCCGCCC AGGGCTACAA GGTGCTGGTG CTGAACCCCA
 701    GCGTGGCCGC CACCCTGGGC TTCGGCGCCT ACATGAGCAA GGCCCACGGC
 751    ATCGACCCCA ACATCCGCAC CGGCGTGCGC ACCATCACCA CCGGCGCCCC
 801    CGTGACCTAC AGCACCTACG GCAAGTTCCT GGCCGACGGC GGCTGCAGCG
 851    GCGGCGCCTA CGACATCATC ATCTGCGACG AGTGCCACAG CACCGACAGC
 901    ACCACCATCC TGGGCATCGG CACCGTGCTG GACCAGGCCG AGACCGCCGG
 951    CGCCCGCCTG GTGGTGCTGG CCACCGCCAC CCCCCCCGGC AGCGTGACCG
1001    TGCCCCACCC CAACATCGAG GAGGTGGCCC TGAGCAACAC CGGCGAGATC
1051    CCCTTCTACG GCAAGGCCAT CCCCATCGAG GCCATCCGCG GCGGCCGCCA
1101    CCTGATCTTC TGCCACAGCA AGAAGAAGTG CGACGAGCTG GCCGCCAAGC
1151    TGAGCGGCCT GGGCATCAAC GCCGTGGCCT ACTACCGCGG CCTGGACGTG
1201    AGCGTGATCC CCACCATCGG CGACGTGGTG GTGGTGGCCA CCGACGCCCT
1251    GATGACCGGC TACACCGGCG ACTTCGACAG CGTGATCGAC TGCAACACCT
1301    GCGTGACCCA GACCGTGGAC TTCAGCCTGG ACCCCACCTT CACCATCGAG
1351    ACCACCACCG TGCCCCAGGA CGCCGTGAGC CGCAGCCAGC GCCGCGGCCG
1401    CACCGGCCGC GGCCGCCGCG GCATCTACCG CTTCGTGACC CCCGGCGAGC
1451    GCCCCAGCGG CATGTTCGAC AGCAGCGTGC TGTGCGAGTG CTACGACGCC
1501    GGCTGCGCCT GGTACGAGCT GACCCCCGCC GAGACCAGCG TGCGCCTGCG
1551    CGCCTACCTG AACACCCCCG GCCTGCCCGT GTGCCAGGAC CACCTGGAGT
1601    TCTGGGAGAG CGTGTTCACC GGCCTGACCC ACATCGACGC CCACTTCCTG
1651    AGCCAGACCA AGCAGGCCGG CGACAACTTC CCCTACCTGG TGGCCTACCA
```

FIG. 3A

| | | | | |
|------|------------|------------|------------|------------|
| 1701 | GGCCACCGTG | TGCGCCCGCG | CCCAGGCCCC | CCCCCCCAGC | TGGGACCAGA |
| 1751 | TGTGGAAGTG | CCTGATCCGC | CTGAAGCCCA | CCCTGCACGG | CCCCACCCCC |
| 1801 | CTGCTGTACC | GCCTGGGCGC | CGTGCAGAAC | GAGGTGACCC | TGACCCACCC |
| 1851 | CATCACCAAG | TACATCATGG | CCTGCATGAG | CGCCGACCTG | GAGGTGGTGA |
| 1901 | CCAGCACCTG | GGTGCTGGTG | GGCGGCGTGC | TGGCCGCCCT | GGCCGCCTAC |
| 1951 | TGCCTGACCA | CCGGCAGCGT | GGTGATCGTG | GCCGCATCA | TCCTGAGCGG |
| 2001 | CCGCCCCGCC | ATCGTGCCCG | ACCGCGAGTT | CCTGTACCAG | GAGTTCGACG |
| 2051 | AGATGGAGGA | GTGCGCCAGC | CACCTGCCCT | ACATCGAGCA | GGGCATGCAG |
| 2101 | CTGGCCGAGC | AGTTCAAGCA | GAAGGCCCTG | GCCTGCTGC | AGACCGCCAC |
| 2151 | CAAGCAGGCC | GAGGCCGCCG | CCCCCGTGGT | GGAGAGCAAG | TGGCGCGCCC |
| 2201 | TGGAGACCTT | CTGGGCCAAG | CACATGTGGA | ACTTCATCAG | CGGCATCCAG |
| 2251 | TACCTGGCCG | GCCTGAGCAC | CCTGCCCGGC | AACCCGCCA | TCGCCAGCCT |
| 2301 | GATGGCCTTC | ACCGCCAGCA | TCACCAGCCC | CCTGACCACC | CAGAGCACCC |
| 2351 | TGCTGTTCAA | CATCCTGGGC | GGCTGGGTGG | CCGCCCAGCT | GGCCCCCCCC |
| 2401 | AGCGCCGCCA | GCGCCTTCGT | GGGCGCCGGC | ATCGCCGGCG | CCGCCGTGGG |
| 2451 | CAGCATCGGC | CTGGGCAAGG | TGCTGGTGGA | CATCCTGGCC | GGCTACGGCG |
| 2501 | CCGGCGTGGC | CGGCGCCCTG | GTGGCCTTCA | AGGTGATGAG | CGGCGAGATG |
| 2551 | CCCAGCACCG | AGGACCTGGT | GAACCTGCTG | CCCGCCATCC | TGAGCCCCGG |
| 2601 | CGCCCTGGTG | GTGGGCGTGG | TGTGCGCCGC | CATCCTGCGC | CGCCACGTGG |
| 2651 | GCCCCGGCGA | GGGCGCCGTG | CAGTGGATGA | ACCGCCTGAT | CGCCTTCGCC |
| 2701 | AGCCGCGGCA | ACCACGTGAG | CCCCACCCAC | TACGTGCCCG | AGAGCGACGC |
| 2751 | CGCCGCCCGC | GTGACCCAGA | TCCTGAGCAG | CCTGACCATC | ACCCAGCTGC |
| 2801 | TGAAGCGCCT | GCACCAGTGG | ATCAACGAGG | ACTGCAGCAC | CCCCTGCAGC |
| 2851 | GGCAGCTGGC | TGCGCGACGT | GTGGGACTGG | ATCTGCACCG | TGCTGACCGA |
| 2901 | CTTCAAGACC | TGGCTGCAGA | GCAAGCTGCT | GCCCCAGCTG | CCCGGCGTGC |
| 2951 | CCTTCTTCAG | CTGCCAGCGC | GGCTACAAGG | GCGTGTGGCG | CGGCGACGGC |
| 3001 | ATCATGCAGA | CCACCTGCCC | CTGCGGCGCC | CAGATCACCG | GCCACGTGAA |
| 3051 | GAACGGCAGC | ATGCGCATCG | TGGGCCCCAA | GACCTGCAGC | AACACCTGGC |
| 3101 | ACGGCACCTT | CCCCATCAAC | GCCTACACCA | CCGGCCCCTG | CACCCCCAGC |
| 3151 | CCCGCCCCCA | ACTACAGCCG | CGCCCTGTGG | CGCGTGGCCG | CCGAGGAGTA |
| 3201 | CGTGGAGGTG | ACCCGCGTGG | GCGACTTCCA | CTACGTGACC | GGCATGACCA |
| 3251 | CCGACAACGT | GAAGTGCCCC | TGCCAGGTGC | CCGCCCCCGA | GTTCTTCACC |
| 3301 | GAGGTGGACG | GCGTGCGCCT | GCACCGCTAC | GCCCCCGCCT | GCCGCCCCCT |
| 3351 | GCTGCGCGAG | GAGGTGACCT | TCCAGGTGGG | CCTGAACCAG | TACCTGGTGG |

FIG. 3B

| | |
|---|---|
| 3401 | GCAGCCAGCT GCCCTGCGAG CCCGAGCCCG ACGTGGCCGT GCTGACCAGC |
| 3451 | ATGCTGACCG ACCCCAGCCA CATCACCGCC GAGACCGCCA AGCGCCGCCT |
| 3501 | GGCCCGCGGC AGCCCCCCCA GCCTGGCCAG CAGCAGCGCC AGCCAGCTGA |
| 3551 | GCGCCCCCAG CCTGAAGGCC ACCTGCACCA CCCACCACGT GAGCCCCGAC |
| 3601 | GCCGACCTGA TCGAGGCCAA CCTGCTGTGG CGCCAGGAGA TGGGCGGCAA |
| 3651 | CATCACCCGC GTGGAGAGCG AGAACAAGGT GGTGGTGCTG ACAGCTTCG |
| 3701 | ACCCCCTGCG CGCCGAGGAG GACGAGCGCG AGGTGAGCGT GCCCGCCGAG |
| 3751 | ATCCTGCGCA AGAGCAAGAA GTTCCCCGCC GCCATGCCCA TCTGGGCCCG |
| 3801 | CCCCGACTAC AACCCCCCCC TGCTGGAGAG CTGGAAGGAC CCCGACTACG |
| 3851 | TGCCCCCCGT GGTGCACGGC TGCCCCCTGC CCCCCATCAA GGCCCCCCCC |
| 3901 | ATCCCCCCCC CCCGCCGCAA GCGCACCGTG GTGCTGACCG AGAGCAGCGT |
| 3951 | GAGCAGCGCC CTGGCCGAGC TGGCCACCAA GACCTTCGGC AGCAGCGAGA |
| 4001 | GCAGCGCCGT GGACAGCGGC ACCGCCACCG CCCTGCCCGA CCAGGCCAGC |
| 4051 | GACGACGGCG ACAAGGGCAG CGACGTGGAG AGCTACAGCA GCATGCCCCC |
| 4101 | CCTGGAGGGC GAGCCCGGCG ACCCCGACCT GAGCGACGGC AGCTGGAGCA |
| 4151 | CCGTGAGCGA GGAGGCCAGC GAGGACGTGG TGTGCTGCAG CATGAGCTAC |
| 4201 | ACCTGGACCG GCGCCCTGAT CACCCCCTGC GCCGCCGAGG AGAGCAAGCT |
| 4251 | GCCCATCAAC GCCCTGAGCA ACAGCCTGCT GCGCCACCAC AACATGGTGT |
| 4301 | ACGCCACCAC CAGCCGCAGC GCCGGCCTGC GCCAGAAGAA GGTGACCTTC |
| 4351 | GACCGCCTGC AGGTGCTGGA CGACCACTAC CGCGACGTGC TGAAGGAGAT |
| 4401 | GAAGGCCAAG GCCAGCACCG TGAAGGCCAA GCTGCTGAGC GTGGAGGAGG |
| 4451 | CCTGCAAGCT GACCCCCCCC CACAGCGCCA AGAGCAAGTT CGGCTACGGC |
| 4501 | GCCAAGGACG TGCGCAACCT GAGCAGCAAG GCCGTGAACC ACATCCACAG |
| 4551 | CGTGTGGAAG GACCTGCTGG AGGACACCGT GACCCCCATC GACACCACCA |
| 4601 | TCATGGCCAA GAACGAGGTG TTCTGCGTGC AGCCCGAGAA GGGCGGCCGC |
| 4651 | AAGCCCGCCC GCCTGATCGT GTTCCCCGAC CTGGGCGTGC GCGTGTGCGA |
| 4701 | GAAGATGGCC CTGTACGACG TGGTGAGCAC CCTGCCCCAG GTGGTGATGG |
| 4751 | GCAGCAGCTA CGGCTTCCAG TACAGCCCCG CCAGCGCGT GGAGTTCCTG |
| 4801 | GTGAACACCT GGAAGAGCAA GAAGAACCCC ATGGGCTTCA GCTACGACAC |
| 4851 | CCGCTGCTTC GACAGCACCG TGACCGAGAA CGACATCCGC GTGGAGGAGA |
| 4901 | GCATCTACCA GTGCTGCGAC CTGGCCCCCG AGGCCCGCCA GGCCATCAAG |
| 4951 | AGCCTGACCG AGCGCCTGTA CATCGGCGGC CCCCTGACCA ACAGCAAGGG |
| 5001 | CCAGAACTGC GGCTACCGCC GCTGCCGCGC CAGCGGCGTG CTGACCACCA |
| 5051 | GCTGCGGCAA CACCCTGACC TGCTACCTGA AGGCCAGCGC CGCCTGCCGC |

FIG. 3C

```
5101    GCCGCCAAGC TGCAGGACTG CACCATGCTG GTGAACGCCG CCGGCCTGGT
5151    GGTGATCTGC GAGAGCGCCG GCACCCAGGA GGACGCCGCC AGCCTGCGCG
5201    TGTTCACCGA GGCCATGACC CGCTACAGCG CCCCCCCCGG CGACCCCCCC
5251    CAGCCCGAGT ACGACCTGGA GCTGATCACC AGCTGCAGCA GCAACGTGAG
5301    CGTGGCCCAC GACGCCAGCG GCAAGCGCGT GTACTACCTG ACCCGCGACC
5351    CCACCACCCC CCTGGCCCGC GCCGCCTGGG AGACCGCCCG CCACACCCCC
5401    GTGAACAGCT GGCTGGGCAA CATCATCATG TACGCCCCCA CCCTGTGGGC
5451    CCGCATGATC CTGATGACCC ACTTCTTCAG CATCCTGCTG GCCCAGGAGC
5501    AGCTGGAGAA GGCCCTGGAC TGCCAGATCT ACGGCGCCTG CTACAGCATC
5551    GAGCCCCTGG ACCTGCCCCA GATCATCGAG CGCCTGCACG GCCTGAGCGC
5601    CTTCAGCCTG CACAGCTACA GCCCCGGCGA GATCAACCGC GTGGCCAGCT
5651    GCCTGCGCAA GCTGGGCGTG CCCCCCCTGC GCGTGTGGCG CCACCGCGCC
5701    CGCAGCGTGC GCGCCCGCCT GCTGAGCCAG GGCGGCCGCG CCGCCACCTG
5751    CGGCAAGTAC CTGTTCAACT GGGCCGTGAA GACCAAGCTG AAGCTGACCC
5801    CCATCCCCGC CGCCAGCCAG CTGGACCTGA GCGGCTGGTT CGTGGCCGGC
5851    TACAGCGGCG GCGACATCTA CCACAGCCTG AGCCGCGCCC GCCCCCGCTG
5901    GTTCATGCTG TGCCTGCTGC TGCTGAGCGT GGGCGTGGGC ATCTACCTGC
5951    TGCCCAACCG CTAAA
```

FIG. 3D

```
   1 catcatcaat aatatacctt attttggatt gaagccaata tgataatgag ggggtggagt
  61 ttgtgacgtg gcgcggggcg tgggaacggg gcgggtgacg tagtagtgtg gcggaagtgt
 121 gatgttgcaa gtgtggcgga acacatgtaa gcgacggatg tggcaaaagt gacgtttttg
 181 gtgtgcgccg tgtacacacg gaagtgacaa ttttcgcgcg gttttaggcg gatgttgtag
 241 taaatttggg cgtaaccgag taagatttgg ccattttcgc gggaaaactg aataagagga
 301 agtgaaatct gaataatttt gtgttactca tagcgcgtaa tatttgtcta gggccgcggg
 361 gactttgacc gtttacgtgg agactcgccc aggtgttttt ctcaggtgtt ttccgcgttc
 421 cgggtcaaag ttggcgtttt attattatag gcggccgcga tccattgcat acgttgtatc
 481 catatcataa tatgtacatt tatattggct catgtccaac attaccgcca tgttgacatt
 541 gattattgac tagttattaa tagtaatcaa ttacggggtc attagttcat agcccatata
 601 tggagttccg cgttacataa cttacggtaa atgggccgcc tggctgaccg cccaacgacc
 661 cccgcccatt gacgtcaata atgacgtatg ttcccatagt aacgccaata gggactttcc
 721 attgacgtca atgggtggag tatttacggt aaactgccca cttggcagta catcaagtgt
 781 atcatatgcc aagtacgccc cctattgacg tcaatgacgg taaatggccc gcctggcatt
 841 atgcccagta catgacctta tgggactttc ctacttggca gtacatctac gtattagtca
 901 tcgctattac catggtgatg cggttttggc agtacatcaa tgggcgtgga tagcggtttg
 961 actcacgggg atttccaagt ctccacccca ttgacgtcaa tgggagtttg ttttggcacc
1021 aaaatcaacg ggactttcca aaatgtcgta acaactccgc cccattgacg caaatgggcg
1081 gtaggcgtgt acggtgggag gtctatataa gcagagctcg tttagtgaac cgtcagatcg
1141 cctggagacg ccatccacgc tgttttgacc tccatagaag acaccgggac cgatccagcc
1201 tccgcggccg ggaacggtgc attggaacgc ggattccccg tgccaagagt gagatctgcc
1261 accatggcgc ccatcacggc ctactcccaa cagacgcggg gcctacttgg ttgcatcatc
1321 actagcctta caggccggga caagaaccag gtcgagggag aggttcaggt ggtttccacc
1381 gcaacacaat ccttcctggc gacctgcgtc aacggcgtgt gttggaccgt ttaccatggt
1441 gctggctcaa agaccttagc cggcccaaag gggccaatca cccagatgta cactaatgtg
1501 gaccaggacc tcgtcggctg gcaggcgccc ccggggcgc gttccttgac accatgcacc
1561 tgtggcagct cagacccttta cttggtcacg agacatgctg acgtcattcc ggtgcgccgg
1621 cggggcgaca gtaggggagg cctgctctcc ccaggcctg tctcctactt gaagggctct
1681 tcgggtggtc cactgctctg cccttcgggg cacgctgtgg gcatcttccg ggctgccgta
1741 tgcacccggg gggttgcgaa ggcggtggac tttgtgcccg tagagtccat ggaaactact
1801 atgcggtctc cggtcttcac ggacaactca tcccccccgg ccgtaccgca gtcatttcaa
1861 gtggcccacc tacacgctcc cactggcagc ggcaagagta ctaaagtgcc ggctgcatat
1921 gcagcccaag ggtacaaggt gctcgtcctc aatccgtccg ttgccgctac cttagggttt
1981 ggggcgtata tgtctaaggc acacggtatt gaccccaaca tcagaactgg ggtaaggacc
2041 attaccacag gcgcccccgt cacatactct acctatggca agtttcttgc cgatggtggt
2101 tgctctgggg gcgcttatga catcataata tgtgatgagt gccattcaac tgactcgact
2161 acaatcttgg gcatcggcac agtcctggac caagcggaga cggctggagc gcggcttgtc
2221 gtgctcgcca ccgctacgcc tccgggatcg gtcaccgtgc cacacccaaa catcgaggag
2281 gtggccctgt ctaatactgg agagatcccc ttctatggca aagccatccc cattgaagcc
2341 atcagggggg gaaggcatct cattttctgt cattccaaga agaagtgcga cgagctcgcc
2401 gcaaagctgt caggcctcgg aatcaacgct gtggcgtatt accgggggct cgatgtgtcc
2461 gtcataccaa ctatcggaga cgtcgttgtc gtggcaacag acgctctgat gacgggctat
2521 acgggcgact ttgactcagt gatcgactgt aacacatgtg tcacccagac agtcgacttc
2581 agcttggatc ccaccttcac cattgagacg acgaccgtgc ctcaagacgc agtgtcgcgc
2641 tcgcagcggc ggggtaggac tggcagggt aggagaggca tctacaggtt tgtgactccg
2701 ggagaacggc cctcgggcat gttcgattcc tcggtcctgt gtgagtgcta tgacgcgggc
2761 tgtgcttggt acgagctcac ccccgccgag acctcggtta ggttgcgggc ctacctgaac
2821 acaccagggt gcccgtttg ccaggaccac ctggagttct gggagagtgt cttcacaggc
2881 ctcacccaca tagatgcaca cttcttgtcc cagaccaagc aggcaggaga caacttcccc
2941 tacctggtag cataccaagc cacggtgtgc gccagggctc aggcccacc tccatcatgg
3001 gatcaaatgt ggaagtgtct catacggctg aaacctacgc tgcacgggcc aacacccttg
3061 ctgtacaggc tgggagccgt ccaaaatgag gtcacccctca cccacccat aaccaaatac
3121 atcatggcat gcatgtcggc tgacctggag gtcgtcacta gcacctgggt gctggtgggc
3181 ggagtccttg cagctctggc cgcgtattgc ctgacaacag cagtgtggt cattgtgggt
3241 aggattatct tgtccgggag gccggctatt gttcccgaca gggagtttct ctaccaggag
```

FIG. 4B

```
3361 gccgagcaat tcaagcagaa agcgctcggg ttactgcaaa cagccaccaa acaagcggag
3421 gctgctgctc ccgtggtgga gtccaagtgg cgagcccttg agacattctg ggcgaagcac
3481 atgtggaatt tcatcagcgg gatacagtac ttagcaggct tatccactct gcctgggaac
3541 cccgcaatag catcattgat ggcattcaca gcctctatca ccagcccgct caccacccaa
3601 agtaccctcc tgtttaacat cttggggggg tgggtggctg cccaactcgc ccccccagc
3661 gccgcttcgg ctttcgtggg cgccggcatc gccggtgcgg ctgttggcag cataggcctt
3721 gggaaggtgc ttgtggacat tctggcgggt tatggagcag gagtggccgg cgcgctcgtg
3781 gccttcaagg tcatgagcgg cgagatgccc tccaccgagg acctggtcaa tctacttcct
3841 gccatcctct ctcctggcgc cctggtcgtc ggggtcgtgt gtgcagcaat actgcgtcga
3901 cacgtgggtc cgggagaggg ggctgtgcag tggatgaacc ggctgatagc gttcgcctcg
3961 cggggtaatc atgtttcccc cacgcactat gtgcctgaga gcgacgccgc agcgcgtgtt
4021 actcagatcc tctccagcct taccatcact cagctgctga aaaggctcca ccagtggatt
4081 aatgaagact gctccacacc gtgttccggc tcgtggctaa gggatgtttg ggactggata
4141 tgcacggtgt tgactgactt caagacctgg ctccagtcca agctcctgcc gcagctaccg
4201 ggagtccctt ttttctcgtg ccaacgcggg tacaagggag tctggcgggg agacggcatc
4261 atgcaaacca cctgcccatg tggagcacag atcaccggac atgtcaaaaa cggttccatg
4321 aggatcgtcg ggcctaagac ctgcagcaac acgtggcatg aacattccc catcaacgca
4381 tacaccacgg gcccctgcac accctctcca gcgccaaact attctagggc gctgtggcgg
4441 gtggccgctg aggagtacgt ggaggtcacg cgggtggggg atttccacta cgtgacgggc
4501 atgaccactg acaacgtaaa gtgcccatgc caggttccgg ctcctgaatt cttcacggag
4561 gtggacggag tgcggttgca caggtacgct ccggcgtgca ggcctctcct acgggaggag
4621 gttacattcc aggtcgggct caaccaatac ctggttgggt cacagctacc atgcgagccc
4681 gaaccggatg tagcagtgct cacttccatg ctcaccgacc cctcccacat cacagcagaa
4741 acggctaagc gtaggttggc caggggtctc cccccctcct tggccagctc ttcagctagc
4801 cagttgtctg cgccttcctt gaaggcgaca tgcactaccc accatgtctc tccggacgct
4861 gacctcatcg aggccaacct cctgtggcgg caggagatgg gcgggaacat cacccgcgtg
4921 gagtcggaga caaggtggt agtcctggac tctttcgacc cgcttcgagc ggaggaggat
4981 gagagggaag tatccgttcc ggcggagatc ctgcggaaat ccaagaagtt ccccgcagcg
5041 atgcccatct gggcgcgccc ggattacaac cctccactgt tagagtcctg gaaggacccg
5101 gactacgtcc ctccggtggt gcacgggtgc ccgttgccac ctatcaaggc ccctccaata
5161 ccacctccac ggagaaagag gacggttgtc ctaacagagt cctccgtgtc ttctgcctta
5221 gcggagctcg ctactaagac cttcggcagc tccgaatcat cggccgtcga cagcggcacg
5281 gcgaccgccc ttcctgacca ggcctccgac gacggtgaca aggatccga cgttgagtcg
5341 tactcctcca tgcccccct tgaggggaa ccggggggacc ccgatctcag tgacgggtct
5401 tggtctaccg tgagcgagga agctagtgag gatgtcgtct gctgctcaat gtcctacaca
5461 tggacaggcg ccttgatcac gccatgcgct gcggaggaaa gcaagctgcc catcaacgcg
5521 ttgagcaact ctttgctgcg ccaccataac atggtttatg ccacaacatc tcgcagcgca
5581 ggcctgcggc agaagaaggt cacctttgac agactgcaag tcctggacga ccactaccgg
5641 gacgtgctca aggagatgaa ggcgaaggcg tccacagtta aggctaaact cctatccgta
5701 gaggaagcct gcaagctgac gccccacat tcggccaaat ccaagtttgg ctatgggca
5761 aaggacgtcc ggaacctatc agcaaggcc gttaaccaca tccactccgt gtggaaggac
5821 ttgctggaag acactgtgac accaattgac accaccatca tggcaaaaa tgaggttttc
5881 tgtgtccaac cagagaaagg aggccgtaag ccagcccgcc ttatcgtatt cccagatctg
5941 ggagtccgtg tatgcgagaa gatggcctc tatgatgtgg tctccaccct tctcaggtc
6001 gtgatgggct cctcatacgg attccagtac tctcctgggc agcgagtcga gttcctggtg
6061 aatacctgga aatcaaagaa aaaccccatg ggcttttcat atgacactcg ctgtttcgac
6121 tcaacggtca ccgagaacga catccgtgtt gaggagtcaa tttaccaatg ttgtgacttg
6181 gcccccgaag ccagacaggc cataaaatcg ctcacagagc ggctttatat cggggtcct
6241 ctgactaatt caaaagggca gaactgcggt tatcgccggt gccgcgcgag cggcgtgctg
6301 acgactagct gcgtaacac cctcacatgt tacttgaagg cctctgcagc ctgtcgagct
6361 gcgaagctcc aggactgcac gatgctcgtg aacgccgccg gccttgtcgt tatctgtgaa
6421 agcgcgggaa cccaagagga cgcggcgagc ctacgagtct tcacggaggc tatgactagg
6481 tactctgccc ccccggggga cccgcccaa ccagaatacg acttggagct gataacatca
6541 tgttcctcca atgtgtcggt cgcccacgat gcatcaggca aagggtgta ctacctcacc
6601 cgtgatccca ccacccccct cgcacgggct gcgtgggaaa cagctagaca cactccagtt
```

FIG. 4C

```
6661 aactcctggc taggcaacat tatcatgtat gcgcccactt tgtgggcaag gatgattctg
6721 atgactcact tcttctccat ccttctagca caggagcaac ttgaaaaagc cctggactgc
6781 cagatctacg gggcctgtta ctccattgag ccacttgacc tacctcagat cattgaacga
6841 ctccatggcc ttagcgcatt ttcactccat agttactctc caggtgagat caatagggtg
6901 gcttcatgcc tcaggaaact tggggtaccc cccttgcgag tctggagaca tcgggccagg
6961 agcgtccgcg ctaggctact gtcccagggg ggagggccg ccacttgtgg caagtacctc
7021 ttcaactggg cagtgaagac caaactcaaa ctcactccaa tcccggctgc gtcccagctg
7081 gacttgtccg gctggttcgt tgctggttac agcggggggag acatatatca cagcctgtct
7141 cgtgcccgac cccgctggtt catgctgtgc ctactcctac tttctgtagg ggtaggcatc
7201 tacctgctcc ccaaccggta aatctagagc tgtgccttct agttgccagc catctgttgt
7261 ttgcccctcc cccgtgcctt ccttgaccct ggaaggtgcc actcccactg tcctttccta
7321 ataaaatgag gaaattgcat cgcattgtct gagtaggtgt cattctattc tgggggtgg
7381 ggtgggcag acagcaagg gggaggattg gaagacaat agcaggcatg ctggggatgc
7441 ggtgggctct atggccgatc ggcgcgccgt actgaaatgt gtgggcgtgg cttaagggtg
7501 ggaaagaata tataaggtgg gggtcttatg tagttttgta tctgttttgc agcagccgcc
7561 gccgccatga gcaccaactc gtttgatgga agcattgtga gctcatattt gacaacgcgc
7621 atgccccat gggccgggt gcgtcagaat gtgatgggct ccagcattga tggtcgcccc
7681 gtcctgcccg caaactctac taccttgacc tacgagaccg tgtctggaac gccgttggag
7741 actgcagcct ccgccgccgc ttcagccgct gcagccaccg cccgcgggat tgtgactgac
7801 tttgctttcc tgagcccgct tgcaagcagt gcagcttccc gttcatccgc ccgcgatgac
7861 aagttgacgg ctcttttggc acaattggat tctttgaccc gggaacttaa tgtcgtttct
7921 cagcagctgt tggatctgcg ccagcaggtt tctgccctga aggcttcctc ccctcccaat
7981 gcggtttaaa acataaataa aaaaccagac tctgtttgga tttggatcaa gcaagtgtct
8041 tgctgtcttt atttaggggt tttgcgcgcg cggtaggccc gggaccagcg gtctcggtcg
8101 ttgagggtcc tgtgtatttt tccaggacg tggtaaaggt gactctggat gttcagatac
8161 atgggcataa gcccgtctct gggtgtgagg tagcaccact gcagagcttc atgctgcggg
8221 gtggtgttgt agatgatcca gtcgtagcag gagcgctggg cgtggtgcct aaaatgtct
8281 tcagtagca agctgattgc caggggcagg cccttggtgt aagtgtttac aaagcggtta
8341 agctgggatg ggtgcatacg tgggatatg atgcatct tggactgtat ttttaggttg
8401 gctatgttcc cagccatatc cctccgggga ttcatgttgt gcagaaccac cagcacagtg
8461 tatccggtgc acttgggaaa tttgtcatgt agcttagaag gaaatgcgtg gaagaacttg
8521 gagacgccct tgtgacctcc aagatttccc atgcattcgt ccataatgat ggcaatgggc
8581 ccacgggcgg cggcctgggc gaagatattt ctgggatcac taacgtcata gttgtgttcc
8641 aggatgagat cgtcataggc cattttttaca aagcgcggc ggagggtgcc agactgcggt
8701 ataatggttc catccggccc aggggcgtag ttaccctcac agatttgcat ttcccacgct
8761 tgagttcag atggggggat catgtctacc tgcggggcga tgaagaaaac ggttccgggg
8821 gtaggggaga tcagctggga agaaagcagg ttcctgagca gctgcgactt accgcagccg
8881 gtgggcccgt aaatcacacc tattaccggc tgcaactggt agttaagaga gctgcagctg
8941 ccgtcatccc tgagcagggg ggccacttcg ttaagcatgt ccctgactcg catgtttcc
9001 ctgaccaaat ccgccagaag gcgctcgccg cccagcgata gcagttcttg caaggaagca
9061 aagtttttca acggtttgag accgtccgcc gtaggcatgc ttttgagcgt ttgaccaagc
9121 agttccaggc ggtcccacag ctcggtcacc tgctctacgg catctcgatc cagcatatct
9181 cctcgtttcg cggggttgggg cggctttcgc tgtacggcag tagtcggtgc tcgtccagac
9241 gggccagggt catgtctttc cacggggcgca gggtcctcgt cagcgtagtc tgggtcacgg
9301 tgaaggggtg cgctccgggc tgcgcgctgg ccaggtgcg cttgaggctg gtcctgctgg
9361 tgctgaagcg ctgccggtct tcgccctgcg cgtcggccag gtagcatttg accatggtgt
9421 catagtccag cccctccgcg cgtggccct tggcgcgcag cttgcccttg gaggaggcgc
9481 cgcacgaggg gcagtgcaga cttttgaggg cgtagagctt ggcgcgaga ataccgatt
9541 ccggggagta ggcatccgcg ccgcaggccc cgcagacggt ctcgcattcc acgagccagg
9601 tgagctctgg ccgttcgggg tcaaaaacca ggtttccccc atgctttttg atgcgtttct
9661 tacctctggt ttccatgagc cggtgtccac gctcggtgac gaaaggctg tccgtgtccc
9721 cgtatacaga cttgagaggc ctgtcctcga gcggtgttcc gcggtcctcc tcgtatagaa
9781 actcggacca ctctgagacg aaggctcgcg tccaggccac acgaaggag gctaagtggg
9841 aggggtagcg tcgttgtcc actaggggt ccactcgctc cagggtgtga agacacatgt
9901 cgccctcttc ggcatcaagg aagtgattg gtttataggt gtaggccacg tgaccgggtg
```

FIG. 4D

```
 9961 ttcctgaagg ggggctataa aagggggtgg gggcgcgttc gtcctcactc tcttccgcat
10021 cgctgtctgc gagggccagc tgttggggtg agtactccct ctcaaaagcg ggcatgactt
10081 ctgcgctaag attgtcagtt tccaaaaacg aggaggattt gatattcacc tggcccgcgg
10141 tgatgccttt gagggtggcc gcgtccatct ggtcagaaaa gacaatcttt ttgttgtcaa
10201 gcttggtggc aaacgacccg tagagggcgt tggacagcaa cttggcgatg gagcgcaggg
10261 tttggttttt gtcgcgatcg gcgcgctcct tggccgcgat gtttagctgc acgtattcgc
10321 gcgcaacgca ccgccattcg ggaaagacgg tggtgcgctc gtcgggcact aggtgcacgc
10381 gccaaccgcg gttgtgcagg gtgacaaggt caacgctggt ggctacctct ccgcgtaggc
10441 gctcgttggt ccagcagagg cggccgccct tgcgcgagca gaatggcggt agtgggtcta
10501 gctgcgtctc gtccgggggg tctgcgtcca cggtaaagac cccgggcagc aggcgcgcgt
10561 cgaagtagtc tatcttgcat ccttgcaagt ctagcgcctg ctgccatgcg cgggcggcaa
10621 gcgcgcgctc gtatgggttg agtggggggac cccatggcat ggggtgggtg agcgcggagg
10681 cgtacatgcc gcaaatgtcg taaacgtaga ggggctctct gagtattcca agatatgtag
10741 ggtagcatct tccaccgcgg atgctggcgc gcacgtaatc gtatagttcg tgcgagggag
10801 cgaggaggtc gggaccgagg ttgctacggg cgggctgctc tgctcggaag actatctgcc
10861 tgaagatggc atgtgagttg gatgatatgg ttggacgctg gaagacgttg aagctggcgt
10921 ctgtgagacc taccgcgtca cgcacgaagg aggcgtagga gtcgcgcagc ttgttgacca
10981 gctcggcggt gacctgcacg tctagggcgc agtagtccag ggtttccttg atgatgtcat
11041 acttatcctg tccctttttt ttccacagct cgcggttgag gacaaactct tcgcggtctt
11101 tccagtactc ttggatcgga aacccgtcgg cctccgaacg gtaagagcct agcatgtaga
11161 actggttgac ggcctggtag gcgcagcatc ccttttctac gggtagcgcg tatgcctgcg
11221 cggccttccg gagcgaggtg tgggtgagcg caaaggtgtc cctaaccatg actttgaggt
11281 actggtattt gaagtcagtg tcgtcgcatc cgccctgctc ccagagcaaa aagtccgtgc
11341 gcttttttgga acgcgggttt gcagggcga aggtgacatc gttgaagagt atctttcccg
11401 cgcgaggcat aaagttgcgt gtgatgcgga agggtcccgg cacctcggaa cggttgttaa
11461 ttacctgggc ggcgagcacg atctcgtcaa agccgttgat gttgtggccc acaatgtaaa
11521 gttccaagaa gcgcgggatg cccttgatgg aaggcaattt tttaagttcc tcgtaggtga
11581 gctcttcagg ggagctgagc ccgtgctctg aaagggccca gtctgcaaga tgagggttgg
11641 aagcgacgaa tgagctccac aggtcacggg ccattagcat ttgcaggtgg tcgcgaaagg
11701 tcctaaactg gcgacctatg gccatttttt ctggggtgat gcagtagaag gtaagcgggt
11761 cttgttccca gcggtcccat ccaaggtccg cggctaggtc tcgcgcggcg gtcactagag
11821 gctcatctcc gccgaacttc atgaccagca tgaagggcac gagctgcttc ccaaaggccc
11881 ccatccaagt ataggtctct acatcgtagg tgacaaagag acgctcggtg cgaggatgcg
11941 agccgatcgg gaagaactgg atctcccgcc accagttgga ggagtggctg ttgatgtggt
12001 gaaagtagaa gtccctgcga cgggccgaac actcgtgctg gcttttgtaa aaacgtgcgc
12061 agtactggca gcggtgcacg ggctgtacat cctgcacgag gttgacctga cgaccgcgca
12121 caaggaagca gagtgggaat ttgagcccct cgcctggcgg gtttggctgg tggtcttcta
12181 cttcggctgc ttgtccttga ccgtctggct gctcgagggg agttacggtg gatcggacca
12241 ccacgccgcg cgagcccaaa gtccagatgt ccgcgcgcgg cggtcggagc ttgatgacaa
12301 catcgcgcag atgggagctg tccatggtct ggagctcccg cggcgtcagg tcaggcggga
12361 gctcctgcag gtttacctcg catagccggg tcagggcgcg ggctaggtcc aggtgatacc
12421 tgatttccag gggctggttg gtggcggcgt cgatggcttg caagaggccg catccccgcg
12481 gcgcgactac ggtaccgcgc ggcgggcggt gggccgcggg ggtgtccttg gatgatgcat
12541 ctaaaagcgg tgacgcgggc gggcccccgg aggtaggggg ggctcgggac ccgccgggag
12601 aggggggcagg ggcacgtcgg cgccgcgcgc gggcaggagc tggtgctgcg cgcggaggtt
12661 gctggcgaac gcgacgacgc ggcggttgat ctcctgaatc tggcgcctct gcgtgaagac
12721 gacgggcccg gtgagcttga acctgaaaga gagttgcgaca gaatcaattt cggtgtcgtt
12781 gacggcggcc tggcgcaaaa tctcctgcac gtctcctgag ttgtcttgat aggcgatctc
12841 ggccatgaac tgctcgatct cttcctcctg gagatctccg cgtccggctc gctccacggt
12901 ggcggcgagg tcgttggaga tgcgggccat gagctgcgag aaggcgttga ggcctccctc
12961 gttccagacg cggctgtaga ccacgccccc ttcggcatcg cgggcgcgca tgaccacctg
13021 cgcgagattg agctccacgt gccgggcgaa gacggcgtag tttcgcaggc gctgaaagag
13081 gtagttgagg gtggtggcgg tgtgttctgc cacgaagaag tacataaccc agcgccgcaa
13141 cgtggattcg ttgatatccc caaggcctc aaggcgctcc atggcctcgt agaagtccac
13201 ggcgaagttg aaaaactggg agttgcgcgc gacacggtt aactcctcct ccagaagacg
```

FIG. 4E

```
13261 gatgagctcg gcgacagtgt cgcgcacctc gcgctcaaag gctacagggg cctcttcttc
13321 ttcttcaatc tcctcttcca taagggcctc cccttcttct tcttctggcg gcggtggggg
13381 agggggggaca cggcggcgac gacggcgcac cgggaggcgg tcgacaaagc gctcgatcat
13441 ctccccgcgg cgacggcgca tggtctcggt gacggcgcgg ccgttctcgc gggggcgcag
13501 ttggaagacg ccgcccgtca tgtcccggtt atgggttggc ggggggctgc cgtgcggcag
13561 ggatacggcg ctaacgatgc atctcaacaa ttgttgtgta ggtactccgc caccgaggga
13621 cctgagcgag tccgcatcga ccggatcgga aaacctctcg agaaaggcgt ctaaccagtc
13681 acagtcgcaa ggtaggctga gcaccgtggc gggcggcagc gggcggcggt cggggttgtt
13741 tctggcggag gtgctgctga tgatgtaatt aaagtaggcg gtcttgagac ggcggatggt
13801 cgacagaagc accatgtcct tgggtccggc ctgctgaatg cgcaggcggt cggccatgcc
13861 ccaggcttcg ttttgacatc ggcgcaggtc tttgtagtag tcttgcatga gcctttctac
13921 cggcacttct tcttctcctt cctcttgtcc tgcatctctt gcatctatcg ctgcggcggc
13981 ggcggagttt ggccgtaggt ggcgccctct tcctcccatg cgtgtgaccc cgaagcccct
14041 catcggctga agcagggcca ggtcggcgac aacgcgctcg gctaatatgg cctgctgcac
14101 ctgcgtgagg gtagactgga agtcgtccat gtccacaaag cggtggtatg cgcccgtgtt
14161 gatggtgtaa gtgcagttgg ccataacgga ccagttaacg gtctggtgac ccggctgcga
14221 gagctcggtg tacctgagac gcgagtaagc ccttgagtca aagacgtagt cgttgcaagt
14281 ccgcaccagg tactggtatc ccaccaaaaa gtgcggcggc ggctggcggt agaggggcca
14341 gcgtagggtg gccggggctc cggggcgag gtcttccaac ataaggcgat gatatccgta
14401 gatgtacctg gacatccagg tgatgccggc ggcggtggtg gaggcgcgcg gaaagtcacg
14461 gacgcggttc cagatgttgc gcagcggcaa aaagtgctcc atggtcggga cgctctggcc
14521 ggtcaggcgc gcgcagtcgt tgacgctcta gaccgtgcaa aggagagcc tgtaagcggg
14581 cactcttccg tggtctggtg gataaattcg caagggtatc atggcggacg accggggttc
14641 gaaccccgga tccggccgtc cgccgtgatc catgcggtta ccgcccgcgt gtcgaaccca
14701 ggtgtgcgac gtcagacaac ggggagcgc tccttttggc ttccttccag gcgcggcgga
14761 tgctgcgcta gcttttttgg ccactggcg cgcgcggcgt aagcggttag gctggaaagc
14821 gaaagcatta agtggctcgc tccctgtagc cggagggtta ttttccaagg gttgagtcgc
14881 gggaccccg gttcgagtct cgggccggcc ggactgcggc gaacggggt ttgcctcccc
14941 gtcatgcaag accccgcttg caaattcctc cggaaacagg gacgagcccc ttttttgctt
15001 ttcccagatg catccggtgc tgcggcagat gcgccccct cctcagcagc ggcaagagca
15061 agagcagcgg cagacatgca gggcaccctc cccttctcct accgcgtcag gaggggcaac
15121 atccgcggct gacgcggcgg cagatggtga ttacgaaccc ccgcggcgcc ggacccggca
15181 ctacttggac ttggaggagg gcgagggcct ggcgcggcta ggagcgccct ctcctgagcg
15241 acacccaagg gtgcagctga agcgtgacac gcgcgaggcg tacgtgccgc ggcagaacct
15301 gtttcgcgac cgcgagggag aggagcccga ggagatgcgg gatcgaaagt tccatgcagg
15361 gcgcgagttg cggcatggcc tgaaccgcga gcggttgctg cgcgaggagg actttgagcc
15421 cgacgcgcgg accgggatta gtcccgcgcg cgcacacgtg gcggccgccg acctggtaac
15481 cgcgtacgag cagacggtga accaggagat taactttcaa aaaagcttta acaaccacgt
15541 gcgcacgctt gtggcgcgcg aggaggtggc tataggactg atgcatctgt gggactttgt
15601 aagcgcgctg gagcaaaacc caaatagcaa gccgctcatg gcgcagctgt tccttatagt
15661 gcagcacagc agggacaacg aggcattcag ggatgcgctg ctaaacatag tagagcccga
15721 gggccgctgg ctgctcgatt tgataaacat tctgcagagc atagtggtgc aggagcgcag
15781 cttgagcctg gctgacaagg tggccgccat taactattcc atgctcagtc tgggcaagtt
15841 ttacgcccgc aagatatacc atacccctta cgttcccata gacaaggagg taaagatcga
15901 ggggttctac atgcgcatgg cgctgaaggt gcttaccttg agcgacgacc tgggcgttta
15961 tcgcaacgag cgcatccaca aggccgtgag cgtcgagccgc cggcgcgagc tcagcgaccg
16021 cgagctgatg cacagcctgc aaagggccct ggctggcacg ggcagcggcg atagagaggc
16081 cgagtcctac tttgacgcgg gcgctgacct gcgctgggcc ccaagccgac gcgccctgga
16141 ggcagctggg gccggacctg ggctggcggt ggcacccgcg cgcgctggca acgtcggcgg
16201 cgtggaggaa tatgacgagg acgatgagta cgagccagag gacggcgagt actaagcggt
16261 gatgtttctg atcagatgat gcaagacgca acggacccgg cggtgcgggc ggcgctgcag
16321 agccagccgt ccggccttaa ctccacggac gactggcgcc aggtcatgga ccgcatcatg
16381 tcgctgactg cgcgcaaccc tgacgcgttc cggcagcagc gcaggccaa ccggctctcc
16441 gcaattctgg aagcggtggt cccggcgcgc gcaaacccca cgcacgagaa ggtgctggcg
16501 atcgtaaacg cgctggccga aaacagggcc atccggcccg atgaggccgg cctggtctac
```

FIG. 4F

```
16561 gacgcgctgc ttcagcgcgt ggctcgttac aacagcagca acgtgcagac caacctggac
16621 cggctggtgg gggatgtgcg cgaggccgtg gcgcagcgtg agcgcgcgca gcagcagggc
16681 aacctgggct ccatggttgc actaaacgcc ttcctgagta cacagcccgc caacgtgccg
16741 cggggacagg aggactacac caactttgtg agcgcactgc ggctaatggt gactgagaca
16801 ccgcaaagtg aggtgtatca gtccgggcca gactattttt tccagaccag tagacaaggc
16861 ctgcagaccg taaacctgag ccaggctttc aagaacttgc aggggctgtg ggggtgcgg
16921 gctcccacag gcgaccgcgc gaccgtgtct agcttgctga cgcccaactc gcgcctgttg
16981 ctgctgctaa tagcgccctt cacggacagt ggcagcgtgt cccgggacac atacctaggt
17041 cacttgctga cactgtaccg cgaggccata ggtcaggcgc atgtggacga gcatactttc
17101 caggagatta caagtgttag ccgcgcgctg gggcaggagg acacgggcag cctggaggca
17161 accctgaact acctgctgac caaccggcgg caaaaaatcc cctcgttgca cagtttaaac
17221 agcgaggagg agcgcatttt gcgctatgtg cagcagagcg tgagccttaa cctgatgcgc
17281 gacggggtaa cgcccagcgt ggcgctggac atgaccgcgc gcaacatgga accgggcatg
17341 tatgcctcaa accggccgtt tatcaatcgc ctaatggact acttgcatcg cgcggccgcc
17401 gtgaacccgg agtatttcac caatgccatc ttgaacccgc actggctacc gccccctggt
17461 ttctacaccg ggggattcga ggtgcccgag ggtaacgatg gattcctctg ggacgacata
17521 gacgacagcg tgttttcccc gcaaccgcag accctgctag agttgcaaca acgcgagcag
17581 gcagaggcgg cgctgcgaaa ggaaagcttc cgcaggccaa gcagcttgtc cgatctaggc
17641 gctgcggccc gcggtcaga tgctagtagc ccatttccaa gcttgatagg gtctcttacc
17701 agcactcgca ccacccgccc gcgcctgctg ggcgaggagg agtacctaaa caactcgctg
17761 ctgcagccgc agcgcgaaaa gaacctgcct ccggcgtttc ccaacaacgg gatagagagc
17821 ctagtggaca agatgagtag atggaagacg tatgcgcagg agcacaggga tgtgcccggc
17881 ccgcgcccgc ccaccccgtcg tcaaaggcac gaccgtcagc ggggtctggt gtgggaggac
17941 gatgactcgg cagacgacag cagcgtcttg gatttgggag ggagtggcaa cccgtttgca
18001 caccttccgc ccaggctggg gagaatgttt taaaaaaag catgatgcaa aataaaaac
18061 tcaccaaggc catggcaccg agcgttggtt ttcttgtatt ccccttagta tgccgcgcgc
18121 ggcgatgtat gaggaaggtc ctcctccctc ctacgagagc gtggtgagcg cggcgccagt
18181 ggcggcggcg ctgggttcac ccttcgatgc tcccctggac ccgccgttcg tgcctccgcg
18241 gtacctgcgg cctaccgggg ggagaaacag catccgttac tctgagttgg cacccctatt
18301 cgacaccacc cgtgtgtacc ttgtggacaa caagtcaacg gatgtggcat ccctgaacta
18361 ccagaacgac cacagcaact ttctaaccac ggtcattcaa aacaatgact acagcccggg
18421 ggaggcaagc acacagacca tcaatcttga cgaccggtcg cactggggcg gcgacctgaa
18481 aaccatcctg cataccaaca tgccaaatgt gaacgagttc atgtttacca ataagtttaa
18541 ggcgcgggtg atggtgtcgc gctcgcttac taaggacaaa caggtggagc tgaaatacga
18601 gtgggtggag ttcacgctgc ccgagggcaa ctactccgag accatgacca tagacctat
18661 gaacaacgcg atcgtggagc actacttgaa agtgggcagg cagaacgggg ttctggaaag
18721 cgacatcggg gtaaagtttg acacccgcaa cttcagactg gggtttgacc cagtcactgg
18781 tcttgtcatg cctggggtat atacaaacga agccttccat ccagacatca ttttgctgcc
18841 aggatgcggg gtggacttca cccacagccg cctgagcaac tgttgggca tccgcaagcg
18901 gcaacccttc caggagggct ttaggatcac ctacgatgac ctggagggtg gtaacattcc
18961 cgcactgttg gatgtggacg cctaccaggc aagcttgaaa gatgacaccg aacagggcgg
19021 gggtggcgca ggcggcggca acaacagtgg cagcggcgcg gaagagaact ccaacgcggc
19081 agctgcggca atgcagccgg tggaggacat gaacgatcat gccattcgcg cgacacctt
19141 tgccacacgg gcggaggaga agcgcgctga ggccgaggca gcggccgaag ctgccgcccc
19201 cgctgcggag gctgcacaac ccaggtcga gaagcctcag aagaaaccgg tgattaaacc
19261 cctgacagag gacagcaaga aacgcagtta caacctaata gcaatgaca gcaccttcac
19321 ccagtaccgc agctggtacc ttgcataaa ctacggcgac cctcaggccg ggatccgctc
19381 atggaccctg ctttgcactc ctgacgtaac ctgcggctcg gagcaggtat actggtcgtt
19441 gcccgacatg atgcaagacc ccgtgacctt ccgctccacg cgccagatca gcaactttcc
19501 ggtggtgggc gccgagctgt tgcccgtgca ctccaagagc ttctacaacg accaggccgt
19561 ctactcccag ctcatccgcc agtttaccct tctgacccac gtgttcaatc gctttcccga
19621 gaaccagatt ttggcgcgcc cgccagcccc caccatcacc accgtcagtg aaaacgttcc
19681 tgctctcaca gatcacggga cgctaccgct gcgcaacagc atcggaggag tccagcgagt
19741 gaccattact gacgccagac gcgcacctg cccctacgtt tacaaggccc tgggcatagt
19801 ctcgccgcgc gtcctatcga gccgcacttt ttgagcaagc atgtccatcc ttatatcgcc
```

FIG. 4G

```
19861 cagcaataac acaggctggg gcctgcgctt cccaagcaag atgtttggcg gggccaagaa
19921 gcgctccgac caacacccag tgcgcgtgcg cgggcactac cgcgcgccct ggggcgcgca
19981 caaacgcggc cgcactgggc gcaccaccgt cgatgacgcc atcgacgcgg tggtggagga
20041 ggcgcgcaac tacacgccca cgccgccgcc agtgtccacc gtggacgcgg ccattcagac
20101 cgtggtgcgc ggagcccggc gctacgctaa aatgaagaga cggcggaggc gcgtagcacg
20161 tcgccaccgc cgccgacccg gcactgccgc caacgcgcg cggcggccc tgcttaaccg
20221 cgcacgtcgc accggccgac gggcggccat gcgagccgct cgaaggctgg ccgcgggtat
20281 tgtcactgtg ccccccaggt ccaggcgacg agcggccgcc gcagcagccg cggccattag
20341 tgctatgact cagggtcgca ggggcaacgt gtactgggtg cgcgactcgg ttagcggcct
20401 gcgcgtgccc gtgcgcaccc gccccccgcg caactagatt gcaataaaaa actacttaga
20461 ctcgtactgt tgtatgtatc cagcggcggc ggcgcgcatc gaagctatgt ccaagcgcaa
20521 aatcaaagaa gagatgctcc aggtcatcgc gccggagatc tatgccccc cgaagaagga
20581 agagcaggat tacaagcccc gaaagctaaa gcgggtcaaa aagaaaaga aagatgatga
20641 tgatgatgaa cttgacgacg aggtggaact gttgcacgcg accgcgccca ggcgacgggt
20701 acagtggaaa ggtcgacgcg taagacgtgt tttgcgaccc ggcaccaccg tagtctttac
20761 gcccggtgag cgctccaccc gcacctacaa gcgcgtgtat gatgaggtgt acggcgacga
20821 ggacctgctt gagcaggcca acgagcgcct cggggagttt gcctacggaa agcggcataa
20881 ggacatgctg gcgttgccgc tggacgaggg caacccaaca cctagcctaa agcccgtgac
20941 actgcagcag gtgctgcccg cgcttgcacc gtccgaagaa agcgcggcc taaagcgcga
21001 gtctggtgac ttggcaccca ccgtgcagct gatggtaccc aagcgtcagc gactggaaga
21061 tgtcttggaa aaaatgaccg tggagcctgg gctggagccc gaggtccgcg tgcggccaat
21121 caagcaggtg gcaccgggac tgggcgtgca gaccgtggac gttcagatac ccaccaccag
21181 tagcactagt attgccactg ccacagaggg catggagaca caaacgtccc cggttgcctc
21241 ggcggtggca gatgccgcgg tgcaggcggc cgctgcggcc gcgtccaaga cctctacgga
21301 ggtgcaaacg gacccgtgga tgtttcgtgt ttcagccccc cggcgtccgc gccgttcaag
21361 gaagtacggc gccgccagcg cgctactgcc cgaatatgcc ctacatcctt ccatcgcgcc
21421 tacccccggc tatcgtggct acacctaccg ccccagaaga cgagcaacta cccgacgccg
21481 aaccaccact ggaacccgcc gccgccgtcg ccgtcgccag cccgtgctgg ccccgatttc
21541 cgtgcgcagg gtggctcgcg aaggaggcag gaccctggtg ctgccaacag cgcgctacca
21601 ccccagcatc gtttaaaagc cggtctttgt ggttcttgca gatatggccc tcacctgccg
21661 cctccgtttc ccggtgccgg gattccgagg aagaatgcac cgtaggaggg gcatggccgg
21721 ccacggcctg acgggcggca tgcgtcgtgc gcaccaccgg cggcggcgcg cgtcgcaccg
21781 tcgcatgcgc ggcggtatcc tgccctcct tattccactg atcgccgcgg cgattggcgc
21841 cgtgcccgga attgcatccg tggccttgca ggcgcagaga cactgattaa aaacaagtta
21901 catgtggaaa aatcaaaata aaagtctgga ctctcacgct cgcttggtcc tgtaactatt
21961 ttgtagaatg gaagacatca actttgcgtc actggccccg cgacacggct cgcgcccgtt
22021 catgggaaac tggcaagata tcggcaccag caatatgagc ggtggcgcct tcagctgggg
22081 ctcgctgtgg agcggcatta aaaatttcgg ttccgccgtt aagaactatg gcagcaaagc
22141 ctggaacagc agcacaggcc agatgctgag gacaagttg aaagagcaaa atttccaaca
22201 aaaggtggta gatggcctgg cctctggcat tagcggggtg gtggacctgg ccaaccaggc
22261 agtgcaaaat aagattaaca gtaagcttga tccccgccct cccgtagagg agcctccacc
22321 ggccgtggag acagtgtctc cagaggggcg tggcgaaaag cgtccgcgac ccgacaggga
22381 agaaactctg gtgacgcaaa tagacgagcc tccctcgtac gaggaggcac taaagcaagg
22441 cctgcccacc acccgtccca tcgcgcccat ggctaccgga gtgctgggcc agcacacacc
22501 cgtaacgctg gacctgcctc cccccgccga cacccagcag aaacctgtgc tgccaggccc
22561 gtccgccgtt gttgtaaccc gtcctagccg cgcgtccctg cgccgcgccg ccagcggtcc
22621 gcgatcgttg cggcccgtag ccagtggcaa ctggcaaagc acactgaaca gcatcgtggg
22681 tttggggtg caatccctga agcgccgacg atgcttctga tagctaacgt gtcgtatgtg
22741 tgtcatgtat gcgtccatgt cgccgccaga ggagctgctg agccgccgcg cgcccgcttt
22801 ccaagatggc tacccccttcg atgatgccgc agtggtctta catgcacatc tcgggccagg
22861 acgcctcgga gtacctgagc cccgggctgg tgcagttcgc ccgcgccacc gagacgtact
22921 tcagcctgaa taacaagttt agaaacccca cggtggcgcc tacgcacgac gtgaccacag
22981 accggtctca gcgtttgacg ctgcggttca tccccgtgga ccgcgaggat actgcgtact
23041 cgtacaaggc gcggttcacc ctagctgtgg gtgataaccg tgtgctagac atggcttcca
23101 cgtactttga catccgcggc gtgctggaca ggggccctac ttttaagccc tactctggca
```

FIG. 4H

```
23161 ctgcctacaa cgcactggcc cccaagggtg cccccaactc gtgcgagtgg gaacaaaatg
23221 aaactgcaca agtggatgct caagaacttg acgaagagga gaatgaagcc aatgaagctc
23281 aggcgcgaga acaggaacaa gctaagaaaa cccatgtata tgcccaggct ccactgtccg
23341 gaataaaaat aactaagaaa ggtctacaaa taggaactgc cgacgccaca gtagcaggtg
23401 ccggcaaaga aattttcgca gacaaaactt ttcaacctga accacaagta ggagaatctc
23461 aatggaacga agcggatgcc acagcagctg gtggaagggt tcttaaaaag acaactccca
23521 tgaaaccctg ctatggctca tacgctagac ccaccaattc caacggcgga cagggcgtta
23581 tggttgaaca aaatggtaaa ttggaaagtc aagtcgaaat gcaattttt tccacatcca
23641 caaatgccac aaatgaagtt aacaatatac aaccaacagt tgtattgtac agcgaagatg
23701 taaacatgga aactccagat actcatcttt cttataaacc taaaatgggg gataaaaatg
23761 ccaaagtcat gcttggacaa caagcaatgc caaacagacc aaattacatt gcttttagag
23821 acaattttat tggtctcatg tattacaaca gcacaggtaa catgggtgtc cttgctggtc
23881 aggcatcgca gttgaacgct gttgtagatt tgcaagacag aaacacagag ctgtcctacc
23941 agcttttgct tgattcaatt ggcgacagaa caagatactt ttcaatgtgg aatcaagctg
24001 ttgacagcta tgatccagat gtcagaatta ttgagaacca tggaactgag gatgagttgc
24061 caaattattg cttttcctctt ggtgaattg ggattactga cacttttcaa gctgttaaaa
24121 caactgctgc taacggggac caaggcaata ctacctggca aaaagattca acatttgcag
24181 aacgcaatga aataggggtg ggaaataact ttgccatgga attaacctg aatgccaacc
24241 tatggagaaa tttcctttac tccaatattg cgctgtacct gccagacaag ctaaaataca
24301 accccaccaa tgtggaaata tctgacaacc caacaccta cgactacatg aacaagcgag
24361 tggtggctcc tgggcttgta gactgctaca ttaaccttgg ggcgcgctgg tctctggact
24421 acatggacaa cgttaatccc tttaaccacc accgcaatgc gggcctgcgt taccgctcca
24481 tgttgttggg aaacggccgc tacgtgccct ttcacattca ggtgccccaa aagtttttg
24541 ccattaaaaa cctcctcctc ctgccaggct catacacata tgaatggaac ttcaggaagg
24601 atgttaacat ggttctgcag agctctctgg gaaacgacct tagagttgac ggggctagca
24661 ttaagtttga cagcatttgt ctttacgcca ccttcttccc catggcccac aacacggcct
24721 ccacgctgga agccatgctc agaaatgaca ccaacgacca gtcctttaat gactaccttt
24781 ccgccgccaa catgctatat cccatacccg ccaacgccac caacgtgccc atctccatcc
24841 catcgcgcaa ctgggcagca tttgcgcggtt gggccttcac acgcttgaag acaaaggaaa
24901 cccctttccct gggatcaggc tacgaccctt actacaccta ctctggctcc ataccatacc
24961 ttgacggaac cttctatctt aatcacacct ttaagaaggt ggccattact tttgactctt
25021 ctgttagctg gccgggcaac gaccgcctgc ttactcccaa tgagtttgag attaagcgct
25081 cagttgacgg ggagggctat aacgtagctc agtgcaacat gacaaaggac tggttcctag
25141 tgcagatgtt ggccaactac aatattggct accagggcct ctacattcca gaaagctaca
25201 aagaccgcat gtactcgttc ttcagaaact tccagcccat gagccggcaa gtggtggacg
25261 atactaaata caaagattat cagcaggttg gaattatcca ccagcataac aactcaggct
25321 tcgtaggcta cctcgctccc accatgcgcg agggacaagc ttaccccgct aatgttccct
25381 acccactaat aggcaaaacc gcggttgata gtattaccca gaaaaagttt ctttgcgacc
25441 gcacctgtgt gcgcatcccc ttctccagta actttatgtc catgggtgcg ctcacagacc
25501 tgggccaaaa ccttctctac gcaaactccg cccacgcgct agacatgacc tttgaggtgg
25561 atcccatgga cgagcccacc ctcttttatg ttttgtttga agtctttgac gtggtccgtg
25621 tgcaccagcc gcaccgcggc gtcatcgaga ccgtgtacct gcgcacgccc ttctcggccg
25681 gcaacgccac aacataaaga agcaagcaac atcaacaaca gctgccgcca tgggctccag
25741 tgagcaggaa ctgaaagcca ttgtcaaaga tcttggttgt gggccatatt ttttgggcac
25801 ctatgacaag cgcttcccag gctttgtttc cccacacaag ctcgcctgcg ccatagttaa
25861 cacggccggt cgcgagactg ggggcgtaca ctgatggcc tttgcctgga cccgcgctc
25921 aaaaacatgc tacctctttg agccctttgg cttttctgac caacgtctca agcaggttta
25981 ccagttgag tacgagtcac tcctgcgccg tagcgccatt gcctcttccc ccgaccgctg
26041 tataacgctg gaaagtccca cccaaagcgt gcagggcccc aactcggccg cctgtggcct
26101 attctgctgc atgtttctcc acgcctttgc caactggccc caaactccca tggatcacaa
26161 ccccaccatg aaccttatta ccggggtacc caactccatg cttaacagtc cccaggtaca
26221 gcccaccctg cgccgcaacc aggaacagct ctacagcttc ctggagcgcc actcgcccta
26281 cttccgcagc cacagtgcgc aaattaggag cgccacttct ttttgtcact tgaaaaacat
26341 gtaaaaataa tgtactagga gacactttca ataaaggcaa atgtttttat ttgtacactc
26401 tcgggtgatt atttacccccc acccttgccg tctgcgccgt ttaaaaatca aagggggttct
```

FIG. 41

```
26461 gccgcgcatc gctatgcgcc actggcaggg acacgttgcg atactggtgt ttagtgctcc
26521 acttaaactc aggcacaacc atccgcggca gctcggtgaa gttttcactc cacaggctgc
26581 gcaccatcac caacgcgttt agcaggtcgg gcgccgatat cttgaagtcg cagttggggc
26641 ctccgccctg cgcgcgcgag ttgcgataca cagggttaca gcactggaac actatcagcg
26701 ccgggtggtg cacgctggcc agcacgctct tgtcggagat cagatccgcg tccaggtcct
26761 ccgcgttgct cagggcgaac ggagtcaact ttggtagctg ccttcccaaa aagggtgcat
26821 gcccaggctt tgagttgcac tcgcaccgta gtggcatcag aaggtgaccg tgcccagtct
26881 gggcgttagg atacagcgcc tgcatgaaag ccttgatctg cttaaaagcc acctgagcct
26941 ttgcgccttc agagaagaac atgccgcaag acttccgga aaactgattg gccggacagg
27001 ccgcgtcatg cacgcagcac cttgcgtcgg tgttggagat ctgcaccaca tttcggcccc
27061 accggttctt cacgatcttg gccttgctag actgctcctt cagcgcgcgc tgcccgtttt
27121 cgctcgtcac atccatttca atcacgtgct ccttatttat cataatgctc ccgtgtagac
27181 acttaagctc gccttcgatc tcagcgcagc ggtgcagcca caacgcgcag cccgtgggct
27241 cgtggtgctt gtaggttacc tctgcaaacg actgcaggta cgcctgcagg aatcgcccca
27301 tcatcgtcac aaaggtcttg ttgctggtga aggtcagctg caacccgcgg tgctcctcgt
27361 ttagccaggt cttgcatacg gccgccagag cttccacttg gtcaggcagt agcttgaagt
27421 ttgcctttag atcgttatcc acgtggtact tgtccatcaa cgcgcgcgca gcctccatgc
27481 ccttctccca cgcagacacg atcggcaggc tcagcgggtt tatcaccgtg cttttcacttt
27541 ccgcttcact ggactcttcc ttttcctctt gcatccgcat accccgcgcc actgggtcgt
27601 cttcattcag ccgccgcacc gtgcgcttac ctcccttgcc gtgcttgatt agcaccggtg
27661 ggttgctgaa acccaccatt tgtagcgcca catcttctct ttcttcctcg ctgtccacga
27721 tcacctctgg ggatggcggg cgctcgggct tgggagaggg gcgcttcttt ttcttttggg
27781 acgcaatggc caaatccgcc gtcgaggtcg atggccgcgg gctgggtgtg cgcggcacca
27841 gcgcatcttg tgacagtctc tcttcgtcct cggactcgag acgccgcctc agccgctttt
27901 ttggggggcgc gcggggaggc ggcggcgacg gcgacgggga cgagacgtcc tccatggttg
27961 gtggacgtcg cgccgcaccg cgtccgcgct cggggggtggt tcgcgctgc tcctcttccc
28021 gactggccat ttccttctcc tataggcaga aaagatcat ggagtcagtc gagaaggagg
28081 acagcctaac cgcccccttt gagttcgcca ccaccgcctc caccgatgcc gccaacgcgc
28141 ctaccacctt ccccgtcgag gcacccccgc ttgaggagga ggaagtgatt atcgagcagg
28201 acccaggttt tgtaagcgaa gacgacgaag atcgctcagt accaacagag gataaaaagc
28261 aagaccagga cgacgcagag gcaaacgagg aacaagtcgg gcgggggggac caaaggcatg
28321 gcgactacct agatgtggga gacgacgtgc tgttgaagca tctgcagcgc cagtgcgcca
28381 ttatctgcga cgcgttgcaa gagcgcagcg atgtgcccct cgccatagcg gatgtcagcc
28441 ttgcctacga acgccacctg ttctcaccgc gcgtaccccc caaacgccaa gaaaacggca
28501 catgcgagcc caacccgcgc ctcaacttct accccgtatt tgccgtgcca gaggtgcttg
28561 ccacctatca catctttttc caaaactgca agatacccct atcctgccgt gccaaccgca
28621 gccgagcgga caagcagctg ccttgcggc agggcgctgt catacctgat atcgcctcgc
28681 tcgacgaagt gccaaaaatc tttgagggtc ttggacgcga cgagaagcgc gcggcaaacg
28741 ctctgcaaca agaaaacagc gaaaatgaaa gtcactgtgg agtgctggtg aacttgagg
28801 gtgacaacgc gcgcctagcc gtgctgaaac gcagcatcga ggtcacccac tttgcctacc
28861 cggcacttaa cctaccccc aaggttatga gcacagtcat gagcgagctg atcgtgcgcc
28921 gtgcacgacc cctggagagg gatgcaaact gcaagaaca aaccgaggag ggcctacccg
28981 cagttggcga tgagcagctg gcgcgctggc ttgagacgcg cgagcctgcc gacttggagg
29041 agcgacgcaa gctaatgatg ccgcagtgc ttgttaccgt ggagcttgag tgcatgcagc
29101 ggttcttgc tgacccggag atgcagcgca agctagagga aacgttgcac tacacctttc
29161 gccagggcta cgtgcgccag gcctgcaaaa tttccaacgt ggagctctgc aacctggtct
29221 cctaccttgg aattttgcac gaaaaccgcc ttgggcaaaa cgtgcttcat tccacgctca
29281 agggcgaggc gcgccgcgac tacgtccgcg actgcgttta cttatttctg tgctacacct
29341 ggcaaacggc catgggcgtg tggcagcagt gcctggagga gcgcaacctg aaggagctgc
29401 agaagctgct aaagcaaaac ttgaaggacc tatggacggc cttcaacgag cgctccgtgg
29461 ccgcgcacct ggcggacatt atcttccccg aacgcctgct taaaaccctg caacagggtc
29521 tgccagactt caccagtcaa agcatgttgc aaaactttag gaactttatc ctagagcgtt
29581 caggaattct gcccgccacc tgctgtgcgc ttcctagcga ctttgtgccc attaagtacc
29641 gtgaatgccc tccgccgctt tggggtcact gctaccttct gcagctagcc aactaccttg
29701 cctaccactc cgacatcatg gaagacgtga gcggtgacgg cctactggag tgtcactgtc
```

FIG. 4J

```
29761 gctgcaacct atgcaccccg caccgctccc tggtctgcaa ttcacaactg cttagcgaaa
29821 gtcaaattat cggtaccttt gagctgcagg gtccctcgcc tgacgaaaag tccgcggctc
29881 cggggttgaa actcactccg gggctgtgga cgtcggctta ccttcgcaaa tttgtacctg
29941 aggactacca cgcccacgag attaggttct acgaagacca atcccgcccg ccaaatgcgg
30001 agcttaccgc ctgcgtcatt acccagggcc acatccttgg ccaattgcaa gccattaaca
30061 aagcccgcca agagtttctg ctacgaaagg acgggggggt ttacttggac ccccagtccg
30121 gcgaggagct caacccaatc ccccgccgc cgcagcccta tcagcagccg cgggcccttg
30181 cttcccagga tggcacccaa aaagaagctg cagctgccgc cgccgccacc cacggacgag
30241 gaggaatact gggacagtca ggcagaggag gttttggacg aggaggagga gatgatggaa
30301 gactgggaca gcctagacga ggaagcttcc gaggccgaag aggtgtcaga cgaaacaccg
30361 tcaccctcgg tcgcattccc ctcgccggcg cccagaaat cggcaaccgt tcccagcatt
30421 gctacaacct ccgctcctca ggcgccgccg gcactgcccg ttcgccgacc caaccgtaga
30481 tgggacacca ctggaaccag ggccggtcag tctaagcagc cgccgccgtt agcccaagag
30541 caacaacagc gccaaggcta ccgctcgtgg cgcgtgcaca agaacgccat agttgcttgc
30601 ttgcaagact gtgggggcaa catctccttc gcccgccgct tcttctcta ccatcacggc
30661 gtggccttcc cccgtaacat cctgcattac taccgtcatc tctacagccc ctactgcacc
30721 ggcggcagcg gcagcaacag cagcggccac gcagaagcaa aggcgaccgg atagcaagac
30781 tctgacaaag cccaagaaat ccacagcggc ggcagcagca ggaggaggag cactgcgtct
30841 ggcgcccaac gaacccgtat cgacccgcga gcttagaaac aggatttttc ccactctgta
30901 tgctatattt caacagagca ggggccaaga caagagctg aaaataaaaa acaggtctct
30961 gcgctccctc acccgcagct gcctgtatca caaaagcgaa gatcagcttc ggcgcacgct
31021 ggaagacgcg gaggctctct tcagcaaata ctgcgcgctg actcttaagg actagtttcg
31081 cgccctttct caaatttaag cgcgaaaact acgtcatctc cagcggccac acccggcgcc
31141 agcacctgtc gtcagcgcca ttatgagcaa ggaaattccc acgccctaca tgtggagtta
31201 ccagccacaa atgggacttg cggctggagc tgcccaagac tactcaaccc gaataaacta
31261 catgagcgcg ggaccccaca tgatatcccg ggtcaacgga atccgcgccc accgaaaccg
31321 aattctcctc gaacaggcgg ctattaccac cacacctcgt aataaccta atccccgtag
31381 ttggcccgct gccctggtgt accaggaaag tcccgctccc accactgtgg tacttcccag
31441 agacgcccag gccgaagttc agatgactaa ctcaggggcg cagcttgcgg gcggctttcg
31501 tcacagggtg cggtcgcccg gcagggtat aactcacctg aaaatcagag ggcgaggtat
31561 tcagctcaac gacgagtcgg tgagctcctc tcttggtctc cgtccggacg ggacatttca
31621 gatcggcggc gctggccgct cttcatttac gccccgtcag gcgatcctaa ctctgcagac
31681 ctcgtcctcg gagccgcgct ccggaggcat tggaactcta caatttattg aggagttcgt
31741 gccttcggtt tacttcaacc ccttttctgg acctcccggc cactaccggg accagtttat
31801 tcccaacttt gacgcggtaa aagactcggc ggacggctac gactgaatga ccagtggaga
31861 ggcagagcaa ctgcgcctga cacacctcga ccactgccgc cgccacaagt gctttgcccg
31921 cggctccggt gagttttgtt actttgaatt gcccgaagag catatcgagg gcccggcgca
31981 cggcgtccgg ctcaccaccc aggtagagct tacacgtagc ctgattcggg agtttaccaa
32041 gcgcccctg ctagtggagc gggagcgggg tccctgtgtt ctgaccgtgg tttgcaactg
32101 tcctaaccct ggattcatc aagatcttat tccattcaac taacaataaa cacacaataa
32161 attcttact taaaatcagt cagcaaatct ttgtccagct tattcagcat cacctccttt
32221 ccctcctccc aactctggta tttcagcagc ctttagctc cgaactttct ccaaagtcta
32281 aatgggatgt caaattcctc atgttcttgt ccctccgcac ccactatctt catattgttg
32341 cagatgaaac gcgccagacc gtctgaagac accttccaacc ctgtgtaccc atatgacacg
32401 gaaaccggcc ctccaactgt gcctttcctt accctccct ttgtgtcgcc aaatgggttc
32461 caagaaagtc ccccggagt gctttctttg cgtcttcag aacctttggt tacctcacac
32521 ggcatgcttg cgctaaaaat gggcagcggc ctgtccctgg atcaggcagg caaccttaca
32581 tcaaatacaa tcactgtttc tcaaccgcta aaaaaacaa agtccaatat aactttggaa
32641 acatccgcgc ccttacagt cagctcaggc gcctaacca tggccacaac ttcgcctttg
32701 gtggtctctg acaacactct taccatgcaa tcacaagcac cgctaaccgt gcaagactca
32761 aaacttagca ttgctaccaa agagccactt acagtgttag atgaaaaact ggccctgcag
32821 acatcagccc cctctctgc cactgataac aacgccctca tatcactgc ctcacctcct
32881 cttactactg caaatggtag tctggctgtt accatgaaaa cccacttta caacaacaat
32941 ggaaaacttg ggctcaaaat tggcggtcct tgcaagtgg ccaccgactc acatgcacta
33001 acactaggta ctggtcaggg ggttgcagtt cataacaatt tgctacatac aaaagttaca
```

FIG. 4K

```
33061  ggcgcaatag ggtttgatac atctggcaac atggaactta aaactggaga tggcctctat
33121  gtggatagcg ccggtcctaa ccaaaaacta catattaatc taaataccac aaaaggcctt
33181  gcttttgaca acaccgcaat aacaattaac gctggaaaag ggttggaatt tgaaacagac
33241  tcctcaaacg gaaatcccat aaaaacaaaa attggatcag gcatacaata taataccaat
33301  ggagctatgg ttgcaaaact tggaacaggc ctcagttttg acagctccgg agccataaca
33361  atgggcagca taaacaatga cagacttact ctttggacaa caccagaccc atccccaaat
33421  tgcagaattg cttcagataa agactgcaag ctaactctgg cgctaacaaa atgtggcagt
33481  caaattttgg gcactgtttc agctttggca gtatcaggta atatggcctc catcaatgga
33541  actctaagca gtgtaaactt ggttcttaga tttgatgaca acggagtgct tatgtcaaat
33601  tcatcactgg acaaacagta ttggaacttt agaaacgggg actccactaa cggtcaacca
33661  tacacttatg ctgttgggtt tatgccaaac ctaaaagctt acccaaaaac tcaaagtaaa
33721  actgcaaaaa gtaatattgt tagccaggtg tatcttaatg gtgacaagtc taaaccattg
33781  cattttacta ttacgctaaa tggaacagat gaaaccaacc aagtaagcaa atactcaata
33841  tcattcagtt ggtcctggaa cagtggacaa tacactaatg acaaatttgc caccaattcc
33901  tatacccttct cctacattgc ccaggaataa agaatcgtga acctgttgca tgttatgttt
33961  caacgtgttt attttttcaat tgcagaaaat ttcaagtcat ttttcattca gtagtatagc
34021  cccaccacca catagcttat actaatcacc gtaccttaat caaactcaca gaaccctagt
34081  attcaacctg ccacctccct ccaacacaca agagtacaca gtcctttctc cccggctggc
34141  cttaaacagc atcatatcat gggtaacaga catattctta ggtgttatat tccacacggt
34201  ctcctgtcga gccaaacgct catcagtgat gttaataaac tccccgggca gctcgcttaa
34261  gttcatgtcg ctgtccagct gctgagccac aggctgctgt ccaacttgcg gttgctcaac
34321  gggcggcgaa ggagaagtcc acgcctacat gggggtagag tcataatcgt gcatcaggat
34381  agggcggtgg tgctgcagca gcgcgcgaat aaactgctgc cgccgccgct ccgtcctgca
34441  ggaatacaac atggcagtgg tctcctcagc gatgattcgc accgcccgca gcataaggcg
34501  ccttgtcctc cgggcacagc agcgcaccct gatctcactt aagtcagcac agtaactgca
34561  gcacagtacc acaatattgt ttaaaatccc acagtgcaag gcgctgtatc aaagctcat
34621  ggcggggacc acagaaccca cgtggccatc ataccacaag cgcaggtaga ttaagtggcg
34681  accctcata aacacgctgg acataaacat tacctctttt ggcatgttgt aattcaccac
34741  ctcccggtac catataaacc tctgattaaa catggcgcca tccaccacca tcctaaacca
34801  gctggccaaa acctgcccgc cggctatgca ctgcagggaa ccgggactgg aacaatgaca
34861  gtggagagcc caggactcgt aaccatggat catcatgctc gtcatgatat caatgttggc
34921  acaacacagg cacacgtgca tacacttcct caggattaca agctcctccc gcgtcagaac
34981  catatcccag ggaacaaccc attcctgaat cagcgtaaat cccacactgc agggaagacc
35041  tcgcacgtaa ctcacgttgt gcattgtcaa agtgttacat tcgggcagca gcggatgatc
35101  ctccagtatg gtagcgcggg tttctgtctc aaaaggaggt agacgatccc tactgtacgg
35161  agtcgccga gacaaccgag atcgtgttgg tcgtagtgtc atgccaaatg gaacgccgga
35221  cgtagtcata ttcctgaag caaaaccagg tgcgggcgtg acaaacagat ctgcgtctcc
35281  ggtctcgccg cttagatcgc tctgtgtagt agttgtagta tatccactct ctcaaagcat
35341  ccaggcgccc cctggcttcg ggttctatgt aaactccttc atgcgccgct gccctgataa
35401  catccaccac cgcagaataa gccacaccca gccaacctac acattcgttc tgcgagtcac
35461  acacgggagg agcgggaaga gctggaagaa ccatgttttt tttttttattc caaaagatta
35521  tccaaaacct caaaatgaag atctattaag tgaacgcgct ccccctccggt ggcgtggtca
35581  aactctacag ccaaagaaca gataatggca tttgtaagat gttgcacaat ggcttccaaa
35641  aggcaaacgg ccctcacgtc caagtggacg taaaggctaa acccttcagg gtgaatctcc
35701  tctataaaca ttccagcacc ttcaaccatg cccaaataat tctcatctcg ccaccttctc
35761  aatatatctc taagcaaatc ccgaatatta agtccggcca ttgtaaaaat ctgctccaga
35821  gcgccctcca ccttcagcct caagcagcga atcatgattg caaaaattca ggttcctcac
35881  agacctgtat aagattcaaa agcggaacat taacaaaaat accgcgatcc cgtaggtccc
35941  ttcgcagggc cagctgaaca taatcgtgca ggtctgcacg gaccagcgcg gccacttccc
36001  cgccaggaac catgacaaaa gaacccacac tgattatgac acgcatactc ggagctatgc
36061  taaccagcgt agccccgatg taagcttgtt gcatgggcgg cgatataaaa tgcaaggtgc
36121  tgctcaaaaa atcaggcaaa gcctcgcgca aaaagaaag cacatcgtag tcatgctcat
36181  gcagataaag gcaggtaagc tccggaacca ccacagaaaa agacaccatt tttctctcaa
36241  acatgtctgc gggtttctgc ataaacacaa aataaaataa caaaaaaaca tttaaacatt
36301  agaagcctgt cttacaacag gaaaaacaac ccttataagc ataagacgga ctacggccat
```

FIG. 4L

```
36361  gccggcgtga ccgtaaaaaa actggtcacc gtgattaaaa agcaccaccg acagctcctc
36421  ggtcatgtcc ggagtcataa tgtaagactc ggtaaacaca tcaggttgat tcacatcggt
36481  cagtgctaaa aagcgaccga aatagcccgg gggaatacat acccgcaggc gtagagacaa
36541  cattacagcc cccataggag gtataacaaa attaatagga gagaaaaaca cataaacacc
36601  tgaaaaccc tcctgcctag gcaaaatagc accctcccgc tccagaacaa catacagcgc
36661  ttccacagcg gcagccataa cagtcagcct taccagtaaa aagaaaacc tattaaaaaa
36721  acaccactcg acacggcacc agctcaatca gtcacagtgt aaaaagggc caagtgcaga
36781  gcgagtatat ataggactaa aaatgacgt aacggttaaa gtccacaaaa aacacccaga
36841  aaaccgcacg cgaacctacg cccagaaacg aaagccaaaa aacccacaac ttcctcaaat
36901  cgtcacttcc gttttcccac gttacgtcac tcccatttt aagaaaacta caattcccaa
36961  cacatacaag ttactccgcc ctaaaaccta cgtcacccgc cccgttccca cgccccgcgc
37021  cacgtcacaa actccacccc ctcattatca tattggcttc aatccaaaat aaggtatatt
37081  attgatgatg
```

FIG. 4M

```
           10                  30                  50
ATGGCGCCCATCACGGCCTACTCCCAACAGACGCGGGGCCTACTTGGTTGCATCATCACT
---------+---------+---------+---------+---------+---------+
MetAlaProIleThrAlaTyrSerGlnGlnThrArgGlyLeuLeuGlyCysIleIleThr
                             10                            20

70                  90                 110
AGCCTTACAGGCCGGGACAAGAACCAGGTCGAGGGAGAGGTTCAGGTGGTTTCCACCGCA
---------+---------+---------+---------+---------+---------+
SerLeuThrGlyArgAspLysAsnGlnValGluGlyGluValGlnValValSerThrAla
                             30                            40

130                 150                 170
ACACAATCCTTCCTGGCGACCTGCGTCAACGGCGTGTGTTGGACCGTTTACCATGGTGCT
---------+---------+---------+---------+---------+---------+
ThrGlnSerPheLeuAlaThrCysValAsnGlyValCysTrpThrValTyrHisGlyAla
                             50                            60

190                 210                 230
GGCTCAAAGACCTTAGCCGGCCCAAAGGGGCCAATCACCCAGATGTACACTAATGTGGAC
---------+---------+---------+---------+---------+---------+
GlySerLysThrLeuAlaGlyProLysGlyProIleThrGlnMetTyrThrAsnValAsp
                             70                            80

250                 270                 290
CAGGACCTCGTCGGCTGGCAGGCGCCCCCCGGGGCGCGTTCCTTGACACCATGCACCTGT
---------+---------+---------+---------+---------+---------+
GlnAspLeuValGlyTrpGlnAlaProProGlyAlaArgSerLeuThrProCysThrCys
                             90                           100

310                 330                 350
GGCAGCTCAGACCTTTACTTGGTCACGAGACATGCTGACGTCATTCCGGTGCGCCGGCGG
---------+---------+---------+---------+---------+---------+
GlySerSerAspLeuTyrLeuValThrArgHisAlaAspValIleProValArgArgArg
                            110                           120

370                 390                 410
GGCGACAGTAGGGGGAGCCTGCTCTCCCCCAGGCCTGTCTCCTACTTGAAGGGCTCTTCG
---------+---------+---------+---------+---------+---------+
GlyAspSerArgGlySerLeuLeuSerProArgProValSerTyrLeuLysGlySerSer
                            130                           140
```

FIG. 5A

```
                430                  450                  470
      GGTGGTCCACTGCTCTGCCCTTCGGGGCACGCTGTGGGCATCTTCCGGGCTGCCGTATGC
      ---------+---------+---------+---------+---------+---------+
      GlyGlyProLeuLeuCysProSerGlyHisAlaValGlyIlePheArgAlaAlaValCys
                                    150                       160

490                  510                  530
      ACCCGGGGGGTTGCGAAGGCGGTGGACTTTGTGCCCGTAGAGTCCATGGAAACTACTATG
      ---------+---------+---------+---------+---------+---------+
      ThrArgGlyValAlaLysAlaValAspPheValProValGluSerMetGluThrThrMet
                                    170                       180

550                  570                  590
      CGGTCTCCGGTCTTCACGGACAACTCATCCCCCCCGGCCGTACCGCAGTCATTTCAAGTG
      ---------+---------+---------+---------+---------+---------+
      ArgSerProValPheThrAspAsnSerSerProProAlaValProGlnSerPheGlnVal
                                    190                       200

610                  630                  650
      GCCCACCTACACGCTCCCACTGGCAGCGGCAAGAGTACTAAAGTGCCGGCTGCATATGCA
      ---------+---------+---------+---------+---------+---------+
      AlaHisLeuHisAlaProThrGlySerGlyLysSerThrLysValProAlaAlaTyrAla
                                    210                       220

670                  690                  710
      GCCCAAGGGTACAAGGTGCTCGTCCTCAATCCGTCCGTTGCCGCTACCTTAGGGTTTGGG
      ---------+---------+---------+---------+---------+---------+
      AlaGlnGlyTyrLysValLeuValLeuAsnProSerValAlaAlaThrLeuGlyPheGly
                                    230                       240

730                  750                  770
      GCGTATATGTCTAAGGCACACGGTATTGACCCCAACATCAGAACTGGGGTAAGGACCATT
      ---------+---------+---------+---------+---------+---------+
      AlaTyrMetSerLysAlaHisGlyIleAspProAsnIleArgThrGlyValArgThrIle
                                    250                       260

790                  810                  830
      ACCACAGGCGCCCCCGTCACATACTCTACCTATGGCAAGTTTCTTGCCGATGGTGGTTGC
      ---------+---------+---------+---------+---------+---------+
      ThrThrGlyAlaProValThrTyrSerThrTyrGlyLysPheLeuAlaAspGlyGlyCys
                                    270                       280
```

FIG. 5B

```
                850                    870                    890
         TCTGGGGGCGCTTATGACATCATAATATGTGATGAGTGCCATTCAACTGACTCGACTACA
         ---------+---------+---------+---------+---------+---------+
         SerGlyGlyAlaTyrAspIleIleIleCysAspGluCysHisSerThrAspSerThrThr
                         290                                    300

910                    930                    950
         ATCTTGGGCATCGGCACAGTCCTGGACCAAGCGGAGACGGCTGGAGCGCGGCTTGTCGTG
         ---------+---------+---------+---------+---------+---------+
         IleLeuGlyIleGlyThrValLeuAspGlnAlaGluThrAlaGlyAlaArgLeuValVal
                         310                                    320

970                    990                   1010
         CTCGCCACCGCTACGCCTCCGGGATCGGTCACCGTGCCACACCCAAACATCGAGGAGGTG
         ---------+---------+---------+---------+---------+---------+
         LeuAlaThrAlaThrProProGlySerValThrValProHisProAsnIleGluGluVal
                         330                                    340

1030                   1050                   1070
         GCCCTGTCTAATACTGGAGAGATCCCCTTCTATGGCAAAGCCATCCCCATTGAAGCCATC
         ---------+---------+---------+---------+---------+---------+
         AlaLeuSerAsnThrGlyGluIleProPheTyrGlyLysAlaIleProIleGluAlaIle
                         350                                    360

1090                   1110                   1130
         AGGGGGGGAAGGCATCTCATTTTCTGTCATTCCAAGAAGAAGTGCGACGAGCTCGCCGCA
         ---------+---------+---------+---------+---------+---------+
         ArgGlyGlyArgHisLeuIlePheCysHisSerLysLysLysCysAspGluLeuAlaAla
                         370                                    380

1150                   1170                   1190
         AAGCTGTCAGGCCTCGGAATCAACGCTGTGGCGTATTACCGGGGGCTCGATGTGTCCGTC
         ---------+---------+---------+---------+---------+---------+
         LysLeuSerGlyLeuGlyIleAsnAlaValAlaTyrTyrArgGlyLeuAspValSerVal
                         390                                    400

1210                   1230                   1250
         ATACCAACTATCGGAGACGTCGTTGTCGTGGCAACAGACGCTCTGATGACGGGCTATACG
         ---------+---------+---------+---------+---------+---------+
         IleProThrIleGlyAspValValValValAlaThrAspAlaLeuMetThrGlyTyrThr
                         410                                    420
```

FIG. 5C

```
      1270                1290               1310
GGCGACTTTGACTCAGTGATCGACTGTAACACATGTGTCACCCAGACAGTCGACTTCAGC
---------+---------+---------+---------+---------+---------+
GlyAspPheAspSerValIleAspCysAsnThrCysValThrGlnThrValAspPheSer
                            430                           440

1330                1350               1370
TTGGATCCCACCTTCACCATTGAGACGACGACCGTGCCTCAAGACGCAGTGTCGCGCTCG
---------+---------+---------+---------+---------+---------+
LeuAspProThrPheThrIleGluThrThrThrValProGlnAspAlaValSerArgSer
                            450                           460

1390                1410               1430
CAGCGGCGGGGTAGGACTGGCAGGGGTAGGAGAGGCATCTACAGGTTTGTGACTCCGGGA
---------+---------+---------+---------+---------+---------+
GlnArgArgGlyArgThrGlyArgGlyArgArgGlyIleTyrArgPheValThrProGly
                            470                           480

1450                1470               1490
GAACGGCCCTCGGGCATGTTCGATTCCTCGGTCCTGTGTGAGTGCTATGACGCGGGCTGT
---------+---------+---------+---------+---------+---------+
GluArgProSerGlyMetPheAspSerSerValLeuCysGluCysTyrAspAlaGlyCys
                            490                           500

1510                1530               1550
GCTTGGTACGAGCTCACCCCCGCCGAGACCTCGGTTAGGTTGCGGGCCTACCTGAACACA
---------+---------+---------+---------+---------+---------+
AlaTrpTyrGluLeuThrProAlaGluThrSerValArgLeuArgAlaTyrLeuAsnThr
                            510                           520

1570                1590               1610
CCAGGGTTGCCCGTTTGCCAGGACCACCTGGAGTTCTGGGAGAGTGTCTTCACAGGCCTC
---------+---------+---------+---------+---------+---------+
ProGlyLeuProValCysGlnAspHisLeuGluPheTrpGluSerValPheThrGlyLeu
                            530                           540

1630                1650               1670
ACCCACATAGATGCACACTTCTTGTCCCAGACCAAGCAGGCAGGAGACAACTTCCCCTAC
---------+---------+---------+---------+---------+---------+
ThrHisIleAspAlaHisPheLeuSerGlnThrLysGlnAlaGlyAspAsnPheProTyr
                            550                           560
```

FIG. 5D

```
              1690                1710                1730
     CTGGTAGCATACCAAGCCACGGTGTGCGCCAGGGCTCAGGCCCCACCTCCATCATGGGAT
     ---------+---------+---------+---------+---------+---------+
     LeuValAlaTyrGlnAlaThrValCysAlaArgAlaGlnAlaProProProSerTrpAsp
                        570                                 580

1750                1770                1790
     CAAATGTGGAAGTGTCTCATACGGCTGAAACCTACGCTGCACGGGCCAACACCCTTGCTG
     ---------+---------+---------+---------+---------+---------+
     GlnMetTrpLysCysLeuIleArgLeuLysProThrLeuHisGlyProThrProLeuLeu
                        590                                 600

1810                1830                1850
     TACAGGCTGGGAGCCGTCCAAAATGAGGTCACCCTCACCCACCCCATAACCAAATACATC
     ---------+---------+---------+---------+---------+---------+
     TyrArgLeuGlyAlaValGlnAsnGluValThrLeuThrHisProIleThrLysTyrIle
                        610                                 620

1870                1890                1910
     ATGGCATGCATGTCGGCTGACCTGGAGGTCGTCACTAGCACCTGGGTGCTGGTGGGCGGA
     ---------+---------+---------+---------+---------+---------+
     MetAlaCysMetSerAlaAspLeuGluValValThrSerThrTrpValLeuValGlyGly
                        630                                 640

1930                1950                1970
     GTCCTTGCAGCTCTGGCCGCGTATTGCCTGACAACAGGCAGTGTGGTCATTGTGGGTAGG
     ---------+---------+---------+---------+---------+---------+
     ValLeuAlaAlaLeuAlaAlaTyrCysLeuThrThrGlySerValValIleValGlyArg
                        650                                 660

1990                2010                2030
     ATTATCTTGTCCGGGAGGCCGGCTATTGTTCCCGACAGGGAGTTTCTCTACCAGGAGTTC
     ---------+---------+---------+---------+---------+---------+
     IleIleLeuSerGlyArgProAlaIleValProAspArgGluPheLeuTyrGlnGluPhe
                        670                                 680

2050                2070                2090
     GATGAAATGGAAGAGTGCGCCTCGCACCTCCCTTACATCGAGCAGGGAATGCAGCTCGCC
     ---------+---------+---------+---------+---------+---------+
     AspGluMetGluGluCysAlaSerHisLeuProTyrIleGluGlnGlyMetGlnLeuAla
                        690                                 700
```

FIG. 5E

```
              2110                2130                2150
     GAGCAATTCAAGCAGAAAGCGCTCGGGTTACTGCAAACAGCCACCAAACAAGCGGAGGCT
     ---------+---------+---------+---------+---------+---------+
     GluGlnPheLysGlnLysAlaLeuGlyLeuLeuGlnThrAlaThrLysGlnAlaGluAla
                       710                                    720

2170                2190                2210
     GCTGCTCCCGTGGTGGAGTCCAAGTGGCGAGCCCTTGAGACATTCTGGGCGAAGCACATG
     ---------+---------+---------+---------+---------+---------+
     AlaAlaProValValGluSerLysTrpArgAlaLeuGluThrPheTrpAlaLysHisMet
                       730                                    740

2230                2250                2270
     TGGAATTTCATCAGCGGGATACAGTACTTAGCAGGCTTATCCACTCTGCCTGGGAACCCC
     ---------+---------+---------+---------+---------+---------+
     TrpAsnPheIleSerGlyIleGlnTyrLeuAlaGlyLeuSerThrLeuProGlyAsnPro
                       750                                    760

2290                2310                2330
     GCAATAGCATCATTGATGGCATTCACAGCCTCTATCACCAGCCCGCTCACCACCCAAAGT
     ---------+---------+---------+---------+---------+---------+
     AlaIleAlaSerLeuMetAlaPheThrAlaSerIleThrSerProLeuThrThrGlnSer
                       770                                    780

2350                2370                2390
     ACCCTCCTGTTTAACATCTTGGGGGGGTGGGTGGCTGCCCAACTCGCCCCCCCCAGCGCC
     ---------+---------+---------+---------+---------+---------+
     ThrLeuLeuPheAsnIleLeuGlyGlyTrpValAlaAlaGlnLeuAlaProProSerAla
                       790                                    800

2410                2430                2450
     GCTTCGGCTTTCGTGGGCGCCGGCATCGCCGGTGCGGCTGTTGGCAGCATAGGCCTTGGG
     ---------+---------+---------+---------+---------+---------+
     AlaSerAlaPheValGlyAlaGlyIleAlaGlyAlaAlaValGlySerIleGlyLeuGly
                       810                                    820

2470                2490                2510
     AAGGTGCTTGTGGACATTCTGGCGGGTTATGGAGCAGGAGTGGCCGGCGCGCTCGTGGCC
     ---------+---------+---------+---------+---------+---------+
     LysValLeuValAspIleLeuAlaGlyTyrGlyAlaGlyValAlaGlyAlaLeuValAla
                       830                                    840
```

FIG. 5F

```
            2530                2550                2570
   TTCAAGGTCATGAGCGGCGAGATGCCCTCCACCGAGGACCTGGTCAATCTACTTCCTGCC
   ---------+---------+---------+---------+---------+---------+
   PheLysValMetSerGlyGluMetProSerThrGluAspLeuValAsnLeuLeuProAla
                               850                           860

2590                2610                2630
   ATCCTCTCTCCTGGCGCCCTGGTCGTCGGGGTCGTGTGTGCAGCAATACTGCGTCGACAC
   ---------+---------+---------+---------+---------+---------+
   IleLeuSerProGlyAlaLeuValValGlyValValCysAlaAlaIleLeuArgArgHis
                               870                           880

2650                2670                2690
   GTGGGTCCGGGAGAGGGGGCTGTGCAGTGGATGAACCGGCTGATAGCGTTCGCCTCGCGG
   ---------+---------+---------+---------+---------+---------+
   ValGlyProGlyGluGlyAlaValGlnTrpMetAsnArgLeuIleAlaPheAlaSerArg
                               890                           900

2710                2730                2750
   GGTAATCATGTTTCCCCCACGCACTATGTGCCTGAGAGCGACGCCGCAGCGCGTGTTACT
   ---------+---------+---------+---------+---------+---------+
   GlyAsnHisValSerProThrHisTyrValProGluSerAspAlaAlaAlaArgValThr
                               910                           920

2770                2790                2810
   CAGATCCTCTCCAGCCTTACCATCACTCAGCTGCTGAAAAGGCTCCACCAGTGGATTAAT
   ---------+---------+---------+---------+---------+---------+
   GlnIleLeuSerSerLeuThrIleThrGlnLeuLeuLysArgLeuHisGlnTrpIleAsn
                               930                           940

2830                2850                2870
   GAAGACTGCTCCACACCGTGTTCCGGCTCGTGGCTAAGGGATGTTTGGGACTGGATATGC
   ---------+---------+---------+---------+---------+---------+
   GluAspCysSerThrProCysSerGlySerTrpLeuArgAspValTrpAspTrpIleCys
                               950                           960

2890                2910                2930
   ACGGTGTTGACTGACTTCAAGACCTGGCTCCAGTCCAAGCTCCTGCCGCAGCTACCGGGA
   ---------+---------+---------+---------+---------+---------+
   ThrValLeuThrAspPheLysThrTrpLeuGlnSerLysLeuLeuProGlnLeuProGly
                               970                           980
```

FIG. 5G

```
              2950                2970                2990
     GTCCCTTTTTTCTCGTGCCAACGCGGGTACAAGGGAGTCTGGCGGGGAGACGGCATCATG
     ---------+---------+---------+---------+---------+---------+
     ValProPhePheSerCysGlnArgGlyTyrLysGlyValTrpArgGlyAspGlyIleMet
                         990                                1000

3010                3030                3050
     CAAACCACCTGCCCATGTGGAGCACAGATCACCGGACATGTCAAAAACGGTTCCATGAGG
     ---------+---------+---------+---------+---------+---------+
     GlnThrThrCysProCysGlyAlaGlnIleThrGlyHisValLysAsnGlySerMetArg
                        1010                                1020

3070                3090                3110
     ATCGTCGGGCCTAAGACCTGCAGCAACACGTGGCATGGAACATTCCCCATCAACGCATAC
     ---------+---------+---------+---------+---------+---------+
     IleValGlyProLysThrCysSerAsnThrTrpHisGlyThrPheProIleAsnAlaTyr
                        1030                                1040

3130                3150                3170
     ACCACGGGCCCCTGCACACCCTCTCCAGCGCCAAACTATTCTAGGGCGCTGTGGCGGGTG
     ---------+---------+---------+---------+---------+---------+
     ThrThrGlyProCysThrProSerProAlaProAsnTyrSerArgAlaLeuTrpArgVal
                        1050                                1060

3190                3210                3230
     GCCGCTGAGGAGTACGTGGAGGTCACGCGGGTGGGGGATTTCCACTACGTGACGGGCATG
     ---------+---------+---------+---------+---------+---------+
     AlaAlaGluGluTyrValGluValThrArgValGlyAspPheHisTyrValThrGlyMet
                        1070                                1080

3250                3270                3290
     ACCACTGACAACGTAAAGTGCCCCATGCCAGGTTCCGGCTCCTGAATTCTTCACGGAGGTG
     ---------+---------+---------+---------+---------+---------+
     ThrThrAspAsnValLysCysProCysGlnValProAlaProGluPhePheThrGluVal
                        1090                                1100

3310                3330                3350
     GACGGAGTGCGGTTGCACAGGTACGCTCCGGCGTGCAGGCCTCTCCTACGGGAGGAGGTT
     ---------+---------+---------+---------+---------+---------+
     AspGlyValArgLeuHisArgTyrAlaProAlaCysArgProLeuLeuArgGluGluVal
                        1110                                1120
```

FIG. 5H

```
              3370                3390                3410
    ACATTCCAGGTCGGGCTCAACCAATACCTGGTTGGGTCACAGCTACCATGCGAGCCCGAA
    ---------+---------+---------+---------+---------+---------+
    ThrPheGlnValGlyLeuAsnGlnTyrLeuValGlySerGlnLeuProCysGluProGlu
                        1130                               1140

3430                3450                3470
    CCGGATGTAGCAGTGCTCACTTCCATGCTCACCGACCCCTCCCACATCACAGCAGAAACG
    ---------+---------+---------+---------+---------+---------+
    ProAspValAlaValLeuThrSerMetLeuThrAspProSerHisIleThrAlaGluThr
                        1150                               1160

3490                3510                3530
    GCTAAGCGTAGGTTGGCCAGGGGGTCTCCCCCCTCCTTGGCCAGCTCTTCAGCTAGCCAG
    ---------+---------+---------+---------+---------+---------+
    AlaLysArgArgLeuAlaArgGlySerProProSerLeuAlaSerSerSerAlaSerGln
                        1170                               1180

3550                3570                3590
    TTGTCTGCGCCTTCCTTGAAGGCGACATGCACTACCCACCATGTCTCTCCGGACGCTGAC
    ---------+---------+---------+---------+---------+---------+
    LeuSerAlaProSerLeuLysAlaThrCysThrThrHisHisValSerProAspAlaAsp
                        1190                               1200

3610                3630                3650
    CTCATCGAGGCCAACCTCCTGTGGCGGCAGGAGATGGGCGGGAACATCACCCGCGTGGAG
    ---------+---------+---------+---------+---------+---------+
    LeuIleGluAlaAsnLeuLeuTrpArgGlnGluMetGlyGlyAsnIleThrArgValGlu
                        1210                               1220

3670                3690                3710
    TCGGAGAACAAGGTGGTAGTCCTGGACTCTTTCGACCCGCTTCGAGCGGAGGAGGATGAG
    ---------+---------+---------+---------+---------+---------+
    SerGluAsnLysValValValLeuAspSerPheAspProLeuArgAlaGluGluAspGlu
                        1230                               1240

3730                3750                3770
    AGGGAAGTATCCGTTCCGGCGGAGATCCTGCGGAAATCCAAGAAGTTCCCCGCAGCGATG
    ---------+---------+---------+---------+---------+---------+
    ArgGluValSerValProAlaGluIleLeuArgLysSerLysLysPheProAlaAlaMet
                        1250                               1260
```

FIG. 5I

```
            3790                3810                3830
CCCATCTGGGCGCGCCCGGATTACAACCCTCCACTGTTAGAGTCCTGGAAGGACCCGGAC
---------+---------+---------+---------+---------+---------+
ProIleTrpAlaArgProAspTyrAsnProProLeuLeuGluSerTrpLysAspProAsp
                1270                                1280

3850                3870                3890
TACGTCCCTCCGGTGGTGCACGGGTGCCCCGTTGCCACCTATCAAGGCCCCTCCAATACCA
---------+---------+---------+---------+---------+---------+
TyrValProProValValHisGlyCysProLeuProProIleLysAlaProProIlePro
                1290                                1300

3910                3930                3950
CCTCCACGGAGAAAGAGGACGGTTGTCCTAACAGAGTCCTCCGTGTCTTCTGCCTTAGCG
---------+---------+---------+---------+---------+---------+
ProProArgArgLysArgThrValValLeuThrGluSerSerValSerSerAlaLeuAla
                1310                                1320

3970                3990                4010
GAGCTCGCTACTAAGACCTTCGGCAGCTCCGAATCATCGGCCGTCGACAGCGGCACGGCG
---------+---------+---------+---------+---------+---------+
GluLeuAlaThrLysThrPheGlySerSerGluSerSerAlaValAspSerGlyThrAla
                1330                                1340

4030                4050                4070
ACCGCCCTTCCTGACCAGGCCTCCGACGACGGTGACAAAGGATCCGACGTTGAGTCGTAC
---------+---------+---------+---------+---------+---------+
ThrAlaLeuProAspGlnAlaSerAspAspGlyAspLysGlySerAspValGluSerTyr
                1350                                1360

4090                4110                4130
TCCTCCATGCCCCCCCTTGAGGGGGAACCGGGGGACCCCGATCTCAGTGACGGGTCTTGG
---------+---------+---------+---------+---------+---------+
SerSerMetProProLeuGluGlyGluProGlyAspProAspLeuSerAspGlySerTrp
                1370                                1380

4150                4170                4190
TCTACCGTGAGCGAGGAAGCTAGTGAGGATGTCGTCTGCTGCTCAATGTCCTACACATGG
---------+---------+---------+---------+---------+---------+
SerThrValSerGluGluAlaSerGluAspValValCysCysSerMetSerTyrThrTrp
                1390                                1400
```

FIG. 5J

```
              4210               4230                4250
     ACAGGCGCCTTGATCACGCCATGCGCTGCGGAGGAAAGCAAGCTGCCCATCAACGCGTTG
     ---------+---------+---------+---------+---------+---------+
     ThrGlyAlaLeuIleThrProCysAlaAlaGluGluSerLysLeuProIleAsnAlaLeu
                        1410               1420

4270               4290                4310
     AGCAACTCTTTGCTGCGCCACCATAACATGGTTTATGCCACAACATCTCGCAGCGCAGGC
     ---------+---------+---------+---------+---------+---------+
     SerAsnSerLeuLeuArgHisHisAsnMetValTyrAlaThrThrSerArgSerAlaGly
                        1430               1440

4330               4350                4370
     CTGCGGCAGAAGAAGGTCACCTTTGACAGACTGCAAGTCCTGGACGACCACTACCGGGAC
     ---------+---------+---------+---------+---------+---------+
     LeuArgGlnLysLysValThrPheAspArgLeuGlnValLeuAspAspHisTyrArgAsp
                        1450               1460

4390               4410                4430
     GTGCTCAAGGAGATGAAGGCGAAGGCGTCCACAGTTAAGGCTAAACTCCTATCCGTAGAG
     ---------+---------+---------+---------+---------+---------+
     ValLeuLysGluMetLysAlaLysAlaSerThrValLysAlaLysLeuLeuSerValGlu
                        1470               1480

4450               4470                4490
     GAAGCCTGCAAGCTGACGCCCCCACATTCGGCCAAATCCAAGTTTGGCTATGGGGCAAAG
     ---------+---------+---------+---------+---------+---------+
     GluAlaCysLysLeuThrProProHisSerAlaLysSerLysPheGlyTyrGlyAlaLys
                        1490               1500

4510               4530                4550
     GACGTCCGGAACCTATCCAGCAAGGCCGTTAACCACATCCACTCCGTGTGGAAGGACTTG
     ---------+---------+---------+---------+---------+---------+
     AspValArgAsnLeuSerSerLysAlaValAsnHisIleHisSerValTrpLysAspLeu
                        1510               1520

4570               4590                4610
     CTGGAAGACACTGTGACACCAATTGACACCACCATCATGGCAAAAAATGAGGTTTTCTGT
     ---------+---------+---------+---------+---------+---------+
     LeuGluAspThrValThrProIleAspThrThrIleMetAlaLysAsnGluValPheCys
                        1530               1540
```

FIG. 5K

```
         4630                4650                4670
GTCCAACCAGAGAAAGGAGGCCGTAAGCCAGCCCGCCTTATCGTATTCCCAGATCTGGGA
---------+---------+---------+---------+---------+---------+
ValGlnProGluLysGlyGlyArgLysProAlaArgLeuIleValPheProAspLeuGly
              1550                1560

4690                4710                4730
GTCCGTGTATGCGAGAAGATGGCCCTCTATGATGTGGTCTCCACCCTTCCTCAGGTCGTG
---------+---------+---------+---------+---------+---------+
ValArgValCysGluLysMetAlaLeuTyrAspValValSerThrLeuProGlnValVal
              1570                1580

4750                4770                4790
ATGGGCTCCTCATACGGATTCCAGTACTCTCCTGGGCAGCGAGTCGAGTTCCTGGTGAAT
---------+---------+---------+---------+---------+---------+
MetGlySerSerTyrGlyPheGlnTyrSerProGlyGlnArgValGluPheLeuValAsn
              1590                1600

4810                4830                4850
ACCTGGAAATCAAAGAAAAACCCCATGGGCTTTTCATATGACACTCGCTGTTTCGACTCA
---------+---------+---------+---------+---------+---------+
ThrTrpLysSerLysLysAsnProMetGlyPheSerTyrAspThrArgCysPheAspSer
              1610                1620

4870                4890                4910
ACGGTCACCGAGAACGACATCCGTGTTGAGGAGTCAATTTACCAATGTTGTGACTTGGCC
---------+---------+---------+---------+---------+---------+
ThrValThrGluAsnAspIleArgValGluGluSerIleTyrGlnCysCysAspLeuAla
              1630                1640

4930                4950                4970
CCCGAAGCCAGACAGGCCATAAAATCGCTCACAGAGCGGCTTTATATCGGGGGTCCTCTG
---------+---------+---------+---------+---------+---------+
ProGluAlaArgGlnAlaIleLysSerLeuThrGluArgLeuTyrIleGlyGlyProLeu
              1650                1660

4990                5010                5030
ACTAATTCAAAAGGGCAGAACTGCGGTTATCGCCGGTGCCGCGCGAGCGGCGTGCTGACG
---------+---------+---------+---------+---------+---------+
ThrAsnSerLysGlyGlnAsnCysGlyTyrArgArgCysArgAlaSerGlyValLeuThr
              1670                1680
```

FIG. 5L

```
         5050                5070                5090
ACTAGCTGCGGTAACACCCTCACATGTTACTTGAAGGCCTCTGCAGCCTGTCGAGCTGCG
---------+---------+---------+---------+---------+---------+
ThrSerCysGlyAsnThrLeuThrCysTyrLeuLysAlaSerAlaAlaCysArgAlaAla
                    1690                1700

5110                5130                5150
AAGCTCCAGGACTGCACGATGCTCGTGAACGGAGACGACCTTGTCGTTATCTGTGAAAGC
---------+---------+---------+---------+---------+---------+
LysLeuGlnAspCysThrMetLeuValAsnGlyAspAspLeuValValIleCysGluSer
                    1710                1720

5170                5190                5210
GCGGGAACCCAAGAGGACGCGGCGAGCCTACGAGTCTTCACGGAGGCTATGACTAGGTAC
---------+---------+---------+---------+---------+---------+
AlaGlyThrGlnGluAspAlaAlaSerLeuArgValPheThrGluAlaMetThrArgTyr
                    1730                1740

5230                5250                5270
TCTGCCCCCCCGGGGACCCGCCCCAACCAGAATACGACTTGGAGCTGATAACATCATGT
---------+---------+---------+---------+---------+---------+
SerAlaProProGlyAspProProGlnProGluTyrAspLeuGluLeuIleThrSerCys
                    1750                1760

5290                5310                5330
TCCTCCAATGTGTCGGTCGCCCACGATGCATCAGGCAAAAGGGTGTACTACCTCACCCGT
---------+---------+---------+---------+---------+---------+
SerSerAsnValSerValAlaHisAspAlaSerGlyLysArgValTyrTyrLeuThrArg
                    1770                1780

5350                5370                5390
GATCCCACCACCCCCCTCGCACGGGCTGCGTGGGAAACAGCTAGACACACTCCAGTTAAC
---------+---------+---------+---------+---------+---------+
AspProThrThrProLeuAlaArgAlaAlaTrpGluThrAlaArgHisThrProValAsn
                    1790                1800

5410                5430                5450
TCCTGGCTAGGCAACATTATCATGTATGCGCCCACTTTGTGGGCAAGGATGATTCTGATG
---------+---------+---------+---------+---------+---------+
SerTrpLeuGlyAsnIleIleMetTyrAlaProThrLeuTrpAlaArgMetIleLeuMet
                    1810                1820
```

FIG. 5M

```
        5470                5490                5510
ACTCACTTCTTCTCCATCCTTCTAGCACAGGAGCAACTTGAAAAAGCCCTGGACTGCCAG
---------+---------+---------+---------+---------+---------+
ThrHisPhePheSerIleLeuLeuAlaGlnGluGlnLeuGluLysAlaLeuAspCysGln
                      1830                1840

5530                5550                5570
ATCTACGGGGCCTGTTACTCCATTGAGCCACTTGACCTACCTCAGATCATTGAACGACTC
---------+---------+---------+---------+---------+---------+
IleTyrGlyAlaCysTyrSerIleGluProLeuAspLeuProGlnIleIleGluArgLeu
                      1850                1860

5590                5610                5630
CATGGCCTTAGCGCATTTTCACTCCATAGTTACTCTCCAGGTGAGATCAATAGGGTGGCT
---------+---------+---------+---------+---------+---------+
HisGlyLeuSerAlaPheSerLeuHisSerTyrSerProGlyGluIleAsnArgValAla
                      1870                1880

5650                5670                5690
TCATGCCTCAGGAAACTTGGGGTACCACCCTTGCGAGTCTGGAGACATCGGGCCAGGAGC
---------+---------+---------+---------+---------+---------+
SerCysLeuArgLysLeuGlyValProProLeuArgValTrpArgHisArgAlaArgSer
                      1890                1900

5710                5730                5750
GTCCGCGCTAGGCTACTGTCCCAGGGGGGGAGGGCCGCCACTTGTGGCAAGTACCTCTTC
---------+---------+---------+---------+---------+---------+
ValArgAlaArgLeuLeuSerGlnGlyGlyArgAlaAlaThrCysGlyLysTyrLeuPhe
                      1910                1920

5770                5790                5810
AACTGGGCAGTGAAGACCAAACTCAAACTCACTCCAATCCCGGCTGCGTCCCAGCTGGAC
---------+---------+---------+---------+---------+---------+
AsnTrpAlaValLysThrLysLeuLysLeuThrProIleProAlaAlaSerGlnLeuAsp
                      1930                1940

5830                5850                5870
TTGTCCGGCTGGTTCGTTGCTGGTTACAGCGGGGGAGACATATATCACAGCCTGTCTCGT
---------+---------+---------+---------+---------+---------+
LeuSerGlyTrpPheValAlaGlyTyrSerGlyGlyAspIleTyrHisSerLeuSerArg
                      1950                1960
```

FIG. 5N

```
              5890                5910                5930
GCCCGACCCCGCTGGTTCATGCTGTGCCTACTCCTACTTTCTGTAGGGGTAGGCATCTAC
---------+---------+---------+---------+---------+---------+
AlaArgProArgTrpPheMetLeuCysLeuLeuLeuLeuSerValGlyValGlyIleTyr
                            1970                        1980

5950 5955
CTGCTCCCCAACCGA    (SEQ. ID. NO. 5)
---------+-----
LeuLeuProAsnArg    (SEQ. ID. NO. 6)
            1985
```

FIG. 5O

```
   1  TCGCGCGTTT CGGTGATGAC GGTGAAAACC TCTGACACAT GCAGCTCCCG
  51  GAGACGGTCA CAGCTTGTCT GTAAGCGGAT GCCGGGAGCA GACAAGCCCG
 101  TCAGGGCGCG TCAGCGGGTG TTGGCGGGTG TCGGGCTGG  CTTAACTATG
 151  CGGCATCAGA GCAGATTGTA CTGAGAGTGC ACCATATGCG GTGTGAAATA
 201  CCGCACAGAT GCGTAAGGAG AAAATACCGC ATCAGATTGG CTATTGGCCA
 251  TTGCATACGT TGTATCCATA TCATAATATG TACATTTATA TTGGCTCATG
 301  TCCAACATTA CCGCCATGTT GACATTGATT ATTGACTAGT TATTAATAGT
 351  AATCAATTAC GGGGTCATTA GTTCATAGCC CATATATGGA GTTCCGCGTT
 401  ACATAACTTA CGGTAAATGG CCCGCCTGGC TGACCGCCCA ACGACCCCCG
 451  CCCATTGACG TCAATAATGA CGTATGTTCC CATAGTAACG CCAATAGGGA
 501  CTTTCCATTG ACGTCAATGG GTGGAGTATT TACGGTAAAC TGCCCACTTG
 551  GCAGTACATC AAGTGTATCA TATGCCAAGT ACGCCCCCTA TTGACGTCAA
 601  TGACGGTAAA TGGCCCGCCT GGCATTATGC CCAGTACATG ACCTTATGGG
 651  ACTTTCCTAC TTGGCAGTAC ATCTACGTAT TAGTCATCGC TATTACCATG
 701  GTGATGCGGT TTTGGCAGTA CATCAATGGG CGTGGATAGC GGTTTGACTC
 751  ACGGGGATTT CCAAGTCTCC ACCCCATTGA CGTCAATGGG AGTTTGTTTT
 801  GGCACCAAAA TCAACGGGAC TTTCCAAAAT GTCGTAACAA CTCCGCCCCA
 851  TTGACGCAAA TGGGCGGTAG GCGTGTACGG TGGGAGGTCT ATATAAGCAG
 901  AGCTCGTTTA GTGAACCGTC AGATCGCCTG GAGACGCCAT CCACGCTGTT
 951  TTGACCTCCA TAGAAGACAC CGGGACCGAT CCAGCCTCCG CGGCCGGGAA
1001  CGGTGCATTG GAACGCGGAT TCCCCGTGCC AAGAGTGACG TAAGTACCGC
1051  CTATAGACTC TATAGGCACA CCCCTTTGGC TCTTATGCAT GCTATACTGT
1101  TTTTGGCTTG GGGCCTATAC ACCCCCGCTT CCTTATGCTA TAGGTGATGG
1151  TATAGCTTAG CCTATAGGTG TGGGTTATTG ACCATTATTG ACCACTCCCC
1201  TATTGGTGAC GATACTTTCC ATTACTAATC CATAACATGG CTCTTTGCCA
1251  CAACTATCTC TATTGGCTAT ATGCCAATAC TCTGTCCTTC AGAGACTGAC
1301  ACGGACTCTG TATTTTTACA GGATGGGGTC CCATTTATTA TTTACAAATT
1351  CACATATACA ACAACGCCGT CCCCCGTGCC CGCAGTTTTT ATTAAACATA
1401  GCGTGGGATC TCCACGCGAA TCTCGGGTAC GTGTTCCGGA CATGGGCTCT
1451  TCTCCGGTAG CGGCGGAGCT TCCACATCCG AGCCCTGGTC CCATGCCTCC
1501  AGCGGCTCAT GGTCGCTCGG CAGCTCCTTG CTCCTAACAG TGGAGGCCAG
1551  ACTTAGGCAC AGCACAATGC CCACCACCAC CAGTGTGCCG CACAAGGCCG
1601  TGGCGGTAGG GTATGTGTCT GAAAATGAGC GTGGAGATTG GGCTCGCACG
1651  GCTGACGCAG ATGGAAGACT TAAGGCAGCG GCAGAAGAAG ATGCAGGCAG
1701  CTGAGTTGTT GTATTCTGAT AAGAGTCAGA GGTAACTCCC GTTGCGGTGC
1751  TGTTAACGGT GGAGGGCAGT GTAGTCTGAG CAGTACTCGT TGCTGCCGCG
1801  CGCGCCACCA GACATAATAG CTGACAGACT AACAGACTGT TCCTTTCCAT
1851  GGGTCTTTTC TGCAGTCACC GTCCTTAGAT CTAGGTACCA GATATCAGAA
1901  TTCAGTCGAC AGCGGCCGCG ATCTGCTGTG CCTTCTAGTT GCCAGCCATC
1951  TGTTGTTTGC CCCTCCCCCG TGCCTTCCTT GACCCTGGAA GGTGCCACTC
2001  CCACTGTCCT TTCCTAATAA AATGAGGAAA TTGCATCGCA TTGTCTGAGT
2051  AGGTGTCATT CTATTCTGGG GGTGGGGTG  GGGCAGGACA GCAAGGGGGA
```

FIG. 6A

```
2101  GGATTGGGAA GACAATAGCA GGCATGCTGG GGATGCGGTG GGCTCTATGG
2151  CCGCTGCGGC CAGGTGCTGA AGAATTGACC CGGTTCCTCC TGGGCCAGAA
2201  AGAAGCAGGC ACATCCCCTT CTCTGTGACA CACCCTGTCC ACGCCCCTGG
2251  TTCTTAGTTC CAGCCCCACT CATAGGACAC TCATAGCTCA GGAGGGCTCC
2301  GCCTTCAATC CCACCCGCTA AGTACTTGG AGCGGTCTCT CCCTCCCTCA
2351  TCAGCCCACC AAACCAAACC TAGCCTCCAA GAGTGGGAAG AAATTAAAGC
2401  AAGATAGGCT ATTAAGTGCA GAGGGAGAGA AAATGCCTCC AACATGTGAG
2451  GAAGTAATGA GAGAAATCAT AGAATTTCTT CCGCTTCCTC GCTCACTGAC
2501  TCGCTGCGCT CGGTCGTTCG GCTGCGGCGA GCGGTATCAG CTCACTCAAA
2551  GGCGGTAATA CGGTTATCCA CAGAATCAGG GGATAACGCA GGAAAGAACA
2601  TGTGAGCAAA AGGCCAGCAA AAGGCCAGGA ACCGTAAAAA GGCCGCGTTG
2651  CTGGCGTTTT TCCATAGGCT CCGCCCCCCT GACGAGCATC ACAAAAATCG
2701  ACGCTCAAGT CAGAGGTGGC GAAACCCGAC AGGACTATAA AGATACCAGG
2751  CGTTTCCCCC TGGAAGCTCC CTCGTGCGCT CTCCTGTTCC GACCCTGCCG
2801  CTTACCGGAT ACCTGTCCGC CTTTCTCCCT TCGGGAAGCG TGGCGCTTTC
2851  TCATAGCTCA CGCTGTAGGT ATCTCAGTTC GGTGTAGGTC GTTCGCTCCA
2901  AGCTGGGCTG TGTGCACGAA CCCCCCGTTC AGCCCGACCG CTGCGCCTTA
2951  TCCGGTAACT ATCGTCTTGA GTCCAACCCG GTAAGCACG ACTTATCGCC
3001  ACTGGCAGCA GCCACTGGTA ACAGGATTAG CAGAGCGAGG TATGTAGGCG
3051  GTGCTACAGA GTTCTTGAAG TGGTGGCCTA ACTACGGCTA CACTAGAAGA
3101  ACAGTATTTG GTATCTGCGC TCTGCTGAAG CCAGTTACCT TCGGAAAAAG
3151  AGTTGGTAGC TCTTGATCCG GCAAACAAAC CACCGCTGGT AGCGGTGGTT
3201  TTTTTGTTTG CAAGCAGCAG ATTACGCGCA GAAAAAAAGG ATCTCAAGAA
3251  GATCCTTTGA TCTTTTCTAC GGGGTCTGAC GCTCAGTGGA ACGAAAACTC
3301  ACGTTAAGGG ATTTTGGTCA TGAGATTATC AAAAAGGATC TTCACCTAGA
3351  TCCTTTTAAA TTAAAAATGA AGTTTTAAAT CAATCTAAAG TATATATGAG
3401  TAAACTTGGT CTGACAGTTA CCAATGCTTA ATCAGTGAGG CACCTATCTC
3451  AGCGATCTGT CTATTTCGTT CATCCATAGT TGCCTGACTC GGGGGGGGGG
3501  GGCGCTGAGG TCTGCCTCGT GAAGAAGGTG TTGCTGACTC ATACCAGGCC
3551  TGAATCGCCC CATCATCCAG CCAGAAAGTG AGGGAGCCAC GGTTGATGAG
3601  AGCTTTGTTG TAGGTGGACC AGTTGGTGAT TTTGAACTTT TGCTTTGCCA
3651  CGGAACGGTC TGCGTTGTCG GGAAGATGCG TGATCTGATC CTTCAACTCA
3701  GCAAAGTTC GATTTATTCA ACAAAGCCGC CGTCCCGTCA AGTCAGCGTA
3751  ATGCTCTGCC AGTGTTACAA CCAATTAACC AATTCTGATT AGAAAAACTC
3801  ATCGAGCATC AAATGAAACT GCAATTTATT CATATCAGGA TTATCAATAC
3851  CATATTTTTG AAAAGCCGT TTCTGTAATG AAGGAGAAAA CTCACCGAGG
3901  CAGTTCCATA GGATGGCAAG ATCCTGGTAT CGGTCTGCGA TTCCGACTCG
3951  TCCAACATCA ATACAACCTA TTAATTTCCC CTCGTCAAAA ATAAGGTTAT
4001  CAAGTGAGAA ATCACCATGA GTGACGACTG AATCCGGTGA GAATGGCAAA
4051  AGCTTATGCA TTTCTTTCCA GACTTGTTCA ACAGGCCAGC CATTACGCTC
4101  GTCATCAAAA TCACTCGCAT CAACCAAACC GTTATTCATT CGTGATTGCG
4151  CCTGAGCGAG ACGAAATACG CGATCGCTGT TAAAAGGACA ATTACAAACA
```

FIG. 6B

```
4201  GGAATCGAAT GCAACCGGCG CAGGAACACT GCCAGCGCAT CAACAATATT
4251  TTCACCTGAA TCAGGATATT CTTCTAATAC CTGGAATGCT GTTTTCCCGG
4301  GGATCGCAGT GGTGAGTAAC CATGCATCAT CAGGAGTACG GATAAAATGC
4351  TTGATGGTCG GAAGAGGCAT AAATTCCGTC AGCCAGTTTA GTCTGACCAT
4401  CTCATCTGTA ACATCATTGG CAACGCTACC TTTGCCATGT TTCAGAAACA
4451  ACTCTGGCGC ATCGGGCTTC CCATACAATC GATAGATTGT CGCACCTGAT
4501  TGCCCGACAT TATCGCGAGC CCATTTATAC CCATATAAAT CAGCATCCAT
4551  GTTGGAATTT AATCGCGGCC TCGAGCAAGA CGTTTCCCGT TGAATATGGC
4601  TCATAACACC CCTTGTATTA CTGTTTATGT AAGCAGACAG TTTTATTGTT
4651  CATGATGATA TATTTTTATC TTGTGCAATG TAACATCAGA GATTTTGAGA
4701  CACAACGTGG CTTTCCCCCC CCCCCCATTA TTGAAGCATT TATCAGGGTT
4751  ATTGTCTCAT GAGCGGATAC ATATTTGAAT GTATTTAGAA AAATAAACAA
4801  ATAGGGGTTC CGCGCACATT TCCCCGAAAA GTGCCACCTG ACGTCTAAGA
4851  AACCATTATT ATCATGACAT TAACCTATAA AAATAGGCGT ATCACGAGGC
4901  CCTTTCGTC
```

FIG. 6C

```
   1  CATCATCAAT AATATACCTT ATTTTGGATT GAAGCCAATA TGATAATGAG GGGGTGGAGT
  61  TTGTGACGTG GCGCGGGGCG TGGGAACGGG GCGGGTGACG TAGTAGTGTG GCGGAAGTGT
 121  GATGTTGTAA GTGTGGCGGA ACACATGTAA GCGCCGGATG TGGTAAAAGT GACGTTTTTG
 181  GTGTGCGCCG GTGTACACGG GAAGTGACAA TTTTCGCGCG GTTTTAGGCG GATGTTGTAG
 241  TAAATTTGGG CGTAACCAAG TAATATTTGG CCATTTTCGC GGGAAAACTG AATAAGAGGA
 301  AGTGAAATCT GAATAATTCT GTGTTACTCA TAGCGCGTAA TATTTGTCTA GGGCCGCGGG
 361  GACTTTGACC GTTTACGTGG AGACTCGCCC AGGTGTTTTT CTCAGGTGTT TTCCGCGTTC
 421  CGGGTCAAAG TTGGCGTTTT ATTATTATAG TCAGCTGACG CGCAGTGTAT TTATACCCGG
 481  TGAGTTCCTC AAGAGGCCAC TCTTGAGTGC CAGCGAGTAG AGTTTTCTCC TCCGAGCCGC
 541  TCCGACACCG GGACTGAAAA TGAGACATAT TATCTGCCAC GGAGGTGTTA TTACCGAAGA
 601  AATGGCCGCC AGTCTTTTGG ACCAGCTGAT CGAAGAGGTA CTGGCTGATA ATCTTCCACC
 661  TCCTAGCCAT TTTGAACCAC CTACCCTTCA CGAACTGTAT GATTTAGACG TGACGGCCCC
 721  CGAAGATCCC AACGAGGAGG CGGTTTCGCA GATTTTTCCC GAGTCTGTAA TGTTGGCGGT
 781  GCAGGAAGGG ATTGACTTAT TCACTTTTCC GCCGGCGCCC GGTTCTCCGG AGCCGCCTCA
 841  CCTTTCCCGG CAGCCCGAGC AGCCGGAGCA GAGAGCCTTG GGTCCGGTTT CTATGCCAAA
 901  CCTTGTGCCG GAGGTGATCG ATCTTACCTG CCACGAGGCT GGCTTTCCAC CCAGTGACGA
 961  CGAGGATGAA GAGGGTGAGG AGTTTGTGTT AGATTATGTG GAGCACCCCG GCACGGTTG
1021  CAGGTCTTGT CATTATCACC GGAGGAATAC GGGGGACCCA GATATTATGT GTTCGCTTTG
1081  CTATATGAGG ACCTGTGGCA TGTTTGTCTA CAGTAAGTGA AAAATTATGG GCAGTGGGTG
1141  ATAGAGTGGT GGGTTTGGTG TGGTAATTTT TTTTTTAATT TTTACAGTTT TGTGGTTTAA
1201  AGAATTTTGT ATTGTGATTT TTTAAAAGGT CCTGTGTCTG AACCTGAGCC TGAGCCCGAG
1261  CCAGAACCGG AGCCTGCAAG ACCTACCCGG CGTCCTAAAT TGGTGCCTGC TATCCTGAGA
1321  CGCCCGACAT CACCTGTGTC TAGAGAATGC AATAGTAGTA CGGATAGCTG TGACTCCGGT
1381  CCTTCTAACA CACCTCCTGA GATACACCCG GTGGTCCCGC TGTGCCCCAT TAAACCAGTT
1441  GCCGTGAGAG TTGGTGGGCG TCGCCAGGCT GTGGAATGTA TCGAGGACTT GCTTAACGAG
1501  TCTGGGCAAC CTTTGGACTT GAGCTGTAAA CGCCCCAGGC CATAAGGTGT AAACCTGTGA
1561  TTGCGTGTGT GGTTAACGCC TTTGTTTGCT GAATGAGTTG ATGTAAGTTT AATAAAGGGT
1621  GAGATAATGT TTAACTTGCA TGGCGTGTTA AATGGGGCGG GGCTTAAAGG GTATATAATG
1681  CGCCGTGGGC TAATCTTGGT TACATCTGAC CTCATGGAGG CTTGGGAGTG TTTGGAAGAT
1741  TTTTCTGCTG TGCGTAACTT GCTGGAACAG AGCTCTAACA GTACCTCTTG GTTTTGGAGG
1801  TTTCTGTGGG GCTCCTCCCA GGCAAAGTTA GTCTGCAGAA TTAAGGAGGA TTACAAGTGG
1861  GAATTTGAAG AGCTTTTGAA ATCCTGTGGT GAGCTGTTTG ATTCTTTGAA TCTGGGTCAC
1921  CAGGCGCTTT TCCAAGAGAA GGTCATCAAG ACTTTGGATT TTTCCACACC GGGGCGCGCT
1981  GCGGCTGCTG TTGCTTTTTT GAGTTTTATA AAGGATAAAT GGAGCGAAGA AACCCATCTG
2041  AGCGGGGGGT ACCTGCTGGA TTTTCTGGCC ATGCATCTGT GGAGAGCGGT GGTGAGACAC
2101  AAGAATCGCC TGCTACTGTT GTCTTCCGTC CGCCCGGCAA TAATACCGAC GGAGGAGCAA
2161  CAGCAGGAGG AAGCCAGGCG GCGGCGGCGG CAGGAGCAGA GCCCATGGAA CCCGAGAGCC
2221  GGCCTGGACC CTCGGGAATG AATGTTGTAC AGGTGGCTGA ACTGTTTCCA GAACTGAGAC
2281  GCATTTTAAC CATTAACGAG GATGGGCAGG GGCTAAAGGG GGTAAAGAAG GAGCGGGGGG
2341  CTTCTGAGGC TACAGAGGAG GCTAGGAATC TAACTTTTAG CTTAATGACC AGACACCGTC
2401  CTGAGTGTGT TACTTTTCAG CAGATTAAGG ATAATTGCGC TAATGAGCTT GATCTGCTGG
2461  CGCAGAAGTA TTCCATAGAG CAGCTGACCA CTTACTGGCT GCAGCCAGGG GATGATTTTG
```

FIG. 7A

```
2521 AGGAGGCTAT TAGGGTATAT GCAAAGGTGG CACTTAGGCC AGATTGCAAG TACAAGATTA
2581 GCAAACTTGT AAATATCAGG AATTGTTGCT ACATTTCTGG GAACGGGCC GAGGTGGAGA
2641 TAGATACGGA GGATAGGGTG GCCTTTAGAT GTAGCATGAT AAATATGTGG CCGGGGGTGC
2701 TTGGCATGGA CGGGGTGGTT ATTATGAATG TGAGGTTTAC TGGTCCCAAT TTTAGCGGTA
2761 CGGTTTTCCT GGCCAATACC AATCTTATCC TACACGGTGT AAGCTTCTAT GGGTTTAACA
2821 ATACCTGTGT GGAAGCCTGG ACCGATGTAA GGGTTCGGGG CTGTGCCTTT TACTGCTGCT
2881 GGAAGGGGGT GGTGTGTCGC CCCAAAAGCA GGGCTTCAAT TAAGAAATGC CTGTTTGAAA
2941 GGTGTACCTT GGGTATCCTG TCTGAGGGTA ACTCCAGGGT GCGCCACAAT GTGGCCTCCG
3001 ACTGTGGTTG CTTTATGCTA GTGAAAAGCG TGGCTGTGAT TAAGCATAAC ATGGTGTGTG
3061 GCAACTGCGA GGACAGGGCC TCTCAGATGC TGACCTGCTC GGACGGCAAC TGTCACTTGC
3121 TGAAGACCAT TCACGTAGCC AGCCACTCTC GCAAGGCCTG GCCAGTGTTT GAGCACAACA
3181 TACTGACCCG CTGTTCCTTG CATTTGGGTA ACAGGAGGGG GGTGTTCCTA CCTTACCAAT
3241 GCAATTTGAG TCACACTAAG ATATTGCTTG AGCCCGAGAG CATGTCCAAG GTGAACCTGA
3301 ACGGGGTGTT TGACATGACC ATGAAGATCT GGAAGGTGCT GAGGTACGAT GAGACCCGCA
3361 CCAGGTGCAG ACCCTGCGAG TGTGGCGGTA ACATATATTAG GAACCAGCCT GTGATGCTGG
3421 ATGTGACCGA GGAGCTGAGG CCCGATCACT TGGTGCTGGC CTGCACCCGC GCTGAGTTTG
3481 GCTCTAGCGA TGAAGATACA GATTGAGGTA CTGAAATGTG TGGGCGTGGC TTAAGGGTGG
3541 GAAAGAATAT ATAAGGTGGG GGTCTCATGT AGTTTTGTAT CTGTTTTGCA GCAGCCGCCG
3601 CCATGAGCGC CAACTCGTTT GATGGAAGCA TTGTGAGCTC ATATTTGACA ACGCGCATGC
3661 CCCCATGGGC CGGGGTGCGT CAGAATGTGA TGGGCTCCAG CATTGATGGT CGCCCCGTCC
3721 TGCCCGCAAA CTCTACTACC TTGACCTACG AGACCGTGTC TGGAACGCCG TTGGAGACTG
3781 CAGCCTCCGC CGCCGCTTCA GCCGCTGCAG CCACCGCCCG CGGGATTGTG ACTGACTTTG
3841 CTTTCCTGAG CCCGCTTGCA AGCAGTGCAG CTTCCCGTTC ATCCGCCCGC GATGACAAGT
3901 TGACGGCTCT TTTGGCACAA TTGGATTCTT TGACCCGGGA ACTTAATGTC GTTTCTCAGC
3961 AGCTGTTGGA TCTGCGCCAG CAGGTTTCTG CCCTGAAGGC TTCCTCCCCT CCCAATGCGG
4021 TTTAAAACAT AAATAAAAAC CAGACTCTGT TTGGATTTGG ATCAAGCAAG TGTCTTGCTG
4081 TCTTTATTTA GGGGTTTTGC GCGCGCGGTA GGCCCGGGAC CAGCGGTCTC GGTCGTTGAG
4141 GGTCCTGTGT ATTTTTTCCA GGACGTGGTA AAGGTGACTC TGGATGTTCA GATACATGGG
4201 CATAAGCCCG TCTCTGGGGT GGAGGTAGCA CCACTGCAGA GCTTCATGCT GCGGGGTGGT
4261 GTTGTAGATG ATCCAGTCGT AGCAGGAGCG CTGGGCGTGG TGCCTAAAAA TGTCTTTCAG
4321 TAGCAAGCTG ATTGCCAGGG GCAGGCCCTT GGTGTAAGTG TTTACAAAGC GGTTAAGCTG
4381 GGATGGGTGC ATACGTGGGG ATATGAGATG CATCTTGGAC TGTATTTTTA GGTTGGCTAT
4441 GTTCCCAGCC ATATCCCTCC GGGGATTCAT GTTGTGCAGA ACCACCAGCA CAGTGTATCC
4501 GGTGCACTTG GGAAATTTGT CATGTAGCTT AGAAGGAAAT GCGTGGAAGA ACTTGGAGAC
4561 GCCCTTGTGA CCTCCAAGAT TTTCCATGCA TTCGTCCATA ATGATGGCAA TGGGCCCACG
4621 GGCGGCGGCC TGGGCGAAGA TATTTCTGGG ATCACTAACG TCATAGTTGT GTTCCAGGAT
4681 GAGATCGTCA TAGGCCATTT TTACAAAGCG CGGGCGGAGG GTGCCAGACT GCGGTATAAT
4741 GGTTCCATCC GGCCCAGGGG CGTAGTTACC CTCACAGATT TGCATTTCCC ACGCTTTGAG
4801 TTCAGATGGG GGGATCATGT CTACCTGCGG GGCGATGAAG AAAACCGTTT CCGGGGTAGG
4861 GGAGATCAGC TGGGAAGAAA GCAGGTTCCT AAGCAGCTGC GACTTACCGC AGCCGGTGGG
4921 CCCGTAAATC ACACCTATTA CCGGCTGCAA CTGGTAGTTA AGAGAGCTGC AGCTGCCGTC
4981 ATCCCTGAGC AGGGGGGCCA CTTCGTTAAG CATGTCCCTG ACTTGCATGT TTTCCCTGAC
```

FIG. 7B

```
5041 CAAATCCGCC AGAAGGCGCT CGCCGCCCAG CGATAGCAGT TCTTGCAAGG AAGCAAAGTT
5101 TTTCAACGGT TTGAGGCCGT CCGCCGTAGG CATGCTTTTG AGCGTTTGAC CAAGCAGTTC
5161 CAGGCGGTCC CACAGCTCGG TCACGTGCTC TACGGCATCT CGATCCAGCA TATCTCCTCG
5221 TTTCGCGGGT TGGGGCGGCT TTCGCTGTAC GGCAGTAGTC GGTGCTCGTC CAGACGGGCC
5281 AGGGTCATGT CTTTCCACGG GCGCAGGGTC CTCGTCAGCG TAGTCTGGGT CACGGTGAAG
5341 GGGTGCGCTC CGGGTTGCGC GCTGGCCAGG GTGCGCTTGA GGCTGGTCCT GCTGGTGCTG
5401 AAGCGCTGCC GGTCTTCGCC CTGCGCGTCG GCCAGGTAGC ATTTGACCAT GGTGTCATAG
5461 TCCAGCCCCT CCGCGGCGTG GCCCTTGGCG CGCAGCTTGC CCTTGGAGGA GGCGCCGCAC
5521 GAGGGGCAGT GCAGACTTTT AAGGGCGTAG AGCTTGGGCG CGAGAAATAC CGATTCCGGG
5581 GAGTAGGCAT CCGCGCCGCA GGCCCCGCAG ACGGTCTCGC ATTCCACGAG CCAGGTGAGC
5641 TCTGGCCGTT CGGGGTCAAA AACCAGGTTT CCCCCATGCT TTTTGATGCG TTTCTTACCT
5701 CTGGTTTCCA TGAGCCGGTG TCCACGCTCG GTGACGAAAA GGCTGTCCGT GTCCCCGTAT
5761 ACAGACTTGA GAGGCCTGTC CTCGAGCGGT GTTCCGCGGT CCTCCTCGTA TAGAAACTCG
5821 GACCACTCTG AGACGAAGGC TCGCGTCCAG GCCAGCACGA AGGAGGCTAA GTGGGAGGGG
5881 TAGCGGTCGT TGTCCACTAG GGGGTCCACT CGCTCCAGGG TGTGAAGACA CATGTCGCCC
5941 TCTTCGGCAT CAAGGAAGGT GATTGGTTTA TAGGTGTAGG CCACGTGACC GGGTGTTCCT
6001 GAAGGGGGGC TATAAAAGGG GGTGGGGCG CGTTCGTCCT CACTCTCTTC CGCATCGCTG
6061 TCTGCGAGGG CCAGCTGTTG GGGTGAGTAC TCCCTCTCAA AAGCGGGCAT GACTTCTGCG
6121 CTAAGATTGT CAGTTTCCAA AAACGAGGAG GATTTGATAT TCACCTGGCC CGCGGTGATG
6181 CCTTTGAGGG TGGCCGCGTC CATCTGGTCA GAAAGACAA TCTTTTTGTT GTCAAGCTTG
6241 GTGGCAAACG ACCCGTAGAG GGCGTTGGAC AGCAACTTGG CGATGGAGCG CAGGGTTTGG
6301 TTTTTGTCGC GATCGGCGCG CTCCTTGGCC GCGATGTTTA GCTGCACGTA TTCGCGCGCA
6361 ACGCACCGCC ATTCGGGAAA GACGGTGGTG CGCTCGTCGG CACTAGGTG CACGCGCCAA
6421 CCGCGGTTGT GCAGGGTGAC AAGGTCAACG CTGGTGGCTA CCTCTCCGCG TAGGCGCTCG
6481 TTGGTCCAGC AGAGGCGGCC GCCCTTGCGC GAGCAGAATG GCGGTAGTGG GTCTAGCTGC
6541 GTCTCGTCCG GGGGTCTGC GTCCACGGTA AGACCCCGG GCAGCAGGCG CGCGTCGAAG
6601 TAGTCTATCT TGCATCCTTG CAAGTCTAGC GCCTGCTGCC ATGCGCGGGC GGCAAGCGCG
6661 CGCTCGTATG GGTTGAGTGG GGGACCCCAT GGCATGGGGT GGGTGAGCGC GGAGGCGTAC
6721 ATGCCGCAAA TGTCGTAAAC GTAGAGGGGC TCTCTGAGTA TTCCAAGATA TGTAGGGTAG
6781 CATCTTCCAC CGCGGATGCT GGCGCGCACG TAATCGTATA GTTCGTGCGA GGGAGCGAGG
6841 AGGTCGGGAC CGAGGTTGCT ACGGGCGGGC TGCTCTGCTC GGAAGACTAT CTGCCTGAAG
6901 ATGGCATGTG AGTTGGATGA TATGGTTGGA CGCTGGAAGA CGTTGAAGCT GGCGTCTGTG
6961 AGACCTACCG CGTCACGCAC GAAGGAGGCG TAGGAGTCGC GCAGCTTGTT GACCAGCTCG
7021 GCGGTGACCT GCACGTCTAG GGCGCAGTAG TCCAGGGTTT CCTTGATGAT GTCATACTTA
7081 TCCTGTCCCT TTTTTTTCCA CAGCTCGCGG TTGAGGACAA ACTCTTCGCG GTCTTTCCAG
7141 TACTCTTGGA TCGGAAACCC GTCGGCCTCC GAACGGTAAG AGCCTAGCAT GTAGAACTGG
7201 TTGACGGCCT GGTAGGCGCA GCATCCCTTT TCTACGGGTA GCGCGTATGC CTGCGCGGCC
7261 TTCCGGAGCG AGGTGTGGGT GAGCGCAAAG GTGTCCCTAA CCATGACTTT GAGGTACTGG
7321 TATTTGAAGT CAGTGTCGTC GCATCCGCCC TGCTCCCAGA GCAAAAAGTC CGTGCGCTTT
7381 TTGAACGCG GGTTTGGCAG GGCGAAGGTG ACATCGTTGA AGAGTATCTT TCCCGCGCGA
7441 GGCATAAAGT TGCGTGTGAT GCGGAAGGGT CCCGGCACCT CGGAACGGTT GTTAATTACC
7501 TGGGCGGCGA GCACGATCTC GTCAAAGCCG TTGATGTTGT GGCCCACAAT GTAAAGTTCC
```

FIG. 7C

```
7561 AAGAAGCGCG GGATGCCCTT GATGGAAGGC AATTTTTTAA GTTCCTCGTA GGTGAGCTCT
7621 TCAGGGGAGC TGAGCCCGTG CTCTGAAAGG GCCCAGTCTG CAAGATGAGG GTTGGAAGCG
7681 ACGAATGAGC TCCACAGGTC ACGGGCCATT AGCATTTGCA GGTGGTCGCG AAAGGTCCTA
7741 AACTGGCGAC CTATGGCCAT TTTTTCTGGG GTGATGCAGT AGAAGGTAAG CGGGTCTTGT
7801 TCCCAGCGGT CCCATCCAAG GTCCGCGGCT AGGTCTCGCG CGGCGGTCAC TAGAGGCTCA
7861 TCTCCGCCGA ACTTCATGAC CAGCATGAAG GCACGAGCT GCTTCCCAAA GGCCCCCATC
7921 CAAGTATAGG TCTCTACATC GTAGGTGACA AAGAGACGCT CGGTGCGAGG ATGCGAGCCG
7981 ATCGGGAAGA ACTGGATCTC CCGCCACCAG TTGGAGGAGT GGCTGTTGAT GTGGTGAAAG
8041 TAGAAGTCCC TGCGACGGGC CGAACACTCG TGCTGGCTTT TGTAAAAACG TGCGCAGTAC
8101 TGGCAGCGGT GCACGGGCTG TACATCCTGC ACGAGGTTGA CCTGACGACC GCGCACAAGG
8161 AAGCAGAGTG GGAATTTGAG CCCCTCGCCT GGCGGGTTTG CTGGTGGTC TTCTACTTCG
8221 GCTGCTTGTC CTTGACCGTC TGGCTGCTCG AGGGGAGTTA CGGTGGATCG GACCACCACG
8281 CCGCGCGAGC CCAAAGTCCA GATGTCCGCG CGCGGCGGTC GGAGCTTGAT GACAACATCG
8341 CGCAGATGGG AGCTGTCCAT GGTCTGGAGC TCCCGCGGCG TCAGGTCAGG CGGGAGCTCC
8401 TGCAGGTTTA CCTCGCATAG CCGGGTCAGG GCGCGGGCTA GGTCCAGGTG ATACCTGATT
8461 TCCAGGGGCT GGTTGGTGGC GGCGTCGATG GCTTGCAAGA GGCCGCATCC CCGCGGCGCG
8521 ACTACGGTAC CGCGCGGCGG GCGGTGGGCC GCGGGGGTGT CCTTGGATGA TGCATCTAAA
8581 AGCGGTGACG CGGGCGGGCC CCCGGAGGTA GGGGGGGCTC GGGACCCGCC GGGAGAGGGG
8641 GCAGGGGCAC GTCGGCGCCG CGCGCGGGCA GGAGCTGGTG CTGCGCGCGG AGGTTGCTGG
8701 CGAACGCGAC GACGCGGCGG TTGATCTCCT GAATCTGGCG CCTCTGCGTG AAGACGACGG
8761 GCCCGGTGAG CTTGAACCTG AAAGAGAGTT CGACAGAATC AATTTCGGTG TCGTTGACGG
8821 CGGCCTGGCG CAAAATCTCC TGCACGTCTC CTGAGTTGTC TTGATAGGCG ATCTCGGCCA
8881 TGAACTGCTC GATCTCTTCC TCCTGGAGAT CTCCGCGTCC GGCTCGCTCC ACGGTGGCGG
8941 CGAGGTCGTT GGAGATGCGG GCCATGAGCT GCGAGAAGGC GTTGAGGCCT CCCTCGTTCC
9001 AGACGCGGCT GTAGACCACG CCCCCTTCGG CATCGCGGGC GCGCATGACC ACCTGCGCGA
9061 GATTGAGCTC CACGTGCCGG GCGAAGACGG CGTAGTTTCG CAGGCGCTGA AGAGGTAGT
9121 TGAGGGTGGT GGCGGTGTGT CTGCCACGA AGAAGTACAT AACCCAGCGC CGCAACGTGG
9181 ATTCGTTGAT ATCCCCCAAG GCCTCAAGGC GCTCCATGGC CTCGTAGAAG TCCACGGCGA
9241 AGTTGAAAAA CTGGGAGTTG CGCGCCGACA CGGTTAACTC CTCCTCCAGA AGACGGATGA
9301 GCTCGGCGAC AGTGTCGCGC ACCTCGCGCT CAAAGGCTAC AGGGGCCTCT TCTTCTTCTT
9361 CAATCTCCTC TTCCATAAGG GCCTCCCCTT CTTCTTCTTC TGGCGGCGGT GGGGGAGGGG
9421 GGACACGGCG GCGACGACGG CGCACCGGGA GGCGGTCGAC AAAGCGCTCG ATCATCTCCC
9481 CGCGGCGACG GCGCATGGTC TCGGTGACGG CGCGGCCGTT CTCGCGGGGG CGCAGTTGGA
9541 AGACGCCGCC CGTCATGTCC CGGTTATGGG TTGGCGGGGG GCTGCCGTGC GGCAGGGATA
9601 CGGCGCTAAC GATGCATCTC AACAATTGTT GTGTAGGTAC TCCGCCACCG AGGGACCTGA
9661 GCGAGTCCGC ATCGACCGGA TCGGAAAACC TCTCGAGAAA GGCGTCTAAC CAGTCACAGT
9721 CGCAAGGTAG GCTGAGCACC GTGGCGGGCG GCAGCGGGCG GCGGTCGGGG TTGTTTCTGG
9781 CGGAGGTGCT GCTGATGATG TAATTAAAGT AGGCGGTCTT GAGACGGCGG ATGGTCGACA
9841 GAAGCACCAT GTCCTTGGGT CCGGCCTGCT GAATGCGCAG GCGGTCGGCC ATGCCCCAGG
9901 CTTCGTTTTG ACATCGGCGC AGGTCTTTGT AGTAGTCTTG CATGAGCCTT TCTACCGGCA
9961 CTTCTTCTTC TCCTTCCTCT TGTCCTGCAT CTCTTGCATC TATCGCTGCG GCGGCGGCGG
10021 AGTTTGGCCG TAGGTGGCGC CCTCTTCCTC CCATGCGTGT GACCCCGAAG CCCCTCATCG
```

FIG. 7D

```
10081 GCTGAAGCAG GGCCAGGTCG GCGACAACGC GCTCGGCTAA TATGGCCTGC TGCACCTGCG
10141 TGAGGGTAGA CTGGAAGTCG TCCATGTCCA CAAAGCGGTG GTATGCGCCC GTGTTGATGG
10201 TGTAAGTGCA GTTGGCCATA ACGGACCAGT TAACGGTCTG GTGACCCGGC TGCGAGAGCT
10261 CGGTGTACCT GAGACGCGAG TAAGCCCTTG AGTCAAAGAC GTAGTCGTTG CAAGTCCGCA
10321 CCAGGTACTG GTATCCCACC AAAAAGTGCG GCGGCGGCTG GCGGTAGAGG GGCCAGCGTA
10381 GGGTGGCCGG GGCTCCGGGG GCGAGGTCTT CCAACATAAG GCGATGATAT CCGTAGATGT
10441 ACCTGGACAT CCAGGTGATG CCGGCGGCGG TGGTGGAGGC GCGCGGAAAG TCACGGACGC
10501 GGTTCCAGAT GTTGCGCAGC GGCAAAAAGT GCTCCATGGT CGGGACGCTC TGGCCGGTCA
10561 GGCGCGCGCA GTCGTTGACG CTCTAGACCG TGCAAAAGGA GAGCCTGTAA GCGGGCACTC
10621 TTCCGTGGTC TGGTGGATAA ATTCGCAAGG GTATCATGGC GGACGACCGG GGTTCGAACC
10681 CCGGATCCGG CCGTCCGCCG TGATCCATGC GGTTACCGCC CGCGTGTCGA ACCCAGGTGT
10741 GCGACGTCAG ACAACGGGGG AGCGCTCCTT TTGGCTTCCT TCCAGGCGCG GCGGATGCTG
10801 CGCTAGCTTT TTTGGCCACT GGCCGCGCGC GGCGTAAGCG GTTAGGCTGG AAAGCGAAAG
10861 CATTAAGTGG CTCGCTCCCT GTAGCCGGAG GGTTATTTTC AAGGGTTGA GTCGCGGGAC
10921 CCCCGGTTCG AGTCTCGGGC CGGCCGGACT GCGGCGAACG GGGGTTTGCC TCCCCGTCAT
10981 GCAAGACCCC GCTTGCAAAT TCCTCCGGAA ACAGGGACGA GCCCCTTTTT TGCTTTTCCC
11041 AGATGCATCC GGTGCTGCGG CAGATGCGCC CCCTCCTCA GCAGCGGCAA GAGCAAGAGC
11101 AGCGGCAGAC ATGCAGGGCA CCCTCCCCTT CTCCTACCGC GTCAGGAGGG GCAACATCCG
11161 CGGCTGACGC GGCGGCAGAT GGTGATTACG AACCCCCGCG GCGCCGGACC CGGCACTACT
11221 TGGACTTGGA GGAGGGCGAG GGCCTGGCGC GGCTAGGAGC GCCCTCTCCT GAGCGACACC
11281 CAAGGGTGCA GCTGAAGCGT GACACGCGCG AGGCGTACGT GCCGCGGCAG AACCTGTTTC
11341 GCGACCGCGA GGGAGAGGAG CCCGAGGAGA TGCGGGATCG AAAGTTCCAT GCAGGGCGCG
11401 AGTTGCGGCA TGGCCTGAAC CGCGAGCGGT TGCTGCGCGA GGAGGACTTT GAGCCCGACG
11461 CGCGGACCGG GATTAGTCCC GCGCGCGCAC ACGTGGCGGC CGCCGACCTG GTAACCGCGT
11521 ACGAGCAGAC GGTGAACCAG GAGATTAACT TTCAAAAAAG CTTTAACAAC CACGTGCGCA
11581 CGCTTGTGGC GCGCGAGGAG GTGGCTATAG GACTGATGCA TCTGTGGGAC TTTGTAAGCG
11641 CGCTGGAGCA AAACCCAAAT AGCAAGCCGC TCATGGCGCA GCTGTTCCTT ATAGTGCAGC
11701 ACAGCAGGGA CAACGAGGCA TTCAGGGATG CGCTGCTAAA CATAGTAGAG CCCGAGGGCC
11761 GCTGGCTGCT CGATTTGATA AACATTCTGC AGAGCATAGT GGTGCAGGAG CGCAGCTTGA
11821 GCCTGGCTGA CAAGGTGGCC GCCATTAACT ATTCCATGCT CAGTCTGGGC AAGTTTTACG
11881 CCCGCAAGAT ATACCATACC CCTTACGTTC CCATAGACAA GGAGGTAAAG ATCGAGGGGT
11941 TCTACATGCG CATGGCGCTG AAGGTGCTTA CCTTGAGCGA CGACCTGGGC GTTTATCGCA
12001 ACGAGCGCAT CCACAAGGCC GTGAGCGTGA GCCGGCGGCG CGAGCTCAGC GACCGCGAGC
12061 TGATGCACAG CCTGCAAAGG GCCCTGGCTG GCACGGGCAG CGGCGATAGA GAGGCCGAGT
12121 CCTACTTTGA CGCGGGCGCT GACCTGCGCT GGGCCCCAAG CCGACGCGCC CTGGAGGCAG
12181 CTGGGGCCGG ACCTGGCTG GCGGTGGCAC CCGCGCGCGC TGGCAACGTC GGCGGCGTGG
12241 AGGAATATGA CGAGGACGAT GAGTACGAGC CAGAGGACGG CGAGTACTAA GCGGTGATGT
12301 TTCTGATCAG ATGATGCAAG ACGCAACGGA CCCGGCGGTG CGGGCGGCGC TGCAGAGCCA
12361 GCCGTCCGGC CTTAACTCCA CGGACGACTG GCGCCAGGTC ATGGACCGCA TCATGTCGCT
12421 GACTGCGCGC AACCCTGACG CGTTCCGGCA GCAGCCGCAG GCCAACCGGC TCTCCGCAAT
12481 TCTGGAAGCG GTGGTCCCGG CGCGCGCAAA CCCCACGCAC GAGAAGGTGC TGGCGATCGT
12541 AAACGCGCTG GCCGAAAACA GGGCCATCCG GCCCGATGAG GCCGGCCTGG TCTACGACGC
```

FIG. 7E

```
12601 GCTGCTTCAG CGCGTGGCTC GTTACAACAG CAGCAACGTG CAGACCAACC TGGACCGGCT
12661 GGTGGGGGAT GTGCGCGAGG CCGTGGCGCA GCGTGAGCGC GCGCAGCAGC AGGGCAACCT
12721 GGGCTCCATG GTTGCACTAA ACGCCTTCCT GAGTACACAG CCCGCCAACG TGCCGCGGGG
12781 ACAGGAGGAC TACACCAACT TTGTGAGCGC ACTGCGGCTA ATGGTGACTG AGACACCGCA
12841 AAGTGAGGTG TATCAGTCCG GCCAGACTA TTTTTTCCAG ACCAGTAGAC AAGGCCTGCA
12901 GACCGTAAAC CTGAGCCAGG CTTTCAAGAA CTTGCAGGGG CTGTGGGGGG TGCGGGCTCC
12961 CACAGGCGAC CGCGCGACCG TGTCTAGCTT GCTGACGCCC AACTCGCGCC TGTTGCTGCT
13021 GCTAATAGCG CCCTTCACGG ACAGTGGCAG CGTGTCCCGG GACACATACC TAGGTCACTT
13081 GCTGACACTG TACCGCGAGG CCATAGGTCA GGCGCATGTG GACGAGCATA CTTTCCAGGA
13141 GATTACAAGT GTTAGCCGCG CGCTGGGGCA GGAGGACACG GGCAGCCTGG AGGCAACCCT
13201 GAACTACCTG CTGACCAACC GGCGGCAAAA AATCCCCTCG TTGCACAGTT TAAACAGCGA
13261 GGAGGAGCGC ATTTTGCGCT ATGTGCAGCA GAGCGTGAGC CTTAACCTGA TGCGCGACGG
13321 GGTAACGCCC AGCGTGGCGC TGGACATGAC CGCGCGCAAC ATGGAACCGG GCATGTATGC
13381 CTCAAACCGG CCGTTTATCA ATCGCCTAAT GGACTACTTG CATCGCGCGG CCGCCGTGAA
13441 CCCCGAGTAT TTCACCAATG CCATCTTGAA CCCGCACTGG CTACCGCCCC CTGGTTTCTA
13501 CACCGGGGGA TTCGAGGTGC CCGAGGGTAA CGATGGATTC CTCTGGGACG ACATAGACGA
13561 CAGCGTGTTT TCCCCGCAAC CGCAGACCCT GCTAGAGTTG CAACAACGCG AGCAGGCAGA
13621 GGCGGCGCTG CGAAAGGAAA GCTTCCGCAG GCCAAGCAGC TTGTCCGATC TAGGCGCTGC
13681 GGCCCCGCGG TCAGATGCTA GTAGCCCATT TCCAAGCTTG ATAGGGTCTC TTACCAGCAC
13741 TCGCACCACC CGCCCGCGCC TGCTGGGCGA GGAGGAGTAC CTAAACAACT CGCTGCTGCA
13801 GCCGCAGCGC GAAAAGAACC TGCCTCCGGC GTTTCCCAAC AACGGGATAG AGAGCCTAGT
13861 GGACAAGATG AGTAGATGGA AGACGTATGC GCAGGAGCAC AGGGATGTGC CCGGCCCGCG
13921 CCCGCCCACC CGTCGTCAAA GGCACGACCG TCAGCGGGGT CTGGTGTGGG AGGACGATGA
13981 CTCGGCAGAC GACAGCAGCG TCTTGGATTT GGGAGGGAGT GGCAACCCGT TTGCACACCT
14041 TCGCCCCAGG CTGGGGAGAA TGTTTTAAAA AAGCATGAT GCAAAATAAA AAACTCACCA
14101 AGGCCATGGC ACCGAGCGTT GGTTTTCTTG TATTCCCCTT AGTATGCGG CGCGCGGCGAT
14161 GTATGAGGAA GGTCCTCCTC CCTCCTACGA GAGCGTGGTG AGCGCGGCGC CAGTGGCGGC
14221 GGCGCTGGGT TCACCCTTCG ATGCTCCCCT GGACCCGCCG TTCGTGCCTC CGCGGTACCT
14281 GCGGCCTACC GGGGGGAGAA ACAGCATCCG TTACTCTGAG TTGGCACCCC TATTCGACAC
14341 CACCCGTGTG TACCTTGTGG ACAACAAGTC AACGGATGTG GCATCCCTGA ACTACCAGAA
14401 CGACCACAGC AACTTTCTAA CCACGGTCAT TCAAAACAAT GACTACAGCC CGGGGGAGGC
14461 AAGCACACAG ACCATCAATC TTGACGACCG GTCGCACTGG GGCGGCGACC TGAAAACCAT
14521 CCTGCATACC AACATGCCAA ATGTGAACGA GTTCATGTTT ACCAATAAGT TTAAGGCGCG
14581 GGTGATGGTG TCGCGCTCGC TTACTAAGGA CAAACAGGTG GAGCTGAAAT ACGAGTGGGT
14641 GGAGTTCACG CTGCCCGAGG GCAACTACTC CGAGACCATG ACCATAGACC TTATGAACAA
14701 CGCGATCGTG GAGCACTACT TGAAAGTGGG CAGGCAGAAC GGGGTTCTGG AAAGCGACAT
14761 CGGGGTAAAG TTTGACACCC GCAACTTCAG ACTGGGGTTT GACCCAGTCA CTGGTCTTGT
14821 CATGCCTGGG GTATATACAA ACGAAGCCTT CCATCCAGAC ATCATTTTGC TGCCAGGATG
14881 CGGGGTGGAC TTCACCCACA GCCGCCTGAG CAACTTGTTG GGCATCCGCA AGCGGCAACC
14941 CTTCCAGGAG GGCTTTAGGA TCACCTACGA TGACCTGGAG GGTGGTAACA TTCCCGCACT
15001 GTTGGATGTG GACGCCTACC AGGCAAGCTT GAAAGATGAC ACCGAACAGG GCGGGGGTGG
15061 CGCAGGCGGC GGCAACAACA GTGGCAGCGG CGCGGAAGAG AACTCCAACG CGGCAGCTGC
```

FIG. 7F

```
15121 GGCAATGCAG CCGGTGGAGG ACATGAACGA TCATGCCATT CGCGGCGACA CCTTTGCCAC
15181 ACGGGCGGAG GAGAAGCGCG CTGAGGCCGA GGCAGCGGCC GAAGCTGCCG CCCCCGCTGC
15241 GGAGGCTGCA CAACCCGAGG TCGAGAAGCC TCAGAAGAAA CCGGTGATTA AACCCCTGAC
15301 AGAGGACAGC AAGAAACGCA GTTACAACCT AATAAGCAAT GACAGCACCT TCACCCAGTA
15361 CCGCAGCTGG TACCTTGCAT ACAACTACGG CGACCCTCAG GCCGGGATCC GCTCATGGAC
15421 CCTGCTTTGC ACTCCTGACG TAACCTGCGG CTCGGAGCAG GTATACTGGT CGTTGCCCGA
15481 CATGATGCAA GACCCCGTGA CCTTCCGCTC CACGCGCCAG ATCAGCAACT TTCCGGTGGT
15541 GGGCGCCGAG CTGTTGCCCG TGCACTCCAA GAGCTTCTAC AACGACCAGG CCGTCTACTC
15601 CCAGCTCATC CGCCAGTTTA CCTCTCTGAC CCACGTGTTC AATCGCTTTC CCGAGAACCA
15661 GATTTTGGCG CGCCCGCCAG CCCCCACCAT CACCACCGTC AGTGAAAACG TTCCTGCTCT
15721 CACAGATCAC GGGACGCTAC CGCTGCGCAA CAGCATCGGA GGAGTCCAGC GAGTGACCAT
15781 TACTGACGCC AGACGCCGCA CCTGCCCCTA CGTTTACAAG GCCCTGGGCA TAGTCTCGCC
15841 GCGCGTCCTA TCGAGCCGCA CTTTTTGAGC AAGCATGTCC ATCCTTATAT CGCCCAGCAA
15901 TAACACAGGC TGGGGCCTGC GCTTCCCAAG CAAGATGTTT GGCGGGGCCA AGAAGCGCTC
15961 CGACCAACAC CCAGTGCGCG TGCGCGGGCA CTACCGCGCG CCCTGGGGCG CGCACAAACG
16021 CGGCCGCACT GGGCGCACCA CCGTCGATGA CGCCATCGAC GCGGTGGTGG AGGAGGCGCG
16081 CAACTACACG CCCACGCCGC CGCCAGTGTC CACCGTGGAC GCGGCCATTC AGACCGTGGT
16141 GCGCGGAGCC CGGCGCTACG CTAAAATGAA GAGACGGCGG AGGCGCGTAG CACGTCGCCA
16201 CCGCCGCCGA CCCGGCACTG CCGCCCAACG CGCGGCGGCG GCCCTGCTTA CCGCGCACG
16261 TCGCACCGGC CGACGGGCGG CCATGCGAGC CGCTCGAAGG CTGGCCGCGG GTATTGTCAC
16321 TGTGCCCCCC AGGTCCAGGC GACGAGCGGC CGCCGCAGCA GCCGCGGCCA TTAGTGCTAT
16381 GACTCAGGGT CGCAGGGGCA ACGTGTACTG GGTGCGCGAC TCGGTTAGCG GCCTGCGCGT
16441 GCCCGTGCGC ACCCGCCCCC CGCGCAACTA GATTGCAATA AAAAACTACT TAGACTCGTA
16501 CTGTTGTATG TATCCAGCGG CGGCGGCGCG CATCGAAGCT ATGTCCAAGC GCAAAATCAA
16561 AGAAGAGATG CTCCAGGTCA TCGCGCCGGA GATCTATGGC CCCCCGAAGA AGGAAGAGCA
16621 GGATTACAAG CCCCGAAAGC TAAAGCGGGT CAAAAAGAAA AGAAAGATG ATGATGATGA
16681 TGAACTTGAC GACGAGGTGG AACTGTTGCA CGCGACCGCG CCCAGGCGAC GGGTACAGTG
16741 GAAAGGTCGA CGCGTAAGAC GTGTTTTGCG ACCCGGCACC ACCGTAGTCT TTACGCCCGG
16801 TGAGCGCTCC ACCCGCACCT ACAAGCGCGT GTATGATGAG GTGTACGGCG ACGAGGACCT
16861 GCTTGAGCAG GCCAACGAGC GCCTCGGGGA GTTTGCCTAC GGAAAGCGGC ATAAGGACAT
16921 GCTGGCGTTG CCGCTGGACG AGGGCAACCC AACACCTAGC CTAAAGCCCG TGACACTGCA
16981 GCAGGTGCTG CCCGCGCTTG CACCGTCCGA AGAAAAGCGC GGCCTAAAGC GCGAGTCTGG
17041 TGACTTGGCA CCCACCGTGC AGCTGATGGT ACCCAAGCGT CAGCGACTGG AAGATGTCTT
17101 GGAAAAAATG ACCGTGGAGC TGGGCTGGA GCCCGAGGTC CGCGTGCGG CAATCAAGCA
17161 GGTGGCACCG GGACTGGGCG TGCAGACCGT GGACGTTCAG ATACCCACCA CCAGTAGCAC
17221 TAGTATTGCC ACTGCCACAG AGGGCATGGA GACACAAACG TCCCCGGTTG CCTCGGCGGT
17281 GGCAGATGCC GCGGTGCAGG CGGCCGCTGC GGCCGCGTCC AAGACCTCTA CGGAGGTGCA
17341 AACGGACCCG TGGATGTTTC GTGTTTCAGC CCCCCGGCGT CCGCGCCGTT CAAGGAAGTA
17401 CGGCGCCGCC AGCGCGCTAC TGCCCGAATA TGCCCTACAT CCTTCCATCG CGCCTACCCC
17461 CGGCTATCGT GGCTACACCT ACCGCCCCAG AAGACGAGCA ACTACCCGAC GCCGAACCAC
17521 CACTGGAACC CGCCGCCGCC GTCGCCGTCG CCAGCCCGTG CTGGCCCCGA TTTCCGTGCG
17581 CAGGGTGGCT CGCGAAGGAG GCAGGACCCT GGTGCTGCCA ACAGCGCGCT ACCACCCCAG
```

FIG. 7G

```
17641 CATCGTTTAA AAGCCGGTCT TTGTGGTTCT TGCAGATATG GCCCTCACCT GCCGCCTCCG
17701 TTTCCCGGTG CCGGGATTCC GAGGAAGAAT GCACCGTAGG AGGGGCATGG CCGGCCACGG
17761 CCTGACGGGC GGCATGCGTC GTGCGCACCA CCGGCGGCGG CGCGCGTCGC ACCGTCGCAT
17821 GCGCGGCGGT ATCCTGCCCC TCCTTATTCC ACTGATCGCC GCGGCGATTG GCGCCGTGCC
17881 CGGAATTGCA TCCGTGGCCT TGCAGGCGCA GAGACACTGA TTAAAAACAA GTTACATGTG
17941 GAAAAATCAA AATAAAAGTC TGGACTCTCA CGCTCGCTTG GTCCTGTAAC TATTTTGTAG
18001 AATGGAAGAC ATCAACTTTG CGTCACTGGC CCCGCGACAC GGCTCGCGCC CGTTCATGGG
18061 AAACTGGCAA GATATCGGCA CCAGCAATAT GAGCGGTGGC GCCTTCAGCT GGGGCTCGCT
18121 GTGGAGCGGC ATTAAAAATT TCGGTTCCGC CGTTAAGAAC TATGGCAGCA AGCCTGGAA
18181 CAGCAGCACA GGCCAGATGC TGAGGGACAA GTTGAAGAG CAAATTTCC AACAAAGGT
18241 GGTAGATGGC CTGGCCTCTG GCATTAGCGG GGTGGTGGAC CTGGCCAACC AGGCAGTGCA
18301 AAATAAGATT AACAGTAAGC TTGATCCCCG CCCTCCCGTA GAGGAGCCTC CACCGGCCGT
18361 GGAGACAGTG TCTCCAGAGG GGCGTGGCGA AAAGCGTCCG CGACCCGACA GGGAAGAAAC
18421 TCTGGTGACG CAAATAGACG AGCCTCCCTC GTACGAGGAG GCACTAAAGC AAGGCCTGCC
18481 CACCACCCGT CCCATCGCGC CCATGGCTAC CGGAGTGCTG GGCCAGCACA CACCCGTAAC
18541 GCTGGACCTG CCTCCCCCCG CCGACACCCA GCAGAAACCT GTGCTGCCAG GCCCGTCCGC
18601 CGTTGTTGTA ACCCGTCCTA GCCGCGCGTC CCTGCGCCGC GCCGCCAGCG GTCCGCGATC
18661 GTTCGGCCCC GTAGCCAGTG GCAACTGGCA AAGCACACTG AACAGCATCG TGGGTTTGGG
18721 GGTGCAATCC CTGAAGCGCC GACGATGCTT CTGATAGCTA ACGTGTCGTA TGTGTGTCAT
18781 GTATGCGTCC ATGTCGCCGC CAGAGGAGCT GCTGAGCCGC CGCGCGCCCG CTTTCCAAGA
18841 TGGCTACCCC TTCGATGATG CCGCAGTGGT CTTACATGCA CATCTCGGGC CAGGACGCCT
18901 CGGAGTACCT GAGCCCCGGG CTGGTGCAGT TCGCCCGCGC CACCGAGACG TACTTCAGCC
18961 TGAATAACAA GTTTAGAAAC CCCACGGTGG CGCCTACGCA CGACGTGACC ACAGACCGGT
19021 CTCAGCGTTT GACGCTGCGG TTCATCCCCG TGGACCGCGA GGATACTGCG TACTCGTACA
19081 AGGCGCGGTT CACCCTAGCT GTGGGTGATA ACCGTGTGCT AGACATGGCT TCCACGTACT
19141 TTGACATCCG CGGCGTGCTG GACAGGGGCC CTACTTTTAA GCCCTACTCT GGCACTGCCT
19201 ACAACGCACT GGCCCCCAAG GGTGCCCCCA ACTCGTGCGA GTGGGAACAA AATGAAACTG
19261 CACAAGTGGA TGCTCAAGAA CTTGACGAAG AGGAGAATGA AGCCAATGAA GCTCAGGCGC
19321 GAGAACAGGA ACAAGCTAAG AAAACCCATG TATATGCCCA GGCTCCACTG TCCGGAATAA
19381 AAATAACTAA AGAAGGTCTA CAAATAGGAA CTGCCGACGC CACAGTAGCA GGTGCCGGCA
19441 AAGAAATTTT CGCAGACAAA ACTTTTCAAC CTGAACCACA AGTAGGAGAA TCTCAATGGA
19501 ACGAAGCGGA TGCCACAGCA GCTGGTGGAA GGGTTCTTAA AAAGACAACT CCCATGAAAC
19561 CCTGCTATGG CTCATACGCT AGACCCACCA ATTCCAACGG CGGACAGGGC GTTATGGTTG
19621 AACAAAATGG TAAATTGGAA AGTCAAGTCG AAATGCAATT TTTTTCCACA TCCACAAATG
19681 CCACAAATGA AGTTAACAAT ATACAACCAA CAGTTGTATT GTACAGCGAA GATGTAAACA
19741 TGGAAACTCC AGATACTCAT CTTTCTTATA AACCTAAAAT GGGGGATAAA AATGCCAAAG
19801 TCATGCTTGG ACAACAAGCA ATGCCAAACA GACCAAATTA CATTGCTTTT AGAGACAATT
19861 TTATTGGTCT CATGTATTAC AACAGCACAG GTAACATGGG TGTCCTTGCT GGTCAGGCAT
19921 CGCAGTTGAA CGCTGTTGTA GATTTGCAAG ACAGAAACAC AGAGCTGTCC TACCAGCTTT
19981 TGCTTGATTC AATTGGCGAC AGAACAAGAT ACTTTCAAT GTGGAATCAA GCTGTTGACA
20041 GCTATGATCC AGATGTCAGA ATTATTGAGA ACCATGGAAC TGAGGATGAG TTGCCAAATT
20101 ATTGCTTTCC TCTTGGTGGA ATTGGGATTA CTGACACTTT TCAAGCTGTT AAAACAACTG
```

FIG. 7H

```
20161 CTGCTAACGG GGACCAAGGC AATACTACCT GGCAAAAAGA TTCAACATTT GCAGAACGCA
20221 ATGAAATAGG GGTGGGAAAT AACTTTGCCA TGGAAATTAA CCTGAATGCC AACCTATGGA
20281 GAAATTTCCT TTACTCCAAT ATTGCGCTGT ACCTGCCAGA CAAGCTAAAA TACAACCCCA
20341 CCAATGTGGA AATATCTGAC AACCCCAACA CCTACGACTA CATGAACAAG CGAGTGGTGG
20401 CTCCTGGGCT TGTAGACTGC TACATTAACC TTGGGGCGCG CTGGTCTCTG GACTACATGG
20461 ACAACGTTAA TCCCTTTAAC CACCACCGCA ATGCGGGCCT GCGTTACCGC TCCATGTTGT
20521 TGGGAAACGG CCGCTACGTG CCCTTTCACA TTCAGGTGCC CCAAAAGTTT TTTGCCATTA
20581 AAAACCTCCT CCTCCTGCCA GGCTCATACA CATATGAATG GAACTTCAGG AAGGATGTTA
20641 ACATGGTTCT GCAGAGCTCT CTGGGAAACG ACCTTAGAGT TGACGGGGCT AGCATTAAGT
20701 TTGACAGCAT TTGTCTTTAC GCCACCTTCT TCCCCATGGC CCACAACACG GCCTCCACGC
20761 TGGAAGCCAT GCTCAGAAAT GACACCAACG ACCAGTCCTT TAATGACTAC CTTTCCGCCG
20821 CCAACATGCT ATATCCCATA CCCGCCAACG CCACCAACGT GCCCATCTCC ATCCCATCGC
20881 GCAACTGGGC AGCATTTCGC GGTTGGGCCT TCACACGCTT GAAGACAAAG GAAACCCCTT
20941 CCCTGGGATC AGGCTACGAC CCTTACTACA CCTACTCTGG CTCCATACCA TACCTTGACG
21001 GAACCTTCTA TCTTAATCAC ACCTTTAAGA AGGTGGCCAT TACTTTTGAC TCTTCTGTTA
21061 GCTGGCCGGG CAACGACCGC CTGCTTACTC CCAATGAGTT TGAGATTAAG CGCTCAGTTG
21121 ACGGGGAGGG CTATAACGTA GCTCAGTGCA ACATGACAAA GGACTGGTTC CTAGTGCAGA
21181 TGTTGGCCAA CTACAATATT GGCTACCAGG GCTTCTACAT TCCAGAAAGC TACAAAGACC
21241 GCATGTACTC GTTCTTCAGA AACTTCCAGC CCATGAGCCG GCAAGTGGTG GACGATACTA
21301 AATACAAAGA TTATCAGCAG GTTGGAATTA TCCACCAGCA TAACAACTCA GGCTTCGTAG
21361 GCTACCTCGC TCCCACCATG CGCGAGGGAC AAGCTTACCC CGCTAATGTT CCCTACCCAC
21421 TAATAGGCAA AACCGCGGTT GATAGTATTA CCCAGAAAAA GTTTCTTTGC GACCGCACCC
21481 TGTGGCGCAT CCCCTTCTCC AGTAACTTTA TGTCCATGGG TGCGCTCACA GACCTGGGCC
21541 AAAACCTTCT CTACGCAAAC TCCGCCCACG CGCTAGACAT GACCTTTGAG GTGGATCCCA
21601 TGGACGAGCC CACCCTTCTT TATGTTTTGT TTGAAGTCTT TGACGTGGTC CGTGTGCACC
21661 AGCCGCACCG CGGCGTCATC GAGACCGTGT ACCTGCGCAC GCCCTTCTCG GCCGGCAACG
21721 CCACAACATA AGAAGCAAG CAACATCAAC AACAGCTGCC GCCATGGGCT CCAGTGAGCA
21781 GGAACTGAAA GCCATTGTCA AAGATCTTGG TTGTGGGCCA TATTTTTGG GCACCTATGA
21841 CAAGCGCTTC CCAGGCTTTG TTTCCCCACA CAAGCTCGCC TGCGCCATAG TTAACACGGC
21901 CGGTCGCGAG ACTGGGGGCG TACACTGGAT GGCCTTTGCC TGGAACCCGC GCTCAAAAAC
21961 ATGCTACCTC TTTGAGCCCT TTGGCTTTTC TGACCAACGT CTCAAGCAGG TTTACCAGTT
22021 TGAGTACGAG TCACTCCTGC GCCGTAGCGC CATTGCCTCT TCCCCCGACC GCTGTATAAC
22081 GCTGGAAAAG TCCACCCAAA GCGTGCAGGG GCCCAACTCG GCCGCCTGTG GCCTATTCTG
22141 CTGCATGTTT CTCCACGCCT TGCCAACTG GCCCCAAACT CCCATGGATC ACAACCCCAC
22201 CATGAACCTT ATTACCGGGG TACCCAACTC CATGCTTAAC AGTCCCCAGG TACAGCCCAC
22261 CCTGCGCCGC AACCAGGAAC AGCTCTACAG CTTCCTGGAG CGCCACTCGC CCTACTTCCG
22321 CAGCCACAGT GCGCAAATTA GGAGCGCCAC TTCTTTTTGT CACTTGAAAA ACATGTAAAA
22381 ATAATGTACT AGGAGACACT TTCAATAAAG GCAAATGTTT TTATTTGTAC ACTCTCGGGT
22441 GATTATTTAC CCCCACCCTT GCCGTCTGCG CCGTTTAAAA ATCAAAGGGG TTCTGCCGCG
22501 CATCGCTATG CGCCACTGGC AGGGACACGT TGCGATACTG GTGTTTAGTG CTCCACTTAA
22561 ACTCAGGCAC AACCATCCGC GGCAGCTCGG TGAAGTTTTC ACTCCACAGG CTGCGCACCA
22621 TCACCAACGC GTTTAGCAGG TCGGGCGCCG ATATCTTGAA GTCGCAGTTG GGGCCTCCGC
```

FIG. 71

```
22681 CCTGCGCGCG CGAGTTGCGA TACACAGGGT TACAGCACTG GAACACTATC AGCGCCGGGT
22741 GGTGCACGCT GGCCAGCACG CTCTTGTCGG AGATCAGATC CGCGTCCAGG TCCTCCGCGT
22801 TGCTCAGGGC GAACGGAGTC AACTTTGGTA GCTGCCTTCC CAAAAAGGGT GCATGCCCAG
22861 GCTTTGAGTT GCACTCGCAC CGTAGTGGCA TCAGAAGGTG ACCGTGCCCA GTCTGGGCGT
22921 TAGGATACAG CGCCTGCATG AAAGCCTTGA TCTGCTTAAA AGCCACCTGA GCCTTTGCGC
22981 CTTCAGAGAA GAACATGCCG CAAGACTTGC CGGAAAACTG ATTGGCCGGA CAGGCCGCGT
23041 CATGCACGCA GCACCTTGCG TCGGTGTTGG AGATCTGCAC CACATTTCGG CCCCACCGGT
23101 TCTTCACGAT CTTGGCCTTG CTAGACTGCT CCTTCAGCGC GCGCTGCCCG TTTTCGCTCG
23161 TCACATCCAT TTCAATCACG TGCTCCTTAT TTATCATAAT GCTCCCGTGT AGACACTTAA
23221 GCTCGCCTTC GATCTCAGCG CAGCGGTGCA GCCACAACGC GCAGCCCGTG GGCTCGTGGT
23281 GCTTGTAGGT TACCTCTGCA AACGACTGCA GGTACGCCTG CAGGAATCGC CCCATCATCG
23341 TCACAAAGGT CTTGTTGCTG GTGAAGGTCA GCTGCAACCC GCGGTGCTCC TCGTTTAGCC
23401 AGGTCTTGCA TACGGCCGCC AGAGCTTCCA CTTGGTCAGG CAGTAGCTTG AAGTTTGCCT
23461 TTAGATCGTT ATCCACGTGG TACTTGTCCA TCAACGCGCG CGCAGCCTCC ATGCCCTTCT
23521 CCCACGCAGA CACGATCGGC AGGCTCAGCG GGTTTATCAC CGTGCTTTCA CTTTCCGCTT
23581 CACTGGACTC TTCCTTTTCC TCTTGCATCC GCATACCCCG CGCCACTGGG TCGTCTTCAT
23641 TCAGCCGCCG CACCGTGCGC TTACCTCCCT TGCCGTGCTT GATTAGCACC GGTGGGTTGC
23701 TGAAACCCAC CATTTGTAGC GCCACATCTT CTCTTTCTTC CTCGCTGTCC ACGATCACCT
23761 CTGGGGATGG CGGGCGCTCG GCTTGGGAG AGGGGCGCTT CTTTTTCTTT TTGGACGCAA
23821 TGGCCAAATC CGCCGTCGAG GTCGATGGCC GCGGGCTGGG TGTGCGCGGC ACCAGCGCAT
23881 CTTGTGACGA GTCTTCTTCG TCCTCGGACT CGAGACGCCG CCTCAGCCGC TTTTTTGGGG
23941 GCGCGCGGGG AGGCGGCGGC GACGGCGACG GGGACGAGAC GTCCTCCATG GTTGGTGGAC
24001 GTCGCGCCGC ACCGCGTCCG CGCTCGGGGG TGGTTTCGCG CTGCTCCTCT TCCCGACTGG
24061 CCATTTCCTT CTCCTATAGG CAGAAAAAGA TCATGGAGTC AGTCGAGAAG GAGGACAGCC
24121 TAACCGCCCC CTTTGAGTTC GCCACCACCG CCTCCACCGA TGCCGCCAAC GCGCCTACCA
24181 CCTTCCCCGT CGAGGCACCC CCGCTTGAGG AGGAGGAAGT GATTATCGAG CAGGACCCAG
24241 GTTTTGTAAG CGAAGACGAC GAAGATCGCT CAGTACCAAC AGAGGATAAA AAGCAAGACC
24301 AGGACGACGC AGAGGCAAAC GAGGAACAAG TCGGGCGGGG GGACCAAAGG CATGGCGACT
24361 ACCTAGATGT GGGAGACGAC GTGCTGTTGA AGCATCTGCA GCGCCAGTGC GCCATTATCT
24421 GCGACGCGTT GCAAGAGCGC AGCGATGTGC CCCTCGCCAT AGCGGATGTC AGCCTTGCCT
24481 ACGAACGCCA CCTGTTCTCA CCGCGCGTAC CCCCCAAACG CCAAGAAAAC GGCACATGCG
24541 AGCCCAACCC GCGCCTCAAC TTCTACCCCG TATTTGCCGT GCCAGAGGTG CTTGCCACCT
24601 ATCACATCTT TTTCCAAAAC TGCAAGATAC CCCTATCCTG CCGTGCCAAC CGCAGCCGAG
24661 CGGACAAGCA GCTGGCCTTG CGGCAGGGCG CTGTCATACC TGATATCGCC TCGCTCGACG
24721 AAGTGCCAAA AATCTTTGAG GGTCTTGGAC GCGACGAGAA GCGCGCGGCA AACGCTCTGC
24781 AACAAGAAAA CAGCGAAAAT GAAAGTCACT GTGGAGTGCT GGTGGAACTT GAGGGTGACA
24841 ACGCGCGCCT AGCCGTGCTG AAACGCAGCA TCGAGGTCAC CCACTTTGCC TACCCGGCAC
24901 TTAACCTACC CCCCAAGGTT ATGAGCACAG TCATGAGCGA GCTGATCGTG CGCCGTGCAC
24961 GACCCCTGGA GAGGGATGCA AACTTGCAAG AACAAACCGA GGAGGGCCTA CCCGCAGTTG
25021 GCGATGAGCA GCTGGCGCGC TGGCTTGAGA CGCGCGAGCC TGCCGACTTG GAGGAGCGAC
25081 GCAAGCTAAT GATGGCCGCA GTGCTTGTTA CCGTGGAGCT TGAGTGCATG CAGCGGTTCT
25141 TTGCTGACCC GGAGATGCAG CGCAAGCTAG AGGAAACGTT GCACTACACC TTTCGCCAGG
```

FIG. 7J

```
25201  GCTACGTGCG CCAGGCCTGC AAAATTTCCA ACGTGGAGCT CTGCAACCTG GTCTCCTACC
25261  TTGGAATTTT GCACGAAAAC CGCCTTGGGC AAAACGTGCT TCATTCCACG CTCAAGGGCG
25321  AGGCGCGCCG CGACTACGTC CGCGACTGCG TTTACTTATT TCTGTGCTAC ACCTGGCAAA
25381  CGGCCATGGG CGTGTGGCAG CAGTGCCTGG AGGAGCGCAA CCTGAAGGAG CTGCAGAAGC
25441  TGCTAAAGCA AAACTTGAAG GACCTATGGA CGGCCTTCAA CGAGCGCTCC GTGGCCGCGC
25501  ACCTGGCGGA CATTATCTTC CCCGAACGCC TGCTTAAAAC CCTGCAACAG GGTCTGCCAG
25561  ACTTCACCAG TCAAAGCATG TTGCAAAACT TTAGGAACTT TATCCTAGAG CGTTCAGGAA
25621  TTCTGCCCGC CACCTGCTGT GCGCTTCCTA GCGACTTTGT GCCCATTAAG TACCGTGAAT
25681  GCCCTCCGCC GCTTTGGGGT CACTGCTACC TTCTGCAGCT AGCCAACTAC CTTGCCTACC
25741  ACTCCGACAT CATGGAAGAC GTGAGCGGTG ACGGCCTACT GGAGTGTCAC TGTCGCTGCA
25801  ACCTATGCAC CCCGCACCGC TCCCTGGTCT GCAATTCACA ACTGCTTAGC GAAAGTCAAA
25861  TTATCGGTAC CTTTGAGCTG CAGGGTCCCT CGCCTGACGA AAAGTCCGCG GCTCCGGGGT
25921  TGAAACTCAC TCCGGGGCTG TGGACGTCGG CTTACCTTCG CAAATTTGTA CCTGAGGACT
25981  ACCACGCCCA CGAGATTAGG TTCTACGAAG ACCAATCCCG CCCGCCAAAT GCGGAGCTTA
26041  CCGCCTGCGT CATTACCCAG GGCCACATCC TTGGCCAATT GCAAGCCATT AACAAAGCCC
26101  GCCAAGAGTT TCTGCTACGA AAGGGACGGG GGGTTTACTT GGACCCCCAG TCCGGCGAGG
26161  AGCTCAACCC AATCCCCCCG CCGCCGCAGC CCTATCAGCA GCCGCGGGCC CTTGCTTCCC
26221  AGGATGGCAC CCAAAAAGAA GCTGCAGCTG CCGCCGCCGC CACCCACGGA CGAGGAGGAA
26281  TACTGGGACA GTCAGGCAGA GGAGGTTTTG GACGAGGAGG AGGAGATGAT GGAAGACTGG
26341  GACAGCCTAG ACGAGGAAGC TTCCGAGGCC GAAGAGGTGT CAGACGAAAC ACCGTCACCC
26401  TCGGTCGCAT TCCCCTCGCC GGCGCCCCAG AAATCGGCAA CCGTTCCCAG CATTGCTACA
26461  ACCTCCGCTC CTCAGGCGCC GCCGGCACTG CCCGTTCGCC GACCCAACCG TAGATGGGAC
26521  ACCACTGGAA CCAGGGCCGG TAAGTCTAAG CAGCCGCCGC CGTTAGCCCA AGAGCAACAA
26581  CAGCGCCAAG GCTACCGCTC GTGGCGCGTG CACAAGAACG CCATAGTTGC TTGCTTGCAA
26641  GACTGTGGGG GCAACATCTC CTTCGCCCGC CGCTTTCTTC TCTACCATCA CGGCGTGGCC
26701  TTCCCCCGTA ACATCCTGCA TTACTACCGT CATCTCTACA GCCCCTACTG CACCGGCGGC
26761  AGCGGCAGCA ACAGCAGCGG CCACGCAGAA GCAAAGGCGA CCGGATAGCA AGACTCTGAC
26821  AAAGCCCAAG AAATCCACAG CGGCGGCAGC AGCAGGAGGA GGAGCACTGC GTCTGGCGCC
26881  CAACGAACCC GTATCGACCC GCGAGCTTAG AAACAGGATT TTTCCCACTC TGTATGCTAT
26941  ATTTCAACAG AGCAGGGGCC AAGAACAAGA GCTGAAAATA AAAAACAGGT CTCTGCGCTC
27001  CCTCACCCGC AGCTGCCTGT ATCACAAAAG CGAAGATCAG CTTCGGCGCA CGCTGGAAGA
27061  CGCGGAGGCT CTCTTCAGCA ATACTGCGC GCTGACTCTT AAGGACTAGT TTCGCGCCCT
27121  TTCTCAAATT TAAGCGCGAA AACTACGTCA TCTCCAGCGG CCACACCCGG CGCCAGCACC
27181  TGTCGTCAGC GCCATTATGA GCAAGGAAAT TCCCACGCCC TACATGTGGA GTTACCAGCC
27241  ACAAATGGGA CTTGCGGCTG GAGCTGCCCA AGACTACTCA ACCCGAATAA ACTACATGAG
27301  CGCGGGACCC CACATGATAT CCCGGGTCAA CGGAATCCGC GCCCACCGAA ACCGAATTCT
27361  CCTCGAACAG GCGGCTATTA CCACCACACC TCGTAATAAC CTTAATCCCC GTAGTTGGCC
27421  CGCTGCCCTG GTGTACCAGG AAAGTCCCGC TCCCACCACT GTGGTACTTC CAGAGACGC
27481  CCAGGCCGAA GTTCAGATGA CTAACTCAGG GGCGCAGCTT GCGGGCGGCT TTCGTCACAG
27541  GGTGCGGTCG CCCGGGCAGG GTATAACTCA CCTGAAAATC AGAGGGCGAG GTATTCAGCT
27601  CAACGACGAG TCGGTGAGCT CCTCTCTTGG TCTCCGTCCG GACGGGACAT TCAGATCGG
27661  CGGCGCTGGC CGCTCTTCAT TTACGCCCCG TCAGGCGATC CTAACTCTGC AGACCTCGTC
```

FIG. 7K

```
27721 CTCGGAGCCG CGCTCCGGAG GCATTGGAAC TCTACAATTT ATTGAGGAGT TCGTGCCTTC
27781 GGTTTACTTC AACCCCTTTT CTGGACCTCC CGGCCACTAC CCGGACCAGT TTATTCCCAA
27841 CTTTGACGCG GTAAAAGACT CGGCGGACGG CTACGACTGA ATGACCAGTG GAGAGGCAGA
27901 GCAACTGCGC CTGACACACC TCGACCACTG CCGCCGCCAC AAGTGCTTTG CCCGCGGCTC
27961 CGGTGAGTTT TGTTACTTTG AATTGCCCGA AGAGCATATC GAGGGCCCGG CGCACGGCGT
28021 CCGGCTCACC ACCCAGGTAG AGCTTACACG TAGCCTGATT CGGGAGTTTA CCAAGCGCCC
28081 CCTGCTAGTG GAGCGGGAGC GGGGTCCCTG TGTTCTGACC GTGGTTTGCA ACTGTCCTAA
28141 CCCTGGATTA CATCAAGATC TTTGTTGTCA TCTCTGTGCT GAGTATAATA AATACAGAAA
28201 TTAGAATCTA CTGGGGCTCC TGTCGCCATC CTGTGAACGC CACCGTTTTT ACCCACCCAA
28261 AGCAGACCAA AGCAAACCTC ACCTCCGGTT TGCACAAGCG GGCCAATAAG TACCTTACCT
28321 GGTACTTTAA CGGCTCTTCA TTTGTAATTT ACAACAGTTT CCAGCGAGAC GAAGTAAGTT
28381 TGCCACACAA CCTTCTCGGC TTCAACTACA CCGTCAAGAA AAACACCACC ACCACCCTCC
28441 TCACCTGCCG GGAACGTACG AGTGCGTCAC CGGTTGCTGC GCCCACACCT ACAGCCTGAG
28501 CGTAACCAGA CATTACTCCC ATTTTCCCAA AACAGGAGGT GAGCTCAACT CCCGGAACTC
28561 AGGTCAAAAA AGCATTTTGC GGGGTGCTGG GATTTTTTAA TTAAGTATAT GAGCAATTCA
28621 AGTAACTCTA CAAGCTTGTC TAATTTTTCT GGAATTGGGG TCGGGGTTAT CCTTACTCTT
28681 GTAATTCTGT TTATTCTTAT ACTAGCACTT CTGTGCCTTA GGGTTGCCGC CTGCTGCACG
28741 CACGTTTGTA CCTATTGTCA GCTTTTAAA CGCTGGGGGC GACATCCAAG ATGAGGTACA
28801 TGATTTTAGG CTTGCTCGCC CTTGCGGCAG TCTGCAGCGC TGCCAAAAAG GTTGAGTTTA
28861 AGGAACCAGC TTGCAATGTT ACATTTAAAT CAGAAGCTAA TGAATGCACT ACTCTTATAA
28921 AATGCACCAC AGAACATGAA AAGCTTATTA TTCGCCACAA AGACAAAATT GGCAAGTATG
28981 CTGTATATGC TATTTGGCAG CCAGGTGACA CTAACGACTA TAATGTCACA GTCTTCCAAG
29041 GTGAAAATCG TAAAACTTTT ATGTATAAAT TTCCATTTTA TGAAATGTGC GATATTACCA
29101 TGTACATGAG CAAACAGTAC AAGTTGTGGC CCCCACAAAA GTGTTTAGAG AACACTGGCA
29161 CCTTTTGTTC CACCGCTCTG CTTATTACAG CGCTTGCTTT GGTATGTACC TTACTTTATC
29221 TCAAATACAA AAGCAGACGC AGTTTATTG ATGAAAAGAA AATGCCTTGA TTTTCCGCTT
29281 GCTTGTATTC CCCTGGACAA TTTACTCTAT GTGGGATATG CGCCAGGCGG GAAAGATTAT
29341 ACCCACAACC TTCAAATCAA ACTTTCCTGG ACGTTAGCGC CTGACTTCTG CCAGCGCCTG
29401 CACTGCAAAT TGATCAAAC CCAGCTTCAG CTTGCCTGCT CCAGAGATGA CCGGCTCAAC
29461 CATCGCGCCC ACAACGGACT ATCGCAACAC CACTGCTACC GGACTAAAAT CTGCCCTAAA
29521 TTTACCCCAA GTTCATGCCT TTGTCAATGA CTGGGCGAGC TTGGGCATGT GGTGGTTTTC
29581 CATAGCGCTT ATGTTTGTTT GCCTTATTAT TATGTGGCTT ATTTGTTGCC TAAAGCGCAG
29641 ACGCGCCAGA CCCCCCATCT ATAGGCCTAT CATTGTGCTC AACCCACACA ATGAAAAAAT
29701 TCATAGATTG GACGGTCTCA ACCATGTTC TCTTCTTTTA CAGTATGATT AAATGAGACA
29761 TGATTCCTCG AGTCCTTATA TTATTGACCC TTGTTGCGCT TTTCTGTGCG TGCTCTACAT
29821 TGGCTGCGGT CGCTCACATC GAAGTAGATT GCATCCCACC TTTCACAGTT TACCTGCTTT
29881 ACGGATTTGT CACCCTTATC CTCATCTGCA GCCTCGTCAC TGTAGTCATC GCCTTCATTC
29941 AGTTCATTGA CTGGATTTGT GTGCGCATTG CGTACCTTAG GCACCATCCG CAATACAGAG
30001 ACAGGACTAT AGCTGATCTT CTCAGAATTC TTTAATTATG AAACGGATTG TCACTTTTGT
30061 TTTGCTGATT TTCTGCGCCC TACCTGTGCT TTGCTCCCAA ACCTCAGCGC CTCCCAAAAG
30121 ACATATTTCC TGCAGATTCA CTCAAATATG GAACATTCCC AGCTGCTACA ACAAACAGAG
30181 CGATTTGTCA GAAGCCTGGT TATACGCCAT CATCTCTGTC ATGGTTTTTT GCAGTACCAT
```

FIG. 7L

```
30241 TTTTGCCCTA GCCATATACC CATACCTTGA CATTGGTTGG AATGCCATAG ATGCCATGAA
30301 CCACCCTACT TTCCCAGCGC CCAATGTCAT ACCACTGCAA CAGGTTATTG CCCCAATCAA
30361 TCAGCCTCGC CCCCCTTCTC CCACCCCCAC TGAGATTAGC TACTTTAATT TGACAGGTGG
30421 AGATGACTGA ATCTCTAGAT CTAGAATTGG ATGGAATTAA CACCGAACAG CGCCTACTAG
30481 AAAGGCGCAA GGCGGCGTCC GAGCGAGAAC GCCTAAAACA AGAAGTTGAA GACATGGTTA
30541 ACCTGCACCA GTGTAAAAGA GGTATCTTTT GTGTGGTCAA GCAGGCCAAA CTTACCTACG
30601 AAAAAACCAC TACCGGCAAC CGCCTTAGCT ACAAGCTACC CACCCAGCGC CAAAAACTGG
30661 TGCTTATGGT GGGAGAAAAA CCTATCACCG TCACCCAGCA CTCGGCAGAA ACAGAAGGCT
30721 GCCTGCACTT CCCCTATCAG GGTCCAGAGG ACCTCTGCAC TCTTATTAAA ACCATGTGTG
30781 GCATTAGAGA TCTTATTCCA TTCAACTAAC AATAAACACA CAATAAATTA CTTACTTAAA
30841 ATCAGTCAGC AAATCTTTGT CCAGCTTATT CAGCATCACC TCCTTTCCCT CCTCCCAACT
30901 CTGGTATTTC AGCAGCCTTT TAGCTGCGAA CTTTCTCCAA AGTCTAAATG GGATGTCAAA
30961 TTCCTCATGT TCTTGTCCCT CCGCACCCAC TATCTTCATA TTGTTGCAGA TGAAACGCGC
31021 CAGACCGTCT GAAGACACCT TCAACCCTGT GTACCCATAT GACACGGAAA CCGGCCCTCC
31081 AACTGTGCCT TTCCTTACCC CTCCCTTTGT GTCGCCAAAT GGGTTCCAAG AAAGTCCCCC
31141 CGGAGTGCTT TCTTTGCGTC TTTCAGAACC TTTGGTTACC TCACACGGCA TGCTTGCGCT
31201 AAAAATGGGC AGCGGCCTGT CCCTGGATCA GGCAGGCAAC CTTACATCAA ATACAATCAC
31261 TGTTTCTCAA CCGCTAAAAA AAACAAAGTC AATATAACT TTGGAAACAT CCGCGCCCCT
31321 TACAGTCAGC TCAGGCGCCC TAACCATGGC CACAACTTCG CCTTTGGTGG TCTCTGACAA
31381 CACTCTTACC ATGCAATCAC AAGCACCGCT AACCGTGCAA GACTCAAAAC TTAGCATTGC
31441 TACCAAAGAG CCACTTACAG TGTTAGATGG AAAACTGGCC CTGCAGACAT CAGCCCCCCT
31501 CTCTGCCACT GATAACAACG CCCTCACTAT CACTGCCTCA CCTCCTCTTA CTACTGCAAA
31561 TGGTAGTCTG GCTGTTACCA TGGAAAACCC ACTTTACAAC AACAATGGAA AACTTGGGCT
31621 CAAAATTGGC GGTCCTTTGC AAGTGGCCAC CGACTCACAT GCACTAACAC TAGGTACTGG
31681 TCAGGGGGTT GCAGTTCATA ACAATTTGCT ACATACAAAA GTTACAGGCG CAATAGGGTT
31741 TGATACATCT GGCAACATGG AACTTAAAAC TGGAGATGGC CTCTATGTGG ATAGCGCCGG
31801 TCCTAACCAA AAACTACATA TTAATCTAAA TACCACAAAA GGCCTTGCTT TTGACAACAC
31861 CGCAATAACA ATTAACGCTG GAAAAGGGTT GGAATTTGAA ACAGACTCCT CAAACGGAAA
31921 TCCCATAAAA ACAAAAATTG GATCAGGCAT ACAATATAAT ACCAATGGAG CTATGGTTGC
31981 AAAACTTGGA ACAGGCCTCA GTTTGACAG CTCCGGAGCC ATAACAATGG GCAGCATAAA
32041 CAATGACAGA CTTACTCTTT GGACAACACC AGACCCATCC CCAAATTGCA GAATTGCTTC
32101 AGATAAAGAC TGCAAGCTAA CTCTGGCGCT AACAAAATGT GGCAGTCAAA TTTTGGGCAC
32161 TGTTTCAGCT TTGGCAGTAT CAGGTAATAT GGCCTCCATC AATGGAACTC TAAGCAGTGT
32221 AAACTTGGTT CTTAGATTTG ATGACAACGG AGTGCTTATG TCAAATTCAT CACTGGACAA
32281 ACAGTATTGG AACTTTAGAA ACGGGGACTC CACTAACGGT CAACCATACA CTTATGCTGT
32341 TGGGTTTATG CCAAACCTAA AAGCTTACCC AAAAACTCAA AGTAAACTG CAAAAAGTAA
32401 TATTGTTAGC CAGGTGTATC TTAATGGTGA CAAGTCTAAA CCATTGCATT TTACTATTAC
32461 GCTAAATGGA ACAGATGAAA CCAACCAAGT AAGCAAATAC TCAATATCAT TCAGTTGGTC
32521 CTGGAACAGT GGACAATACA CTAATGACAA ATTTGCCACC AATTCCTATA CCTTCTCCTA
32581 CATTGCCCAG GAATAAAGAA TCGTGAACCT GTTGCATGTT ATGTTTCAAC GTGTTTATTT
32641 TTCAATTGCA GAAAATTTCA AGTCATTTTT CATTCAGTAG TATAGCCCCA CCACCACATA
32701 GCTTATACTA ATCACCGTAC CTTAATCAAA CTCACAGAAC CCTAGTATTC AACCTGCCAC
```

FIG. 7M

```
32761 CTCCCTCCCA ACACACAGAG TACACAGTCC TTTCTCCCCG GCTGGCCTTA AACAGCATCA
32821 TATCATGGGT AACAGACATA TTCTTAGGTG TTATATTCCA CACGGTCTCC TGTCGAGCCA
32881 AACGCTCATC AGTGATGTTA ATAAACTCCC CGGGCAGCTC GCTTAAGTTC ATGTCGCTGT
32941 CCAGCTGCTG AGCCACAGGC TGCTGTCCAA CTTGCGGTTG CTCAACGGGC GGCGAAGGAG
33001 AAGTCCACGC CTACATGGGG GTAGAGTCAT AATCGTGCAT CAGGATAGGG CGGTGGTGCT
33061 GCAGCAGCGC GCGAATAAAC TGCTGCCGCC GCCGCTCCGT CCTGCAGGAA TACAACATGG
33121 CAGTGGTCTC CTCAGCGATG ATTCGCACCG CCCGCAGCAT AAGGCGCCTT GTCCTCCGGG
33181 CACAGCAGCG CACCCTGATC TCACTTAAGT CAGCACAGTA ACTGCAGCAC AGTACCACAA
33241 TATTGTTTAA AATCCCACAG TGCAAGGCGC TGTATCCAAA GCTCATGGCG GGACCACAG
33301 AACCCACGTG GCCATCATAC CACAAGCGCA GGTAGATTAA GTGGCGACCC CTCATAAACA
33361 CGCTGGACAT AAACATTACC TCTTTTGGCA TGTTGTAATT CACCACCTCC CGGTACCATA
33421 TAAACCTCTG ATTAAACATG GCGCCATCCA CCACCATCCT AAACCAGCTG GCCAAAACCT
33481 GCCCGCCGGC TATGCACTGC AGGGAACCGG GACTGGAACA ATGACAGTGG AGAGCCCAGG
33541 ACTCGTAACC ATGGATCATC ATGCTCGTCA TGATATCAAT GTTGGCACAA CACAGGCACA
33601 CGTGCATACA CTTCCTCAGG ATTACAAGCT CCTCCCGCGT CAGAACCATA TCCCAGGGAA
33661 CAACCCATTC CTGAATCAGC GTAAATCCCA CACTGCAGGG AAGACCTCGC ACGTAACTCA
33721 CGTTGTGCAT TGTCAAAGTG TTACATTCGG GCAGCAGCGG ATGATCCTCC AGTATGGTAG
33781 CGCGTGTCTC TGTCTCAAAA GGAGGTAGGC GATCCCTACT GTACGGAGTG CGCCGAGACA
33841 ACCGAGATCG TGTTGGTCGT AGTGTCATGC CAAATGGAAC GCCGGACGTA GTCATATTTC
33901 CTGAAGCAAA ACCAGGTGCG GGCGTGACAA ACAGATCTGC GTCTCCGGTC TCGTCGCTTA
33961 GCTCGCTCTG TGTAGTAGTT GTAGTATATC CACTCTCTCA AAGCATCCAG GCGCCCCCTG
34021 GCTTCGGGTT CTATGTAAAC TCCTTCATGC GCCGCTGCCC TGATAACATC CACCACCGCA
34081 GAATAAGCCA CACCCAGCCA ACCTACACAT TCGTTCTGCG AGTCACACAC GGGAGGAGCG
34141 GGAAGAGCTG GAAGAACCAT GTTTTTTTTT TTTATTCCAA AAGATTATCC AAAACCTCAA
34201 AATGAAGATC TATTAAGTGA ACGCGCTCCC CTCCGGTGGC GTGGTCAAAC TCTACAGCCA
34261 AAGAACAGAT AATGGCATTT GTAAGATGTT GCACAATGGC TTCCAAAAGG CAAACTGCCC
34321 TCACGTCCAA GTGGACGTAA AGGCTAAACC CTTCAGGGTG AATCTCCTCT ATAAACATTC
34381 CAGCACCTTC AACCATGCCC AATAATTTTT CATCTCGCCA CCTTATCAAT ATGTCTCTAA
34441 GCAAATCCCG AATATTAAGT CCGGCCATTG TAAAAATCTG CTCCAGAGCG CCCTCCACCT
34501 TCAGCCTCAA GCAGCGAATC ATGATTGCAA AAATTCAGGT TCCTCACAGA CCTGTATAAG
34561 ATTCAAAAGC GGAACATTAA CAAAATATACC GCGATCCCGT AGGTCCCTTC GCAGGGCCAG
34621 CTGAACATAA TCGTGCAGGT CTGCACGGAC CAGCGCGGCC ACTTCCCCGC CAGGAACCAT
34681 GACAAAAGAA CCCACACTGA TTATGACACG CATACTCGGA GCTATGCTAA CCAGCGTAGC
34741 CCCGATGTAA GCTTGTTGCA TGGGCGGCGA TATAAAATGC AAGGTACTGC TCAAAAAATC
34801 AGGCAAAGCC TCGCGCAAAA AAGCAAGCAC ATCGTAGTCA TGCTCATGCA GATAAAGGCA
34861 GGTAAGTTCC GGAACCACCA CAGAAAAAGA CACCATTTTT CTCTCAAACA TGTCTGCGGG
34921 TTCCTGCATA AACACAAAAT AAAATAACAA AAAAAAAAA ACATTTAAAC ATTAGAAGCC
34981 TGTNTTACAA CAGGAAAAAC AACCCTTATA AGCATAAGAC GGACTACGGC CATGCCGGCG
35041 TGACCGTAAA AAAACTGGTC ACCGTGATTA AAAGCACCA CCGACAGTTC CTCGGTCATG
35101 TCCGGAGTCA TAATGTAAGA CTCGGTAAAC ACATCAGGTT GGTTAACATC GGTCAGTGCT
35161 AAAAGCGAC CGAAATAGCC CGGGGAATA CATACCCGCA GGCGTAGAGA CAACATTACA
35221 GCCCCCATAG GAGGTATAAC AAAATTAATA GGAGAGAAAA ACACATAAAC ACCTGAAAAA
```

FIG. 7N

```
35281 CCCTCCTGCC TAGGCAAAAT AGCACCCTCC CGCTCCAGAA CAACATACAG CGCTTCCACA
35341 GCGGCAGCCA TAACAGTCAG CCTTACCAGT AAAAAAACCT ATTAAAAAAC ACCACTCGAC
35401 ACGGCACCAG CTCAATCAGT CACAGTGTAA AAAGGGCCAA GTACAGAGCG AGTATATATA
35461 GGACTAAAAA ATGACGTAAC GGTTAAAGTC CACAAAAACC ACCCAGAAAA CCGCACGCGA
35521 ACCTACGCCC AGAAACGAAA GCCAAAAAAC CCACAACTTC CTCAAATCTT CACTTCCGTT
35581 TTCCCACGAT ACGTCACTTC CCATTTTAAA AAAAAACTAC AATTCCCAAT ACATGCAAGT
35641 TACTCCGCCC TAAAACCTAC GTCACCCGCC CCGTTCCCAC GCCCCGCGCC ACGTCACAAA
35701 CTCCACCCCC TCATTATCAT ATTGGCTTCA ATCCAAAATA AGGTATATTA TTGATGATG
```

FIG. 7O

```
   1 CATCATCAAT AATATACCTT ATTTTGGATT GAAGCCAATA TGATAATGAG GGGGTGGAGT
  61 TTGTGACGTG GCGCGGGGCG TGGGAACGGG GCGGGTGACG TAGTAGTGTG GCGGAAGTGT
 121 GATGTTGCAA GTGTGGCGGA ACACATGTAA GCGACGGATG TGGCAAAAGT GACGTTTTTG
 181 GTGTGCGCCG GTGTACACAG GAAGTGACAA TTTTCGCGCG GTTTTAGGCG GATGTTGTAG
 241 TAAATTTGGG CGTAACCGAG TAAGATTTGG CCATTTCGC GGGAAAACTG AATAAGAGGA
 301 AGTGAAATCT GAATAATTTT GTGTTACTCA TAGCGCGTAA TATTTGTCTA GGGCCGCGGG
 361 GACTTTGACC GTTTACGTGG AGACTCGCCC AGGTGTTTTT CTCAGGTGTT TTCCGCGTTC
 421 CGGGTCAAAG TTGGCGTTTT ATTATTATAG TCAGCTGACG TGTAGTGTAT TTATACCCGG
 481 TGAGTTCCTC AAGAGGCCAC TCTTGAGTGC CAGCGAGTAG AGTTTTCTCC TCCGAGCCGC
 541 TCCGACACCG GGACTGAAAA TGAGACATAT TATCTGCCAC GGAGGTGTTA TTACCGAAGA
 601 AATGGCCGCC AGTCTTTTGG ACCAGCTGAT CGAAGAGGTA CTGGCTGATA ATCTTCCACC
 661 TCCTAGCCAT TTGAACCAC CTACCCTTCA CGAACTGTAT GATTTAGACG TGACGGCCCC
 721 CGAAGATCCC AACGAGGAGG CGGTTTCGCA GATTTTCCC GACTCTGTAA TGTTGGCGGT
 781 GCAGGAAGGG ATTGACTTAC TCACTTTTCC GCCGGCGCCC GGTTCTCCGG AGCCGCCTCA
 841 CCTTTCCCGG CAGCCCGAGC AGCCGGAGCA GAGAGCCTTG GGTCCGGTTT CTATGCCAAA
 901 CCTTGTACCG GAGGTGATCG ATCTTACCTG CCACGAGGCT GGCTTTCCAC CCAGTGACGA
 961 CGAGGATGAA GAGGGTGAGG AGTTTGTGTT AGATTATGTG GAGCACCCCG GGCACGGTTG
1021 CAGGTCTTGT CATTATCACC GGAGGAATAC GGGGGACCCA GATATTATGT GTTCGCTTTG
1081 CTATATGAGG ACCTGTGGCA TGTTTGTCTA CAGTAAGTGA AAATTATGGG CAGTGGGTGA
1141 TAGAGTGGTG GGTTTGGTGT GGTAATTTTT TTTTAATTT TTACAGTTTT GTGGTTTAAA
1201 GAATTTTGTA TTGTGATTTT TTTAAAAGGT CCTGTGTCTG AACCTGAGCC TGAGCCCGAG
1261 CCAGAACCGG AGCCTGCAAG ACCTACCCGC CGTCCTAAAA TGGCGCCTGC TATCCTGAGA
1321 CGCCCGACAT CACCTGTGTC TAGAGAATGC AATAGTAGTA CGGATAGCTG TGACTCCGGT
1381 CCTTCTAACA CACCTCCTGA GATACACCCG GTGGTCCCGC TGTGCCCCAT TAAACCAGTT
1441 GCCGTGAGAG TTGGTGGGCG TCGCCAGGCT GTGGAATGTA TCGAGGACTT GCTTAACGAG
1501 CCTGGGCAAC CTTTGGACTT GAGCTGTAAA CGCCCCAGGC CATAAGGTGT AAACCTGTGA
1561 TTGCGTGTGT GGTTAACGCC TTTGTTTGCT GAATGAGTTG ATGTAAGTTT AATAAAGGGT
1621 GAGATAATGT TTAACTTGCA TGGCGTGTTA AATGGGGCGG GGCTTAAAGG GTATATAATG
1681 CGCCGTGGGC TAATCTTGGT TACATCTGAC CTCATGGAGG CTTGGGAGTG TTTGGAAGAT
1741 TTTTCTGCTG TGCGTAACTT GCTGGAACAG AGCTCTAACA GTACCTCTTG GTTTTGGAGG
1801 TTTCTGTGGG GCTCATCCCA GGCAAAGTTA GTCTGCAGAA TTAAGGAGGA TTACAAGTGG
1861 GAATTTGAAG AGCTTTTGAA ATCCTGTGGT GAGCTGTTTG ATTCTTTGAA TCTGGGTCAC
1921 CAGGCGCTTT TCCAAGAGAA GGTCATCAAG ACTTTGGATT TTTCCACACC GGGGCGCGCT
1981 GCGGCTGCTG TTGCTTTTTT GAGTTTTATA AAGGATAAAT GGAGCGAAGA AACCCATCTG
2041 AGCGGGGGGT ACCTGCTGGA TTTTCTGGCC ATGCATCTGT GGAGAGCGGT TGTGAGACAC
2101 AAGAATCGCC TGCTACTGTT GTCTTCCGTC CGCCCGGCGA TAATACCGAC GGAGGAGCAG
2161 CAGCAGCAGC AGGAGGAAGC CAGGCGGCGG CGGCAGGAGC AGAGCCCATG GAACCCGAGA
2221 GCCGGCCTGG ACCCTCGGGA ATGAATGTTG TACAGGTGGC TGAACTGTAT CCAGAACTGA
2281 GACGCATTTT GACAATTACA GAGGATGGGC AGGGGCTAAA GGGGGTAAAG AGGGAGCGGG
2341 GGCTTGTGA GGCTACAGAG GAGGCTAGGA ATCTAGCTTT TAGCTTAATG ACCAGACACC
2401 GTCCTGAGTG TATTACTTTT CAACAGATCA AGGATAATTG CGCTAATGAG CTTGATCTGC
2461 TGGCGCAGAA GTATTCCATA GAGCAGCTGA CCACTTACTG GCTGCAGCCA GGGGATGATT
2521 TTGAGGAGGC TATTAGGGTA TATGCAAAGG TGGCACTTAG GCCAGATTGC AAGTACAAGA
2581 TCAGCAAACT TGTAAATATC AGGAATTGTT GCTACATTTC TGGGAACGGG GCCGAGGTGG
2641 AGATAGATAC GGAGGATAGG GTGGCCTTTA GATGTAGCAT GATAAATATG TGGCCGGGGG
2701 TGCTTGGCAT GGACGGGGTG TTATTATGA ATGTAAGGTT TACTGGCCCC AATTTTAGCG
2761 GTACGGTTTT CCTGGCCAAT ACCAACCTTA TCCTACACGG TGTAAGCTTC TATGGGTTTA
2821 ACAATACCTG TGTGGAAGCC TGGACCGATG TAAGGGTTCG GGCTGTGCC TTTTACTGCT
2881 GCTGGAAGGG GGTGGTGTGT CGCCCAAAA GCAGGGCTTC AATTAAGAAA TGCCTCTTTG
2941 AAAGGTGTAC CTTGGGTATC CTGTCTGAGG GTAACTCCAG GGTGCGCCAC AATGTGGCCT
3001 CCGACTGTGG TTGCTTCATG CTAGTGAAAA GCGTGGCTGT GATTAAGCAT AACATGGTAT
3061 GTGGCAACTG CGAGGACAGG GCCTCTCAGA TGCTGACCTG CTCGGACGGC AACTGTCACC
3121 TGCTGAAGAC CATTCACGTA GCCAGCCACT CTCGCAAGGC CTGGCCAGTG TTTGAGCATA
3181 ACATACTGAC CCGCTGTTCC TTGCATTTGG GTAACAGGAG GGGGGTGTTC CTACCTTACC
3241 AATGCAATTT GAGTCACACT AAGATATTGC TTGAGCCCGA GAGCATGTCC AAGGTGAACC
```

FIG. 8A

```
3301 TGAACGGGGT GTTTGACATG ACCATGAAGA TCTGGAAGGT GCTGAGGTAC GATGAGACCC
3361 GCACCAGGTG CAGACCCTGC GAGTGTGGCG GTAAACATAT TAGGAACCAG CCTGTGATGC
3421 TGGATGTGAC CGAGGAGCTG AGGCCCGATC ACTTGGTGCT GGCCTGCACC CGCGCTGAGT
3481 TTGGCTCTAG CGATGAAGAT ACAGATTGAG GTACTGAAAT GTGTGGGCGT GGCTTAAGGG
3541 TGGGAAAGAA TATATAAGGT GGGGGTCTTA TGTAGTTTTG TATCTGTTTT GCAGCAGCCG
3601 CCGCCGCCAT GAGCACCAAC TCGTTTGATG GAAGCATTGT GAGCTCATAT TTGACAACGC
3661 GCATGCCCCC ATGGGCCGGG GTGCGTCAGA ATGTGATGGG CTCCAGCATT GATGGTCGCC
3721 CCGTCCTGCC CGCAAACTCT ACTACCTTGA CCTACGAGAC CGTGTCTGGA ACGCCGTTGG
3781 AGACTGCAGC CTCCGCCGCC GCTTCAGCCG CTGCAGCCAC CGCCCGCGGG ATTGTGACTG
3841 ACTTTGCTTT CCTGAGCCCG CTTGCAAGCA GTGCAGCTTC CCGTTCATCC GCCCGCGATG
3901 ACAAGTTGAC GGCTCTTTTG GCACAATTGG ATTCTTTGAC CCGGGAACTT AATGTCGTTT
3961 CTCAGCAGCT GTTGGATCTG CGCCAGCAGG TTTCTGCCCT GAAGGCTTCC TCCCCTCCCA
4021 ATGCGGTTTA AAACATAAAT AAAAAACCAG ACTCTGTTTG GATTTGGATC AAGCAAGTGT
4081 CTTGCTGTCT TTATTTAGGG GTTTTGCGCG CGCGGTAGGC CCGGGTCTCG GGTCTCGGT
4141 CGTTGAGGGT CCTGTGTATT TTTTCCAGGA CGTGGTAAAG GTGACTCTGG ATGTTCAGAT
4201 ACATGGGCAT AAGCCCGTCT CTGGGGTGGA GGTAGCACCA CTGCAGAGCT TCATGCTGCG
4261 GGGTGGTGTT GTAGATGATC CAGTCGTAGC AGGAGCGCTG GGCGTGGTGC CTAAAAATGT
4321 CTTTCAGTAG CAAGCTGATT GCCAGGGGCA GGCCCTTGGT GTAAGTGTTT ACAAAGCGGT
4381 TAAGCTGGGA TGGGTGCATA CGTGGGGATA TGAGATGCAT CTTGCAGAACC ATTTTTAGGT
4441 TGGCTATGTT CCCAGCCATA TCCCTCCGGG GATTCATGTT GTGCAGAACC ACCAGCACAG
4501 TGTATCCGGT GCACTTGGA AATTTGTCAT GTAGCTTAGA AGGAAATGCG TGGAAGAACT
4561 TGGAGACGCC CTTGTGACCT CCAAGATTTT CCATGCATTC GTCCATAATG ATGGCAATGG
4621 GCCCACGGGC GGCGGCCTGG GCGAAGATAT TTCTGGGATC ACTAACGTCA TAGTTGTGTT
4681 CCAGGATGAG ATCGTCATAG GCCATTTTTA CAAAGCGCGG GCGGAGGGTG CCAGACTGCG
4741 GTATAATGGT TCCATCCGGC CCAGGGGCGT AGTTACCCTC ACAGATTTGC ATTTCCCACG
4801 CTTTGAGTTC AGATGGGGGG ATCATGTCTA CCTGCGGGGC GATGAAGAAA ACGGTTTCCG
4861 GGGTAGGGGA GATCAGCTGG GAAGAAAGCA GGTTCCTGAG CAGCTGCGAC TTACCGCAGC
4921 CGGTGGGCCC GTAAATCACA CCTATTACCG GGTGCAACTG GTAGTTAAGA GAGCTGCAGC
4981 TGCCGTCATC CCTGAGCAGG GGGGCCACTT CGTTAAGCAT GTCCCTGACT CGCATGTTTT
5041 CCCTGACCAA ATCCGCCAGA AGGCGCTCGC CGCCCAGCAT TAGCAGTTCT TGCAAGGAAG
5101 CAAAGTTTTT CAACGGTTTG AGACCGTCCG CCGTAGGCAT GCTTTTGAGC GTTTGACCAA
5161 GCAGTTCCAG GCGGTCCCAC AGCTCGGTCA CCTGCTACAC GGCATCTCGA TCCAGCATAT
5221 CTCCTCGTTT CGCGGGTTGG GGCGGCTTTC GCTGTACGGC AGTAGTCGGT GCTCGTCCAG
5281 ACGGGCCAGG GTCATGTCTT TCCACGGGCG CAGGGCAGGGTG CGCTTGAGGC TGGTCCTGCT
5341 GGTGAAGGGG TGCGCTCCGG GCTGCGCGCT GGCGTCGGCC AGGTAGCATT TGACCATGGT
5401 GGTGCTGAAG CGCTGCCGGT CTTCGCCCTG CTTGGCGCGC AGCTTGCCCT TGGAGGAGGC
5461 GTCATAGTCC AGCCCCTCCG CGGCGTGGCC GGCGTAGAGC TTGGGCGCGA GAAATACCGA
5521 GCCGCACGAG GGGCAGTGCA GACTTTTGAG GGCCGCAGACG GTCTCGCATT CCACGAGCCA
5581 TTCCGGGGAG TAGGCATCCG CGCCGCAGGC CAGGTTTCCC CCATGCTTTT TGATGCGTTT
5641 GGTGAGCTCT GGCCGTTCGG GGTCAAAAAC ACGCTCGGTG ACGAAAAGGC TGTCCGTGTC
5701 CTTACCTCTG GTTTCCATGA GCCGGTGTCC GAGCGGTGTT CCGCGGTCCT CCTCGTATAG
5761 CCCGTATACA GACTTGAGAG GCCTGTCCTC CGTCCAGGCC AGCACGAAGG AGGCTAAGTG
5821 AAACTCGGAC CACTCTGAGA CAAAGGCTCG GTCCACTCGC TCCAGGGTGT GAAGACACAT
5881 GGAGGGGTAG CGGTCGTTGT CCACTAGGGG GTCCACTCGC TCCAGGGTGT GAAGACACAT
5941 GTCGCCCTCT TCGGCATCAA GGAAGGTGAT TGGTTTGTAG GTGTAGGCCA CGTGACCGGG
6001 TGTTCCTGAA GGGGGCTAT AAAAGGGGGT GGGGGCGCGT TCGTCCTCAC TCTCTTCCGC
6061 ATCGCTGTCT GCGAGGGCCA GCTGTTGGGG TGAGTACTCC CTCTGAAAAG CGGGCATGAC
6121 TTCTGCGCTA AGATTGTCAG TTTCCAAAAA CGAGGAGGAT TTGATATTCA CCTGGCCCGC
6181 GGTGATGCCT TTGAGGGTGG CCGCATCCAT CTGGTCAGAA AAGCAAATCT TTTTGTTGTC
6241 AAGCTTGGTG GCAAACGACC CGTAGAGGGC GTTGGACAGC AACTTGGCGA TGGAGCGCAG
6301 GGTTTGGTTT TTGTCGCGAT CGGCGCGCTC CTTGGCCGCG ATGTTTAGCT GCACGTATTC
6361 GCGCGCAACG CACCGCCATT CGGGAAAGAC GGTGGTGCGC TCGTCGGGCA CCAGGTGCAC
6421 GCGCCAACCG CGGTTGTGCA GGGTGACAAG GTCAACGCTG GTGGCTACCT CTCCGCGTAG
6481 GCGCTCGTTG GTCCAGCAGA GGCGGCCGCC CTTGCGCGAG CAGAATGGCG GTAGGGGGTC
6541 TAGCTGCGTC TCGTCCGGGG GGTCTGCGTC CACGGTAAAG ACCCCGGGCA GCAGGCGCGC
```

FIG. 8B

```
6601 GTCGAAGTAG TCTATCTTGC ATCCTTGCAA GTCTAGCGCC TGCTGCCATG CGCGGGCGGC
6661 AAGCGCGCGC TCGTATGGGT TGAGTGGGGG ACCCCATGGC ATGGGGTGGG TGAGCGCGGA
6721 GGCGTACATG CCGCAAATGT CGTAAACGTA GAGGGGCTCT CTGAGTATTC CAAGATATGT
6781 AGGGTAGCAT CTTCCACCGC GGATGCTGGC GCGCACGTAA TCGTATAGTT CGTGCGAGGG
6841 AGCGAGGAGG TCGGGACCGA GGTTGCTACG GGCGGGCTGC TCTGCTCGGA AGACTATCTG
6901 CCTGAAGATG GCATGTGAGT TGGATGATAT GGTTGGACGC TGGAAGACGT TGAAGCTGGC
6961 GTCTGTGAGA CCTACCGCGT CACGCACGAA GGAGGCGTAG GAGTCGCGCA GCTTGTTGAC
7021 CAGCTCGGCG GTGACCTGCA CGTCTAGGGC GCAGTAGTCC AGGGTTTCCT TGATGATGTC
7081 ATACTTATCC TGTCCCTTTT TTTTCCACAG CTCGCGGTTG AGGACAAACT CTTCGCGGTC
7141 TTTCCAGTAC TCTTGGATCG GAAACCCGTC GGCCTCCGAA CGGTAAGAGC CTAGCATGTA
7201 GAACTGGTTG ACGGCCTGGT AGGCGCAGCA TCCCTTTTCT ACGGGTAGCG CGTATGCCTG
7261 CGCGGCCTTC CGGAGCGAGG TGTGGGTGAG CGCAAAGGTG TCCCTGACCA TGACTTTGAG
7321 GTACTGGTAT TTGAAGTCAG TGTCGTCGCA TCCGCCCTGC TCCCAGAGCA AAAAGTCCGT
7381 GCGCTTTTTG GAACGCGGAT TTGGCAGGGC GAAGGTGACA TCGTTGAAGA GTATCTTTCC
7441 CGCGCGAGGC ATAAAGTTGC GTGTGATGCG GAAGGGTCCC GGCACCTCGG AACGGTTGTT
7501 AATTACCTGG GCGGCGAGCA CGATCTCGTC AAAGCCGTTG ATGTTGTGGC CCACAATGTA
7561 AAGTTCCAAG AAGCGCGGGA TGCCCTTGAT GGAAGGCAAT TTTTTAAGTT CCTCGTAGGT
7621 GAGCTCTTCA GGGGAGCTGA GCCCGTGCTC TGAAAGGGCC CAGTCTGCAA GATGAGGGTT
7681 GGAAGCGACG AATGAGCTCC ACAGGTCACG GGCCATTAGC ATTTGCAGGT GGTCGCGAAA
7741 GGTCCTAAAC TGGCGACCTA TGGCCATTTT TTCTGGGGTG ATGCAGTAGA AGGTAAGCGG
7801 GTCTTGTTCC CAGCGGTCCC ATCCAAGGTT CGCGGCTAGG TCTCGCGCGG CAGTCACTAG
7861 AGGCTCATCT CCGCCGAACT TCATGACCAG CATGAAGGGC ACGAGCTGCT TCCCAAAGGC
7921 CCCCATCCAA GTATAGGTCT CTACATCGTA GGTGACAAAG AGACGCTCGG TGCGAGGATG
7981 CGAGCCGATC GGGAAGAACT GGATCTCCCG CCACCAATTG GAGGAGTGGC TATTGATGTG
8041 GTGAAAGTAG AAGTCCCTGC GACGGGCCGA ACACTCGTGC TGGCTTTTGT AAAAACGTGC
8101 GCAGTACTGG CAGCGGTGCA CGGGCTGTAC ATCCTGCACG AGGTTGACCT GACGACGCGC
8161 CACAAGGAAG CAGAGTGGGA ATTTGAGCCC CTCGCCTGGC GGGTTTGGCT GGTGGTCTTC
8221 TACTTCGGCT GCTTGTCCTT GACCGTCTGG CTGCTCGAGG GGAGTTACGG TGGATCGGAC
8281 CACCACGCCG CGCGAGCCCA AGTCCAGAT GTCCGCGCGC GGCGGTCGGA GCTTGATGAC
8341 AACATCGCGC AGATGGGAGC TGTCCATGGT CTGGAGCTCC CGCGGCGTCA GGTCAGGCGG
8401 GAGCTCCTGC AGGTTTACCT CGCATAGACG GGTCAGGGCG CGGGCTAGAT CCAGGTGATA
8461 CCTAATTTCC AGGGGCTGGT TGGTGGCGGC GTCGATGGCT TGCAAGAGGC CGCATCCCCG
8521 CGGCGCGACT ACGGTACCGC GCGGCGGGCG GTGGGCCGCG GGGGTGTCCT TGGATGATGC
8581 ATCTAAAAGC GGTGACGCGG GCGAGCCCCC GGAGGTAGGG GGGGCTCCGG ACCCGCCGGG
8641 AGAGGGGGCA GGGGCACGTC GGCGCCGCGC GCGGGCAGGA GCTGGTGCTG CGCGCGTAGG
8701 TTGCTGGCGA ACGCGACGAC GCGGCGGTTG ATCTCCTGAA TCTGCCGCCT CTGCGTGAAG
8761 ACGACGGGCC CGGTGAGCTT GAGCCTGAAA GAGAGTTCGA CAGAATCAAT TTCGGTGTCG
8821 TTGACGGCGG CCTGGCGCAA AATCTCCTGC ACGTCTCCTG AGTTGTCTTG ATAGGCGATC
8881 TCGGCCATGA ACTGCTCGAT CTCTTCCTCC TGGAGATCTC CGCGTCCGGC TCGCTCCACG
8941 GTGGCGGCGA GGTCGTTGGA AATGCGGGCC ATGAGCTGCG AGAAGGCGTT GAGGCCTCCC
9001 TCGTTCCAGA CGCGGCTGTA GACCACGCCC CCTTCGGCAT CGCGGGCGCG CATGACCACC
9061 TGCGCGAGAT TGAGCTCCAC GTGCCGGGCG AAGACGGCGT AGTTTCGCAG GCGCTGAAAG
9121 AGGTAGTTGA GGGTGGTGGC GGTGTGTTCT GCCACGAAGA AGTACATAAC CCAGCGTCGC
9181 AACGTGGATT CGTTGATATC CCCCAAGGCC TCAAGGCGCT CCATGGCCTC GTAGAAGTCC
9241 ACGGCGAAGT TGAAAAACTG GGAGTTGCGC GCCGACACGG TTAACTCCTC CTCCAGAAGA
9301 CGGATGAGCT CGGCGACAGT GTCGCGCACC TCGCGCTCAA AGGCTACAGG GGCCTCTTCT
9361 TCTTCTTCAA TCTCCTCTTC CATAAGGGCC TCCCCTTCTT CTTCTTCTGG CGGCGGTGGG
9421 GGAGGGGGGA CACGGCGGCG ACGACGGCGC ACCGGGAGGC GGTCGACAAA GCGCTCGATC
9481 ATCTCCCCGC GGCGACGGCG CATGGTCTCG GTGACGGCGC GGCCGTTCTC GCGGGGCGC
9541 AGTTGGAAGA CGCCGCCCGT CATGTCCCGG TTATGGGTTG GCGGGGGGCT GCCATGCGGC
9601 AGGGATACGG CGCTAACGAT GCATCTCAAC AATTGTTGTG TAGGTACTCC GCCGCCGAGG
9661 GACCTGAGCG AGTCCGCATC GACCGGATCG GAAAACCTCT CGAGAAAGGC GTCTAACCAG
9721 TCACAGTCGC AAGGTAGGCT GAGCACCGTG GCGGGCGGCA GCGGGCGGCG GTCGGGTTG
9781 TTTCTGGCGG AGGTGCTGCT GATGATGTAA TTAAAGTAGG CGGTCTTGAG ACGGCGGATG
9841 GTCGACAGAA GCACCATGTC CTTGGGTCCG GCCTGCTGAA TGCGCAGGCG GTCGGCCATG
```

FIG. 8C

```
9901  CCCCAGGCTT CGTTTTGACA TCGGCGCAGG TCTTTGTAGT AGTCTTGCAT GAGCCTTTCT
9961  ACCGGCACTT CTTCTTCTCC TTCCTCTTGT CCTGCATCTC TTGCATCTAT CGCTGCGGCG
10021 GCGGCGGAGT TTGGCCGTAG GTGGCGCCCT CTTCCTCCCA TGCGTGTGAC CCCGAAGCCC
10081 CTCATCGGCT GAAGCAGGGC TAGGTCGGCG ACAACGCGCT CGGCTAATAT GGCCTGCTGC
10141 ACCTGCGTGA GGGTAGACTG GAAGTCATCC ATGTCCACAA AGCGGTGGTA TGCGCCCGTG
10201 TTGATGGTGT AAGTGCAGTT GGCCATAACG GACCAGTTAA CGGTCTGGTG ACCCGGCTGC
10261 GAGAGCTCGG TGTACCTGAG ACGCGAGTAA GCCCTCGAGT CAAATACGTA GTCGTTGCAA
10321 GTCCGCACCA GGTACTGGTA TCCCACCAAA AAGTGCGGCG GCGGCTGGCG GTAGAGGGGC
10381 CAGCGTAGGG TGGCCGGGGC TCCGGGGGCG AGATCTTCCA ACATAAGGCG ATGATATCCG
10441 TAGATGTACC TGGACATCCA GGTGATGCCG GCGGCGGTGG TGGAGGCGCG CGGAAAGTCG
10501 CGGACGCGGT TCCAGATGTT GCGCAGCGGC AAAAAGTGCT CCATGGTCGG GACGCTCTGG
10561 CCGGTCAGGC GCGCGCAATC GTTGACGCTC TAGACCGTGC AAAAGGAGAG CCTGTAAGCG
10621 GGCACTCTTC CGTGGTCTGG TGGATAAATT CGCAAGGGTA TCATGGCGGA CGACCGGGGT
10681 TCGAGCCCCG TATCCGGCCG TCCGCCGTGA TCCATGCGGT TACCGCCCGC GTGTCGAACC
10741 CAGGTGTGCG ACGTCAGACA ACGGGGGAGT GCTCCTTTTG GCTTCCTTCC AGGCGCGGCG
10801 GCTGCTGCGC TAGCTTTTTT GGCCACTGGC CGCGCGCAGC GTAAGCGGTT AGGCTGGAAA
10861 GCGAAAGCAT TAAGTGGCTC GCTCCCTGTA GCCGGAGGGT TATTTTCAA GGGTTGAGTC
10921 GCGGGACCCC CGGTTCGAGT CTCGGACCGG CCGGACTGCG GCGAACGGGG GTTTGCCTCC
10981 CCGTCATGCA AGACCCCGCT TGCAAATTCC TCCGGAAACA GGGACGAGCC CCTTTTTTGC
11041 TTTTCCCAGA TGCATCCGGT GCTGCGGCAG ATGCGCCCCC CTCCTCAGCA GCGGCAAGAG
11101 CAAGAGCAGC GGCAGACATG CAGGGCACCC TCCCCTCCTC CTACCGCGTC AGGAGGGGCG
11161 ACATCCGCGG TTGACGCGGC AGCAGATGGT GATTACGAAC CCCCGCGGCG CCGGGCCCGG
11221 CACTACCTGG ACTTGGAGGA GGGCGAGGGC CTGGCGCGGC TAGGAGCGCC CTCTCCTGAG
11281 CGGTACCCAA GGGTGCAGCT GAAGCGTGAT ACGCGTGAGG CGTACGTGCC GCGGCAGAAC
11341 CTGTTTCGCG ACCGCGAGGG AGAGGAGCCC GAGGAGATGC GGGATCGAAA GTTCCACGCA
11401 GGGCGCGAGC TGCGGCATGG CCTGAATCGC GAGCGGTTGC TGCGCGAGGA GGACTTTGAG
11461 CCCGACGCGC GAACCGGGAT TAGTCCCGCG CGCGCACACG TGGCGGCCGC CGACCTGGTA
11521 ACCGCATACG AGCAGACGGT GAACCAGGAG ATTAACTTTC AAAAAAGCTT TAACAACCAC
11581 GTGCGTACGC TTGTGGCGCG CGAGGAGGTG GCTATAGGAC TGATGCATCT GTGGGACTTT
11641 GTAAGCGCGC TGGAGCAAAA CCCAAATAGC AAGCCGCTCA TGGCGCAGCT GTTCCTTATA
11701 GTGCAGCACA GCAGGGACAA CGAGGCATTC AGGGATGCGC TGCTAAACAT AGTAGAGCCC
11761 GAGGGCCGCT GGCTGCTCGA TTTGATAAAC ATCCTGCAGA GCATAGTGGT GCAGGAGCGC
11821 AGCTTGAGCC TGGCTGACAA GGTGGCCGCC ATCAACTATT CCATGCTTAG CCTGGGCAAG
11881 TTTTACGCCC GCAAGATATA CCATACCCCT TACGTTCCCA TAGACAAGGA GGTAAAGATC
11941 GAGGGGTTCT ACATGCGCAT GGCGCATCCA CAAGGCCGTG AGCGTGAGCC GGCGGCGCGA GCTCAGCGAC
12001 TATCGCAACG AGCGCATCCA CAAGGCCGTG AGCGTGAGCC GGCGGCGCGA GCTCAGCGAC
12061 CGCGAGCTGA TGCACGAGCT GCAAAGGGCC CTGGCTGGCA CGGGCAGCGG CGATAGAGAG
12121 GCCGAGTCCT ACTTTGACGC GGGCGCTGAC CTGCGCTGGG CCCCAAGCCG ACGCGCCCTG
12181 GAGGCAGCTG GGGCCGGACC TGGGCTGGCG GTGGCACCCG CGCGCGCTGG CAACGTCGGC
12241 GGCGTGGAGG AATATGACGA GGACGATGAG TACGAGCCAG AGGACGGCGA GTACTAAGCG
12301 GTGATGTTTC TGATCAGATG ATGCAAGACG CAACGGACCC GGCGGTGCGG GCGGCGCTGC
12361 AGAGCCAGCC GTCCGGCCTT AACTCCACGG ACGACTGGCG CCAGGTCATG GACCGCATCA
12421 TGTCGCTGAC TGCGCGCAAT CCTGACGCGT TCCGGCAGCA GCCGCAGGCC AACCGGCTCT
12481 CCGCAATTCT GGAAGCGGTG GTCCCGGCGC GCGCAAACCC CACGCACGAG AAGGTGCTGG
12541 CGATCGTAAA CGCGCTGGCC GAAAACAGGG CCATCCGGCC CGACGAGGCC GGCCTGGTCT
12601 ACGACGCGCT GCTTCAGCGC GTGGCTCGTT ACAACAGCGG CAACGTGCAG ACCAACCTGG
12661 ACCGGCTGGT GGGGGATGTG CGCGAGGCCG TGGCGCAGCG TGAGCGCGCG CAGCAGCAGG
12721 GCAACCTGGG CTCCATGGTT GCACTAAACG CCTTCCTGAG TACACAGCCC GCCAACGTGC
12781 CGCGGGGACA GGAGGACTAC ACCAACTTTG TGAGCGCACT GCGGCTAATG GTGACTGAGA
12841 CACCGCAAAG TGAGGTGTAC CAGTCTGGGC CAGACTATTT TTTCCAGACC AGTAGACAAG
12901 GCCTGCAGAC CGTAAACCTG AGCCAGGCTT TCAAAAACTT GCAGGGGCTG TGGGGGGTGC
12961 GGGCTCCCAC AGGCGACCGC GCGACCGTGT CTAGCTTGCT GACGCCCAAC TCGCGCCTGT
13021 TGCTGCTGCT AATAGCGCCC TTCACGGACA GTGGCAGCGT GTCCCGGGAC ACATACCTAG
13081 GTCACTTGCT GACACTGTAC CGCGAGGCCA TAGGTCAGGC GCATGTGGAC GAGCATACTT
13141 TCCAGGAGAT TACAAGTGTC AGCCGCGCGC TGGGGCAGGA GGACACGGGC AGCCTGGAGG
```

FIG. 8D

```
13201 CAACCCTAAA CTACCTGCTG ACCAACCGGC GGCAGAAGAT CCCCTCGTTG CACAGTTTAA
13261 ACAGCGAGGA GGAGCGCATT TTGCGCTACG TGCAGCAGAG CGTGAGCCTT AACCTGATGC
13321 GCGACGGGGT AACGCCCAGC GTGGCGCTGG ACATGACCGC GCGCAACATG GAACCGGGCA
13381 TGTATGCCTC AAACCGGCCG TTTATCAACC GCCTAATGGA CTACTTGCAT CGCGCGGCCG
13441 CCGTGAACCC CGAGTATTTC ACCAATGCCA TCTTGAACCC GCACTGGCTA CCGCCCCCTG
13501 GTTTCTACAC CGGGGGATTC GAGGTGCCCG AGGGTAACGA TGGATTCCTC TGGGACGACA
13561 TAGACGACAG CGTGTTTTCC CCGCAACCGC AGACCCTGCT AGAGTTGCAA CAGCGCGAGC
13621 AGGCAGAGGC GGCGCTGCGA AAGGAAAGCT TCCGCAGGCC AAGCAGCTTG TCCGATCTAG
13681 GCGCTGCGGC CCCGCGGTCA GATGCTAGTA GCCCATTTCC AAGCTTGATA GGGTCTCTTA
13741 CCAGCACTCG CACCACCCGC CCGCGCCTGC TGGGCGAGGA GGAGTACCTA AACAACTCGC
13801 TGCTGCAGCC GCAGCGCGAA AAAAACCTGC CTCCGGCATT TCCCAACAAC GGGATAGAGA
13861 GCCTAGTGGA CAAGATGAGT AGATGGAAGA CGTACGCGCA GGAGCACAGG GACGTGCCAG
13921 GCCCGCGCCC GCCCACCCGT CGTCAAAGGC ACGACCGTCA GCGGGGTCTG GTGTGGGAGG
13981 ACGATGACTC GGCAGACGAC AGCAGCGTCC TGGATTTGGG AGGGAGTGGC AACCCGTTTG
14041 CGCACCTTCG CCCCAGGCTG GGGAGAATGT TTTAAAAAAA AAAAAGCATG ATGCAAAATA
14101 AAAAACTCAC CAAGGCCATG GCACCGAGCG TTGGTTTTCT TGTATTCCCC TTAGTATGCG
14161 GCGCGCGGCG ATGTATGAGG AAGGTCCTCC TCCCTCCTAC GAGAGTGTGG TGAGCGCGGC
14221 GCCAGTGGCG GCGGCGCTGG GTTCTCCCTT CGATGCTCCC CTGGACCCGC CGTTTGTGCC
14281 TCCGCGGTAC CTGCGGCCTA CCGGGGGGAG AAACAGCATC CGTTACTCTG AGTTGGCACC
14341 CCTATTCGAC ACCACCCGTG TGTACCTGGT GGACAACAAG TCAACGGATG TGGCATCCCT
14401 GAACTACCAG AACGACCACA GCAACTTTCT GACCACGGTC ATTCAAAACA ATGACTACAG
14461 CCCGGGGGAG GCAAGCACAC AGACCATCAA TCTTGACGAC CGGTCGCACT GGGGCGGCGA
14521 CCTGAAAACC ATCCTGCATA CCAACATGCC AAATGTGAAC GAGTTCATGT TTACCAATAA
14581 GTTTAAGGCG CGGGTGATGG TGTCGCGCTT GCCTACTAAG GACAATCAGG TGGAGCTGAA
14641 ATACGAGTGG GTGGAGTTCA CGCTGCCCGA GGGCAACTAC TCCGAGACCA TGACCATAGA
14701 CCTTATGAAC AACGCGATCG TGGAGCACTA CTTGAAAGTG GGCAGACAGA ACGGGGTTCT
14761 GGAAAGCGAC ATCGGGGTAA AGTTTGACAC CCGCAACTTC AGACTGGGGT TTGACCCCGT
14821 CACTGGTCTT GTCATGCCTG GGGTATATAC AAACGAAGCC TTCCATCCAG ACATCATTTT
14881 GCTGCCAGGA TGCGGGGTGG ACTTCACCCA CAGCCGCCTG AGCAACTTGT TGGGCATCCG
14941 CAAGCGGCAA CCCTTCCAGG AGGGCTTTAG GATCACCTAC GATGATCTGG AGGGTGGTAA
15001 CATTCCCGCA CTGTTGGATG TGGACGCCTA CCAGGCGAGC TTGAAAGATG ACACCGAACA
15061 GGGCGGGGGT GGCGCAGGCG GCAGCAACAG CAGTGGCAGC GGCGCGGAAG AGAACTCCAA
15121 CGCGGCAGCC GCGGCAATGC AGCCGGTGGA GGACATGAAC GATCATGCCA TTCGCGGCGA
15181 CACCTTTGCC ACACGGGCTG AGGAGAAGCG CGCTGAGGCC GAAGCAGCGG CCGAAGCTGC
15241 CGCCCCCGCT GCGCAACCCG AGGTCGAGAA GCCTCAGAAG AAACCGGTGA TCAAACCCCT
15301 GACAGAGGAC AGCAAGAAAC GCAGTTACAA CCTAATAAGC AATGACAGCA CCTTCACCCA
15361 GTACCGCAGC TGGTACCTTG CATACAACTA CGGCGACCCT CAGACCGGAA TCCGCTCATG
15421 GACCCTGCTT TGCACTCCTG ACGTAACCTG CGGCTCGGAG CAGGTCTACT GGTCGTTGCC
15481 AGACATGATG CAAGACCCCG TGACCTTCCG CTCCACGCGC CAGATCAGCA ACTTTCCGGT
15541 GGTGGGCGCC GAGCTGTTGC CCGTGCACTC CAAGAGCTTC TACAACGACC AGGCCGTCTA
15601 CTCCCAACTC ATCCGCCAGT TTACCTCTCT GACCCACGTG TTCAATCGCT TTCCCGAGAA
15661 CCAGATTTTG GCGCGCCCGC CAGCCCCCAC CATCACCACC GTCAGTGAAA ACGTTCCTGC
15721 TCTCACAGAT CACGGGACGC TACCGCTGCG CAACAGCATC GGAGGAGTCC AGCGAGTGAC
15781 CATTACTGAC GCCAGACGCC GCACCTGCCC CTACGTTTAC AAGGCCCTGG GCATAGTCTC
15841 GCCGCGCGTC CTATCGAGCC GCACTTTTTG AGCAAGCATG TCCATCCTTA TATCGCCCAG
15901 CAATAACACA GGCTGGGGCC TGCGCTTCCC AAGCAAGATG TTTGGCGGGG CCAAGAAGCG
15961 CTCCGACCAA CACCCAGTGC GCGTGCGCGG GCACTACCGC GCGCCTGGG GCGCGCACAA
16021 ACGCGGCCGC ACTGGGCGCA CCACCGTCGA TGACGCCATC GACGCGGTGG TGGAGGAGGC
16081 GCGCAACTAC ACGCCCACGC CGCCACCAGT GTCCACAGTG GACGCGGCCA TTCAGACCGT
16141 GGTGCGCGGA GCCCGGCGCT ATGCTAAAAT GAAGAGACGG CGGAGGCGCG TAGCACGTCG
16201 CCACCGCCGC CGACCCGGCA CTGCCGCCCA ACGCGCGGCG GCGGCCCTGC TTAACCGCGC
16261 ACGTCGCACC GGCCGACGGG CGGCCATGCG GGCCGCTCGA AGGCTGGCCG CGGGTATTGT
16321 CACTGTGCCC CCCAGGTCCA GGCGACGAGC GGCCGCCGCA GCAGCCGCGG CCATTAGTGC
16381 TATGACTCAG GGTCGCAGGG CAACGTGTA TTGGGTGCGC GACTCGGTTA GCGGCCTGCG
16441 CGTGCCCGTG CGCACCCGCC CCCCGCGCAA CTAGATTGCA AGAAAAAACT ACTTAGACTC
```

FIG. 8E

```
16501 GTACTGTTGT ATGTATCCAG CGGCGGCGGC GCGCAACGAA GCTATGTCCA AGCGCAAAAT
16561 CAAAGAAGAG ATGCTCCAGG TCATCGCGCC GGAGATCTAT GGCCCCCCGA AGAAGGAAGA
16621 GCAGGATTAC AAGCCCCGAA AGCTAAAGCG GGTCAAAAAG AAAAAGAAAG ATGATGATGA
16681 TGAACTTGAC GACGAGGTGG AACTGCTGCA CGCTACCGCG CCCAGGCGAC GGGTACAGTG
16741 GAAAGGTCGA CGCGTAAAAC GTGTTTTGCG ACCCGGCACC ACCGTAGTCT TTACGCCCGG
16801 TGAGCGCTCC ACCCGCACCT ACAAGCGCGT GTATGATGAG GTGTACGGCG ACGAGGACCT
16861 GCTTGAGCAG GCCAACGAGC GCCTCGGGGA GTTTGCCTAC GGAAAGCGGC ATAAGGACAT
16921 GCTGGCGTTG CCGCTGGACG AGGGCAACCC AACACCTAGC CTAAAGCCCG TAACACTGCA
16981 GCAGGTGCTG CCCGCGCTTG CACCGTCCGA AGAAAAGCGC GGCCTAAAGC GCGAGTCTGG
17041 TGACTTGGCA CCCACCGTGC AGCTGATGGT ACCCAAGCGC CAGCGACTGG AAGATGTCTT
17101 GGAAAAAATG ACCGTGGAAC CTGGGCTGGA GCCCGAGGTC CGCGTGCGGC CAATCAAGCA
17161 GGTGGCGCCG GGACTGGGCG TGCAGACCGT GGACGTTCAG ATACCCACTA CCAGTAGCAC
17221 CAGTATTGCC ACCGCCACAG AGGGCATGGA GACACAAACG TCCCCGGTTG CCTCAGCGGT
17281 GGCGGATGCC GCGGTGCAGG CGGTCGCTGC GGCCGCGTCC AAGACCTCTA CGGAGGTGCA
17341 AACGGACCCG TGGATGTTTC GCGTTTCAGC CCCCCGGCGC CCGCGCGGTT CGAGGAAGTA
17401 CGGCGCCGCC AGCGCGCTAC TGCCCGAATA TGCCCTACAT CCTTCCATTG CGCCTACCCC
17461 CGGCTATCGT GGCTACACCT ACCGCCCCAG AAGACGAGCA ACTACCCGAC GCCGAACCAC
17521 CACTGGAACC CGCCGCCGCC GTCGCCGTCG CCAGCCCGTG CTGGCCCCGA TTTCCGTGCG
17581 CAGGGTGGCT CGCGAAGGAG GCAGGACCCT GGTGCTGCCA ACAGCGCGCT ACCACCCCAG
17641 CATCGTTTAA AAGCCGGTCT TTGTGGTTCT TGCAGATATG GCCCTCACCT GCCGCCTCCG
17701 TTTCCCGGTG CCGGGATTCC GAGGAAGAAT GCACCGTAGG AGGGGCATGG CCGGCCACGG
17761 CCTGACGGGC GGCATGCGTC GTGCGCACCA CCGGCGGCGG CGCGCGTCGC ACCGTCGCAT
17821 GCGCGGCGGT ATCCTGCCCC TCCTTATTCC ACTGATCGCC GCGGCGATTG GCGCCGTGCC
17881 CGGAATTGCA TCCGTGGCCT TGCAGGCGCA GAGACACTGA TTAAAAACAA GTTGCATGTG
17941 GAAAAATCAA AATAAAAAGT CTGGACTCTC ACGCTCGCTT GGTCCTGTAA CTATTTTGTA
18001 GAATGGAAGA CATCAACTTT GCGTCTCTGG CCCCGCGACA CGGCTCGCGC CCGTTCATGG
18061 GAAACTGGCA AGATATCGGC ACCAGCAATA TGAGCGGTGG CGCCTTCAGC TGGGCTCGC
18121 TGTGGAGCGG CATTAAAAAT TTCGGTTCCA CCGTTAAGAA CTATGGCAGC AAGGCCTGGA
18181 ACAGCAGCAC AGGCCAGATG CTGAGGGATA AGTTGAAAGA GCAAAATTTC CAACAAAAGG
18241 TGGTAGATGG CCTGGCCTCT GGCATTAGCG GGGTGGTGGA CCTGGCCAAC CAGGCAGTGC
18301 AAAATAAGAT TAACAGTAAG CTTGATCCCC GCCCTCCCGT AGAGGAGCCT CCACCGGCCG
18361 TGGAGACAGT GTCTCCAGAG GGGCGTGGCG AAAAGCGTCC GCGCCCCGAC AGGGAAGAAA
18421 CTCTGGTGAC GCAAATAGAC GAGCCTCCCT CGTACGAGGA GGCACTAAAG CAAGGCCTGC
18481 CCACCACCCG TCCCATCGCG CCCATGGCTA CCGGAGTGCT GGGCCAGCAC ACACCCGTAA
18541 CGCTGGACCT GCCTCCCCCC GCCGACACCC AGCAGAAACC TGTGCTGCCA GGCCCGACCG
18601 CCGTTGTTGT AACCCGTCCT AGCCGCGCGT CCCTGCGCCG CGCCGCCAGC GGTCCGCGAT
18661 CGTTGCGGCC CGTAGCCAGT GGCAACTGGC AAAGCACACT GAACAGCATC GTGGGTCTGG
18721 GGGTGCAATC CCTGAAGCGC CGACGATGCT TCTGAATAGC TAACGTGTCG TATGTGTGTC
18781 ATGTATGCGT CCATGTCGCC GCCAGAGGAG CTGCTGAGCC GCCGCGCGCC CGCTTTCCAA
18841 GATGGCTACC CCTTCGATGA TGCCGCAGTG GTCTTACATG CACATCTCGG GCCAGGACGC
18901 CTCGGAGTAC CTGAGCCCCG GCTGGTGCA GTTTGCCCGC CCACCGAGA CGTACTTCAG
18961 CCTGAATAAC AAGTTTAGAA ACCCACGGT GGCGCCTACG CACGACGTGA CCACAGACCG
19021 GTCCCAGCGT TTGACGCTGC GGTTCATCCC TGTGGACCGT GAGGATACTG CGTACTCGTA
19081 CAAGGCGCGG TTCACCCTAG CTGTGGGTGA TAACCGTGTG CTGGACATGG CTTCCACGTA
19141 CTTTGACATC CGCGGCGTGC TGGACAGGGG CCCTACTTTT AAGCCCTACT CTGGCACTGC
19201 CTACAACGCC CTGGCTCCCA AGGGTGCCCC AAATCCTTGC GAATGGGATG AAGCTGCTAC
19261 TGCTCTTGAA ATAAACCTAG AAGAAGAGGA CGATGACAAC GAAGACGAAG TAGACGAGCA
19321 AGCTGAGCAG CAAAAAACTC ACGTATTTGG GCAGGCGCCT TATTCTGGTA TAAATATTAC
19381 AAAGGAGGGT ATTCAAATAG GTGTCGAAGG TCAAACACCT AAATATGCCG ATAAAACATT
19441 TCAACCTGAA CCTCAAATAG GAGAATCTCA GTGGTACGAA ACTGAAATTA ATCATGCAGC
19501 TGGGAGAGTC CTTAAAAAGA CTACCCCAAT GAAACCATGT TACGGTTCAT ATGCAAAACC
19561 CACAAATGAA AATGGAGGGC AAGGCATTCT TGTAAAGCAA CAAAATGGAA AGCTAGAAAG
19621 TCAAGTGGAA ATGCAATTTT TCTCAACTAC TGAGGCGACC GCAGGCAATG GTGATAACTT
19681 GACTCCTAAA GTGGTATTGT ACAGTGAAGA TGTAGATATA GAAACCCCAG ACACTCATAT
19741 TTCTTACATG CCCACTATTA AGGAAGGTAA CTCACGAGAA CTAATGGGCC AACAATCTAT
```

FIG. 8F

```
19801 GCCCAACAGG CCTAATTACA TTGCTTTTAG GGACAATTTT ATTGGTCTAA TGTATTACAA
19861 CAGCACGGGT AATATGGGTG TTCTGGCGGG CCAAGCATCG CAGTTGAATG CTGTTGTAGA
19921 TTTGCAAGAC AGAAACACAG AGCTTTCATA CCAGCTTTTG CTTGATTCCA TTGGTGATAG
19981 AACCAGGTAC TTTTCTATGT GGAATCAGGC TGTTGACAGC TATGATCCAG ATGTTAGAAT
20041 TATTGAAAAT CATGGAACTG AAGATGAACT TCCAAATTAC TGCTTTCCAC TGGGAGGTGT
20101 GATTAATACA GAGACTCTTA CCAAGGTAAA ACCTAAAACA GGTCAGGAAA ATGGATGGGA
20161 AAAAGATGCT ACAGAATTTT CAGATAAAAA TGAAATAAGA GTTGGAAATA ATTTTGCCAT
20221 GGAAATCAAT CTAAATGCCA ACCTGTGGAG AAATTTCCTG TACTCCAACA TAGCGCTGTA
20281 TTTGCCCGAC AAGCTAAAGT ACAGTCCTTC CAACGTAAAA ATTTCTGATA ACCCAAACAC
20341 CTACGACTAC ATGAACAAGC GAGTGGTGGC TCCCGGGTTA GTGGACTGCT ACATTAACCT
20401 TGGAGCACGC TGGTCCCTTG ACTATATGGA CAACGTCAAC CCATTTAACC ACCACCGCAA
20461 TGCTGGCCTG CGCTACCGCT CAATGTTGCT GGGCAATGGT CGCTATGTGC CCTTCCACAT
20521 CCAGGTGCCT CAGAAGTTCT TTGCCATTAA AAACCTCCTT CTCCTGCCGG GCTCATACAC
20581 CTACGAGTGG AACTTCAGGA AGGATGTTAA CATGGTTCTG CAGAGCTCCC TAGGAAATGA
20641 CCTAAGGGTT GACGGAGCCA GCATTAAGTT TGATAGCATT TGCCTTTACG CCACCTTCTT
20701 CCCCATGGCC CACAACACCG CCTCCACGCT TGAGGCCATG CTTAGAAACG ACACCAACGA
20761 CCAGTCCTTT AACGACTATC TCTCCGCCGC CAACATGCTC TACCCTATAC CCGCCAACGC
20821 TACCAACGTG CCCATATCCA TCCCCTCCCG CAACTGGGCG GCTTTCCGCG GCTGGGCCTT
20881 CACGCGCCTT AAGACTAAGG AAACCCATCA CTGGGCTCGG GCTACGACC CTTATTACAC
20941 CTACTCTGGC TCTATACCCT ACCTAGATGG AACCTTTTAC CTCAACCACA CCTTTAAGAA
21001 GGTGGCCATT ACCTTTGACT CTTCTGTCAG CTGGCCTGGC AATGACCGCC TGCTTACCCC
21061 CAACGAGTTT GAAATTAAGC GCTCAGTTGA CGGGGAGGGT TACAACGTTG CCCAGTGTAA
21121 CATGACCAAA GACTGGTTCC TGGTACAAAT GCTAGCTAAC TACAACATTG CTACCAGGG
21181 CTTCTATATC CCAGAGAGCT ACAAGGACCG CATGTACTCC TTCTTTAGAA ACTTCCAGCC
21241 CATGAGCCGT CAGGTGGTGG ATGATACTAA ATACAAGGAC TACCAACAGG TGGGCATCCT
21301 ACACCAACAC AACAACTCTG GATTTGTTGG CTACCTTGCC CCCACCATGC GCGAAGGACA
21361 GGCCTACCCT GCTAACTTCC CCTATCCGCT TATAGGCAAG ACCGCAGTTG ACAGCATTAC
21421 CCAGAAAAAG TTTCTTTGCG ATCGCACCCT TTGGCGCATC CCATTCTCCA GTAACTTTAT
21481 GTCCATGGGC GCACTCACAG ACCTGGGCCA AAACCTTCTC TACGCCAACT CCGCCCACGC
21541 GCTAGACATG ACTTTTGAGG TGGATCCCAT GGACGAGCCC ACCCTTCTTT ATGTTTTGTT
21601 TGAAGTCTTT GACGTGGTCC GTGTGCACCG GCCGCACCGC GGCGTCATCG AAACCGTGTA
21661 CCTGCGCACG CCCTTCTCGG CCGGCAACGC CACAACATAA AGAAGCAAGC AACATCAACA
21721 ACAGCTGCCG CCATGGGCTC CAGTGAGCAG GAACTGAAAG CCATTGTCAA AGATCTTGGT
21781 TGTGGGCCAT ATTTTTTGGG CACCTATGAC AAGCGCTTTC CAGGCTTTGT TTCTCCACAC
21841 AAGCTCGCCT GCGCCATAGT CAATACGGCC GGTCGCGAGA CTGGGGGCGT ACACTGGATG
21901 GCCTTTGCCT GGAACCCGCA CTCAAAAACA TGCTACCTCT TTGAGCCCTT TGGCTTTTCT
21961 GACCAGCGAC TCAAGCAGGT TTACCAGTTT GAGTACGAGT CACTCCTGCG CCGTAGCGCC
22021 ATTGCTTCTT CCCCCGACCG CTGTATAACG CTGGAAAAGT CCACCCAAAG CGTACAGGGG
22081 CCCAACTCGG CCGCCTGTGG ACTATTCTGC TGCATGTTTC TCCACGCCTT TGCCAACTGG
22141 CCCCAAACTC CCATGGATCA CAACCCCACC ATGAACCTTA TTACCGGGGT ACCCAACTCC
22201 ATGCTCAACA GTCCCCACGC CTACTTCCGC AGCCACAGTG CGCAGATTAG GAGCGCCACT
22261 TTCCTGGAGC GCCACTCGCC CTACTTCCGC AGCCACAGTG CGCAGATTAG GAGCGCCACT
22321 TCTTTTTGTC ACTTGAAAAA CATGTAAAAA TAATGTACTA GAGACACTTT CAATAAAGGC
22381 AAAATGCTTTT ATTTGTACAC TCTCGGGTGA TTATTTACCC CCACCCTTGC CGTCTGCGCC
22441 GTTTAAAAAT CAAAGGGGTT CTGCCGCGCA TCGCTATGCG CCACTGGCAG GGACACGTTG
22501 CGATACTGGT GTTTAGTGCT CCACTTAAAC TCAGGCACAA CCATCCGCGG CAGCTCGGTG
22561 AAGTTTTCAC TCCACAGGCT GCGCACCATC ACCAACGCGT TTAGCAGGTC GGGCGCCGAT
22621 ATCTTGAAGT CGCAGTTGGG GCCTCCGCCC TGCGCGCGCG AGTTGCGATA CACAGGGTTG
22681 CAGCACTGGA ACACTATCAG CGCCGGGTGG TGCACGCTGG CCAGCACGCT CTTGTCGGAG
22741 ATCAGATCCG CGTCCAGGTC CTCCGCGTTG CTCAGGGCGA ACGGAGTCAA CTTTGGTAGC
22801 TGCCTTCCCA AAAAGGGCGC GTGCCCAGGC TTTGAGTTGC ACTCGCACCG TAGTGGCATC
22861 AAAAGGTGAC CGTGCCCGGT CTGGGCGTTA GGATACAGCG CCTGCATAAA AGCCTTGATC
22921 TGCTTAAAAG CCACCTGAGC CTTTGCGCCT TCAGAGAAGA ACATGCCGCA AGACTTGCCG
22981 GAAAACTGAT GGCCGGACA GGCCGCGTCG TGCACGCAGC ACCTTGCGTC GGTGTTGGAG
23041 ATCTGCACCA CATTTCGGCC CCACCGGTTC TTCACGATCT TGGCCTTGCT AGACTGCTCC
```

FIG. 8G

```
23101 TTCAGCGCGC GCTGCCCGTT TTCGCTCGTC ACATCCATTT CAATCACGTG CTCCTTATTT
23161 ATCATAATGC TTCCGTGTAG ACACTTAAGC TCGCCTTCGA TCTCAGCGCA GCGGTGCAGC
23221 CACAACGCGC AGCCCGTGGG CTCGTGATGC TTGTAGGTCA CCTCTGCAAA CGACTGCAGG
23281 TACGCCTGCA GGAATCGCCC CATCATCGTC ACAAAGGTCT TGTTGCTGGT GAAGGTCAGC
23341 TGCAACCCGC GGTGCTCCTC GTTCAGCCAG GTCTTGCATA CGGCCGCCAG AGCTTCCACT
23401 TGGTCAGGCA GTAGTTTGAA GTTCGCCTTT AGATCGTTAT CCACGTGGTA CTTGTCCATC
23461 AGCGCGCGCG CAGCCTCCAT GCCCTTCTCC CACGCAGACA CGATCGGCAC ACTCAGCGGG
23521 TTCATCACCG TAATTTCACT TTCCGCTTCG CTGGGCTCTT CCTCTTCCTC TTGCGTCCGC
23581 ATACCACGCG CCACTGGGTC GTCTTCATTC AGCCGCCGCA CTGTGCGCTT ACCTCCTTTG
23641 CCATGCTTGA TTAGCACCGG TGGGTTGCTG AAACCCACCA TTTGTAGCGC CACATCTTCT
23701 CTTTCTTCCT CGCTGTCCAC GATTACCTCT GGTGATGGCG GGCGCTCGGG CTTGGGAGAA
23761 GGGCGCTTCT TTTTCTTCTT GGGCGCAATG GCCAAATCCG CCGCCGAGGT CGATGGCCGC
23821 GGGCTGGGTG TGCGCGGCAC CAGCGCGTCT TGTGATGAGT CTTCCTCGTC CTCGGACTCG
23881 ATACGCCGCC TCATCCGCTT TTTTGGGGGC GCCGGGGAG GCGGCGGCGA CGGGGACGGG
23941 GACGACACGT CCTCCATGGT TGGGGGACGT CGCGCCGCAC CGCGTCCGCG CTCGGGGGTG
24001 GTTTCGCGCT GCTCCTCTTC CCGACTGGCC ATTTCCTTCT CCTATAGGCA GAAAAAGATC
24061 ATGGAGTCAG TCGAGAAGAA GGACAGCCTA ACCGCCCCCT CTGAGTTCGC CACCACCGCC
24121 TCCACCGATG CCGCCAACGC GCCTACCACC TTCCCCGTCG AGGCACCCCC GCTTGAGGAG
24181 GAGGAAGTGA TTATCGAGCA GGACCCAGGT TTTGTAAGCG AAGACGACGA GGACCGCTCA
24241 GTACCAACAG AGGATAAAAA GCAAGACCAG GACAACGCAG AGGCAAACGA GGAACAAGTC
24301 GGGCGGGGGG ACGAAAGGCA TGGCGACTAC CTAGATGTGG GAGACGACGT GCTGTTGAAG
24361 CATCTGCAGC GCCAGTGCGC CATTATCTGC GACGCGTTGC AAGAGCGCAG CGATGTGCCC
24421 CTCGCCATAG CGGATGTCAG CCTTGCCTAC GAACGCCACC TATTCTCACC GCGCGTACCC
24481 CCCAAACGCC AAGAAAACGG CACATGCGAG CCCAACCCGC GCCTCAACTT CTACCCCGTA
24541 TTTGCCGTGC CAGAGGTGCT TGCCACCTAT CACATCTTTT TCCAAAACTG CAAGATACCC
24601 CTATCCTGCC GTGCCAACCG CAGCCGAGCG ACAAGCAGC TGGCCTTGCG GCAGGGCGCT
24661 GTCATACCTG ATATCGCCTC GCTCAACGAA GTGCCAAAAA TCTTTGAGGG TCTTGGACGC
24721 GACGAGAAGC GCGCGGCAAA CGCTCTGCAA CAGGAAAACA GCGAAAATGA AAGTCACTCT
24781 GGAGTGTTGG TGGAACTCGA GGGTGACAAC GCGCGCCTAG CCGTACTAAA ACGCAGCATC
24841 GAGGTCACCC ACTTTGCCTA CCCGGCACTT AACCTACCCC CAAGGTCAT GAGCACAGTC
24901 ATGAGTGAGC TGATCGTGCG CCGTGCGCAG CCCCTGGAGA GGGATGCAAA TTTGCAAGAA
24961 CAAACAGAGG AGGGCCTACC CGCAGTTGGC GACGAGCAGC TAGCGCGCTG GCTTCAAACG
25021 CGCGAGCCTG CCGACTTGGA GGAGCGACGC AAACTAATGA TGGCCGCAGT GCTCGTTACC
25081 GTGGAGCTTG AGTGCATGCA GCGGTTCTTT GCTGACCCGG AGATGCAGCG CAAGCTAGAG
25141 GAAACATTGC ACTACACCTT TCGACAGGGC TACGTACGCC AGGCCTGCAA GATCTCCAAC
25201 GTGGAGCTCT GCAACCTGGT CTCCTACCTT GGAATTTTGC ACGAAAACCG CCTTGGGCAA
25261 AACGTGCTTC ATTCCACGCT CAAGGGCGAG GCGCGCCGCG ACTACGTCCG CGACTGCGTT
25321 TACTTATTTC TATGCTACAC CTGGCAGACG GCCATGGGCG TTTGGCAGCA GTGCTTGGAG
25381 GAGTGCAACC TCAAGGAGCT GCAGAAACTG CTAAAGCAAA ACTTGAAGGA CCTATGGACG
25441 GCCTTCAACG AGCGCTCCGT GGCCGCGCAC CTGGCGGACA TCATTTTCCC CGAACGCCTG
25501 CTTAAAACCC TGCAACAGGG TCTGCCAGAC TTCACCAGTC AAAGCATGTT GCAGAACTTT
25561 AGGAACTTTA TCCTAGAGCG CTCAGGAATC TTGCCCGCCA CCTGCTGTGC ACTTCCTAGC
25621 GACTTTGTGC CCATTAAGTA CCGCGAATGC CCTCCGCCGC TTTGGGGCCA CTGCTACCTT
25681 CTGCAGCTAG CCAACTACCT TGCCTACCAC TCTGACATAA TGGAAGACGT GAGCGGTGAC
25741 GGTCTACTGG AGTGTCACTG TCGCTGCAAC CTATGCACCC CGCACCGCTC CCTGGTTTGC
25801 AATTCGCAGC TGCTTAACGA AAGTCAAATT ATCGGTACCT TTGAGCTGCA GGGTCCCTCG
25861 CCTGACGAAA AGTCCGCGGC TCCGGGGTTG AAACTCACTC CGGGGCTGTG GACGTCGGCT
25921 TACCTTCGCA AATTTGTACC TGAGGACTAC CACGCCCACG AGATTAGGTT CTACGAAGAC
25981 CAATCCCGCC CGCCAAATGC GGAGCTTACC GCCTGCGTCA TTACCCAGGG CCACATTCTT
26041 GGCCAATTGC AAGCCATCAA CAAAGCCCGC CAAGAGTTTC TGCTACGAAA GGGACGGGGG
26101 GTTTACTTGG ACCCCCAGTC CGGCGAGGAG CTCAACCCAA TCCCCCCGCC GCCGCAGCCC
26161 TATCAGCAGC AGCCGCGGGC CCTTGCTTCC CAGGATGGCA CCCAAAAAGA AGCTGCAGCT
26221 GCCGCCGCCA CCCACGGACG AGGAGGAATA CTGGGACAGT CAGGCAGAGG AGGTTTTGGA
26281 CGAGGAGGAG GAGGACATGA TGGAAGACTG GAGAGCCTA GACGAGGAAG CTTCCGAGGT
26341 CGAAGAGGTG TCAGACGAAA CACCGTCACC CTCGGTCGCA TTCCCCTCGC CGGCGCCCCA
```

FIG. 8H

```
26401 GAAATCGGCA ACCGGTTCCA GCATGGCTAC AACCTCCGCT CCTCAGGCGC CGCCGGCACT
26461 GCCCGTTCGC CGACCCAACC GTAGATGGGA CACCACTGGA ACCAGGGCCG GTAAGTCCAA
26521 GCAGCCGCCG CCGTTAGCCC AAGAGCAACA ACAGCGCCAA GGCTACCGCT CATGGCGCGG
26581 GCACAAGAAC GCCATAGTTG CTTGCTTGCA AGACTGTGGG GGCAACATCT CCTTCGCCCG
26641 CCGCTTTCTT CTCTACCATC ACGGCGTGGC CTTCCCCCGT AACATCCTGC ATTACTACCG
26701 TCATCTCTAC AGCCCATACT GCACCGGCGG CAGCGGCAGC GGCAGCAACA GCAGCGGCCA
26761 CACAGAAGCA AAGGCGACCG GATAGCAAGA CTCTGACAAA GCCCAAGAAA TCCACAGCGG
26821 CGGCAGCAGC AGGAGGAGGA GCGCTGCGTC TGGCGCCCAA CGAACCCGTA TCGACCCGCG
26881 AGCTTAGAAA CAGGATTTTT CCCACTCTGT ATGCTATATT TCAACAGAGC AGGGGCCAAG
26941 AACAAGAGCT GAAAATAAAA ACAGGTCTC TGCGATCCCT CACCCGCAGC TGCCTGTATC
27001 ACAAAAGCGA AGATCAGCTT CGGCGCACGC TGGAAGACGC GGAGGCTCTC TTCAGTAAAT
27061 ACTGCGCGCT GACTCTTAAG GACTAGTTTC GCGCCCTTTC TCAAATTTAA GCGCGAAAAC
27121 TACGTCATCT CCAGCGGCCA CACCCGGCGC CAGCACCTGT CGTCAGCGCC ATTATGAGCA
27181 AGGAAATTCC CACGCCCTAC ATGTGGAGTT ACCAGCCACA AATGGGACTT GCGGCTGGAG
27241 CTGCCCAAGA CTACTCAACC CGAATAAACT ACATGAGCGC GGGACCCCAC ATGATATCCC
27301 GGGTCAACGG AATCCGCGCC CACCGAAACC GAATTCTCTT GGAACAGGCG GCTATTACCA
27361 CCACACCTCG TAATAACCTT AATCCCCGTA GTTGGCCCGC TGCCCTGGTG TACCAGGAAA
27421 GTCCGCTCC CACCACTGTG GTACTTCCCA GAGACGCCCA GGCCGAAGTT CAGATGACTA
27481 ACTCAGGGGC GCAGCTTGCG GGCGGCTTTC GTCACAGGGT GCGGTCGCCC GGGCAGGGTA
27541 TAACTCACCT GACAATCAGA GGGCGAGGTA TTCAGCTCAA CGACGAGTCG GTGAGCTCCT
27601 CGCTTGGTCT CCGTCCGGAC GGGACATTTC AGATCGGCGG CGCCGGCCGT CCTTCATTCA
27661 CGCCTCGTCA GGCAATCCTA ACTCTGCAGA CCTCGTCCTC TGAGCCGCGC TCTGGAGGCA
27721 TTGGAACTCT GCAATTTATT GAGGAGTTTG TGCCATCGGT CTACTTTAAC CCCTTCTCGG
27781 GACCTCCCGG CCACTATCCG GATCAATTTA TTCCTAACTT TGACGCGGTA AAGGACTCGG
27841 CGGACGGCTA CGACTGAATG TTAAGTGGAG AGGCAGAGCA ACTGCGCCTG AAACACCTGG
27901 TCCACTGTCG CCGCCACAAG TGCTTTGCCC GCGACTCCGG TGAGTTTTGC TACTTTGAAT
27961 TGCCCGAGGA TCATATCGAG GGCCCGGCGC ACGGCGTCCG GCTTACCGCC CAGGGAGAGC
28021 TTGCCCGTAG CCTGATTCGG GAGTTTACCC AGCGCCCCT GCTAGTTGAG CGGGACAGGG
28081 GACCCTGTGT TCTCACTGTG ATTTGCAACT GTCCTAACCT TGGATTACAT CAAGATCTTT
28141 GTTGCCATCT CTGTGCTGAG TATAATAAAT ACAGAAATTA AATATACTG GGGCTCCTAT
28201 CGCCATCCTG TAAACGCCAC CGTCTTCACC CGCCAAGCA AACCAAGGCG AACCTTACCT
28261 GGTACTTTTA ACATCTCTCC CTCTGTGATT TACAACAGTT TCAACCCAGA CGGAGTGAGT
28321 CTACGAGAGA ACCTCTCCGA GCTACGCTAC TCCATCAGAA AAAACACCAC CCTCCTTACC
28381 TGCCGGGAAC GTACGAGTGC GTCACCGGCC GCTGCACCAC ACCTACCGCC TGACCGTAAA
28441 CCAGACTTTT TCCGGACAGA CCTCAATAAC TCTGTTTACC AGAACAGGAG GTGAGCTTAG
28501 AAAACCCTTA GGGTATTAGG CCAAAGGCGC AGCTACTGTG GGGTTTATGA ACAATTCAAG
28561 CAACTCTACG GGCTATTCTA ATTCAGGTTT CTCTAGAATC GGGGTTGGGG TTATTCTCTG
28621 TCTTGTGATT CTCTTTATTC TTATACTAAC GCTTCTCTGC CTAAGGCTCG CCGCCTGCTG
28681 TGTGCACATT TGCATTTATT GTCAGCTTTT TAAACGCTGG GGTCGCCACC CAAGATGATT
28741 AGGTACATAA TCCTAGGTTT ACTCACCCTT GCGTCAGCCC ACGGTACCAC CCAAAAGGTG
28801 GATTTTAAGG AGCCAGCCTG TAATGTTACA TTCGCAGCTG AAGCTAATGA GTGCACCACT
28861 CTTATAAAAT GCACCACAGA ACATGAAAAG CTGCTTATTC GCCACAAAAA CAAAATTGGC
28921 AAGTATGCTG TTTATGCTAT TTGGCAGCCA GGTGACACTA CAGAGTATAA TGTTACAGTT
28981 TTCCAGGGTA AAAGTCATAA AACTTTTATG TATACTTTTC CATTTTATGA AATGTGCGAC
29041 ATTACCATGT ACATGAGCAA ACAGTATAAG TTGTGGCCCC CACAAAATTG TGTGGAAAAC
29101 ACTGGCACTT TCTGCTGCAC TGCTATGCTA ATTACAGTGC TCGCTTTGGT CTGTACCCTA
29161 CTCTATATTA AATACAAAAG CAGACGCAGC TTTATTGAGG AAAAGAAAAT GCCTTAATTT
29221 ACTAAGTTAC AAAGCTAATG TCACCACTAA CTGCTTTACT CGCTGCTTGC AAAACAAATT
29281 CAAAAAGTTA GCATTATAAT TAGAATAGGA TTTAAACCCC CCGGTCATTT CCTGCTCAAT
29341 ACCATTCCCC TGAACAATTG ACTCTATGTG GGATATGCTC CAGCGCTACA ACCTTGAAGT
29401 CAGGCTTCCT GGATGTCAGC ATCTGACTTT GGCCAGCACC TGTCCCGCGG ATTTGTTCCA
29461 GTCCAACTAC AGCGACCCAC CCTAACAGAG ATGACCAACA CAACCAACGC GGCCGCCGCT
29521 ACCGGACTTA CATCTACCAC AAATACACCC CAAGTTTCTG CCTTTGTCAA TAACTGGGAT
29581 AACTTGGGCA TGTGGTGGTT CTCCATAGCG CTTATGTTTG TATGCCTTAT TATTATGTGG
29641 CTCATCTGCT GCCTAAAGCG CAAACGCGCC CGACCACCCA TCTATAGTCC CATCATTGTG
```

FIG. 81

```
29701 CTACACCCAA ACAATGATGG AATCCATAGA TTGGACGGAC TGAAACACAT GTTCTTTTCT
29761 CTTACAGTAT GATTAAATGA GACATGATTC CTCGAGTTTT TATATTACTG ACCCTTGTTG
29821 CGCTTTTTTG TGCGTGCTCC ACATTGGCTG CGGTTTCTCA CATCGAAGTA GACTGCATTC
29881 CAGCCTTCAC AGTCTATTTG CTTTACGGAT TTGTCACCCT CACGCTCATC TGCAGCCTCA
29941 TCACTGTGGT CATCGCCTTT ATCCAGTGCA TTGACTGGGT CTGTGTGCGC TTTGCATATC
30001 TCAGACACCA TCCCCAGTAC AGGGACAGGA CTATAGCTGA GCTTCTTAGA ATTCTTTAAT
30061 TATGAAATTT ACTGTGACTT TTCTGCTGAT TATTTGCACC CTATCTGCGT TTTGTTCCCC
30121 GACCTCCAAG CCTCAAAGAC ATATATCATG CAGATTCACT CGTATATGGA ATATTCCAAG
30181 TTGCTACAAT GAAAAAGCG ATCTTTCCGA AGCCTGGTTA TATGCAATCA TCTCTGTTAT
30241 GGTGTTCTGC AGTACCATCT TAGCCCTAGC TATATATCCC TACCTTGACA TTGGCTGGAA
30301 ACGAATAGAT GCCATGAACC ACCCAACTTT CCCCGCGCCC GCTATGCTTC CACTGCAACA
30361 AGTTGTTGCC GGCGGCTTTG TCCCAGCCAA TCAGCCTCGC CCCACTTCTC CCACCCCCAC
30421 TGAAATCAGC TACTTTAATC TAACAGGAGG AGATGACTGA CACCCTAGAT CTAGAAATGG
30481 ACGGAATTAT TACAGAGCAG CGCCTGCTAG AAAGACGCAG GGCAGCGGCC GAGCAACAGC
30541 GCATGAATCA AGAGCTCCAA GACATGGTTA ACTTGCACCA GTGCAAAAGG GGTATCTTTT
30601 GTCTGGTAAA GCAGGCCAAA GTCACCTACG ACAGTAATAC CACCGGACAC CGCCTTAGCT
30661 ACAAGTTGCC AACCAAGCGT CAGAAATTGG TGGTCATGGT GGGAGAAAAG CCCATTACCA
30721 TAACTCAGCA CTCGGTAGAA ACCGAAGGCT GCATTCACTC ACCTTGTCAA GGACCTGAGG
30781 ATCTCTGCAC CCTTATTAAG ACCCTGTGCG GTCTCAAAGA TCTTATTCCC TTTAACTAAT
30841 AAAAAAAAAT AATAAAGCAT CACTTACTTA AAATCAGTTA GCAAATTTCT GTCCAGTTTA
30901 TTCAGCAGCA CCTCCTTGCC CTCCTCCCAG CTCTGGTATT GCAGCTTCCT CCTGGCTGCA
30961 AACTTTCTCC ACAATCTAAA TGGAATGTCA GTTTCCTCCT GTTCCTGTCC ATCCGCACCC
31021 ACTATCTTCA TGTTGTTGCA GATGAAGCGC GCAAGACCGT CTGAAGATAC CTTCAACCCC
31081 GTGTATCCAT ATGCACGGA AACCGGTCCT CCAACTGTGC CTTTTCTTAC TCCTCCCTTT
31141 GTATCCCCCA ATGGGTTTCA AGAGAGTCCC CCTGGGGTAC TCTCTTTGCG CCTATCCGAA
31201 CCTCTAGTTA CCTCCAATGG CATGCTTGCG CTCAAAATGG GCAACGGCCT CTCTCTGGAC
31261 GAGGCCGGCA ACCTTACCTC CCAAAATGTA ACCACTGTGA GCCCACCTCT CAAAAAAACC
31321 AAGTCAAACA TAAACCTGGA AATATCTGCA CCCCTCACAG TTACCTCAGA AGCCCTAACT
31381 GTGGCTGCCG CCGCACCTCT AATGGTCGCG GGCAACACAC TCACCATGCA ATCACAGGCC
31441 CCGCTAACCG TGCACGACTC CAAACTTAGC ATTGCCACCC AAGGACCCCT CACAGTGTCA
31501 GAAGGAAAGC TAGCCCTGCA AACATCAGGC CCCCTCACCA CCACCGATAG CAGTACCCTT
31561 ACTATCACTG CCTCACCCCC TCTAACTACT GCCACTGGTA GCTTGGGCAT TGACTTGAAA
31621 GAGCCCATTT ATACACAAAA TGGAAAACTA GGACTAAAGT ACGGGCTCC TTTGCATGTA
31681 ACAGACGACC TAAACACTTT GACCGTAGCA ACTGGTCCAG GTGTGACTAT TAATAATACT
31741 TCCTTGCAAA CTAAAGTTAC TGGAGCCTTG GGTTTTGATT CACAAGGCAA TATGCAACTT
31801 AATGTAGCAG GAGGACTAAG GATTGATTCT CAAAACAGAC GCCTTATACT TGATGTTAGT
31861 TATCCGTTTG ATGCTCAAAA CCAACTAAAT CTAAGACTAG GACAGGGCCC TCTTTTTATA
31921 AACTCAGCCC ACAACTTGGA TATTAACTAC AACAAAGGCC TTTACTTGTT TACAGCTTCA
31981 AACAATTCCA AAAAGCTTGA GGTTAACCTA AGCACTGCCA AGGGGTTGAT GTTTGACGCT
32041 ACAGCCATAG CCATTAATGC AGGAGATGGG CTTGAATTTG GTTCACCTAA TGCACCAAAC
32101 ACAAATCCCC TCAAAACAAA AATTGGCCAT GGCCTAGAAT TTGATTCAAA CAAGGCTATG
32161 GTTCCTAAAC TAGGAACTGG CCTTAGTTTT TGACAGCACAG GTGCCATTAC AGTAGGAAAC
32221 AAAAATAATG ATAAGCTAAC TTTGTGGACC ACACCAGCTC CATCTCCTAA CTGTAGACTA
32281 AATGCAGAGA AGATGCTAAC ACTCACTTTG GTCTTAACAA AATGTGGCAG TCAAATACTT
32341 GCTACAGTTT CAGTTTTGGC TGTTAAAGGC AGTTTGGCTC CAATATCTGG AACAGTTCAA
32401 AGTGCTCATC TTATTATAAG ATTTGACGAA AATGGAGTGC TACTAAACAA TTCCTTCCTG
32461 GACCCAGAAT ATTGGAACTT TAGAAATGGA GATCTTACTG AAGGCACAGC CTATACAAAC
32521 GCTGTTGGAT TTATGCCTAA CCTATCAGCT TATCCAAAAT CTCACGGTAA AACTGCCAAA
32581 AGTAACATTG TCAGTCAAGT TTACTTAAAC GGAGACAAAA CTAAACCTGT AACACTAACC
32641 ATTACACTAA ACGGTACACA GGAAACAGGA GACACAACTC CAAGTGCATA CTCTATGTCA
32701 TTTTCATGGG ACTGGTCTGG CCACAACTAC ATTAATGAAA TATTTGCCAC ATCCTCTTAC
32761 ACTTTTTCAT ACATTGCCCA AGAATAAAGA ATCGTTTGTG TTATGTTTCA ACGTGTTTAT
32821 TTTTCAATTG CAGAAAATTT CAAGTCATTT TTCATTCAGT AGTATAGCCC CACCACCACA
32881 TAGCTTATAC AGATCACCGT ACCTTAATCA AACTCACAGA ACCCTAGTAT TCAACCTGCC
32941 ACCTCCCTCC CAACACACAG AGTACACAGT CCTTTCTCCC CGGCTGGCCT TAAAAAGCAT
```

FIG. 8J

```
33001 CATATCATGG GTAACAGACA TATTCTTAGG TGTTATATTC CACACGGTTT CCTGTCGAGC
33061 CAAACGCTCA TCAGTGATAT TAATAAACTC CCCGGGCAGC TCACTTAAGT TCATGTCGCT
33121 GTCCAGCTGC TGAGCCACAG GCTGCTGTCC AACTTGCGGT TGCTTAACGG GCGGCGAAGG
33181 AGAAGTCCAC GCCTACATGG GGGTAGAGTC ATAATCGTGC ATCAGGATAG GGCGGTGGTG
33241 CTGCAGCAGC GCGCGAATAA ACTGCTGCCG CCGCCGCTCC GTCCTGCAGG AATACAACAT
33301 GGCAGTGGTC TCCTCAGCGA TGATTCGCAC CGCCCGCAGC ATAAGGCGCC TTGTCCTCCG
33361 GGCACAGCAG CGCACCCTGA TCTCACTTAA ATCAGCACAG TAACTGCAGC ACAGCACCAC
33421 AATATTGTTC AAAATCCCAC AGTGCAAGGC GCTGTATCCA AAGCTCATGG CGGGGACCAC
33481 AGAACCCACG TGGCCATCAT ACCACAAGCG CAGGTAGATT AAGTGGCGAC CCCTCATAAA
33541 CACGCTGGAC ATAAACATTA CCTCTTTTGG CATGTTGTAA TTCACCACCT CCCGGTACCA
33601 TATAAACCTC TGATTAAACA TGGCGCCATC CACCACCATC CTAAACCAGC TGGCCAAAAC
33661 CTGCCCGCCG GCTATACACT GCAGGGAACC GGGACTGGAA CAATGACAGT GGAGAGCCCA
33721 GGACTCGTAA CCATGGATCA TCATGCTCGT CATGATATCA ATGTTGGCAC AACACAGGCA
33781 CACGTGCATA CACTTCCTCA GGATTACAAG CTCCTCCCGC GTTAGAACCA TATCCCAGGG
33841 AACAACCCAT TCCTGAATCA GCGTAAATCC CACACTGCAG GGAAGACCTC GCACGTAACT
33901 CACGTTGTGC ATTGTCAAAG TGTTACATTC GGGCAGCAGC GGATGATCCT CCAGTATGGT
33961 AGCGCGGGTT TCTGTCTCAA AAGGAGGTAG ACGATCCCTA CTGTACGGAG TGCGCCGAGA
34021 CAACCGAGAT CGTGTTGGTC GTAGTGTCAT GCCAAATGGA ACGCCGGACG TAGTCATATT
34081 TCCTGAAGCA AAACCAGGTG CGGGCGTGAC AAACAGATCT GCGTCTCCGG TCTCGCCGCT
34141 TAGATCGCTC TGTGTAGTAG TTGTAGTATA TCCACTCTCT CAAAGCATCC AGGCGCCCCC
34201 TGGCTTCGGG TTCTATGTAA ACTCCTTCAT GCGCCGCTGC CCTGATAACA TCCACCACCG
34261 CAGAATAAGC CACACCCAGC CAACCTACAC ATTCGTTCTG CGAGTCACAC ACGGGAGGAG
34321 CGGGAAGAGC TGGAAGAACC ATGTTTTTTT TTTTATTCCA AAAGATTATC CAAAACCTCA
34381 AAATGAAGAT CTATTAAGTG AACGCGCTCC CCTCCGGTGG CGTGGTCAAA CTCTACAGCC
34441 AAAGAACAGA TAATGGCATT TGTAAGATGT TGCACAATGG CTTCCAAAAG GCAAACGGCC
34501 CTCACGTCCA AGTGGACGTA AAGGCTAAAC CCTTCAGGGT GAATCTCCTC TATAAACATT
34561 CCAGCACCTT CAACCATGCC CAAATAATTC TCATCTCGCC ACCTTCTCAA TATATCTCTA
34621 AGCAAATCCC GAATATTAAG TCCGGCCATT GTAAAAATCT GCTCCAGAGC GCCCTCCACC
34681 TTCAGCCTCA AGCAGCGAAT CATGATTCCA AAAATTCAGG TTCCTCACAG ACCTGTATAA
34741 GATTCAAAAG CGGAACATTA ACAAAATAC CGCGATCCCC TAGGTCCCTT CGCAGGGCCA
34801 GCTGAACATA ATCGTGCAGG TCTGCACGGA CCAGCGCGGC CACTTCCCCG CCAGGAACCT
34861 TGACAAAAGA ACCCACACTG ATTATGACAC GCATACTCGG AGCTATGCTA ACCAGCGTAG
34921 CCCCGATGTA AGCTTTGTTG CATGGGCGGC GATATAAAAT GCAAGGTGCT GCTCAAAAAA
34981 TCAGGCAAAG CCTCGCGCAA AAAAGAAAGC ACATCGTAGT CATGCTCATG CAGATAAAGG
35041 CAGGTAAGCT CCGGAACCAC CACAGAAAAA GACACCATTT TTCTCTCAAA CATGTCTGCG
35101 GGTTTCTGCA TAAACACAAA ATAAATAAC AAAAAAACAT TTAAACATTA GAAGCCTGTC
35161 TTACAACAGG AAAAACAACC CTTATAAGCA TAAGACGGAC TACGGCCATG CCGGCGTGAC
35221 CGTAAAAAAA CTGGTCACCG TGATTAAAAA GCACCACCGA CAGCTCCTCG GTCATGTCCG
35281 GAGTCATAAT GTAAGACTCG GTAAACACAT CAGGTTGATT CATCGGTCAG TGCTAAAAAG
35341 CGACCGAAAT AGCCCGGGGG AATACATACC CGCAGGCGTA GAGACAACAT TACAGCCCCC
35401 ATAGGAGGTA TAACAAAATT AATAGGAGAG AAAACACAT AAACACCTGA AAAACCCTCC
35461 TGCCTAGGCA AAATAGCACC CTCCCGCTCC AGAACAACAT ACAGCGCTTC ACAGCGGCAG
35521 CCTAACAGTC AGCCTTACCA GTAAAAAGA AAACCTATTA AAAAACACC ACTCGACACG
35581 GCACCAGCTC AATCAGTCAC AGTGTAAAAA AGGGCAAGT GCAGAGCGAG TATATATAGG
35641 ACTAAAAAAT GACGTAACGG TTAAAGTCCA CAAAAACAC CCAGAAAACC GCACGCGAAC
35701 CTACGCCCAG AAACGAAAGC CAAAAAACCC ACAACTTCCT CAAATCGTCA CTTCCGTTTT
35761 CCCACGTTAC GTAACTTCCC ATTTTAAGAA AACTACAATT CCCAACACAT ACAAGTTACT
35821 CCGCCCTAAA ACCTACGTCA CCCGCCCCGT TCCCACGCCC CGCGCCACGT CACAAACTCC
35881 ACCCCCTCAT TATCATATTG GCTTCAATCC AAAATAAGGT ATATTATTGA TGATG
```

FIG. 8K

Western blot on whole-cell extracts from 293 cells transfected with plasmid DNA expressing the different HCV NS cassettes. Mature NS3 and NS5A products were detected with specific antibodies.

|  | | Pep pool | | | | | | | |
|---|---|---|---|---|---|---|---|---|---|
|  | mouse | F(NS3p) | G(NS3h) | H(NS4) | I(NS5a) | L(NS35b) | M(NS5b) | 1480(CD8 ep) | DMSO |
|  | #31 | 41 | 135 | 19 | 44 | 25 | 17 | 137 | 8 |
|  | #32 | 121 | 783 | 77 | 144 | 13 | 22 | 604 | 4 |
|  | #33 | 8 | 32 | 3 | 11 | 6 | 6 | 43 | 3 |
|  | #34 | 16 | 139 | 13 | 47 | 31 | 25 | 151 | 2 |
| pV1jns-NS | #35 | 21 | 101 | 40 | 32 | 21 | 20 | 75 | 1 |
|  | #36 | 18 | 26 | 24 | 25 | 5 | 7 | 29 | 6 |
|  | #37 | 19 | 73 | 15 | 39 | 8 | 20 | 49 | 2 |
|  | #38 | 133 | 575 | 74 | 345 | 75 | 63 | 515 | 5 |
|  | #39 | 40 | 183 | 10 | 85 | 14 | 9 | 148 | 2 |
|  | #40 | 66 | 465 | 29 | 111 | 15 | 16 | 189 | 0 |
|  | Geomean | 33 | 146 | 21 | 57 | 15 | 16 | 123 | na |

|  | | Pep pool | | | | | | | |
|---|---|---|---|---|---|---|---|---|---|
|  | mouse | F(NS3p) | G(NS3h) | H(NS4) | I(NS5a) | L(NS35b) | M(NS5b) | 1480(CD8 ep) | DMSO |
|  | #41 | 39 | 293 | 58 | 187 | 5 | 4 | 248 | 1 |
|  | #42 | 21 | 220 | 46 | 107 | 26 | 10 | 189 | 4 |
|  | #43 | 76 | 134 | 12 | 78 | 8 | 6 | 144 | 2 |
|  | #44 | 30 | 45 | 20 | 52 | 4 | 8 | 40 | 4 |
| pV1jns-NSmut | #45 | 36 | 100 | 17 | 56 | 4 | 6 | 116 | 3 |
|  | #46 | 67 | 172 | 16 | 138 | 8 | 9 | 145 | 3 |
|  | #47 | 34 | 131 | 28 | 38 | 9 | 5 | 118 | 1 |
|  | #48 | 55 | 316 | 43 | 107 | 9 | 7 | 277 | 5 |
|  | #49 | 6 | 131 | 5 | 25 | 4 | 1 | 91 | 0 |
|  | #50 | 13 | 93 | 11 | 11 | 5 | 1 | 76 | 1 |
|  | Geomean | 30 | 142 | 20 | 61 | 7 | 5 | 126 | na |

|  | | Pep pool | | | | | | | |
|---|---|---|---|---|---|---|---|---|---|
|  | mouse | F(NS3p) | G(NS3h) | H(NS4) | I(NS5a) | L(NS35b) | M(NS5b) | 1480(CD8 ep) | DMSO |
|  | #51 | 53 | 409 | 34 | 84 | 11 | 25 | 271 | 4 |
|  | #52 | 140 | 660 | 65 | 276 | 23 | 36 | 377 | 2 |
|  | #53 | 58 | 553 | 48 | 105 | 23 | 18 | 564 | 1 |
|  | #54 | 50 | 105 | 35 | 134 | 10 | 16 | 80 | 2 |
| pV1jns-NSOPTmut | #55 | 14 | 80 | 11 | 35 | 4 | 7 | 91 | 6 |
|  | #56 | 14 | 342 | 30 | 101 | 23 | 14 | 207 | 1 |
|  | #57 | 63 | 325 | 66 | 239 | 17 | 24 | 123 | 1 |
|  | #58 | 75 | 542 | 66 | 168 | 127 | 93 | 191 | 0 |
|  | #59 | 65 | 468 | 40 | 124 | 18 | 23 | 344 | 4 |
|  | #60 | 27 | 142 | 48 | 16 | 7 | 8 | 77 | 0 |
|  | Geomean | 45 | 295 | 40 | 99 | 16 | 20 | 188 | na |

IFNγ ELIspot on splenocytes from C57black6 mice immunized with two injections of 25μg DNA/dose with GET of plasmid vectors expressing the different HCV NS cassettes. Data are expressed as SFC/10$^6$ PBMC.

FIG. 13A

|  | | Pep pool | | | | | | |
|---|---|---|---|---|---|---|---|---|
|  | mouse | F(NS3p) | G(NS3h) | H(NS4) | I(NS5a) | L(NS35b) | M(NS5b) | DMSO |
| pV1jns-NS | #51 | 219 | 699 | 634 | 486 | 487 | 264 | 34 |
|  | #52 | 67 | 302 | 347 | 167 | 111 | 87 | 9 |
|  | #53 | 59 | 460 | 400 | 246 | 244 | 136 | 26 |
|  | #54 | 139 | 817 | 685 | 236 | 547 | 223 | 24 |
|  | #55 | 96 | 904 | 542 | 277 | 256 | 337 | 17 |
|  | #56 | 225 | 603 | 686 | 156 | 350 | 240 | 56 |
|  | #57 | 44 | 288 | 211 | 148 | 100 | 141 | 4 |
|  | #58 | 37 | 262 | 221 | 53 | 58 | 62 | 3 |
|  | #59 | 131 | 975 | 928 | 159 | 305 | 284 | 14 |
|  | #60 | 93 | 475 | 464 | 77 | 206 | 113 | 12 |
|  | geo mean | 111 | 579 | 512 | 201 | 266 | 189 | 20 |

|  | | Pep pool | | | | | | |
|---|---|---|---|---|---|---|---|---|
|  | mouse | F(NS3p) | G(NS3h) | H(NS4) | I(NS5a) | L(NS35b) | M(NS5b) | DMSO |
| pV1jns-NSmut | #61 | 72 | 840 | 515 | 219 | 278 | 249 | 19 |
|  | #62 | 294 | 1881 | 1266 | 365 | 434 | 411 | 63 |
|  | #63 | 73 | 415 | 422 | 103 | 141 | 99 | 41 |
|  | #64 | 66 | 824 | 486 | 175 | 162 | 144 | 18 |
|  | #66 | 24 | 313 | 168 | 53 | 47 | 42 | 5 |
|  | #67 | 15 | 230 | 253 | 94 | 25 | 39 | 2 |
|  | #68 | 53 | 354 | 252 | 89 | 101 | 86 | 15 |
|  | #69 | 271 | 895 | 909 | 518 | 322 | 285 | 74 |
|  | #70 | 417 | 1303 | 1186 | 468 | 557 | 267 | 34 |
|  | geo mean | 143 | 784 | 606 | 232 | 230 | 180 | 30 |

|  | | Pep pool | | | | | | |
|---|---|---|---|---|---|---|---|---|
|  | mouse | F(NS3p) | G(NS3h) | H(NS4) | I(NS5a) | L(NS35b) | M(NS5b) | DMSO |
| pV1jns-NSOPTmut | #71 | 206 | 944 | 890 | 342 | 207 | 397 | 47 |
|  | #72 | 393 | 1655 | 1151 | 575 | 626 | 401 | 72 |
|  | #73 | 123 | 522 | 515 | 319 | 223 | 198 | 21 |
|  | #74 | 500 | 1414 | 1419 | 878 | 1035 | 1122 | 137 |
|  | #75 | 286 | 812 | 873 | 382 | 543 | 267 | 31 |
|  | #76 | 224 | 1143 | 942 | 218 | 420 | 281 | 22 |
|  | #77 | 95 | 643 | 630 | 169 | 385 | 218 | 15 |
|  | #78 | 401 | 1302 | 1068 | 538 | 608 | 623 | 12 |
|  | #79 | 108 | 1190 | 914 | 199 | 265 | 215 | 4 |
|  | #80 | 122 | 511 | 546 | 189 | 286 | 190 | 13 |
|  | geo mean | 209 | 941 | 854 | 331 | 406 | 329 | 24 |

IFNγ ELIspot on splenocytes from BalbC mice immunized with two injections of 50μg DNA/dose with GET of plasmid vectors expressing the different HCV NS cassettes. Data are expressed as SFC/$10^6$ PBMC.

FIG. 13B

Western blot on whole-cell extracts from HeLa cells infected at different multiplicity of infection (m.o.i.; indicated at the top) with Adenovectors expressing the different HCV NS cassettes. Mature NS5B and NS5A products were detected with specific antibodies.

|  | mouse | Pep pool | | | | | | |
|---|---|---|---|---|---|---|---|---|
|  |  | F(NS3p) | G(NS3h) | H(NS4) | I(NS5a) | L+M(NS35b) | 1480(CD8 ep) | DMSO |
| Ad5-NS | #1 | 14 | 492 | 9 | 27 | 10 | 554 | 7 |
|  | #2 | 8 | 440 | 2 | 26 | 5 | 438 | 0 |
|  | #3 | 12 | 92 | 5 | 12 | 7 | 73 | 4 |
|  | #4 | 16 | 388 | 6 | 40 | 6 | 228 | 2 |
|  | #6 | 8 | 210 | 4 | 31 | 3 | 238 | 3 |
|  | #7 | 7 | 133 | 13 | 16 | 0 | 128 | 9 |
|  | #8 | 11 | 342 | 25 | 55 | 22 | 267 | 12 |
|  | #9 | 5 | 345 | 0 | 45 | 5 | 285 | 3 |
|  | #10 | 22 | 888 | 3 | 65 | 25 | 799 | 1 |
|  | Geomean | 10 | 305 | na | 31 | na | 269 | na |

|  | mouse | Pep pool | | | | | | |
|---|---|---|---|---|---|---|---|---|
|  |  | F(NS3p) | G(NS3h) | H(NS4) | I(NS5a) | L+M(NS35b) | 1480(CD8 ep) | DMSO |
| MRKAd5-NSmut | #11 | 14 | 1009 | 13 | 75 | 7 | 751 | 6 |
|  | #12 | 15 | 695 | 3 | 39 | 9 | 552 | 1 |
|  | #13 | 12 | 389 | 4 | 20 | 7 | 352 | 3 |
|  | #14 | 7 | 459 | 6 | 50 | 1 | 274 | 1 |
|  | #15 | 5 | 549 | 3 | 22 | 6 | 485 | 0 |
|  | #16 | 10 | 631 | 1 | 6 | 4 | 600 | 3 |
|  | #17 | 5 | 257 | 3 | 9 | 1 | 245 | 3 |
|  | #18 | 13 | 659 | 6 | 43 | 7 | 555 | 1 |
|  | #19 | 12 | 758 | 1 | 37 | 5 | 669 | 0 |
|  | #20 | 22 | 1380 | 5 | 163 | 8 | 1003 | 4 |
|  | Geomean | 10 | 615 | 3 | 31 | 4 | 504 | na |

|  | mouse | Pep pool | | | | | | |
|---|---|---|---|---|---|---|---|---|
|  |  | F(NS3p) | G(NS3h) | H(NS4) | I(NS5a) | L+M(NS35b) | 1480(CD8 ep) | DMSO |
| MRKAd6-NSmut | #21 | 6 | 584 | 5 | 27 | 4 | 491 | 2 |
|  | #22 | 6 | 231 | 3 | 12 | 3 | 235 | 0 |
|  | #23 | 8 | 482 | 1 | 18 | 1 | 511 | 0 |
|  | #24 | 14 | 1120 | 6 | 38 | 10 | 1004 | 5 |
|  | #25 | 1 | 311 | 3 | 9 | 0 | 382 | 1 |
|  | #26 | 29 | 903 | 3 | 60 | 5 | 751 | 5 |
|  | #27 | 35 | 1573 | 4 | 40 | 4 | 1277 | 4 |
|  | #28 | 7 | 406 | 5 | 15 | 1 | 443 | 3 |
|  | #29 | 4 | 461 | 3 | 12 | 3 | 515 | 3 |
|  | Geomean | 8 | 567 | 3 | 21 | na | 554 | na |

IFNγ ELISPOT on splenocytes from C57black6 mice immunized with two injections of $10^9$ vp/dose of Adenovectors expressing the different HCV NS cassettes. Data are expressed as SFC/$10^6$ PBMC.

FIG. 15

| Pep pools | Ad5-NS $10^{10}$ vp/dose | | |
|---|---|---|---|
| | 96074 | 134T | 063Q |
| F (NS3p) | 374 | 11 | 74 |
| G (NS3h) | 359 | 1070 | 1455 |
| H (NS4) | 376 | 30 | 64 |
| I (NS5a) | 240 | 40 | 63 |
| L (NS5b) | 226 | 29 | 121 |
| M (NS5b) | 511 | 23 | 35 |
| DMSO | 128 | 3 | 31 |

| Pep pools | MRK Ad6-NSmut $10^{10}$ vp/dose | | |
|---|---|---|---|
| | S207 | 035Q | 057Q |
| F (NS3p) | 363 | 382 | 150 |
| G (NS3h) | 180 | 316 | 119 |
| H (NS4) | 126 | 113 | 62 |
| I (NS5a) | 1780 | 688 | 114 |
| L (NS5b) | 447 | 111 | 81 |
| M (NS5b) | 153 | 38 | 16 |
| DMSO | 9 | 6 | 9 |

IFNγ ELISPOT on PBMC from Rhesus monkeys immunized with one injection of $10^{10}$ vp/dose of Adenovectors expressing the different HCV NS cassettes. Data are expressed as SFC/$10^6$ PBMC.

FIG. 16A

| Pep pools | MRK Ad5-NSmut $10^{10}$ vp/dose | | |
|---|---|---|---|
| | S201 | 075Q | 137Q |
| F (NS3p) | 928 | 69 | 254 |
| G (NS3h) | 317 | 436 | 98 |
| H (NS4) | 56 | 101 | 45 |
| I (NS5a) | 1530 | 1100 | 413 |
| L (NS5b) | 149 | 23 | 92 |
| M (NS5b) | 398 | 32 | 80 |
| DMSO | 29 | 6 | 29 |

| Pep pools | MRK Ad6-NSOPTmut $10^{10}$ vp/dose | | |
|---|---|---|---|
| | 98D209 | 106Q | 113Q |
| F (NS3p) | 3110 | 263 | 404 |
| G (NS3h) | 2115 | 642 | 1008 |
| H (NS4) | 373 | 72 | 19 |
| I (NS5a) | 103 | 37 | 347 |
| L (NS5b) | 149 | 22 | 10 |
| M (NS5b) | 314 | 428 | 19 |
| DMSO | 0 | 1 | 3 |

IFNγ ELISPOT on PBMC from Rhesus monkeys immunized with one injection of $10^{10}$ vp/dose of Adenovectors expressing the different HCV NS cassettes. Data are expressed as SFC/$10^6$ PBMC.

FIG. 16B

| | Ad5-NS $10^{11}$ vp/dose | | | |
|---|---|---|---|---|
| Pep pools | 99C008 | 97N104 | 97X008 | 99C026 |
| F (NS3p) | 28 | 1026 | 579 | 889 |
| G (NS3h) | 1279 | 188 | 103 | 2453 |
| H (NS4) | 18 | 39 | 138 | 109 |
| I (NS5a) | 131 | 1068 | 172 | 141 |
| L (NS5b) | 78 | 144 | 103 | 32 |
| M (NS5b) | 24 | 68 | 47 | 84 |
| DMSO | 3 | 16 | 1 | 19 |

| | MRKAd6-NSmut $10^{11}$ vp/dose | | | |
|---|---|---|---|---|
| Pep pools | 98C047 | 97C055 | 93G | 97X014 |
| F (NS3p) | 477 | 25 | 93 | 1022 |
| G (NS3h) | 959 | 398 | 81 | 1513 |
| H (NS4) | 36 | 14 | 99 | 53 |
| I (NS5a) | 171 | 45 | 1237 | 98 |
| L (NS5b) | 18 | 32 | 23 | 51 |
| M (NS5b) | 88 | 4 | 13 | 40 |
| DMSO | 8 | 3 | 1 | 5 |

IFNγ ELISPOT on PBMC from Rhesus monkeys immunized with two injections of $10^{11}$ vp/dose of Adenovectors expressing the different HCV NS cassettes. Data are expressed as SFC/$10^6$ PBMC.

FIG. 16C

| Pep pools | MRKAd5-NSmut 10$^{11}$ vp/dose | | | |
|---|---|---|---|---|
| | 99C059 | 99C060 | 97X009 | 96069 |
| F (NS3p) | 28 | 81 | 1308 | 1618 |
| G (NS3h) | 2600 | 161 | 1008 | 123 |
| H (NS4) | 31 | 74 | 101 | 40 |
| I (NS5a) | 181 | 99 | 69 | 96 |
| L (NS5b) | 24 | 31 | 40 | 20 |
| M (NS5b) | 11 | 58 | 38 | 164 |
| DMSO | 6 | 15 | 1 | 16 |

IFNγ ELISPOT on PBMC from Rhesus monkeys immunized with two injections of 10$^{11}$ vp/dose of Adenovectors expressing the different HCV NS cassettes. Data are expressed as SFC/10$^6$ PBMC.

FIG. 16D

| Pep pools | MRK Ad5-NSmut 10$^{10}$ vp/dose | | |
|---|---|---|---|
| | S201 | 075Q | 137Q |
| pool F (NS3p) | 881 | 1755 | 73 |
| pool G (NS3h) | 573 | | |
| pool H (NS4) | | 3541 | |
| pool I (NS5a) | 2094 | | 39 |
| pool L (NS5b) | | | |
| pool M (NS5b) | 756 | | |
| DMSO | 319 | 117 | 44 |

| Pep pools | MRK Ad6-NSOPTmut 10$^{10}$ vp/dose | | |
|---|---|---|---|
| | 98D209 | 106Q | 113Q |
| pool F (NS3p) | 5073 | 84 | 952 |
| pool G (NS3h) | 2376 | 160 | 3325 |
| pool H (NS4) | 700 | | |
| pool I (NS5a) | | | 1106 |
| pool L (NS5b) | | | |
| pool M (NS5b) | 530 | 706 | |
| DMSO | 43 | 47 | 28 |

| Pep pools | MRK Ad6-NSmut 10$^{10}$ vp/dose | | |
|---|---|---|---|
| | S207 | 035Q | 057Q |
| pool F (NS3p) | 118 | 480 | |
| pool G (NS3h) | | 196 | |
| pool H (NS4) | | | |
| pool I (NS5a) | 3340 | 933 | |
| pool L (NS5b) | 118 | | |
| pool M (NS5b) | | | |
| DMSO | 145 | 34 | |

IFNγ ICS on PBMC from Rhesus monkeys immunized with two injections at four weeks interval with 10$^{10}$ vp/dose of Adenovectors expressing the different HCV NS cassettes. Data are expressed as number of positive IFNγ/CD3/CD8 per 10$^6$ lymphocytes.

FIG. 17A

| Pep pools | Ad5-NS 10$^{11}$ vp/dose | | | |
|---|---|---|---|---|
| | 99C008 | 97N104 | 97X008 | 99C026 |
| F (NS3p) | | 1703 | 1136 | 615 |
| G (NS3h) | 3153 | | | 2787 |
| H (NS4) | | | | |
| I (NS5a) | | 2233 | | |
| L (NS5b) | | | | |
| M (NS5b) | | | | |
| DMSO | 125 | 98 | 130 | 0 |

| Pep pools | MRKAd6-NSmut 10$^{11}$ vp/dose | | | |
|---|---|---|---|---|
| | 98C047 | 97C055 | 93G | 97X014 |
| F (NS3p) | 1024 | | | 948 |
| G (NS3h) | 3246 | 353 | | 1074 |
| H (NS4) | | | 316 | |
| I (NS5a) | | | 6224 | |
| L (NS5b) | | | | |
| M (NS5b) | | | | |
| DMSO | 49 | 23 | 37 | 93 |

| Pep pools | MRKAd5-NSmut 10$^{11}$ vp/dose | | | |
|---|---|---|---|---|
| | 99C059 | 99C060 | 97X009 | 96069 |
| F (NS3p) | | | 2266 | 5053 |
| G (NS3h) | 2434 | 316 | 1018 | |
| H (NS4) | | | | |
| I (NS5a) | | | | |
| L (NS5b) | | | | |
| M (NS5b) | | | | 205 |
| DMSO | 13 | 110 | 119 | 15 |

IFNγ ICS on PBMC from Rhesus monkeys immunized with two injections at four weeks interval with 10$^{11}$ vp/dose of Adenovectors expressing the different HCV NS cassettes. Data are expressed as number of positive IFNγ/CD3/CD8 per 10$^6$ lymphocytes.

FIG. 17B

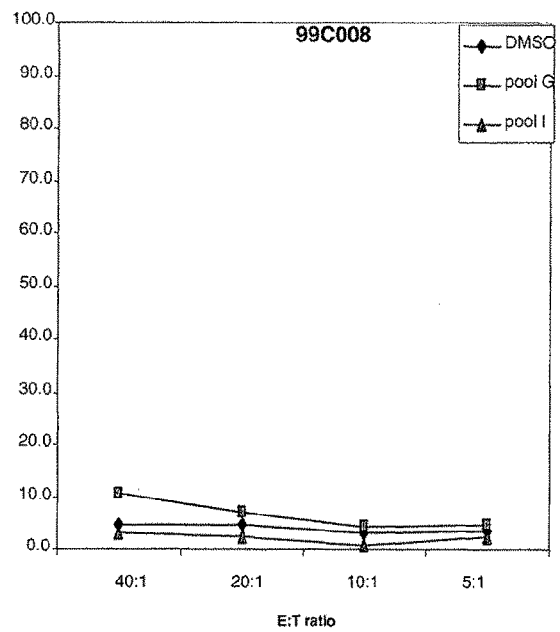
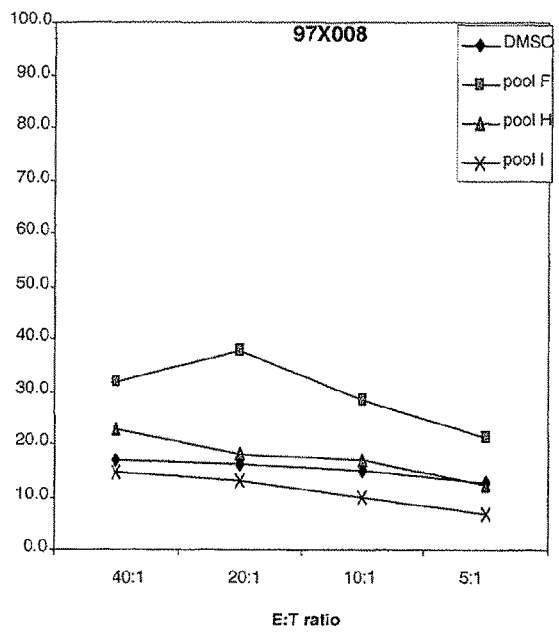
Bulk CTL assays on PBMC from Rhesus monkeys immunized with two injections of $10^{11}$vp/dose of Ad5-NS.
FIG. 18A

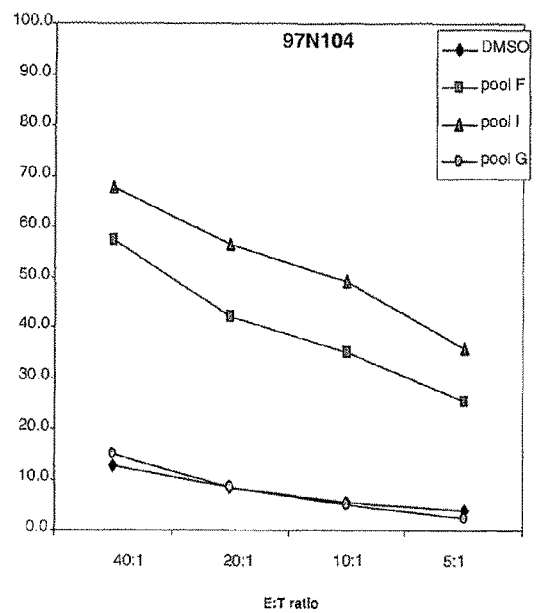
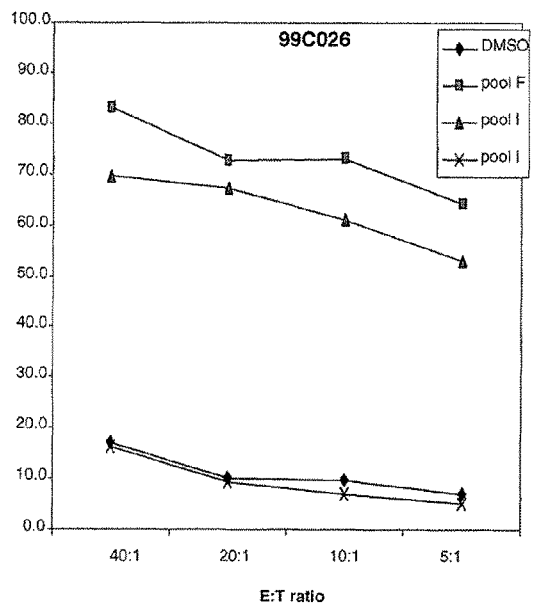
Bulk CTL assays on PBMC from Rhesus monkeys immunized with two injections of $10^{11}$ vp/dose of Ad5-NS.
FIG. 18B

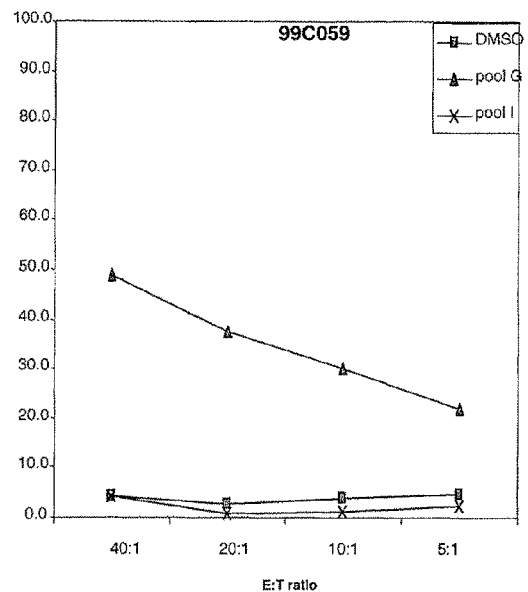
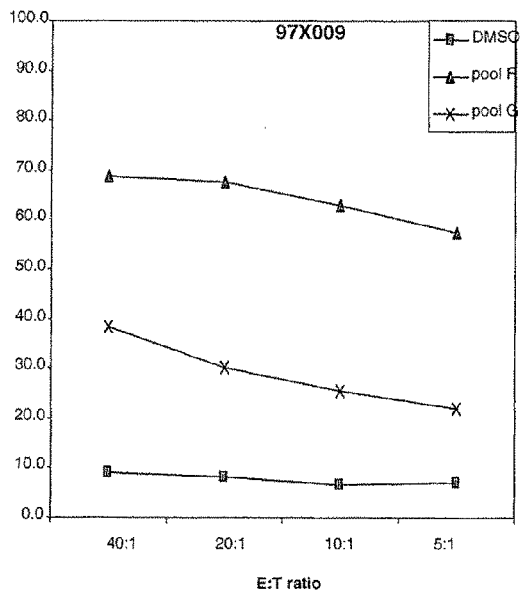
Bulk CTL assays on PBMC from Rhesus monkeys immunized with two injections of $10^{11}$ vp/dose of MRKAd5-NSmut.
FIG. 18C

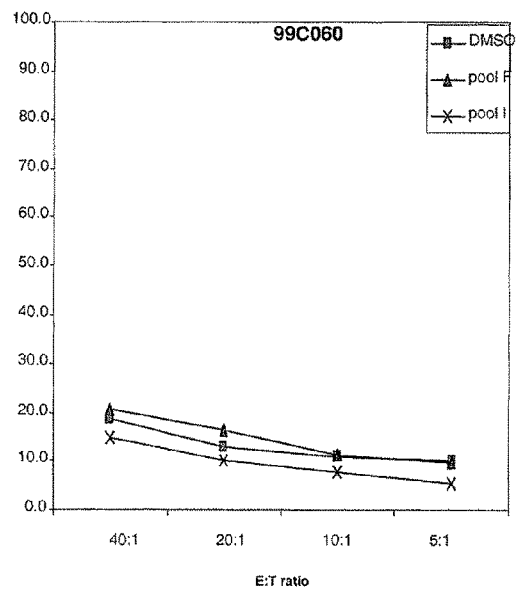
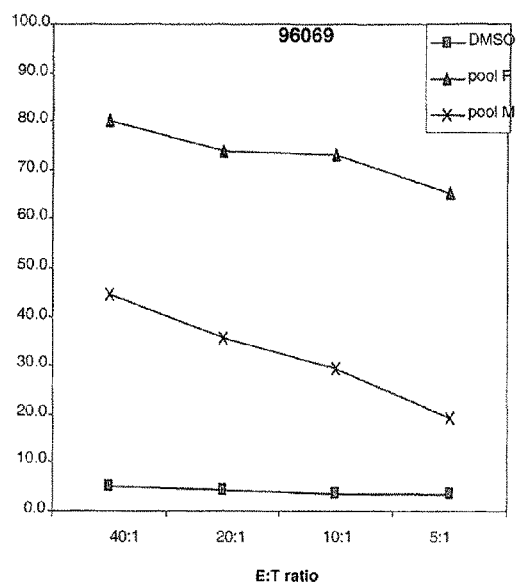
Bulk CTL assays on PBMC from Rhesus monkeys immunized with two injections of $10^{11}$ vp/dose of MRKAd5-NSmut
FIG. 18D

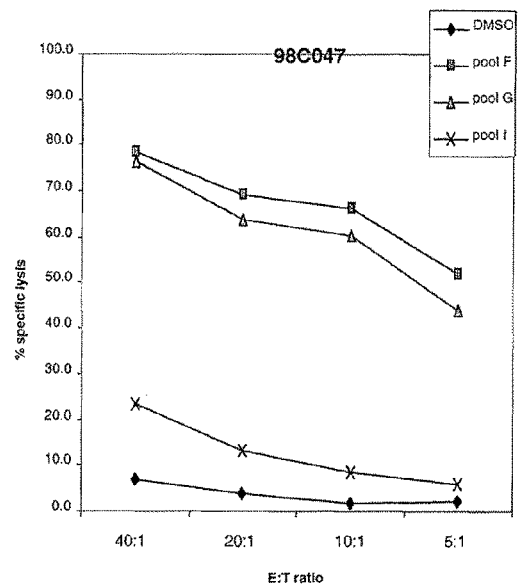
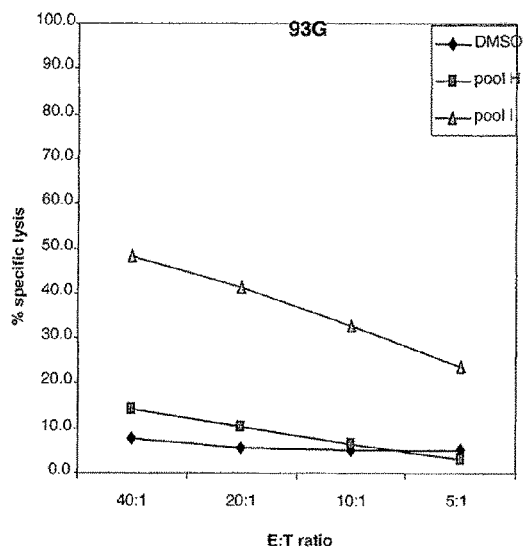
Bulk CTL assays on PBMC from Rhesus monkeys immunized with two injections of $10^{11}$ vp/dose of MRKAd6-NSmut.
FIG. 18E

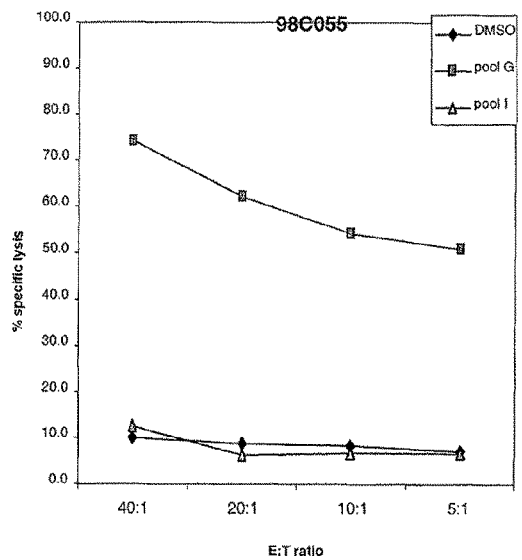
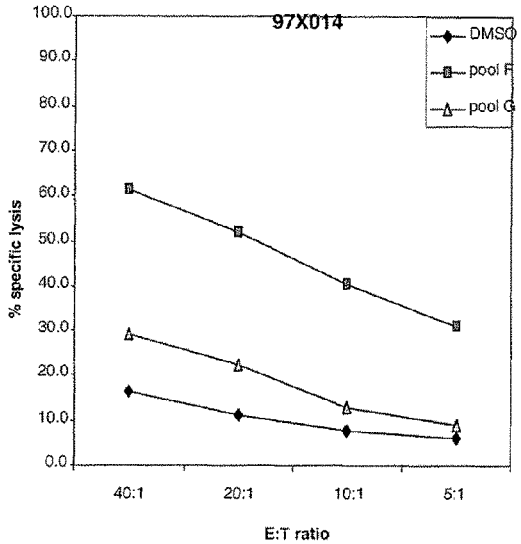
Bulk CTL assays on PBMC from Rhesus monkeys immunized with two injections of $10^{11}$ vp/dose of MRKAd6-NSmut.
FIG. 18F

```
   1  GCCACCATGG CCCCCATCAC CGCCTACAGC CAGCAGACCA GGGGCCTGCT
  51  GGGCTGCATC ATCACCAGCC TGACCGGACG CGACAAGAAC CAGGTGGAGG
 101  GAGAGGTGCA GGTGGTGAGC ACCGCTACCC AGAGCTTCCT GGCCACCTGC
 151  GTGAACGGCG TGTGCTGGAC CGTGTACCAC GGAGCCGGAA GCAAGACCCT
 201  GGCCGGACCC AAGGGCCCTA TCACCCAGAT GTACACCAAT GTGGATCAGG
 251  ATCTGGTGGG CTGGCAGGCC CCTCCCGGAG CCAGGAGCCT GACACCCTGT
 301  ACCTGTGGAA GCAGCGACCT GTACCTGGTG ACACGCCACG CCGATGTGAT
 351  CCCCGTGAGG CGCAGGGGCG ATTCTCGCGG AAGCCTGCTG AGCCCTAGGC
 401  CCGTGAGCTA CCTGAAGGGC AGCAGCGGAG GACCCCTGCT GTGTCCTTCT
 451  GGCCATGCCG TGGGCATTTT TCGCGCTGCC GTGTGTACCA GGGGCGTGGC
 501  CAAAGCCGTG GATTTTGTGC CGTGGAAAG CATGGAGACC ACCATGCGCA
 551  GCCCTGTGTT CACCGACAAC AGCTCTCCCC CTGCCGTGCC CCAATCATTC
 601  CAGGTGGCTC ACCTGCACGC CCCTACCGGA TCTGGCAAGA GCACCAAGGT
 651  GCCCGCTGCC TACGCCGCTC AGGGCTACAA GGTGCTGGTG CTGAACCCCA
 701  GCGTGGCCGC TACCCTGGGC TTCGGCGCTT ACATGAGCAA GGCCCATGGC
 751  ATCGACCCCA ACATCCGCAC AGGCGTGCGC ACCATCACCA CCGGAGCTCC
 801  CGTGACCTAC AGCACCTACG GCAAGTTCCT GGCCGATGGA GGCTGCAGCG
 851  GAGGAGCCTA CGACATCATC ATCTGCGACG AGTGCCACAG CACCGACAGC
 901  ACCACCATCC TGGGCATTGG CACCGTGCTG GATCAGGCCG AAACAGCTGG
 951  AGCCAGGCTG GTGGTGCTGG CCACAGCTAC CCCTCCTGGC AGCGTGACCG
1001  TGCCCCATCC CAATATCGAG GAGGTGGCCC TGAGCAACAC AGGCGAGATC
1051  CCCTTCTACG GCAAGGCCAT CCCCATCGAG GCCATCCGCG GAGGCAGGCA
1101  CCTGATCTTC TGCCACAGCA AGAAGAAGTG CGACGAGCTG GCTGCCAAGC
1151  TGAGCGGACT GGGCATCAAC GCCGTGGCCT ACTACAGGGG CCTGGACGTG
1201  TCAGTGATCC CCACCATCGG CGATGTGGTG GTGGTGGCCA CCGACGCCCT
1251  GATGACAGGC TACACCGGAG ACTTCGACAG CGTGATCGAC TGCAACACCT
1301  GCGTGACCCA GACCGTGGAC TTCAGCCTGG ACCCCACCTT CACCATCGAA
1351  ACCACCACCG TGCCTCAGGA TGCTGTGAGC AGGAGCCAGA GGCGCGGACG
1401  CACCGGAAGG GGCAGGCGCG GAATTTATCG CTTTGTGACC CCTGGCGAAA
1451  GGCCCTCTGG CATGTTCGAC AGCAGCGTGC TGTGCGAGTG CTACGACGCT
1501  GGCTGCGCTT GGTACGAGCT GACACCCGCT GAAACCAGCG TGCGCCTGCG
1551  CGCTTATCTG AATACCCCTG GCCTGCCCGT GTGTCAGGAC CACCTGGAGT
```

FIG. 20A

```
1601  TCTGGGAGAG CGTGTTCACA GGACTGACCC ACATCGACGC CCATTTCCTG
1651  AGCCAGACCA AGCAGGCTGG CGACAACTTC CCCTATCTGG TGGCCTATCA
1701  GGCCACCGTG TGTGCTAGGG CCCAAGCTCC ACCTCCTTCA TGGGACCAGA
1751  TGTGGAAGTG CCTGATCCGC CTGAAGCCCA CCCTGCACGG CCCTACCCCT
1801  CTGCTGTACC GCCTGGGAGC CGTGCAGAAC GAGGTGACCC TGACCCACCC
1851  CATCACCAAG TACATCATGG CCTGCATGAG CGCTGATCTG GAAGTGGTGA
1901  CCAGCACCTG GGTGCTGGTG GGAGGCGTGC TGGCCGCTCT GGCTGCCTAC
1951  TGCCTGACCA CCGGAAGCGT GGTGATCGTG GGACGCATCA TCCTGAGCGG
2001  AAGGCCCGCT ATCGTGCCCG ATCGCGAGTT CCTGTACCAG GAGTTCGACG
2051  AGATGGAGGA GTGTGCCAGC CACCTGCCCT ACATCGAGCA GGGCATGCAG
2101  CTGGCCGAAC AGTTCAAGCA GAAGGCCCTG GGCCTGCTGC AGACAGCCAC
2151  CAAACAGGCC GAAGCTGCCG CTCCCGTGGT GGAAAGCAAG TGGAGGGCCC
2201  TGGAGACCTT CTGGGCTAAG CACATGTGGA ACTTCATCTC TGGCATCCAG
2251  TACCTGGCCG GACTGAGCAC CCTGCCTGGC AACCCCGCTA TCGCCAGCCT
2301  GATGGCCTTC ACCGCTAGCA TCACCTCTCC CCTGACCACC CAGAGCACCC
2351  TGCTGTTCAA CATTCTGGGC GGATGGGTGG CCGCTCAGCT GGCCCCTCCT
2401  TCAGCTGCTT CTGCCTTTGT GGGCGCTGGC ATTGCCGGAG CCGCTGTGGG
2451  CAGCATTGGC CTGGGCAAAG TGCTGGTGGA TATTCTGGCT GGCTATGGCG
2501  CTGGCGTGGC CGGAGCCCTG GTGGCCTTCA AGGTGATGAG CGGAGAGATG
2551  CCCAGCACCG AGGACCTGGT GAACCTGCTG CCTGCCATTC TGAGCCCTGG
2601  AGCCCTGGTG GTGGGCGTGG TGTGTGCTGC CATTCTGAGG CGCCATGTGG
2651  GACCCGGAGA GGGCGCTGTG CAGTGGATGA ACCGCCTGAT CGCCTTCGCC
2701  TCTCGCGGAA ACCACGTGAG CCCTACCCAC TACGTGCCTG AGAGCGACGC
2751  CGCTGCCAGG GTGACCCAGA TCCTGAGCAG CCTGACCATC ACCCAGCTGC
2801  TGAAGCGCCT GCACCAGTGG ATCAACGAGG ACTGCAGCAC ACCCTGCAGC
2851  GGAAGCTGGC TGAGGGACGT GTGGGACTGG ATCTGCACCG TGCTGACCGA
2901  CTTCAAGACC TGGCTGCAGA GCAAGCTGCT GCCCCAACTG CCTGGCGTGC
2951  CCTTCTTCTC ATGCCAGCGC GGATACAAGG GCGTGTGGAG GGGCGATGGC
3001  ATCATGCAGA CCACCTGTCC CTGCGGAGCC CAGATCACAG GCCACGTGAA
3051  GAACGGCAGC ATGCGCATCG TGGGCCCTAA GACCTGCAGC AACACCTGGC
3101  ACGGCACCTT CCCCATCAAC GCCTACACCA CCGGACCCTG CACACCCAGC
3151  CCTGCTCCCA ACTACAGCAG GGCCCTGTGG AGGGTGGCTG CCGAGGAGTA
```

FIG. 20B

```
3201  CGTGGAGGTG ACCAGGGTGG GAGACTTCCA CTACGTGACC GGAATGACCA
3251  CCGACAACGT GAAGTGTCCC TGTCAGGTGC CCGCTCCCGA ATTTTTTACC
3301  GAAGTGGATG GCGTGCGCCT GCATCGCTAT GCCCCTGCCT GTAGGCCCCT
3351  GCTGCGCGAA GAAGTGACCT TCCAGGTGGG CCTGAACCAG TACCTGGTGG
3401  GCAGCCAGCT GCCCTGCGAG CCTGAGCCCG ATGTGGCCGT GCTGACCAGC
3451  ATGCTGACCG ACCCCAGCCA CATCACAGCC GAAACCGCTA AAAGGCGCCT
3501  GGCCAGGGGC TCTCCTCCAA GCCTGGCCTC AAGCAGCGCT AGCCAGCTGT
3551  CTGCTCCCAG CCTGAAGGCC ACCTGCACCA CCCACCACGT GAGCCCCGAC
3601  GCCGACCTGA TCGAGGCCAA CCTGCTGTGG CGCCAGGAGA TGGGCGGCAA
3651  CATCACCCGC GTGGAGAGCG AGAACAAGGT GGTGGTGCTG GACAGCTTCG
3701  ACCCCCTGCG CGCCGAGGAG GACGAGCGCG AGGTGAGCGT GCCCGCCGAG
3751  ATCCTGCGCA AGAGCAAGAA GTTCCCCGCT GCCATGCCCA TCTGGGCTAG
3801  ACCTGATTAC AACCCTCCCC TGCTGGAGAG CTGGAAGGAC CCTGATTACG
3851  TGCCTCCAGT GGTGCATGGC TGTCCTCTGC CTCCCATTAA AGCCCCTCCT
3901  ATTCCACCTC CTAGGCGCAA AAGGACCGTG GTGCTGACAG AAAGCAGCGT
3951  GAGCTCTGCT CTGGCCGAAC TGGCCACCAA GACCTTTGGC AGCAGCGAGA
4001  GCTCTGCCGT GGACAGCGGA ACAGCCACCG CTCTGCCTGA CCAGGCCAGC
4051  GACGACGGCG ATAAGGGCAG CGATGTGGAG AGCTATAGCA GCATGCCTCC
4101  CCTGGAAGGC GAACCTGGCG ATCCCGATCT GAGCGATGGC AGCTGGAGCA
4151  CCGTGAGCGA AGAGGCCAGC GAGGACGTGG TGTGTTGCAG CATGAGCTAC
4201  ACCTGGACAG GCGCTCTGAT CACACCCTGC GCTGCCGAGG AGAGCAAGCT
4251  GCCCATCAAC GCCCTGAGCA ACAGCCTGCT GAGGCACCAC AACATGGTGT
4301  ACGCCACCAC CAGCAGGTCT GCCGGACTGA GGCAGAAGAA GGTGACCTTC
4351  GACCGCCTGC AGGTGCTGGA CGACCACTAC CGCGATGTGC TGAAGGAGAT
4401  GAAGGCCAAG GCCAGCACCG TGAAGGCCAA GCTGCTGAGC GTGGAGGAGG
4451  CCTGCAAGCT GACCCCCCCC CACAGCGCCA AGAGCAAGTT CGGCTACGGC
4501  GCCAAGGACG TGCGCAACCT GAGCAGCAAG GCCGTGAACC ACATCCACAG
4551  CGTGTGGAAG GACCTGCTGG AGGACACCGT GACCCCCATC GACACCACCA
4601  TCATGGCCAA GAACGAGGTG TTCTGCGTGC AGCCCGAGAA GGGCGGCCGC
4651  AAGCCCGCTC GCCTGATCGT GTTCCCCGAT CTGGGCGTGC GCGTGTGCGA
4701  GAAGATGGCC CTGTACGACG TGGTGAGCAC CCTGCCTCAG GTGGTGATGG
4751  GCTCAAGCTA CGGCTTCCAG TACAGCCCTG GCCAGCGCGT GGAGTTCCTG
```

FIG. 20C

```
4801  GTGAACACCT GGAAGAGCAA GAAGAACCCC ATGGGCTTCA GCTACGACAC
4851  ACGCTGCTTC GACAGCACCG TGACCGAGAA CGACATCCGC GTGGAGGAGA
4901  GCATCTACCA GTGCTGCGAC CTGGCCCCTG AGGCCAGGCA GGCCATCAAG
4951  AGCCTGACCG AGCGCCTGTA CATCGGAGGC CCTCTGACCA ACAGCAAGGG
5001  ACAGAACTGC GGATACAGGC GCTGTAGGGC CTCTGGCGTG CTGACCACCA
5051  GCTGTGGCAA CACCCTGACC TGCTACCTGA AGGCCAGCGC TGCCTGTCGC
5101  GCTGCCAAGC TGCAGGACTG CACCATGCTG GTGAACGCCG CTGGCCTGGT
5151  GGTGATTTGT GAAAGCGCTG GCACCCAGGA AGATGCTGCC AGCCTGCGCG
5201  TGTTCACCGA GGCCATGACC AGGTACTCTG CCCCTCCCGG AGACCCCCCT
5251  CAGCCCGAAT ACGACCTGGA GCTGATCACC AGCTGCTCAA GCAACGTGAG
5301  CGTGGCTCAC GACGCCAGCG GAAAGCGCGT GTACTACCTG ACACGCGATC
5351  CCACCACCCC TCTGGCTCGC GCTGCCTGGG AAACCGCTCG CCATACACCC
5401  GTGAACAGCT GGCTGGGCAA CATCATCATG TACGCCCCTA CCCTGTGGGC
5451  TCGCATGATC CTGATGACCC ACTTCTTCAG CATCCTGCTG GCTCAGGAGC
5501  AGCTGGAGAA GGCCCTGGAC TGCCAGATTT ACGGCGCTTG CTACAGCATC
5551  GAGCCCCTGG ACCTGCCCCA AATCATCGAG CGCCTGCACG GCCTGTCTGC
5601  CTTCAGCCTG CACAGCTACA GCCCTGGCGA AATTAATCGC GTGGCCAGCT
5651  GTCTGCGCAA ACTGGGCGTG CCTCCTCTGC GCGTGTGGAG GCATAGGGCT
5701  AGGAGCGTGA GGGCTAGGCT GCTGAGCCAG GGAGGCAGGG CCGCTACCTG
5751  TGGAAAGTAC CTGTTCAACT GGGCCGTGAA GACCAAGCTG AAGCTGACCC
5801  CTATCCCTGC CGCTAGCCAG CTGGACCTGA GCGGATGGTT CGTGGCTGGC
5851  TACAGCGGAG GCGACATCTA CCACAGCCTG TCTCGCGCTC GCCCTCGCTG
5901  GTTCATGCTG TGCCTGCTGC TGCTGAGCGT GGGCGTGGGC ATCTACCTGC
5951  TGCCCAACCG CTAAA
```

FIG. 20D

HEPATITIS C VIRUS VACCINE

RELATED APPLICATIONS

The present application is a divisional application of U.S. Ser. No. 12/396,747, filed Mar. 3, 2009 now U.S. Pat. No. 8,142,794, which is a divisional application of U.S. Ser. No. 10/492,178, filed on Apr. 7, 2004, now U.S. Pat. No. 7,598,362, which is a §371 National Stage application of PCT/US02/32512, filed Oct. 10, 2002, which claims priority to provisional applications U.S. Ser. No. 60/363,774, filed Mar. 13, 2002, and U.S. Ser. No. 60/328,655, filed Oct. 11, 2001, each of which are hereby incorporated by reference herein.

REFERENCE TO SEQUENCE LISTING SUBMITTED ELECTRONICALLY

The sequence listing of the present application is submitted electronically via EFS-Web as an ASCII formatted sequence listing with a file name "IRRIFD0015YPDBUSPCD_SEQLIST_29JANUARY2010.TXT," creation date of Jan. 29, 2010, and a size of 222 KB. This sequence listing submitted via EFS-Web is part of the specification and is herein incorporated by reference in its entirety.

BACKGROUND OF THE INVENTION

The references cited in the present application are not admitted to be prior art to the claimed invention.

About 3% of the world's population are infected with the Hepatitis C virus (HCV). (Wasley a al., *Semin. Liver Dis.* 20, 1-16, 2000.) Exposure to HCV results in an overt acute disease in a small percentage of cases, while in most instances the virus establishes a chronic infection causing liver inflammation and slowly progresses into liver failure and cirrhosis. (Iwarson, *FEMS Microbiol. Rev.* 14, 201-204, 1994.) In addition, epidemiological surveys indicate an important role of HCV in the pathogenesis of hepatocellular carcinoma. (Kew, *FEMS Microbial. Rev.* 14, 211-220, 1994, Alter, *Blood* 85, 1681-1695, 1995.)

Prior to the implementation of routine blood screening for HCV in 1992, most infections were contracted by inadvertent exposure to contaminated blood, blood products or transplanted organs. In those areas where blood screening of HCV is carried out, HCV is primarily contracted through direct percutaneous exposure to infected blood, i.e., intravenous drug use. Less frequent methods of transmission include perinatal exposure, hemodialysis, and sexual contact with an HCV infected person. (Alter et al., *N. Engl. J. Med.* 341(8), 556-562, 1999, Alter, *J. Hepatol.* 31 *Suppl.* 88-91, 1999. *Semin. Liver. Dis.* 201, 1-16, 2000.)

The HCV genome consists of a single strand RNA about 9.5 kb encoding a precursor polyprotein of about 3000 amino acids. (Choo a al., *Science* 244, 362-364, 1989, Choo et al., *Science* 244, 359-362, 1989, Takamizawa et al., *J. Virol.* 65, 1105-1113, 1991.) The HCV polyprotein contains the viral proteins in the order: C-E1-E2-p7-NS2-NS3-NS4A-NS4B-NS5A-NS5B.

Individual viral proteins are produced by proteolysis of the HCV polyprotein. Host cell proteases release the putative structural proteins C, E1, E2, and p7, and create the N-terminus of NS2 at amino acid 810. (Mizushima et al., *J. Virol.* 68, 2731-2734, 1994, Hijikata et al., *P.N.A.S. USA* 90, 10773-10777, 1993.)

The non-structural proteins NS3, NS4A, NS4B, NS5A and NS5B presumably form the virus replication machinery and are released from the polyprotein. A zinc-dependent protease associated with NS2 and the N-terminus of NS3 is responsible for cleavage between NS2 and NS3. (Grakoui et al., *J. Virol.* 67, 1385-1395, 1993, Hijikata et al., *P.N.A.S. USA* 90, 10773-10777, 1993.) A distinct serine protease located in the N-terminal domain of NS3 is responsible for proteolytic cleavages at the NS3/NS4A, NS4A/NS4B, NS4B/NS5A and NS5A/NS5B junctions. (Bartenschlager et al., *J. Virol.* 67, 3835-3844, 1993, Grakoui et al., *Proc. Natl. Acad. Sci. USA* 90, 10583-10587, 1993, Tomei et al., *J. Virol.* 67, 4017-4026, 1993.) NS4A provides a cofactor for NS3 activity. (Failla et al., *J. Virol.* 68, 3753-3760, 1994, De Francesco et al., U.S. Pat. No. 5,739,002.)

NS5A is a highly phosphorylated protein conferring interferon resistance. (De Francesco et al., *Semin. Liver Dis.*, 20(1), 69-83, 2000, Pawlotsky, *Viral Hepat. Suppl.* 1, 47-48, 1999.)

NS5B provides an RNA-dependent RNA polymerase. (De Francesco et al., International Publication Number WO 96/37619, Behrens et al., *EMBO* 15, 12-22, 1996, Lohmann et al., *Virology* 249, 108-118, 1998.)

SUMMARY OF THE INVENTION

The present invention features Ad6 vectors and a nucleic acid encoding a Met-NS3-NS4A-NS4B-NS5A-NS5B polypeptide containing an inactive NS5B RNA-dependent RNA polymerase region. The nucleic acid is particularly useful as a component of an adenovector or DNA plasmid vaccine providing a broad range of antigens for generating an HCV specific cell mediated immune (CMI) response against HCV.

A HCV specific CMI response refers to the production of cytotoxic T lymphocytes and T helper cells that recognize an HCV antigen. The CMI response may also include non-HCV specific immune effects.

Preferred nucleic acids encode a Met-NS3-NS4A-NS4B-NS5A-NS5B polypeptide that is substantially similar to SEQ. ID. NO. 1 and has sufficient protease activity to process itself to produce at least a polypeptide substantially similar to the NS5B region present in SEQ. ID. NO. 1. The produced polypeptide corresponding to NS5B is enzymatically inactive. More preferably, the HCV polypeptide has sufficient protease activity to produce polypeptides substantially similar to the NS3, NS4A, NS4B, NS5A, and NS5B regions present in SEQ. ID. NO. 1.

Reference to a "substantially similar sequence" indicates an identity of at least about 65% to a reference sequence. Thus, for example, polypeptides having an amino acid sequence substantially similar to SEQ. ID. NO. 1 have an overall amino acid identity of at least about 65% to SEQ. ID. NO. 1.

Polypeptides corresponding to NS3, NS4A, NS4B, NS5A, and NS5B have an amino acid sequence identity of at least about 65% to the corresponding region in SEQ. ID. NO. 1. Such corresponding polypeptides are also referred to herein as NS3, NS4A, NS4B, NS5A, and NS5B polypeptides.

Thus, a first aspect of the present invention describes a nucleic acid comprising a nucleotide sequence encoding a Met-NS3-NS4A-NS4B-NS5A-NS5B polypeptide substantially similar to SEQ. ID. NO. 1. The encoded polypeptide has sufficient protease activity to process itself to produce an NS5B polypeptide that is enzymatically inactive.

In a preferred embodiment, the nucleic acid is an expression vector capable of expressing the Met-NS3-NS4A-NS4B-NS5A-NS5B polypeptide in a desired human cell. Expression inside a human cell has therapeutic applications for actively treating an HCV infection and for prophylactically treating against an HCV infection.

An expression vector contains a nucleotide sequence encoding a polypeptide along with regulatory elements for proper transcription and processing. The regulatory elements that may be present include those naturally associated with the nucleotide sequence encoding the polypeptide and exogenous regulatory elements not naturally associated with the nucleotide sequence. Exogenous regulatory elements such as an exogenous promoter can be useful for expression in a particular host, such as in a human cell. Examples of regulatory elements useful for functional expression include a promoter, a terminator, a ribosome binding site, and a polyadenylation signal.

Another aspect of the present invention describes a nucleic acid comprising a gene expression cassette able to express in a human cell a Met-NS3-NS4A-NS4B-NS5A-NS5B polypeptide substantially similar to SEQ. ID. NO. 1. The polypeptide can process itself to produce an enzymatically inactive NS5B protein. The gene expression cassette contains at least the following:

a) a promoter transcriptionally coupled to a nucleotide sequence encoding a polypeptide;

b) a 5' ribosome binding site functionally coupled to the nucleotide sequence, c) a terminator joined to the 3' end of the nucleotide sequence, and d) a 3' polyadenylation signal functionally coupled to the nucleotide sequence.

Reference to "transcriptionally coupled" indicates that the promoter is positioned such that transcription of the nucleotide sequence can be brought about by RNA polymerase binding at the promoter. Transcriptionally coupled does not require that the sequence being transcribed is adjacent to the promoter.

Reference to "functionally coupled" indicates the ability to mediate an effect on the nucleotide sequence. Functionally coupled does not require that the coupled sequences be adjacent to each other. A 3' polyadenylation signal functionally coupled to the nucleotide sequence facilitates cleavage and polyadenylation of the transcribed RNA. A 5' ribosome binding site functionally coupled to the nucleotide sequence facilitates ribosome binding.

In preferred embodiments the nucleic acid is a DNA plasmid vector or an adenovector suitable for either therapeutic application in treating HCV or as an intermediate in the production of a therapeutic vector. Treating HCV includes actively treating an HCV infection and prophylactically treating against an HCV infection.

Another aspect of the present invention describes an adenovector comprising a Met-NS3-NS4A-NS4B-NS5A-NS5B expression cassette able to express a polypeptide substantially similar to SEQ. ID. NO. 1 that is produced by a process involving (a) homologous recombination and (b) adenovector rescue. The homologous recombinant step produces an adenovirus genome plasmid. The adenovector rescue step produces the adenovector from the adenogenome plasmid.

Adenovirus genome plasmids described herein contain a recombinant adenovirus genome having a deletion in the E1 region and optionally in the E3 region and a gene expression cassette inserted into one of the deleted regions. The recombinant adenovirus genome is made of regions substantially similar to one or more adenovirus serotypes.

Another aspect of the present invention describes an adenovector consisting of the nucleic acid sequence of SEQ. ID. NO. 4 or a derivative thereof, wherein said derivative thereof has the HCV polyprotein encoding sequence present in SEQ. ID. NO. 4 replaced with the HCV polyprotein encoding sequence of either SEQ. ID. NO. 3, SEQ. ID. NO. 10 or SEQ. ID. NO. 11.

Another aspect of the present invention describes a cultured recombinant cell comprising a nucleic acid containing a sequence encoding a Met-NS3-NS4A-NS4B-NS5A-NS5B polypeptide substantially similar to SEQ. ID. NO. 1. The recombinant cell has a variety of uses such as being used to replicate nucleic acid encoding the polypeptide in vector construction methods.

Another aspect of the present invention describes a method of making an adenovector comprising a Met-NS3-NS4A-NS4B-NS5A-NS5B expression cassette able to express a polypeptide substantially similar to SEQ. ID. NO. 1. The method involves the steps of (a) producing an adenovirus genome plasmid containing a recombinant adenovirus genome with deletions in the E1 and E3 regions and a gene expression cassette inserted into one of the deleted regions and (b) rescuing the adenovector from the adenovirus genome plasmid.

Another aspect of the present invention describes a pharmaceutical composition comprising a vector for expressing a Met-NS3-NS4A-NS4B-NS5A-NS5B polypeptide substantially similar to SEQ. ID. NO. 1 and a pharmaceutically acceptable carrier. The vector is suitable for administration and polypeptide expression in a patient.

A "patient" refers to a mammal capable of being infected with HCV. A patient may or may not be infected with HCV. Examples of patients are humans and chimpanzees.

Another aspect of the present invention describes a method of treating a patient comprising the step of administering to the patient an effective amount of a vector expressing a Met-NS3-NS4A-NS4B-NS5A-NS5B polypeptide substantially similar to SEQ. ID. NO. 1. The vector is suitable for administration and polypeptide expression in the patient.

The patient undergoing treatment may or may not be infected with HCV. For a patient infected with HCV, an effective amount is sufficient to achieve one or more of the following effects: reduce the ability of HCV to replicate, reduce HCV load, increase viral clearance, and increase one or more HCV specific CMI responses. For a patient not infected with HCV, an effective amount is sufficient to achieve one or more of the following: an increased ability to produce one or more components of a HCV specific CMI response to a HCV infection, a reduced susceptibility to HCV infection, and a reduced ability of the infecting virus to establish persistent infection for chronic disease.

Another aspect of the present invention features a recombinant nucleic acid comprising an Ad6 region and a region not present in Ad6. Reference to "recombinant" nucleic acid indicates the presence of two or more nucleic acid regions not naturally associated with each other. Preferably, the Ad6 recombinant nucleic acid contains Ad6 regions and a gene expression cassette coding for a polypeptide heterologous to Ad6.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIGS. 1A and 1B illustrate SEQ. ID. NO. 1,

FIGS. 2A, 2B, 2C, and 2D illustrate SEQ. ID. NO. 2. SEQ. ID. NO. 2 provides a nucleotide sequence coding for SEQ. ID. NO. 1 along with an optimized internal ribosome entry site and TAAA termination. Nucleotides 1-6 provides an optimized internal ribosome entry site. Nucleotides 7-5961 code for a HCV Met-NS3-NS4A-NS4B-NS5A-NS5B polypeptide with nucleotides in positions 5137 to 5145 providing a AlaAlaGly sequence in amino acid positions 1711 to 1713 that renders NS5B inactive. Nucleotides 5962-5965 provide a TAAA termination.

FIGS. 3A, 3B, 3C, and 3D illustrate SEQ. ID. NO. 3. SEQ. ID. NO. 3 is a codon optimized version of SEQ. ID. NO. 2, Nucleotides 7-5961 encode a HCV Met-NS3-NS4A-NS4B-NS5A-NS5B polypeptide.

Figure 4A:
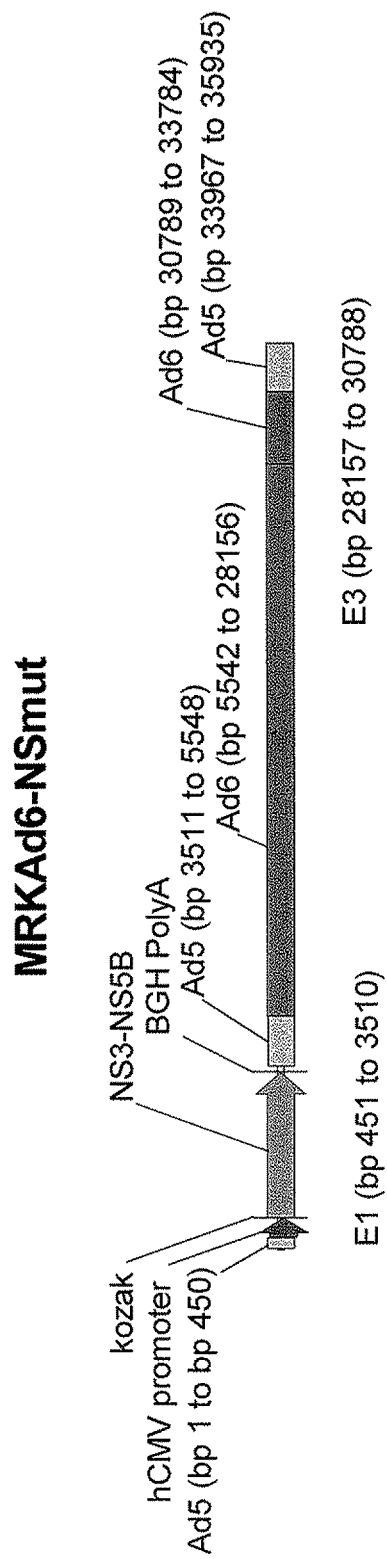

FI tions, most of them mediated by Th1 and Th2 cytokines. HCV specific Th cells assist in the activation and differentiation of B cells and induction and stimulation of virus-specific cytotoxic T cells. Together with CTL, Th cells may also secrete IFN-γ and TNF-α that inhibit replication and gene expression of several viruses. Additionally, Th cells and CTL, the main effector cells, can induce apoptosis and lysis of virus infected cells.

HCV specific CTL are generated from antigens processed by professional antigen presenting cells (pAPCs). Antigens can be either synthesized within or introduced into pAPCs. Antigen synthesis in a pAPC can be brought about by introducing into the cell an expression cassette encoding the antigen.

A preferred route of nucleic acid vaccine administration is an intramuscular route. Intramuscular administration appears to result in the introduction and expression of nucleic acid into somatic cells and pAPCs. HCV antigens produced in the somatic cells can be transferred to pAPCs for presentation in the context of MHC class I molecules. (Donnelly et al., *Annu. Rev. Immunol.* 15:617-648, 1997.)

pAPCs process longer length antigens into smaller peptide antigens in the proteasome complex. The antigen is translocated into the endoplasmic reticulum/Golgi complex secretory pathway for association with MHC class I proteins. CD8+ T lymphocytes recognize antigen associated with class I MHC via the T cell receptor (TCR) and the CD8 cell surface protein.

Using a nucleic acid encoding a Met-NS3-NS4A-NS4B-NS5A-NS5B polypeptide as a vaccine component allows for production of a broad range of antigens capable of generating CMI responses from a single vector. The polypeptide should be able to process itself sufficiently to produce at least a region corresponding to NS5B. Preferred nucleic acids encode an amino acid sequence substantially similar to SEQ. ID. NO. 1 that has sufficient protease activity to process itself to produce individual HCV polypeptides substantially similar to the NS3, NS4A, NS4B, NS5A, and NS5B regions present in SEQ. ID. NO. 1.

A polypeptide substantially similar to SEQ. ID. NO. 1 with sufficient protease activity to process itself in a cell provides the cell with T cell epitopes that are present in several different HCV strains. Protease activity is provided by NS3 and NS3/NS4A proteins digesting the Met-NS3-NS4A-NS4B-NS5A-NS5B polypeptide at the appropriate cleavage sites to release polypeptides corresponding to NS3, NS4A, NS4B, NS5A, and NS5B. Self-processing of the Met-NS3-NS4A-NS4B-NS5A-NS5B generates polypeptides that approximate naturally occurring HCV polypeptides.

Based on the guidance provided herein a sufficiently strong immune response can be generated to achieve beneficial effects in a patient. The provided guidance includes information concerning HCV sequence selection, vector selection, vector production, combination treatment, and administration.

I. HCV SEQUENCES

A variety of different nucleic acid sequences can be used as a vaccine component to supply a HCV Met-NS3-NS4A-NS4B-NS5A-NS5B polypeptide to a cell or as an intermediate to produce vaccine components. The starting point for obtaining suitable nucleic acid sequences are preferably naturally occurring NS3-NS4A-NS4B-NS5A-NS5B polypeptide sequences modified to produce an inactive NS5B.

The use of a HCV nucleic acid sequence providing HCV non-structural antigens to generate a CMI response is mentioned by Cho et al., *Vaccine* 17:1136-1144, 1999, Paliard et al., International Publication Number WO 01/30812 (not admitted to be prior art to the claimed invention), and Coit et al., International Publication Number WO 01/38360 (not admitted to be prior art to the claimed invention). Such references fail to describe, for example, a polypeptide that processes itself to produce an inactive NS5B, and the particular combinations of HCV sequences and delivery vehicles employed herein.

Modifications to a HCV Met-NS3-NS4A-NS4B-NS5A-NS5B polypeptide sequence can be produced by altering the encoding nucleic acid. Alterations can be performed to create deletions, insertions and substitutions.

Small modifications can be made in NS5B to produce an inactive polymerase by targeting motifs essentially for replication. Examples of motifs critical for NS5B activity and modifications that can be made to produce an inactive NS5B are described by Lohmann et al., *Journal of Virology* 71:8416-8426, 1997, and Kolykhalov et al., *Journal of Virology* 74:2046-2051, 2000.

Additional factors to take into account when producing modifications to a HCV Met-NS3-NS4A-NS4B-NS5A-NS5B polypeptide include maintaining the ability to self-process and maintaining T cell antigens. The ability of the HCV polypeptide to process itself is determined to a large extent by a functional NS3 protease. Modifications that maintain NS3 activity protease activity can be obtained by taking into account the NS3 protein, NS4A which serves as a cofactor for NS3, and NS3 protease recognition sites present within the NS3-NS4A-NS4B-NS5A-NS5B polypeptide.

Different modifications can be made to naturally occurring NS3-NS4A-NS4B-NS5A-NS5B polypeptide sequences to produce polypeptides able to elicit a broad range of T cell responses. Factors influencing the ability of a polypeptide to elicit a broad T cell response include the preservation or introduction of HCV specific T cell antigen regions and prevalence of different T cell antigen regions in different HCV isolates.

Numerous examples of naturally occurring HCV isolates are well known in the art. HCV isolates can be classified into the following six major genotypes comprising one or more subtypes: HCV-1/(1a,1b,1c), HCV-2/(2a,2b,2c), HCV-3/(3a,3b,10a), HCV-4/(4a), HCV-5/(5a) and HCV-6/(6a,6b,7b,8b,9a,11a). (Simmonds, *J. Gen. Virol.*, 693-712, 2001.) Examples of particular HCV sequences such as HCV-BK, HCV-J, HCV-N, HCV-H, have been deposited in GenBank and described in various publications. (See, for example, Chamberlain et al., *J. Gen. Virol.*, 1341-1347, 1997.)

HCV T cell antigens can be identified by, for example, empirical experimentation. One way of identifying T cell antigens involves generating a series of overlapping short peptides from a longer length polypeptide and then screening the T-cell populations from infected patients for positive clones. Positive clones are activated/primed by a particular peptide. Techniques such as IFNγ-ELISPOT, IFNγ-Intracellular staining and bulk CTL assays can be used to measure peptide activity. Peptides thus identified can be considered to represent T-cell epitopes of the respective pathogen.

HCV T cell antigen regions from different HCV isolates can be introduced into a single sequence by, for example, producing a hybrid NS3-NS4A-NS4B-NS5A-NS5B polypeptide containing regions from two or more naturally occurring sequences. Such a hybrid can contain additional modifications, which preferably do not reduce the ability of the polypeptide to produce an HCV CMI response.

The ability of a modified Met-NS3-NS4A-NS4B-NS5A-NS5B polypeptide to process itself and produce a CMI response can be determined using techniques described herein or well known in the art. Such techniques include the use of IFNγ-ELISPOT, IFNγ-Intracellular staining and bulk CTL assays to measure a HCV specific CMI response.

A. Met-NS3-NS4A-NS4B-NS5A-NS5B Sequences

SEQ. ID. NO. 1 provides a preferred Met-NS3-NS4A-NS4B-NS5A-NS5B sequence. SEQ. ID. NO. 1 contains a large number of HCV specific T cell antigens that are present in several different HCV isolates. SEQ. ID. NO. 1 is similar to the NS3-NS4A-NS4B-NS5A-NS5B portion of the HCV BK strain nucleotide sequence (GenBank accession number M58335).

In SEQ. ID. NO. 1 anchor positions important for recognition by MHC class I molecules are conserved or represent conservative substitutions for 18 out of 20 known T-cell epitopes in the NS3-NS4A-NS4B-NS5A-NS5B portion of HCV polyproteins. With respect to the remaining two known T-cell epitopes, one has a non-conservative anchor substitution in SEQ. ID. NO. 1 that may still be recognized by a different HLA supertype and one epitope has one anchor residue not conserved. HCV T-cell epitopes are described in Chisari et al., *Curr Top. Microbial Immunol.,* 242:299-325, 2000, and Lechner et al. *J. Exp. Med.* 9:1499-1512, 2000.

Differences between the HCV-BK NS3-NS4A-NS4B-NS5A-NS5B nucleotide sequence and SEQ. ID. NO. 1 include the introduction of a methionine at the 5' end and the presence of modified NS5B active site residues in SEQ. ID. NO. 1. The modification replaces GlyAspAsp with AlaAlaGly (residues 1711-1713) to inactivate NS5B.

The encoded HCV Met-NS3-NS4A-NS4B-NS5A-NS5B polypeptide preferably has an amino acid sequence substantially similar to SEQ. ID. NO. 1. In different embodiments, the encoded HCV Met-NS3-NS4A-NS4B-NS5A-NS5B polypeptide has an amino acid identify to SEQ. ID. NO. 1 of at least 65%, at least 75%, at least 85%, at least 95%, at least 99% or 100%; or differs from SEQ. ID. NO. 1 by 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, or 1-20 amino acids.

Amino acid differences between a Met-NS3-NS4A-NS4B-NS5A-NS5B polypeptide and SEQ. ID. NO. 1 are calculated by determining the minimum number of amino acid modifications in which the two sequences differ. Amino acid modifications can be deletions, additions, substitutions or any combination thereof.

Amino acid sequence identity is determined by methods well known in the art that compare the amino acid sequence of one polypeptide to the amino acid sequence of a second polypeptide and generate a sequence alignment. Amino acid identity is calculated from the alignment by counting the number of aligned residue pairs that have identical amino acids.

Methods for determining sequence identity include those described by Schuler, G. D. in *Bioinformatics: A Practical Guide to the Analysis of Genes and Proteins*, Baxevanis, A. D. and Ouelette, B. F. F., eds., John Wiley & Sons, Inc, 2001; Yona, et al., in *Bioinformatics: Sequence, structure and databanks*, Higgins, D. and Taylor, W. eds, Oxford University Press, 2000; and *Bioinformatics: Sequence and Genome Analysis*, Mount, D. W., ed., Cold Spring Harbor Laboratory Press, 2001). Methods to determine amino acid sequence identity are codified in publicly available computer programs such as GAP (Wisconsin Package Version 10.2, Genetics Computer Group (GCG), Madison, Wis.), BLAST (Altschul et al., *J. Mol. Biol.* 215(3):403-10, 1990), and FASTA (Pearson, *Methods in Enzymology* 183:63-98, 1990, R. F. Doolittle, ed.). In an embodiment of the present invention sequence identity between two polypeptides is determined using the GAP program (Wisconsin Package Version 10.2, Genetics Computer Group (GCG), Madison, Wis.). GAP uses the alignment method of Needleman and Wunsch. (Needleman, et al., *J. Mol. Biol.* 48:443-453, 1970.) GAP considers all possible alignments and gap positions between two sequences and creates a global alignment that maximizes the number of matched residues and minimizes the number and size of gaps. A scoring matrix is used to assign values for symbol matches. In addition, a gap creation penalty and a gap extension penalty are required to limit the insertion of gaps into the alignment. Default program parameters for polypeptide comparisons using GAP are the BLOSUM62 (Henikoff et al., *Proc. Natl. Acad. Sci. USA,* 89:10915-10919, 1992) amino acid scoring matrix (MATrix=blosum62.cmp), a gap creation parameter (GAPweight=8) and a gap extension parameter (LENgthweight=2).

More preferred HCV Met-NS3-NS4A-NS4B-NS5A-NS5B polypeptides in addition to being substantially similar to SEQ. ID. NO. 1 across their entire length produce individual NS3, NS4A, NS4B, NS5A and NS5B regions that are substantially similar to the corresponding regions present in SEQ. ID. NO. 1. The corresponding regions in SEQ. ID. NO. 1 are provided as follows: Met-NS3 amino acids 1-632; NS4A amino acids 633-686; NS4B amino acids 687-947; NS5A amino acids 948-1394; and NS5B amino acids 1395-1985.

In different embodiments a NS3, NS4A, NS4B, NS5A and/or NS5B region has an amino acid identity to the corresponding region in SEQ. ID. NO. 1 of at least 65%, at least 75%, at least 85%, at least 95%, at least 99%, or 100%; or an amino acid difference of 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, or 1-20 amino acids.

Amino acid modifications to SEQ. ID. NO. 1 preferably maintain all or most of the T-cell antigen regions. Differences in naturally occurring amino acids are due to different amino acid side chains (R groups). An R group affects different properties of the amino acid such as physical size, charge, and hydrophobicity. Amino acids can be divided into different groups as follows: neutral and hydrophobic (alanine, valine, leucine, isoleucine, proline, tyrptophan, phenylalanine, and methionine); neutral and polar (glycine, serine, threonine, tryosine, cysteine, asparagine, and glutamine); basic (lysine, arginine, and histidine); and acidic (aspartic acid and glutamic acid).

Generally, in substituting different amino acids it is preferable to exchange amino acids having similar properties. Substituting different amino acids within a particular group, such as substituting valine for leucine, arginine for lysine, and asparagine for glutamine are good candidates for not causing a change in polypeptide tertiary structure.

Starting with a particular amino acid sequence and the known degeneracy of the genetic code, a large number of different encoding nucleic acid sequences can be obtained. The degeneracy of the genetic code arises because almost all amino acids are encoded by different combinations of nucleotide triplets or "codons". The translation of a particular codon into a particular amino acid is well known in the art (see, e.g., Lewin GENES IV, p. 119, Oxford University Press, 1990). Amino acids are encoded by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU.

Nucleic acid sequences can be optimized in an effort to enhance expression in a host. Factors to be considered include C:G content, preferred codons, and the avoidance of inhibitory secondary structure. These factors can be combined in different ways in an attempt to obtain nucleic acid sequences having enhanced expression in a particular host. (See, for example, Donnelly et al., International Publication Number WO 97/47358.)

The ability of a particular sequence to have enhanced expression in a particular host involves some empirical experimentation. Such experimentation involves measuring expression of a prospective nucleic acid sequence and, if needed, altering the sequence.

B. Encoding Nucleotide Sequences

SEQ. ID. NOs. 2 and 3 provide two examples of nucleotide sequences encoding a Met-NS3-NS4A-NS4B-NS5A-NS5B sequence. The coding sequence of SEQ. ID, NO. 2 is similar (99.4% nucleotide sequence identity) to the NS3-NS4A-NS4B-NS5A-NS5B region of the naturally occurring HCV-BK sequence (GenBank accession number M58335). SEQ. ID. NO. 3 is a codon-optimized version of SEQ. ID, NO. 2. SEQ. ID. NOs. 2 and 3 have a nucleotide sequence identity of 78.3%.

Differences between the HCV-BK NS3-NS4A-NS4B-NS5A-NS5B nucleotide (GenBank accession number M58335) and SEQ. ID. NO. 2, include SEQ. ID. NO. 2 having a ribosome binding site, an ATG methionine codon, a region coding for a modified NS5B catalytic domain, a TAAA stop signal and an additional 30 nucleotide differences. The modified catalytic domain codes for a AlaAlaGly (residues 1711-1713) instead of GlyAspAsp to inactivate NS5B.

A nucleotide sequence encoding a HCV Met-NS3-NS4A-NS4B-NS5A-NS5B polypeptide is preferably substantially similar to the SEQ. ID. NO. 2 coding region. In different embodiments, the nucleotide sequence encoding a HCV Met-NS3-NS4A-NS4B-NS5A-NS5B polypeptide has a nucleotide sequence identify to the SEQ. ID. NO. 2 coding region of at least 65%, at least 75%, at least 85%, at least 95%, at least 99%, or 100%; or differs from SEQ. ID. NO. 2 by 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-25, 1-30, 1-35, 1-40, 1-45, or 1-50 nucleotides.

Nucleotide differences between a sequence coding Met-NS3-NS4A-NS4B-NS5A-NS5B and the SEQ. ID. NO. 2 coding region are calculated by determining the minimum number of nucleotide modifications in which the two sequences differ. Nucleotide modifications can be deletions, additions, substitutions or any combination thereof.

Nucleotide sequence identity is determined by methods well known in the art that compare the nucleotide sequence of one sequence to the nucleotide sequence of a second sequence and generate a sequence alignment. Sequence identity is determined from the alignment by counting the number of aligned positions having identical nucleotides.

Methods for determining nucleotide sequence identity between two polynucleotides include those described by Schuler, in *Bioinformatics: A Practical Guide to the Analysis of Genes and Proteins*, Baxevanis, A. D. and Ouelette, B. F. F., eds., John Wiley & Sons, Inc, 2001; Yona et al., in *Bioinformatics: Sequence, structure and databanks*, Higgins, D. and Taylor, W. eds, Oxford University Press, 2000; and *Bioinformatics: Sequence and Genome Analysis*, Mount, D. W., ed., Cold Spring Harbor Laboratory Press, 2001). Methods to determine nucleotide sequence identity are codified in publicly available computer programs such as GAP (Wisconsin Package Version 10.2, Genetics Computer Group (GCG), Madison, Wis.), BLAST (Altschul et al., *J. Mol. Biol.* 215(3): 403-10, 1990), and FASTA (Pearson, W. R., *Methods in Enzymology* 183:63-98, 1990, R. F. Doolittle, ed.).

In an embodiment of the present invention, sequence identity between two polynucleotides is determined by application of GAP (Wisconsin Package Version 10.2, Genetics Computer Group (GCG), Madison, Wis.). GAP uses the alignment method of Needleman and Wunsch. (Needleman et al., *J. Mol. Biol.* 48:443-453, 1970.) GAP considers all possible alignments and gap positions between two sequences and creates a global alignment that maximizes the number of matched residues and minimizes the number and size of gaps. A scoring matrix is used to assign values for symbol matches. In addition, a gap creation penalty and a gap extension penalty are required to limit the insertion of gaps into the alignment. Default program parameters for polynucleotide comparisons using GAP are the nwsgapdna.cmp scoring matrix (MATrix=nwsgapdna.cmp), a gap creation parameter (GAPweight=50) and a gap extension pararameter (LENgthweight=3).

More preferred HCV Met-NS3-NS4A-NS4B-NS5A-NS5B nucleotide sequences in addition to being substantially similar across its entire length, produce individual NS3, NS4A, NS4B, NS5A and NS5B regions that are substantially similar to the corresponding regions present in SEQ. ID. NO. 2. The corresponding coding regions in SEQ. ID. NO. 2 are provided as follows: Met-NS3, nucleotides 7-1902; NS4A nucleotides 1903-2064; NS4B nucleotides 2065-2847; NS5A nucleotides 2848-4188: NS5B nucleotides 4189-5661.

In different embodiments a NS3, NS4A, NS4B, NS5A and/or NS5B encoding region has a nucleotide sequence identity to the corresponding region in SEQ. ID. NO. 2 of at least 65%, at least 75%, at least 85%, at least 95%, at least 99% or 100%; or a nucleotide difference to SEQ. ID. NO. 2 of 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-25, 1-30, 1-35, 1-40, 1-45, or 1-50 nucleotides.

C. Gene Expression Cassettes

A gene expression cassette contains elements needed for polypeptide expression. Reference to "polypeptide" does not provide a size limitation and includes protein. Regulatory elements present in a gene expression cassette generally include: (a) a promoter transcriptionally coupled to a nucleotide sequence encoding the polypeptide, (b) a 5' ribosome binding site functionally coupled to the nucleotide sequence, (c) a terminator joined to the 3' end of the nucleotide sequence, and (d) a 3' polyadenylation signal functionally coupled to the nucleotide sequence. Additional regulatory elements useful for enhancing or regulating gene expression or polypeptide processing may also be present.

Promoters are genetic elements that are recognized by an RNA polymerase and mediate transcription of downstream regions. Preferred promoters are strong promoters that provide for increased levels of transcription. Examples of strong promoters are the immediate early human cytomegalovirus promoter (CMV), and CMV with intron A. (Chapman et al, *Nucl. Acids Res.* 19:3979-3986, 1991.) Additional examples of promoters include naturally occurring promoters such as the EF1 alpha promoter, the murine CMV promoter, Rous sarcoma virus promoter, and SV40 early/late promoters and the β-actin promoter; and artificial promoters such as a synthetic muscle specific promoter and a chimeric muscle-specific/CMV promoter (Li et al., *Nat. Biotechnol.* 17:241-245, 1999, Hagstrom et al., *Blood* 95:2536-2542, 2000).

The ribosome binding site is located at or near the initiation codon. Examples of preferred ribosome binding sites include CCACCAUGG, CCGCCAUGG, and ACCAUGG, where AUG is the initiation codon. (Kozak, *Cell* 44:283-292, 1986). Another example of a ribosome binding site is GCCACCAUGG (SEQ. ID. NO. 12).

The polyadenylation signal is responsible for cleaving the transcribed RNA and the addition of a poly (A) tail to the RNA. The polyadenylation signal in higher eukaryotes contains an AAUAAA sequence about 11-30 nucleotides from the polyadenylation addition site. The AAUAAA sequence is involved in signaling RNA cleavage. (Lewin, Genes IV, Oxford University Press, NY, 1990.) The poly (A) tail is important for the mRNA processing.

Polyadenylation signals that can be used as part of a gene expression cassette include the minimal rabbit β-globin polyadenylation signal and the bovine growth hormone polyadenylation (BGH). (Xu et al., *Gene* 272:149-156, 2001, Post et al., U.S. Pat. No. 5,122,458.) Additional examples include the Synthetic Polyadenylation Signal (SPA) and SV40 polyadenylation signal. The SPA sequence is as follows: AAUAAAAGAUCUUUAUUUUCAUUAGAUCUGUGUGUUGGUUUUUUGUGUG (SEQ. ID. NO. 13).

Examples of additional regulatory elements useful for enhancing or regulating gene expression or polypeptide processing that may be present include an enhancer, a leader sequence and an operator. An enhancer region increases transcription. Examples of enhancer regions include the CMV enhancer and the SV40 enhancer. (Hitt et al., *Methods in Molecular Genetics* 7:13-30, 1995, Xu, et al., *Gene* 272:149-156, 2001.) An enhancer region can be associated with a promoter.

A leader sequence is an amino acid region on a polypeptide that directs the polypeptide into the proteasome. Nucleic acid encoding the leader sequence is 5' of a structural gene and is transcribed along the structural gene. An example of a leader sequences is tPA.

An operator sequence can be used to regulate gene expression. For example, the Tet operator sequence can be used to repress gene expression.

II. THERAPEUTIC VECTORS

Nucleic acid encoding a Met-NS3-NS4A-NS4B-NS5A-NS5B polypeptide can be introduced into a patient using vectors suitable for therapeutic administration. Suitable vectors can deliver nucleic acid into a target cell without causing an unacceptable side effect.

Cellular expression is achieved using a gene expression cassette encoding a Met-NS3-NS4A-NS4B-NS5A-NS5B polypeptide. The gene expression cassette contains regulatory elements for producing and processing a sufficient amount of nucleic acid inside a target cell to achieve a beneficial effect.

Examples of vectors that can be used for therapeutic applications include first and second generation adenovectors, helper dependent adenovectors, adeno-associated viral vectors, retroviral vectors, alpha virus vectors, Venezuelan Equine Encephalitis virus vector, and plasmid vectors. (Hitt, et al., *Advances in Pharmacology* 40:137-206, 1997, Johnston et al., U.S. Pat. No. 6,156,588, and Johnston et al., International Publication Number WO 95/32733.) Preferred vectors for introducing a Met-NS3-NS4A-NS4B-NS5A-NS5B polypeptide into a subject are first generation adenoviral vectors and plasmid DNA vectors.

A. First Generation Adenovectors

First generation adenovector for expressing a gene expression cassette contain the expression cassette in an E1 and optionally E3 deleted recombinant adenovirus genome. The deletion in the E1 region is sufficiently large to remove elements needed for adenoviral replication.

First generation adenovectors for expressing a Met-NS3-NS4A-NS4B-NS5A-NS5B polypeptide contain a E1 and E3 deleted recombinant adenovirus genome. The deletion in the E1 region is sufficiently large to remove elements needed for adenoviral replication. The combinations of deletions of the E1 and E3 regions are sufficiently large to accommodate a gene expression cassette encoding a Met-NS3-NS4A-NS4B-NS5A-NS5B polypeptide.

The adenovirus has a double-stranded linear genome with inverted terminal repeats at both ends. During viral replication, the genome is packaged inside a viral capsid to form a virion. The virus enters its target cell through viral attachment followed by internalization. (Hitt et al., *Advances in Pharmacology* 40:137-206, 1997.)

Adenovectors can be based on different adenovirus serotypes such as those found in humans or animals. Examples of animal adenoviruses include bovine, porcine, chimp, murine, canine, and avian (CELO). Preferred adenovectors are based on human serotypes, more preferably Group B, C, or D serotypes. Examples of human adenovirus Group B, C, D, or E serotypes include types 2 ("Ad2"), 4 ("Ad4"), ("Ad5"), 6 ("Ad6"), 24 ("Ad24"), 26 ("Ad26"), 34 ("Ad34") and 35 ("Ad35"). Adenovectors can contain regions from a single adenovirus or from two or more adenovirus.

In different embodiments adenovectors are based on Ad5, Ad6, or a combination thereof. Ad5 is described by Chroboczek, et al., *J. Virology* 186:280-285, 1992. Ad6 is described in FIGS. 7A-7N. An Ad6 based vector containing Ad5 regions is described in the Example section provided below.

Adenovectors do not need to have their E1 and E3 regions completely removed. Rather, a sufficient amount the E1 region is removed to render the vector replication incompetent in the absence of the E1 proteins being supplied in trans; and the E1 deletion or the combination of the E1 and E3 deletions are sufficiently large enough to accommodate a gene expression cassette.

E1 deletions can be obtained starting at about base pair 342 going up to about base pair 3523 of Ad5, or a corresponding region from other adenoviruses. Preferably, the deleted region involves removing a region from about base pair 450 to about base pair 3511 of Ad5, or a corresponding region from other adenoviruses. Larger E1 region deletions starting at about base pair 341 removes elements that facilitate virus packaging.

E3 deletions can be obtained starting at about base pair 27865 to about base pair 30995 of Ad5, or the corresponding region of other adenovectors. Preferably the deletion region involves removing a region from about base pair 28134 up to about base pair 30817 of Ad5, or the corresponding region of other adenovectors.

The combination of deletions to the E1 region and optionally the E3 region should be sufficiently large so that the overall size of the recombinant genome containing the gene expression cassette does not exceed about 105% of the wild type adenovirus genome. For example, as recombinant adenovirus Ad5 genomes increase size above about 105% the genome becomes unstable. (Rett et al., *Journal of Virology* 67:5911-5921, 1993.)

Preferably, the size of the recombinant adenovirus genome containing the gene expression cassette is about 85% to about 105% the size of the wild type adenovirus genome. In different embodiments, the size of the recombinant adenovirus genome containing the expression cassette is about 100% to about 105.2%, or about 100%, the size of the wild type genome.

Approximately 7,500 kb can be inserted into an adenovirus genome with a E1 and E3 deletion. Without any deletion, the Ad5 genome is 35,935 base pairs and the Ad6 genome is 35,759 base pairs.

Replication of first generation adenovectors can be performed by supplying the E1 gene products in trans. The E1 gene product can be supplied in trans, for example, by using cell lines that have been transformed with the adenovirus E1 region. Examples of cells and cells lines transformed with the adenovirus E1 region are HEK 293 cells, 911 cells, PERC.6™ cells, and transfected primary human aminocytes cells. (Graham et al., *Journal of Virology* 36:59-72, 1977, Schiedner et al., *Human Gene Therapy* 11:2105-2116, 2000, Fallaux et al., *Human Gene Therapy* 9:1909-1917, 1998, Bout et al., U.S. Pat. No. 6,033,908.)

A Met-NS3-NS4A-NS4B-NS5A-NS5B expression cassette should be inserted into a recombinant adenovirus genome in the region corresponding to the deleted E1 region or the deleted E3 region. The expression cassette can have a parallel or anti-parallel orientation. In a parallel orientation the transcription direction of the inserted gene is the same direction as the deleted E1 or E3 gene. In an anti-parallel orientation transcription the opposite strand serves as a template and the transcription direction is in the opposite direction.

In an embodiment of the present invention the adenovector has a gene expression cassette inserted in the E1 deleted region. The vector contains:

a) a first adenovirus region from about base pair 1 to about base pair 450 corresponding to either Ad5 or Ad6;

b) a gene expression cassette in a E1 parallel or E1 anti-parallel orientation joined to the first region;

c) a second adenovirus region from about base pair 3511 to about base pair 5548 corresponding to Ad5 or from about base pair 3508 to about base pair 5541 corresponding to Ad6, joined to the expression cassette;

d) a third adenovirus region from about base pair 5549 to about base pair 28133 corresponding to Ad5 or from about base pair 5542 to about base pair 28156 corresponding to Ad6, joined to the second region;

e) a fourth adenovirus region from about base pair 30818 to about base pair 33966 corresponding to Ad5 or from about base pair 30789 to about base pair 33784 corresponding to Ad6, joined to the third region; and f) a fifth adenovirus region from about base pair 33967 to about base pair 35935 corresponding to Ad5 or from about base pair 33785 to about base pair 35759 corresponding to Ad6 joined to the fourth region.

In another embodiment of the present invention the adenovector has an expression cassette inserted in the E3 deleted region. The vector contains:

a) a first adenovirus region from about base pair 1 to about base pair 450 corresponding to either Ad5 or Ad6;

b) a second adenovirus region from about base pair 3511 to about base pair 5548 corresponding to Ad5 or from about base pair 3508 to about base pair 5541 corresponding to Ad6, joined to the first region;

c) a third adenovirus region from about base pair 5549 to about base pair 28133 corresponding to Ad5 or from about base pair 5542 to about base pair 28156 corresponding to Ad6, joined to the second region;

d) a gene expression cassette in a E3 parallel or E3 anti-parallel orientation joined to the third region;

e) a fourth adenovirus region from about base pair 30818 to about base pair 33966 corresponding to Ad5 or from about base pair 30789 to about base pair 33784 corresponding to Ad6, joined to the gene expression cassette; and f) fifth adenovirus region from about base pair 33967 to about base pair 35935 corresponding to Ad5 or from about base pair 33785 to about base pair 35759 corresponding to Ad6, joined to the fourth region.

In preferred different embodiments concerning adenovirus regions that are present: (1) the first, second, third, fourth, and fifth region corresponds to Ad5; (2) the first, second, third, fourth, and fifth region corresponds to Ad6; and (3) the first region corresponds to Ad5, the second region corresponds to Ad5, the third region corresponds to Ad6, the fourth region corresponds to Ad6, and the fifth region corresponds to Ad5.

B. DNA Plasmid Vectors

DNA vaccine plasmid vectors contain a gene expression cassette along with elements facilitating replication and preferably vector selection. Preferred elements provide for replication in non-mammalian cells and a selectable marker. The vectors should not contain elements providing for replication in human cells or for integration into human nucleic acid.

The selectable marker facilitates selection of nucleic acids containing the marker. Preferred selectable markers are those that confer antibiotic resistance. Examples of antibiotic selection genes include nucleic acid encoding resistance to ampicillin, neomycin, and kanamycin.

Suitable DNA vaccine vectors can be produced starting with a plasmid containing a bacterial origin of replication and a selectable marker. Examples of bacterial origins of replication providing for higher yields include the ColE1 plasmid-derived bacterial origin of replication. (Donnelly et al., *Annu. Rev. Immunol.* 15:617-648, 1997.)

The presence of the bacterial origin of replication and selectable marker allows for the production of the DNA vector in a bacterial strain such as *E. coli*. The selectable marker is used to eliminate bacteria not containing the DNA vector.

III. AD6 RECOMBINANT NUCLEIC ACID

Ad6 recombinant nucleic acid comprises an Ad6 region substantially similar to an Ad6 region found in SEQ. ID. NO. 8, and a region not present in Ad6 nucleic acid. Recombinant nucleic acid comprising Ad6 regions have different uses such as in producing different Ad6 regions, as intermediates in the production of Ad6 based vectors, and as a vector for delivering a recombinant gene.

Figure 9:
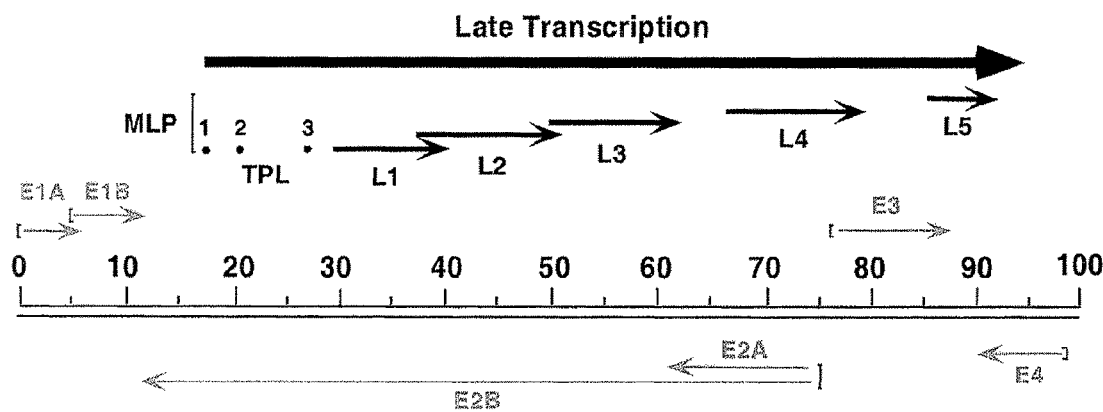

As depicted in FIG. 9, the genomic organization of Ad6 is very similar to the genomic organization of Ad5. The homology between Ad5 and Ad6 is approximately 98%.

In different embodiments, the Ad6 recombinant nucleic acid comprises a nucleotide region substantially similar to E1A, E1B, E2B, E2A, E3, E4, L1, L2, L3, or L4, or any combination thereof. A substantially similar nucleic acid region to an Ad6 region has a nucleotide sequence identity of at least 65%, at least 75%, at least 85%, at least 95%, at least 99% or 100%; or a nucleotide difference of 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-25, 1-30, 1-35, 1-40, 1-45, or 1-50 nucleotides. Techniques and embodiments for determining substantially similar nucleic acid sequences are described in Section I.B. supra.

Preferably, the recombinant Ad6 nucleic acid contains an expression cassette coding for a polypeptide not found in Ad6. Examples of expression cassettes include those coding for HCV regions and those coding for other types of polypeptides.

Different types of adenoviral vectors can be produced incorporating different amounts of Ad6, such as first and second generation adenovectors. As noted in Section II.A, supra. first generation adenovectors are defective in E1 and can replicate when E1 is supplied in trans.

Second generation adenovectors contain less adenoviral genome than first generation vectors and can be used in conjugation with complementing cell lines and/or helper vectors supplying adenoviral proteins. Second generation adenovectors are described in different references such as Russell, *Journal of General Virology* 81:2573-2604, 2000; Hitt et al., 1997, Human Ad vectors for Gene Transfer, Advances in Pharmacology, Vol 40 Academic Press.

In an embodiment of the present invention, the Ad6 recombinant nucleic acid is an adenovirus vector defective in E1 that is able to replicate when E1 is supplied in trans. Expression cassettes can be inserted into a deleted E1 region and/or a deleted E3 region.

An example of an Ad6 based adenoviral vector with an expression cassette provided in a deleted E1 region comprises or consists of:

a) a first adenovirus region from about base pair 1 to about base pair 450 corresponding to either Ad5 or Ad6;

b) a gene expression cassette in a E1 parallel or E1 anti-parallel orientation joined to the first region;

c) a second adenovirus region from about base pair 3511 to about base pair 5548 corresponding to Ad5 or from about base pair 3508 to about base pair 5541 corresponding to Ad6, joined to the expression cassette;

d) a third adenovirus region from about base pair 5549 to about base pair 28133 corresponding to Ad5 or from about base pair 5542 to about base pair 28156 corresponding to Ad6, joined to the second region;

e) an optionally present fourth region from about base pair 28134 to about base pair 30817 corresponding to Ad5, or from about base pair 28157 to about base pair 30788 corresponding to Ad6, joined to the third region;

f) a fifth adenovirus region from about base pair 30818 to about base pair 33966 corresponding to Ad5 or from about base pair 30789 to about base pair 33784 corresponding to Ad6, wherein the fifth region is joined to the fourth region if the fourth region is present, or the fifth is joined to the third region if the fourth region is not present; and g) a sixth adenovirus region from about base pair 33967 to about base pair 35935 corresponding to Ad5 or from about base pair 33785 to about base pair 35759 corresponding to Ad6, joined to the fifth region;

wherein at least one Ad6 region is present.

In different embodiments of the invention, all of the regions are from Ad6; all of the regions expect for the first and second are from Ad6; and 1, 2, 3, or 4 regions selected from the second, third, fourth, and fifth regions are from Ad6.

An example of an Ad6 based adenoviral vector with an expression cassette provided in a deleted E3 region comprises or consists of:

a) a first adenovirus region from about base pair 1 to about base pair 450 corresponding to either Ad5 or Ad6;

b) a second adenovirus region from about base pair 3511 to about base pair 5548 corresponding to Ad5 or from about base pair 3508 to about base pair 5541 corresponding to Ad6, joined to the first region;

c) a third adenovirus region from about base pair 5549 to about base pair 28133 corresponding to Ad5 or from about base pair 5542 to about base pair 28156 corresponding to Ad6, joined to the second region;

d) a gene expression cassette in a E3 parallel or E3 anti-parallel orientation joined to the third region;

e) a fourth adenovirus region from about base pair 30818 to about base pair 33966 corresponding to Ad5 or from about base pair 30789 to about base pair 33784 corresponding to Ad6, joined to the gene expression cassette; and f) a fifth adenovirus region from about base pair 33967 to about base pair 35935 corresponding to Ad5 or from about base pair 33785 to about base pair 35759 corresponding to Ad6, joined to the fourth region;

wherein at least one Ad6 region is present.

In different embodiment of the invention, all of the regions are from Ad6; all of the regions expect for the first and second are from Ad6; and 1, 2, 3, or 4 regions selected from the second, third, fourth and fifth regions are from Ad6.

IV. VECTOR PRODUCTION

Vectors can be produced using recombinant nucleic acid techniques such as those involving the use of restriction enzymes, nucleic acid ligation, and homologous recombination. Recombinant nucleic acid techniques are well known in the art. (Ausubel, *Current Protocols in Molecular Biology*, John Wiley, 1987-1998, and Sambrook et al., *Molecular Cloning, A Laboratory Manual*, $2^{nd}$ Edition, Cold Spring Harbor Laboratory Press, 1989.)

Intermediate vectors are used to derive a therapeutic vector or to transfer an expression cassette or portion thereof from one vector to another vector. Examples of intermediate vectors include adenovirus genome plasmids and shuttle vectors.

Useful elements in an intermediate vector include an origin of replication, a selectable marker, homologous recombination regions, and convenient restriction sites. Convenient restriction sites can be used to facilitate cloning or release of a nucleic acid sequence.

Homologous recombination regions provide nucleic acid sequence regions that are homologous to a target region in another nucleic acid molecule. The homologous regions flank the nucleic acid sequence that is being inserted into the target region. In different embodiments homologous regions are preferably about 150 to 600 nucleotides in length, or about 100 to 500 nucleotides in length.

An embodiment of the present invention describes a shuttle vector containing a Met-NS3-NS4A-NS4B-NS5A-NS5B expression cassette, a selectable marker, a bacterial origin of replication, a first adenovirus homology region and a second adenovirus homology region that target the expression cassette to insert in or replace an E1 region. The first and second homology regions flank the expression cassette. The first homology region contains at least about 100 base pairs substantially homologous to at least the right end (3' end) of a wild-type adenovirus region from about base pairs 4-450. The second homology contains at least about 100 base pairs substantially homologous to at least the left end (5' end) of Ad5 from about base pairs 3511-5792, or the corresponding region from another adenovirus.

Reference to "substantially homologous" indicates a sufficient degree of homology to specifically recombine with a target region. In different embodiments substantially homologous refers to at least 85%, at least 95%, or 100% sequence identity. Sequence identity can be calculated as described in Section I.B. supra.

One method of producing adenovectors is through the creation of an adenovirus genome plasmid containing an expression cassette. The pre-Adenovirus plasmid contains all the adenovirus sequences needed for replication in the desired complimenting cell line. The pre-Adenovirus plasmid is then digested with a restriction enzyme to release the viral ITR's and transfected into the complementing cell line for virus rescue. The ITR's must be released from plasmid sequences to allow replication to occur. Adenovector rescue results in the production on an adenovector containing the expression cassette.

A. Adenovirus Genome Plasmids

Adenovirus genome plasmids contain an adenovector sequence inside a longer-length plasmid (which may be a cosmid). The longer-length plasmid may contain additional elements such as those facilitating growth and selection in eukaryotic or bacterial cells depending upon the procedures employed to produce and maintain the plasmid. Techniques for producing adenovirus genome plasmids include those involving the use of shuttle vectors and homologous recombination, and those involving the insertion of a gene expression cassette into an adenovirus cosmid. (Hitt et al., *Methods in Molecular Genetics* 7:13-30, 1995, Danthinne et al., *Gene Therapy* 7:1707-1714, 2000.)

Adenovirus genome plasmids preferably have a gene expression cassette inserted into a E1 or E3 deleted region. In an embodiment of the present invention, the adenovirus genome plasmid contains a gene expression cassette inserted in the E1 deleted region, an origin of replication, a selectable marker, and the recombinant adenovirus region is made up of:

a) a first adenovirus region from about base pair 1 to about base 450 corresponding to either Ad5 or Ad6;

b) a gene expression cassette in a E1 parallel or E1 anti-parallel orientation joined to the first region;

c) a second adenovirus region from about base pair 3511 to about base pair 5548 corresponding to Ad5 or from about base pair 3508 to about base pair 5541 corresponding to Ad6, joined to the expression cassette;

d) a third adenovirus region from about base pair 5549 to about base pair 28133 corresponding to Ad5 or from about base pair 5542 to about base pair 28156 corresponding to Ad6, joined to the second region;

e) a fourth adenovirus region from about base pair 30818 to about base pair 33966 corresponding to Ad5 or from about base pair 30789 to about base pair 33784 corresponding to Ad6, joined to the third region;

f) a fifth adenovirus region from about base pair 33967 to about base pair 35935 corresponding to Ad5 or from about base pair 33785 to about base pair 35759 corresponding to Ad6, joined to the fourth region, and g) an optionally present E3 region corresponding to all or part of the E3 region present in Ad5 or Ad6, which may be present for smaller inserts taking into account the overall size of the desired adenovector.

In another embodiment of the present invention the recombinant adenovirus genome plasmid has the gene expression cassette inserted in the E3 deleted region. The vector contains an origin of replication, a selectable marker, and the following:

a) a first adenovirus region from about base pair 1 to about base pair 450 corresponding to either Ad5 or Ad6;

b) a second adenovirus region from about base pair 3511 to about base pair 5548 corresponding to Ad5 or from about base pair 3508 to about base pair 5541 corresponding to Ad6, joined to the expression cassette;

c) a third adenovirus region from about base pair 5549 to about base pair 28133 corresponding to Ad5 or from about base pair 5542 to about base pair 28156 corresponding to Ad6, joined to the second region;

d) the gene expression cassette in a E3 parallel or E3 anti-parallel orientation joined to the third region;

e) a fourth adenovirus region from about base pair 30818 to about base pair 33966 corresponding to Ad5 or from about base pair 30789 to about base pair 33784 corresponding to Ad6, joined to the gene expression cassette; and f) a fifth adenovirus region from about base pair 33967 to about base pair 35935 corresponding to Ad5 or from about base pair 33785 to about base pair 35759 corresponding to Ad6, joined to the fourth region.

In different embodiments concerning adenovirus regions that are present: (1) the first, second, third, fourth, and fifth region corresponds to Ad5; (2) the first, second, third, fourth, and fifth region corresponds to Ad6; and (3) the first region corresponds to Ad5, the second region corresponds to Ad5, the third region corresponds to Ad6, the fourth region corresponds to Ad6, and the fifth region corresponds to Ad5.

An embodiment of the present invention describes a method of making an adenovector involving a homologous recombination step to produce a adenovirus genome plasmid and an adenovirus rescue step. The homologous recombination step involves the use of a shuttle vector containing a Met-NS3-NS4A-NS4B-NS5A-NS5B expression cassette flanked by adenovirus homology regions. The adenovirus homology regions target the expression cassette into either the E1 or E3 deleted region.

In an embodiment of the present invention concerning the production of an adenovirus genome plasmid, the gene expression cassette is inserted into a vector comprising: a first adenovirus region from about base pair 1 to about base pair 450 corresponding to either Ad5 or Ad6; a second adenovirus region from about base pair 3511 to about base pair 5548 corresponding to Ad5 or from about base pair 3508 to about base pair 5541 corresponding to Ad6, joined to the second region; a third adenovirus region from about base pair 5549 to about base pair 28133 corresponding to Ad5 or from about base pair 5542 to about base pair 28156 corresponding to Ad6, joined to the second region; a fourth adenovirus region from about base pair 30818 to about base pair 33966 corresponding to Ad5 or from about base pair 30789 to about base pair 33784 corresponding to Ad6, joined to the third region; and a fifth adenovirus region from about 33967 to about 35935 corresponding to Ad5 or from about base pair 33785 to about base pair 35759 corresponding to Ad6, joined to the fourth region. The adenovirus genome plasmid should contain an origin of replication and a selectable marker, and may contain all or part of the Ad5 or Ad6 E3 region.

In different embodiments concerning adenovirus regions that are present: (1) the first, second, third, fourth, and fifth region corresponds to Ad5; (2) the first, second, third, fourth, and fifth region corresponds to Ad6; and (3) the first region corresponds to Ad5, the second region corresponds to Ad5, the third region corresponds to Ad6, the fourth region corresponds to Ad6, and the fifth region corresponds to Ad5.

B. Adenovector Rescue

An adenovector can be rescued from a recombinant adenovirus genome plasmid using techniques known in the art or described herein. Examples of techniques for adenovirus rescue well known in the art are provided by Hitt et al., *Methods in Molecular Genetics* 7:13-30, 1995, and Danthinne et al., *Gene Therapy* 7:1707-1714, 2000.

A preferred method of rescuing an adenovector described herein involves boosting adenoviral replication. Boosting adenoviral replication can be performed, for example, by supplying adenoviral functions such as E2 proteins (polymerase, pre-terminal protein and DNA binding protein) as well as E4 orf6 on a separate plasmid. Example 10 infra. illustrates the boosting of adenoviral replication to rescue an adenovector containing a codon optimized Met-NS3-NS4A-NS4B-NS5A-NS5B expression cassette.

V. PARTIAL-OPTIMIZED HCV ENCODING SEQUENCES

Partial optimization of HCV polyprotein encoding nucleic acid provides for a lesser amount of codons optimized for expression in a human than complete optimization. The overall objective is to provide the benefits of increased expression due to codon optimization, while facilitating the production of an adenovector containing HCV polyprotein encoding nucleic acid having optimized codons.

Complete optimization of an HCV polyprotein encoding sequence provides the most frequently observed human codon for each amino acid. Complete optimization can be performed using codon frequency tables well known in the art and using programs such as the BACKTRANSLATE program (Wisconsin Package version 10, Genetics Computer Group, GCG, Madison, Wis.).

Partial optimization can be preformed on an entire HCV polyprotein encoding sequence that is present (e.g., NS3-NS5B), or one or more local regions that are present. In different embodiments the GC content for the entire HCV encoded polyprotein that is present is no greater than at least about 65%; and the GC content for one or more local regions is no greater than about 70%.

Local regions are regions present in HCV encoding nucleic acid, and can vary in size. For example, local regions can be about 60, about 70, about 80, about 90 or about 100 nucleotides in length.

Partial optimization can be achieved by initially constructing an HCV encoding polyprotein sequence to be partially optimized based on a naturally occurring sequence. Alternatively, an optimized HCV encoding sequence can be used as basis of comparison to produce a partial optimized sequence.

VI. HCV COMBINATION TREATMENT

The HCV Met-NS3-NS4A-NS4B-NS5A-NS5B vaccine can be used by itself to treat a patient, can be used in conjunction with other HCV therapeutics, and can be used with agents targeting other types of diseases. Additional therapeutics include additional therapeutic agents to treat HCV and diseases having a high prevalence in HCV infected persons. Agents targeting other types of disease include vaccines directed against HIV and HBV.

Additional therapeutics for treating HCV include vaccines and non-vaccine agents. (Zein, Expert Opin. Investig. Drugs 10:1457-1469, 2001.) Examples of additional HCV vaccines include vaccines designed to elicit an immune response against an HCV core antigen and the HCV E1, E2 or p7 region. Vaccine components can be naturally occurring HCV polypeptides, HCV mimotope polypeptides or nucleic acid encoding such polypeptides.

HCV mimotope polypeptides contain HCV epitopes, but have a different sequence than a naturally occurring HCV antigen. A HCV mimotope can be fused to a naturally occurring HCV antigen. References describing techniques for producing mimotopes in general and describing different HCV mimotopes are provided in Felici et al. U.S. Pat. No. 5,994,083 and Nicosia et al., International Application Number WO 99/60132.

VII. PHARMACEUTICAL ADMINISTRATION

HCV vaccines can be formulated and administered to a patient using the guidance provided herein along with techniques well known in the art. Guidelines for pharmaceutical administration in general are provided in, for example, *Modern Vaccinology*, Ed. Kurstak, Plenum Med. Co. 1994; *Remington's Pharmaceutical Sciences* $18^{th}$ Edition, Ed. Gennaro, Mack Publishing, 1990; and *Modern Pharmaceutics* $2^{nd}$ Edition, Eds. Banker and Rhodes, Marcel Dekker, Inc., 1990, each of which are hereby incorporated by reference herein.

HCV vaccines can be administered by different routes such intravenous, intraperitoneal, subcutaneous, intramuscular, intradermal, impression through the skin, or nasal. A preferred route is intramuscular.

Intramuscular administration can be preformed using different techniques such as by injection with or without one or more electric pulses. Electric mediated transfer can assist genetic immunization by stimulating both humoral and cellular immune responses.

Vaccine injection can be performed using different techniques, such as by employing a needle or a needless injection system. An example of a needless injection system is a jet injection device. (Donnelly et al., International Publication Number WO 99/52463.)

A. Electrically Mediated Transfer

Electrically mediated transfer or Gene Electra-Transfer (GET) can be performed by delivering suitable electric pulses after nucleic acid injection. (See Mathiesen, International Publication Number WO 98/43702). Plasmid injection and electroporation can be performed using stainless needles. Needles can be used in couples, triplets or more complex patterns. In one configuration the needles are soldered on a printed circuit board that is a mechanical support and connects the needles to the electrical field generator by means of suitable cables.

The electrical stimulus is given in the form of electrical pulses. Pulses can be of different forms (square, sinusoidal, triangular, exponential decay) and different polarity (monopolar of positive or negative polarity, bipolar). Pulses can be delivered either at constant voltage or constant current modality.

Different patterns of electric treatment can be used to introduce nucleic acid vaccines including HCV and other nucleic acid vaccines into a patient. Possible patterns of electric treatment include the following:

Treatment 1: 10 trains of 1000 square bipolar pulses delivered every other second, pulse length 0.2 msec/phase, frequency 1000 Hz, constant voltage mode, 45 Volts/phase, floating current.

Treatment 2: 2 trains of 100 square bipolar pulses delivered every other second, pulse length 2 msec/phase, frequency 100 Hz, constant current mode, 100 mA/phase, floating voltage.

Treatment 3: 2 trains of bipolar pulses at a pulse length of about 2 msec/phase, for a total length of about 3 seconds, where the actual current going through the tissue is fixed at about 50 mA.

Electric pulses are delivered through an electric field generator. A suitable generator can be composed of three independent hardware elements assembled in a common chassis and driven by a portable PC which runs the driving program.

The software manages both basic and accessory functions. The elements of the device are: (1) signal generator driven by a microprocessor, (2) power amplifier and (3) digital oscilloscope.

The signal generator delivers signals having arbitrary frequency and shape in a given range under software control. The same software has an interactive editor for the waveform to be delivered. The generator features a digitally controlled current limiting device (a safety feature to control the maximal current output). The power amplifier can amplify the signal generated up to +/−150 V. The oscilloscope is digital and is able to sample both the voltage and the current being delivered by the amplifier.

B. Pharmaceutical Carriers

Pharmaceutically acceptable carriers facilitate storage and administration of a vaccine to a subject. Examples of pharmaceutically acceptable carriers are described herein. Additional pharmaceutical acceptable carriers are well known in the art.

Pharmaceutically acceptable carriers may contain different components such a buffer, normal saline or phosphate buffered saline, sucrose, salts and polysorbate. An example of a pharmaceutically acceptable carrier is follows: 2.540 mM TRIS buffer, preferably about 5 mM TRIS buffer; 25400 mM NaCl, preferably about 75 mM NaCl; 2.540% sucrose, preferably about 5% sucrose; 0.01-2 mM $MgCl_2$; and 0.001%-0.01% polysorbate 80 (plant derived). The pH is preferably from about 7.0-9.0, more preferably about 8.0. A specific example of a carrier contains 5 mM TRIS, 75 mM NaCl, 5% sucrose, 1 mM $MgCl_2$, 0.005% polysorbate 80 at pH 8.0.

C. Dosing Regimes

Suitable dosing regimens can be determined taking into account the efficacy of a particular vaccine and factors such as age, weight, sex and medical condition of a patient; the route of administration; the desired effect; and the number of doses. The efficacy of a particular vaccine depends on different factors such as the ability of a particular vaccine to produce polypeptide that is expressed and processed in a cell and presented in the context of MHC class I and II complexes.

HCV encoding nucleic acid administered to a patient can be part of different types of vectors including viral vectors such as adenovector, and DNA plasmid vaccines. In different embodiments concerning administration of a DNA plasmid, about 0.1 to 10 mg of plasmid is administered to a patient, and about 1 to 5 mg of plasmid is administered to a patient. In different embodiments concerning administration of a viral vector, preferably an adenoviral vector, about $10^5$ to $10^{11}$ viral particles are administered to a patient, and about $10^7$ to $10^{10}$ viral particles are administered to a patient.

Viral vector vaccines and DNA plasmid vaccines may be administered alone, or may be part of a prime and boost administration regimen. A mixed modality priming and booster inoculation involves either priming with a DNA vaccine and boosting with viral vector vaccine, or priming with a viral vector vaccine and boosting with a DNA vaccine.

Multiple priming, for example, about to 2-4 or more may be used. The length of time between priming and boost may typically vary from about four months to a year, but other time frames may be used. The use of a priming regimen with a DNA vaccine may be preferred in situations where a person has a pre-existing anti-adenovirus immune response.

In an embodiment of the present invention, $1 \times 10^7$ to $1 \times 10^{12}$ particles and preferably about $1 \times 10^{10}$ to $1 \times 10^{11}$ particles of adenovector is administered directly into muscle tissue. Following initial vaccination a boost is performed with an adenovector or DNA vaccine.

In another embodiment of the present invention initial vaccination is performed with a DNA vaccine directly into muscle tissue. Following initial vaccination a boost is performed with an adenovector or DNA vaccine.

Agents such as interleukin-12, GM-CSF, B7-1, B7-2, IP10, Mig-1 can be coadministered to boost the immune response. The agents can be coadministered as proteins or through use of nucleic acid vectors.

D. Heterologous Prime-Boost

Heterologous prime-boost is a mixed modality involving the use of one type of viral vector for priming and another type of viral vector for boosting. The heterologous prime-boost can involve related vectors such as vectors based on different adenovirus serotypes and more distantly related viruses such adenovirus and poxvirus. The use of poxvirus and adenovirus vectors to protect mice against malaria is illustrated by Gilbert et al., *Vaccine* 20:1039-1045, 2002.

Different embodiments concerning priming and boosting involve the following types of vectors expressing desired antigens such as Met-NS3-NS4A-NS4B-NS5A-NS5B: Ad5 vector followed by Ad6 vector; Ad6 vector followed by Ad5 vector; Ad5 vector followed by poxvirus vector; poxvirus vector followed by Ad5 vector; Ad6 vector followed by poxvirus vector; and poxvirus vector followed by Ad6 vector.

The length of time between priming and boosting typically varies from about four months to a year, but other time frames may be used. The minimum time frame should be sufficient to allow for an immunological rest. In an embodiment, this rest is for a period of at least 6 months. Priming may involve multiple priming with one type of vector, such as 2-4 primings.

Expression cassettes present in a poxvirus vector should contain a promoter either native to, or derived from, the poxvirus of interest or another poxvirus member. Different strategies for constructing and employing different types of poxvirus based vectors including those based on vaccinia virus, modified vaccinia virus, avipoxvirus, raccoon poxvirus, modified vaccinia virus Ankara, canarypoxviruses (such as ALVAC), fowlpoxviruses, cowpoxviruses, and NYVAC are well known in the art. (Moss, *Current Topics in Microbiology and Immunology* 158:25-38, 1982; Earl et al., In *Current Protocols in Molecular Biology*, Ausubel et al. eds., New York: Greene Publishing Associates & Wiley Interscience; 1991:16.16.1-16.16.7, Child et al., *Virology* 174(2):625-9, 1990; Tartaglia et al., *Virology* 188:217-232, 1992; U.S. Pat. Nos. 4,603,112, 4,722,848, 4,769,330, 5,110,587, 5,174,993, 5,185,146, 5,266,313, 5,505,941, 5,863,542, and 5,942,235.

E. Adjuvants

HCV vaccines can be formulated with an adjuvant. Adjuvants are particularly useful for DNA plasmid vaccines. Examples of adjuvants are alum, $AlPO_4$, alhydrogel, Lipid-A and derivatives or variants thereof, Freund's incomplete adjuvant, neutral liposomes, liposomes containing the vaccine and cytokines, non-ionic block copolymers, and chemokines.

Non-ionic block polymers containing polyoxyethylene (POE) and polyxylpropylene (POP), such as POE-POP-POE block copolymers may be used as an adjuvant. (Newman et al., *Critical Reviews in Therapeutic Drug Carrier Systems* 15:89-142, 1998.) The immune response of a nucleic acid can be enhanced using a non-ionic block copolymer combined with an anionic surfactant.

A specific example of an adjuvant formulation is one containing CRL-1005 (CytRx Research Laboratories), DNA, and benzylalkonium chloride (BAK). The formulation can be prepared by adding pure polymer to a cold (<5° C.) solution of plasmid DNA in PBS using a positive displacement pipette. The solution is then vortexed to solubilize the polymer. After complete solubilization of the polymer a clear solution is obtained at temperatures below the cloud point of the polymer (~6-7° C.). Approximately 4 mM BAK is then added to the DNA/CRL-1005 solution in PBS, by slow addition of a dilute solution of BAK dissolved in PBS. The initial DNA concentration is approximately 6 mg/mL before the addition of polymer and BAK, and the final DNA concentration is about 5 mg/mL. After BAK addition the formulation is vortexed extensively, while the temperature is allowed to increase from ~2° C. to above the cloud point. The formulation is then placed on ice to decrease the temperature below the cloud point. Then, the formulation is vortexed while the temperature is allowed to increase from ~2° C. to above the cloud point. Cooling and mixing while the temperature is allowed to increase from ~2° C. to above the cloud point is repeated several times, until the particle size of the formulation is about 200-500 nm, as measured by dynamic light scattering. The formulation is then stored on ice until the solution is clear, then placed in storage at −70° C. Before use, the formulation is allowed to thaw at room temperature.

F. Vaccine Storage

Adenovector and DNA vaccines can be stored using different types of buffers. For example, buffer A105 described in Example 9 infra, can be used to for vector storage.

Storage of DNA can be enhanced by removal or chelation of trace metal ions. Reagents such as succinic or malic acid, and chelators can be used to enhance DNA vaccine stability. Examples of chelators include multiple phosphate ligands and EDTA. The inclusion of non-reducing free radical scavengers, such as ethanol or glycerol, can also be useful to prevent damage of DNA plasmid from free radical production. Furthermore, the buffer type, pH, salt concentration, light exposure, as well as the type of sterilization process used to prepare the vials, may be controlled in the formulation to optimize the stability of the DNA vaccine.

VII. EXAMPLES

Examples are provided below to further illustrate different features of the present invention. The examples also illustrate useful methodology for practicing the invention. These examples do not limit the claimed invention.

Example 1

Met-NS3-NS4A-NS4B-NS5A-NS5B Expression Cassettes

Different gene expression cassettes encoding HCV NS3-NS4A-NS4B-NS5A-NS5B were constructed based on a 1b subtype HCV BK strain. The encoded sequences had either (1) an active NS5B sequence ("NS"), (2) an inactive NS5B sequence ("NSmut"), (3) a codon optimized sequence with an inactive NS5B sequence ("NSOPTmut"). The expression cassettes also contained a CMV promoter/enhancer and the BGH polyadenylation The NS nucleotide sequence (SEQ. ID. NO. 5) differs from HCV BK strain GenBank accession number M58335 by 30 out of 5952 nucleotides. The NS amino acid sequence (SEQ. ID. NO. 6) differs from the corresponding 1b genotype HCV BK strain by 7 out of 1984 amino acids. To allow for initiation of translation an ATG codon is present at the 5' end of the NS sequence. A TGA termination sequence is present at the 3' end of the NS sequence.

The NSmut nucleotide sequence (SEQ. ID. NO. 2, FIG. 2), is similar to the NS sequence. The differences between NSmut and NS include NSmut having an altered NS5B catalytic site; an optimal ribosome binding site at the 5' end; and a TAAA termination sequence at the 3' end. The alterations in NS5B comprise bases 5138 to 5146, which encode amino acids 1711 to 1713. The alterations result in a change of amino acids GlyAspAsp into AlaAlaGly and creates an inactive form of the NS5B RNA-dependent RNA-polymerase NS5B.

The NSOPTmut sequence (SEQ. ID. NO. 3, FIG. 3) was designed based on the amino acid sequence encoded by NSmut. The NSmut amino acid sequence was back translated into a nucleotide sequence with the GCG (Wisconsin Package version 10, Genetics Computer Group, GCG, Madison, Wis.) BACKTRANSLATE program. To generate a NSOPTmut nucleotide sequence where each amino acid is coded for by the corresponding most frequently observed human codon, the program was run choosing as parameter the generation of the most probable nucleotide sequence and specifying the codon frequency table of highly expressed human genes (human_high.cod) available within the GCG Package as translation scheme.

Example 2

Generation pV1Jns plasmid with NS, NSmut or NSOPTmut Sequences pV1Jns plasmids containing either the NS sequence, NSmut sequence or NSOPTmut sequences were generated and characterised as follows:

pV1Jns Plasmid with the NS Sequence

The coding region Met-NS3-NS4A-NS4B-NS5A and the coding region Met-NS3-NS4A-NS4B-NS5A-NS5B from a HCV BK type strain (Tomei et al., *J. Virol.* 67:4017-4026, 1993) were cloned into pcDNA3 plasmid (Invitrogen), generating pcD3-5a and pcD3-5b vectors, respectively. PcD3-5A was digested with Hind III, blunt-ended with Klenow fill-in and subsequently digested with Xba I, to generate a fragment corresponding to the coding region of Met-NS3-NS4A-NS4B-NS5A. The fragment was cloned into pV1Jns-poly, digested with Bgl II blunt-ended with Klenow fill-in and subsequently digested with Xba I, generating pV1JnsNS3-5A.

pV1Jns-poly is a derivative of pV1JnsA plasmid (Montgomery et al., *DNA and Cell Biol.* 12:777-783, 1993), modified by insertion of a polylinker containing recognition sites for XbaI, PmeI, PacI into the unique BglII and NotI restriction sites. The pV1Jns plasmid with the NS sequence (pV1JnsNS3-5B) was obtained by homologous recombination into the bacterial strain BJ5183, co-transforming pV1JNS3-5A linearized with XbaI and NotI digestion and a PCR fragment containing approximately 200 bp of NS5A, NS5B coding sequence and approximately 60 bp of the BGH polyadenylation signal. The resulting plasmid represents pV1Jns-NS.

pV1Jns-NS can be summarized as follows:

| | |
|---|---|
| Bases | 1 to 1881 of pV1JnsA |
| an additional | AGCTT |
| then the | Met-NS3-NS5B sequence (SEQ. ID. NO. 5) |
| then the | wt TGA stop |

| an additional | TCTAGAGCGTTTAAACCCTTAATTAAGG (SEQ. ID. NO. 14) |
|---|---|
| Bases | 1912 to 4909 of pV1JnsA | pV1Jns Plasmid with the NSmut Sequence

The V1JnsNS3-5A plasmid was modified at the 5' of the NS3 coding sequence by addition of a full Kozak sequence. The plasmid (V1JNS3-5Akozak) was obtained by homologous recombination into the bacterial strain BJ5183, co-transforming V1JNS3-5A linearized by AflII digestion and a PCR fragment containing the proximal part of Intron A, the restriction site BglII, a full Kozak translation initiation sequence and part of the NS3 coding sequence.

The resulting plasmid (V1JNS3-5Akozak) was linearized with Xba digestion and co-transformed into the bacterial strain BJ5183 with a PCR fragment, containing approximately 200 bp of NS5A, the NS5B mutated sequence, the strong translation termination TAAA and approximately 60 bp of the BGH polyadenylation signal. The PCR fragment was obtained by assembling two 22 bp-overlapping fragments where mutations were introduced by the oligonucleotides used for their amplification. The resulting plasmid represents pV1Jns-NSmut.

pV1Jns-NSmut can be summarized as follows:

| Bases | 1 to 1882 of pV1JnsA |
|---|---|
| then the | kozak Met4-4S3-NS5B(mut) TAAA sequence (SEQ. ID. NO. 2) |
| an additional | TCTAGA |
| Bases | 1925 to 4909 of pV1JnsA | pV1Jns Plasmid with the NSOPTmut Sequence

The human codon-optimized synthetic gene (NSOPTmut) with mutated NS5B to abrogate enzymatic activity, full Kozak translation initiation sequence and a strong translation termination was digested with BamHI and SalI restriction sites present at the 5' and 3' end of the gene. The gene was then cloned into the BglII and SalI restriction sites present in the polylinker of pV1JnsA plasmid, generating pV1Jns-NSOPTmut.

pV1Jns-NSOPTmut can be summarized as follows:

| Bases | 1 to 1881 of pV1JnsA |
|---|---|
| an additional | C |
| then | kozak Met-NS3-NS5B(optmut) TAAA sequence (SEQ. ID. NO. 3) |
| an additional | TTTAAATGTTTAAAC (SEQ. ID. NO. 15) |
| Bases | 1905 to 4909 of pV1JnsA |

Plasmids Characterization

Expression of HCV NS proteins was tested by transfection of HEK 293 cells, grown in 10% FCS/DMEM supplemented by L-glutamine (final 4 mM). Twenty-four hours before transfection, cells were plated in 6-well 35 mm diameter, to reach 90-95% confluence on the day of transfection. Forty nanograms of plasmid DNA (previously assessed as a non-saturating DNA amount) were co-transfected with 100 ng of pRSV-Luc plasmid containing the luciferase reporter gene under the control of Rous sarcoma virus promoter, using the LIPOPECTAMINE 2000 reagent. Cells were kept in a $CO_2$ incubator for 48 hours at 37° C.

Figure 12:
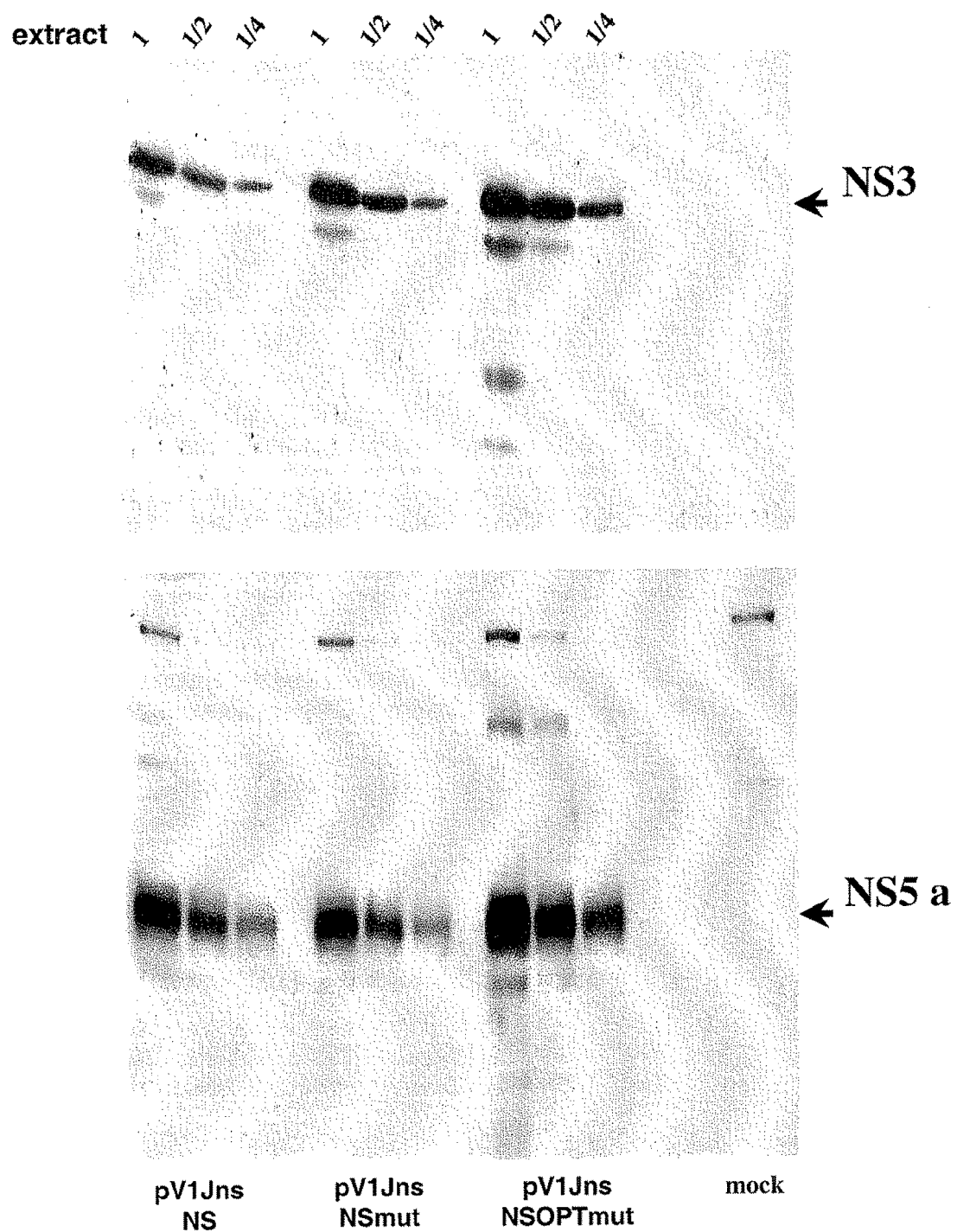

Cell extracts were prepared in 1% Triton/TEN buffer. The extracts were normalized for Luciferase activity, and run in serial dilution on 10% SDS-acrylamide gel. Proteins were transferred on nitrocellulose and assayed with antibodies directed against NS3, NS5A and NS5B to assess strength of expression and correct proteolytic cleavage. Mock-transfected cells were used as a negative control. Results from representative experiments testing pV1JnsNS, pV1JnsNSmut and pV1JnsNSOPTmut are shown in FIG. 12.

Example 3

Mice Immunization with Plasmid DNA Vectors

The DNA plasmids pV1Jns-NS, pV1Jns-NSmut and pV1Jns-NSOPTmut were injected in different mice strains to evaluate their potential to elicit anti-HCV immune responses. Two different strains (Balb/C and C57Black6, N=9-10) were injected intramuscularly with 25 or 50 mg of DNA followed by electrical pluses. Each animal received two doses at three weeks interval.

Humoral immune response elicited in C57Black6 mice against the NS3 protein was measured in post dose two sera by ELISA on bacterially expressed NS3 protease domain. Antibodies specific for the tested antigen were detected in animals immunized with all three vectors with geometric mean titers (GMT) ranging from 94000 to 133000 (Tables 1-3).

TABLE 1

| | pV1jns-NS | | | | | | | | | |
|---|---|---|---|---|---|---|---|---|---|---|
| Mice n. | 1 | 2 | 3 | 4 | 5 | 6 | 7 | 8 | 9 | GMT |
| Titer | 105466 | 891980 | 78799 | 39496 | 543542 | 182139 | 32351 | 95028 | 67800 | 94553 |

TABLE 2

| | pV1jns-NSmut | | | | | | | | | | |
|---|---|---|---|---|---|---|---|---|---|---|---|
| Mice n. | 11 | 12 | 13 | 14 | 15 | 16 | 17 | 18 | 19 | 20 | GMT |
| Titer | 202981 | 55670 | 130786 | 49748 | 17672 | 174958 | 44304 | 37337 | 78182 | 193695 | 75083 |

TABLE 3

| | pV1jns-NSOPTmut | | | | | | | | | | |
|---|---|---|---|---|---|---|---|---|---|---|---|
| Mice n. | 21 | 22 | 23 | 24 | 25 | 26 | 27 | 28 | 29 | 30 | GMT |
| Titer | 310349 | 43645 | 63496 | 82174 | 630778 | 297259 | 66861 | 146735 | 173506 | 77732 | 133165 |

A T cell response was measured in C57Black6 mice immunized with two intramuscular injections at three weeks interval with 25 µg of plasmid DNA. Quantitative ELIspot assay was performed to determine the number of IFNγ secreting T cells in response to five pools of 20mer peptides overlapping by ten residues encompassing the NS3-NS5B sequence. Specific CD8+ response was analyzed by the same assay using a 20mer peptide encompassing a CD8+ epitope for C57Black6 mice (pep1480).

Cells secreting IFNγ in an antigen specific-manner were detected using a standard ELIspot assay. T cell response in C57Black6 mice immunized with two intramuscular injections at three weeks interval with 50 µg of plasmid DNA, was analyzed by the same ELIspot assay measuring the number of IFNγ secreting T cells in response to five pools of 20mer peptides overlapping by ten residues encompassing the NS3-NS5B sequence.

Spleen cells were prepared from immunized mice and re-suspended in R10 medium (RPMI 1640 supplemented with 10% FCS, 2 mM L-Glutamine, 50 U/ml-50 µg/ml Penicillin/Streptomycin, 10 mM Hepes, 50 µM 2-mercapto-ethanol). Multiscreen 96-well Filtration Plates (Millipore, Cat. No. MAIPS4510, Millipore Corporation, 80 Ashby Road Bedford, Mass.) were coated with purified rat anti-mouse INFγ antibody (PharMingen, Cat. No. 18181D, PharmiMingen, 10975 Torreyana Road, San Diego, Calif. 92121-1111 USA). After overnight incubation, plates were washed with PBS 1×/0.005% Tween and blocked with 250 µl/well of R10 medium.

Splenocytes from immunized mice were prepared and incubated for twenty-four hours in the presence or absence of 10 µM peptide at a density of $2.5\times10^5$/well or $5\times10^5$/well. After extensive washing (PBS 1×/0.005% Tween), biotinylated rat anti-mouse IFNγ antibody (PharMingen, Cat. No. 18112D, PharMingen, 10975 Torreyana Road, San Diego, Calif. 92121-1111 USA) was added and incubated overnight at 4° C. For development, streptavidin-AKP (PharMingen, Cat. No. 13043E, PharMingen, 10975 Torreyana Road, San Diego, Calif. 92121-1111 USA) and 1-Step™ NBT-BCIP development solution (Pierce, Cat. No. 34042, Pierce, P.O. Box 117, Rockford, Ill. 61105 USA) were added.

Pools of 20mer overlapping peptides encompassing the entire sequence of the HCV BK strain NS3 to NS5B were used to reveal HCV-specific IFNγ-secreting T cells. Similarly a single 20mer peptide encompassing a CD8+ epitope for C57Black6 mice was used to detect CD8 response. Representative data from groups of C57Black6 and Balb/C mice (N=9-10) immunized with two injections of 25 or 50 µg of plasmid vectors pV1Jns-NS, pV1Jns-NSmut and pV1Jns-NSOPTmut are shown in FIGS. 13A and 13B.

Example 4

Immunization of Rhesus Macaques

Rhesus macaques (N=3) were immunized by intramuscular injection with 5 mg of plasmid pV1Jns-NSOPTmut in 7.5 mg/ml CRL1005, Benzalkonium chloride 0.6 mM. Each animal received two doses in the deltoid muscle at 0, and 4 weeks.

CMI was measured at different time points by IFN-γ ELISPOT. This assay measures HCV antigen-specific CD8+ and CD4+ T lymphocyte responses, and can be used for a variety of mammals, such as humans, rhesus monkeys, mice, and rats.

The use of a specific peptide or a pool of peptides can simplify antigen presentation in CTL cytotoxicity assays, interferon-gamma ELISPOT assays and interferon-gamma intracellular staining assays. Peptides based on the amino acid sequence of various HCV proteins (core, E2, NS3, NS4A, NS4B, NS5A, NS5B) were prepared for use in these assays to measure immune responses in HCV DNA and adenovirus vector vaccinated rhesus monkeys, as well as in HCV-infected humans. The individual peptides are overlapping 20-mers, offset by 10 amino acids. Large pools of peptides can be used to detect an overall response to HCV proteins while smaller pools and individual peptides may be used to define the epitope specificity of a response.

IFNγ ELISPOT

The IFNγ-ELISPOT assay provides a quantitative determination of HCV-specific T lymphocyte responses. PBMC are serially diluted and placed in microplate wells coated with anti-rhesus IFN-γ antibody (MD-1 U-Cytech). They are cultured with a HCV peptide pool for 20 hours, resulting in the restimulation of the precursor cells and secretion of IFN-γ. The cells are washed away, leaving the secreted IFN bound to the antibody-coated wells in concentrated areas where the cells were sitting. The captured IFN is detected with biotinylated anti-rhesus IFN antibody (detector Ab U-Cytech) followed by alkaline phosphatase-conjugated streptavidin (Pharmingen 13043E). The addition of insoluble alkaline phosphatase substrate results in dark spots in the wells at the sites where the cells were located, leaving one spot for each T cell that secreted IFN-γ.

The number of spots per well is directly related to the precursor frequency of antigen-specific T cells. Gamma interferon was selected as the cytokine visualized in this assay (using species specific anti-gamma interferon monoclonal antibodies) because it is the most common, and one of the most abundant cytokines synthesized and secreted by activated T lymphocytes. For this assay, the number of spot forming cells (SFC) per million PBMCs is determined for samples in the presence and absence (media control) of peptide antigens. Data from Rhesus macaques on PBMC from post dose two material are shown in Table 4.

TABLE 4

| Pep pools | PV1J-NSOPTmut | | |
|---|---|---|---|
| | 21G | 99C161 | 99C166 |
| F (NS3p) | 8 | 10 | 170 |
| G (NS3h) | 7 | 592 | 229 |
| H (NS4) | 3 | 14 | 16 |
| I (NS5a) | 5 | 71 | 36 |
| L (NS5b) | 14 | 23 | 11 |
| M (NS5b) | 3 | 35 | 8 |
| DMSO | 2 | 4 | 5 |

INFyELISPOT on PBMC from Rhesus monkeys immunized with two injections of 5 mg DNA/dose in OPTIVAX/BAK of plasmid pV1Jns-NSOPTmut. Data are expressed as SFC7 $10^6$ PBMC.

Example 5

Construction of Ad6 Pre-Adenovirus Plasmids

Ad6 pre-adenovirus plasmids were obtained as follows:
Construction of pAd6 E1-E3+ Pre-Adenovirus Plasmid An Ad6 based pre-adenovirus plasmid which can be used to generate first generation Ad6 vectors was constructed either taking advantage of the extensive sequence identity (approx. 98%) between Ad5 and Ad6 or containing only Ad6 regions, Homologous recombination was used to clone wtAd6 sequences into a bacterial plasmid.

Figure 10:
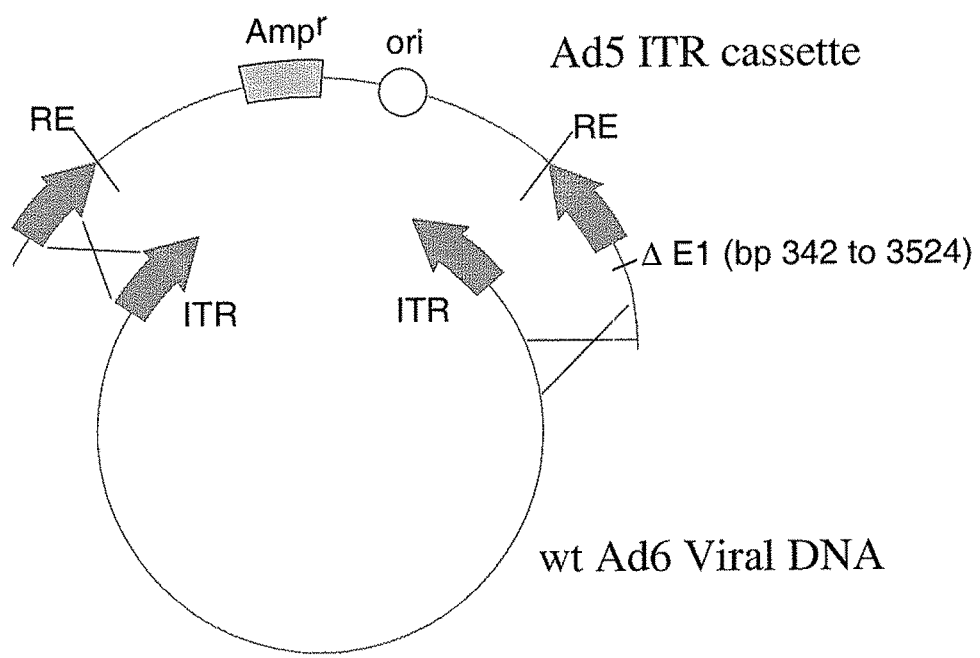

A general strategy used to recover pAd6E1-E3+ as a bacterial plasmid containing Ad5 and Ad6 regions is illustrated in FIG. 10. Cotransformation of BJ 5183 bacteria with purified wt Ad6 viral DNA and a second DNA fragment termed the Ad5 ITR cassette resulted in the circularization of the viral genome by homologous recombination. The ITR cassette contains sequences from the right (bp 33798 to 35935) and left (bp 1 to 341 and by 3525 to 5767) end of the Ad5 genome separated by plasmid sequences containing a bacterial origin of replication and an ampicillin resistance gene. The ITR cassette contains a deletion of E1 sequences from Ad5 342 to 3524. The Ad5 sequences in the ITR cassette provide regions of homology with the purified Ad6 viral DNA in which recombination can occur.

Potential clones were screened by restriction analysis and one clone was selected as pAd6E1-E3+. This clone was then sequenced in it entirety. pAd6E1-E3+ contains Ad5 sequences from bp 1 to 341 and from bp 3525 to 5548, Ad6 bp 5542 to 33784, and Ad5 bp 33967 to 35935 (bp numbers refer to the wt sequence for both Ad5 and Ad6). pAd6E1-E3+ contains the coding sequences for all Ad6 virion structural proteins which constitute its serotype specificity.

Figure 11:
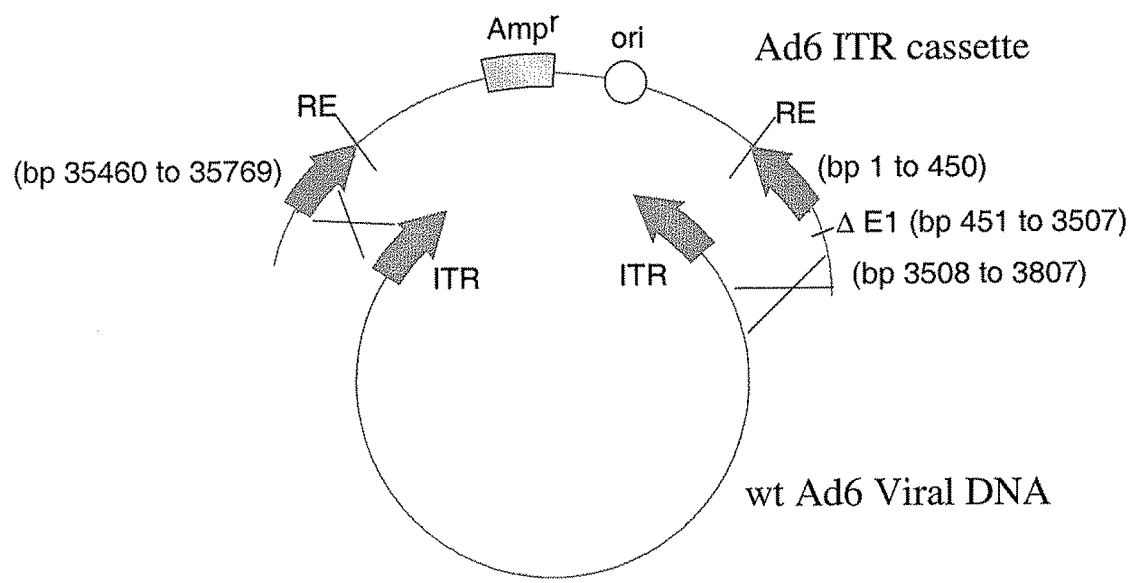

A general strategy used to recover pAd6E1-E3+ as a bacterial plasmid containing Ad6 regions is illustrated in FIG. 11. Cotransformation of BJ 5183 bacteria with purified wt Ad6 viral DNA and a second DNA fragment termed the Ad6 ITR cassette resulted in the circularization of the viral genome by homologous recombination. The ITR cassette contains sequences from the right (bp 35460 to 35759) and left (bp 1 to 450 and bp 3508 to 3807) end of the Ad6 genome separated by plasmid sequences containing a bacterial origin of replication and an ampicillin resistance gene. These three segments were generated by PCR and cloned sequentially into pNEB193, generating pNEBAd6-3 (the ITR cassette). The ITR cassette contains a deletion of E1 sequences from Ad5 451 to 3507. The Ad6 sequences in the ITR cassette provide regions of homology with the purified Ad6 viral DNA in which recombination can occur.

Construction of pAd6 E1-E3-Pre-Adenovirus Plasmids

Ad6 based vectors containing A5 regions and deleted in the E3 region were constructed starting with pAd6E1-E3+ containing Ad5 regions. A 5322 bp subfragment of pAd6E1-E3+ containing the E3 region (Ad6 bp 25871 to 31192) was subcloned into pABS.3 generating pABSAd6E3. Three E3 deletions were then made in this plasmid generating three new plasmids pABSAd6E3 (1.8 Kb) (deleted for Ad6 bp 28602 to 30440), pABSAd6E3 (2.3 Kb) (deleted for Ad6 bp 28157 to 30437) and pABSAd6E3 (2.6 Kb) (deleted for Ad6 bp 28157 to 30788). Bacterial recombination was then used to substitute the three E3 deletions back into pAd6E1-E3+ generating the Ad6 genome plasmids pAd6E1-E3-1.8 Kb, pAd6E1-E3-2.3 Kb and pAd6E1-E3-2.6 Kb.

Example 6

Generation of Ad5 Genome Plasmid with the NS Sequence

A pcDNA3 plasmid (Invitrogen) containing the coding region NS3-NS4A-NS4B-NS5A was digested with XmnI and NruI restriction sites and the DNA fragment containing the CMV promoter, the NS3-NS4A-NS4B-NS5A coding sequence and the Bovine Growth Hormone (BGH) polyadenylation signal was cloned into the unique EcorV restriction site of the shuttle vector pDelE1Spa, generating the Sva3-5A vector.

A pcDNA3 plasmid containing the coding region NS3-NS4A-NS4B-NS5A-NS5B was digested with XmnI and EcorI (partial digestion), and the DNA fragment containing part of NS5A, NS5B gene and the BGH polyadenylation signal was cloned into the Sva3-5A vector, digested EcorI and BglII blunted with Klenow, generating the Sva3-5B vector.

The Sva3-5B vector was finally digested SspI and Bst1107I restriction sites and the DNA fragment containing the expression cassette (CMV promoter, NS3-NS4A-NS4B-NS5A-NS5B coding sequence and the BGH polyadenylation signal) flanked by adenovirus sequences was co-transformed with pAd5HVO (E1-, E3-) ClaI linearized genome plasmid into the bacterial strain BJ5183, to generate pAd5HVONS. pAd5HVO contains Ad5 bp 1 to 341, bp 3525 to 28133 and bp 30818 to 35935.

Example 7

Generation of Adenovirus Genome Plasmids with the NSmut Sequence

Adenovirus genome plasmids containing an NS-rut sequence were generated in an Ad5 or Ad6 background. The Ad6 background contained Ad5 regions at bases 1 to 450, 3511 to 5548 and 33967 to 35935.

pV1JNS3-5Akozak was digested with BglII and XbaI restriction enzymes and the DNA fragment containing the Kozak sequence and the sequence coding NS3-NS4A-NS4B-NS5A was cloned into a BglII and XbaI digested polypM-RKpdelE1 shuttle vector. The resulting vector was designated shNS3-5Akozak.

PolypMRKpdelE1 is a derivative of RKpdelE1(Pac/pIX/pack450)+CMVmin+BGHpA(str.) modified by the insertion of a polylinker containing recognition sites for BglII, PmeI, Swat, XbaI, SalI, into the unique BglII restriction site present downstream the CMV promoter. MRKpdelE1 (Pac/pa/ pack450)+CMVmin+BGHpA(str.) contains Ad5 sequences from bp 1 to 5792 with a deletion of E1 sequences from bp 451 to 3510. The human CMV promoter and BGH polyadenylation signal were inserted into the E1 deletion in an E1 parallel orientation with a unique BglII site separating them.

The NS5B fragment, mutated to abrogate enzymatic activity and with a strong translation termination at the 3' end, was obtained by assembly PCR and inserted into the shNS3-5Akozak vector via homologous recombination, generating polypMRKpdelE1NSmut. In polypMRKpdelE1NSmut the NS-mut coding sequence is under the control of CMV promoter and the BGH polyadenylation signal is present downstream.

The gene expression cassette and the flanking regions which contain adenovirus sequences allowing homologous recombination were excised by digestion with PacI and Bst1107I restriction enzymes and co-transformed with either pAd5HVO (E1-, E3-) or pAd6E1-E3-2.6 Kb ClaI linearized genome plasmids into the bacterial strain BJ5183, to generate pAd5HVONSmut and pAd6E1-, E3-NSmut, respectively.

pAd6E1-E3-2.6 Kb contains Ad5 bp 1 to 341 and from bp 3525 to 5548, Ad6 bp 5542 to 28157 and from bp 30788 to 33784, and Ad5 bp 33967 to 35935 (bp numbers refer to the wt sequence for both Ad5 and Ad6). In both plasmids the viral ITR's are joined by plasmid sequences that contain the bacterial origin of replication and an ampicillin resistance gene.

Example 8

Generation of Adenovirus Genome Plasmids with the NSOPTmut

The human codon-optimized synthetic gene (NSOPTmut) provided by SEQ. ID. NO. 3 cloned into a pCRBlunt vector (Invitrogen) was digested with BamH1 and SalI restriction enzymes and cloned into BglII and SaiI restriction sites present in the shuttle vector polypMRKpdelE1. The resulting clone (polypMRKpdelE1NSOPTmut) was digested with PadI and Bst1107I restriction enzymes and co-transformed with either pAd5HVO (E1-, E3-) or pAd6E1-E3-2.6 Kb ClaI linearized genome plasmids, into the bacterial strain BJ5183, to generate pAd5HVONSOPTmut and pAd6E1-, E3-NSOPTmut, respectively.

Example 9

Rescue and Amplification of Adenovirus Vectors

Adenovectors were rescued in Per.6 cells. Per.C6 were grown in 10% FCS/DMEM supplemented by L-glutamine (final 4 mM), penicillin/streptomycin (final 100 IU/ml) and 10 mM $MgCl_2$. After infection, cells were kept in the same medium supplemented by 5% horse serum (HS). For viral rescue, $2.5\times10^6$ Per.C6 were plated in 6 cm ø Petri dishes.

Twenty-four hours after plating, cells were transfected by calcium phosphate method with 10 µg of the Pac I linearized adenoviral DNA. The DNA precipitate was left on the cells for 4 hours. The medium was removed and 5% HS/DMEM was added.

Cells were kept in a $CO_2$ incubator until a cytopathic effect was visible (1 week). Cells and supernatant were recovered and subjected to 3× freeze/thawing cycles (liquid nitrogen/water bath at 37° C.). The lysate was centrifuged at 3000 rpm at −4° C. for 20 minutes and the recovered supernatant (corresponding to a cell lysate containing virus passed on cells only once; P1) was used, in the amount of 1 ml/dish, to infect 80-90% confluent Per.C6 in 10 cm ø Petri dishes. The infected cells were incubated until a cytopathic effect was visible, cells and supernatant recovered and the lysate prepared as described above (P2).

P2 lysate (4 ml) were used to infect 2×15 cm ø Petri dishes. The lysate recovered from this infection (P3) was kept in aliquots at −80° C. as a stock of virus to be used as starting point for big viral preparations. In this case, 1 ml of the stock was enough to infect 2×15 cm ø Petri dishes and resulting lysate (P4) was used for the infection of the Petri dishes devoted to the large scale infection.

Further amplification was obtained from the P4 lysate which was diluted in medium without FCS and used to infect 30×15 cm ø Petri dishes (with Per.C6 80%-90% confluent) in the amount of 10 ml/dish. Cells were incubated 1 hour in the $CO_2$ incubator, mixing gently every 20 minutes. 12 ml/dish of 5% HS/DMEM was added and cells were incubated until a cytopathic effect was visible (about 48 hours).

Cells and supernatant were collected and centrifuged at 2K rpm for 20 minutes at 4° C. The pellet was resuspended in 15 ml of 0.1 M Tris pH=8.0. Cells were lysed by 3× freeze/thawing cycles (liquid nitrogen/water bath at 37° C.). 150 µl of 2 M $MgCl_2$ and 75 µl of DNAse (10 mg of bovine pancreatic deoxyribonuclease in 10 ml of 20 mM Tris-HCl pH=7.4, 50 mM NaCl, 1 mM dithiothreitol, 0.1 mg/ml bovine serum albumin, 50% glycerol) were added. After a 1 hour incubation at 37° C. in a water bath (vortex every 15 minutes) the lysate was centrifuged at 4K rpm for 15 minutes at 4° C. The recovered supernatant was ready to be applied on CsCl gradient.

The CsCl gradients were prepared in SW40 ultra-clear tubes as follows:
0.5 ml of 1.5d CsCl
3 ml of 1.35d CsCl
3 ml of 1.25d CsCl
5-ml/tube of viral supernatant was applied.

If necessary, the tubes were topped up with 0.1 M tris-Cl Tubes were centrifuged at 35K rpm for 1 hour at −10° C. with rotor SW40. The viral bands (located at the 1.25/1.35 interface) were collected using a syringe.

The virus was transferred into a new SW40 ultraclear tube and 1.35d CsCl was added to top the tube up. After centrifugation at 35K rpm for 24 hours at 10° C. in the rotor SW40, the virus was collected in the smallest possible volume and dialyzed extensively against buffer A105 (5 mM Tris, 5% sucrose, 75 mM NaCl, 1 mM $MgCl_2$, 0.005% polysorbate 80 pH=8.0). After dialysis, glycerol was added to final 10% and the virus was stored in aliquots at ±80° C.

Example 10

Enhanced Adenovector Rescue

First generation Ad5 and Ad6 vectors carrying HCV NSOPTmut transgene were found to be difficult to rescue. A possible block in the rescue process might be attributed to an inefficient replication of plasmid DNA that is a sub-optimal template for the replication machinery of adenovirus. The absence of the terminal protein linked to the 5' ends of the DNA (normally present in the viral DNA), associated with the very high G-C content of the transgene inserted in the E1 region of the vector, may be causing a substantial reduction in replication rate of the plasmid-derived adenovirus.

Figure 19:
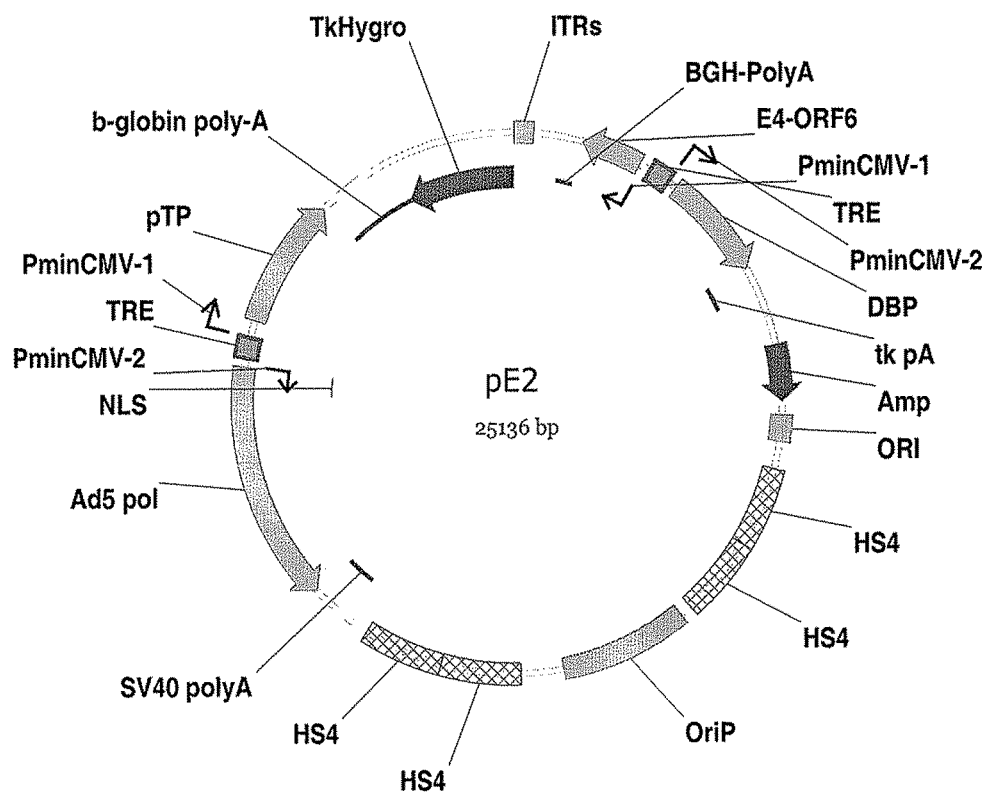

To set up a more efficient and reproducible procedure for rescuing Ad vectors, an expression vector (pE2; FIG. 19) containing all E2 proteins (polymerase, pre-terminal protein and DNA binding protein) as well as E4 orf6 under the control of tet-inducible promoter was employed. The transfection of pE2 in combination with a normal preadeno plasmid in PerC6 and in 293 leads to a strong increase of Ad DNA replication and to a more efficient production of complete infectious adenovirus particles.

Plasmid Construction pE2 is based on the cloning vector pBI (CLONTECH) with the addition of two elements to allow episomal replication and selection in cell culture: (1) the EBV-OriP (EBV [nt] 7421-8042) region permitting plasmid replication in synchrony with the cell cycle when EBNA-1 is expressed and (2) the hygromycin-B phosphotransferase (HPH)-resistance gene allowing a positive selection of transformed cells. The two transcriptional units for the adenoviral genes E2 a and b and E4-Orf6 were constructed and assembled in pE2 as described below.

The Ad5-Polymerase ClaI/SphI fragment and the Ad5-pTP Acc65/EcoRV fragment were obtained from pVac-Pol and pVac-pTP (Stunnenberg et al. *NAR* 16:2431-2444, 1988). Both fragments were filled with Klenow and cloned into the SalI (filled) and EcoR V sites of pBI, respectively obtaining pBI-Pol/pTP.

EBV-OriP element from pCEP4 (Invitrogen) was first inserted within two chicken β-globin insulator dimers by cloning it into BamHI site of pJC13-1 (Chung et al., *Cell* 74(3):505-14, 1993). HS4-OriP fragment from pJC13-OriP was then cloned inside pSA1mv (a plasmid containing tk-Hygro-B resistance gene expression cassette as well as Ad5 replication origin), the ITR's arranged as head-to-tail junction, obtained by PCR from pFG140 (Graham, *EMBO J.* 3:2917-2922, 1984) using the following primers: 5'-TCGAATCGATACGCGAACCTACGC-3' (SEQ. ID. NO. 16) and 5'-TCGACGTGTCGACTTCGAAGCGCACAC-CAAAAACGTC-3' (SEQ. ID. NO. 17), thus generating pMVHS4Orip. A DNA fragment from pMVHS4Orip, containing the insulated OriP, Ad5 ITR junction and tk-HygroB cassette, was then inserted into pBI-Pol/pTP vector restricted AseI/AatII generating pBI-Pol/pTPHS4

To construct the second transcriptional unit expressing Ad5-Orf6 as well as Ad5-DBP, E4orf6 (Ad 5 [nt] 33193-34077) obtained by PCR was first inserted into pBI vector, generating pBI-Orf6. Subsequently, DBP coding DNA sequence (Ad 5 [nt] 22443-24032) was inserted into pBI-Orf6 obtaining the second bi-directional Tet-regulated expression vector (pBI-DBP/E4orf6). The original polyA signals present in pBI were substituted with BGH and SV40 polyA. pBI-DBP/E4orf6 was then modified by inserting a DNA fragment containing the Adeno5-ITRs arranged in head-to-tail junction plus the hygromycin B resistance gene obtained from plasmid pSA-1mv. The new plasmid pBI-DBP/E4orf6shuttle was then used as donor plasmid to insert the second tet-regulated transcriptional unit into pBI-Pol/pTPHS4 by homologous recombination using *E. coli* strain BJ5183 obtaining pE2.

Cell lines, Transfections and Virus Amplification

PerC6 cells were cultured in Dulbecco's modified Eagle's Medium (DMEM) plus 10% fetal bovine serum (FBS), 10 mM $MgCl_2$, penicillin (100 U/ml), streptomycin (100 μg/ml) and 2 mM glutamine.

All transient transfections were performed using Lipofectamine-2000 (Invitrogen) as described by the manufacturer. 90% confluent PERC.6™ planted in 6-cm plates were transfected with 3.5 μg of Ad5/6NSOPTmut pre-adeno plasmids, digested with PadI, alone or in combination with 5 μg pE2 plus 1 μg pUHD52.1. pUHD52.1 is the expression vector for the reverse tet transactivator 2 (rtTA2) (Urlinger et al., *Proc. Natl. Acad. Sci.* 97(14):7963-7968, 2000). Upon transfection, cells were cultivated in the presence of 1 μg/ml of doxycycline to activate pE2 expression. 7 days post-transfection cells were harvested and cell lysate was obtained by three cycles of freeze-thaw. Two ml of cell lysate were used to infect a second 6-cm dish of PerC6. Infected cells were cultivated until a full CPE was observed then harvested. The virus was serially passaged five times as described above, then purified on CsCl gradient. The DNA structure of the purified virus was controlled by endonuclease digestion and agarose gel electrophoresis analysis and compared to the original pre-adeno plasmid restriction pattern.

Example 11

Partial Optimization of HCV Polyprotein Encoding Nucleic Acid

Partial optimization of HCV polyprotein encoding nucleic acid was performed to facilitate the production of adenovectors containing codons optimized for expression in a human host. The overall objective was to provide for increased expression due to codon optimization, while facilitating the production of an adenovector encoding HCV polyprotein.

Several difficulties were encountered in producing an adenovector encoding HCV polyprotein with codons optimized for expression in a human host. An adenovector containing an optimized sequence (SEQ. ID. NO. 3) was found to be more difficult to synthesize and rescue than an adenovector containing a non-optimized sequence (SEQ. ID. NO. 2).

The difficulties in producing an adenovector containing SEQ. ID. NO. 3 were attributed to a high GC content. A particularly problemetic region was the region at about position 3900 of NSOPTmut (SEQ. ID. NO. 3).

Alternative versions of optimized HCV encoding nucleic acid sequence were designed to facilitate its use in an adenovector. The alternative versions, compared to NSOPTmut, were designed to have a lower overall GC content, to reduce/avoid the presence of potentially problematic motifs of consecutive G's or C's, while maintaining a high level of codon optimization to allow improved expression of the encoded polyprotein and the individual cleavage products.

A starting point for the generation of a suboptimally codon-optimized sequence is the coding region of the NSOPTmut nucleotide sequence (bases 7 to 5961 of SEQ. ID. NO. 3). Values for codon usage frequencies (normalized to a total of 1.0 for each amino acid) were taken from the file human_high.cod available in the Wisconsin Package Version 10.3 (Accelrys Inc., a wholly owned subsidiary of Pharmacopeia, Inc).

To reduce the local and overall GC content a table defining preferred codon substitutions for each amino acid was manually generated. For each amino acid the codon having 1) a lower GC content as compared to the most frequent codon and 2) a relatively high observed codon usage frequency (as defined in human_high.cod) was chosen as the replacement codon. For example for Arg the codon with the highest frequency is CGC. Out of the other five alternative codons encoding Arg (COG, AGG, AGA, CGT, CGA) three (AGG, CGT, CGA) reduce the GC content by 1 base, one (AGA) by two bases and one (CGG) by 0 bases. Since the AGA codon is listed in human_high.cod as having a relatively low usage frequency (0.1), the codon substituting CGC was therefore chosen to be AGG with a relative frequency of 0.18. Similar criteria were applied in order to establish codon replacements for the other amino acids resulting in the list shown in Table 5. Parameters applied in the following optimization procedure were determined empirically such that the resulting sequence maintained a considerably improved codon usage (for each amino acid) and the GC content (overall and in fowl of local stretches of consecutive G's and/or C's) was decreased.

Two examples of partial optimized HCV encoding sequences are provided by SEQ. ID. NO. 10 and SEQ. ID. NO. 11. SEQ. ID. NO. 10 provides a HCV encoding sequence that is partially optimized throughout. SEQ. ID. NO. 11 provides an HCV encoding sequence fully optimized for codon usage with the exception of a region that was partially optimized.

Codon optimization was performed using the following procedure:

Step 1) The coding region of the input fully optimized NSOPTmut sequence was analyzed using a sliding window of 3 codons (9 bases) shifting the window by one codon after each cycle. Whenever a stretch containing 5 or more consecutive C's and/or G's was detected in the window the following replacement rule was applied: Let N indicate the number of codon replacements previously performed. If N is odd replace the middle codon in the window with the codon specified in Table 5, if N is even replace the third terminal codon in the window with the codon specified in a codon optimization table such as human_high.cod. If Leu or Val is present at the second or third codon do not apply any replacement in order not to introduce Leu or Val codons with very low relative codon usage frequency (see, for example, human_high.cod). In the following cycle analysis of the shifted window was then applied to a sequence containing the replacements of the previous cycle.

The alternating replacement of the middle and terminal codon in the 3 codon window was found empirically to give a more satisfying overall maintenance of optimized codon usage while also reducing GC content (as judged from the final sequence after the procedure). In general, however, the precise replacement strategy depends on the amino acid sequence encoded by the nucleotide sequence under analysis and will have to be determined empirically.

Step 2) The sequence containing all the codon replacements performed during step 1) was then subjected to an additional analysis using a sliding window of 21 codons (63 bases) in length: according to an adjustable parameter the overall GC content in the window was determined. If the GC content in the window was higher than 70% the following codon replacement strategy was applied: In the window replace the codons for the amino acids Asn, Asp, Cys, Glu, His, He, Lys, Phe, Tyr by the codons given in Table 5. Restriction of the replacement to this set of amino acids was motivated by the fact that a) the replacement codon still has an acceptably high frequency of usage in human_high.cod and b) the average overall human codon usage in CUTG for the replacement codon is nearly as high as the most frequent codon. In the following cycle analysis of the shifted window is then applied to a sequence containing the replacements of the previous cycle.

The threshold 70% was determined empirically by compromising between an overall reduction in GC content and maintenance of a high codon optimization for the individual amino acids. As in step 1) the precise replacement strategy (choice of amino acids and GC content threshold value) will again depend on the amino acid sequence encoded by the nucleotide sequence under analysis and will have to be determined empirically.

Step 3) The sequence generated by steps 1) and 2) was then manually edited and additional codons were changed according to the following criteria: Regions still having a GC content higher than 70% over a window of 21 codons were examined manually and a few codons were replaced again following the scheme given in Table 5.

Subsequent steps were performed to provide for useful restriction sites, remove possible open reading frames on the complementary strand, to add homologous recombinant regions, to add a Kozac signal, and to add a terminator. These steps are numbered 4-7

Step 4) The sequence generated in step 3 was examined for the absence of certain restriction sites (BglII, PmeI and XbaI) and presence of only 1 StuI site to allow a subsequent cloning strategy using a subset of restriction enzymes. Two sites (one for BglII and one for StuI) were removed from the sequence by replacing codons that were part of the respective recognition sites.

Step 5) The sequence generated by steps 1) through 4) was then modified according to allow subsequent generation of a modified NSOPTmut sequence (by homologous recombination). In the sequence obtained from steps 1) through 4) the segment comprising base 3556 to 3755 and the segment comprising base 4456 to 4656 were replaced by the corresponding segments from NSOPTmut. The segment comprising bases 3556 to 4656 of SEQ. ID. NO. 10 can be used to replace the problematic region in NSOPTmut (around position 3900) by homologous recombination thus creating the variant of NSOPTmut having the sequence of SEQ. ID. NO. 11.

Step 6) Analysis of the sequence generated through steps 1) to 5) revealed a potential open reading frame spanning nearly the complete fragment on the complementary strand. Removal of all codons CTA and TTA (Leu) and TCA (Ser) from the sense strand effectively removed all stop codons in one of the reading frames on the complementary strand. Although the likelihood for transcription of this complementary strand open reading frame and subsequent translation into protein is very small, in order to exclude a potential interference with the transcription and subsequent translation of the sequence encoded on the sense strand, TCA codons for Ser were introduced on the sense approximately every 500 bases. No changes were introduced in the segments introduced during step 5) to allow homologous recombination. The TCA codon for Ser was preferred over the CTA and TTA codons for Leu because of the higher relative frequency for TCA (0.05) as compared to CTA (0.02) and TTA (0.03) in human_high.cod. In addition, the average human codon usage from CUTG favored TCA (0.14 against 0.07 for CTA and TTA).

Step 7) In a final step GCCACC was added at the 5' end of the sequence to generate an optimized internal ribosome entry site (Kozak signal) and a TAAA stop signal was added at the 3'. To maintain the initiation of translation properties of NSsuboptmut the first 8 codons of the coding region were kept identical to the NSOPTmut sequence. The resulting sequence was again checked for the absence of BglII, PmeI and XbaI recognition sites and the presence of only 1 StuI site.

The NSsuboptmut sequence (SEQ. ID. NO. 10) has an overall reduced GC content (63.5%) as compared to NSOPTmut (703%) and maintains a well optimized level of codon usage optimization. Nucleotide sequence identity of NSsuboptmut is 77.2% with respect to NSmut.

TABLE 5

Definition of codon replacements performed during steps 1) and 2).

| Amino Acid | Most frequent codon | Relative frequency | Reduction in GC content (bases) | Replacement codon | Relative frequency |
|---|---|---|---|---|---|
| | Amino Acids where the replacement codon reduces the codon GC-content by 1 base |
| Ala | GCC | 0.51 | 1 | GCT | 0.17 |
| Arg | CGC | 0.37 | 1 | AGG | 0.18 |
| Asn | AAC | 0.78 | 1 | AAT | 0.22 |
| Asp | GAC | 0.75 | 1 | GAT | 0.25 |
| Cys | TGC | 0.68 | 1 | TGT | 0.32 |
| Glu | GAG | 0.75 | 1 | GAA | 0.25 |
| Gln | CAG | 0.88 | 1 | CAA | 0.12 |
| Gly | GGC | 0.50 | 1 | GGA | 0.14 |
| His | CAC | 0.79 | 1 | CAT | 0.21 |
| Ile | ATC | 0.77 | 1 | ATT | 0.18 |
| Lys | AAG | 0.82 | 1 | AAA | 0.18 |
| Phe | TTC | 0.80 | 1 | TTT | 0.20 |
| Pro | CCC | 0.48 | 1 | CCT | 0.19 |
| Ser | AGC | 0.34 | 1 | TCT | 0.13 |
| Thr | ACC | 0.51 | 1 | ACA | 0.14 |
| Tyr | TAC | 0.74 | 1 | TAT | 0.26 |
| | Amino Acids with no alternative codon |
| Met | ATG | 1.00 | 0 | ATG | 1.00 |
| Trp | TGG | 1.00 | 0 | TGG | 1.00 |
| | Amino Acids where the replacement codon has a very low relative frequency. These amino acids were excluded from the replacement procedure |
| Leu | CTG | 0.58 | 1 | TTG | 0.06 |
| Val | GTG | 0.64 | 1 | GTT | 0.07 |

Example 12

Virus Characterization

Adenovectors were characterized by: (a) measuring the physical particles/ml; (b) running a TaqMan PCR assay; and (c) checking protein expression after infection of HeLa cells.

a) Physical Particles Determination

CsCl purified virus was diluted 1/10 and 1/100 in 0.1% SDS PBS. As a control, buffer A105 was used. These dilutions were incubated 10 minutes at 55° C. After spinning the tubes briefly, O.D. at 260 nm was measured. The amount of viral particles was calculated as follows: 1 OD 260 nm=1.1× $10^{12}$ physical particles/ml. The results were typically between $5 \times 10^{11}$ and $1 \times 10^{12}$ physical particles/ml.

b) TaqMan PCR Assay

TaqMan PCR assay was used for adenovectors genome quantification (Q-PCR particles/ml). TaqMan PCR assay was performed using the ABI Prism 7700-sequence detector. The reaction was performed in a final 50 µl volume in the presence of oligonucleotides (at final 200 nM) and probe (at final 200 µM) specific for the adenoviral backbone. The virus was diluted 1/10 in 0.1% SDS PBS and incubated 10 minutes at 55° C. After spinning the tube briefly, serial 1/10 dilutions (in water) were prepared. 10 µl the $10^{-3}$, $10^{-5}$ and $10^{-7}$ dilutions were used as templates in the PCR assay.

The amount of particles present in each sample was calculated on the basis of a standard curve run in the same experiment. Typically results were between $1 \times 10^{12}$ and $3 \times 10^{12}$ Q-PCR particles/ml.

c) Expression of HCV Non-Structural Proteins

Expression of HCV NS proteins was tested by infection of HeLa cells. Cells were plated the day before the infection at $1.5 \times 10^6$ cells/dish (10 cm ø Petri dishes). Different amounts of CsCl purified virus corresponding to m.o.i. of 50, 250 and 1250 pp/cell were diluted in medium (FCS free) up to a final volume of 5 ml. The diluted virus was added on the cells and incubated for 1 hour at 37° C. in a $CO_2$ incubator (gently mixing every 20 minutes). 5 ml of 5% HS-DMEM was added and the cells were incubated at 37° C. for 48 hours.

Figure 14:
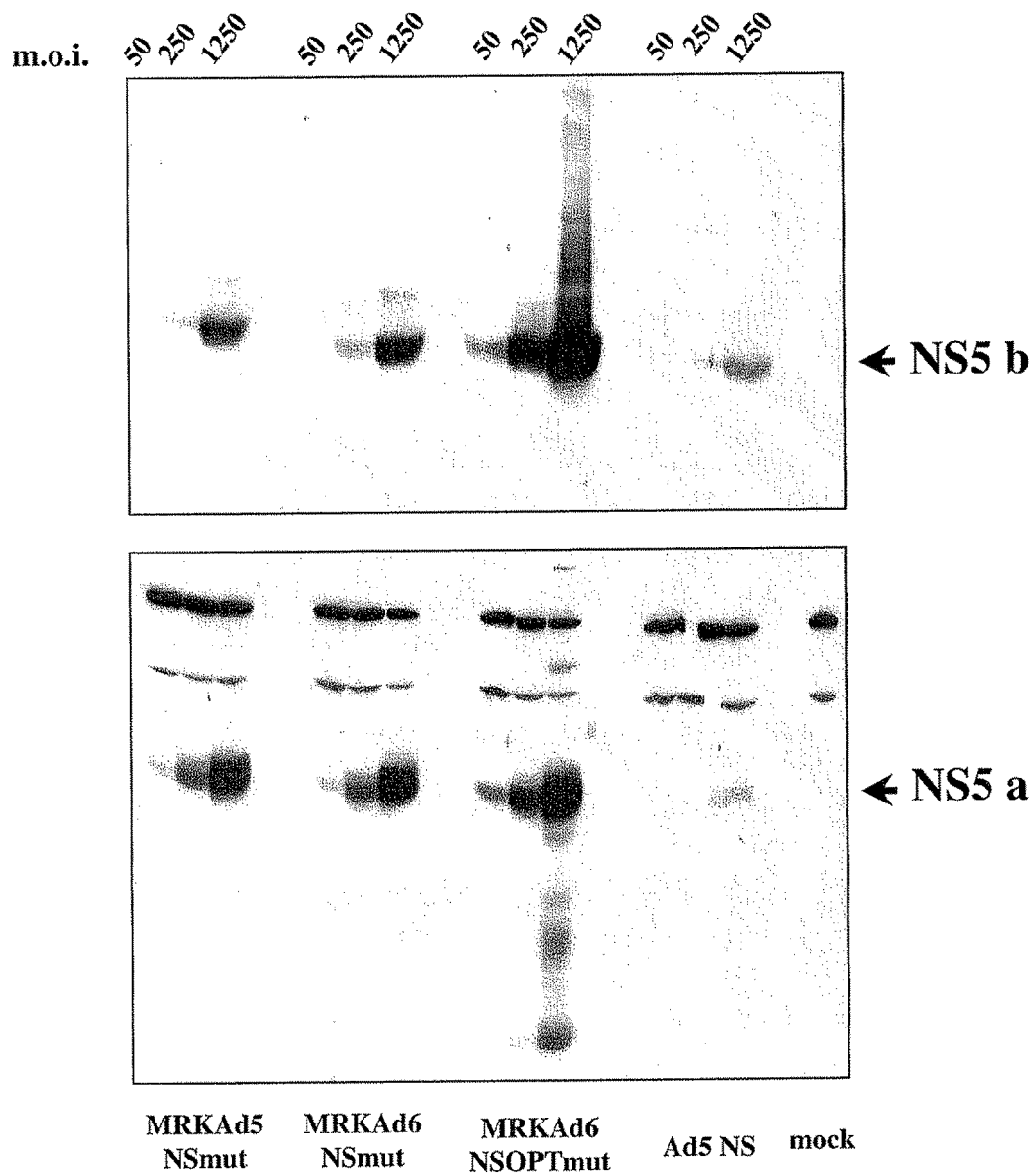

Cell extracts were prepared in 1% Triton/TEN buffer. The extracts were run on 10% SDS-acrylamide gel, blotted on nitrocellulose and assayed with antibodies directed against NS3, NS5a and NS5b in order to check the correct polyprotein cleavage. Mock-infected cells were used as a negative control. Results from representative experiments testing the Ad5-NS, MRKAd5-NSmut, MRKAd6-NSmut and MRKAd6-NSOPTmut are shown in FIG. 14.

Example 13

Mice Immunization with Adenovectors Encoding Different NS Cassettes

The adenovectors Ad5-NS, MRKAd5-NSmut, MRKAd6-NSmut and MRKAd6-NSOPTmut were injected in C57Black6 mice strains to evaluate their potential to elicit anti-HCV immune responses. Groups of animals (N=9-10) were injected intramuscularly with $10^9$ pp of CsCl purified virus. Each animal received two doses at three weeks interval.

Humoral immune response against the NS3 protein was measured in post dose two sera from C57Black6 immunized mice by ELISA on bacterially expressed NS3 protease domain. Antibodies specific for the tested antigen were detected with geometric mean titers (GMT) ranging from 100 to 46000 (Tables 6, 7, 8 and 9).

TABLE 6

| | Ad5-NS | | | | | | | | | | |
|---|---|---|---|---|---|---|---|---|---|---|---|
| Mice n. | 1 | 2 | 3 | 4 | 5 | 6 | 7 | 8 | 9 | 10 | GMT |
| Titer | 50 | 253 | 50 | 50 | 50 | 2257 | 504 | 50 | 50 | 50 | 108 |

TABLE 7

| | Ad5-NSmut | | | | | | | | | | |
|---|---|---|---|---|---|---|---|---|---|---|---|
| Mice n. | 11 | 12 | 13 | 14 | 15 | 16 | 17 | 18 | 19 | 20 | GMT |
| Titer | 3162 | 78850 | 87241 | 6796 | 12134 | 3340 | 18473 | 13093 | 76167 | 49593 | 23645 |

TABLE 8

| | MRKAd6-NSmut | | | | | | | | | | |
|---|---|---|---|---|---|---|---|---|---|---|---|
| Mice n. | 21 | 22 | 23 | 24 | 25 | 26 | 27 | 28 | 29 | 30 | GMT |
| Titer | 125626 | 39751 | 40187 | 65834 | 60619 | 69933 | 21555 | 49348 | 29290 | 26859 | 46461 |

TABLE 9

| | MRKAd6-NSOPTmut | | | | | | | |
|---|---|---|---|---|---|---|---|---|
| Mice n. | 31 | 32 | 33 | 34 | 35 | 36 | 37 | GMT |
| Titer | 25430 | 3657 | 893 | 175 | 10442 | 49540 | 173 | 2785 |

T cell response in C57Black6 mice was analyzed by the quantitative ELISPOT assay measuring the number of IFNγ secreting T cells in response to five pools (named from F to L+M) of 20mer peptides overlapping by ten residues encompassing the NS3-NS5B sequence. Specific CD8+ response induced in C57Black6 mice was analyzed by the same assay using a 20mer peptide encompassing a CD8+ epitope for C57Black6 mice (pep1480). Cells secreting IFNγ in an antigen specific-manner were detected using a standard ELIspot assay.

Spleen cells, splenocytes and peptides were produced and treated as described in Example 3, supra. Representative data from groups of C57Black6 mice (N=9-10) immunized with two injections of $10^9$ viral particles of vectors Ad5-NS, MRKAd5-NSmut and MRKAd6-NSmut are shown in FIG. 15.

Example 14

Immunization of Rhesus macaques with Adenovectors

Rhesus macaques (N=3-4) were immunized by intramuscular injection of CsCl purified Ad5-NS, MRKAd5-NSmut, MRKAd6-NSmut or MRKAd6-NSOPTmut virus. Each animal received two doses of $10^{11}$ or $10^{10}$ vp in the deltoid muscle at 0, and 4 weeks.

CMI was measured at different time points by a) IFN-γ ELISPOT (see Example 3, supra), b) IFN-γ ICS and c) bulk CTL assays. These assays measure HCV antigen-specific CD8+ and CD4+ T lymphocyte responses, and can be used for a variety of mammals, such as humans, rhesus monkeys, mice, and rats.

The use of a specific peptide or a pool of peptides can simplify antigen presentation in CTL cytotoxicity assays, interferon-gamma ELISPOT assays and interferon-gamma intracellular staining assays. Peptides based on the amino acid sequence of various HCV proteins (core, E2, NS3, NS4A, NS4B, NS5a, NS5b) were prepared for use in these assays to measure immune responses in HCV DNA and adenovirus vector vaccinated rhesus monkeys, as well as in HCV-infected humans. The individual peptides are overlapping 20-mers, offset by 10 amino acids. Large pools of peptides can be used to detect an overall response to HCV proteins while smaller pools and individual peptides may be used to define the epitope specificity of a response.

IFN-γICS

For IFN-γ ICS, $2\times10^6$ PBMC in 1 ml R10 (RPMI medium, supplemented with 10% FCS) were stimulated with peptide pool antigens. Final concentration of each peptide was 2 μg/ml. Cells were incubated for 1 hour in a $CO_2$ incubator at 37° C. and then Brefeldin A was added to a final concentration of 10 μg/ml to inhibit the secretion of soluble cytokines. Cells were incubated for additional 14-16 hours at 37° C.

Stimulation was done in the presence of co-stimulatory antibodies: CD28 and CD49d (anti-humanCD28 BD340975 and anti-humanCD49d BD340976). After incubation, cells were stained with fluorochrome-conjugated antibodies for surface antigens: anti-CD3, anti-CD4, anti-CD8 (CD3-APC Biosource APS0301, CD4-PE BD345769, CD8-PerCP BD345774).

To detect intracellular cytokines, cells were treated with FACS permeabilization buffer 2 (BD340973), 2× final concentration. Once fixed and permeabilized, cells were incubated with an antibody against human IFN-γ, IFN-γFITC (Biosource AHC4338).

Cells were resuspended in 1% formaldehyde in PBS and analyzed at FACS within 24 hours. Four color FACS analysis was performed on a FACSCalibur instrument (Becton Dickinson) equipped with two lasers. Acquisition was done gating on the lymphocyte population in the Forward versus Side Scatter plot coupled with the CD3, CD8 positive populations. At least 30,000 events of the gate were taken. The positive cells are expressed as number of IFN-γ expressing cells over $10^6$ lymphocytes.

IFN-γ ELISPOT and IFN-γ ICS data from immunized monkeys after one or two injections of $10^{10}$ or $10^{11}$ vp of the different adenovectors are reported in FIGS. 16A-16D, 17A, and 17B.

Bulk CTL Assays

A distinguishing effector function of T lymphocytes is the ability of subsets of this cell population to directly lyse cells exhibiting appropriate MHC-associated antigenic peptides. This cytotoxic activity is most often associated with CD8+ T lymphocytes.

PBMC samples were infected with recombinant vaccine viruses expressing HCV antigens in vitro for approximately 14 days to provide antigen restimulation and expansion of memory T cells. Cytotoxicity against autologous B cell lines treated with peptide antigen pools was tested.

The lytic function of the culture is measured as a percentage of specific lysis resulted from chromium released from target cells during 4 hours incubation with CTL effector cells. Specific cytotoxicity is measured and compared to irrelevant antigen or excipient-treated B cell lines. This assay is semi-quantitative and is the preferred means for determining whether CTL responses were elicited by the vaccine. Data after two injections from monkeys immunized with $10^{11}$ vp/dose with adenovectors Ad5-NS, MRKAd5-NSmut and MRKAd6-NSmut are reported in FIGS. 18A-18F.

Other embodiments are within the following claims. While several embodiments have been shown and described, various modifications may be made without departing from the spirit and scope of the present invention.

What is claimed is:

1. A recombinant nucleic acid comprising one or more Ad6 regions and a region not present in Ad6, wherein at least one Ad6 region is selected from the group consisting of: E1A, E1B, E2B, E2A, E4, L1, L2, L4, and L5, wherein said region not present in Ad6, is an expression cassette coding for a polypeptide not found in Ad6 and wherein said recombinant nucleic acid is an adenovirus vector defective in at least E1 that is able to replicate when E1 is supplied in trans, wherein the Ad6 region E2A, E2B, or both E2A and E2B are present in the nucleic acid.

2. A recombinant nucleic acid comprising one or more Ad6 regions and a region not present in Ad6, wherein said region not present in Ad6 is an expression cassette coding for a polypeptide not found in Ad6, wherein said recombinant nucleic acid is an adenovirus vector defective in at least E1 that is able to replicate when E1 is supplied in trans, wherein said vector consists of:

a) a first adenovirus region from about base pair 1 to about base pair 450 corresponding to either Ad5 or Ad6; the base pairs corresponding to SEQ ID NO:8 representing Ad6 adenovirus or SEQ ID NO:9 representing Ad5 adenovirus;

b) said gene expression cassette in an E1 parallel or E1 anti-parallel orientation joined to said first region;

c) a second adenovirus region from about base pair 3511 to about base pair 5548 corresponding to Ad5, the base pairs corresponding to SEQ ID NO:9, or from about base pair 3508 to about base pair 5541 corresponding to Ad6, the base pairs corresponding to SEQ ID NO:8, joined to said gene expression cassette;

d) a third adenovirus region from about base pair 5549 to about base pair 28133 corresponding to Ad5, the base pairs corresponding to SEQ ID NO:9, or from about base pair 5542 to about base pair 28156 corresponding to Ad6, the base pairs corresponding to SEQ ID NO:8, joined to said second region;

e) an optionally present fourth region from about base pair 28134 to about base pair 30817 corresponding to Ad5, the base pairs corresponding to SEQ ID NO:9, or from about base pair 28157 to about 30789 corresponding to Ad6, the base pairs corresponding to SEQ ID NO:8, joined to said third region;

f) a fifth adenovirus region from about base pair 30818 to about base pair 33966 corresponding to Ad5, the base pairs corresponding to SEQ ID NO:9, or from about base pair 30789 to about base pair 33784 corresponding to Ad6, the base pairs corresponding to SEQ ID NO:8, wherein said fifth region is joined to said fourth region if said fourth region is present, or said fifth is joined to said third region if said fourth region is not present; and g) a sixth adenovirus region from about base pair 33967 to about base pair 35935 corresponding to Ad5, the base pairs corresponding to SEQ ID NO:9, or from about base pair 33785 to about base pair 35759 corresponding to Ad6, the base pairs corresponding to SEQ ID NO:8, joined to said fourth region;

provided that at least one of said second, third, and fifth regions is from Ad6.

3. A recombinant nucleic acid comprising one or more Ad6 regions and a region not present in Ad6, wherein said region not present in Ad6 is an expression cassette coding for a polypeptide not found in Ad6, wherein said recombinant nucleic acid is an adenovirus vector defective in at least E1 that is able to replicate when E1 is supplied in trans., wherein said vector consists of:

a) a first adenovirus region from about base pair to about base pair 450 corresponding to either Ad5 or Ad6, the base pairs corresponding to SEQ ID NO:8 representing Ad6 adenovirus or SEQ ID NO:9 representing Ad5 adenovirus;

b) a second adenovirus region from about base pair 3511 to about base pair 5548 corresponding to Ad5, the base pairs corresponding to SEQ ID NO:9, or from about base pair 3508 to about base pair 5541 corresponding to Ad6, the base pairs corresponding to SEQ ID NO:8, joined to said first region;

c) a third adenovirus region from about base pair 5549 to about base pair 28133 corresponding to Ad5, the base pairs corresponding to SEQ ID NO:9, or from about base pair 5542 to about base pair 28156 corresponding to Ad6, the base pairs corresponding to SEQ ID NO:8, joined to said second region;

d) said gene expression cassette in a E3 parallel or E3 anti-parallel orientation joined to said third region;

e) a fourth adenovirus region from about base pair 30818 to about base pair 33966 corresponding to Ad5, the base pairs corresponding to SEQ ID NO:9, or from about base pair 30789 to about base pair 33784 corresponding to Ad6, the base pairs corresponding to SEQ ID NO:8, joined to said gene expression cassette; and f) a fifth adenovirus region from about base pair 33967 to about base pair 35935 corresponding to Ad5, the base pairs corresponding to SEQ ID NO:9, or from about base pair 33785 to about base pair 35759 corresponding to Ad6, the base pairs corresponding to SEQ ID NO:8, joined to said fourth region;

provided that at least one of said second, third, and fourth regions is from Ad6.

* * * * *

SEQUENCE LISTING

<160> NUMBER OF SEQ ID NOS: 17

<210> SEQ ID NO 1
<211> LENGTH: 1985
<212> TYPE: PRT
<213> ORGANISM: Artificial Sequence
<220> FEATURE:
<223> OTHER INFORMATION: Met-NS3-NS4A-NS4B-NS5A-NS5B polypeptide

<400> SEQUENCE: 1

```
Met Ala Pro Ile Thr Ala Tyr Ser Gln Gln Thr Arg Gly Leu Leu Gly
 1               5                  10                  15

Cys Ile Ile Thr Ser Leu Thr Gly Arg Asp Lys Asn Gln Val Glu Gly
             20                  25                  30

Glu Val Gln Val Val Ser Thr Ala Thr Gln Ser Phe Leu Ala Thr Cys
         35                  40                  45

Val Asn Gly Val Cys Trp Thr Val Tyr His Gly Ala Gly Ser Lys Thr
     50                  55                  60

Leu Ala Gly Pro Lys Gly Pro Ile Thr Gln Met Tyr Thr Asn Val Asp
 65                  70                  75                  80

Gln Asp Leu Val Gly Trp Gln Ala Pro Pro Gly Ala Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Val Ser Tyr Leu Lys Gly Ser Ser Gly Gly Pro Leu
    130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
            180                 185                 190

Ala Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ala Pro Val Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ser Thr Thr Ile Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Asn Thr Gly Glu Ile Pro Phe Tyr Gly
            340                 345                 350
```

-continued

```
Lys Ala Ile Pro Ile Glu Ala Ile Arg Gly Gly Arg His Leu Ile Phe
            355                 360                 365
Cys His Ser Lys Lys Cys Asp Glu Leu Ala Ala Lys Leu Ser Gly
        370                 375                 380
Leu Gly Ile Asn Ala Val Ala Tyr Tyr Arg Gly Leu Asp Val Ser Val
385                 390                 395                 400
Ile Pro Thr Ile Gly Asp Val Val Val Ala Thr Asp Ala Leu Met
            405                 410                 415
Thr Gly Tyr Thr Gly Asp Phe Asp Ser Val Ile Asp Cys Asn Thr Cys
            420                 425                 430
Val Thr Gln Thr Val Asp Phe Ser Leu Asp Pro Thr Phe Thr Ile Glu
            435                 440                 445
Thr Thr Thr Val Pro Gln Asp Ala Val Ser Arg Ser Gln Arg Arg Gly
        450                 455                 460
Arg Thr Gly Arg Gly Arg Arg Gly Ile Tyr Arg Phe Val Thr Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Gly Thr Ser Val
            500                 505                 510
Arg Leu Arg Ala Tyr Leu Asn Thr Pro Gly Leu Pro Val Cys Gln Asp
        515                 520                 525
His Leu Glu Phe Trp Glu Ser Val Phe Thr Gly Leu Thr His Ile Asp
        530                 535                 540
Ala His Phe Leu Ser Gln Thr Lys Gln Ala Gly Asp Asn Phe Pro Tyr
545                 550                 555                 560
Leu Val Ala Tyr Gln Ala Thr Val Cys Ala Arg Ala Gln Ala Pro Pro
                565                 570                 575
Pro Ser Trp Asp Gln Met Trp Lys Cys Leu Ile Arg Leu Lys Pro Thr
            580                 585                 590
Leu His Gly Pro Thr Pro Leu Leu Tyr Arg Leu Gly Ala Val Gln Asn
        595                 600                 605
Glu Val Thr Leu Thr His Pro Ile Thr Lys Tyr Ile Met Ala Cys Met
610                 615                 620
Ser Ala Asp Leu Glu Val Val Thr Ser Thr Trp Val Leu Val Gly Gly
625                 630                 635                 640
Val Leu Ala Ala Leu Ala Ala Tyr Cys Leu Thr Thr Gly Ser Val Val
                645                 650                 655
Ile Val Gly Arg Ile Ile Leu Ser Gly Arg Pro Ala Ile Val Pro Asp
            660                 665                 670
Arg Glu Phe Leu Tyr Gln Glu Phe Asp Glu Met Glu Glu Cys Ala Ser
            675                 680                 685
His Leu Pro Tyr Ile Glu Gln Gly Met Gln Leu Ala Glu Gln Phe Lys
        690                 695                 700
Gln Lys Ala Leu Gly Leu Leu Gln Thr Ala Thr Lys Gln Ala Glu Ala
705                 710                 715                 720
Ala Ala Pro Val Val Glu Ser Lys Trp Arg Ala Leu Glu Thr Phe Trp
                725                 730                 735
Ala Lys His Met Trp Asn Phe Ile Ser Gly Ile Gln Tyr Leu Ala Gly
            740                 745                 750
Leu Ser Thr Leu Pro Gly Asn Pro Ala Ile Ala Ser Leu Met Ala Phe
        755                 760                 765
Thr Ala Ser Ile Thr Ser Pro Leu Thr Thr Gln Ser Thr Leu Leu Phe
        770                 775                 780
```

```
Asn Ile Leu Gly Gly Trp Val Ala Ala Gln Leu Ala Pro Pro Ser Ala
785                 790                 795                 800

Ala Ser Ala Phe Val Gly Ala Gly Ile Ala Gly Ala Ala Val Gly Ser
            805                 810                 815

Ile Gly Leu Gly Lys Val Leu Val Asp Ile Leu Ala Gly Tyr Gly Ala
            820                 825                 830

Gly Val Ala Gly Ala Leu Val Ala Phe Lys Val Met Ser Gly Glu Met
            835                 840                 845

Pro Ser Thr Glu Asp Leu Val Asn Leu Leu Pro Ala Ile Leu Ser Pro
            850                 855                 860

Gly Ala Leu Val Val Gly Val Val Cys Ala Ala Ile Leu Arg Arg His
865                 870                 875                 880

Val Gly Pro Gly Glu Gly Ala Val Gln Trp Met Asn Arg Leu Ile Ala
            885                 890                 895

Phe Ala Ser Arg Gly Asn His Val Ser Pro Thr His Tyr Val Pro Glu
            900                 905                 910

Ser Asp Ala Ala Ala Arg Val Thr Gln Ile Leu Ser Ser Leu Thr Ile
            915                 920                 925

Thr Gln Leu Leu Lys Arg Leu His Gln Trp Ile Asn Glu Asp Cys Ser
            930                 935                 940

Thr Pro Cys Ser Gly Ser Trp Leu Arg Asp Val Trp Asp Trp Ile Cys
945                 950                 955                 960

Thr Val Leu Thr Asp Phe Lys Thr Trp Leu Gln Ser Lys Leu Leu Pro
            965                 970                 975

Gln Leu Pro Gly Val Pro Phe Phe Ser Cys Gln Arg Gly Tyr Lys Gly
            980                 985                 990

Val Trp Arg Gly Asp Gly Ile Met Gln Thr Thr Cys Pro Cys Gly Ala
            995                 1000                1005

Gln Ile Thr Gly His Val Lys Asn Gly Ser Met Arg Ile Val Gly Pro
1010                1015                1020

Lys Thr Cys Ser Asn Thr Trp His Gly Thr Phe Pro Ile Asn Ala Tyr
1025                1030                1035                1040

Thr Thr Gly Pro Cys Thr Pro Ser Pro Ala Pro Asn Tyr Ser Arg Ala
            1045                1050                1055

Leu Trp Arg Val Ala Ala Glu Glu Tyr Val Glu Val Thr Arg Val Gly
            1060                1065                1070

Asp Phe His Tyr Val Thr Gly Met Thr Thr Asp Asn Val Lys Cys Pro
            1075                1080                1085

Cys Gln Val Pro Ala Pro Glu Phe Phe Thr Glu Val Asp Gly Val Arg
            1090                1095                1100

Leu His Arg Tyr Ala Pro Ala Cys Arg Pro Leu Leu Arg Glu Glu Val
1105                1110                1115                1120

Thr Phe Gln Val Gly Leu Asn Gln Tyr Leu Val Gly Ser Gln Leu Pro
            1125                1130                1135

Cys Glu Pro Glu Pro Asp Val Ala Val Leu Thr Ser Met Leu Thr Asp
            1140                1145                1150

Pro Ser His Ile Thr Ala Glu Thr Ala Lys Arg Arg Leu Ala Arg Gly
            1155                1160                1165

Ser Pro Pro Ser Leu Ala Ser Ser Ser Ala Ser Gln Leu Ser Ala Pro
            1170                1175                1180

Ser Leu Lys Ala Thr Cys Thr Thr His His Val Ser Pro Asp Ala Asp
1185                1190                1195                1200

Leu Ile Glu Ala Asn Leu Leu Trp Arg Gln Glu Met Gly Gly Asn Ile
```

```
                1205                1210                1215
Thr Arg Val Glu Ser Glu Asn Lys Val Val Leu Asp Ser Phe Asp
            1220                1225                1230

Pro Leu Arg Ala Glu Glu Asp Glu Arg Glu Val Ser Val Pro Ala Glu
            1235                1240                1245

Ile Leu Arg Lys Ser Lys Lys Phe Pro Ala Ala Met Pro Ile Trp Ala
            1250                1255                1260

Arg Pro Asp Tyr Asn Pro Pro Leu Leu Glu Ser Trp Lys Asp Pro Asp
1265                1270                1275                1280

Tyr Val Pro Pro Val Val His Gly Cys Pro Leu Pro Pro Ile Lys Ala
                1285                1290                1295

Pro Pro Ile Pro Pro Pro Arg Arg Lys Arg Thr Val Val Leu Thr Glu
                1300                1305                1310

Ser Ser Val Ser Ser Ala Leu Ala Glu Leu Ala Thr Lys Thr Phe Gly
            1315                1320                1325

Ser Ser Glu Ser Ser Ala Val Asp Ser Gly Thr Ala Thr Ala Leu Pro
            1330                1335                1340

Asp Gln Ala Ser Asp Asp Gly Asp Lys Gly Ser Asp Val Glu Ser Tyr
1345                1350                1355                1360

Ser Ser Met Pro Pro Leu Glu Gly Glu Pro Gly Asp Pro Asp Leu Ser
                1365                1370                1375

Asp Gly Ser Trp Ser Thr Val Ser Glu Glu Ala Ser Glu Asp Val Val
            1380                1385                1390

Cys Cys Ser Met Ser Tyr Thr Trp Thr Gly Ala Leu Ile Thr Pro Cys
            1395                1400                1405

Ala Ala Glu Glu Ser Lys Leu Pro Ile Asn Ala Leu Ser Asn Ser Leu
1410                1415                1420

Leu Arg His His Asn Met Val Tyr Ala Thr Thr Ser Arg Ser Ala Gly
1425                1430                1435                1440

Leu Arg Gln Lys Lys Val Thr Phe Asp Arg Leu Gln Val Leu Asp Asp
            1445                1450                1455

His Tyr Arg Asp Val Leu Lys Glu Met Lys Ala Lys Ala Ser Thr Val
            1460                1465                1470

Lys Ala Lys Leu Leu Ser Val Glu Glu Ala Cys Lys Leu Thr Pro Pro
            1475                1480                1485

His Ser Ala Lys Ser Lys Phe Gly Tyr Gly Ala Lys Asp Val Arg Asn
            1490                1495                1500

Leu Ser Ser Lys Ala Val Asn His Ile His Ser Val Trp Lys Asp Leu
1505                1510                1515                1520

Leu Glu Asp Thr Val Thr Pro Ile Asp Thr Thr Ile Met Ala Lys Asn
            1525                1530                1535

Glu Val Phe Cys Val Gln Pro Glu Lys Gly Gly Arg Lys Pro Ala Arg
            1540                1545                1550

Leu Ile Val Phe Pro Asp Leu Gly Val Arg Val Cys Glu Lys Met Ala
            1555                1560                1565

Leu Tyr Asp Val Val Ser Thr Leu Pro Gln Val Met Gly Ser Ser
        1570                1575                1580

Tyr Gly Phe Gln Tyr Ser Pro Gly Gln Arg Val Glu Phe Leu Val Asn
1585                1590                1595                1600

Thr Trp Lys Ser Lys Lys Asn Pro Met Gly Phe Ser Tyr Asp Thr Arg
                1605                1610                1615

Cys Phe Asp Ser Thr Val Thr Glu Asn Asp Ile Arg Val Glu Glu Ser
            1620                1625                1630
```

Ile Tyr Gln Cys Cys Asp Leu Ala Pro Glu Ala Arg Gln Ala Ile Lys
        1635                1640                1645

Ser Leu Thr Glu Arg Leu Tyr Ile Gly Gly Pro Leu Thr Asn Ser Lys
    1650                1655                1660

Gly Gln Asn Cys Gly Tyr Arg Arg Cys Arg Ala Ser Gly Val Leu Thr
1665                1670                1675                1680

Thr Ser Cys Gly Asn Thr Leu Thr Cys Tyr Leu Lys Ala Ser Ala Ala
            1685                1690                1695

Cys Arg Ala Ala Lys Leu Gln Asp Cys Thr Met Leu Val Asn Ala Ala
                1700                1705                1710

Gly Leu Val Val Ile Cys Glu Ser Ala Gly Thr Gln Glu Asp Ala Ala
            1715                1720                1725

Ser Leu Arg Val Phe Thr Glu Ala Met Thr Arg Tyr Ser Ala Pro Pro
        1730                1735                1740

Gly Asp Pro Pro Gln Pro Glu Tyr Asp Leu Glu Leu Ile Thr Ser Cys
1745                1750                1755                1760

Ser Ser Asn Val Ser Val Ala His Asp Ala Ser Gly Lys Arg Val Tyr
            1765                1770                1775

Tyr Leu Thr Arg Asp Pro Thr Thr Pro Leu Ala Arg Ala Ala Trp Glu
        1780                1785                1790

Thr Ala Arg His Thr Pro Val Asn Ser Trp Leu Gly Asn Ile Ile Met
            1795                1800                1805

Tyr Ala Pro Thr Leu Trp Ala Arg Met Ile Leu Met Thr His Phe Phe
        1810                1815                1820

Ser Ile Leu Leu Ala Gln Glu Gln Leu Glu Lys Ala Leu Asp Cys Gln
1825                1830                1835                1840

Ile Tyr Gly Ala Cys Tyr Ser Ile Glu Pro Leu Asp Leu Pro Gln Ile
            1845                1850                1855

Ile Glu Arg Leu His Gly Leu Ser Ala Phe Ser Leu His Ser Tyr Ser
            1860                1865                1870

Pro Gly Glu Ile Asn Arg Val Ala Ser Cys Leu Arg Lys Leu Gly Val
        1875                1880                1885

Pro Pro Leu Arg Val Trp Arg His Arg Ala Arg Ser Val Arg Ala Arg
    1890                1895                1900

Leu Leu Ser Gln Gly Gly Arg Ala Ala Thr Cys Gly Lys Tyr Leu Phe
1905                1910                1915                1920

Asn Trp Ala Val Lys Thr Lys Leu Lys Leu Thr Pro Ile Pro Ala Ala
            1925                1930                1935

Ser Gln Leu Asp Leu Ser Gly Trp Phe Val Ala Gly Tyr Ser Gly Gly
        1940                1945                1950

Asp Ile Tyr His Ser Leu Ser Arg Ala Arg Pro Arg Trp Phe Met Leu
        1955                1960                1965

Cys Leu Leu Leu Leu Ser Val Gly Val Gly Ile Tyr Leu Leu Pro Asn
    1970                1975                1980

Arg
1985

<210> SEQ ID NO 2
<211> LENGTH: 5965
<212> TYPE: DNA
<213> ORGANISM: Artificial Sequence
<220> FEATURE:
<223> OTHER INFORMATION: Non-optimized cDNA sequence encoding SEQ. ID. NO.
      1

<400> SEQUENCE: 2

```
gccaccatgg cgcccatcac ggcctactcc aacagacgc ggggcctact tggttgcatc      60
atcactagcc ttacaggccg ggacaagaac caggtcgagg gagaggttca ggtggtttcc    120
accgcaacac aatccttcct ggcgacctgc gtcaacggcg tgtgttggac cgtttaccat    180
ggtgctggct caaagacctt agccggccca aaggggccaa tcacccagat gtacactaat    240
gtggaccagg acctcgtcgg ctggcaggcg ccccccgggg cgcgttcctt gacaccatgc    300
acctgtggca gctcagacct ttacttggtc acgagacatg ctgacgtcat tccggtgcgc    360
cggcggggcg acagtagggg gagcctgctc tcccccaggc ctgtctccta cttgaagggc    420
tcttcgggtg gtccactgct ctgcccttcg gggcacgctg tgggcatctt ccgggctgcc    480
gtatgcaccc gggggttgc gaaggcggtg gactttgtgc ccgtagagtc catggaaact    540
actatgcggt ctccggtctt cacgacaac tcatccccccc cggccgtacc gcagtcattt    600
caagtggccc acctacacgc tcccactggc agcggcaaga gtactaaagt gccggctgca    660
tatgcagccc aagggtacaa ggtgctcgtc ctcaatccgt ccgttgccgc taccttaggg    720
tttggggcgt atatgtctaa ggcacacggt attgacccca acatcagaac tggggtaagg    780
accattacca caggcgcccc cgtcacatac tctacctatg caagtttct tgccgatggt    840 ggttgctctg ggggcgctta tgacatcata atatgtgatg agtgccattc aactgactcg    900
actacaatct tgggcatcgg cacagtcctg gaccaagcgg agacggctgg agcgcggctt    960
gtcgtgctcg ccaccgctac gcctccggga tcggtcaccg tgccacaccc aaacatcgag   1020
gaggtggccc tgtctaatac tggagagatc cccttctatg gcaaagccat ccccattgaa   1080
gccatcaggg ggggaaggca tctcattttc tgtcattcca agaagaagtg cgacgagctc   1140
gccgcaaagc tgtcaggcct cggaatcaac gctgtggcgt attaccgggg gctcgatgtg   1200
tccgtcatac caactatcgg agacgtcgtt gtcgtggcaa cagacgctct gatgacgggc   1260
tatacgggcg actttgactc agtgatcgac tgtaacacat gtgtcaccca gacagtcgac   1320
ttcagcttgg atcccaccct caccattgag acgacgaccg tgcctcaaga cgcagtgtcg   1380
cgctcgcagc ggcggggtag gactggcagg ggtaggagag gcatctacag gtttgtgact   1440
ccgggagaac ggccctcggg catgttcgat tcctcggtcc tgtgtgagtg ctatgacgcg   1500
ggctgtgctt ggtacgagct caccccccgcc gagacctcgg ttaggttgcg ggcctacctg   1560
aacacaccag ggttgcccgt ttgccaggac cacctggagt tctgggagag tgtcttcaca   1620
ggcctcaccc acatagatgc acacttcttg tcccagacca agcaggcagg agacaacttc   1680
ccctacctgg tagcatacca agccacggtg tgcgccaggg ctcaggcccc acctccatca   1740
tgggatcaaa tgtggaagtg tctcatacgg ctgaaaccta cgctgcacgg gccaacaccc   1800
ttgctgtaca ggctgggagc cgtccaaaat gaggtcaccc tcacccaccc cataaccaaa   1860
tacatcatgg catgcatgtc ggctgacctg gaggtcgtca ctagcacctg ggtgctggtg   1920
ggcggagtcc ttgcagctct ggccgcgtat tgcctgacaa caggcagtgt ggtcattgtg   1980
ggtaggatta tcttgtccgg gaggccggct attgttcccg acagggagtt tctctaccag   2040
gagttcgatg aaatggaaga gtgcgcctcg cacctccctt acatcgagca gggaatgcag   2100
ctcgccgagc aattcaagca gaaagcgctc gggttactgc aaacagccac caaacaagcg   2160
gaggctgctg ctcccgtggt ggagtccaag tggcagcccc ttgagacatt ctgggcgaag   2220
cacatgtgga atttcatcag cgggatacag tacttagcag gcttatccac tctgcctggg   2280
aaccccgcaa tagcatcatt gatggcattc acagcctcta tcaccagccc gctcaccacc   2340
caaagtaccc tcctgtttta acatcttgggg gggtgggtgg ctgcccaact cgccccccccc   2400
```

-continued

```
agcgccgctt cggctttcgt gggcgccggc atcgccggtg cggctgttgg cagcataggc    2460
cttgggaagg tgcttgtgga cattctggcg ggttatggag caggagtggc cggcgcgctc    2520
gtggccttca aggtcatgag cggcgagatg ccctccaccg aggacctggt caatctactt    2580
cctgccatcc tctctcctgg cgccctggtc gtcggggtcg tgtgtgcagc aatactgcgt    2640
cgacacgtgg gtccgggaga gggggctgtg cagtggatga accggctgat agcgttcgcc    2700
tcgcggggta atcatgtttc ccccacgcac tatgtgcctg agagcgacgc cgcagcgcgt    2760
gttactcaga tcctctccag ccttaccatc actcagctgc tgaaaaggct ccaccagtgg    2820
attaatgaag actgctccac accgtgttcc ggctcgtggc taagggatgt ttgggactgg    2880
atatgcacgg tgttgactga cttcaagacc tggctccagt ccaagctcct gccgcagcta    2940
ccggagtcc cttttttctc gtgccaacgc gggtacaagg gagtctggcg gggagacggc     3000
atcatgcaaa ccacctgccc atgtggagca cagatcaccg gacatgtcaa aaacggttcc    3060
atgaggatcg tcgggcctaa gacctgcagc aacacgtggc atggaacatt ccccatcaac    3120
gcatacacca cgggcccctg cacaccctct ccagcgccaa actattctag ggcgctgtgg    3180
cgggtggccg ctgaggagta cgtggaggtc acgcgggtgg gggatttcca ctacgtgacg    3240
ggcatgacca ctgacaacgt aaagtgccca tgccaggttc cggctcctga attcttcacg    3300
gaggtggacg gagtgcggtt gcacaggtac gctccggcgt gcaggcctct cctacgggag    3360
gaggttacat tccaggtcgg gctcaaccaa tacctggttg ggtcacagct accatgcgag    3420
cccgaaccgg atgtagcagt gctcacttcc atgctcaccg accctcccca catcacagca    3480
gaaacggcta agcgtaggtt ggccagggggg tctcccccct ccttggccag ctcttcagct    3540
agccagttgt ctgcgccttc cttgaaggcg acatgcacta cccaccatgt ctctccggac    3600
gctgacctca tcgaggccaa cctcctgtgg cggcaggaga tgggcgggaa catcacccgc    3660
gtggagtcgg agaacaaggt ggtagtcctg gactcttttcg acccgcttcg agcggaggag    3720
gatgagaggg aagtatccgt tccggcggag atcctgcgga aatccaagaa gttccccgca    3780
gcgatgccca tctgggcgcg cccggattac aaccctccac tgttagagtc ctggaaggac    3840
ccggactacg tccctccggt ggtgcacggg tgccgcttgc cacctatcaa ggcccctcca    3900
ataccacctc cacggagaaa gaggacggtt gtcctaacag agtcctccgt gtcttctgcc    3960
ttagcggagc tcgctactaa gaccttcggc agctccgaat catcggccgt cgacagcggc    4020
acggcgaccg cccttcctga ccaggcctcc gacgacggtg acaaaggatc cgacgttgag    4080
tcgtactcct ccatgccccc ccttgagggg gaaccggggg accccgatct cagtgacggg    4140
tcttggtcta ccgtgagcga ggaagctagt gaggatgtcg tctgctgctc aatgtcctac    4200
acatggacag gcgccttgat cacgccatgc gctgcgagg aaagcaagct gcccatcaac     4260
gcgttgagca actctttgct gcgccaccat aacatggttt atgccacaac atctcgcagc    4320
gcaggcctgc ggcagaagaa ggtcaccttt gacagactgc aagtcctgga cgaccactac    4380
cgggacgtgc tcaaggagat gaaggcgaag gcgtccacag ttaaggctaa actcctatcc    4440
gtagaggaag cctgcaagct gacgcccca cattcggcca atccaagtt tggctatggg     4500
gcaaaggacg tccggaacct atccagcaag gccgttaacc acatccactc cgtgtggaag    4560
gacttgctgg aagacactgt gacaccaatt gacaccacca tcatggcaaa aaatgaggtt    4620
ttctgtgtcc aaccagagaa aggaggccgt aagccagccc gccttatcgt attcccagat    4680
ctgggagtcc gtgtatgcga gaagatggcc ctctatgatg tggtctccac ccttcctcag    4740
gtcgtgatgg gctcctcata cggattccag tactctcctg ggcagcgagt cgagttcctg    4800
```

-continued

```
gtgaatacct ggaaatcaaa gaaaaacccc atgggctttt catatgacac tcgctgtttc      4860
gactcaacgg tcaccgagaa cgacatccgt gttgaggagt caatttacca atgttgtgac      4920
ttggcccccg aagccagaca ggccataaaa tcgctcacag agcggcttta tcgggggt       4980
cctctgacta attcaaaagg gcagaactgc ggttatcgcc ggtgccgcgc gagcggcgtg      5040
ctgacgacta gctgcggtaa caccctcaca tgttacttga aggcctctgc agcctgtcga      5100
gctgcgaagc tccaggactg cacgatgctc gtgaacgccg ccggccttgt cgttatctgt      5160
gaaagcgcgg gaacccaaga ggacgcggcg agcctacgag tcttcacgga ggctatgact      5220
aggtactctg ccccccccgg ggacccgccc caaccagaat acgacttgga gctgataaca      5280
tcatgttcct ccaatgtgtc ggtcgcccac gatgcatcag gcaaagggt gtactacctc       5340
acccgtgatc ccaccacccc cctcgcacgg gctgcgtggg aaacagctag acacactcca      5400
gttaactcct ggctaggcaa cattatcatg tatgcgccca ctttgtgggc aaggatgatt      5460
ctgatgactc acttcttctc catccttcta gcacaggagc aacttgaaaa agccctggac      5520
tgccagatct acggggcctg ttactccatt gagccacttg acctacctca gatcattgaa      5580
cgactccatg gccttagcgc attttcactc catagttact ctccaggtga gatcaatagg      5640
gtggcttcat gcctcaggaa acttggggta ccacccttgc gagtctggag acatcgggcc      5700
aggagcgtcc gcgctaggct actgtcccag ggggggaggg ccgccacttg tggcaagtac      5760
ctcttcaact gggcagtgaa gaccaaactc aaactcactc caatcccggc tgcgtcccag      5820
ctggacttgt ccggctggtt cgttgctggt tacagcgggg gagacatata tcacagcctg      5880
tctcgtgccc gaccccgctg gttcatgctg tgcctactcc tactttctgt aggggtaggc      5940
atctacctgc tccccaaccg ataaa                                           5965

<210> SEQ ID NO 3
<211> LENGTH: 5965
<212> TYPE: DNA
<213> ORGANISM: Artificial Sequence
<220> FEATURE:
<223> OTHER INFORMATION: Optimized cDNA encoding SEQ ID NO: 1

<400> SEQUENCE: 3
gccaccatgg cccccatcac cgcctacagc cagcagaccc gcggcctgct gggctgcatc       60
atcaccagcc tgaccggccg cgacaagaac caggtggagg cgcaggtgca ggtggtgagc      120
accgccaccc agagcttcct ggccacctgc gtgaacggcg tgtgctggac cgtgtaccac      180
ggcgccggca gcaagaccct ggccggcccc aagggcccca tcacccagat gtacaccaac      240
gtggaccagg acctggtggg ctggcaggcc ccccccggcg cccgcagcct gaccccctgc      300
acctgcggca gcagcgacct gtacctggtg acccgccacg ccgacgtgat ccccgtgcgc      360
cgccgcggcg acagccgcgg cagcctgctg agccccccgcc ccgtgagcta cctgaagggc      420
agcagcggcg gccccctgct gtgccccagc ggccacgccg tgggcatctt ccgcgccgcc      480
gtgtgcaccc gcggcgtggc caaggccgtg gacttcgtgc ccgtggagag catggagacc      540
accatgcgca gccccgtgtt caccgacaac agcagccccc ccgccgtgcc ccagagcttc      600
caggtggccc cctgcacgc ccccaccggc agcggcaaga gcaccaaggt gcccgccgcc      660
tacgccgccc agggctacaa ggtgctggtg ctgaacccca gcgtggccgc cacccctgggc      720
ttcggcgcct acatgagcaa ggcccacggc atcgacccca acatccgcac cggcgtgcgc      780
accatcacca ccggcgcccc cgtgacctac agcacctacg gcaagttcct ggccgacggc      840
ggctgcagcg gcggcgccta cgacatcatc atctgcgacg agtgccacag caccgacagc      900
```

```
accaccatcc tgggcatcgg caccgtgctg gaccaggccg agaccgccgg cgcccgcctg    960
gtggtgctgg ccaccgccac cccccccggc agcgtgaccg tgcccacccc caacatcgag   1020
gaggtggccc tgagcaacac cggcgagatc cccttctacg gcaaggccat ccccatcgag   1080
gccatccgcg gcgccgccca cctgatcttc tgccacagca agaagaagtg cgacgagctg   1140
gccgccaagc tgagcggcct gggcatcaac gccgtggcct actaccgcgg cctggacgtg   1200
agcgtgatcc ccaccatcgg cgacgtggtg gtggtggcca ccgacgccct gatgaccggc   1260
tacaccggcg acttcgacag cgtgatcgac tgcaacacct gcgtgaccca gaccgtggac   1320
ttcagcctgg accccacctt caccatcgag accaccaccg tgccccagga cgccgtgagc   1380
cgcagccagc gccgcggccg caccggccgc ggccgccgcg gcatctaccg cttcgtgacc   1440
cccgcgagc gccccagcgg catgttcgac agcagcgtgc tgtgcgagtg ctacgacgcc   1500
ggctgcgcct ggtacgagct gaccccccgc cgagaccagcg tgcgcctgcg cgcctacctg   1560
aacacccccg gcctgccgt gtgccaggac cacctggagt tctgggagag cgtgttcacc   1620
ggcctgaccc acatcgacgc ccacttcctg agccagacca gcaggccgg cgacaacttc   1680
ccctacctgg tggcctacca ggccaccgtg tgcgcccgcg cccaggcccc ccccccagc   1740
tgggaccaga tgtggaagtg cctgatccgc ctgaagccca cctgcacgg ccccacccc   1800
ctgctgtacc gcctgggcgc cgtgcagaac gaggtgaccc tgacccaccc catcaccaag   1860
tacatcatgg cctgcatgag cgccgacctg gaggtggtga ccagcacctg ggtgctggtg   1920
ggcggcgtgc tggccgccct ggccgcctac tgcctgacca ccggcagcgt ggtgatcgtg   1980
ggccgcatca tcctgagcgg ccgccccgcc atcgtgcccg accgcgagtt cctgtaccag   2040
gagttcgacg agatggagga gtgcgccagc cacctgcccct acatcgagca gggcatgcag   2100
ctggccgagc agttcaagca gaaggccctg ggcctgctgc agaccgccac caagcaggcc   2160
gaggccgccg cccccgtggt ggagagcaag tggcgcgccc tggagacctt ctgggccaag   2220
cacatgtgga acttcatcag cggcatccag tacctggccg gcctgagcac cctgccggc   2280
aaccccgcca tcgccagcct gatggccttc accgccagca tcaccagccc cctgaccacc   2340
cagagcaccc tgctgttcaa catcctgggc ggctgggtgg ccgcccagct ggccccccc   2400
agcgccgcca gcgccttcgt gggcgccggc atcgccggcg ccgccgtggg cagcatcggc   2460
ctgggcaagg tgctggtgga catcctggcc ggctacggcg ccggcgtggc cggcgccctg   2520
gtggccttca aggtgatgag cggcgagatg cccagcaccg aggacctggt gaacctgctg   2580
cccgccatcc tgagccccgg cgccctggtg gtgggcgtgg tgtgcgccgc catcctgcgc   2640
cgccacgtgg gccccggcga gggcgccgtg cagtggatga accgcctgat cgccttcgcc   2700
agccgcggca accacgtgag ccccacccac tacgtgcccg agagcgacgc cgccgcccgc   2760
gtgacccaga tcctgagcag cctgaccatc acccagctgc tgaagcgcct gcaccagtgg   2820
atcaacgagg actgcagcac ccccgcagc ggcagctggc tgcgcgacgt gtgggactgg   2880
atctgcaccg tgctgaccga cttcaagacc tggctgcaga gcaagctgct gccccagctg   2940
cccggcgtgc ccttcttcag ctgccagcgc ggctacaagg gcgtgtggcg cggcgacggc   3000
atcatgcaga ccacctgccc ctgcggcgcc cagatcaccg gccacgtgaa gaacggcagc   3060
atgcgcatcg tgggccccaa gacctgcagc aacacctggc acggcacctt ccccatcaac   3120
gcctacacca ccggcccctg caccccagc ccgcccccca actacagccg cgccctgtgg   3180
cgcgtggccg ccgaggagta cgtggaggtg accgcgtgg gcgacttcca ctacgtgacc   3240
ggcatgacca ccgacaacgt gaagtgcccc tgccaggtgc ccgcccccga gttcttcacc   3300
```

```
gaggtggacg gcgtgcgcct gcaccgctac gcccccgcct gccgcccccct gctgcgcgag    3360
gaggtgacct tccaggtggg cctgaaccag tacctggtgg cagccagct gccctgcgag      3420
cccgagcccg acgtggccgt gctgaccagc atgctgaccg accccagcca catcaccgcc    3480
gagaccgcca agcgccgcct ggcccgcggc agccccccca gcctggccag cagcagcgcc    3540
agccagctga gcgcccccag cctgaaggcc acctgcacca cccaccacgt gagccccgac    3600
gccgacctga tcgaggccaa cctgctgtgg cgccaggaga tgggcggcaa catcacccgc    3660
gtggagagcg agaacaaggt ggtggtgctg gacagcttcg acccctgcg cgccgaggag     3720
gacgagcgcg aggtgagcgt gcccgccgag atcctgcgca gagcaagaa gttccccgcc     3780
gccatgccca tctgggcccg ccccgactac aaccccccc tgctggagag ctggaaggac     3840
cccgactacg tgcccccgt ggtgcacggc tgccccctgc ccccatcaa ggccccccc      3900
atccccccccc cccgccgcaa gcgcaccgtg gtgctgaccg agagcagcgt gagcagcgcc   3960
ctggccgagc tggccaccaa gaccttcggc agcagcgaga gcagcgccgt ggacagcggc   4020
accgccaccg ccctgcccga ccaggccagc gacgacggcg acaagggcag cgacgtggag   4080
agctacagca gcatgccccc cctggagggc gagcccggcg accccgacct gagcgacggc    4140
agctggagca ccgtgagcga ggaggccagc gaggacgtgg tgtgctgcag catgagctac    4200
acctggaccg cgccctgat cacccccgc gccgccgagg agagcaagct gcccatcaac     4260
gccctgagca acagcctgct gcgccaccac aacatggtgt acgccaccac cagccgcagc    4320
gccggcctgc gccagaagaa ggtgaccttc gaccgcctgc aggtgctgga cgaccactac    4380
cgcgacgtgc tgaaggagat gaaggccaag gccagcaccg tgaaggccaa gctgctgagc    4440
gtggaggagg cctgcaagct gaccccccc cacagcgcca agagcaagtt cggctacggc     4500
gccaaggacg tgcgcaacct gagcagcaag gccgtgaacc acatccacag cgtgtggaag    4560
gacctgctgg aggacaccgt gacccccatc gacaccacca tcatggccaa gaacgaggtg     4620
ttctgcgtgc agcccgagaa gggcggccgc aagcccgccc gctgatcgt gttccccgac    4680
ctgggcgtgc gcgtgtgcga gaagatggcc ctgtacgacg tggtgagcac cctgccccag    4740
gtggtgatgg gcagcagcta cggcttccag tacagccccg ccagcgcgt ggagttcctg    4800
gtgaacacct ggaagagcaa gaagaacccc atgggcttca gctacgacac ccgctgcttc    4860
gacagcaccg tgaccgagaa cgacatccgc gtggaggaga gcatctacca gtgctgcgac    4920
ctggccccg aggcccgcca ggccatcaag agcctgaccg agcgcctgta catcggcggc    4980
cccctgacca acagcaaggg ccagaactgc ggctaccgcc gctgccgcgc cagcggcgtg    5040
ctgaccacca gctgcggcaa caccctgacc tgctacctga aggccagcgc cgcctgccgc    5100
gccgccaagc tgcaggactg caccatgctg gtgaacgccg ccggcctggt ggtgatctgc    5160
gagagcgccg gcacccagga ggacgccgcc agcctgcgcg tgttcaccga ggccatgacc    5220
cgctacagcg ccccccccgg cgacccccc cagcccgagt acgacctgga gctgatcacc    5280
agctgcagca gcaacgtgag cgtggcccac gacgccagcg caagcgcgt gtactacctg    5340
acccgcgacc ccaccacccc cctggcccgc gcgcctggg agaccgcccg ccacacccc     5400
gtgaacagct ggctgggcaa catcatcatg tacgcccca ccctgtgggc ccgcatgatc     5460
ctgatgaccc acttcttcag catcctgctg gcccaggagc agctggagaa ggccctggac    5520
tgccagatct acggcgcctg ctacagcatc gagcccctgg acctgcccca gatcatcgag    5580
cgcctgcacg gcctgagcgc cttcagcctg cacagctaca gccccggcga gatcaaccgc    5640
gtggccagct gcctgcgcaa gctgggcgtg ccccccctgc gcgtgtggcg ccaccgcgcc    5700
```

-continued

| | |
|---|---|
| cgcagcgtgc gcgcccgcct gctgagccag ggcggccgcg ccgccacctg cggcaagtac | 5760 |
| ctgttcaact gggccgtgaa gaccaagctg aagctgaccc ccatccccgc cgccagccag | 5820 |
| ctggacctga gcggctggtt cgtggccggc tacagcggcg gcgacatcta ccacagcctg | 5880 |
| agccgcgccc gcccccgctg gttcatgctg tgcctgctgc tgctgagcgt gggcgtgggc | 5940 |
| atctacctgc tgcccaaccg ctaaa | 5965 |

<210> SEQ ID NO 4
<211> LENGTH: 37090
<212> TYPE: DNA
<213> ORGANISM: Artificial Sequence
<220> FEATURE:
<223> OTHER INFORMATION: MRKAd6-NSmut nucleic acid

<400> SEQUENCE: 4

| | |
|---|---|
| catcatcaat aatataccct attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgtttttg | 180 |
| gtgtgcgccg tgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tatttgtcta gggccgcggg | 360 |
| gactttgacc gtttacgtgg agactcgccc aggtgttttt ctcaggtgtt ttccgcgttc | 420 |
| cgggtcaaag ttggcgtttt attattatag gcggccgcga tccattgcat acgttgtatc | 480 |
| catatcataa tatgtacatt tatattggct catgtccaac attaccgcca tgttgacatt | 540 |
| gattattgac tagttattaa tagtaatcaa ttacggggtc attagttcat agcccatata | 600 |
| tggagttccg cgttacataa cttacggtaa atggcccgcc tggctgaccg cccaacgacc | 660 |
| cccgcccatt gacgtcaata atgacgtatg ttcccatagt aacgccaata gggactttcc | 720 |
| attgacgtca atgggtggag tatttacggt aaactgccca cttggcagta catcaagtgt | 780 |
| atcatatgcc aagtacgccc cctattgacg tcaatgacgg taaatggccc gcctggcatt | 840 |
| atgcccagta catgacctta tgggactttc ctacttggca gtacatctac gtattagtca | 900 |
| tcgctattac catggtgatg cggttttggc agtacatcaa tgggcgtgga tagcggtttg | 960 |
| actcacgggg atttccaagt ctccacccca ttgacgtcaa tgggagtttg ttttggcacc | 1020 |
| aaaatcaacg ggactttcca aaatgtcgta acaactccgc cccattgacg caaatgggcg | 1080 |
| gtaggcgtgt acggtgggag gtctatataa gcagagctcg tttagtgaac cgtcagatcg | 1140 |
| cctggagacg ccatccacgc tgttttgacc tccatagaag acaccgggac cgatccagcc | 1200 |
| tccgcggccg gaacggtgc attggaacgc ggattccccg tgccaagagt gagatctgcc | 1260 |
| accatggcgc ccatcacggc ctactcccaa cagacgcggg gcctacttgg ttgcatcatc | 1320 |
| actagcctta caggccggga caagaaccag gtcgagggga aggttcaggt ggtttccacc | 1380 |
| gcaacacaat ccttcctggc gacctgcgtc aacggcgtgt gttggaccgt ttaccatggt | 1440 |
| gctggctcaa agaccttagc cggcccaaag gggccaatca cccagatgta cactaatgtg | 1500 |
| gaccaggacc tcgtcggctg gcaggcgccc cccgggcgc gttccttgac accatgcacc | 1560 |
| tgtggcagct cagaccttta cttggtcacg agacatgctg acgtcattcc ggtgcgccgg | 1620 |
| cggggcgaca gtagggggag cctgctctcc cccaggcctg tctcctactt gaagggctct | 1680 |
| tcgggtggtc cactgctctg cccttcgggg cacgctgtgg gcatcttccg ggctgccgta | 1740 |
| tgcacccggg gggttgcgaa ggcggtggac tttgtgcccg tagagtccat ggaaactact | 1800 |

```
atgcggtctc cggtcttcac ggacaactca tcccccccgg ccgtaccgca gtcatttcaa   1860
gtggcccacc tacacgctcc cactggcagc ggcaagagta ctaaagtgcc ggctgcatat   1920
gcagcccaag ggtacaaggt gctcgtcctc aatccgtccg ttgccgctac cttagggttt   1980
ggggcgtata tgtctaaggc acacggtatt gaccccaaca tcagaactgg ggtaaggacc   2040
attaccacag gcgccccgt cacatactct acctatggca gtttcttgc cgatggtggt    2100 tgctctgggg gcgcttatga catcataata tgtgatgagt gccattcaac tgactcgact   2160
acaatcttgg gcatcggcac agtcctggac caagcggaga cggctggagc gcggcttgtc   2220
gtgctcgcca ccgctacgcc tccgggatcg gtcaccgtgc cacacccaaa catcgaggag   2280
gtggccctgt ctaatactgg agagatcccc ttctatggca aagccatccc cattgaagcc   2340 atcaggggg gaaggcatct cattttctgt cattccaaga gaagtgcga cgagctcgcc    2400 gcaaagctgt caggcctcgg aatcaacgct gtggcgtatt accgggggct cgatgtgtcc   2460
gtcataccaa ctatcggaga cgtcgttgtc gtggcaacag acgctctgat gacgggctat   2520
acgggcgact ttgactcagt gatcgactgt aacacatgtg tcacccagac agtcgacttc   2580
agcttggatc ccaccttcac cattgagacg acgaccgtgc ctcaagacgc agtgtcgcgc   2640
tcgcagcggc ggggtaggac tggcaggggt aggagaggca tctacaggtt tgtgactccg   2700
ggagaacggc cctcgggcat gttcgattcc tcggtcctgt gtgagtgcta tgacgcgggc   2760
tgtgcttggt acgagctcac ccccgccgag acctcggtta ggttgcgggc ctacctgaac   2820
acaccagggt tgcccgtttg ccaggaccac ctggagttct gggagagtgt cttcacaggc   2880
ctcacccaca tagatgcaca cttcttgtcc cagaccaagc aggcaggaga caacttcccc   2940
tacctggtag cataccaagc cacggtgtgc gccagggctc aggccccacc tccatcatgg   3000
gatcaaatgt ggaagtgtct catacggctg aaacctacgc tgcacgggcc aacacccttg   3060
ctgtacaggc tgggagccgt ccaaaatgag gtcacccctca cccacccat aaccaaatac   3120 atcatggcat gcatgtcggc tgacctggag gtcgtcacta gcacctgggt gctggtgggc   3180
ggagtccttg cagctctggc cgcgtattgc ctgacaacag gcagtgtggt cattgtgggt   3240
aggattatct tgtccgggag gccggctatt gttcccgaca gggagtttct ctaccaggag   3300
ttcgatgaaa tggaagagtg cgcctcgcac ctcccttaca tcgagcaggg aatgcagctc   3360
gccgagcaat tcaagcagaa agcgctcggg ttactgcaaa cagccaccaa acaagcggag   3420
gctgctgctc ccgtggtgga gtccaagtgg cgagcccttg agacattctg gcgaagcac   3480 atgtggaatt tcatcagcgg gatacagtac ttagcaggct tatccactct gcctgggaac   3540
cccgcaatag catcattgat ggcattcaca gcctctatca ccagcccgct caccacccaa   3600
agtaccctcc tgtttaacat cttggggggg tgggtggctg cccaactcgc ccccccagc    3660 gccgcttcgg ctttcgtggg cgccggcatc gccggtgcgg ctgttggcag cataggcctt   3720
gggaaggtgc ttgtggacat tctggcgggt tatggagcag gagtggccgg cgcgctcgtg   3780
gccttcaagg tcatgagcgg cgagatgccc tccaccgagg acctggtcaa tctacttcct   3840
gccatcctct ctcctggcgc cctggtcgtc ggggtcgtgt gtgcagcaat actgcgtcga   3900
cacgtgggtc cgggagaggg ggctgtgcag tggatgaacc ggctgatagc gttcgcctcg   3960
cggggtaatc atgtttcccc cacgcactat gtgcctgaga gcgacgccgc agcgcgtgtt   4020
actcagatcc tctccagcct taccatcact cagctgctga aaaggctcca ccagtggatt   4080
aatgaagact gctccacacc gtgttccggc tcgtggctaa gggatgtttg ggactggata   4140
tgcacggtgt tgactgactt caagacctgg ctccagtcca agctcctgcc gcagctaccg   4200
```

```
ggagtccctt ttttctcgtg ccaacgcggg tacaagggag tctggcgggg agacggcatc    4260
atgcaaacca cctgcccatg tggagcacag atcaccggac atgtcaaaaa cggttccatg    4320
aggatcgtcg ggcctaagac ctgcagcaac acgtggcatg gaacattccc catcaacgca    4380
tacaccacgg gcccctgcac accctctcca gcgccaaact attctagggc gctgtggcgg    4440
gtggccgctg aggagtacgt ggaggtcacg cgggtggggg atttccacta cgtgacgggc    4500
atgaccactg acaacgtaaa gtgcccatgc caggttccgg ctcctgaatt cttcacggag    4560
gtggacggag tgcggttgca caggtacgct ccggcgtgca ggcctctcct acgggaggag    4620
gttacattcc aggtcgggct caaccaatac ctggttgggt cacagctacc atgcgagccc    4680
gaaccggatg tagcagtgct cacttccatg ctcaccgacc cctcccacat cacagcagaa    4740
acggctaagc gtaggttggc caggggctct ccccctcct tggccagctc ttcagctagc    4800
cagttgtctg cgccttcctt gaaggcgaca tgcactaccc accatgtctc tccggacgct    4860
gacctcatcg aggccaacct cctgtggcgg caggagatgg gcgggaacat cacccgcgtg    4920
gagtcggaga acaaggtggt agtcctggac tctttcgacc cgcttcgagc ggaggaggat    4980
gagagggaag tatccgttcc ggcggagatc ctgcggaaat ccaagaagtt ccccgcagcg    5040
atgcccatct gggcgcgccc ggattacaac cctccactgt tagagtcctg aaggacccg    5100 gactacgtcc ctccggtggt gcacgggtgc ccgttgccac ctatcaaggc ccctccaata    5160
ccacctccac ggagaaagag gacggttgtc ctaacagagt cctccgtgtc ttctgcctta    5220
gcggagctcg ctactaagac cttcggcagc tccgaatcat cggccgtcga cagcggcacg    5280
gcgaccgccc ttcctgacca ggcctccgac gacggtgaca aggatccga cgttgagtcg    5340 tactcctcca tgcccccccct tgagggggaa ccggggggacc ccgatctcag tgacgggtct    5400
tggtctaccg tgagcgagga agctagtgag gatgtcgtct gctgctcaat gtcctacaca    5460
tggacaggcg ccttgatcac gccatgcgct gcggaggaaa gcaagctgcc catcaacgcg    5520
ttgagcaact ctttgctgcg ccaccataac atggtttatg ccacaacatc tcgcagcgca    5580
ggcctgcggc agaagaaggt cacctttgac agactgcaag tcctggacga ccactaccgg    5640
gacgtgctca aggagatgaa ggcgaaggcg tccacagtta aggctaaaac tctatccgta    5700
gaggaagcct gcaagctgac gccccccacat tcggccaaat ccaagtttgg ctatggggca    5760
aaggacgtcc ggaacctatc cagcaaggcc gttaaccaca tccactccgt gtggaaggac    5820
ttgctggaag acactgtgac accaattgac accaccatca tggcaaaaaa tgaggttttc    5880
tgtgtccaac cagagaaagg aggccgtaag ccagcccgcc ttatcgtatt cccagatctg    5940
ggagtccgtg tatgcgagaa gatggccctc tatgatgtgg tctccaccct tcctcaggtc    6000
gtgatgggct cctcatacgg attccagtac tctcctgggc agcgagtcga gttcctggtg    6060
aatacctgga aatcaaagaa aaaccccatg gcttttcat atgacactcg ctgtttcgac    6120
tcaacggtca ccgagaacga catccgtgtt gaggagtcaa tttaccaatg ttgtgacttg    6180
gcccccgaag ccagacaggc cataaaatcg ctcacagagc ggctttatat cgggggtcct    6240
ctgactaatt caaagggca gaactgcggt tatcgccggt gccgcgcgag cggcgtgctg    6300
acgactagct gcggtaacac cctcacatgt tacttgaagg cctctgcagc ctgtcgagct    6360
gcgaagctcc aggactgcac gatgctcgtg aacgccgccg gccttgtcgt tatctgtgaa    6420
agcgcgggaa cccaagagga cgcggcgagc ctacgagtct tcacgaggc tatgactagg    6480 tactctgccc ccccgggga cccgcccaa ccagaatacg acttggagct gataacatca    6540
tgttcctcca atgtgtcggt cgcccacgat gcatcaggca aaagggtgta ctacctcacc    6600
```

-continued

```
cgtgatccca ccacccccct cgcacgggct gcgtgggaaa cagctagaca cactccagtt    6660
aactcctggc taggcaacat tatcatgtat gcgcccactt tgtgggcaag gatgattctg    6720
atgactcact tcttctccat ccttctagca caggagcaac ttgaaaaagc cctggactgc    6780
cagatctacg gggcctgtta ctccattgag ccacttgacc tacctcagat cattgaacga    6840
ctccatggcc ttagcgcatt ttcactccat agttactctc caggtgagat caatagggtg    6900
gcttcatgcc tcaggaaact tggggtacca cccttgcgag tctggagaca tcgggccagg    6960
agcgtccgcg ctaggctact gtcccagggg gggagggccg ccacttgtgg caagtacctc    7020
ttcaactggg cagtgaagac caaactcaaa ctcactccaa tcccggctgc gtcccagctg    7080
gacttgtccg gctggttcgt tgctggttac agcgggggag acatatatca cagcctgtct    7140
cgtgcccgac cccgctggtt catgctgtgc ctactcctac tttctgtagg ggtaggcatc    7200
tacctgctcc ccaaccggta aatctagagc tgtgccttct agttgccagc catctgttgt    7260
ttgcccctcc ccgtgccttc cttgaccct ggaaggtgcc actcccactg tcctttccta    7320
ataaaatgag gaaattgcat cgcattgtct gagtaggtgt cattctattc tggggggtgg    7380
ggtggggcag gacagcaagg gggaggattg gaagacaat agcaggcatg ctggggatgc    7440
ggtgggctct atggccgatc ggcgcgccgt actgaaatgt gtgggcgtgg cttaagggtg    7500
ggaaagaata tataaggtgg gggtcttatg tagttttgta tctgttttgc agcagccgcc    7560
gccgccatga gcaccaactc gtttgatgga agcattgtga gctcatattt gacaacgcgc    7620
atgcccccat gggccgggt gcgtcagaat gtgatgggct ccagcattga tggtcgcccc    7680
gtcctgcccg caaactctac taccttgacc tacgagaccg tgtctggaac gccgttggag    7740
actgcagcct ccgccgccgc ttcagccgct gcagccaccg cccgcgggat tgtgactgac    7800
tttgctttcc tgagcccgct tgcaagcagt gcagcttccc gttcatccgc ccgcgatgac    7860
aagttgacgg ctcttttggc acaattggat tctttgaccc gggaacttaa tgtcgtttct    7920
cagcagctgt tggatctgcg ccagcaggtt tctgccctga aggcttcctc ccctcccaat    7980
gcggtttaaa acataaataa aaaaccagac tctgtttgga tttggatcaa gcaagtgtct    8040
tgctgtcttt atttaggggt tttgcgcgcg cggtaggccc gggaccagcg gtctcggtcg    8100
ttgagggtcc tgtgtatttt ttccaggacg tggtaaaggt gactctggat gttcagatac    8160
atgggcataa gcccgtctct ggggtggagg tagcaccact gcagagcttc atgctgcggg    8220
gtggtgttgt agatgatcca gtcgtagcag gagcgctggg cgtggtgcct aaaaatgtct    8280
ttcagtagca agctgattgc caggggcagg cccttggtgt aagtgtttac aaagcggtta    8340
agctgggatg ggtgcatacg tggggatatg agatgcatct tggactgtat ttttaggttg    8400
gctatgttcc cagccatatc cctccgggga ttcatgttgt gcagaaccac cagcacagtg    8460
tatccggtgc acttgggaaa tttgtcatgt agcttagaag gaaatgcgtg gaagaacttg    8520
gagacgccct tgtgacctcc aagatttttcc atgcattcgt ccataatgat ggcaatgggc    8580
ccacgggcgg cggcctgggc gaagatattt ctgggatcac taacgtcata gttgtgttcc    8640
aggatgagat cgtcataggc cattttttaca aagcgcgggc ggagggtgcc agactgcggt    8700
ataatggttc catccggccc aggggcgtag ttaccctcac agatttgcat ttcccacgct    8760
ttgagttcag atggggggat catgtctacc tgcgggcga tgaagaaaac ggtttccggg    8820
gtaggggaga tcagctggga agaaagcagg ttcctgagca gctgcgactt accgcagccg    8880
gtgggcccga aaatcacacc tattaccggc tgcaactggt agttaagaga gctgcagctg    8940
ccgtcatccc tgagcagggg ggccacttcg ttaagcatgt ccctgactcg catgttttcc    9000
```

```
ctgaccaaat ccgccagaag gcgctcgccg cccagcgata gcagttcttg caaggaagca   9060
aagttttca  acggtttgag accgtccgcc gtaggcatgc ttttgagcgt ttgaccaagc   9120
agttccaggc ggtcccacag ctcggtcacc tgctctacgg catctcgatc cagcatatct   9180
cctcgtttcg cgggttgggg cggctttcgc tgtacggcag tagtcggtgc tcgtccagac   9240
gggccagggt catgtctttc cacgggcgca gggtcctcgt cagcgtagtc tgggtcacgg   9300
tgaaggggtg cgctccgggc tgcgcgctgg ccagggtgcg cttgaggctg gtcctgctgg   9360
tgctgaagcg ctgccggtct tcgccctgcg cgtcggccag gtagcatttg accatggtgt   9420
catagtccag cccctccgcg gcgtggccct tggcgcgcag cttgcccttg gaggaggcgc   9480
cgcacgaggg gcagtgcaga cttttgaggg cgtagagctt gggcgcgaga aataccgatt   9540
ccggggagta ggcatccgcg ccgcaggccc cgcagacggt ctcgcattcc acgagccagg   9600
tgagctctgg ccgttcgggg tcaaaaacca ggtttccccc atgcttttg  atgcgtttct   9660
tacctctggt ttccatgagc cggtgtccac gctcggtgac gaaaaggctg tccgtgtccc   9720
cgtatacaga cttgagaggc ctgtcctcga gcggtgttcc gcggtcctcc tcgtatagaa   9780
actcggacca ctctgagacg aaggctcgcg tccaggccag cacgaaggag gctaagtggg   9840
aggggtagcg gtcgttgtcc actagggggt ccactcgctc cagggtgtga agacacatgt   9900
cgccctcttc ggcatcaagg aaggtgattg gtttataggt gtaggccacg tgaccgggtg   9960
ttcctgaagg ggggctataa aaggggtgg  gggcgcgttc gtcctcactc tcttccgcat   10020
cgctgtctgc gagggccagc tgttggggtg agtactccct ctcaaaagcg ggcatgactt   10080
ctgcgctaag attgtcagtt ccaaaaacg  aggaggattg gatattcacc tggcccgcgg   10140
tgatgccttt gagggtggcc gcgtccatct ggtcagaaaa gacaatcttt ttgttgtcaa   10200
gcttggtggc aaacgacccg tagagggcgt tggacagcaa cttggcgatg gagcgcaggg   10260
tttggtttt  gtcgcgatcg gcgcgctcct tggccgcgat gtttagctgc acgtattcgc   10320
gcgcaacgca ccgccattcg ggaaagacgg tggtgcgctc gtcgggcact aggtgcacgc   10380
gccaaccgcg gttgtgcagg gtgacaaggt caacgctggt ggctacctct ccgcgtaggc   10440
gctcgttggt ccagcagagg cggccgccct tgcgcgagca gaatggcggt agtgggtcta   10500
gctgcgtctc gtccgggggg tctgcgtcca cggtaaagac cccgggcagc aggcgcgcgt   10560
cgaagtagtc tatcttgcat ccttgcaagt ctagcgcctg ctgccatgcg cgggcggcaa   10620
gcgcgcgctc gtatgggttg agtgggggac cccatggcat ggggtgggtg agcgcggagg   10680
cgtacatgcc gcaaatgtcg taaacgtaga ggggctctct gagtattcca agatatgtag   10740
ggtagcatct tccaccgcgg atgctggcgc gcacgtaatc gtatagttcg tgcgagggag   10800
cgaggaggtc gggaccgagg ttgctacggg cgggctgctc tgctcggaag actatctgcc   10860
tgaagatggc atgtgagttg gatgatatgg ttggacgctg gaagacgttg aagctggcgt   10920
ctgtgagacc taccgcgtca cgcacgaagg aggcgtagga gtcgcgcagc ttgttgacca   10980
gctcggcggt gacctgcacg tctagggcgc agtagtccag ggtttccttg atgatgtcat   11040
acttatcctg tccctttttt ttccacagct cgcggttgag gacaaactct tcgcggtctt   11100
tccagtactc ttggatcgga aacccgtcgg cctccgaacg gtaagagcct agcatgtaga   11160
actggttgac ggcctggtag gcgcagcatc cttttctac  gggtagcgcg tatgcctgcg   11220
cggccttccg gagcgaggtg tgggtgagcg caaaggtgtc cctaaccatg actttgaggt   11280
actggtattt gaagtcagtg tcgtcgcatc cgccctgctc ccagagcaaa agtccgtgc   11340
gcttttggga acgcgggttt ggcagggcga aggtgacatc gttgaagagt atcttcccg   11400
```

```
cgcgaggcat aaagttgcgt gtgatgcgga agggtcccgg cacctcggaa cggttgttaa   11460
ttacctgggc ggcgagcacg atctcgtcaa agccgttgat gttgtggccc acaatgtaaa   11520
gttccaagaa gcgcgggatg cccttgatgg aaggcaattt tttaagttcc tcgtaggtga   11580
gctcttcagg ggagctgagc ccgtgctctg aaagggccca gtctgcaaga tgagggttgg   11640
aagcgacgaa tgagctccac aggtcacggg ccattagcat ttgcaggtgg tcgcgaaagg   11700
tcctaaactg gcgacctatg gccattttt ctggggtgat gcagtagaag gtaagcgggt   11760
cttgttccca gcggtcccat ccaaggtccg cggctaggtc tcgcgcggcg gtcactagag   11820
gctcatctcc gccgaacttc atgaccagca tgaagggcac gagctgcttc ccaaaggccc   11880
ccatccaagt ataggtctct acatcgtagg tgacaaagag acgctcggtg cgaggatgcg   11940
agccgatcgg gaagaactgg atctcccgcc accagttgga ggagtggctg ttgatgtggt   12000
gaaagtagaa gtccctgcga cgggccgaac actcgtgctg gcttttgtaa aaacgtgcgc   12060
agtactggca gcggtgcacg ggctgtacat cctgcacgag gttgacctga cgaccgcgca   12120
caaggaagca gagtgggaat tgagcccct cgcctggcgg gtttggctgg tggtcttcta   12180
cttcggctgc ttgtccttga ccgtctggct gctcgagggg agttacggtg gatcggacca   12240
ccacgccgcg cgagcccaaa gtccagatgt ccgcgcgcgg cggtcggagc ttgatgacaa   12300
catcgcgcag atgggagctg tccatggtct ggagctcccg cggcgtcagg tcaggcggga   12360
gctcctgcag gtttacctcg catagccggg tcagggcgcg ggctaggtcc aggtgatacc   12420
tgatttccag gggctggttg gtggcggcgt cgatggcttg caagaggccg catccccgcg   12480
gcgcgactac ggtaccgcgc ggcgggcggt gggccgcggg ggtgtccttg gatgatgcat   12540
ctaaaagcgg tgacgcgggc gggccccgg aggtaggggg ggctcgggac ccgccgggag   12600 aggggggcagg ggcacgtcgg cgccgcgcgc gggcaggagc tggtgctgcg cgcggaggtt   12660
gctggcgaac gcgacgacgc ggcggttgat ctcctgaatc tggcgcctct gcgtgaagac   12720
gacgggcccg gtgagcttga acctgaaaga gagttcgaca gaatcaattt cggtgtcgtt   12780
gacggcggcc tggcgcaaaa tctcctgcac gtctcctgag ttgtcttgat aggcgatctc   12840
ggccatgaac tgctcgatct cttcctcctg gagatctccg cgtccggctc gctccacggt   12900
ggcggcgagg tcgttggaga tgcgggccat gagctgcgag aaggcgttga ggcctccctc   12960
gttccagacg cggctgtaga ccacgccccc ttcggcatcg cgggcgcgca tgaccacctg   13020
cgcgagattg agctccacgt gccgggcgaa gacggcgtag tttcgcaggc gctgaaagag   13080
gtagttgagg gtggtggcgg tgtgttctgc cacgaagaag tacataaccc agcgccgcaa   13140
cgtggattcg ttgatatccc ccaaggcctc aaggcgctcc atggcctcgt agaagtccac   13200
ggcgaagttg aaaaactggg agttgcgcgc cgacacggtt aactcctcct ccagaagacg   13260
gatgagctcg gcgacagtgt cgcgcacctc gcgctcaaag gctacagggg cctcttcttc   13320
ttcttcaatc tcctcttcca taagggcctc cccttcttct tcttctggcg gcggtggggg   13380
aggggggaca cggcggcgac gacggcgcac cgggaggcgg tcgacaaagc gctcgatcat   13440
ctccccgcgg cgacgcgca tggtctcggt gacggcgcgg ccgttctcgc ggggcgcag   13500 ttggaagacg ccgcccgtca tgtcccggtt atgggttggc gggggctgc cgtgcggcag   13560 ggatacggcg ctaacgatgc atctcaacaa ttgttgtgta ggtactccgc caccgaggga   13620
cctgagcgag tccgcatcga ccggatcgga aaacctctcg agaaaggcgt ctaaccagtc   13680
acagtcgcaa ggtaggctga gcaccgtggc gggcggcagc gggcggcggt cggggttgtt   13740
tctggcggag gtgctgctga tgatgtaatt aaagtaggcg tcttgagac ggcggatggt   13800
```

```
cgacagaagc accatgtcct tgggtccggc ctgctgaatg cgcaggcggt cggccatgcc    13860
ccaggcttcg ttttgacatc ggcgcaggtc tttgtagtag tcttgcatga gcctttctac    13920
cggcacttct tcttctcctt cctcttgtcc tgcatctctt gcatctatcg ctgcggcggc    13980
ggcggagttt ggccgtaggt ggcgccctct tcctcccatg cgtgtgaccc cgaagcccct    14040
catcggctga agcagggcca ggtcggcgac aacgcgctcg gctaatatgg cctgctgcac    14100
ctgcgtgagg gtagactgga agtcgtccat gtccacaaag cggtggtatg cgcccgtgtt    14160
gatggtgtaa gtgcagttgg ccataacgga ccagttaacg gtctggtgac ccggctgcga    14220
gagctcggtg tacctgagac gcgagtaagc ccttgagtca aagacgtagt cgttgcaagt    14280
ccgcaccagg tactggtatc ccaccaaaaa gtgcggcggc ggctggcggt agaggggcca    14340
gcgtagggtg gccggggctc cggggcgagg tcttccaac ataaggcgat gatatccgta    14400
gatgtacctg gacatccagg tgatgccggc ggcggtggtg gaggcgcgcg gaaagtcacg    14460
gacgcggttc cagatgttgc gcagcggcaa aaagtgctcc atggtcggga cgctctggcc    14520
ggtcaggcgc gcgcagtcgt tgacgctcta gaccgtgcaa aaggagagcc tgtaagcggg    14580
cactcttccg tggtctggtg gataaattcg caagggtatc atggcggacg accgggttc    14640
gaaccccgga tccggccgtc cgccgtgatc catgcggtta ccgcccgcgt gtcgaaccca    14700
ggtgtgcgac gtcagacaac gggggagcgc tccttttggc ttccttccag gcgcggcgga    14760
tgctgcgcta gcttttttgg ccactggccg cgcgcggcgt aagcggttag gctggaaagc    14820
gaaagcatta agtggctcgc tccctgtagc cggagggtta ttttccaagg gttgagtcgc    14880
gggaccccg gttcgagtct cgggccggcc ggactgcggc gaacgggggt ttgcctcccc    14940
gtcatgcaag accccgcttg caaattcctc cggaaacagg gacgagcccc ttttttgctt    15000
ttcccagatg catccggtgc tgcggcagat gcgccccct cctcagcagc ggcaagagca    15060
agagcagcgg cagacatgca gggcaccctc cccttctcct accgcgtcag gaggggcaac    15120
atccgcggct gacgcggcgg cagatggtga ttacgaaccc ccgcggcgcc ggacccggca    15180
ctacttggac ttggaggagg gcagggcct ggcgcggcta ggagcgccct ctcctgagcg    15240
acacccaagg gtgcagctga agcgtgacac gcgcgaggcg tacgtgccgc ggcagaacct    15300
gtttcgcgac cgcgagggag aggagcccga ggagatgcgg gatcgaaagt tccatgcagg    15360
gcgcgagttg cggcatggcc tgaaccgcga gcggttgctg cgcgaggagg actttgagcc    15420
cgacgcgcgg accgggatta gtcccgcgcg cgcacacgtg gcggccgccg acctggtaac    15480
cgcgtacgag cagacggtga accaggagat taacttcaa aaaagcttta acaaccacgt    15540
gcgcacgctt gtggcgcgcg aggaggtggc tataggactg atgcatctgt gggactttgt    15600
aagcgcgctg gagcaaaaacc caaatagcaa gccgctcatg gcgcagctgt tccttatagt    15660
gcagcacagc agggacaacg aggcattcag ggatgcgctg ctaaacatag tagagcccga    15720
gggccgctgg ctgctcgatt tgataaacat tctgcagagc atagtggtgc aggagcgcag    15780
cttgagcctg gctgacaagg tggccgccat taactattcc atgctcagtc tgggcaagtt    15840
ttacgcccgc aagatatacc ataccccctta cgttccata gacaaggagg taaagatcga    15900
ggggttctac atgcgcatgg cgctgaaggt gcttaccttg agcgacgacc tgggcgttta    15960
tcgcaacgag cgcatccaca aggccgtgag cgtgagccgg cggcgcgagc tcagcgaccg    16020
cgagctgatg cacagcctgc aaagggccct ggctggcacg ggcagcggcg atagagaggc    16080
cgagtcctac tttgacgcgg gcgctgacct cgcgctgggcc caagccgac gcgccctgga    16140
ggcagctggg gccggacctg ggctggcggt ggcacccgcg cgcgctggca acgtcggcgg    16200
```

```
cgtggaggaa tatgacgagg acgatgagta cgagccagag gacggcgagt actaagcggt   16260
gatgtttctg atcagatgat gcaagacgca acggacccgg cggtgcgggc ggcgctgcag   16320
agccagccgt ccggccttaa ctccacggac gactggcgcc aggtcatgga ccgcatcatg   16380
tcgctgactg cgcgcaaccc tgacgcgttc cggcagcagc cgcaggccaa ccggctctcc   16440
gcaattctgg aagcggtggt cccggcgcgc gcaaacccca cgcacgagaa ggtgctggcg   16500
atcgtaaacg cgctggccga aaacagggcc atccggcccg atgaggccgg cctggtctac   16560
gacgcgctgc ttcagcgcgt ggctcgttac aacagcagca acgtgcagac caacctggac   16620
cggctggtgg gggatgtgcg cgaggccgtg gcgcagcgtg agcgcgcgca gcagcagggc   16680
aacctgggct ccatggttgc actaaacgcc ttcctgagta cacagcccgc caacgtgccg   16740
cggggacagg aggactacac caactttgtg agcgcactgc ggctaatggt gactgagaca   16800
ccgcaaagtg aggtgtatca gtccgggcca gactattttt tccagaccag tagacaaggc   16860
ctgcagaccg taaacctgag ccaggctttc aagaacttgc aggggctgtg ggggtgcgg   16920 gctcccacag gcgaccgcgc gaccgtgtct agcttgctga cgcccaactc gcgcctgttg   16980
ctgctgctaa tagcgcccct cacggacagt ggcagcgtgt cccgggacac ataccctaggt   17040 cacttgctga cactgtaccg cgaggccata ggtcaggcgc atgtggacga gcatactttc   17100
caggagatta caagtgttag ccgcgcgctg gggcaggagg acacgggcag cctggaggca   17160
accctgaact acctgctgac caaccggcgg caaaaaatcc cctcgttgca cagtttaaac   17220
agcgaggagg agcgcatttt gcgctatgtg cagcagagcg tgagccttaa cctgatgcgc   17280
gacggggtaa cgcccagcgt ggcgctggac atgaccgcgc gcaacatgga accgggcatg   17340
tatgcctcaa accggccgtt tatcaatcgc ctaatggact acttgcatcg cgcggccgcc   17400
gtgaaccccg agtatttcac caatgccatc ttgaacccgc actggctacc gccccctggt   17460
ttctacaccg ggggattcga ggtgcccgag ggtaacgatg gattcctctg gacgacata   17520 gacgacagcg tgttttcccc gcaaccgcag accctgctag agttgcaaca acgcgagcag   17580
gcagaggcgg cgctgcgaaa ggaaagcttc cgcaggccaa gcagcttgtc cgatctaggc   17640
gctgcggccc cgcggtcaga tgctagtagc ccatttccaa gcttgatagg gtctcttacc   17700
agcactcgca ccacccgccc gcgcctgctg ggcgaggagg agtacctaaa caactcgctg   17760
ctgcagccgc agcgcgaaaa gaacctgcct ccggcgtttc caacaacgg atagagagc   17820 ctagtggaca agatgagtag atggaagacg tatgcgcagg agcacaggga tgtgcccggc   17880
ccgcgcccgc ccaccgtcg tcaaaggcac gaccgtcagc ggggtctggt gtgggaggac   17940
gatgactcgg cagacgacag cagcgtcttg gatttgggag ggagtggcaa cccgtttgca   18000
caccttcgcc ccaggctggg gagaatgttt taaaaaaaag catgatgcaa aataaaaaac   18060
tcaccaaggc catggcaccg agcgttggtt ttcttgtatt ccccttagta tgcggcgcgc   18120
ggcgatgtat gaggaaggtc ctcctccctc ctacgagagc gtggtgagcg cggcgccagt   18180
ggcggcggcg ctgggttcac ccttcgatgc tcccctggac ccgccgttcg tgcctccgcg   18240
gtacctgcgg cctaccgggg ggagaaacag catccgttac tctgagttgg cacccctatt   18300
cgacaccacc cgtgtgtacc ttgtggacaa caagtcaacg gatgtggcat ccctgaacta   18360
ccagaacgac cacagcaact ttctaaccac ggtcattcaa aacaatgact acagcccggg   18420
ggaggcaagc acacagacca tcaatcttga cgaccggtcg cactggggcg cgacctgaa   18480 aaccatcctg cataccaaca tgccaaatgt gaacgagttc atgtttacca ataagtttaa   18540
ggcgcgggtg atggtgtcgc gctcgcttac taaggacaaa caggtggagc tgaaatacga   18600
```

```
gtgggtggag ttcacgctgc ccgagggcaa ctactccgag accatgacca tagaccttat   18660
gaacaacgcg atcgtggagc actacttgaa agtgggcagg cagaacgggg ttctggaaag   18720
cgacatcggg gtaaagtttg acacccgcaa cttcagactg gggtttgacc cagtcactgg   18780
tcttgtcatg cctggggtat atacaaacga agccttccat ccagacatca ttttgctgcc   18840
aggatgcggg gtggacttca cccacagccg cctgagcaac ttgttgggca tccgcaagcg   18900
gcaacccttc caggagggct ttaggatcac ctacgatgac ctggagggtg gtaacattcc   18960
cgcactgttg gatgtggacg cctaccaggc aagcttgaaa gatgacaccg aacagggcgg   19020
gggtggcgca ggcggcggca acaacagtgg cagcggcgcg aagagaaact ccaacgcggc   19080
agctgcggca atgcagccgg tggaggacat gaacgatcat gccattcgcg gcgacacctt   19140
tgccacacgg gcgaaggaga agcgcgctga ggccgaggca gcggccgaag ctgccgcccc   19200
cgctgcggag gctgcacaac ccgaggtcga gaagcctcag aagaaaccgg tgattaaacc   19260
cctgacagag gacagcaaga aacgcagtta caacctaata agcaatgaca gcaccttcac   19320
ccagtaccgc agctggtacc ttgcatacaa ctacggcgac cctcaggccg ggatccgctc   19380
atggaccctg ctttgcactc ctgacgtaac ctgcggctcg gagcaggtat actggtcgtt   19440
gcccgacatg atgcaagacc ccgtgacctt ccgctccacg cgccagatca gcaactttcc   19500
ggtggtgggc gccgagctgt tgcccgtgca ctccaagagc ttctacaacg accaggccgt   19560
ctactcccag ctcatccgcc agtttacctc tctgacccac gtgttcaatc gctttcccga   19620
gaaccagatt ttggcgcgcc cgccagcccc caccatcacc accgtcagtg aaaacgttcc   19680
tgctctcaca gatcacggga cgctaccgct gcgcaacagc atcggaggag tccagcgagt   19740
gaccattact gacgccagac gccgcacctg cccctacgtt tacaaggccc tgggcatagt   19800
ctcgccgcgc gtcctatcga gccgcacttt ttgagcaagc atgtccatcc ttatatcgcc   19860
cagcaataac acaggctggg gcctgcgctt cccaagcaag atgtttggcg ggccaagaa   19920 gcgctccgac caacacccag tgcgcgtgcg cgggcactac cgcgcgccct ggggcgcgca   19980
caaacgcggc cgcactgggc gcaccaccgt cgatgacgcc atcgacgcgg tggtggagga   20040
ggcgcgcaac tacacgccca cgccgccgcc agtgtccacc gtggacgcgg ccattcagac   20100
cgtggtgcgc ggagcccggc gctacgctaa aatgaagaga cggcggaggc gcgtagcacg   20160
tcgccaccgc cgccgacccg gcactgccgc ccaacgcgcg gcggcggccc tgcttaaccg   20220
cgcacgtcgc accggccgac gggcggccat gcgagccgct cgaaggctgg ccgcgggtat   20280
tgtcactgtg cccccaggt ccaggcgacg agcggccgcc gcagcagccg cggccattag   20340
tgctatgact cagggtcgca ggggcaacgt gtactgggtg cgcgactcgg ttagcggcct   20400
gcgcgtgccc gtgcgcaccc gccccccgcg caactagatt gcaataaaaa actacttaga   20460
ctcgtactgt tgtatgtatc cagcggcggc ggcgcgcatc gaagctatgt ccaagcgcaa   20520
aatcaaagaa gagatgctcc aggtcatcgc gccgagatc tatggccccc cgaagaagga   20580
agagcaggat tacaagcccc gaaagctaaa gcgggtcaaa agaaaaaga aagatgatga   20640 tgatgatgaa cttgacgacg aggtggaact gttcacgcg accgcgccca ggcgacgggt   20700
acagtggaaa ggtcgacgcg taagacgtgt tttgcgaccc ggcaccaccg tagtctttac   20760
gcccggtgag cgctccaccc gcacctacaa gcgcgtgtat gatgaggtgt acggcgacga   20820
ggacctgctt gagcaggcca acgagcgcct cggggagttt gcctacggaa agcggcataa   20880
ggacatgctg gcgttgccgc tggacagggg caacccaaca cctagcctaa agcccgtgac   20940
actgcagcag gtgctgcccg cgcttgcacc gtccgaagaa aagcgcggcc taaagcgcga   21000
```

```
gtctggtgac ttggcaccca ccgtgcagct gatggtaccc aagcgtcagc gactggaaga   21060
tgtcttggaa aaaatgaccg tggagcctgg gctggagccc gaggtccgcg tgcggccaat   21120
caagcaggtg gcaccgggac tgggcgtgca gaccgtggac gttcagatac ccaccaccag   21180
tagcactagt attgccactg ccacagaggg catggagaca caaacgtccc cggttgcctc   21240
ggcggtggca gatgccgcgg tgcaggcggc cgctgcggcc gcgtccaaga cctctacgga   21300
ggtgcaaacg gacccgtgga tgtttcgtgt ttcagccccc cggcgtccgc gccgttcaag   21360
gaagtacggc gccgccagcg cgctactgcc cgaatatgcc ctacatcctt ccatcgcgcc   21420
tacccccggc tatcgtggct acacctaccg ccccagaaga cgagcaacta cccgacgccg   21480
aaccaccact ggaacccgcc gccgccgtcg ccgtcgccag cccgtgctgg ccccgatttc   21540
cgtgcgcagg gtggctcgcg aaggaggcag gaccctggtg ctgccaacag cgcgctacca   21600
ccccagcatc gtttaaaagc cggtcttttgt ggttcttgca gatatggccc tcacctgccg   21660
cctccgtttc ccggtgccgg gattccgagg aagaatgcac cgtaggaggg gcatggccgg   21720
ccacggcctg acgggcggca tgcgtcgtgc gcaccaccgg cggcggcgcg cgtcgcaccg   21780
tcgcatgcgc ggcggtatcc tgcccctcct tattccactg atcgccgcgg cgattggcgc   21840
cgtgcccgga attgcatccg tggccttgca ggcgcagaga cactgattaa aaacaagtta   21900
catgtggaaa aatcaaaata aaagtctgga ctctcacgct cgcttggtcc tgtaactatt   21960
ttgtagaatg gaagacatca actttgcgtc actggccccg cgacacggct cgcgcccgtt   22020
catgggaaac tggcaagata tcggcaccag caatatgagc ggtggcgcct tcagctgggg   22080
ctcgctgtgg agcggcatta aaaatttcgg ttccgccgtt aagaactatg gcagcaaagc   22140
ctggaacagc agcacaggcc agatgctgag ggacaagttg aaagagcaaa atttccaaca   22200
aaaggtggta gatggcctgg cctctggcat tagcggggtg gtggacctgg ccaaccaggc   22260
agtgcaaaat aagattaaca gtaagcttga tccccgccct cccgtagagg agcctccacc   22320
ggccgtggag acagtgtctc cagaggggcg tggcgaaaag cgtccgcgac ccgacaggga   22380
agaaactctg gtgacgcaaa tagacgagcc tccctcgtac gaggaggcac taaagcaagg   22440
cctgcccacc acccgtccca tcgcgcccat ggctaccgga gtgctgggcc agcacacacc   22500
cgtaacgctg gacctgcctc cccccgccga cacccagcag aaacctgtgc tgccaggccc   22560
gtccgccgtt gttgtaaccc gtcctagccg cgcgtccctg cgccgcgccg ccagcggtcc   22620
gcgatcgttg cggcccgtag ccagtggcaa ctggcaaagc acactgaaca gcatcgtggg   22680
tttgggggtg caatccctga agcgccgacg atgcttctga tagctaacgt gtcgtatgtg   22740
tgtcatgtat gcgtccatgt cgccgccaga ggagctgctg agccgccgcg cgcccgcttt   22800
ccaagatggc tacccctttcg atgatgccgc agtggtctta catgcacatc tcgggccagg   22860
acgcctcgga gtacctgagc cccgggctgg tgcagttcgc ccgcgccacc gagacgtact   22920
tcagcctgaa taacaagttt agaaaccccca cggtggcgcc tacgcacgac gtgaccacag   22980
accggtctca gcgtttgacg ctgcggttca tccccgtgga ccgcgaggat actgcgtact   23040
cgtacaaggc gcggttcacc ctagctgtgg gtgataaccg tgtgctagac atggcttcca   23100
cgtactttga catccgcggc gtgctggaca ggggccctac ttttaagccc tactctggca   23160
ctgcctacaa cgcactggcc cccaagggtg ccccaactc gtgcgagtgg gaacaaaatg   23220
aaactgcaca agtggatgct caagaacttg acgaagagga gaatgaagcc aatgaagctc   23280
aggcgcgaga acaggaacaa gctaagaaaa cccatgtata tgcccaggct ccactgtccg   23340
gaataaaaat aactaaagaa ggtctacaaa taggaactgc cgacgccaca gtagcaggtg   23400
```

```
ccggcaaaga aattttcgca gacaaaactt ttcaacctga accacaagta ggagaatctc   23460
aatgaaacga agcggatgcc acagcagctg gtggaagggt tcttaaaaag acaactccca   23520
tgaaaccctg ctatggctca tacgctagac ccaccaattc caacggcgga cagggcgtta   23580
tggttgaaca aaatggtaaa ttggaaagtc aagtcgaaat gcaattttt tccacatcca    23640 caaatgccac aaatgaagtt aacaatatac aaccaacagt tgtattgtac agcgaagatg   23700
taaacatgga aactccagat actcatcttt cttataaacc taaaatgggg gataaaaatg   23760
ccaaagtcat gcttggacaa caagcaatgc caaacagacc aaattacatt gcttttagag   23820
acaattttat tggtctcatg tattacaaca gcacaggtaa catgggtgtc cttgctggtc   23880
aggcatcgca gttgaacgct gttgtagatt tgcaagacag aaacacagag ctgtcctacc   23940
agcttttgct tgattcaatt ggcgacagaa caagatactt ttcaatgtgg aatcaagctg   24000
ttgacagcta tgatccagat gtcagaatta ttgagaacca tggaactgag gatgagttgc   24060
caaattattg ctttcctctt ggtggaattg ggattactga cacttttcaa gctgttaaaa   24120
caactgctgc taacggggac caaggcaata ctacctggca aaaagattca acatttgcag   24180
aacgcaatga aataggggtg ggaaataact ttgccatgga aattaacctg aatgccaacc   24240
tatggagaaa tttcctttac tccaatattg cgctgtacct gccagacaag ctaaaataca   24300
accccaccaa tgtggaaata tctgacaacc ccaacaccta cgactacatg aacaagcgag   24360
tggtggctcc tgggcttgta gactgctaca ttaaccttgg ggcgcgctgg tctctggact   24420
acatggacaa cgttaatccc tttaaccacc accgcaatgc gggcctgcgt taccgctcca   24480
tgttgttggg aaacggccgc tacgtgccct ttcacattca ggtgccccaa aagttttttg   24540
ccattaaaaa cctcctcctc ctgccaggct catacacata tgaatggaac ttcaggaagg   24600
atgttaacat ggttctgcag agctctctgg gaaacgacct tagagttgac ggggctagca   24660
ttaagtttga cagcatttgt ctttacgcca ccttcttccc catggcccac aacacgcct    24720 ccacgctgga agccatgctc agaaatgaca ccaacgacca gtcctttaat gactacctt    24780 ccgccgccaa catgctatat cccataccc g ccaacgccac caacgtgccc atctccatcc   24840
catcgcgcaa ctgggcagca tttcgcggtt gggccttcac acgcttgaag acaaaggaaa   24900
ccccttccct gggatcaggc tacgacccct actacaccta ctctggctcc ataccatacc   24960
ttgacggaac cttctatctt aatcacacct ttaagaaggt ggccattact tttgactctt   25020
ctgttagctg gccgggcaac gaccgcctgc ttactcccaa tgagtttgag attaagcgct   25080
cagttgacgg ggagggctat aacgtagctc agtgcaacat gacaaaggac tggttcctag   25140
tgcagatgtt ggccaactac aatattggct accagggctt ctacattcca gaaagctaca   25200
aagaccgcat gtactcgttc ttcagaaact tccagcccat gagccggcaa gtggtggacg   25260
atactaaata caaagattat cagcaggttg gaattatcca ccagcataac aactcaggct   25320
tcgtaggcta cctcgctccc accatgcgcg agggacaagc ttaccccgct aatgttccct   25380
acccactaat aggcaaaacc gcggttgata gtattaccca gaaaaagttt ctttgcgacc   25440
gcaccctgtg gcgcatcccc ttctccagta actttatgtc catgggtgcg ctcacagacc   25500
tgggccaaaa ccttctctac gcaaactccg cccacgcgct agacatgacc tttgaggtgg   25560
atcccatgga cgagcccacc cttctttatg ttttgtttga agtctttgac gtggtccgtg   25620
tgcaccagcc gcaccgcggc gtcatcgaga ccgtgtacct gcgcacgccc ttctcggccg   25680
gcaacgccac aacataaaga agcaagcaac atcaacaaca gctgccgcca tgggctccag   25740
tgagcaggaa ctgaaagcca ttgtcaaaga tcttggttgt gggccatatt ttttgggcac   25800
```

```
ctatgacaag cgcttcccag gctttgtttc cccacacaag ctcgcctgcg ccatagttaa    25860
cacggccggt cgcgagactg ggggcgtaca ctggatggcc tttgcctgga acccgcgctc    25920
aaaaacatgc tacctctttg agcccttttgg cttttctgac caacgtctca agcaggttta   25980
ccagtttgag tacgagtcac tcctgcgccg tagcgccatt gcctcttccc ccgaccgctc    26040
tataacgctg gaaaagtcca cccaaagcgt gcaggggccc aactcggccg cctgtggcct    26100
attctgctgc atgtttctcc acgcctttgc caactggccc caaactccca tggatcacaa    26160
ccccaccatg aaccttatta ccggggtacc caactccatg cttaacagtc cccaggtaca    26220 gcccacccctg cgccgcaacc aggaacagct ctacagcttc ctggagcgcc actcgcccta   26280
cttccgcagc cacagtgcgc aaattaggag cgccacttct ttttgtcact tgaaaaacat    26340
gtaaaaataa tgtactagga gacactttca ataaaggcaa atgtttttat ttgtacactc    26400
tcgggtgatt atttacccccc acccttgccg tctgcgccgt ttaaaaatca agggggttct    26460
gccgcgcatc gctatgcgcc actggcaggg acacgttgcg atactggtgt ttagtgctcc    26520
acttaaactc aggcacaacc atccgcggca gctcggtgaa gttttcactc cacaggctgc    26580
gcaccatcac caacgcgttt agcaggtcgg gcgccgatat cttgaagtcg cagttggggc    26640
ctccgccctg cgcgcgcgag ttgcgataca cagggttaca gcactggaac actatcagcg    26700
ccgggtggtg cacgctggcc agcacgctct tgtcggagat cagatccgcg tccaggtcct    26760
ccgcgttgct cagggcgaac ggagtcaact ttggtagctg ccttcccaaa aagggtgcat    26820
gcccaggctt tgagttgcac tcgcaccgta gtggcatcag aaggtgaccg tgcccagtct    26880
gggcgttagg atacagcgcc tgcatgaaag ccttgatctg cttaaaagcc acctgagcct    26940
ttgcgccttc agagaagaac atgccgcaag acttgccgga aaactgattg gccggacagg    27000
ccgcgtcatg cacgcagcac cttgcgtcgg tgttggagat ctgcaccaca tttcggcccc    27060
accggttctt cacgatcttg gccttgctag actgctcctt cagcgcgcgc tgcccgtttt    27120
cgctcgtcac atccatttca atcacgtgct ccttatttat cataatgctc ccgtgtagac    27180
acttaagctc gccttcgatc tcagcgcagc ggtgcagcca caacgcgcag cccgtgggct    27240
cgtggtgctt gtaggttacc tctgcaaacg actgcaggta cgcctgcagg aatcgcccca    27300
tcatcgtcac aaaggtcttg ttgctggtga aggtcagctg caaccgcgcg tgctcctcgt    27360
ttagccaggt cttgcatacg gccgccagag cttccacttg gtcaggcagt agcttgaagt    27420
ttgcctttag atcgttatcc acgtggtact tgtccatcaa cgcgcgcgca gcctccatgc    27480
ccttctccca cgcagacacg atcggcaggc tcagcgggtt tatcaccgtg ctttcacttt    27540
ccgcttcact ggactcttcc ttttcctctt gcatccgcat accccgcgcc actgggtcgt    27600
cttcattcag ccgccgcacc gtgcgcttac ctcccttgcc gtgcttgatt agcaccggtg    27660
ggttgctgaa acccaccatt tgtagcgcca catcttctct ttcttcctcg ctgtccacga    27720
tcacctctgg ggatgcgggg cgctcggggct tgggagaggg gcgcttctttt ttcttttttgg  27780 acgcaatggc caaatccgcc gtcgaggtcg atggccgcgg gctgggtgtg cgcggcacca    27840
gcgcatcttg tgacgagtct tcttcgtcct cggactcgag acgccgcctc agccgctttt    27900
ttgggggcgc gcggggaggc ggcggcgacg gcgacgggga cgagacgtcc tccatggttg    27960
gtggacgtcg cgccgcaccg cgtccgcgct cggggggtggt ttcgcgctgc tcctcttccc   28020
gactggccat ttccttctcc tataggcaga aaaagatcat ggagtcagtc gagaaggagg    28080
acagcctaac cgcccccttt gagttcgcca ccaccgcctc caccgatgcc gccaacgcgc    28140
ctaccacctt ccccgtcgag gcaccccgc ttgaggagga ggaagtgatt atcgagcagg     28200
```

```
acccaggttt tgtaagcgaa gacgacgaag atcgctcagt accaacagag gataaaaagc   28260
aagaccagga cgacgcagag gcaaacgagg aacaagtcgg gcgggggggac caaaggcatg   28320 gcgactacct agatgtggga gacgacgtgc tgttgaagca tctgcagcgc cagtgcgcca   28380
ttatctgcga cgcgttgcaa gagcgcagcg atgtgcccct cgccatagcg gatgtcagcc   28440
ttgcctacga acgccacctg ttctcaccgc gcgtaccccc caaacgccaa gaaaacggca   28500
catgcgagcc caacccgcgc ctcaacttct accccgtatt tgccgtgcca gaggtgcttg   28560
ccacctatca catcttttc caaaactgca agatacccct atcctgccgt gccaaccgca   28620
gccgagcgga caagcagctg gccttgcggc agggcgctgt catacctgat atcgcctcgc   28680
tcgacgaagt gccaaaaatc tttgagggtc ttggacgcga cgagaagcgc gcggcaaacg   28740
ctctgcaaca agaaaacagc gaaaatgaaa gtcactgtgg agtgctggtg aacttgagg    28800 gtgacaacgc gcgcctagcc gtgctgaaac gcagcatcga ggtcacccac tttgcctacc   28860
cggcacttaa cctaccccc aaggttatga gcacagtcat gagcgagctg atcgtgcgcc    28920
gtgcacgacc cctggagagg gatgcaaact gcaagaaca aaccgaggag ggcctacccg    28980
cagttggcga tgagcagctg gcgcgctggc ttgagacgcg cgagcctgcc gacttggagg   29040
agcgacgcaa gctaatgatg gccgcagtgc ttgttaccgt ggagcttgag tgcatgcagc   29100
ggttctttgc tgacccggag atgcagcgca agctagagga aacgttgcac tacacctttc   29160
gccagggcta cgtgcgccag gcctgcaaaa tttccaacgt ggagctctgc aacctggtct   29220
cctaccttgg aatttgcac gaaaccgcc ttgggcaaaa cgtgcttcat tccacgctca     29280
agggcgaggc gcgccgcgac tacgtccgcg actgcgttta cttatttctg tgctacacct   29340
ggcaaacggc catgggcgtg tggcagcagt gcctggagga gcgcaacctg aaggagctgc   29400
agaagctgct aaagcaaaac ttgaaggacc tatgacggc cttcaacgag cgctccgtgg    29460
ccgcgcacct ggcggacatt atcttccccg aacgcctgct taaaaccctg caacagggtc   29520
tgccagactt caccagtcaa agcatgttgc aaaactttag gaactttatc ctagagcgtt   29580
caggaattct gcccgccacc tgctgtgcgc ttcctagcga cttgtgccc attaagtacc     29640 gtgaatgccc tccgccgctt tggggtcact gctaccttct gcagctagcc aactaccttg   29700
cctaccactc cgacatcatg gaagacgtga gcggtgacgg cctactggag tgtcactgtc   29760
gctgcaacct atgcacccc caccgctccc tggtctgcaa ttcacaactg cttagcgaaa    29820
gtcaaattat cggtacctt gagctgcagg gtccctcgcc tgacgaaaag tccgcggctc    29880
cggggttgaa actcactccg gggctgtgga cgtcggctta ccttcgcaaa tttgtacctg   29940
aggactacca cgcccacgag attaggttct acgaagacca atcccgcccg ccaaatgcgg   30000
agcttaccgc ctgcgtcatt acccaggcc acatccttgg ccaattgcaa gccattaaca    30060
aagcccgcca agagtttctg ctacgaaagg gacgggggt ttacttggac ccccagtccg    30120
gcgaggagct caacccaatc cccccgccgc cgcagcccta tcagcagccg gggcccttg    30180 cttcccagga tggcacccaa aaagaagctg cagctgccgc cgccgccacc cacggacgag   30240
gaggaatact gggacagtca ggcagaggag gttttggacg aggaggagga gatgatgaa    30300 gactgggaca gcctagacga ggaagcttcc gaggccgaag aggtgtcaga cgaaacaccg   30360
tcaccctcgg tcgcattccc ctcgccggcg ccccagaaat cggcaaccgt tcccagcatt   30420
gctacaacct ccgctcctca ggcgccgccg gcactgcccg ttcgccgacc caaccgtaga   30480
tgggacacca ctggaaccag ggccggtaag tctaagcagc cgccgccgtt agcccaagag   30540
caacaacagc gccaaggcta ccgctcgtgg cgcgtgcaca agaacgccat agttgcttgc   30600
```

-continued

```
ttgcaagact gtgggggcaa catctccttc gcccgccgct ttcttctcta ccatcacggc   30660
gtggccttcc cccgtaacat cctgcattac taccgtcatc tctacagccc ctactgcacc   30720
ggcggcagcg gcagcaacag cagcggccac gcagaagcaa aggcgaccgg atagcaagac   30780
tctgacaaag cccaagaaat ccacagcggc ggcagcagca ggaggaggag cactgcgtct   30840
ggcgcccaac gaacccgtat cgacccgcga gcttagaaac aggattttc ccactctgta   30900 tgctatattt caacagagca ggggccaaga acaagagctg aaaataaaaa acaggtctct   30960
gcgctccctc acccgcagct gcctgtatca caaaagcgaa gatcagcttc ggcgcacgct   31020
ggaagacgcg gaggctctct tcagcaaata ctgcgcgctg actcttaagg actagtttcg   31080 cgcccttct caaatttaag cgcgaaaact acgtcatctc cagcggccac acccggcgcc   31140
agcacctgtc gtcagcgcca ttatgagcaa ggaaattccc acgccctaca tgtggagtta   31200
ccagccacaa atgggacttg cggctggagc tgcccaagac tactcaaccc gaataaacta   31260
catgagcgcg ggaccccaca tgatatcccg ggtcaacgga atccgcgccc accgaaaccg   31320
aattctcctc gaacaggcgg ctattaccac cacacctcgt aataaccta atccccgtag   31380 ttggcccgct gccctggtgt accaggaaag tcccgctccc accactgtgg tacttcccag   31440
agacgcccag gccgaagttc agatgactaa ctcaggggcg cagcttgcgg gcggctttcg   31500
tcacagggtg cggtcgcccg ggcagggtat aactcacctg aaaatcagag ggcgaggtat   31560
tcagctcaac gacgagtcgg tgagctcctc tcttggtctc cgtccggacg ggacatttca   31620
gatcggcggc gctggccgct cttcatttac gccccgtcag gcgatcctaa ctctgcagac   31680
ctcgtcctcg gagccgcgct ccggaggcat tggaactcta caatttattg aggagttcgt   31740
gccttcggtt tacttcaacc ccttttctgg acctcccggc cactaccggg accagtttat   31800
tcccaacttt gacgcggtaa aagactcggc ggacggctac gactgaatga ccagtggaga   31860
ggcagagcaa ctgcgcctga cacacctcga ccactgccgc cgccacaagt gctttgcccg   31920
cggctccggt gagttttgtt actttgaatt gccccgaagag catatcgagg gcccggcgca   31980
cggcgtccgg ctcaccaccc aggtagagct tacacgtagc ctgattcggg agttaccaa    32040 gcgcccccctg ctagtggagc gggagcgggg tccctgtgtt ctgaccgtgg tttgcaactg   32100
tcctaaccct ggattacatc aagatcttat tccattcaac taacaataaa cacacaataa   32160
attacttact taaaatcagt cagcaaatct ttgtccagct tattcagcat cacctccttt   32220
ccctcctccc aactctggta tttcagcagc ctttttagctg cgaactttct ccaaagtcta   32280
aatgggatgt caaattcctc atgttcttgt ccctccgcac ccactatctt catattgttg   32340
cagatgaaac gcgccagacc gtctgaagac accttcaacc ctgtgtaccc atatgacacg   32400
gaaaccggcc ctccaactgt gccttttcctt acccctccct ttgtgtcgcc aaatgggttc   32460
caagaaagtc cccccggagt gctttctttg cgtctttcag aacctttggt tacctcacac   32520
ggcatgcttg cgctaaaaat gggcagcggc ctgtccctgg atcaggcagg caaccttaca   32580
tcaaatacaa tcactgtttc tcaaccgcta aaaaaacaa agtccaatat aactttggaa   32640
acatccgcgc cccttacagt cagctcaggc gccctaacca tggccacaac ttcgcctttg   32700
gtggtctctg acaacactct taccatgcaa tcacaagcac cgctaaccgt gcaagactca   32760
aaacttagca ttgctaccaa agagccactt acagtgttag atggaaaact ggccctgcag   32820
acatcagccc cctctctgc cactgataac aacgccctca ctatcactgc ctcacctcct   32880
cttactactg caaatggtag tctggctgtt accatggaaa acccactta caacaacaat   32940 ggaaaacttg ggctcaaaat tggcggtcct ttgcaagtgg ccaccgactc acatgcacta   33000
```

```
acactaggta ctggtcaggg ggttgcagtt cataacaatt tgctacatac aaaagttaca   33060
ggcgcaatag ggtttgatac atctggcaac atggaactta aaactggaga tggcctctat   33120
gtggatagcg ccgtcctaa ccaaaaacta catattaatc taaataccac aaaaggcctt    33180
gcttttgaca acaccgcaat aacaattaac gctggaaaag ggttggaatt tgaaacagac   33240
tcctcaaacg gaaatcccat aaaaacaaaa attggatcag gcatacaata taataccaat   33300
ggagctatgg ttgcaaaact tggaacaggc ctcagttttg acagctccgg agccataaca   33360
atgggcagca taaacaatga cagacttact cttttggacaa caccagaccc atccccaaat   33420
tgcagaattg cttcagataa agactgcaag ctaactctgg cgctaacaaa atgtggcagt   33480
caaatttttgg gcactgtttc agctttggca gtatcaggta atatggcctc catcaatgga   33540
actctaagca gtgtaaactt ggttcttaga tttgatgaca acggagtgct tatgtcaaat   33600
tcatcactgg acaaacagta ttggaacttt agaaacgggg actccactaa cggtcaacca   33660
tacacttatg ctgttgggtt tatgccaaac ctaaaagctt acccaaaaac tcaaagtaaa   33720
actgcaaaaa gtaatattgt tagccaggtg tatcttaatg gtgacaagtc taaaccattg   33780
cattttacta ttacgctaaa tggaacagat gaaaccaacc aagtaagcaa atactcaata   33840
tcattcagtt ggtcctggaa cagtggacaa tacactaatg acaaatttgc caccaattcc   33900
tataccttct cctacattgc ccaggaataa agaatcgtga acctgttgca tgttatgttt   33960
caacgtgttt atttttcaat tgcagaaaat ttcaagtcat ttttcattca gtagtatagc   34020
cccaccacca catagcttat actaatcacc gtaccttaat caaactcaca gaaccctagt   34080
attcaacctg ccacctccct cccaacacac agagtacaca gtcctttctc cccggctggc   34140
cttaaacagc atcatatcat gggtaacaga catattctta ggtgttatat tccacacggt   34200
ctcctgtcga gccaaacgct catcagtgat gttaataaac tccccgggca gctcgcttaa   34260
gttcatgtcg ctgtccagct gctgagccac aggctgctgt ccaacttgcg gttgctcaac   34320
gggcggcgaa ggagaagtcc acgcctacat gggggtagag tcataatcgt gcatcaggat   34380
agggcggtgg tgctgcagca gcgcgcgaat aaactgctgc cgccgccgct ccgtcctgca   34440
ggaatacaac atggcagtgg tctcctcagc gatgattcgc accgcccgca gcataaggcg   34500
ccttgtcctc cgggcacagc agcgcaccct gatctcactt aagtcagcac agtaactgca   34560
gcacagtacc acaatattgt ttaaaatccc acagtgcaag gcgctgtatc caagctcat   34620
ggcggggacc acagaaccca cgtggccatc ataccacaag cgcaggtaga ttaagtggcg   34680
acccctcata aacacgctgg acataaacat tacctctttt ggcatgttgt aattcaccac   34740
ctcccggtac catataaacc tctgattaaa catggcgcca tccaccacca tcctaaacca   34800
gctggccaaa acctgcccgc cggctatgca ctgcagggaa ccgggactgg aacaatgaca   34860
gtggagagcc caggactcgt aaccatggat catcatgctc gtcatgatat caatgttggc   34920
acaacacagg cacacgtgca tacacttcct caggattaca agctcctccc gcgtcagaac   34980
catatcccag ggaacaaccc attcctgaat cagcgtaaat cccacactgc agggaagacc   35040
tcgcacgtaa ctcacgttgt gcattgtcaa agtgttacat tcgggcagca gcggatgatc   35100
ctccagtatg gtagcgcggg tttctgtctc aaaaggaggt agacgatccc tactgtacgg   35160
agtgcgccga gacaaccgag atcgtgttgg tcgtagtgtc atgccaaatg gaacgccgga   35220
cgtagtcata tttcctgaag caaaaccagg tgcgggcgtg acaaacagat ctgcgtctcc   35280
ggtctcgccg cttagatcgc tctgtgtagt agttgtagta tatccactct ctcaaagcat   35340
ccaggcgccc cctggcttcg ggttctatgt aaactccttc atgcgccgct gccctgataa   35400
```

-continued

| | |
|---|---|
| catccaccac cgcagaataa gccacaccca gccaacctac acattcgttc tgcgagtcac | 35460 |
| acacgggagg agcgggaaga gctggaagaa ccatgttttt ttttttattc caaaagatta | 35520 |
| tccaaaacct caaaatgaag atctattaag tgaacgcgct cccctccggt ggcgtggtca | 35580 |
| aactctacag ccaagaaca gataatggca tttgtaagat gttgcacaat ggcttccaaa | 35640 |
| aggcaaacgg ccctcacgtc caagtggacg taaaggctaa acccttcagg gtgaatctcc | 35700 |
| tctataaaca ttccagcacc ttcaaccatg cccaaataat tctcatctcg ccaccttctc | 35760 |
| aatatatctc taagcaaatc ccgaatatta agtccggcca ttgtaaaaat ctgctccaga | 35820 |
| gcgcccctcca ccttcagcct caagcagcga atcatgattg caaaaattca ggttcctcac | 35880 |
| agacctgtat aagattcaaa agcggaacat taacaaaaat accgcgatcc cgtaggtccc | 35940 |
| ttcgcagggc cagctgaaca taatcgtgca ggtctgcacg gaccagcgcg gccacttccc | 36000 |
| cgccaggaac catgacaaaa gaacccacac tgattatgac acgcatactc ggagctatgc | 36060 |
| taaccagcgt agccccgatg taagcttgtt gcatgggcgg cgatataaaa tgcaaggtgc | 36120 |
| tgctcaaaaa atcaggcaaa gcctcgcgca aaaagaaag cacatcgtag tcatgctcat | 36180 |
| gcagataaag gcaggtaagc tccggaacca ccacagaaaa agacaccatt tttctctcaa | 36240 |
| acatgtctgc gggtttctgc ataaacacaa aataaaataa caaaaaaaca tttaaacatt | 36300 |
| agaagcctgt cttacaacag gaaaaacaac ccttataagc ataagacgga ctacggccat | 36360 |
| gccggcgtga ccgtaaaaaa actggtcacc gtgattaaaa agcaccaccg acagctcctc | 36420 |
| ggtcatgtcc ggagtcataa tgtaagactc ggtaaacaca tcaggttgat tcacatcggt | 36480 |
| cagtgctaaa aagcgaccga aatagcccgg gggaatacat acccgcaggc gtagagacaa | 36540 |
| cattacagcc cccataggag gtataacaaa attaatagga gagaaaaaca cataaacacc | 36600 |
| tgaaaaaccc tcctgcctag gcaaaatagc accctcccgc tccagaacaa catacagcgc | 36660 |
| ttccacagcg gcagccataa cagtcagcct taccagtaaa aagaaaacc tattaaaaaa | 36720 |
| acaccactcg acacggcacc agctcaatca gtcacagtgt aaaaagggc caagtgcaga | 36780 |
| gcgagtatat ataggactaa aaatgacgt aacggttaaa gtccacaaaa acacccaga | 36840 |
| aaaccgcacg cgaacctacg cccagaaacg aaagccaaaa aacccacaac ttcctcaaat | 36900 |
| cgtcacttcc gttttcccac gttacgtcac ttcccatttt aagaaaacta caattcccaa | 36960 |
| cacatacaag ttactccgcc ctaaaaccta cgtcacccgc cccgttccca cgccccgcgc | 37020 |
| cacgtcacaa actccacccc ctcattatca tattggcttc aatccaaaat aaggtatatt | 37080 |
| attgatgatg | 37090 |

<210> SEQ ID NO 5
<211> LENGTH: 5955
<212> TYPE: DNA
<213> ORGANISM: Artificial Sequence
<220> FEATURE:
<223> OTHER INFORMATION: NS cDNA sequence
<220> FEATURE:
<221> NAME/KEY: CDS
<222> LOCATION: (1)...(5955)

<400> SEQUENCE: 5

| | |
|---|---|
| atg gcg ccc atc acg gcc tac tcc caa cag acg cgg ggc cta ctt ggt<br>Met Ala Pro Ile Thr Ala Tyr Ser Gln Gln Thr Arg Gly Leu Leu Gly<br>1               5                   10                  15 | 48 |
| tgc atc atc act agc ctt aca ggc cgg gac aag aac cag gtc gag gga<br>Cys Ile Ile Thr Ser Leu Thr Gly Arg Asp Lys Asn Gln Val Glu Gly<br>            20                  25                  30 | 96 |
| gag gtt cag gtg gtt tcc acc gca aca caa tcc ttc ctg gcg acc tgc<br>Glu Val Gln Val Val Ser Thr Ala Thr Gln Ser Phe Leu Ala Thr Cys | 144 |

|     |     |     |     |     |     |     |     |     |     |     |     |     |     |     |     |     |
|---|---|---|---|---|---|---|---|---|---|---|---|---|---|---|---|---|
| Glu | Val | Gln | Val | Val | Ser | Thr | Ala | Thr | Gln | Ser | Phe | Leu | Ala | Thr | Cys | |
| | 35 | | | | | 40 | | | | | 45 | | | | | |

| gtc | aac | ggc | gtg | tgt | tgg | acc | gtt | tac | cat | ggt | gct | ggc | tca | aag | acc | 192 |
|---|---|---|---|---|---|---|---|---|---|---|---|---|---|---|---|---|
| Val | Asn | Gly | Val | Cys | Trp | Thr | Val | Tyr | His | Gly | Ala | Gly | Ser | Lys | Thr | |
| 50 | | | | | 55 | | | | | 60 | | | | | | |

| tta | gcc | ggc | cca | aag | ggg | cca | atc | acc | cag | atg | tac | act | aat | gtg | gac | 240 |
|---|---|---|---|---|---|---|---|---|---|---|---|---|---|---|---|---|
| Leu | Ala | Gly | Pro | Lys | Gly | Pro | Ile | Thr | Gln | Met | Tyr | Thr | Asn | Val | Asp | |
| 65 | | | | 70 | | | | | 75 | | | | | 80 | | |

| cag | gac | ctc | gtc | ggc | tgg | cag | gcg | ccc | ccg | gcg | cgt | tcc | ttg | aca | | 288 |
|---|---|---|---|---|---|---|---|---|---|---|---|---|---|---|---|---|
| Gln | Asp | Leu | Val | Gly | Trp | Gln | Ala | Pro | Pro | Gly | Ala | Arg | Ser | Leu | Thr | |
| | | | | 85 | | | | | 90 | | | | | 95 | | |

| cca | tgc | acc | tgt | ggc | agc | tca | gac | ctt | tac | ttg | gtc | acg | aga | cat | gct | 336 |
|---|---|---|---|---|---|---|---|---|---|---|---|---|---|---|---|---|
| Pro | Cys | Thr | Cys | Gly | Ser | Ser | Asp | Leu | Tyr | Leu | Val | Thr | Arg | His | Ala | |
| | | | 100 | | | | | 105 | | | | | 110 | | | |

| gac | gtc | att | ccg | gtg | cgc | cgg | cgg | ggc | gac | agt | agg | ggg | agc | ctg | ctc | 384 |
|---|---|---|---|---|---|---|---|---|---|---|---|---|---|---|---|---|
| Asp | Val | Ile | Pro | Val | Arg | Arg | Arg | Gly | Asp | Ser | Arg | Gly | Ser | Leu | Leu | |
| | | | 115 | | | | | 120 | | | | | 125 | | | |

| tcc | ccc | agg | cct | gtc | tcc | tac | ttg | aag | ggc | tct | tcg | ggt | ggt | cca | ctg | 432 |
|---|---|---|---|---|---|---|---|---|---|---|---|---|---|---|---|---|
| Ser | Pro | Arg | Pro | Val | Ser | Tyr | Leu | Lys | Gly | Ser | Ser | Gly | Gly | Pro | Leu | |
| | 130 | | | | | 135 | | | | | 140 | | | | | |

| ctc | tgc | cct | tcg | ggg | cac | gct | gtg | ggc | atc | ttc | cgg | gct | gcc | gta | tgc | 480 |
|---|---|---|---|---|---|---|---|---|---|---|---|---|---|---|---|---|
| Leu | Cys | Pro | Ser | Gly | His | Ala | Val | Gly | Ile | Phe | Arg | Ala | Ala | Val | Cys | |
| 145 | | | | | 150 | | | | | 155 | | | | | 160 | |

| acc | cgg | ggg | gtt | gcg | aag | gcg | gtg | gac | ttt | gtg | ccc | gta | gag | tcc | atg | 528 |
|---|---|---|---|---|---|---|---|---|---|---|---|---|---|---|---|---|
| Thr | Arg | Gly | Val | Ala | Lys | Ala | Val | Asp | Phe | Val | Pro | Val | Glu | Ser | Met | |
| | | | | 165 | | | | | 170 | | | | | 175 | | |

| gaa | act | act | atg | cgg | tct | ccg | gtc | ttc | acg | gac | aac | tca | tcc | ccc | ccg | 576 |
|---|---|---|---|---|---|---|---|---|---|---|---|---|---|---|---|---|
| Glu | Thr | Thr | Met | Arg | Ser | Pro | Val | Phe | Thr | Asp | Asn | Ser | Ser | Pro | Pro | |
| | | | 180 | | | | | 185 | | | | | 190 | | | |

| gcc | gta | ccg | cag | tca | ttt | caa | gta | gcc | cac | cta | cac | gct | ccc | act | ggc | 624 |
|---|---|---|---|---|---|---|---|---|---|---|---|---|---|---|---|---|
| Ala | Val | Pro | Gln | Ser | Phe | Gln | Val | Ala | His | Leu | His | Ala | Pro | Thr | Gly | |
| | | 195 | | | | | 200 | | | | | 205 | | | | |

| agc | ggc | aag | agt | act | aaa | gtg | ccg | gct | gca | tat | gca | gcc | caa | ggg | tac | 672 |
|---|---|---|---|---|---|---|---|---|---|---|---|---|---|---|---|---|
| Ser | Gly | Lys | Ser | Thr | Lys | Val | Pro | Ala | Ala | Tyr | Ala | Ala | Gln | Gly | Tyr | |
| | 210 | | | | | 215 | | | | | 220 | | | | | |

| aag | gtg | ctc | gtc | ctc | aat | ccg | tcc | gtt | gcc | gct | acc | tta | ggg | ttt | ggg | 720 |
|---|---|---|---|---|---|---|---|---|---|---|---|---|---|---|---|---|
| Lys | Val | Leu | Val | Leu | Asn | Pro | Ser | Val | Ala | Ala | Thr | Leu | Gly | Phe | Gly | |
| 225 | | | | | 230 | | | | | 235 | | | | | 240 | |

| gcg | tat | atg | tct | aag | gca | cac | ggt | att | gac | ccc | aac | atc | aga | act | ggg | 768 |
|---|---|---|---|---|---|---|---|---|---|---|---|---|---|---|---|---|
| Ala | Tyr | Met | Ser | Lys | Ala | His | Gly | Ile | Asp | Pro | Asn | Ile | Arg | Thr | Gly | |
| | | | | 245 | | | | | 250 | | | | | 255 | | |

| gta | agg | acc | att | acc | aca | ggc | gcc | ccc | gtc | aca | tac | tct | acc | tat | ggc | 816 |
|---|---|---|---|---|---|---|---|---|---|---|---|---|---|---|---|---|
| Val | Arg | Thr | Ile | Thr | Thr | Gly | Ala | Pro | Val | Thr | Tyr | Ser | Thr | Tyr | Gly | |
| | | | 260 | | | | | 265 | | | | | 270 | | | |

| aag | ttt | ctt | gcc | gat | ggt | ggt | tgc | tct | ggg | ggc | gct | tat | gac | atc | ata | 864 |
|---|---|---|---|---|---|---|---|---|---|---|---|---|---|---|---|---|
| Lys | Phe | Leu | Ala | Asp | Gly | Gly | Cys | Ser | Gly | Gly | Ala | Tyr | Asp | Ile | Ile | |
| | | 275 | | | | | 280 | | | | | 285 | | | | |

| ata | tgt | gat | gag | tgc | cat | tca | act | gac | tcg | act | aca | atc | ttg | ggc | atc | 912 |
|---|---|---|---|---|---|---|---|---|---|---|---|---|---|---|---|---|
| Ile | Cys | Asp | Glu | Cys | His | Ser | Thr | Asp | Ser | Thr | Thr | Ile | Leu | Gly | Ile | |
| | 290 | | | | | 295 | | | | | 300 | | | | | |

| ggc | aca | gtc | ctg | gac | caa | gcg | gag | acg | gct | gga | gcg | cgg | ctt | gtc | gtg | 960 |
|---|---|---|---|---|---|---|---|---|---|---|---|---|---|---|---|---|
| Gly | Thr | Val | Leu | Asp | Gln | Ala | Glu | Thr | Ala | Gly | Ala | Arg | Leu | Val | Val | |
| 305 | | | | | 310 | | | | | 315 | | | | | 320 | |

| ctc | gcc | acc | gct | acg | cct | ccg | gga | tcg | gtc | acc | gtg | cca | cac | cca | aac | 1008 |
|---|---|---|---|---|---|---|---|---|---|---|---|---|---|---|---|---|
| Leu | Ala | Thr | Ala | Thr | Pro | Pro | Gly | Ser | Val | Thr | Val | Pro | His | Pro | Asn | |
| | | | | 325 | | | | | 330 | | | | | 335 | | |

| atc | gag | gag | gtg | gcc | ctg | tct | aat | act | gga | gag | atc | ccc | ttc | tat | ggc | 1056 |
|---|---|---|---|---|---|---|---|---|---|---|---|---|---|---|---|---|
| Ile | Glu | Glu | Val | Ala | Leu | Ser | Asn | Thr | Gly | Glu | Ile | Pro | Phe | Tyr | Gly | |
| | | | 340 | | | | | 345 | | | | | 350 | | | |

| aaa | gcc | atc | ccc | att | gaa | gcc | atc | agg | ggg | gga | agg | cat | ctc | att | ttc | 1104 |

```
                    -continued

Lys Ala Ile Pro Ile Glu Ala Ile Arg Gly Gly Arg His Leu Ile Phe
                      355                 360                 365 tgt cat tcc aag aag aag tgc gac gag ctc gcc gca aag ctg tca ggc      1152
Cys His Ser Lys Lys Lys Cys Asp Glu Leu Ala Ala Lys Leu Ser Gly
    370                 375                 380 ctc gga atc aac gct gtg gcg tat tac cgg ggg ctc gat gtg tcc gtc      1200
Leu Gly Ile Asn Ala Val Ala Tyr Tyr Arg Gly Leu Asp Val Ser Val
385                 390                 395                 400 ata cca act atc gga gac gtc gtt gtg gca aca gac gct ctg atg          1248
Ile Pro Thr Ile Gly Asp Val Val Val Ala Thr Asp Ala Leu Met
                405                 410                 415 acg ggc tat acg ggc gac ttt gac tca gtg atc gac tgt aac aca tgt      1296
Thr Gly Tyr Thr Gly Asp Phe Asp Ser Val Ile Asp Cys Asn Thr Cys
            420                 425                 430 gtc acc cag aca gtc gac ttc agc ttg gat ccc acc ttc acc att gag      1344
Val Thr Gln Thr Val Asp Phe Ser Leu Asp Pro Thr Phe Thr Ile Glu
        435                 440                 445 acg acg acc gtg cct caa gac gca gtg tcg cgc tcg cag cgg cgg ggt      1392
Thr Thr Thr Val Pro Gln Asp Ala Val Ser Arg Ser Gln Arg Arg Gly
    450                 455                 460 agg act ggc agg ggt agg aga ggc atc tac agg ttt gtg act ccg gga      1440
Arg Thr Gly Arg Gly Arg Arg Gly Ile Tyr Arg Phe Val Thr Pro Gly
465                 470                 475                 480 gaa cgg ccc tcg ggc atg ttc gat tcc tcg gtc ctg tgt gag tgc tat      1488
Glu Arg Pro Ser Gly Met Phe Asp Ser Ser Val Leu Cys Glu Cys Tyr
                485                 490                 495 gac gcg ggc tgt gct tgg tac gag ctc acc ccc gcc gag acc tcg gtt      1536
Asp Ala Gly Cys Ala Trp Tyr Glu Leu Thr Pro Ala Glu Thr Ser Val
            500                 505                 510 agg ttg cgg gcc tac ctg aac aca cca ggg ttg ccc gtt tgc cag gac      1584
Arg Leu Arg Ala Tyr Leu Asn Thr Pro Gly Leu Pro Val Cys Gln Asp
        515                 520                 525 cac ctg gag ttc tgg gag agt gtc ttc aca ggc ctc acc cac ata gat      1632
His Leu Glu Phe Trp Glu Ser Val Phe Thr Gly Leu Thr His Ile Asp
    530                 535                 540 gca cac ttc ttg tcc cag acc aag cag gca gga gac aac ttc ccc tac      1680
Ala His Phe Leu Ser Gln Thr Lys Gln Ala Gly Asp Asn Phe Pro Tyr
545                 550                 555                 560 ctg gta gca tac caa gcc acg gtg tgc gcc agg gct cag gcc cca cct      1728
Leu Val Ala Tyr Gln Ala Thr Val Cys Ala Arg Ala Gln Ala Pro Pro
                565                 570                 575 cca tca tgg gat caa atg tgg aag tgt ctc ata cgg ctg aaa cct acg      1776
Pro Ser Trp Asp Gln Met Trp Lys Cys Leu Ile Arg Leu Lys Pro Thr
            580                 585                 590 ctg cac ggg cca aca ccc ttg ctg tac agg ctg gga gcc gtc caa aat      1824
Leu His Gly Pro Thr Pro Leu Leu Tyr Arg Leu Gly Ala Val Gln Asn
        595                 600                 605 gag gtc acc ctc acc cac ccc ata acc aaa tac atc atg gca tgc atg      1872
Glu Val Thr Leu Thr His Pro Ile Thr Lys Tyr Ile Met Ala Cys Met
    610                 615                 620 tcg gct gac ctg gag gtc gtc act agc acc tgg gtg ctg gtg ggc gga      1920
Ser Ala Asp Leu Glu Val Val Thr Ser Thr Trp Val Leu Val Gly Gly
625                 630                 635                 640 gtc ctt gca gct ctg gcc gcg tat tgc ctg aca aca ggc agt gtg gtc      1968
Val Leu Ala Ala Leu Ala Ala Tyr Cys Leu Thr Thr Gly Ser Val Val
                645                 650                 655 att gtg ggt agg att atc ttg tcc ggg agg ccg gct att gtt ccc gac      2016
Ile Val Gly Arg Ile Ile Leu Ser Gly Arg Pro Ala Ile Val Pro Asp
            660                 665                 670 agg gag ttt ctc tac cag gag ttc gat gaa atg gaa gag tgc gcc tcg      2064
```

```
                  -continued

Arg Glu Phe Leu Tyr Gln Glu Phe Asp Glu Met Glu Glu Cys Ala Ser
            675                 680                 685 cac ctc cct tac atc gag cag gga atg cag ctc gcc gag caa ttc aag    2112
His Leu Pro Tyr Ile Glu Gln Gly Met Gln Leu Ala Glu Gln Phe Lys
            690                 695                 700 cag aaa gcg ctc ggg tta ctg caa aca gcc acc aaa caa gcg gag gct    2160
Gln Lys Ala Leu Gly Leu Leu Gln Thr Ala Thr Lys Gln Ala Glu Ala
705                 710                 715                 720 gct gct ccc gtg gtg gag tcc aag tgg cga gcc ctt gag aca ttc tgg    2208
Ala Ala Pro Val Val Glu Ser Lys Trp Arg Ala Leu Glu Thr Phe Trp
                725                 730                 735 gcg aag cac atg tgg aat ttc atc agc ggg ata cag tac tta gca ggc    2256
Ala Lys His Met Trp Asn Phe Ile Ser Gly Ile Gln Tyr Leu Ala Gly
            740                 745                 750 tta tcc act ctg cct ggg aac ccc gca ata gca tca ttg atg gca ttc    2304
Leu Ser Thr Leu Pro Gly Asn Pro Ala Ile Ala Ser Leu Met Ala Phe
        755                 760                 765 aca gcc tct atc acc agc ccg ctc acc acc caa agt acc ctc ctg ttt    2352
Thr Ala Ser Ile Thr Ser Pro Leu Thr Thr Gln Ser Thr Leu Leu Phe
770                 775                 780 aac atc ttg ggg ggg tgg gtg gct gcc caa ctc gcc ccc ccc agc gcc    2400
Asn Ile Leu Gly Gly Trp Val Ala Ala Gln Leu Ala Pro Pro Ser Ala
785                 790                 795                 800 gct tcg gct ttc gtg ggc gcc ggc atc gcc ggt gcg gct gtt ggc agc    2448
Ala Ser Ala Phe Val Gly Ala Gly Ile Ala Gly Ala Ala Val Gly Ser
                805                 810                 815 ata ggc ctt ggg aag gtg ctt gtg gac att ctg gcg ggt tat gga gca    2496
Ile Gly Leu Gly Lys Val Leu Val Asp Ile Leu Ala Gly Tyr Gly Ala
            820                 825                 830 gga gtg gcc ggc gcg ctc gtg gcc ttc aag gtc atg agc ggc gag atg    2544
Gly Val Ala Gly Ala Leu Val Ala Phe Lys Val Met Ser Gly Glu Met
        835                 840                 845 ccc tcc acc gag gac ctg gtc aat cta ctt cct gcc atc ctc tct cct    2592
Pro Ser Thr Glu Asp Leu Val Asn Leu Leu Pro Ala Ile Leu Ser Pro
850                 855                 860 ggc gcc ctg gtc gtc ggg gtc gtg tgt gca gca ata ctg cgt cga cac    2640
Gly Ala Leu Val Val Gly Val Val Cys Ala Ala Ile Leu Arg Arg His
865                 870                 875                 880 gtg ggt ccg gga gag ggg gct gtg cag tgg atg aac cgg ctg ata gcg    2688
Val Gly Pro Gly Glu Gly Ala Val Gln Trp Met Asn Arg Leu Ile Ala
                885                 890                 895 ttc gcc tcg cgg ggt aat cat gtt tcc ccc acg cac tat gtg cct gag    2736
Phe Ala Ser Arg Gly Asn His Val Ser Pro Thr His Tyr Val Pro Glu
            900                 905                 910 agc gac gcc gca gcg cgt gtt act cag atc ctc tcc agc ctt acc atc    2784
Ser Asp Ala Ala Ala Arg Val Thr Gln Ile Leu Ser Ser Leu Thr Ile
        915                 920                 925 act cag ctg ctg aaa agg ctc cac cag tgg att aat gaa gac tgc tcc    2832
Thr Gln Leu Leu Lys Arg Leu His Gln Trp Ile Asn Glu Asp Cys Ser
930                 935                 940 aca ccg tgt tcc ggc tcg tgg cta agg gat gtt tgg gac tgg ata tgc    2880
Thr Pro Cys Ser Gly Ser Trp Leu Arg Asp Val Trp Asp Trp Ile Cys
945                 950                 955                 960 acg gtg ttg act gac ttc aag acc tgg ctc cag tcc aag ctc ctg ccg    2928
Thr Val Leu Thr Asp Phe Lys Thr Trp Leu Gln Ser Lys Leu Leu Pro
                965                 970                 975 cag cta ccg gga gtc cct ttt ttc tcg tgc caa cgc ggg tac aag gga    2976
Gln Leu Pro Gly Val Pro Phe Phe Ser Cys Gln Arg Gly Tyr Lys Gly
            980                 985                 990 gtc tgg cgg gga gac ggc atc atg caa acc acc tgc cca tgt gga gca    3024
```

-continued

|  |  |
|---|---|
| Val Trp Arg Gly Asp Gly Ile Met Gln Thr Thr Cys Pro Cys Gly Ala<br>     995                          1000                     1005 |  |
| cag atc acc gga cat gtc aaa aac ggt tcc atg agg atc gtc ggg cct<br>Gln Ile Thr Gly His Val Lys Asn Gly Ser Met Arg Ile Val Gly Pro<br>          1010                         1015                     1020 | 3072 |
| aag acc tgc agc aac acg tgg cat gga aca ttc ccc atc aac gca tac<br>Lys Thr Cys Ser Asn Thr Trp His Gly Thr Phe Pro Ile Asn Ala Tyr<br>1025                    1030                       1035                    1040 | 3120 |
| acc acg ggc ccc tgc aca ccc tct cca gcg cca aac tat tct agg gcg<br>Thr Thr Gly Pro Cys Thr Pro Ser Pro Ala Pro Asn Tyr Ser Arg Ala<br>                    1045                       1050                    1055 | 3168 |
| ctg tgg cgg gtg gcc gct gag gag tac gtg gag gtc acg cgg gtg ggg<br>Leu Trp Arg Val Ala Ala Glu Glu Tyr Val Glu Val Thr Arg Val Gly<br>                 1060                       1065                    1070 | 3216 |
| gat ttc cac tac gtg acg ggc atg acc act gac aac gta aag tgc cca<br>Asp Phe His Tyr Val Thr Gly Met Thr Thr Asp Asn Val Lys Cys Pro<br>                    1075                       1080                    1085 | 3264 |
| tgc cag gtt ccg gct cct gaa ttc ttc acg gag gtg gac gga gtg cgg<br>Cys Gln Val Pro Ala Pro Glu Phe Phe Thr Glu Val Asp Gly Val Arg<br>          1090                         1095                    1100 | 3312 |
| ttg cac agg tac gct ccg gcg tgc agg cct ctc cta cgg gag gag gtt<br>Leu His Arg Tyr Ala Pro Ala Cys Arg Pro Leu Leu Arg Glu Glu Val<br>1105                    1110                       1115                    1120 | 3360 |
| aca ttc cag gtc ggg ctc aac caa tac ctg gtt ggg tca cag cta cca<br>Thr Phe Gln Val Gly Leu Asn Gln Tyr Leu Val Gly Ser Gln Leu Pro<br>                    1125                       1130                    1135 | 3408 |
| tgc gag ccc gaa ccg gat gta gca gtg ctc act tcc atg ctc acc gac<br>Cys Glu Pro Glu Pro Asp Val Ala Val Leu Thr Ser Met Leu Thr Asp<br>                 1140                       1145                    1150 | 3456 |
| ccc tcc cac atc aca gca gaa acg gct aag cgt agg ttg gcc agg ggg<br>Pro Ser His Ile Thr Ala Glu Thr Ala Lys Arg Arg Leu Ala Arg Gly<br>               1155                       1160                    1165 | 3504 |
| tct ccc ccc tcc ttg gcc agc tct tca gct agc cag ttg tct gcg cct<br>Ser Pro Pro Ser Leu Ala Ser Ser Ser Ala Ser Gln Leu Ser Ala Pro<br>1170                    1175                       1180 | 3552 |
| tcc ttg aag gcg aca tgc act acc cac cat gtc tct ccg gac gct gac<br>Ser Leu Lys Ala Thr Cys Thr Thr His His Val Ser Pro Asp Ala Asp<br>1185                    1190                       1195                    1200 | 3600 |
| ctc atc gag gcc aac ctc ctg tgg cgg cag gag atg ggc ggg aac atc<br>Leu Ile Glu Ala Asn Leu Leu Trp Arg Gln Glu Met Gly Gly Asn Ile<br>                    1205                       1210                    1215 | 3648 |
| acc cgc gtg gag tcg gag aac aag gtg gta gtc ctg gac tct ttc gac<br>Thr Arg Val Glu Ser Glu Asn Lys Val Val Val Leu Asp Ser Phe Asp<br>          1220                         1225                    1230 | 3696 |
| ccg ctt cga gcg gag gag gat gag agg gaa gta tcc gtt ccg gcg gag<br>Pro Leu Arg Ala Glu Glu Asp Glu Arg Glu Val Ser Val Pro Ala Glu<br>                 1235                       1240                    1245 | 3744 |
| atc ctg cgg aaa tcc aag aag ttc ccc gca gcg atg ccc atc tgg gcg<br>Ile Leu Arg Lys Ser Lys Lys Phe Pro Ala Ala Met Pro Ile Trp Ala<br>                    1250                       1255                    1260 | 3792 |
| cgc ccg gat tac aac cct cca ctg tta gag tcc tgg aag gac ccg gac<br>Arg Pro Asp Tyr Asn Pro Pro Leu Leu Glu Ser Trp Lys Asp Pro Asp<br>1265                    1270                       1275                    1280 | 3840 |
| tac gtc cct ccg gtg gtg cac ggg tgc ccg ttg cca cct atc aag gcc<br>Tyr Val Pro Pro Val Val His Gly Cys Pro Leu Pro Pro Ile Lys Ala<br>                    1285                       1290                    1295 | 3888 |
| cct cca ata cca cct cca cgg aga aag agg acg gtt gtc cta aca gag<br>Pro Pro Ile Pro Pro Pro Arg Arg Lys Arg Thr Val Val Leu Thr Glu<br>                 1300                       1305                    1310 | 3936 |
| tcc tcc gtg tct tct gcc tta gcg gag ctc gct act aag acc ttc ggc | 3984 |

-continued

```
                Ser Ser Val Ser Ser Ala Leu Ala Glu Leu Ala Thr Lys Thr Phe Gly
                        1315                1320                1325 agc tcc gaa tca tcg gcc gtc gac agc ggc acg gcg acc gcc ctt cct         4032
Ser Ser Glu Ser Ser Ala Val Asp Ser Gly Thr Ala Thr Ala Leu Pro
    1330                1335                1340 gac cag gcc tcc gac gac ggt gac aaa gga tcc gac gtt gag tcg tac         4080
Asp Gln Ala Ser Asp Asp Gly Asp Lys Gly Ser Asp Val Glu Ser Tyr
1345                1350                1355                1360 tcc tcc atg ccc ccc ctt gag ggg gaa ccg ggg gac ccc gat ctc agt         4128
Ser Ser Met Pro Pro Leu Glu Gly Glu Pro Gly Asp Pro Asp Leu Ser
                1365                1370                1375 gac ggg tct tgg tct acc gtg agc gag gaa gct agt gag gat gtc gtc         4176
Asp Gly Ser Trp Ser Thr Val Ser Glu Glu Ala Ser Glu Asp Val Val
            1380                1385                1390 tgc tgc tca atg tcc tac aca tgg aca ggc gcc ttg atc acg cca tgc         4224
Cys Cys Ser Met Ser Tyr Thr Trp Thr Gly Ala Leu Ile Thr Pro Cys
        1395                1400                1405 gct gcg gag gaa agc aag ctg ccc atc aac gcg ttg agc aac tct ttg         4272
Ala Ala Glu Glu Ser Lys Leu Pro Ile Asn Ala Leu Ser Asn Ser Leu
    1410                1415                1420 ctg cgc cac cat aac atg gtt tat gcc aca aca tct cgc agc gca ggc         4320
Leu Arg His His Asn Met Val Tyr Ala Thr Thr Ser Arg Ser Ala Gly
1425                1430                1435                1440 ctg cgg cag aag aag gtc acc ttt gac aga ctg caa gtc ctg gac gac         4368
Leu Arg Gln Lys Lys Val Thr Phe Asp Arg Leu Gln Val Leu Asp Asp
                1445                1450                1455 cac tac cgg gac gtg ctc aag gag atg aag gcg aag gcg tcc aca gtt         4416
His Tyr Arg Asp Val Leu Lys Glu Met Lys Ala Lys Ala Ser Thr Val
            1460                1465                1470 aag gct aaa ctc cta tcc gta gag gaa gcc tgc aag ctg acg ccc cca         4464
Lys Ala Lys Leu Leu Ser Val Glu Glu Ala Cys Lys Leu Thr Pro Pro
        1475                1480                1485 cat tcg gcc aaa tcc aag ttt ggc tat ggg gca aag gac gtc cgg aac         4512
His Ser Ala Lys Ser Lys Phe Gly Tyr Gly Ala Lys Asp Val Arg Asn
    1490                1495                1500 cta tcc agc aag gcc gtt aac cac atc cac tcc gtg tgg aag gac ttg         4560
Leu Ser Ser Lys Ala Val Asn His Ile His Ser Val Trp Lys Asp Leu
1505                1510                1515                1520 ctg gaa gac act gtg aca cca att gac acc acc atc atg gca aaa aat         4608
Leu Glu Asp Thr Val Thr Pro Ile Asp Thr Thr Ile Met Ala Lys Asn
                1525                1530                1535 gag gtt ttc tgt gtc caa cca gag aaa gga ggc cgt aag cca gcc cgc         4656
Glu Val Phe Cys Val Gln Pro Glu Lys Gly Gly Arg Lys Pro Ala Arg
            1540                1545                1550 ctt atc gta ttc cca gat ctg gga gtc cgt gta tgc gag aag atg gcc         4704
Leu Ile Val Phe Pro Asp Leu Gly Val Arg Val Cys Glu Lys Met Ala
        1555                1560                1565 ctc tat gat gtg gtc tcc acc ctt cct cag gtc gtg atg ggc tcc tca         4752
Leu Tyr Asp Val Val Ser Thr Leu Pro Gln Val Val Met Gly Ser Ser
    1570                1575                1580 tac gga ttc cag tac tct cct ggg cag cga gtc gag ttc ctg gtg aat         4800
Tyr Gly Phe Gln Tyr Ser Pro Gly Gln Arg Val Glu Phe Leu Val Asn
1585                1590                1595                1600 acc tgg aaa tca aag aaa aac ccc atg ggc ttt tca tat gac act cgc         4848
Thr Trp Lys Ser Lys Lys Asn Pro Met Gly Phe Ser Tyr Asp Thr Arg
                1605                1610                1615 tgt ttc gac tca acg gtc acc gag aac gac atc cgt gtt gag gag tca         4896
Cys Phe Asp Ser Thr Val Thr Glu Asn Asp Ile Arg Val Glu Glu Ser
            1620                1625                1630 att tac caa tgt tgt gac ttg gcc ccc gaa gcc aga cag gcc ata aaa         4944
```

-continued

| | | |
|---|---|---|
| Ile Tyr Gln Cys Cys Asp Leu Ala Pro Glu Ala Arg Gln Ala Ile Lys<br>        1635                1640               1645 | | |
| tcg ctc aca gag cgg ctt tat atc ggg ggt cct ctg act aat tca aaa<br>Ser Leu Thr Glu Arg Leu Tyr Ile Gly Gly Pro Leu Thr Asn Ser Lys<br>1650                 1655               1660 | | 4992 |
| ggg cag aac tgc ggt tat cgc cgg tgc cgc gcg agc ggc gtg ctg acg<br>Gly Gln Asn Cys Gly Tyr Arg Arg Cys Arg Ala Ser Gly Val Leu Thr<br>1665              1670             1675             1680 | | 5040 |
| act agc tgc ggt aac acc ctc aca tgt tac ttg aag gcc tct gca gcc<br>Thr Ser Cys Gly Asn Thr Leu Thr Cys Tyr Leu Lys Ala Ser Ala Ala<br>        1685                1690             1695 | | 5088 |
| tgt cga gct gcg aag ctc cag gac tgc acg atg ctc gtg aac gga gac<br>Cys Arg Ala Ala Lys Leu Gln Asp Cys Thr Met Leu Val Asn Gly Asp<br>1700                1705             1710 | | 5136 |
| gac ctt gtc gtt atc tgt gaa agc gcg gga acc caa gag gac gcg gcg<br>Asp Leu Val Val Ile Cys Glu Ser Ala Gly Thr Gln Glu Asp Ala Ala<br>        1715              1720              1725 | | 5184 |
| agc cta cga gtc ttc acg gag gct atg act agg tac tct gcc ccc ccc<br>Ser Leu Arg Val Phe Thr Glu Ala Met Thr Arg Tyr Ser Ala Pro Pro<br>1730                1735             1740 | | 5232 |
| ggg gac ccg ccc caa cca gaa tac gac ttg gag ctg ata aca tca tgt<br>Gly Asp Pro Pro Gln Pro Glu Tyr Asp Leu Glu Leu Ile Thr Ser Cys<br>1745                1750             1755             1760 | | 5280 |
| tcc tcc aat gtg tcg gtc gcc cac gat gca tca ggc aaa agg gtg tac<br>Ser Ser Asn Val Ser Val Ala His Asp Ala Ser Gly Lys Arg Val Tyr<br>                1765              1770              1775 | | 5328 |
| tac ctc acc cgt gat ccc acc acc ccc ctc gca cgg gct gcg tgg gaa<br>Tyr Leu Thr Arg Asp Pro Thr Thr Pro Leu Ala Arg Ala Ala Trp Glu<br>        1780                1785             1790 | | 5376 |
| aca gct aga cac act cca gtt aac tcc tgg cta ggc aac att atc atg<br>Thr Ala Arg His Thr Pro Val Asn Ser Trp Leu Gly Asn Ile Ile Met<br>        1795                1800             1805 | | 5424 |
| tat gcg ccc act ttg tgg gca agg atg att ctg atg act cac ttc ttc<br>Tyr Ala Pro Thr Leu Trp Ala Arg Met Ile Leu Met Thr His Phe Phe<br>1810                1815             1820 | | 5472 |
| tcc atc ctt cta gca cag gag caa ctt gaa aaa gcc ctg gac tgc cag<br>Ser Ile Leu Leu Ala Gln Glu Gln Leu Glu Lys Ala Leu Asp Cys Gln<br>1825                1830             1835             1840 | | 5520 |
| atc tac ggg gcc tgt tac tcc att gag cca ctt gac cta cct cag atc<br>Ile Tyr Gly Ala Cys Tyr Ser Ile Glu Pro Leu Asp Leu Pro Gln Ile<br>                1845              1850              1855 | | 5568 |
| att gaa cga ctc cat ggc ctt agc gca ttt tca ctc cat agt tac tct<br>Ile Glu Arg Leu His Gly Leu Ser Ala Phe Ser Leu His Ser Tyr Ser<br>                1860              1865              1870 | | 5616 |
| cca ggt gag atc aat agg gtg gct tca tgc ctc agg aaa ctt ggg gta<br>Pro Gly Glu Ile Asn Arg Val Ala Ser Cys Leu Arg Lys Leu Gly Val<br>        1875                1880             1885 | | 5664 |
| cca ccc ttg cga gtc tgg aga cat cgg gcc agg agc gtc cgc gct agg<br>Pro Pro Leu Arg Val Trp Arg His Arg Ala Arg Ser Val Arg Ala Arg<br>1890                1895             1900 | | 5712 |
| cta ctg tcc cag ggg ggg agg gcc gcc act tgt ggc aag tac ctc ttc<br>Leu Leu Ser Gln Gly Gly Arg Ala Ala Thr Cys Gly Lys Tyr Leu Phe<br>1905                1910             1915             1920 | | 5760 |
| aac tgg gca gtg aag acc aaa ctc aaa ctc act cca atc ccg gct gcg<br>Asn Trp Ala Val Lys Thr Lys Leu Lys Leu Thr Pro Ile Pro Ala Ala<br>                1925              1930             1935 | | 5808 |
| tcc cag ctg gac ttg tcc ggc tgg ttc gtt gct ggt tac agc ggg gga<br>Ser Gln Leu Asp Leu Ser Gly Trp Phe Val Ala Gly Tyr Ser Gly Gly<br>                1940              1945              1950 | | 5856 |
| gac ata tat cac agc ctg tct cgt gcc cga ccc cgc tgg ttc atg ctg | | 5904 |

-continued

```
                Asp Ile Tyr His Ser Leu Ser Arg Ala Arg Pro Arg Trp Phe Met Leu
                    1955                1960                1965 tgc cta ctc cta ctt tct gta ggg gta ggc atc tac ctg ctc ccc aac    5952
Cys Leu Leu Leu Leu Ser Val Gly Val Gly Ile Tyr Leu Leu Pro Asn
1970                1975                1980 cga                                                                5955
Arg
1985

<210> SEQ ID NO 6
<211> LENGTH: 1985
<212> TYPE: PRT
<213> ORGANISM: Artificial Sequence
<220> FEATURE:
<223> OTHER INFORMATION: NS sequence

<400> SEQUENCE: 6

Met Ala Pro Ile Thr Ala Tyr Ser Gln Gln Thr Arg Gly Leu Leu Gly
 1               5                   10                  15

Cys Ile Ile Thr Ser Leu Thr Gly Arg Asp Lys Asn Gln Val Glu Gly
            20                  25                  30

Glu Val Gln Val Val Ser Thr Ala Thr Gln Ser Phe Leu Ala Thr Cys
        35                  40                  45

Val Asn Gly Val Cys Trp Thr Val Tyr His Gly Ala Gly Ser Lys Thr
    50                  55                  60

Leu Ala Gly Pro Lys Gly Pro Ile Thr Gln Met Tyr Thr Asn Val Asp
65                  70                  75                  80

Gln Asp Leu Val Gly Trp Gln Ala Pro Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Val Ser Tyr Leu Lys Gly Ser Ser Gly Gly Pro Leu
    130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
            180                 185                 190

Ala Val Pro Gln Ser Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ala Pro Val Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ser Thr Thr Ile Leu Gly Ile
    290                 295                 300

Gly Thr Val Leu Asp Gln Ala Glu Thr Ala Gly Ala Arg Leu Val Val
305                 310                 315                 320
```

```
Leu Ala Thr Ala Thr Pro Pro Gly Ser Val Thr Val Pro His Pro Asn
                325                 330                 335

Ile Glu Glu Val Ala Leu Ser Asn Thr Gly Glu Ile Pro Phe Tyr Gly
                340                 345                 350

Lys Ala Ile Pro Ile Glu Ala Ile Arg Gly Gly Arg His Leu Ile Phe
                355                 360                 365

Cys His Ser Lys Lys Cys Asp Glu Leu Ala Ala Lys Leu Ser Gly
                370                 375                 380

Leu Gly Ile Asn Ala Val Ala Tyr Tyr Arg Gly Leu Asp Val Ser Val
385                 390                 395                 400

Ile Pro Thr Ile Gly Asp Val Val Val Ala Thr Asp Ala Leu Met
                    405                 410                 415

Thr Gly Tyr Thr Gly Asp Phe Asp Ser Val Ile Asp Cys Asn Thr Cys
                420                 425                 430

Val Thr Gln Thr Val Asp Phe Ser Leu Asp Pro Thr Phe Thr Ile Glu
                435                 440                 445

Thr Thr Thr Val Pro Gln Asp Ala Val Ser Arg Ser Gln Arg Gly
                450                 455                 460

Arg Thr Gly Arg Gly Arg Gly Ile Tyr Arg Phe Val Thr Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Ser Val
                500                 505                 510

Arg Leu Arg Ala Tyr Leu Asn Thr Pro Gly Leu Pro Val Cys Gln Asp
                515                 520                 525

His Leu Glu Phe Trp Glu Ser Val Phe Thr Gly Leu Thr His Ile Asp
                530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
                580                 585                 590

Leu His Gly Pro Thr Pro Leu Leu Tyr Arg Leu Gly Ala Val Gln Asn
                595                 600                 605

Glu Val Thr Leu Thr His Pro Ile Thr Lys Tyr Ile Met Ala Cys Met
                610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Thr Thr Gly Ser Val Val
                645                 650                 655

Ile Val Gly Arg Ile Ile Leu Ser Gly Arg Pro Ala Ile Val Pro Asp
                660                 665                 670

Arg Glu Phe Leu Tyr Gln Glu Phe Asp Glu Met Glu Glu Cys Ala Ser
                675                 680                 685

His Leu Pro Tyr Ile Glu Gln Gly Met Gln Leu Ala Glu Gln Phe Lys
                690                 695                 700

Gln Lys Ala Leu Gly Leu Leu Gln Thr Ala Thr Lys Gln Ala Glu Ala
705                 710                 715                 720

Ala Ala Pro Val Val Glu Ser Lys Trp Arg Ala Leu Glu Thr Phe Trp
                    725                 730                 735

Ala Lys His Met Trp Asn Phe Ile Ser Gly Ile Gln Tyr Leu Ala Gly
```

740                 745                 750
Leu Ser Thr Leu Pro Gly Asn Pro Ala Ile Ala Ser Leu Met Ala Phe
                755                 760                 765
Thr Ala Ser Ile Thr Ser Pro Leu Thr Thr Gln Ser Thr Leu Leu Phe
                770                 775                 780
Asn Ile Leu Gly Gly Trp Val Ala Ala Gln Leu Ala Pro Pro Ser Ala
785                 790                 795                 800
Ala Ser Ala Phe Val Gly Ala Gly Ile Ala Gly Ala Ala Val Gly Ser
                805                 810                 815
Ile Gly Leu Gly Lys Val Leu Val Asp Ile Leu Ala Gly Tyr Gly Ala
                820                 825                 830
Gly Val Ala Gly Ala Leu Val Ala Phe Lys Val Met Ser Gly Glu Met
                835                 840                 845
Pro Ser Thr Glu Asp Leu Val Asn Leu Leu Pro Ala Ile Leu Ser Pro
                850                 855                 860
Gly Ala Leu Val Val Gly Val Val Cys Ala Ala Ile Leu Arg Arg His
865                 870                 875                 880
Val Gly Pro Gly Glu Gly Ala Val Gln Trp Met Asn Arg Leu Ile Ala
                885                 890                 895
Phe Ala Ser Arg Gly Asn His Val Ser Pro Thr His Tyr Val Pro Glu
                900                 905                 910
Ser Asp Ala Ala Ala Arg Val Thr Gln Ile Leu Ser Ser Leu Thr Ile
                915                 920                 925
Thr Gln Leu Leu Lys Arg Leu His Gln Trp Ile Asn Glu Asp Cys Ser
                930                 935                 940
Thr Pro Cys Ser Gly Ser Trp Leu Arg Asp Val Trp Asp Trp Ile Cys
945                 950                 955                 960
Thr Val Leu Thr Asp Phe Lys Thr Trp Leu Gln Ser Lys Leu Leu Pro
                965                 970                 975
Gln Leu Pro Gly Val Pro Phe Phe Ser Cys Gln Arg Gly Tyr Lys Gly
                980                 985                 990
Val Trp Arg Gly Asp Gly Ile Met Gln Thr Thr Cys Pro Cys Gly Ala
                995                 1000                1005
Gln Ile Thr Gly His Val Lys Asn Gly Ser Met Arg Ile Val Gly Pro
                1010                1015                1020
Lys Thr Cys Ser Asn Thr Trp His Gly Thr Phe Pro Ile Asn Ala Tyr
1025                1030                1035                1040
Thr Thr Gly Pro Cys Thr Pro Ser Pro Ala Pro Asn Tyr Ser Arg Ala
                1045                1050                1055
Leu Trp Arg Val Ala Ala Glu Glu Tyr Val Glu Val Thr Arg Val Gly
                1060                1065                1070
Asp Phe His Tyr Val Thr Gly Met Thr Thr Asp Asn Val Lys Cys Pro
                1075                1080                1085
Cys Gln Val Pro Ala Pro Glu Phe Phe Thr Glu Val Asp Gly Val Arg
                1090                1095                1100
Leu His Arg Tyr Ala Pro Ala Cys Arg Pro Leu Leu Arg Glu Glu Val
1105                1110                1115                1120
Thr Phe Gln Val Gly Leu Asn Gln Tyr Leu Val Gly Ser Gln Leu Pro
                1125                1130                1135
Cys Glu Pro Glu Pro Asp Val Ala Val Leu Thr Ser Met Leu Thr Asp
                1140                1145                1150
Pro Ser His Ile Thr Ala Glu Thr Ala Lys Arg Arg Leu Ala Arg Gly
                1155                1160                1165

-continued

```
Ser Pro Pro Ser Leu Ala Ser Ser Ala Ser Gln Leu Ser Ala Pro
        1170                1175                1180

Ser Leu Lys Ala Thr Cys Thr Thr His His Val Ser Pro Asp Ala Asp
1185                1190                1195                1200

Leu Ile Glu Ala Asn Leu Leu Trp Arg Gln Glu Met Gly Gly Asn Ile
            1205                1210                1215

Thr Arg Val Glu Ser Glu Asn Lys Val Val Leu Asp Ser Phe Asp
        1220                1225                1230

Pro Leu Arg Ala Glu Glu Asp Glu Arg Glu Val Ser Val Pro Ala Glu
        1235                1240                1245

Ile Leu Arg Lys Ser Lys Lys Phe Pro Ala Ala Met Pro Ile Trp Ala
        1250                1255                1260

Arg Pro Asp Tyr Asn Pro Pro Leu Leu Glu Ser Trp Lys Asp Pro Asp
1265                1270                1275                1280

Tyr Val Pro Pro Val Val His Gly Cys Pro Leu Pro Pro Ile Lys Ala
            1285                1290                1295

Pro Pro Ile Pro Pro Arg Arg Lys Arg Thr Val Val Leu Thr Glu
        1300                1305                1310

Ser Ser Val Ser Ser Ala Leu Ala Glu Leu Ala Thr Lys Thr Phe Gly
        1315                1320                1325

Ser Ser Glu Ser Ser Ala Val Asp Ser Gly Thr Ala Thr Ala Leu Pro
        1330                1335                1340

Asp Gln Ala Ser Asp Asp Gly Asp Lys Gly Ser Asp Val Glu Ser Tyr
1345                1350                1355                1360

Ser Ser Met Pro Pro Leu Glu Gly Glu Pro Gly Asp Pro Asp Leu Ser
            1365                1370                1375

Asp Gly Ser Trp Ser Thr Val Ser Glu Glu Ala Ser Glu Asp Val Val
            1380                1385                1390

Cys Cys Ser Met Ser Tyr Thr Trp Thr Gly Ala Leu Ile Thr Pro Cys
            1395                1400                1405

Ala Ala Glu Glu Ser Lys Leu Pro Ile Asn Ala Leu Ser Asn Ser Leu
        1410                1415                1420

Leu Arg His His Asn Met Val Tyr Ala Thr Thr Ser Arg Ser Ala Gly
1425                1430                1435                1440

Leu Arg Gln Lys Lys Val Thr Phe Asp Arg Leu Gln Val Leu Asp Asp
            1445                1450                1455

His Tyr Arg Asp Val Leu Lys Glu Met Lys Ala Lys Ala Ser Thr Val
        1460                1465                1470

Lys Ala Lys Leu Leu Ser Val Glu Glu Ala Cys Lys Leu Thr Pro Pro
        1475                1480                1485

His Ser Ala Lys Ser Lys Phe Gly Tyr Gly Ala Lys Asp Val Arg Asn
        1490                1495                1500

Leu Ser Ser Lys Ala Val Asn His Ile His Ser Val Trp Lys Asp Leu
1505                1510                1515                1520

Leu Glu Asp Thr Val Thr Pro Ile Asp Thr Thr Ile Met Ala Lys Asn
            1525                1530                1535

Glu Val Phe Cys Val Gln Pro Glu Lys Gly Gly Arg Lys Pro Ala Arg
            1540                1545                1550

Leu Ile Val Phe Pro Asp Leu Gly Val Arg Val Cys Glu Lys Met Ala
        1555                1560                1565

Leu Tyr Asp Val Val Ser Thr Leu Pro Gln Val Val Met Gly Ser Ser
        1570                1575                1580

Tyr Gly Phe Gln Tyr Ser Pro Gly Gln Arg Val Glu Phe Leu Val Asn
1585                1590                1595                1600
```

Thr Trp Lys Ser Lys Lys Asn Pro Met Gly Phe Ser Tyr Asp Thr Arg
            1605                1610                1615
Cys Phe Asp Ser Thr Val Thr Glu Asn Asp Ile Arg Val Glu Glu Ser
            1620                1625                1630
Ile Tyr Gln Cys Cys Asp Leu Ala Pro Glu Ala Arg Gln Ala Ile Lys
            1635                1640                1645
Ser Leu Thr Glu Arg Leu Tyr Ile Gly Gly Pro Leu Thr Asn Ser Lys
            1650                1655                1660
Gly Gln Asn Cys Gly Tyr Arg Arg Cys Arg Ala Ser Gly Val Leu Thr
1665                1670                1675                1680
Thr Ser Cys Gly Asn Thr Leu Thr Cys Tyr Leu Lys Ala Ser Ala Ala
            1685                1690                1695
Cys Arg Ala Ala Lys Leu Gln Asp Cys Thr Met Leu Val Asn Gly Asp
            1700                1705                1710
Asp Leu Val Val Ile Cys Glu Ser Ala Gly Thr Gln Glu Asp Ala Ala
            1715                1720                1725
Ser Leu Arg Val Phe Thr Glu Ala Met Thr Arg Tyr Ser Ala Pro Pro
            1730                1735                1740
Gly Asp Pro Pro Gln Pro Glu Tyr Asp Leu Glu Leu Ile Thr Ser Cys
1745                1750                1755                1760
Ser Ser Asn Val Ser Val Ala His Asp Ala Ser Gly Lys Arg Val Tyr
            1765                1770                1775
Tyr Leu Thr Arg Asp Pro Thr Thr Pro Leu Ala Arg Ala Ala Trp Glu
            1780                1785                1790
Thr Ala Arg His Thr Pro Val Asn Ser Trp Leu Gly Asn Ile Ile Met
            1795                1800                1805
Tyr Ala Pro Thr Leu Trp Ala Arg Met Ile Leu Met Thr His Phe Phe
            1810                1815                1820
Ser Ile Leu Leu Ala Gln Glu Gln Leu Glu Lys Ala Leu Asp Cys Gln
1825                1830                1835                1840
Ile Tyr Gly Ala Cys Tyr Ser Ile Glu Pro Leu Asp Leu Pro Gln Ile
            1845                1850                1855
Ile Glu Arg Leu His Gly Leu Ser Ala Phe Ser Leu His Ser Tyr Ser
            1860                1865                1870
Pro Gly Glu Ile Asn Arg Val Ala Ser Cys Leu Arg Lys Leu Gly Val
            1875                1880                1885
Pro Pro Leu Arg Val Trp Arg His Arg Ala Arg Ser Val Arg Ala Arg
            1890                1895                1900
Leu Leu Ser Gln Gly Gly Arg Ala Ala Thr Cys Gly Lys Tyr Leu Phe
1905                1910                1915                1920
Asn Trp Ala Val Lys Thr Lys Leu Lys Leu Thr Pro Ile Pro Ala Ala
            1925                1930                1935
Ser Gln Leu Asp Leu Ser Gly Trp Phe Val Ala Gly Tyr Ser Gly Gly
            1940                1945                1950
Asp Ile Tyr His Ser Leu Ser Arg Ala Arg Pro Arg Trp Phe Met Leu
            1955                1960                1965
Cys Leu Leu Leu Leu Ser Val Gly Val Gly Ile Tyr Leu Leu Pro Asn
            1970                1975                1980
Arg
1985

<210> SEQ ID NO 7
<211> LENGTH: 4909
<212> TYPE: DNA

<213> ORGANISM: Artificial Sequence
<220> FEATURE:
<223> OTHER INFORMATION: pV1J nucleic acid

<400> SEQUENCE: 7

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
tccccgtgcc aagagtgacg taagtaccgc ctatagactc tataggcaca ccctttggc     1080
tcttatgcat gctatactgt ttttggcttg gggcctatac accccgctt ccttatgcta     1140
taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccatttatta tttacaaatt cacatataca acaacgccgt ccccgtgcc    1380
cgcagttttt attaaacata gcgtgggatc tccacgcgaa tctcgggtac gtgttccgga    1440
catgggctct tctccggtag cggcggagct tccacatccg agccctggtc ccatgcctcc    1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtccttagat ctaggtacca gatatcagaa ttcagtcgac agcggccgcg    1920
atctgctgtg ccttctagtt gccagccatc tgttgtttgc ccctcccccg tgccttcctt    1980
gaccctggaa ggtgccactc ccactgtcct ttcctaataa aatgaggaaa ttgcatcgca    2040
ttgtctgagt aggtgtcatt ctattctggg gggtggggtg gggcaggaca gcaagggga     2100
ggattgggaa gacaatagca ggcatgctgg ggatgcggtg ggctctatgg ccgctgcggc    2160
caggtgctga agaattgacc cggttcctcc tgggccagaa agaagcaggc acatcccctt    2220
```

```
ctctgtgaca cacccctgtcc acgccctgg ttcttagttc cagccccact cataggacac      2280
tcatagctca ggagggctcc gccttcaatc ccacccgcta agtacttgg agcggtctct       2340 ccctccctca tcagcccacc aaaccaaacc tagcctccaa gagtgggaag aaattaaagc      2400
aagataggct attaagtgca gagggagaga aaatgcctcc aacatgtgag gaagtaatga     2460
gagaaatcat agaatttctt ccgcttcctc gctcactgac tcgctgcgct cggtcgttcg     2520
gctgcggcga gcggtatcag ctcactcaaa ggcggtaata cggttatcca cagaatcagg    2580
ggataacgca ggaaagaaca tgtgagcaaa aggccagcaa aaggccagga accgtaaaaa   2640
ggccgcgttg ctggcgtttt tccataggct ccgccccct gacgagcatc acaaaaatcg     2700
acgctcaagt cagaggtggc gaaacccgac aggactataa agataccagg cgtttccccc    2760
tggaagctcc ctcgtgcgct ctcctgttcc gaccctgccg cttaccggat acctgtccgc    2820 cttctccct tcgggaagcg tggcgctttc tcatagctca cgctgtaggt atctcagttc     2880
ggtgtaggtc gttcgctcca agctgggctg tgtgcacgaa ccccccgttc agcccgaccg   2940
ctgcgcctta tccggtaact atcgtcttga gtccaacccg gtaagacacg acttatcgcc    3000
actggcagca gccactggta acaggattag cagagcgagg tatgtaggcg gtgctacaga   3060
gttcttgaag tggtggccta actacggcta cactagaaga acagtatttg gtatctgcgc   3120
tctgctgaag ccagttacct tcggaaaaag agttggtagc tcttgatccg gcaaacaaac   3180
caccgctggt agcggtggtt tttttgtttg caagcagcag attacgcgca gaaaaaaagg  3240
atctcaagaa gatcctttga tcttttctac ggggtctgac gctcagtgga acgaaaactc   3300
acgttaaggg attttggtca tgagattatc aaaaaggatc ttcacctaga tccttttaaa  3360
ttaaaaatga agttttaaat caatctaaag tatatatgag taaacttggt ctgacagtta   3420
ccaatgctta atcagtgagg cacctatctc agcgatctgt ctatttcgtt catccatagt   3480
tgcctgactc gggggggggg ggcgctgagg tctgcctcgt gaagaaggtg ttgctgactc   3540
ataccaggcc tgaatcgccc catcatccag ccagaaagtg agggagccac ggttgatgag  3600
agctttgttg taggtggacc agttggtgat tttgaacttt tgctttgcca cggaacggtc    3660
tgcgttgtcg ggaagatgcg tgatctgatc cttcaactca gcaaaagttc gatttattca   3720
acaaagccgc cgtcccgtca gtcagcgta atgctctgcc agtgttacaa ccaattaacc   3780
aattctgatt agaaaactc atcgagcatc aaatgaaact gcaatttatt catatcagga    3840
ttatcaatac catatttttg aaaaagccgt ttctgtaatg aaggagaaaa ctcaccgagg   3900
cagttccata ggatgcaag atcctggtat cggtctgcga ttccgactcg tccaacatca   3960
atacaaccta ttaatttccc ctcgtcaaaa ataaggttat caagtgagaa atcaccatga  4020
gtgacgactg aatccggtga atgggcaaa agcttatgca tttctttcca gacttgttca    4080
acaggccagc cattacgctc gtcatcaaaa tcactcgcat caaccaaacc gttattcatt   4140
cgtgattgcg cctgagcgag acgaaatacg cgatcgctgt taaaaggaca attacaaaca  4200
ggaatcgaat gcaaccggcg caggaacact gccagcgcat caacaatatt ttcacctgaa   4260
tcaggatatt cttctaatac ctggaatgct gttttcccgg ggatcgcagt ggtgagtaac   4320
catgcatcat caggagtacg gataaaatgc ttgatggtcg gaagaggcat aaattccgtc    4380
agccagttta gtctgaccat ctcatctgta acatcattgg caacgctacc tttgccatgt   4440
ttcagaaaca actctggcgc atcgggcttc ccatacaatc gatagattgt cgcacctgat   4500
tgcccgacat tatcgcgagc ccatttatac ccatataaat cagcatccat gttggaattt    4560
aatcgcggcc tcgagcaaga cgtttcccgt tgaatatggc tcataacacc ccttgtatta    4620
```

-continued

```
ctgtttatgt aagcagacag ttttattgtt catgatgata tattttttatc ttgtgcaatg    4680 taacatcaga gattttgaga cacaacgtgg ctttccccccc cccccccatta ttgaagcatt    4740 tatcagggtt attgtctcat gagcggatac atatttgaat gtatttagaa aaataaacaa    4800
ataggggttc cgcgcacatt tccccgaaaa gtgccacctg acgtctaaga aaccattatt    4860
atcatgacat taacctataa aaataggcgt atcacgaggc cctttcgtc              4909
```

```
<210> SEQ ID NO 8
<211> LENGTH: 35759
<212> TYPE: DNA
<213> ORGANISM: Adenovirus serotype 6
<220> FEATURE:
<221> NAME/KEY: misc_feature
<222> LOCATION: (34984)...(34984)
<223> OTHER INFORMATION: n = a, c, t or g

<400> SEQUENCE: 8
```

```
catcatcaat aatataccttt attttggatt gaagccaata tgataatgag ggggtggagt      60
ttgtgacgtg gcgcggggcg tgggaacggg gcgggtgacg tagtagtgtg gcggaagtgt     120
gatgttgtaa gtgtggcgga acacatgtaa gcgccggatg tggtaaaagt gacgttttg     180 gtgtgcgccg gtgtacacgg gaagtgacaa ttttcgcgcg gttttaggcg gatgttgtag     240
taaatttggg cgtaaccaag taatatttgg ccattttcgc gggaaaactg aataagagga     300
agtgaaatct gaataattct gtgttactca tagcgcgtaa tatttgtcta gggccgcggg     360
gactttgacc gtttacgtgg agactcgccc aggtgttttt ctcaggtgtt ttccgcgttc     420
cgggtcaaag ttggcgtttt attattatag tcagctgacg cgcagtgtat ttatacccgg     480
tgagttcctc aagaggccac tcttgagtgc cagcgagtag agttttctcc tccgagccgc     540
tccgacaccg ggactgaaaa tgagacatat tatctgccac ggaggtgtta ttaccgaaga     600
aatggccgcc agtcttttgg accagctgat cgaagaggta ctggctgata atcttccacc     660
tcctagccat tttgaaccac ctacccttca cgaactgtat gatttagacg tgacggcccc     720
cgaagatccc aacgaggagg cggtttcgca gattttttccc gagtctgtaa tgttggcggt     780
gcaggaaggg attgacttat tcactttttcc gccggcgccc ggttctccgg agccgcctca     840 ccttttcccgg cagcccgagc agccggagca gagagccttg ggtccggttt ctatgccaaa     900
ccttgtgccg gaggtgatcg atcttacctg ccacgaggct ggctttccac ccagtgacga     960
cgaggatgaa gagggtgagg agtttgtgtt agattatgtg gagcaccccg ggcacggttg    1020
caggtcttgt cattatcacc ggaggaatac gggggaccca gatattatgt gttcgctttg    1080
ctatatgagg acctgtggca tgtttgtcta cagtaagtga aaaattatgg gcagtgggtg    1140
atagagtggt gggtttggtg tggtaatttt ttttttaatt tttacagttt tgtggtttaa    1200
agaattttgt attgtgattt tttaaaaggt cctgtgtctg aacctgagcc tgagcccgag    1260
ccagaaccgg agcctgcaag acctacccgg cgtcctaaat tggtgcctgc tatcctgaga    1320
cgcccgacat cacctgtgtc tagagaatgc aatagtagta cggatagctg tgactccggt    1380
ccttctaaca cacctcctga gatacacccg gtggtcccgc tgtgccccat taaaccagtt    1440
gccgtgagag ttggtgggcg tcgccaggct gtggaatgta tcgaggactt gcttaacgag    1500
tctgggcaac ctttggactt gagctgtaaa cgccccaggc cataaggtgt aaacctgtga    1560
ttgcgtgtgt ggttaacgcc tttgtttgct gaatgagttg atgtaagttt aataaagggt    1620
gagataatgt ttaacttgca tggcgtgtta aatgggcggg gcttaaaggg gtatataatg    1680
cgccgtgggc taatccttggt tacatctgac ctcatggagg cttgggagtg tttggaagat    1740
```

-continued

```
ttttctgctg tgcgtaactt gctggaacag agctctaaca gtacctcttg gttttggagg    1800
tttctgtggg gctcctccca ggcaaagtta gtctgcagaa ttaaggagga ttacaagtgg    1860
gaatttgaag agcttttgaa atcctgtggt gagctgtttg attctttgaa tctgggtcac    1920
caggcgcttt tccaagagaa ggtcatcaag actttggatt tttccacacc ggggcgcgct    1980
gcggctgctg ttgctttttt gagttttata aaggataaat ggagcgaaga aacccatctg    2040 agcgggggt acctgctgga tttctggcc atgcatctgt ggagagcggt ggtgagacac      2100
aagaatcgcc tgctactgtt gtcttccgtc cgcccggcaa taataccgac ggaggagcaa    2160
cagcaggagg aagccaggcg gcggcggcgg caggagcaga gcccatggaa cccgagagcc    2220
ggcctggacc ctcgggaatg aatgttgtac aggtggctga actgtttcca gaactgagac    2280
gcattttaac cattaacgag gatgggcagg ggctaaaggg ggtaaagaag gagcgggggg    2340
cttctgaggc tacagaggag gctaggaatc taacttttag cttaatgacc agacaccgtc    2400
ctgagtgtgt tactttttcag cagattaagg ataattgcgc taatgagctt gatctgctgg    2460
cgcagaagta ttccatagag cagctgacca cttactggct gcagccaggg gatgattttg    2520
aggaggctat tagggtatat gcaaaggtgg cacttaggcc agattgcaag tacaagatta    2580
gcaaacttgt aaatatcagg aattgttgct acatttctgg gaacggggcc gaggtggaga    2640
tagatacgga ggatagggtg gcctttagat gtagcatgat aaatatgtgg ccggggggtgc   2700 ttggcatgga cggggtggtt attatgaatg tgaggtttac tggtcccaat tttagcggta    2760
cggttttcct ggccaatacc aatcttatcc tacacggtgt aagcttctat gggtttaaca    2820
atacctgtgt ggaagcctgg accgatgtaa gggttcgggg ctgtgccttt tactgctgct    2880 ggaaggggt ggtgtgtcgc cccaaaagca gggcttcaat taagaaatgc ctgttttgaaa    2940 ggtgtacctt gggtatcctg tctgagggta actccagggt gcgccacaat gtggcctccg    3000
actgtggttg ctttatgcta gtgaaaagcg tggctgtgat taagcataac atggtgtgtg    3060
gcaactgcga ggacagggcc tctcagatgc tgacctgctc ggacggcaac tgtcacttgc    3120
tgaagaccat tcacgtagcc agccactctc gcaaggcctg gccagtgttt gagcacaaca    3180
tactgacccg ctgttccttg catttgggta acaggagggg ggtgttccta ccttaccaat    3240
gcaatttgag tcacactaag atattgcttg agcccgagag catgtccaag gtgaacctga    3300
acggggtgtt tgacatgacc atgaagatct ggaaggtgct gaggtacgat gagacccgca    3360
ccaggtgcag accctgcgag tgtggcggta acatattag gaaccagcct gtgatgctgg    3420
atgtgaccga ggagctgagg cccgatcact tggtgctggc ctgcacccgc gctgagtttg    3480
gctctagcga tgaagataca gattgaggta ctgaaatgtg tgggcgtggc ttaagggtgg    3540
gaaagaatat ataaggtggg ggtctcatgt agttttgtat ctgttttgca gcagccgccg    3600
ccatgagcgc caactcgttt gatggaagca ttgtgagctc atatttgaca acgcgcatgc    3660
ccccatgggc cggggtgcgt cagaatgtga tgggctccag cattgatggt cgccccgtcc    3720
tgcccgcaaa ctctactacc ttgacctacg agaccgtgtc tggaacgccg ttggagactg    3780
cagcctccgc cgccgcttca gccgctgcag ccaccgcccg cgggattgtg actgactttg    3840 cttcctgag cccgcttgca agcagtgcag cttcccgttc atccgcccgc gatgacaagt    3900
tgacggctct tttggcacaa ttggattctt tgacccggga acttaatgtc gtttctcagc    3960
agctgttgga tctgcgccag caggtttctg ccctgaaggc ttcctcccct cccaatgcgg    4020
tttaaaacat aaataaaaac cagactctgt ttggatttgg atcaagcaag tgtcttgctg    4080
tctttattta ggggttttgc gcgcgcggta ggcccgggac cagcggtctc ggtcgttgag    4140
```

```
ggtcctgtgt atttttttcca ggacgtggta aaggtgactc tggatgttca gatacatggg    4200
cataagcccg tctctggggt ggaggtagca ccactgcaga gcttcatgct gcggggtggt    4260
gttgtagatg atccagtcgt agcaggagcg ctgggcgtgg tgcctaaaaa tgtctttcag    4320
tagcaagctg attgccaggg gcaggccctt ggtgtaagtg tttacaaagc ggttaagctg    4380
ggatgggtgc atacgtgggg atatgagatg catcttggac tgtattttta ggttggctat    4440
gttcccagcc atatccctcc ggggattcat gttgtgcaga accaccagca cagtgtatcc    4500
ggtgcacttg ggaaatttgt catgtagctt agaaggaaat gcgtggaaga acttggagac    4560
gcccttgtga cctccaagat tttccatgca ttcgtccata atgatggcaa tgggcccacg    4620
ggcggcggcc tgggcgaaga tatttctggg atcactaacg tcatagttgt gttccaggat    4680
gagatcgtca taggccattt ttacaaagcg cgggcggagg tgccagact gcggtataat    4740 ggttccatcc ggcccagggg cgtagttacc ctcacagatt tgcatttccc acgctttgag    4800
ttcagatggg gggatcatgt ctacctgcgg ggcgatgaag aaaaccgttt ccggggtagg    4860
ggagatcagc tgggaagaaa gcaggttcct aagcagctgc gacttaccgc agccggtggg    4920
cccgtaaatc acacctatta ccggctgcaa ctggtagtta agagagctgc agctgccgtc    4980
atccctgagc agggggggcca cttcgttaag catgtccctg acttgcatgt tttccctgac    5040
caaatccgcc agaaggcgct cgccgcccag cgatagcagt tcttgcaagg aagcaaagtt    5100
tttcaacggt ttgaggccgt ccgccgtagg catgcttttg agcgtttgac caagcagttc    5160
caggcggtcc cacagctcgg tcacgtgctc tacggcatct cgatccagca tatctcctcg    5220
tttcgcgggt tgggggcggct ttcgctgtac ggcagtagtc ggtgctcgtc cagacgggcc    5280 aggtcatgt cttcccacgg gcgcagggtc ctcgtcagcg tagtctgggt cacggtgaag    5340
gggtgcgctc cgggttgcgc gctggccagg gtgcgcttga ggctggtcct gctggtgctg    5400
aagcgctgcc ggtcttcgcc ctgcgcgtcg gccaggtagc atttgaccat ggtgtcatag    5460
tccagcccct ccgcggcgtg gcccttggcg cgcagcttgc ccttggagga ggcgccgcac    5520
gaggggcagt gcagactttt aagggcgtag agcttgggcg cgagaaatac cgattccggg    5580
gagtaggcat ccgcgccgca ggccccgcag acggtctcgc attccacgag ccaggtgagc    5640
tctggccgtt cggggtcaaa aaccaggttt ccccccatgct ttttgatgcg tttcttacct    5700
ctggtttcca tgagcggtg tccacgcctcg gtgacgaaaa ggctgtccgt gtccccgtat    5760
acagacttga gaggcctgtc ctcgagcggt gttccgcggt cctcctcgta tagaaactcg    5820
gaccactctg agacgaaggc tcgcgtccag gccagcacga aggaggctaa gtgggagggg    5880
tagcggtcgt tgtccactag ggggtccact cgctccaggg tgtgaagaca catgtcgccc    5940
tcttcggcat caaggaaggt gattggttta taggtgtagg ccacgtgacc gggtgttcct    6000 gaagggggggc tataaaaggg ggtgggggcg cgttcgtcct cactctcttc cgcatcgctg    6060
tctgcgaggc ccagctgttg gggtgagtac tccctctcaa aagcgggcat gacttctgcg    6120
ctaagattgt cagtttccaa aaacgaggag gatttgatat tcacctggcc cgcggtgatg    6180
cctttgaggg tggccgcgtc catctggtca gaaaagacaa tcttttttgtt gtcaagcttg    6240 gtggcaaacg acccgtagag ggcgttggac agcaacttgg cgatggagcg cagggtttgg    6300
tttttgtcgc gatcggcgcg ctccttggcc gcgatgttta gctgcacgta ttcgcgcgca    6360
acgcaccgcc attcgggaaa gacggtggtg cgctcgtcgg gcactaggtg cacgcgccaa    6420
ccgcggttgt gcagggtgac aaggtcaacg ctggtggcta cctctccgcg taggcgctcg    6480
ttggtccagc agaggcggcc gcccttgcgc gagcagaatg gcggtagtgg gtctagctgc    6540
```

```
gtctcgtccg gggggtctgc gtccacggta agaccccgg gcagcaggcg cgcgtcgaag    6600
tagtctatct tgcatccttg caagtctagc gcctgctgcc atgcgcgggc ggcaagcgcg    6660
cgctcgtatg ggttgagtgg gggaccccat ggcatggggt gggtgagcgc ggaggcgtac    6720
atgccgcaaa tgtcgtaaac gtagaggggc tctctgagta ttccaagata tgtagggtag    6780
catcttccac cgcggatgct ggcgcgcacg taatcgtata gttcgtgcga gggagcgagg    6840
aggtcgggac cgaggttgct acgggcgggc tgctctgctc ggaagactat ctgcctgaag    6900
atggcatgtg agttggatga tatggttgga cgctggaaga cgttgaagct ggcgtctgtg    6960
agacctaccg cgtcacgcac gaaggaggcg taggagtcgc gcagcttgtt gaccagctcg    7020
gcggtgacct gcacgtctag ggcgcagtag tccagggttt ccttgatgat gtcatactta    7080
tcctgtccct ttttttttcca cagctcgcgg ttgaggacaa actcttcgcg gtctttccag    7140
tactcttgga tcggaaaccc gtcggcctcc gaacggtaag agcctagcat gtagaactgg    7200
ttgacggcct ggtaggcgca gcatcccttt tctacgggta gcgcgtatgc ctgcgcggcc    7260
ttccggagcg aggtgtgggt gagcgcaaag gtgtccctaa ccatgacttt gaggtactgg    7320
tatttgaagt cagtgtcgtc gcatccgccc tgctcccaga gcaaaaagtc cgtgcgcttt    7380
ttggaacgcg ggtttggcag ggcgaaggtg acatcgttga agagtatctt tcccgcgcga    7440
ggcataaagt tgcgtgtgat gcggaaggggt cccggcacct cggaacggtt gttaattacc    7500
tgggcggcga gcacgatctc gtcaaagccg ttgatgttgt ggcccacaat gtaaagttcc    7560
aagaagcgcg ggatgccctt gatggaaggc aatttttaa gttcctcgta ggtgagctct    7620
tcaggggagc tgagcccgtg ctctgaaagg gcccagtctg caagatgagg gttggaagcg    7680
acgaatgagc tccacaggtc acgggccatt agcatttgca ggtggtcgcg aaaggtccta    7740
aactggcgac ctatggccat ttttctgggg gtgatgcagt agaaggtaag cgggtcttgt    7800
tcccagcggt cccatccaag gtccgcggct aggtctcgcg cggcggtcac tagaggctca    7860
tctccgccga acttcatgac cagcatgaag ggcacgagct gcttcccaaa ggcccccatc    7920
caagtatagg tctctacatc gtaggtgaca aagagacgct cggtgcgagg atgcgagccg    7980
atcgggaaga actggatctc ccgccaccag ttggaggagt ggctgttgat gtggtgaaag    8040
tagaagtccc tgcgacgggc cgaacactcg tgctggcttt tgtaaaaacg tgcgcagtac    8100
tggcagcggt gcacgggctg tacatcctgc acgaggttga cctgacgacc gcgcacaagg    8160
aagcagagtg ggaatttgag cccctcgcct ggcgggtttg gctggtggtc ttctacttcg    8220
gctgcttgtc cttgaccgtc tggctgctcg agggagtta cggtggatcg gaccaccacg    8280
ccgcgcgagc ccaaagtcca gatgtccgcg cgcggcggtc ggagcttgat gacaacatcg    8340
cgcagatggg agctgtccat ggtctggagc tcccgcggcg tcaggtcagg cgggagctcc    8400
tgcaggttta cctcgcatag ccgggtcagg gcgcgggcta ggtccaggtg atacctgatt    8460
tccaggggct ggttggtggc ggcgtcgatg gcttgcaaga ggccgcatcc ccgcggcgcg    8520
actacggtac cgcgcggcgg gcggtgggcc gcggggtgt ccttggatga tgcatctaaa    8580
agcggtgacg cgggcgggcc cccggaggta ggggggggctc gggacccgcc gggagagggg    8640
gcaggggcac gtcggcgccg cgcgcgggca ggagctggtg ctgcgcgcgg aggttgctgg    8700
cgaacgcgac gacgcggcgg ttgatctcct gaatctggcg cctctgcgtg aagacgacgg    8760
gcccggtgag cttgaacctg aaagagagtt cgacagaatc aatttcggtg tcgttgacgg    8820
cggcctggcg caaaatctcc tgcacgtctc ctgagttgtc ttgataggcg atctcggcca    8880
tgaactgctc gatctcttcc tcctggagat ctccgcgtcc ggctcgctcc acggtggcgg    8940
```

```
cgaggtcgtt ggagatgcgg gccatgagct gcgagaaggc gttgaggcct ccctcgttcc    9000
agacgcggct gtagaccacg cccccttcgg catcgcgggc gcgcatgacc acctgcgcga    9060
gattgagctc cacgtgccgg gcgaagacgg cgtagtttcg caggcgctga aagaggtagt    9120
tgagggtggt ggcggtgtgt tctgccacga agaagtacat aacccagcgc cgcaacgtgg    9180
attcgttgat atcccccaag gcctcaaggc gctccatggc ctcgtagaag tccacggcga    9240
agttgaaaaa ctgggagttg cgcgccgaca cggttaactc ctcctccaga agacggatga    9300
gctcggcgac agtgtcgcgc acctcgcgct caaaggctac agggcctct tcttcttctt    9360
caatctcctc ttccataagg gcctcccctt cttcttcttc tggcggcggt ggggagggg    9420
ggacacggcg gcgacgacgg cgcaccggga ggcggtcgac aaagcgctcg atcatctccc    9480
cgcggcgacg gcgcatggtc tcggtgacgg cgcggccgtt ctcgcggggg cgcagttgga    9540
agacgccgcc cgtcatgtcc cggttatggg ttggcggggg gctgccgtgc ggcagggata    9600
cggcgctaac gatgcatctc aacaattgtt gtgtaggtac tccgccaccg agggacctga    9660
gcgagtccgc atcgaccgga tcggaaaacc tctcgagaaa ggcgtctaac cagtcacagt    9720
cgcaaggtag gctgagcacc gtggcgggcg gcagcgggcg gcggtcgggg ttgtttctgg    9780
cggaggtgct gctgatgatg taattaaagt aggcggtctt gagacggcgg atggtcgaca    9840
gaagcaccat gtccttgggt ccggcctgct gaatgcgcag gcggtcggcc atgcccagg    9900
cttcgttttg acatcggcgc aggtctttgt agtagtcttg catgagcctt tctaccggca    9960
cttcttcttc tccttcctct tgtcctgcat ctcttgcatc tatcgctgcg gcggcggcg   10020
agtttggccg taggtggcgc cctcttcctc ccatgcgtgt gaccccgaag cccctcatcg   10080
gctgaagcag ggccaggtcg gcgacaacgc gctcggctaa tatggcctgc tgcacctgcg   10140
tgagggtaga ctggaagtcg tccatgtcca caaagcggtg gtatgcgccc gtgttgatgg   10200
tgtaagtgca gttggccata acggaccagt taacggtctg gtgacccggc tgcgagagct   10260
cggtgtacct gagacgcgag taagcccttg agtcaaagac gtagtcgttg caagtccgca   10320
ccaggtactg gtatcccacc aaaaagtgcg gcggcggctg gcggtagagg gccagcgta   10380
gggtggccgg ggctccgggg gcgaggtctt ccaacataag gcgatgatat ccgtagatgt   10440
acctggacat ccaggtgatg ccggcggcgg tggtggaggc gcgcggaaag tcacggacgc   10500
ggttccagat gttgcgcagc ggcaaaaagt gctccatggt cgggacgctc tggccggtca   10560
ggcgcgcgca gtcgttgacg ctctagaccg tgcaaaagga gagcctgtaa gcgggcactc   10620
ttccgtggtc tggtggataa attcgcaagg gtatcatggc ggacgaccgg ggttcgaacc   10680
ccggatccgg ccgtccgccg tgatccatgc ggttaccgcc cgcgtgtcga acccaggtgt   10740
gcgacgtcag acaacggggg agcgctcctt ttggcttcct tccaggcgcg gcggatgctg   10800
cgctagcttt tttggccact ggccgcgcgc ggcgtaagcg gttaggctgg aaagcgaaag   10860
cattaagtgg ctcgctccct gtagccgag ggttattttc caagggttga gtcgcgggac   10920
ccccggttcg agtctcgggc cggccggact gcggcgaacg ggggtttgcc tccccgtcat   10980
gcaagacccc gcttgcaaat tcctccggaa acagggacga gccccttttt tgcttttccc   11040
agatgcatcc ggtgctgcgg cagatgcgcc cccctcctca gcagcggcaa gagcaagagc   11100
agcggcagac atgcagggca ccctcccctt tcctaccgc gtcaggaggg gcaacatccg   11160
cggctgacgc ggcggcagat ggtgattacg aaccccgcg gcgccggacc cggcactact   11220
tggacttgga ggagggcgag ggcctggcgc ggctaggagc gccctctcct gagcgacacc   11280
caagggtgca gctgaagcgt gacacgcgcg aggcgtacgt gccgcggcag aacctgtttc   11340
```

```
gcgaccgcga gggagaggag cccgaggaga tgcgggatcg aaagttccat gcagggcgcg    11400
agttgcggca tggcctgaac cgcgagcggt tgctgcgcga ggaggacttt gagcccgacg    11460
cgcggaccgg gattagtccc gcgcgcgcac acgtggcggc cgccgacctg gtaaccgcgt    11520
acgagcagac ggtgaaccag gagattaact ttcaaaaaag ctttaacaac cacgtgcgca    11580
cgcttgtggc gcgcgaggag gtggctatag gactgatgca tctgtgggac tttgtaagcg    11640
cgctggagca aaacccaaat agcaagccgc tcatggcgca gctgttcctt atagtgcagc    11700
acagcaggga caacgaggca ttcagggatg cgctgctaaa catagtagag cccgagggcc    11760
gctggctgct cgatttgata aacattctgc agagcatagt ggtgcaggag cgcagcttga    11820
gcctggctga caaggtggcc gccattaact attccatgct cagtctgggc aagttttacg    11880
cccgcaagat ataccatacc ccttacgttc ccatagacaa ggaggtaaag atcgagggt    11940 tctacatgcg catggcgctg aaggtgctta ccttgagcga cgacctgggc gtttatcgca    12000
acgagcgcat ccacaaggcc gtgagcgtga ccggcggcg cgagctcagc gaccgcgagc    12060
tgatgcacag cctgcaaagg gccctggctg gcacgggcag cggcgataga gaggccgagt    12120
cctactttga cgcgggcgct gacctgcgct gggccccaag ccgacgcgcc ctggaggcag    12180
ctggggccgg acctgggctg gcggtggcac ccgcgcgcgc tggcaacgtc ggcggcgtgg    12240
aggaatatga cgaggacgat gagtacgagc cagaggacgg cgagtactaa gcggtgatgt    12300
ttctgatcag atgatgcaag acgcaacgga cccggcggtg cgggcggcgc tgcagagcca    12360
gccgtccggc cttaactcca cggacgactg cgccaggtc atggaccgca tcatgtcgct    12420
gactgcgcgc aaccctgacg cgttccggca gcagccgcag gccaaccggc tctccgcaat    12480
tctggaagcg gtggtcccgg cgcgcgcaaa ccccacgcac gagaaggtgc tggcgatcgt    12540
aaacgcgctg gccgaaaaca gggccatccg gcccgatgag gccggcctgg tctacgacgc    12600
gctgcttcag cgcgtggctc gttacaacag cagcaacgtg cagaccaacc tggaccggct    12660
ggtgggggat gtgcgcgagg ccgtggcgca gcgtgagcgc gcgcagcagc agggcaaccT    12720
gggctccatg gttgcactaa acgccttcct gagtacacag cccgccaacg tgccgcgggg    12780
acaggaggac tacaccaact tgtgagcgc actgcggcta atggtgactg agacaccgca    12840
aagtgaggtg tatcagtccg ggccagacta tttttttccag accagtagac aaggcctgca    12900
gaccgtaaac ctgagccagg cttttcaagaa cttgcagggg ctgtgggggg tgcgggctcc    12960
cacaggcgac cgcgcgaccg tgtctagctt gctgacgccc aactcgcgcc tgttgctgct    13020
gctaatagcg cccttcacgg acagtggcag cgtgtcccgg gacacatacc taggtcactt    13080
gctgacactg taccgcgagg ccataggtca ggcgcatgtg gacgagcata ctttccagga    13140
gattacaagt gttagccgcg cgctgggca ggaggacacg ggcagcctgg aggcaaccct    13200
gaactacctg ctgaccaacc ggcggcaaaa aatcccctcg ttgcacagtt taaacagcga    13260
ggaggagcgc attttgcgct atgtgcagca gagcgtgagc cttaacctga tgcgcgacg    13320 ggtaacgccc agcgtggcgc tggacatgac cgcgcgcaac atggaaccgg gcatgtatgc    13380
ctcaaaccgg ccgtttatca atcgcctaat ggactacttg catcgcgcgg ccgccgtgaa    13440
ccccgagtat ttcaccaatg ccatcttgaa cccgcactgg ctaccgcccc tggtttcta    13500 caccggggga ttcgaggtgc ccgagggtaa cgatggattc ctctgggacg acatagacga    13560
cagcgtgttt tcccgcaac cgcagaccct gctagagttg caacaacgcg agcaggcaga    13620
ggcggcgctg cgaaaggaaa gcttccgcag gccaagcagc ttgtccgatc taggcgctgc    13680
ggccccgcgg tcagatgcta gtagcccatt tccaagcttg atagggtctc ttaccagcac    13740
```

```
tcgcaccacc cgcccgcgcc tgctgggcga ggaggagtac ctaaacaact cgctgctgca    13800
gccgcagcgc gaaaagaacc tgcctccggc gtttcccaac aacgggatag agagcctagt    13860
ggacaagatg agtagatgga agacgtatgc gcaggagcac agggatgtgc ccggcccgcg    13920
cccgcccacc cgtcgtcaaa ggcacgaccg tcagcgggt ctggtgtggg aggacgatga     13980
ctcggcagac gacagcagcg tcttggattt gggagggagt ggcaacccgt tgcacacct    14040 tcgcccagg ctggggagaa tgttttaaaa aaagcatgat gcaaataaa aaactcacca      14100 aggccatggc accgagcgtt ggttttcttg tattcccctt agtatgcggc gcgcggcgat    14160
gtatgaggaa ggtcctcctc cctcctacga gagcgtggtg agcgcggcgc cagtggcggc    14220
ggcgctgggt tcacccttcg atgctcccct ggacccgccg ttcgtgcctc cgcggtacct    14280
gcggcctacc gggggagaa acagcatccg ttactctgag ttggcacccc tattcgacac     14340
cacccgtgtg taccttgtgg acaacaagtc aacggatgtg gcatccctga actaccagaa    14400
cgaccacagc aactttctaa ccacggtcat tcaaaacaat gactacagcc cgggggaggc    14460
aagcacacag accatcaatc ttgacgaccg gtcgcactgg ggcggcgacc tgaaaaccat    14520
cctgcatacc aacatgccaa atgtgaacga gttcatgttt accaataagt ttaaggcgcg    14580
ggtgatggtg tcgcgctcgc ttactaagga caaacaggtg gagctgaaat acgagtgggt    14640
ggagttcacg ctgcccgagg gcaactactc cgagaccatg accatagacc ttatgaacaa    14700
cgcgatcgtg gagcactact tgaaagtggg caggcagaac ggggttctgg aaagcgacat    14760
cggggtaaag tttgacaccc gcaacttcag actggggttt gacccagtca ctggtcttgt    14820
catgcctggg gtatatacaa acgaagcctt ccatccagac atcattttgc tgccaggatg    14880
cggggtggac ttcacccaca gccgcctgag caacttgttg ggcatccgca agcggcaacc    14940
cttccaggag ggctttagga tcacctacga tgacctggag ggtggtaaca ttcccgcact    15000
gttggatgtg gacgcctacc aggcaagctt gaaagatgac accgaacagg gcggggtgg    15060 cgcaggcggc ggcaacaaca gtggcagcgg cgcggaagag aactccaacg cggcagctgc    15120
ggcaatgcag ccggtggagg acatgaacga tcatgccatt cgcggcgaca cctttgccac    15180
acgggcggag gagaagcgcg ctgaggccga ggcagcggcc gaagctgccg ccccccgctgc   15240 ggaggctgca aacccgagg tcgagaagcc tcagaagaaa ccggtgatta aaccctgac     15300 agaggacagc aagaaacgca gttacaacct aataagcaat gacagcacct tcacccagta    15360
ccgcagctgg taccttgcat acaactacgg cgaccctcag gccgggatcc gctcatggac    15420
cctgctttgc actcctgacg taacctgcgg ctcggagcag gtatactggt cgttgcccga    15480
catgatgcaa gaccccgtga ccttccgctc cacgcgccag atcagcaact ttccggtggt    15540
gggcgccgag ctgttgcccg tgcactccaa gagcttctac aacgaccagg ccgtctactc    15600
ccagctcatc cgccagttta cctctctgac ccacgtgttc aatcgctttc cgagaaacca    15660
gattttggcg cgcccgccag cccccaccat caccaccgtc agtgaaaacg ttcctgctct    15720
cacagatcac gggacgctac cgctgcgcaa cagcatcgga ggagtccagc gagtgaccat    15780
tactgacgcc agacgccgca cctgccccta cgtttacaag gccctgggca tagtctcgcc    15840
gcgcgtccta tcgagccgca ctttttgagc aagcatgtcc atccttatat cgcccagcaa    15900
taacacaggc tggggcctgc gcttcccaag caagatgttt ggcggggcca agaagcgctc    15960
cgaccaacac ccagtgcgcg tgcgcgggca ctaccgcgcg ccctggggcg cgcacaaacg    16020
cggccgcact gggcgcacca ccgtcgatga cgccatcgac gcggtggtgg aggaggcgcg    16080
caactacacg cccacgccgc cgccagtgtc caccgtggac gcggccattc agaccgtggt    16140
```

```
gcgcggagcc cggcgctacg ctaaaatgaa gagacggcgg aggcgcgtag cacgtcgcca    16200
ccgccgccga cccggcactg ccgcccaacg cgcggcggcg gccctgctta accgcgcacg    16260
tcgcaccggc cgacgggcgg ccatgcgagc cgctcgaagg ctggccgcgg gtattgtcac    16320
tgtgccccca aggtccaggc gacgagcggc cgccgcagca gccgcggcca ttagtgctat    16380
gactcagggt cgcaggggca acgtgtactg ggtgcgcgac tcggttagcg gcctgcgcgt    16440
gcccgtgcgc acccgccccc cgcgcaacta gattgcaata aaaaactact tagactcgta    16500
ctgttgtatg tatccagcgg cggcggcgcg catcgaagct atgtccaagc gcaaaatcaa    16560
agaagagatg ctccaggtca tcgcgccgga gatctatggc cccccgaaga aggaagagca    16620
ggattacaag ccccgaaagc taaagcgggt caaaaagaaa aagaagatg atgatgatga    16680 tgaacttgac gacgaggtgg aactgttgca cgcgaccgcg cccaggcgac gggtacagtg    16740
gaaaggtcga cgcgtaagac gtgttttgcg acccggcacc accgtagtct ttacgcccgg    16800
tgagcgctcc acccgcacct acaagcgcgt gtatgatgag gtgtacggcg acgaggacct    16860
gcttgagcag gccaacgagc gcctcgggga gtttgcctac ggaaagcggc ataaggacat    16920
gctggcgttg ccgctggacg agggcaaccc aacacctagc ctaaagcccg tgacactgca    16980
gcaggtgctg cccgcgcttg caccgtccga agaaaagcgc ggcctaaagc gcgagtctgg    17040
tgacttggca cccaccgtgc agctgatggt acccaagcgt cagcgactgg aagatgtctt    17100
ggaaaaaatg accgtggagc ctgggctgga gcccgaggtc cgcgtgcggc caatcaagca    17160
ggtggcaccg ggactgggcg tgcagaccgt ggacgttcag ataccccacca ccagtagcac    17220 tagtattgcc actgccacag agggcatgga gacacaaacg tccccggttg cctcggcggt    17280
ggcagatgcc gcggtgcagg cggccgctgc ggccgcgtcc aagacctcta cggaggtgca    17340
aacggacccg tggatgtttc gtgtttcagc cccccggcgt ccgcgccgtt caaggaagta    17400
cggcgccgcc agcgcgctac tgcccgaata tgccctacat ccttccatcg cgcctacccc    17460
cggctatcgt ggctacacct accgcccag aagacgagca actacccgac gccgaaccac    17520
cactggaacc cgccgccgcc gtcgcgtcg ccagcccgtg ctggccccga tttccgtgcg    17580
cagggtggct cgcgaaggag gcaggaccct ggtgctgcca acagcgcgct accaccccag    17640
catcgtttaa aagccggtct ttgtggttct tgcagatatg ccctcacct gccgcctccg    17700 tttcccggtg ccgggattcc gaggaagaat gcaccgtagg aggggcatgg ccggccacgg    17760
cctgacgggc ggcatgcgtc gtgcgcacca ccggcggcgg cgcgcgtcgc accgtcgcat    17820
gcgcggcggt atcctgcccc tccttattcc actgatcgcc gcggcgattg gcgccgtgcc    17880
cggaattgca tccgtggcct tgcaggcgca gagacactga ttaaaaacaa gttacatgtg    17940
gaaaaatcaa aataaaagtc tggactctca cgctcgcttg gtcctgtaac tatttttgtag    18000 aatggaagac atcaactttg cgtcactggc cccgcgacac ggctcgcgcc cgttcatggg    18060
aaactggcaa gatatcggca ccagcaatat gagcggtggc gccttcagct ggggctcgct    18120
gtggagcggc attaaaaatt tcggttccgc cgttaagaac tatggcagca agcctggaa    18180 cagcagcaca ggccagatgc tgagggacaa gttgaaagag caaatttcc aacaaaaggt    18240 ggtagatggc ctggcctctg gcattagcgg ggtggtggac ctggccaacc aggcagtgca    18300
aaataagatt aacagtaagc ttgatccccg ccctcccgta gaggagcctc caccggccgt    18360
ggagacagtg tctccagagg ggcgtggcga aaagcgtccg cgacccgaca gggaagaaac    18420
tctggtgacg caaatagacg agcctccctc gtacgaggag gcactaaagc aaggcctgcc    18480
caccacccgt cccatcgcgc ccatggctac cggagtgctg ggccagcaca cacccgtaac    18540
```

```
gctggacctg cctcccccg  ccgacaccca gcagaaacct gtgctgccag gcccgtccgc    18600
cgttgttgta acccgtccta gccgcgcgtc cctgcgccgc gccgccagcg gtccgcgatc    18660
gttgcggccc gtagccagtg gcaactggca aagcacactg aacagcatcg tgggtttggg    18720
ggtgcaatcc ctgaagcgcc gacgatgctt ctgatagcta acgtgtcgta tgtgtgtcat    18780
gtatgcgtcc atgtcgccgc cagaggagct gctgagccgc cgcgcgcccg ctttccaaga    18840
tggctacccc ttcgatgatg ccgcagtggt cttacatgca catctcgggc caggacgcct    18900
cggagtacct gagccccggg ctggtgcagt tcgcccgcgc caccgagacg tacttcagcc    18960
tgaataacaa gtttagaaac cccacggtgg cgcctacgca cgacgtgacc acagaccggt    19020
ctcagcgttt gacgctgcgg ttcatccccg tggaccgcga ggatactgcg tactcgtaca    19080
aggcgcggtt caccctagct gtgggtgata accgtgtgct agacatggct tccacgtact    19140
ttgacatccg cggcgtgctg acaggggcc  ctacttttaa gccctactct ggcactgcct    19200
acaacgcact ggcccccaag ggtgccccca actcgtgcga gtgggaacaa aatgaaactg    19260
cacaagtgga tgctcaagaa cttgacgaag aggagaatga agccaatgaa gctcaggcgc    19320
gagaacagga acaagctaag aaaacccatg tatatgccca ggctccactg tccggaataa    19380
aaataactaa agaaggtcta caaataggaa ctgccgacgc cacagtagca ggtgccggca    19440 aagaaaatttt cgcagacaaa acttttcaac ctgaaccaca agtaggagaa tctcaatgga    19500
acgaagcgga tgccacagca gctggtggaa gggttcttaa aaagacaact cccatgaaac    19560
cctgctatgg ctcatacgct agacccacca attccaacgg cggacagggc gttatggttg    19620
aacaaaatgg taaattggaa agtcaagtcg aaatgcaatt ttttccaca  tccacaaatg    19680 ccacaaatga agttaacaat atacaaccaa cagttgtatt gtacagcgaa gatgtaaaca    19740
tggaaactcc agatactcat ctttcttata aacctaaaat ggggataaa aatgccaaag    19800 tcatgcttgg acaacaagca atgccaaaca gaccaaatta cattgctttt agagacaatt    19860
ttattggtct catgtattac aacagcacag gtaacatggg tgtccttgct ggtcaggcat    19920
cgcagttgaa cgctgttgta gatttgcaag acagaaacac agagctgtcc taccagcttt    19980
tgcttgattc aattggcgac agaacaagat acttttcaat gtggaatcaa gctgttgaca    20040
gctatgatcc agatgtcaga attattgaga accatggaac tgaggatgag ttgccaaatt    20100
attgctttcc tcttggtgga attgggatta ctgacacttt tcaagctgtt aaaacaactg    20160
ctgctaacgg ggaccaaggc aatactacct ggcaaaaaga ttcaacattt gcagaacgca    20220
atgaaatagg ggtgggaaat aacttttgcca tggaaattaa cctgaatgcc aacctatgga    20280
gaaatttcct ttactccaat attgcgctgt acctgccaga caagctaaaa tacaacccca    20340
ccaatgtgga aatatctgac aaccccaaca cctacgacta catgaacaag cgagtggtgg    20400
ctcctgggct tgtagactgc tacattaacc ttggggcgcg ctggtctctg gactacatgg    20460
acaacgttaa tcccttaac caccaccgca atgcgggcct gcgttaccgc tccatgttgt    20520
tgggaaacgg ccgctacgtg ccctttcaca ttcaggtgcc ccaaaagttt tttgccatta    20580
aaaacctcct cctcctgcca ggctcataca catatgaatg gaacttcagg aaggatgtta    20640
acatggttct gcagagctct ctgggaaacg accttagagt tgacggggct agcattaagt    20700
ttgacagcat ttgtctttac gccaccttct tccccatggc ccacaacacg gcctccacgc    20760
tggaagccat gctcagaaat gacaccaacg accagtcctt taatgactac ctttccgccg    20820
ccaacatgct atatcccata cccgccaacg ccaccaacgt gcccatctcc atcccatcgc    20880
gcaactgggc agcatttcgc ggttgggcct tcacacgctt gaagacaaag gaaacccctt    20940
```

```
cnctgggatc aggctacgac ccttactaca cctactctgg ctccatacca taccttgacg   21000
gaaccttcta tcttaatcac acctttaaga aggtggccat tacttttgac tcttctgtta   21060
gctggccggg caacgaccgc ctgcttactc ccaatgagtt tgagattaag cgctcagttg   21120
acggggaggg ctataacgta gctcagtgca acatgacaaa ggactggttc ctagtgcaga   21180
tgttggccaa ctacaatatt ggctaccagg gcttctacat tccagaaagc tacaaagacc   21240
gcatgtactc gttcttcaga aacttccagc ccatgagccg gcaagtggtg gacgatacta   21300
aatacaaaga ttatcagcag gttggaatta ccaccagca taacaactca ggcttcgtag   21360
gctacctcgc tcccaccatg cgcgagggac aagcttaccc cgctaatgtt ccctacccac   21420
taataggcaa aaccgcggtt gatagtatta cccagaaaaa gtttctttgc gaccgcaccc   21480
tgtggcgcat cccttctcc agtaacttta tgtccatggg tgcgctcaca gacctgggcc   21540
aaaaccttct ctacgcaaac tccgcccacg cgctagacat gaccttfgag gtggatccca   21600 tggacgagcc caccccttctt tatgtttfgt ttgaagtctt tgacgtggtc cgtgtgcacc   21660
agccgcaccg cggcgtcatc gagaccgtgt acctgcgcac gcccttctcg gccggcaacg   21720
ccacaacata aagaagcaag caacatcaac aacagctgcc gccatgggct ccagtgagca   21780
ggaactgaaa gccattgtca aagatcttgg ttgtgggcca tattttttgg gcacctatga   21840
caagcgcttc ccaggctttg tttccccaca caagctcgcc tgcgccatag ttaacacggc   21900
cggtcgcgag actgggggcg tacactggat ggccttfgcc tggaacccgc gctcaaaaac   21960
atgctacctc tttgagccct ttggcttttc tgaccaacgt ctcaagcagg tttaccagtt   22020
tgagtacgag tcactcctgc gccgtagcgc cattgcctct tcccccgacc gctgtataac   22080
gctggaaaag tccacccaaa gcgtgcaggg gcccaactcg gccgcctgtg gcctattctg   22140 ctgcatgtttt ctccacgcct ttgccaactg gccccaaact cccatggatc acaacccac   22200 catgaacctt attaccgggg tacccaactc catgcttaac agtccccagg tacagcccac   22260
cctgcgccgc aaccaggaac agctctacag cttcctggag cgccactcgc cctacttccg   22320
cagccacagt gcgcaaatta ggagcgccac ttctttttgt cacttgaaaa acatgtaaaa   22380
ataatgtact aggagacact ttcaataaag gcaaatgttt ttatttgtac actctcgggt   22440
gattatttac ccccacccct gccgtctgcg ccgtttaaaa atcaaagggg ttctgccgcg   22500
catcgctatg cgccactggc agggacacgt tgcgatactg gtgtttagtg ctccacttaa   22560
actcaggcac aaccatccgc ggcagctcgg tgaagttttc actccacagg ctgcgcacca   22620
tcaccaacgc gtttagcagg tcgggcgccg atatcttgaa gtcgcagttg gggctccgc   22680 cctgcgcgcg cgagttgcga tacacagggt tacagcactg gaacactatc agcgccgggt   22740
ggtgcacgct ggccagcacg ctcttgtcgg agatcagatc cgcgtccagg tcctccgcgt   22800
tgctcagggc gaacggagtc aactttggta gctgccttcc caaaagggt gcatgcccag   22860 gctttgagtt gcactcgcac cgtagtggca tcagaaggtg accgtgccca gtctgggcgt   22920
taggatacag cgcctgcatg aaagccttga tctgcttaaa agccacctga gcctttgcgc   22980
cttcagagaa gaacatgccg caagacttgc cggaaaactg attggccgga caggccgcgt   23040
catgcacgca gcaccttgcg tcggtgttgg agatctgcac cacatttcgg ccccaccggt   23100
tcttcacgat cttggccttg ctagactgct ccttcagcgc gcgctgcccg ttttcgctcg   23160
tcacatccat ttcaatcacg tgctccttat ttatcataat gctcccgtgt agacacttaa   23220
gctcgccttc gatctcagcg cagcggtgca gccacaacgc gcagcccgtg ggctcgtggt   23280
gcttgtaggt tacctctgca aacgactgca ggtacgcctg caggaatcgc cccatcatcg   23340
```

```
tcacaaaggt cttgttgctg gtgaaggtca gctgcaaccc gcggtgctcc tcgtttagcc    23400
aggtcttgca tacggccgcc agagcttcca cttggtcagg cagtagcctg aagtttgcct    23460
ttagatcgtt atccacgtgg tacttgtcca tcaacgcgcg cgcagcctcc atgcccttct    23520
cccacgcaga cacgatcggc aggctcagcg ggtttatcac cgtgctttca ctttccgctt    23580
cactggactc ttccttttcc tcttgcatcc gcataccccg cgccactggg tcgtcttcat    23640
tcagccgccg caccgtgcgc ttacctccct gccgtgctt gattagcacc ggtgggttgc     23700
tgaaacccac catttgtagc gccacatctt ctctttcttc ctcgctgtcc acgatcacct    23760
ctggggatgg cgggcgctcg ggcttgggag aggggcgctt ctttttcttt ttggacgcaa    23820
tggccaaatc cgccgtcgag gtcgatggcc gcgggctggg tgtgcgcggc accagcgcat    23880
cttgtgacga gtcttcttcg tcctcggact cgagacgccg cctcagccgc ttttttgggg    23940
gcgcgcgggg aggcggcggc gacggcgacg gggacgagac gtcctccatg gttggtggac    24000
gtcgcgccgc accgcgtccg cgctcggggg tggtttcgcg ctgctcctct tcccgactgg    24060
ccatttcctt ctcctatagg cagaaaaaga tcatggagtc agtcgagaag gaggacagcc    24120
taaccgcccc ctttgagttc gccaccaccg cctccaccga tgccgccaac gcgcctacca    24180
ccttcccgt cgaggcaccc ccgcttgagg aggaggaagt gattatcgag caggacccag     24240
gttttgtaag cgaagacgac gaagatcgct cagtaccaac agaggataaa aagcaagacc    24300
aggacgacgc agaggcaaac gaggaacaag tcgggcgggg ggaccaaagg catggcgact    24360
acctagatgt gggagacgac gtgctgttga agcatctgca gcgccagtgc gccattatct    24420
gcgacgcgtt gcaagagcgc agcgatgtgc ccctcgccat agcggatgtc agccttgcct    24480
acgaacgcca cctgttctca ccgcgcgtac cccccaaacg ccaagaaaac ggcacatgcg    24540
agcccaaccc gcgcctcaac ttctaccccg tatttgccgt gccagaggtg cttgccacct    24600
atcacatctt ttttccaaaac tgcaagatac ccctatcctg ccgtgccaac cgcagccgag   24660
cggacaagca gctggccttg cggcagggcg ctgtcatacc tgatatcgcc tcgctcgacg    24720
aagtgccaaa aatctttgag ggtcttggac gcgacgagaa gcgcgcggca aacgctctgc    24780
aacaagaaaa cagcgaaaat gaaagtcact gtggagtgct ggtggaactt gagggtgaca    24840
acgcgcgcct agccgtgctg aaacgcagca tcgaggtcac ccactttgcc tacccggcac    24900
ttaacctacc ccccaaggtt atgagcacag tcatgagcga gctgatcgtg cgccgtgcac    24960
gaccctgga gagggatgca aacttgcaag aacaaaccga ggagggccta cccgcagttg     25020
gcgatgagca gctggcgcgc tggcttgaga cgcgcgagcc tgccgacttg gaggagcgac    25080
gcaagctaat gatggccgca gtgcttgtta ccgtggagct tgagtgcatg cagcgggttct   25140
ttgctgaccc ggagatgcag cgcaagctag aggaaacgtt gcactacacc tttcgccagg    25200
gctacgtgcg ccaggcctgc aaaatttcca acgtggagct ctgcaacctg gtctcctacc    25260
ttggaatttt gcacgaaaac cgccttgggc aaaacgtgct tcattccacg ctcaagggcg    25320
aggcgcgccg cgactacgtc cgcgactgcg tttacttatt tctgtgctac acctggcaaa    25380
cggccatggg cgtgtggcag cagtgcctgg aggagcgcaa cctgaaggag ctgcagaagc    25440
tgctaaagca aaacttgaag gacctatgga cggccttcaa cgagcgctcc gtggccgcgc    25500
acctggcgga cattatcttc cccgaacgcc tgcttaaaac cctgcaacag ggtctgccaa    25560
acttcaccag tcaaagcatg ttgcaaaact ttaggaactt tatcctagag cgttcaggaa    25620
ttctgccccgc cacctgctgt gcgcttccta gcgactttgt gcccattaag taccgtgaat   25680
gccctccgcc gctttggggt cactgctacc ttctgcagct agccaactac cttgcctacc    25740
```

```
actccgacat catggaagac gtgagcggtg acggcctact ggagtgtcac tgtcgctgca    25800
acctatgcac cccgcaccgc tccctggtct gcaattcaca actgcttagc gaaagtcaaa    25860
ttatcggtac ctttgagctg cagggtccct cgcctgacga aaagtccgcg gctccggggt    25920
tgaaactcac tccggggctg tggacgtcgg cttaccttcg caaatttgta cctgaggact    25980
accacgccca cgagattagg ttctacgaag accaatcccg cccgccaaat gcggagctta    26040
ccgcctgcgt cattacccag ggccacatcc ttggccaatt gcaagccatt aacaaagccc    26100
gccaagagtt tctgctacga aagggacggg gggtttactt ggaccccag tccggcgagg     26160 agctcaaccc aatcccccg ccgccgcagc cctatcagca gccgcgggcc cttgcttccc      26220
aggatggcac ccaaaaagaa gctgcagctg ccgccgccgc cacccacgga cgaggaggaa    26280
tactgggaca gtcaggcaga ggaggttttg gacgaggagg aggagatgat ggaagactgg    26340
gacagcctag acgaggaagc ttccgaggcc gaagaggtgt cagacgaaac accgtcaccc    26400
tcggtcgcat tcccctcgcc ggcgcccag aaatcggcaa ccgttcccag cattgctaca      26460
acctccgctc ctcaggcgcc gccggcactg cccgttcgcc gacccaaccg tagatgggac    26520
accactggaa ccagggccgg taagtctaag cagccgccgc cgttagccca agagcaacaa    26580
cagcgccaag gctaccgctc gtggcgcgtg cacaagaacg ccatagttgc ttgcttgcaa    26640
gactgtgggg gcaacatctc cttcgcccgc cgctttcttc tctaccatca cggcgtggcc    26700 ttccccgta acatcctgca ttactaccgt catctctaca gccctactg caccggcggc       26760 agcggcagca acagcagcgg ccacgcagaa gcaaaggcga ccggatagca agactctgac    26820
aaagcccaag aaatccacag cggcggcagc agcaggagga ggagcactgc gtctggcgcc    26880
caacgaaccc gtatcgaccc gcgagcttag aaacaggatt ttttcccactc tgtatgctat    26940 atttcaacag agcaggggcc aagaacaaga gctgaaaata aaaacaggt ctctgcgctc      27000 cctcacccgc agctgcctgt atcacaaaag cgaagatcag cttcggcgca cgctggaaga    27060
cgcggaggct ctcttcagca aatactgcgc gctgactctt aaggactagt ttcgcgccct    27120
ttctcaaatt taagcgcgaa aactacgtca tctccagcgg ccacacccgg cgccagcacc    27180
tgtcgtcagc gccattatga gcaaggaaat tcccacgccc tacatgtgga gttaccagcc    27240
acaaatggga cttgcggctg gagctgccca agactactca acccgaataa actacatgag    27300
cgcgggaccc cacatgatat cccgggtcaa cggaatccgc gcccaccgaa accgaattct    27360
cctcgaacag gcggctatta ccaccacacc tcgtaataac cttaatcccc gtagttggcc    27420
cgctgccctg tgtaccagg aaagtcccgc tcccaccact gtggtacttc ccagagacgc      27480
ccaggccgaa gttcagatga ctaactcagg ggcgcagctt gcgggcggct ttcgtcacag    27540
ggtgcggtcg cccgggcagg gtataactca cctgaaaatc agagggcgag gtattcagct    27600
caacgacgag tcggtgagct cctctcttgg tctccgtccg gacgggacat ttcagatcgg    27660
cggcgctggc cgctcttcat ttacgccccg tcaggcgatc ctaactctgc agacctcgtc    27720
ctcggagccg cgctccggag gcattggaac tctacaattt attgaggagt tcgtgccttc    27780
ggtttacttc aacccctttt ctggacctcc cggccactac ccggaccagt ttattcccaa    27840
ctttgacgcg gtaaaagact cggcggacgg ctacgactga atgaccagtg gagaggcaga    27900
gcaactgcgc ctgacacacc tcgaccactg ccgccgccac aagtgctttg cccgcggctc    27960
cggtgagttt tgttactttg aattgcccga agagcatatc gagggcccgg cgcacggcgt    28020
ccggctcacc acccaggtag agcttacacg tagcctgatt cggagtttta ccaagcgccc    28080
cctgctagtg gagcgggagc ggggtccctg tgttctgacc gtggtttgca actgtcctaa    28140
```

```
ccctggatta catcaagatc tttgttgtca tctctgtgct gagtataata aatacagaaa    28200
ttagaatcta ctggggctcc tgtcgccatc ctgtgaacgc caccgttttt acccacccaa    28260
agcagaccaa agcaaacctc acctccggtt tgcacaagcg ggccaataag taccttacct    28320
ggtactttaa cggctcttca tttgtaattt acaacagttt ccagcgagac gaagtaagtt    28380
tgccacacaa ccttctcggc ttcaactaca ccgtcaagaa aaacaccacc accaccctcc    28440
tcacctgccg ggaacgtacg agtgcgtcac cggttgctgc gcccacacct acagcctgag    28500
cgtaaccaga cattactccc attttcccaa aacaggaggt gagctcaact cccggaactc    28560
aggtcaaaaa agcattttgc ggggtgctgg gattttttaa ttaagtatat gagcaattca    28620
agtaactcta caagcttgtc taattttttct ggaattgggg tcggggttat ccttactctt    28680
gtaattctgt ttattcttat actagcactt ctgtgcctta gggttgccgc ctgctgcacg    28740
cacgtttgta cctattgtca gcttttttaaa cgctggggc gacatccaag atgaggtaca    28800
tgattttagg cttgctcgcc cttgcggcag tctgcagcgc tgccaaaaag gttgagttta    28860
aggaaccagc ttgcaatgtt acatttaaat cagaagctaa tgaatgcact actcttataa    28920
aatgcaccac agaacatgaa aagcttatta ttcgccacaa agacaaaatt ggcaagtatg    28980
ctgtatatgc tatttggcag ccaggtgaca ctaacgacta taatgtcaca gtcttccaag    29040
gtgaaaatcg taaaacttttt atgtataaat ttccatttta tgaaatgtgc gatattacca    29100
tgtacatgag caaacagtac aagttgtggc ccccacaaaa gtgtttagag aacactggca    29160
ccttttgttc caccgctctg cttattacag cgcttgcttt ggtatgtacc ttactttatc    29220
tcaaatacaa aagcagacgc agtttttattg atgaaaagaa aatgccttga ttttccgctt    29280
gcttgtattc ccctggacaa tttactctat gtgggatatg cgccaggcgg gaaagattat    29340
acccacaacc ttcaaatcaa acttttcctgg acgttagcgc ctgacttctg ccagcgcctg    29400
cactgcaaat ttgatcaaac ccagcttcag cttgcctgct ccagagatga ccggctcaac    29460
catcgcgccc acaacggact atcgcaacac cactgctacc ggactaaaat ctgccctaaa    29520
tttaccccaa gttcatgcct ttgtcaatga ctgggcgagc ttgggcatgt ggtggttttc    29580
catagcgctt atgtttgttt gccttattat tatgtggctt atttgttgcc taaagcgcag    29640
acgcgccaga ccccccatct ataggcctat cattgtgctc aacccacaca atgaaaaaat    29700
tcatagattg gacggtctca aaccatgttc tcttctttta cagtatgatt aaatgagaca    29760
tgattcctcg agtccttata ttattgaccc ttgttgcgct tttctgtgcg tgctctacat    29820
tggctgcggt cgctcacatc gaagtagatt gcatcccacc tttcacagtt tacctgcttt    29880
acggatttgt caccccttatc ctcatctgca gcctcgtcac tgtagtcatc gccttcattc    29940
agttcattga ctgatttgt gtgcgcattg cgtaccttag gcaccatccg caatacagag    30000
acaggactat agctgatctt ctcagaattc tttaattatg aaacggattg tcactttgt    30060
tttgctgatt ttctgcgccc tacctgtgct ttgctcccaa acctcagcgc ctcccaaaag    30120
acatatttcc tgcagattca ctcaaatatg gaacattccc agctgctaca acaaacagag    30180
cgatttgtca gaagcctggt tatacgccat catctctgtc atggttttt gcagtaccat    30240
ttttgcccta gccatatacc cataccttga cattggttgg aatgccatag atgccatgaa    30300
ccaccctact ttcccagcgc ccaatgtcat accactgcaa caggttattg ccccaatcaa    30360
tcagcctcgc cccccttctc ccacccccac tgagattagc tactttaatt tgacaggtgg    30420
agatgactga atctctagat ctagaattgg atggaattaa caccgaacag cgcctactag    30480
aaaggcgcaa ggcggcgtcc gagcgagaac gcctaaaaca agaagttgaa gacatggtta    30540
```

```
acctgcacca gtgtaaaaga ggtatctttt gtgtggtcaa gcaggccaaa cttacctacg   30600
aaaaaaccac taccggcaac cgccttagct acaagctacc cacccagcgc caaaaactgg   30660
tgcttatggt gggagaaaaa cctatcaccg tcacccagca ctcggcagaa acagaaggct   30720
gcctgcactt cccctatcag ggtccagagg acctctgcac tcttattaaa accatgtgtg   30780
gcattagaga tcttattcca ttcaactaac aataaacaca caataaatta cttacttaaa   30840
atcagtcagc aaatctttgt ccagcttatt cagcatcacc tcctttccct cctcccaact   30900
ctggtatttc agcagccttt tagctgcgaa cttttctcca agtctaaatg ggatgtcaaa   30960
ttcctcatgt tcttgtccct ccgcacccac tatcttcata ttgttgcaga tgaaacgcgc   31020
cagaccgtct gaagacacct tcaaccctgt gtacccatat gacacggaaa ccggccctcc   31080
aactgtgcct ttccttaccc ctcccttttgt gtcgccaaat gggttccaag aaagtccccc   31140
cggagtgctt tctttgcgtc tttcagaacc tttggttacc tcacacggca tgcttgcgct   31200
aaaaatgggc agcggcctgt ccctggatca ggcaggcaac cttacatcaa atacaatcac   31260
tgtttctcaa ccgctaaaaa aaacaaagtc caatataact ttggaaacat ccgcgcccct   31320
tacagtcagc tcaggcgccc taaccatggc cacaacttcg cctttggtgg tctctgacaa   31380
cactcttacc atgcaatcac aagcaccgct aaccgtgcaa gactcaaaac ttagcattgc   31440
taccaaagag ccacttacag tgttagatgg aaaactggcc ctgcagacat cagccccccct   31500 ctctgccact gataacaacg ccctcactat cactgcctca cctcctctta ctactgcaaa   31560
tggtagtctg gctgttacca tggaaaaccc actttacaac aacaatggaa aacttgggct   31620
caaaattggc ggtcctttgc aagtggccac cgactcacat gcactaacac taggtactgg   31680
tcagggggtt gcagttcata acaatttgct acatacaaaa gttacaggcg caataggggtt   31740 tgatacatct ggcaacatgg aacttaaaac tggagatggc ctctatgtgg atagcgccgg   31800
tcctaaccaa aaactacata ttaatctaaa taccacaaaa ggccttgctt ttgacaacac   31860
cgcaataaca attaacgctg gaaaagggtt ggaatttgaa acagactcct caaacggaaa   31920
tcccataaaa acaaaaattg gatcaggcat acaatataat accaatggag ctatggttgc   31980
aaaacttgga acaggcctca gttttgacag ctccggagcc ataacaatgg gcagcataaa   32040
caatgacaga cttactcttt ggacaacacc agacccatcc ccaaattgca gaattgcttc   32100
agataaagac tgcaagctaa ctctggcgct aacaaaatgt ggcagtcaaa tttttgggcac   32160 tgtttcagct ttggcagtat caggtaatat ggcctccatc aatggaactc taagcagtgt   32220
aaacttggtt cttagatttg atgacaacgg agtgcttatg tcaaattcat cactggacaa   32280
acagtattgg aactttagaa acggggactc cactaacggt caaccataca cttatgctgt   32340
tgggtttatg ccaaacctaa aagcttaccc aaaaactcaa agtaaaactg caaaaagtaa   32400
tattgttagc caggtgtatc ttaatggtga caagtctaaa ccattgcatt ttactattac   32460
gctaaatgga acagatgaaa ccaaccaagt aagcaaatac tcaatatcat tcagttggtc   32520
ctggaacagt ggacaataca ctaatgacaa atttgccacc aattcctata ccttctccta   32580
cattgcccag gaataaagaa tcgtgaacct gttgcatgtt atgtttcaac gtgtttattt   32640
ttcaattgca gaaaatttca agtcattttt cattcagtag tatagcccca ccaccacata   32700
gcttatacta atcaccgtac cttaatcaaa ctcacagaac cctagtattc aacctgccac   32760
ctccctccca acacacagag tacacagtcc tttctccccg gctggcctta aacagcatca   32820
tatcatgggt aacagacata ttcttaggtg ttatattcca cacggtctcc tgtcgagcca   32880
aacgctcatc agtgatgtta ataaactccc cgggcagctc gcttaagttc atgtcgctgt   32940
```

```
ccagctgctg agccacaggc tgctgtccaa cttgcggttg ctcaacgggc ggcgaaggag   33000
aagtccacgc ctacatgggg gtagagtcat aatcgtgcat caggataggg cggtggtgct   33060
gcagcagcgc gcgaataaac tgctgccgcc gccgctccgt cctgcaggaa tacaacatgg   33120
cagtggtctc ctcagcgatg attcgcaccg cccgcagcat aaggcgcctt gtcctccggg   33180
cacagcagcg caccctgatc tcacttaagt cagcacagta actgcagcac agtaccacaa   33240
tattgtttaa atcccacag tgcaaggcgc tgtatccaaa gctcatggcg gggaccacag    33300
aacccacgtg gccatcatac cacaagcgca ggtagattaa gtggcgaccc ctcataaaca   33360
cgctggacat aaacattacc tcttttggca tgttgtaatt caccacctcc cggtaccata   33420
taaacctctg attaaacatg gcgccatcca ccaccatcct aaaccagctg gccaaaacct   33480
gcccgccggc tatgcactgc agggaaccgg gactggaaca atgacagtgg agagcccagg   33540
actcgtaacc atggatcatc atgctcgtca tgatatcaat gttggcacaa cacaggcaca   33600
cgtgcataca cttcctcagg attacaagct cctcccgcgt cagaaccata tcccagggaa   33660
caacccattc ctgaatcagc gtaaatccca cactgcaggg aagacctcgc acgtaactca   33720
cgttgtgcat tgtcaaagtg ttacattcgg gcagcagcgg atgatcctcc agtatggtag   33780
cgcgtgtctc tgtctcaaaa ggaggtaggc gatccctact gtacggagtg cgccgagaca   33840
accgagatcg tgttggtcgt agtgtcatgc caaatggaac gccggacgta gtcatatttc   33900
ctgaagcaaa accaggtgcg ggcgtgacaa acagatctgc gtctccggtc tcgtcgctta   33960
gctcgctctg tgtagtagtt gtagtatatc cactctctca aagcatccag gcgcccctg    34020
gcttcgggtt ctatgtaaac tccttcatgc gccgctgccc tgataacatc caccaccgca   34080
gaataagcca cacccagcca acctacacat tcgttctgcg agtcacacac gggaggagcg   34140
ggaagagctg gaagaaccat gttttttttt tttattccaa aagattatcc aaaacctcaa   34200
aatgaagatc tattaagtga acgcgctccc ctccggtggc gtggtcaaac tctacagcca   34260
aagaacagat aatggcattt gtaagatgtt gcacaatggc ttccaaaagg caaactgccc   34320
tcacgtccaa gtggacgtaa aggctaaacc cttcagggtg aatctcctct ataaacattc   34380
cagcaccttc aaccatgccc aaataatttt catctcgcca ccttatcaat atgtctctaa   34440
gcaaatcccg aatattaagt ccggccattg taaaaatctg ctccagagcg ccctccacct   34500
tcagcctcaa gcagcgaatc atgattgcaa aaattcaggt tcctcacaga cctgtataag   34560
attcaaaagc ggaacattaa caaaaatacc gcgatcccgt aggtcccttc gcagggccag   34620
ctgaacataa tcgtgcaggt ctgcacggac cagcgcggcc acttccccgc caggaaccat   34680
gacaaaagaa cccacactga ttatgacacg catactcgga gctatgctaa ccagcgtagc   34740
cccgatgtaa gcttgttgca tgggcggcga tataaaatgc aaggtactgc tcaaaaaatc   34800
aggcaaagcc tcgcgcaaaa aagcaagcac atcgtagtca tgctcatgca gataaaggca   34860
ggtaagttcc ggaaccacca cagaaaaaga caccatttt ctctcaaaca tgtctgcggg    34920
ttcctgcata acacaaaat aaaataacaa aaaaaaaaaa acatttaaac attagaagcc    34980
tgtnttacaa caggaaaaac aacccttata agcataagac ggactacggc catgccggcg   35040
tgaccgtaaa aaaactggtc accgtgatta aaaagcacca ccgacagttc ctcggtcatg   35100
tccggagtca taatgtaaga ctcggtaaac acatcaggtt ggttaacatc ggtcagtgct   35160
aaaaagcgac cgaaatagcc cgggggaata catcccgca ggcgtagaga caacattaca    35220
gcccccatag gaggtataac aaaattaata ggagagaaaa acacataaac acctgaaaaa   35280
ccctcctgcc taggcaaaat agcacccctcc cgctccagaa caacatacag cgcttccaca   35340
```

| | |
|---|---:|
| gcggcagcca taacagtcag ccttaccagt aaaaaaacct attaaaaaac accactcgac | 35400 |
| acggcaccag ctcaatcagt cacagtgtaa aaagggccaa gtacagagcg agtatatata | 35460 |
| ggactaaaaa atgacgtaac ggttaaagtc cacaaaaacc acccagaaaa ccgcacgcga | 35520 |
| acctacgccc agaaacgaaa gccaaaaaac ccacaacttc ctcaaatctt cacttccgtt | 35580 |
| ttcccacgat acgtcacttc ccattttaaa aaaaaactac aattcccaat acatgcaagt | 35640 |
| tactccgccc taaaacctac gtcacccgcc ccgttcccac gccccgcgcc acgtcacaaa | 35700 |
| ctccacccccc tcattatcat attggcttca atccaaaata aggtatatta ttgatgatg | 35759 |

<210> SEQ ID NO 9
<211> LENGTH: 35935
<212> TYPE: DNA
<213> ORGANISM: Adenovirus serotype 5

<400> SEQUENCE: 9

| | |
|---|---:|
| catcatcaat aatataccttt attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgtttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tatttgtcta gggccgcggg | 360 |
| gactttgacc gtttacgtgg agactcgccc aggtgttttt ctcaggtgtt ttccgcgttc | 420 |
| cgggtcaaag ttggcgtttt attattatag tcagctgacg tgtagtgtat ttatacccgg | 480 |
| tgagttcctc aagaggccac tcttgagtgc cagcgagtag agttttctcc tccgagccgc | 540 |
| tccgacaccg ggactgaaaa tgagacatat tatctgccac ggaggtgtta ttaccgaaga | 600 |
| aatggccgcc agtctttttgg accagctgat cgaagaggta ctggctgata atcttccacc | 660 |
| tcctagccat tttgaaccac ctacccttca cgaactgtat gatttagacg tgacggcccc | 720 |
| cgaagatccc aacgaggagg cggtttcgca gattttcccc gactctgtaa tgttggcggt | 780 |
| gcaggaaggg attgacttac tcacttttcc gccggcgccc ggttctccgg agccgcctca | 840 |
| cctttcccgg cagcccgagc agccggagca gagagccttg ggtccggttt ctatgccaaa | 900 |
| ccttgtaccg gaggtgatcg atcttacctg ccacgaggct ggctttccac ccagtgacga | 960 |
| cgaggatgaa gagggtgagg agtttgtgtt agattatgtg gagcaccccg gcacggttg | 1020 |
| caggtcttgt cattatcacc ggaggaatac ggggacccca gatattatgt gttcgctttg | 1080 |
| ctatatgagg acctgtggca tgtttgtcta cagtaagtga aaattatggg cagtgggtga | 1140 |
| tagagtggtg ggtttggtgt ggtaattttt tttttaattt ttacagtttt gtggtttaaa | 1200 |
| gaattttgta ttgtgatttt tttaaaggt cctgtgtctg aacctgagcc tgagcccgag | 1260 |
| ccagaaccgg agcctgcaag acctacccgc cgtcctaaaa tggcgcctgc tatcctgaga | 1320 |
| cgcccgacat cacctgtgtc tagagaatgc aatagtagta cggatagctg tgactccggt | 1380 |
| ccttctaaca cacctcctga gatacacccg gtggtcccgc tgtgccccat aaaccagtt | 1440 |
| gccgtgagag ttggtgggcg tcgccaggct gtggaatgta tcgaggactt gcttaacgag | 1500 |
| cctgggcaac ctttggactt gagctgtaaa cgccccaggc cataaggtgt aaacctgtga | 1560 |
| ttgcgtgtgt ggttaacgcc tttgtttgct gaatgagttg atgtaagttt aataaagggt | 1620 |
| gagataatgt ttaacttgca tggcgtgtta aatgggcgg ggcttaaagg gtatataatg | 1680 |
| cgccgtgggc taatcttggt tacatctgac ctcatggagg cttgggagtg tttggaagat | 1740 |

```
ttttctgctg tgcgtaactt gctggaacag agctctaaca gtacctcttg gttttggagg    1800
tttctgtggg gctcatccca ggcaaagtta gtctgcagaa ttaaggagga ttacaagtgg    1860
gaatttgaag agcttttgaa atcctgtggt gagctgtttg attctttgaa tctgggtcac    1920
caggcgcttt tccaagagaa ggtcatcaag actttggatt tttccacacc ggggcgcgct    1980
gcggctgctg ttgctttttt gagttttata aaggataaat ggagcgaaga aacccatctg    2040 agcgggggt  acctgctgga ttttctggcc atgcatctgt ggagagcggt tgtgagacac    2100
aagaatcgcc tgctactgtt gtcttccgtc cgcccggcga taataccgac ggaggagcag    2160
cagcagcagc aggaggaagc caggcggcgg cggcaggagc agagcccatg gaacccgaga    2220
gccggcctgg accctcggga atgaatgttg tacaggtggc tgaactgtat ccagaactga    2280
gacgcatttt gacaattaca gaggatgggc aggggctaaa gggggtaaag agggagcggg    2340
gggcttgtga ggctacagag gaggctagga atctagcttt tagcttaatg accagacacc    2400
gtcctgagtg tattactttt caacagatca aggataattg cgctaatgag cttgatctgc    2460
tggcgcagaa gtattccata gagcagctga ccacttactg gctgcagcca ggggatgatt    2520
ttgaggaggc tattagggta tatgcaaagg tggcacttag gccagattgc aagtacaaga    2580
tcagcaaact tgtaaatatc aggaattgtt gctacatttc tgggaacggg gccgaggtgg    2640
agatagatac ggaggatagg gtggccttta gatgtagcat gataaatatg tggccgggg    2700 tgcttggcat ggacggggtg gttattatga atgtaaggtt tactggcccc aattttagcg    2760
gtacggtttt cctggccaat accaacctta tcctacacgg tgtaagcttc tatgggttta    2820
acaatacctg tgtggaagcc tggaccgatg taagggttcg gggctgtgcc ttttactgct    2880
gctggaaggg ggtggtgtgt cgccccaaaa gcagggcttc aattaagaaa tgcctctttg    2940
aaaggtgtac cttgggtatc ctgtctgagg gtaactccag ggtgcgccac aatgtggcct    3000
ccgactgtgg ttgcttcatg ctagtgaaaa gcgtggctgt gattaagcat aacatggtat    3060
gtggcaactg cgaggacagg gcctctcaga tgctgacctg ctcggacggc aactgtcacc    3120
tgctgaagac cattcacgta gccagccact ctcgcaaggc ctggccagtg tttgagcata    3180
acatactgac ccgctgttcc ttgcatttgg gtaacaggag gggggtgttc ctaccttacc    3240
aatgcaattt gagtcacact aagatattgc ttgagcccga gagcatgtcc aaggtgaacc    3300
tgaacggggt gtttgacatg accatgaaga tctggaaggt gctgaggtac gatgagaccc    3360
gcaccaggtg cagaccctgc gagtgtggcg gtaaacatat taggaaccag cctgtgatgc    3420
tggatgtgac cgaggagctg aggcccgatc acttggtgct ggcctgcacc cgcgctgagt    3480
ttggctctag cgatgaagat acagattgag gtactgaaat gtgtgggcgt ggcttaaggg    3540
tgggaaagaa tatataaggt gggggtctta tgtagttttg tatctgtttt gcagcagccg    3600
ccgccgccat gagcaccaac tcgtttgatg gaagcattgt gagctcatat ttgacaacgc    3660
gcatgccccc atgggccggg gtgcgtcaga atgtgatggg ctccagcatt gatggtcgcc    3720
ccgtcctgcc cgcaaactct actaccttga cctacgagac cgtgtctgga acgccgttgg    3780
agactgcagc ctccgccgcc gcttcagccg ctgcagccac cgcccgcggg attgtgactg    3840
actttgcttt cctgagcccg cttgcaagca gtgcagcttc ccgttcatcc gcccgcgatg    3900
acaagttgac ggctcttttg gcacaattgg attctttgac ccgggaactt aatgtcgttt    3960
ctcagcagct gttggatctg cgccagcagg tttctgccct gaaggcttcc tcccctccca    4020
atgcggttta aacataaat  aaaaaaccag actctgtttg gatttggatc aagcaagtgt    4080
cttgctgtct ttatttaggg gttttgcgcg cgcggtaggc ccgggaccag cggtctcggt    4140
```

-continued

```
cgttgagggt cctgtgtatt ttttccagga cgtggtaaag gtgactctgg atgttcagat    4200
acatgggcat aagcccgtct ctggggtgga ggtagcacca ctgcagagct tcatgctgcg    4260
gggtggtgtt gtagatgatc cagtcgtagc aggagcgctg ggcgtggtgc ctaaaaatgt    4320 cttttcagtag caagctgatt gccagggggca ggcccttggt gtaagtgttt acaaagcggt    4380
taagctggga tgggtgcata cgtggggata tgagatgcat cttggactgt attttttaggt    4440 tggctatgtt cccagccata tccctccggg gattcatgtt gtgcagaacc accagcacag    4500
tgtatccggt gcacttggga aatttgtcat gtagcttaga aggaaatgcg tggaagaact    4560
tggagacgcc cttgtgacct ccaagatttt ccatgcattc gtccataatg atggcaatgg    4620
gcccacgggc ggcggcctgg gcgaagatat ttctgggatc actaacgtca tagttgtgtt    4680
ccaggatgag atcgtcatag gccatttttta caaagcgcgg gcggagggtg ccagactgcg    4740
gtataatggt tccatccggc ccaggggcgt agttaccctc acagatttgc atttcccacg    4800
ctttgagttc agatgggggg atcatgtcta cctgcgggcg gatgaagaaa acggtttccg    4860 gggtaggggga gatcagctgg gaagaaagca ggttcctgag cagctgcgac ttaccgcagc    4920
cggtgggccc gtaaatcaca cctattaccg ggtgcaactg gtagttaaga gagctgcagc    4980
tgccgtcatc cctgagcagg ggggccactt cgttaagcat gtccctgact cgcatgtttt    5040
ccctgaccaa atccgccaga aggcgctcgc cgcccagcga tagcagttct tgcaaggaag    5100
caaagttttt caacggtttg agaccgtccg ccgtaggcat gcttttgagc gtttgaccaa    5160
gcagttccag gcggtcccac agctcggtca cctgctctac ggcatctcga tccagcatat    5220
ctcctcgttt cgcgggttgg ggcggctttc gctgtacggc agtagtcggt gctcgtccag    5280
acgggccagg gtcatgtctt tccacggggcg cagggtcctc gtcagcgtag tctgggtcac    5340
ggtgaagggg tgcgctccgg gctgcgcgct ggccagggtg cgcttgaggc tggtcctgct    5400
ggtgctgaag cgctgccggt cttcgccctg cgcgtcggcc aggtagcatt tgaccatggt    5460
gtcatagtcc agcccctccg cggcgtggcc cttggcgcgc agcttgccct tggaggaggc    5520
gccgcacgag gggcagtgca gacttttgag ggcgtagagc ttgggcgcga gaaataccga    5580
ttccggggag taggcatccg cgccgcaggc cccgcagacg gtctcgcatt ccacgagcca    5640
ggtgagctct ggccgttcgg ggtcaaaaac caggtttccc ccatgctttt tgatgcgttt    5700
cttacctctg gtttccatga gccggtgtcc acgctcggtg acgaaaaggc tgtccgtgtc    5760
cccgtataca gacttgagag gcctgtcctc gagcggtgtt ccgcggtcct cctcgtatag    5820
aaactcggac cactctgaga caaaggctcg cgtccaggcc agcacgaagg aggctaagtg    5880
ggaggggtag cggtcgttgt ccactagggg gtccactcgc tccagggtgt gaagacacat    5940
gtcgccctct tcggcatcaa ggaaggtgat tggtttgtag gtgtaggcca cgtgaccggg    6000
tgttcctgaa gggggggctat aaaaggggggt gggggcgcgt tcgtcctcac tctcttccgc    6060
atcgctgtct gcgagggcca gctgttgggg tgagtactcc ctctgaaaag cgggcatgac    6120
ttctgcgcta agattgtcag tttccaaaaa cgaggaggat ttgatattca cctggcccgc    6180
ggtgatgcct ttgagggtgg ccgcatccat ctggtcagaa aagacaatct ttttgttgtc    6240
aagcttggtg gcaaacgacc cgtagagggc gttggacagc aacttggcga tggagcgcag    6300
ggtttggttt ttgtcgcgat cggcgcgctc cttggccgcg atgtttagct gcacgtattc    6360
gcgcgcaacg caccgccatt cgggaaagac ggtggtgcgc tcgtcgggca ccaggtgcac    6420
gcgccaaccg cggttgtgca gggtgacaag gtcaacgctg gtggctacct ctccgcgtag    6480
gcgctcgttg gtccagcaga ggcggccgcc cttgcgcgag cagaatggcg gtaggggtc    6540
```

-continued

```
tagctgcgtc tcgtccgggg ggtctgcgtc cacggtaaag accccgggca gcaggcgcgc    6600
gtcgaagtag tctatcttgc atccttgcaa gtctagcgcc tgctgccatg cgcgggcggc    6660
aagcgcgcgc tcgtatgggt tgagtggggg accccatggc atggggtggg tgagcgcgga    6720
ggcgtacatg ccgcaaatgt cgtaaacgta gaggggctct ctgagtattc caagatatgt    6780
agggtagcat cttccaccgc ggatgctggc gcgcacgtaa tcgtatagtt cgtgcgaggg    6840
agcgaggagg tcgggaccga ggttgctacg ggcgggctgc tctgctcgga agactatctg    6900
cctgaagatg gcatgtgagt tggatgatat ggttggacgc tggaagacgt tgaagctggc    6960
gtctgtgaga cctaccgcgt cacgcacgaa ggaggcgtag gagtcgcgca gcttgttgac    7020
cagctcggcg gtgacctgca cgtctagggc gcagtagtcc agggtttcct tgatgatgtc    7080
atacttatcc tgtcccttt ttttccacag ctcgcggttg aggacaaact cttcgcggtc    7140
tttccagtac tcttggatcg gaaacccgtc ggcctccgaa cggtaagagc ctagcatgta    7200
gaactggttg acgcctggt aggcgcagca tcccttttct acgggtagcg cgtatgcctg    7260
cgcggccttc cggagcgagg tgtgggtgag cgcaaaggtg tccctgacca tgactttgag    7320
gtactggtat ttgaagtcag tgtcgtcgca tccgccctgc tcccagagca aaaagtccgt    7380 gcgcttttg gaacgcggat ttggcagggc gaaggtgaca tcgttgaaga gtatctttcc    7440
cgcgcgaggc ataaagttgc gtgtgatgcg gaagggtccc ggcacctcgg aacggttgtt    7500
aattacctgg gcggcgagca cgatctcgtc aaagccgttg atgttgtggc ccacaatgta    7560
aagttccaag aagcgcggga tgcccttgat ggaaggcaat tttttaagtt cctcgtaggt    7620
gagctcttca ggggagctga gcccgtgctc tgaaagggcc cagtctgcaa gatgagggtt    7680
ggaagcgacg aatgagctcc acaggtcacg ggccattagc atttgcaggt ggtcgcgaaa    7740
ggtcctaaac tggcgaccta tggccatttt ttctggggtg atgcagtaga aggtaagcgg    7800
gtcttgttcc cagcggtccc atccaaggtt cgcggctagg tctcgcgcgg cagtcactag    7860
aggctcatct ccgccgaact tcatgaccag catgaagggc acgagctgct tcccaaaggc    7920
ccccatccaa gtataggtct ctacatcgta ggtgacaaag agacgctcgg tgcgaggatg    7980
cgagccgatc gggaagaact ggatctcccg ccaccaattg gaggagtggc tattgatgtg    8040
gtgaaagtag aagtccctgc gacgggccga acactcgtgc tggcttttgt aaaaacgtgc    8100
gcagtactgg cagcggtgca cgggctgtac atcctgcacg aggttgacct gacgaccgcg    8160
cacaaggaag cagagtggga atttgagccc ctcgcctggc gggtttggct ggtggtcttc    8220
tacttcggct gcttgtcctt gaccgtctgg ctgctcgagg ggagttacgg tggatcggac    8280
caccacgccg cgcgagccca agtccagat gtccgcgcgc ggcggtcgga gcttgatgac    8340
aacatcgcgc agatgggagc tgtccatggt ctggagctcc cgcggcgtca ggtcaggcgg    8400
gagctcctgc aggtttacct cgcatagacg ggtcagggcg cgggctagat ccaggtgata    8460
cctaatttcc aggggctggt tggtggcggc gtcgatggct tgcaagaggc cgcatccccg    8520
cggcgcgact acggtaccgc gcggcgggcg gtgggccgcg ggggtgtcct tggatgatgc    8580
atctaaaagc ggtgacgcgg gcgagccccc ggaggtaggg ggggctccgg acccgccggg    8640
agagggggca ggggcacgtc ggcgccgcgc gcgggcagga gctggtgctg cgcgcgtagg    8700
ttgctggcga acgcgacgac gcggcggttg atctcctgaa tctggcgcct ctgcgtgaag    8760
acgacgggcc cggtgagctt gagcctgaaa gagagttcga cagaatcaat ttcggtgtcg    8820 ttgacgcgcgg cctggcgcaa aatcctctgc acgtctcctg agttgtcttg ataggcgatc    8880
tcggccatga actgctcgat ctcttcctcc tggagatctc cgcgtccggc tcgctccacg    8940
```

```
gtggcggcga ggtcgttgga aatgcgggcc atgagctgcg agaaggcgtt gaggcctccc    9000
tcgttccaga cgcggctgta gaccacgccc ccttcggcat cgcgggcgcg catgaccacc    9060
tgcgcgagat tgagctccac gtgccgggcg aagacggcgt agtttcgcag gcgctgaaag    9120
aggtagttga gggtggtggc ggtgtgttct gccacgaaga agtacataac ccagcgtcgc    9180
aacgtggatt cgttgatatc ccccaaggcc tcaaggcgct ccatggcctc gtagaagtcc    9240
acggcgaagt tgaaaaactg ggagttgcgc gccgacacgg ttaactcctc ctccagaaga    9300
cggatgagct cggcgacagt gtcgcgcacc tcgcgctcaa aggctacagg ggcctcttct    9360
tcttcttcaa tctcctcttc cataaggggc tccccttctt cttcttctgg cggcggtggg    9420
ggagggggga cacggcggcg acgacggcgc accgggaggc ggtcgacaaa gcgctcgatc    9480
atctccccgc ggcgacggcg catggtctcg gtgacggcgc ggccgttctc gcgggggcgc    9540
agttggaaga cgccgcccgt catgtcccgg ttatggggttg gcgggggggct gccatgcggc    9600 agggatacgg cgctaacgat gcatctcaac aattgttgtg taggtactcc gccgccgagg    9660
gacctgagcg agtccgcatc gaccggatcg gaaaacctct cgagaaaggc gtctaaccag    9720
tcacagtcgc aaggtaggct gagcaccgtg gcgggcggca gcgggcggcg gtcggggttg    9780
tttctggcgg aggtgctgct gatgatgtaa ttaaagtagg cggtcttgag acggcggatg    9840
gtcgacagaa gcaccatgtc cttgggtccg gcctgctgaa tgcgcaggcg gtcggccatg    9900
ccccaggctt cgttttgaca tcggcgcagg tctttgtagt agtcttgcat gagcctttct    9960
accggcactt cttcttctcc ttcctcttgt cctgcatctc ttgcatctat cgctgcggcg   10020
gcggcggagt ttggccgtag gtggcgccct cttcctccca tgcgtgtgac cccgaagccc   10080
ctcatcggct gaagcagggc taggtcggcg acaacgcgct cggctaatat ggcctgctgc   10140
acctgcgtga gggtagactg gaagtcatcc atgtccacaa agcggtggta tgcgcccgtg   10200
ttgatggtgt aagtgcagtt ggccataacg gaccagttaa cggtctggtg acccggctgc   10260
gagagctcgg tgtacctgag acgcgagtaa gccctcgagt caaatacgta gtcgttgcaa   10320
gtccgcacca ggtactggta tcccaccaaa aagtgcggcg gcggctggcg gtagaggggc   10380
cagcgtaggg tggccggggc tccggggggcg agatcttcca acataaggcg atgatatccg   10440
tagatgtacc tggacatcca ggtgatgccg gcggcggtgg tggaggcgcg cggaaagtcg   10500
cggacgcggt tccagatgtt gcgcagcggc aaaaagtgct ccatggtcgg gacgctctgg   10560
ccggtcaggc gcgcgcaatc gttgacgctc tagaccgtgc aaaaggagag cctgtaagcg   10620
ggcactcttc cgtggtctgg tggataaatt cgcaagggta tcatggcgga cgaccggggt   10680
tcgagccccg tatccggccg tccgccgtga tccatgcggt taccgcccgc gtgtcgaacc   10740
caggtgtgcg acgtcagaca acgggggagt gctcctttgt gcttccttcc aggcgcggcg   10800
gctgctgcgc tagcttttt ggccactggc cgcgcgcagc gtaagcggtt aggctggaaa   10860
gcgaaagcat taagtggctc gctccctgta gccgagggt tattttccaa gggttgagtc   10920
gcgggacccc cggttcgagt ctcggaccgg ccggactgcg gcgaacgggg gtttgcctcc   10980
ccgtcatgca agacccgcct tgcaaattcc tccggaaaca gggacgagcc cctttttgc   11040 tttttcccaga tgcatccggt gctgcggcag atgcgccccc ctcctcagca gcggcaagag   11100
caagagcagc ggcagacatg cagggcaccc tcccctcctc ctaccgcgtc aggaggggcg   11160
acatccgcgg ttgacgcggc agcagatggt gattacgaac cccgcggcg ccgggcccgg   11220 cactacctgg acttggagga gggcgagggc ctggcgcggc taggagcgcc ctctcctgag   11280
cggtacccaa gggtgcagct gaagcgtgat acgcgtgagg cgtacgtgcc gcggcagaac   11340
```

```
ctgtttcgcg accgcgaggg agaggagccc gaggagatgc gggatcgaaa gttccacgca   11400
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaaagctt taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatgcgc tgctaaacat agtagagccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
ttttacgccc gcaagatata ccatacccct tacgttccca tagacaagga ggtaaagatc   11940
gaggggttct acatgcgcat ggcgctgaag gtgcttacct tgagcgacga cctgggcgtt   12000
tatcgcaacg agcgcatcca caaggccgtg agcgtgagcc ggcggcgcga gctcagcgac   12060
cgcgagctga tgcacagcct gcaaagggcc ctggctggca cgggcagcgg cgatagagag   12120
gccgagtcct actttgacgc gggcgctgac ctgcgctggg ccccaagccg acgcgccctg   12180
gaggcagctg gggccggacc tgggctggcg gtggcacccg cgcgcgctgg caacgtcggc   12240
ggcgtggagg aatatgacga ggacgatgag tacgagccag aggacggcga gtactaagcg   12300
gtgatgtttc tgatcagatg atgcaagacg caacggaccc ggcggtgcgg gcggcgctgc   12360
agagccagcc gtccggcctt aactccacgg acgactggcg ccaggtcatg gaccgcatca   12420
tgtcgctgac tgcgcgcaat cctgacgcgt tccggcagca gccgcaggcc aaccggctct   12480
ccgcaattct ggaagcggtg gtcccggcgc gcgcaaaccc cacgcacgag aaggtgctgg   12540
cgatcgtaaa cgcgctggcc gaaaacaggg ccatccggcc cgacgaggcc ggcctggtct   12600
acgacgcgct gcttcagcgc gtggctcgtt acaacagcgg caacgtgcag accaacctgg   12660
accggctggt gggggatgtg cgcgaggccg tggcgcagcg tgagcgcgcg cagcagcagg   12720
gcaacctggg ctccatggtt gcactaaacg ccttcctgag tacacagccc gccaacgtgc   12780
cgcggggaca ggaggactac accaactttg tgagcgcact gcggctaatg gtgactgaga   12840
caccgcaaag tgaggtgtac cagtctgggc cagactattt tttccagacc agtagacaag   12900
gcctgcagac cgtaaacctg agccaggctt tcaaaaactt gcaggggctg tggggggtgc   12960
gggctcccac aggcgaccgc gcgaccgtgt ctagcttgct gacgcccaac tcgcgcctgt   13020
tgctgctgct aatagcgccc ttcacggaca gtggcagcgt gtcccgggac acatacctag   13080
gtcacttgct gacactgtac cgcgaggcca taggtcaggc gcatgtggac gagcatactt   13140
tccaggagat tacaagtgtc agccgcgcgc tggggcagga ggacacgggc agcctggagg   13200
caaccctaaa ctacctgctg accaaccggc ggcagaagat cccctcgttg cacagtttaa   13260
acagcgagga ggagcgcatt ttgcgctacg tgcagcagag cgtgagcctt aacctgatgc   13320
gcgacggggt aacgcccagc gtggcgctgg acatgaccgc gcgcaacatg gaaccgggca   13380
tgtatgcctc aaaccggccg tttatcaacc gcctaatgga ctacttgcat cgcgcggccg   13440
ccgtgaaccc cgagtatttc accaatgcca tcttgaaccc gcactggcta ccgccccctg   13500
gtttctacac cggggggattc gaggtgcccg agggtaacga tggattcctc tgggacgaca   13560
tagacgacag cgtgtttttcc ccgcaaccgc agaccctgct agagttgcaa cagcgcgagc   13620
aggcagaggc ggcgctgcga aaggaaagct tccgcaggcc aagcagcttg tccgatctag   13680
gcgctgcggc cccgcggtca gatgctagta gcccatttcc aagcttgata gggtctctta   13740
```

```
ccagcactcg caccacccgc ccgcgcctgc tgggcgagga ggagtaccta aacaactcgc  13800
tgctgcagcc gcagcgcgaa aaaaacctgc ctccggcatt tcccaacaac gggatagaga  13860
gcctagtgga caagatgagt agatggaaga cgtacgcgca ggagcacagg gacgtgccag  13920
gcccgcgccc gcccacccgt cgtcaaaggc acgaccgtca gcggggtctg gtgtgggagg  13980
acgatgactc ggcagacgac agcagcgtcc tggatttggg agggagtggc aacccgtttg  14040
cgcaccttcg ccccaggctg gggagaatgt tttaaaaaaa aaaaagcatg atgcaaaata  14100
aaaaactcac caaggccatg gcaccgagcg ttggttttct tgtattcccc ttagtatgcg  14160
gcgcgcggcg atgtatgagg aaggtcctcc tccctcctac gagagtgtgg tgagcgcggc  14220
gccagtggcg gcggcgctgg gttctccctt cgatgctccc ctggaccgc cgtttgtgcc  14280
tccgcggtac ctgcggccta ccgggggag aaacagcatc cgttactctg agttggcacc  14340
cctattcgac accacccgtg tgtacctggt ggacaacaag tcaacggatg tggcatccct  14400
gaactaccag aacgaccaca gcaacttttct gaccacggtc attcaaaaca atgactacag  14460
cccgggggag gcaagcacac agaccatcaa tcttgacgac cggtcgcact ggggcggcga  14520
cctgaaaacc atcctgcata ccaacatgcc aaatgtgaac gagttcatgt ttaccaataa  14580
gtttaaggcg cgggtgatgg tgtcgcgctt gcctactaag gacaatcagg tggagctgaa  14640
atacgagtgg gtggagttca cgctgcccga gggcaactac tccgagacca tgaccataga  14700
ccttatgaac aacgcgatcg tggagcacta cttgaaagtg ggcagacaga acggggttct  14760
ggaaagcgac atcggggtaa agtttgacac ccgcaacttc agactggggt ttgaccccgt  14820
cactggtctt gtcatgcctg ggtatatac aaacgaagcc ttccatccag acatcatttt  14880
gctgccagga tgcggggtgg acttcaccca cagccgcctg agcaacttgt tgggcatccg  14940
caagcggcaa cccttccagg agggctttag gatcacctac gatgatctgg agggtggtaa  15000
cattcccgca ctgttggatg tggacgccta ccaggcgagc ttgaaagatg acaccgaaca  15060
gggcggggt ggcgcaggcg gcagcaacag cagtggcagc ggcgcggaag agaactccaa  15120
cgcggcagcc gcggcaatgc agccggtgga ggacatgaac gatcatgcca ttcgcggcga  15180
cacctttgcc acacgggctg aggagaagcg cgctgaggcc gaagcagcgg ccgaagctgc  15240
cgcccccgct gcgcaacccg aggtcgagaa gcctcagaag aaaccggtga tcaaacccct  15300
gacagaggac agcaagaaac gcagttacaa cctaataagc aatgacagca ccttcaccca  15360
gtaccgcagc tggtaccttg catacaacta cggcgaccct cagaccggaa tccgctcatg  15420
gacctgctt tgcactcctg acgtaacctg cggctcggag caggtctact ggtcgttgcc  15480
agacatgatg caagaccccg tgaccttccg ctccacgcgc cagatcagca actttccggt  15540
ggtgggcgcc gagctgttgc ccgtgcactc caagagcttc tacaacgacc aggccgtcta  15600
ctcccaactc atccgccagt ttacctctct gacccacgtg ttcaatcgct ttcccgagaa  15660
ccagattttg gcgcgcccgc cagccccac catcaccacc gtcagtgaaa acgttcctgc  15720
tctcacagat cacgggacgc taccgctgcg caacagcatc ggaggagtcc agcgagtgac  15780
cattactgac gccagacgcc gcacctgccc ctacgtttac aaggccctgg gcatagtctc  15840
gccgcgcgtc ctatcgagcc gcactttttg agcaagcatg tccatcctta tatcgcccag  15900
caataacaca ggctggggcc tgcgcttccc aagcaagatg tttggcgggg ccaagaagcg  15960
ctccgaccaa cacccagtgc gcgtgcgcgg gcactaccgc gcgccctggg gcgcgcacaa  16020
acgcggccgc actgggcgca ccaccgtcga tgacgccatc gacgcggtgg tggaggaggc  16080
gcgcaactac acgcccacgc cgccaccagt gtccacagtg gacgcggcca ttcagaccgt  16140
```

```
ggtgcgcgga gcccggcgct atgctaaaat gaagagacgg cggaggcgcg tagcacgtcg    16200
ccaccgccgc cgacccggca ctgccgccca acgcgcggcg gcggccctgc ttaaccgcgc    16260
acgtcgcacc ggccgacggg cggccatgcg ggccgctcga aggctggccg cgggtattgt    16320
cactgtgccc cccaggtcca ggcgacgagc ggccgccgca gcagccgcgg ccattagtgc    16380
tatgactcag ggtcgcaggg gcaacgtgta ttgggtgcgc gactcggtta gcggcctgcg    16440
cgtgcccgtg cgcacccgcc ccccgcgcaa ctagattgca agaaaaaact acttagactc    16500
gtactgttgt atgtatccag cggcggcggc gcgcaacgaa gctatgtcca agcgcaaaat    16560
caaagaagag atgctccagg tcatcgcgcc ggagatctat ggcccccccga agaaggaaga   16620 gcaggattac aagccccgaa agctaaagcg ggtcaaaaag aaaagaaag atgatgatga    16680 tgaacttgac gacgaggtgg aactgctgca cgctaccgcg cccaggcgac gggtacagtg    16740
gaaaggtcga cgcgtaaaac gtgttttgcg acccggcacc accgtagtct ttacgcccgg    16800
tgagcgctcc acccgcacct acaagcgcgt gtatgatgag gtgtacggcg acgaggacct    16860
gcttgagcag gccaacgagc gcctcgggga gtttgcctac ggaaagcggc ataaggacat    16920
gctggcgttg ccgctggacg agggcaaccc aacacctagc ctaaagcccg taacactgca    16980
gcaggtgctg cccgcgcttg caccgtccga agaaaagcgc ggcctaaagc gcgagtctgg    17040
tgacttggca cccaccgtgc agctgatggt acccaagcgc cagcgactgg aagatgtctt    17100
ggaaaaaatg accgtggaac ctgggctgga gcccgaggtc cgcgtgcggc aatcaagca    17160 ggtggcgccg ggactgggcg tgcagaccgt ggacgttcag ataccactca ccagtagcac    17220
cagtattgcc accgccacag agggcatgga gacacaaacg tccccggttg cctcagcggt    17280
ggcggatgcc gcggtgcagg cggtcgctgc ggccgcgtcc aagacctcta cggaggtgca    17340
aacggacccg tggatgtttc gcgtttcagc ccccgcgcgc cgcgcggtt cgaggaagta    17400 cggcgccgcc agcgcgctac tgcccgaata tgccctacat ccttccattg cgcctacccc    17460
cggctatcgt ggctacacct accgccccag aagacgagca actacccgac gccgaaccac    17520
cactggaacc cgccgccgcc gtcgccgtcg ccagccccgtg ctggccccga tttccgtgcg    17580
cagggtggct cgcgaaggag gcaggaccct ggtgctgcca acagcgcgct accaccccag    17640
catcgtttaa aagccggtct ttgtggttct tgcagatatg gccctcacct gccgcctccg    17700
tttcccggtg ccgggattcc gaggaagaat gcaccgtagg aggggcatgg ccggccacgg    17760
cctgacgggc ggcatgcgtc gtgcgcacca ccggcggcgg cgcgcgtcgc accgtcgcat    17820
gcgcggcggt atcctgcccc tccttattcc actgatcgcc gcggcgattg gcgccgtgcc    17880
cggaattgca tccgtggcct tgcaggcgca gagacactga ttaaaaacaa gttgcatgtg    17940
gaaaaatcaa aataaaaagt ctggactctc acgctcgctt ggtcctgtaa ctattttgta    18000
gaatggaaga catcaacttt gcgtctctgg ccccgcgaca cggctcgcgc ccgttcatgg    18060
gaaactggca agatatcggc accagcaata tgagcggtgg cgccttcagc tggggctcgc    18120
tgtggagcgg cattaaaaat ttcggttcca ccgttaagaa ctatggcagc aaggcctgga    18180
acagcagcac aggccagatg ctgagggata agttgaaaga gcaaaatttc caacaaaagg    18240
tggtagatgg cctggcctct ggcattagcg gggtggtgga cctggccaac caggcagtgc    18300
aaaataagat taacagtaag cttgatcccc gccctcccgt agaggagcct ccaccggccg    18360
tggagacagt gtctccagag gggcgtggcg aaaagcgtcc gcgcccgac agggaagaaa    18420 ctctggtgac gcaaatagac gagcctcct cgtacgagga ggcactaaag caaggcctgc    18480
ccaccacccg tcccatcgcg cccatggcta ccggagtgct gggccagcac acacccgtaa    18540
```

```
cgctggacct gcctcccccc gccgacaccc agcagaaacc tgtgctgcca ggcccgaccg   18600
ccgttgttgt aacccgtcct agccgcgcgt ccctgcgccg cgccgccagc ggtccgcgat   18660
cgttgcggcc cgtagccagt ggcaactggc aaagcacact gaacagcatc gtgggtctgg   18720
gggtgcaatc cctgaagcgc cgacgatgct tctgaatagc taacgtgtcg tatgtgtgtc   18780
atgtatgcgt ccatgtcgcc gccagaggag ctgctgagcc gccgcgcgcc cgctttccaa   18840
gatggctacc ccttcgatga tgccgcagtg gtcttacatg cacatctcgg gccaggacgc   18900
ctcggagtac ctgagccccg ggctggtgca gtttgcccgc gccaccgaga cgtacttcag   18960
cctgaataac aagtttagaa accccacggt ggcgcctacg cacgacgtga ccacagaccg   19020
gtcccagcgt ttgacgctgc ggttcatccc tgtggaccgt gaggatactg cgtactcgta   19080
caaggcgcgg ttcaccctag ctgtgggtga taaccgtgtg ctggacatgg cttccacgta   19140
ctttgacatc cgcggcgtgc tggacagggg ccctactttt aagccctact ctggcactgc   19200
ctacaacgcc ctggctccca ggtgccccc aaatccttgc gaatgggatg aagctgctac   19260
tgctcttgaa ataaacctag aagaagagga cgatgacaac aagacgaag tagacgagca   19320 agctgagcag caaaaaactc acgtatttgg gcaggcgcct tattctggta taaatattac   19380
aaaggagggt attcaaatag gtgtcgaagg tcaaacacct aaatatgccg ataaaacatt   19440
tcaacctgaa cctcaaatag gagaatctca gtggtacgaa actgaaatta atcatgcagc   19500
tgggagagtc cttaaaaaga ctaccccaat gaaaccatgt tacggttcat atgcaaaacc   19560
cacaaatgaa aatggagggc aaggcattct tgtaaagcaa caaatggaa agctagaaag   19620 tcaagtggaa atgcaatttt tctcaactac tgaggcgacc gcaggcaatg gtgataactt   19680
gactcctaaa gtggtattgt acagtgaaga tgtagatata gaaacccag acactcatat   19740 ttcttacatg cccactatta aggaaggtaa ctcacgagaa ctaatgggcc aacaatctat   19800
gcccaacagg cctaattaca ttgcttttag ggacaatttt attggtctaa tgtattacaa   19860
cagcacgggt aatatgggtg ttctggcggg ccaagcatcg cagttgaatg ctgttgtaga   19920
tttgcaagac agaaacacag agctttcata ccagcttttg cttgattcca ttggtgatag   19980
aaccaggtac tttcctatgt ggaatcaggc tgttgacagc tatgatccag atgttagaat   20040
tattgaaaat catggaactg aagatgaact tccaaattac tgcttccac tgggaggtgt   20100 gattaataca gagactctta ccaaggtaaa acctaaaaca ggtcaggaaa atggatggga   20160
aaaagatgct acagaatttt cagataaaaa tgaaataaga gttggaaata attttgccat   20220
ggaaatcaat ctaaatgcca acctgtggag aaatttcctg tactccaaca tagcgctgta   20280
tttgcccgac aagctaaagt acagtccttc caacgtaaaa atttctgata acccaaacac   20340
ctacgactac atgaacaagc gagtggtggc tcccgggtta gtggactgct acattaacct   20400
tggagcacgc tggtcccttg actatatgga caacgtcaac ccatttaacc accaccgcaa   20460
tgctggcctg cgctaccgct caatgttgct gggcaatggt cgctatgtgc ccttccacat   20520
ccaggtgcct cagaagttct ttgccattaa aaacctcctt ctcctgccgg gctcatacac   20580
ctacgagtgg aacttcagga aggatgttaa catggttctg cagagctccc taggaaatga   20640
cctaagggtt gacggagcca gcattaagtt tgatagcatt tgcctttacg ccaccttctt   20700
ccccatggcc cacaacaccg cctccacgct gaggccatg cttagaaacg acaccaacga   20760
ccagtccttt aacgactatc tctccgccgc caacatgctc taccctatac cgccaacgc   20820 taccaacgtg cccatatcca tcccctcccg caactgggcg gctttccgcg gctgggcctt   20880
cacgcgcctt aagactaagg aaacccccatc actgggctcg ggctacgacc cttattacac   20940
```

```
ctactctggc tctatacccct acctagatgg aacctttac ctcaaccaca cctttaagaa    21000
ggtggccatt acctttgact cttctgtcag ctggcctggc aatgaccgcc tgcttacccc    21060
caacgagttt gaaattaagc gctcagttga cggggagggt tacaacgttg cccagtgtaa    21120
catgaccaaa gactggttcc tggtacaaat gctagctaac tacaacattg gctaccaggg    21180
cttctatatc ccagagagct acaaggaccg catgtactcc ttctttagaa acttccagcc    21240
catgagccgt caggtggtgg atgatactaa atacaaggac taccaacagg tgggcatcct    21300
acaccaacac aacaactctg gatttgttgg ctaccttgcc cccaccatgc gcgaaggaca    21360
ggcctaccct gctaacttcc cctatccgct tataggcaag accgcagttg acagcattac    21420
ccagaaaaag tttctttgcg atcgcaccct ttggcgcatc ccattctcca gtaactttat    21480
gtccatgggc gcactcacag acctgggcca aaaccttctc tacgccaact ccgcccacgc    21540
gctagacatg acttttgagg tggatcccat ggacgagccc acccttcttt atgttttgtt    21600
tgaagtcttt gacgtggtcc gtgtgcaccg gccgcaccgc ggcgtcatcg aaaccgtgta    21660
cctgcgcacg cccttctcgg ccggcaacgc cacaacataa agaagcaagc aacatcaaca    21720
acagctgccg ccatgggctc cagtgagcag gaactgaaag ccattgtcaa agatcttggt    21780
tgtgggccat attttttggg cacctatgac aagcgctttc caggctttgt ttctccacac    21840
aagctcgcct gcgccatagt caatacggcc ggtcgcgaga ctgggggcgt acactggatg    21900
gcctttgcct ggaacccgca ctcaaaaaca tgctacctct ttgagccctt tggcttttct    21960
gaccagcgac tcaagcaggt ttaccagttt gagtacgagt cactcctgcg ccgtagcgcc    22020
attgcttctt cccccgaccg ctgtataacg ctggaaaagt ccacccaaag cgtacagggg    22080
cccaactcgg ccgcctgtgg actattctgc tgcatgtttc tccacgcctt tgccaactgg    22140
ccccaaactc ccatggatca aaccccaccc atgaaccta ttaccggggt acccaactcc    22200
atgctcaaca gtccccaggt acagcccacc ctgcgtcgca accaggaaca gctctacagc    22260
ttcctggagc gccactcgcc ctacttccgc agccacagtg cgcagattag gagcgccact    22320
tcttttttgtc acttgaaaaa catgtaaaaa taatgtacta gagacacttt caataaaggc    22380
aaatgctttt atttgtacac tctcgggtga ttatttaccc ccaccttgc cgtctgcgcc    22440
gtttaaaaat caaggggtt ctgccgcgca tcgctatgcg ccactggcag ggacacgttg    22500
cgatactggt gtttagtgct ccacttaaac tcaggcacaa ccatccgcgg cagctcggtg    22560
aagttttcac tccacaggct gcgcaccatc accaacgcgt ttagcaggtc gggcgccgat    22620
atcttgaagt cgcagttggg gcctccgccc tgcgcgcgcg agttgcgata cacagggttg    22680
cagcactgga acactatcag cgccgggtgg tgcacgctgg ccagcacgct cttgtcggag    22740
atcagatccg cgtccaggtc ctccgcgttg ctcaggcga acggagtcaa ctttggtagc    22800
tgccttccca aaaagggcgc gtgcccaggc tttgagttgc actcgcaccg tagtggcatc    22860
aaaaggtgac cgtgcccggt ctgggcgtta ggatacagcg cctgcataaa gccttgatc    22920
tgcttaaaag ccacctgagc ctttgcgcct tcagagaaga acatgccgca agacttgccg    22980
gaaaactgat tggccggaca ggccgcgtcg tgcacgcagc accttgcgtc ggtgttggag    23040
atctgcacca catttcggcc ccaccggttc ttcacgatct tggccttgct agactgctcc    23100
ttcagcgcgc gctgcccgtt ttcgctcgtc acatccattt caatcacgtg ctccttattt    23160
atcataatgc ttccgtgtag acacttaagc tcgccttcga tctcagcgca gcggtgcagc    23220
cacaacgcgc agcccgtggg ctcgtgatgc ttgtaggtca cctctgcaaa cgactgcagg    23280
tacgcctgca ggaatcgccc catcatcgtc acaaaggtct tgttgctggt gaaggtcagc    23340
```

```
tgcaacccgc ggtgctcctc gttcagccag gtcttgcata cggccgccag agcttccact   23400
tggtcaggca gtagtttgaa gttcgccttt agatcgttat ccacgtggta cttgtccatc   23460
agcgcgcgcg cagcctccat gcccttctcc cacgcagaca cgatcggcac actcagcggg   23520
ttcatcaccg taatttcact ttccgcttcg ctgggctctt cctcttcctc ttgcgtccgc   23580
ataccacgcg ccactgggtc gtcttcattc agccgccgca ctgtgcgctt acctcctttg   23640
ccatgcttga ttagcaccgg tgggttgctg aaacccacca tttgtagcgc cacatcttct   23700
ctttcttcct cgctgtccac gattacctct ggtgatggcg ggcgctcggg cttgggagaa   23760
gggcgcttct ttttcttctt gggcgcaatg gccaaatccg ccgccgaggt cgatggccgc   23820
gggctgggtg tgcgcggcac cagcgcgtct tgtgatgagt cttcctcgtc ctcggactcg   23880
atacgccgcc tcatccgctt ttttgggggc gcccggggag cgcgcggcga cggggacggg   23940
gacgacacgt cctccatggt tgggggacgt cgcgccgcac cgcgtccgcg ctcggggtg    24000
gtttcgcgct gctcctcttc ccgactggcc atttccttct cctataggca gaaaaagatc   24060
atggagtcag tcgagaagaa ggacagccta accgccccct ctgagttcgc caccaccgcc   24120
tccaccgatg ccgccaacgc gcctaccacc ttccccgtcg aggcacccc  gcttgaggag   24180
gaggaagtga ttatcgagca ggacccaggt tttgtaagcg aagacgacga ggaccgctca   24240
gtaccaacag aggataaaaa gcaagaccag gacaacgcag aggcaaacga ggaacaagtc   24300
gggcgggggg acgaaaggca tggcgactac ctagatgtgg gagacgacgt gctgttgaag   24360
catctgcagc gccagtgcgc cattatctgc gacgcgttgc aagagcgcag cgatgtgccc   24420
ctcgccatag cggatgtcag ccttgcctac gaacgccacc tattctcacc gcgcgtaccc   24480
cccaaacgcc aagaaaacgg cacatgcgag cccaacccgc gcctcaactt ctaccccgta   24540
tttgccgtgc cagaggtgct tgccacctat cacatctttt tccaaaactg caagatacc   24600
ctatcctgcc gtgccaaccg cagccgagcg gacaagcagc tggccttgcg gcagggcgct   24660
gtcataccctg atatcgcctc gctcaacgaa gtgccaaaaa tctttgaggg tcttggacgc   24720
gacgagaagc gcgcggcaaa cgctctgcaa caggaaaaca gcgaaaatga aagtcactct   24780
ggagtgttgg tggaactcga gggtgacaac gcgcgcctag ccgtactaaa acgcagcatc   24840
gaggtcaccc actttgccta cccggcactt aacctacccc ccaaggtcat gagcacagtc   24900
atgagtgagc tgatcgtgcg ccgtgcgcag ccccctggaga gggatgcaaa tttgcaagaa   24960
caaacagagg agggcctacc cgcagttggc gacgagcagc tagcgcgctg gcttcaaacg   25020
cgcgagcctg ccgacttgga ggagcgacgc aaactaatga tggccgcagt gctcgttacc   25080
gtggagcttg agtgcatgca gcggttcttt gctgacccgg agatgcagcg caagctagag   25140
gaaacattgc actacacctt tcgacagggc tacgtacgcc aggcctgcaa gatctccaac   25200
gtggagctct gcaacctggt ctcctacctt ggaattttgc acgaaaaccg ccttgggcaa   25260
aacgtgcttc attccacgct caagggcgag gcgcgccgcg actacgtccg cgactgcgtt   25320
tacttatttc tatgctacac ctggcagacg gccatgggcg tttggcagca gtgcttggag   25380
gagtgcaacc tcaaggagct gcagaaactg ctaaagcaaa acttgaagga cctatggacg   25440
gccttcaacg agcgctccgt ggccgcgcac ctggcggaca tcatttttccc cgaacgcctg   25500
cttaaaaccc tgcaacaggg tctgccagac ttcaccagtc aaagcatgtt gcagaacttt   25560
aggaactttta tcctagagcg ctcaggaatc ttgcccgcca cctgctgtgc acttcctagc   25620
gactttgtgc ccattaagta ccgcgaatgc cctccgccgc tttggggcca ctgctacctt   25680
ctgcagctag ccaactacct tgcctaccac tctgacataa tggaagacgt gagcggtgac   25740
```

```
ggtctactgg agtgtcactg tcgctgcaac ctatgcaccc cgcaccgctc cctggtttgc    25800
aattcgcagc tgcttaacga aagtcaaatt atcggtacct tgagctgca gggtccctcg    25860
cctgacgaaa agtccgcggc tccggggttg aaactcactc cggggctgtg gacgtcggct    25920
taccttcgca aatttgtacc tgaggactac cacgcccacg agattaggtt ctacgaagac    25980
caatcccgcc cgccaaatgc ggagcttacc gcctgcgtca ttacccaggg ccacattctt    26040
ggccaattgc aagccatcaa caaagcccgc caagagtttc tgctacgaaa gggacggggg    26100
gtttacttgg accccagtc cggcgaggag ctcaacccaa tcccccgcc gccgcagccc    26160
tatcagcagc agccgcgggc ccttgcttcc caggatggca cccaaaaaga agctgcagct    26220
gccgccgcca cccacggacg aggaggaata ctgggacagt caggcagagg aggttttgga    26280
cgaggaggag gaggacatga tggaagactg ggagagccta gacgaggaag cttccgaggt    26340
cgaagaggtg tcagacgaaa caccgtcacc ctcggtcgca ttcccctcgc cggcgcccca    26400
gaaatcggca accggttcca gcatggctac aacctccgct cctcaggcgc cgccggcact    26460
gcccgttcgc cgacccaacc gtagatggga caccactgga accagggccg gtaagtccaa    26520
gcagccgccg ccgttagccc aagagcaaca acagcgccaa ggctaccgct catggcgcgg    26580
gcacaagaac gccatagttg cttgcttgca agactgtggg ggcaacatct ccttcgcccg    26640
ccgctttctt ctctaccatc acggcgtggc cttcccccgt aacatcctgc attactaccg    26700
tcatctctac agcccatact gcaccggcgg cagcggcagc ggcagcaaca gcagcggcca    26760
cacagaagca aaggcgaccg gatagcaaga ctctgacaaa gcccaagaaa tccacagcgg    26820
cggcagcagc aggaggagga gcgctgcgtc tggcgcccaa cgaacccgta tcgacccgcg    26880
agcttagaaa caggattttt cccactctgt atgctatatt tcaacagagc aggggccaag    26940
aacaagagct gaaaataaaa aacaggtctc tgcgatccct caccccgcagc tgcctgtatc    27000
acaaaagcga agatcagctt cggcgcacgc tggaagacgc ggaggctctc ttcagtaaat    27060
actgcgcgct gactcttaag gactagtttc gcgcccttc tcaaatttaa gcgcgaaaac    27120
tacgtcatct ccagcggcca cacccggcgc cagcacctgt cgtcagcgcc attatgagca    27180
aggaaattcc cacgccctac atgtggagtt accagccaca aatgggactt gcggctggag    27240
ctgcccaaga ctactcaacc cgaataaact acatgagcgc gggaccccac atgatatccc    27300
gggtcaacgg aatccgcgcc caccgaaacc gaattctctt ggaacaggcg ctattacca    27360
ccacacctcg taataacctt aatccccgta gttggcccgc tgccctggtg taccaggaaa    27420
gtcccgctcc caccactgtg gtacttccca gagacgccca ggccgaagtt cagatgacta    27480
actcaggggc gcagcttgcg ggcggctttc gtcacagggt gcggtcgccc gggcagggta    27540
taactcacct gacaatcaga gggcgaggta ttcagctcaa cgacgagtcg gtgagctcct    27600
cgcttggtct ccgtccggac gggacatttc agatcggcgg cgccggccgt ccttcattca    27660
cgcctcgtca ggcaatccta actctgcaga cctcgtcctc tgagccgcgc tctgaggca    27720
ttggaactct gcaatttatt gaggagtttg tgccatcggt ctactttaac cccttctcgg    27780
gacctcccgg ccactatccg gatcaatttta ttcctaactt tgacgcggta aaggactcgg    27840
cggacggcta cgactgaatg ttaagtggag aggcagagca actgcgcctg aaacacctgg    27900
tccactgtcg ccgccacaag tgcttttgccc gcgactccgg tgagttttgc tactttgaat    27960
tgcccgagga tcatatcgag ggcccggcgc acggcgtccg gcttaccgcc cagggagagc    28020
ttgcccgtag cctgattcgg gagtttaccc agcgccccct gctagttgag cgggacaggg    28080
gaccctgtgt tctcactgtg atttgcaact gtcctaacct tggattacat caagatcttt    28140
```

```
gttgccatct ctgtgctgag tataataaat acagaaatta aaatatactg gggctcctat    28200
cgccatcctg taaacgccac cgtcttcacc cgcccaagca aaccaaggcg aaccttacct    28260
ggtactttta acatctctcc ctctgtgatt tacaacagtt tcaacccaga cggagtgagt    28320
ctacgagaga acctctccga gctcagctac tccatcagaa aaaacaccac cctccttacc    28380
tgccgggaac gtacgagtgc gtcaccggcc gctgcaccac acctaccgcc tgaccgtaaa    28440
ccagactttt tccggacaga cctcaataac tctgtttacc agaacaggag gtgagcttag    28500
aaaacccttc gggtattagg ccaaaggcgc agctactgtg gggtttatga acaattcaag    28560
caactctacg ggctattcta attcaggttt ctctagaatc ggggttgggg ttattctctg    28620
tcttgtgatt ctctttattc ttatactaac gcttctctgc ctaaggctcg ccgcctgctg    28680
tgtgcacatt tgcatttatt gtcagctttt taaacgctgg ggtcgccacc caagatgatt    28740
aggtacataa tcctaggttt actcacccc tgcgtcagccc acggtaccac ccaaaaggtg    28800
gattttaagg agccagcctg taatgttaca ttcgcagctg aagctaatga gtgcaccact    28860
cttataaaat gcaccacaga acatgaaaag ctgcttattc gccacaaaaa caaaattggc    28920
aagtatgctg tttatgctat ttggcagcca ggtgacacta cagagtataa tgttacagtt    28980
ttccagggta aaagtcataa aacttttatg tatacttttc cattttatga aatgtgcgac    29040
attaccatgt acatgagcaa acagtataag ttgtggcccc cacaaaattg tgtggaaaac    29100
actggcactt tctgctgcac tgctatgcta attacagtgc tcgctttggt ctgtacccta    29160
ctctatatta aatacaaaag cagacgcagc tttattgagg aaaagaaaat gccttaattt    29220
actaagttac aaagctaatg tcaccactaa ctgctttact cgctgcttgc aaaacaaatt    29280
caaaaagtta gcattataat tagaatagga tttaaacccc ccggtcattt cctgctcaat    29340
accattcccc tgaacaattg actctatgtg ggatatgctc cagcgctaca accttgaagt    29400
caggcttcct ggatgtcagc atctgacttt ggccagcacc tgtcccgcgg atttgttcca    29460
gtccaactac agcgacccac cctaacagag atgaccaaca caaccaacgc ggccgccgct    29520
accggactta catctaccac aaatacaccc caagtttctg cctttgtcaa taactgggat    29580
aacttgggca tgtggtggtt ctccatagcg cttatgtttg tatgccttat tattatgtgg    29640
ctcatctgct gcctaaagcg caaacgcgcc cgaccaccca tctatagtcc catcattgtg    29700
ctacacccaa acaatgatgg aatccataga ttggacggac tgaaacacat gttcttttct    29760
cttacagtat gattaaatga gacatgattc ctcgagtttt tatattactg accttgttg     29820 cgcttttttg tgcgtgctcc acattggctg cggtttctca catcgaagta gactgcattc    29880
cagccttcac agtctatttg ctttacggat ttgtcaccct cacgctcatc tgcagcctca    29940
tcactgtggt catcgccttt atccagtgca ttgactggg ctgtgtgcgc tttgcatatc     30000
tcagacacca tccccagtac agggacagga ctatagctga gcttcttaga attctttaat    30060
tatgaaattt actgtgactt ttctgctgat tatttgcacc ctatctgcgt tttgttcccc    30120
gacctccaag cctcaaagac atatatcatg cagattcact cgtatatgga atattccaag    30180
ttgctacaat gaaaaaagcg atctttccga agcctggtta tatgcaatca tctctgttat    30240
ggtgttctgc agtaccatct tagccctagc tatatatccc taccttgaca ttggctggaa    30300
acgaatagat gccatgaacc acccaacttt ccccgcgccc gctatgcttc cactgcaaca    30360
agttgttgcc ggcggctttg tcccagccaa tcagcctcgc cccacttctc ccaccccac     30420 tgaaatcagc tactttaatc taacaggagg agatgactga cacccagatc ctagaaatgg    30480
acggaattat tacagagcag cgcctgctag aaagacgcag ggcagcggcc gagcaacagc    30540
```

```
gcatgaatca agagctccaa gacatggtta acttgcacca gtgcaaaagg ggtatctttt    30600
gtctggtaaa gcaggccaaa gtcacctacg acagtaatac caccggacac cgccttagct    30660
acaagttgcc aaccaagcgt cagaaattgg tggtcatggt gggagaaaag cccattacca    30720
taactcagca ctcggtagaa accgaaggct gcattcactc accttgtcaa ggacctgagg    30780
atctctgcac ccttattaag accctgtgcg gtctcaaaga tcttattccc tttaactaat    30840
aaaaaaaaat aataaagcat cacttactta aaatcagtta gcaaatttct gtccagttta    30900
ttcagcagca cctccttgcc ctcctcccag ctctggtatt gcagcttcct cctggctgca    30960
aactttctcc acaatctaaa tggaatgtca gtttcctcct gttcctgtcc atccgcaccc    31020
actatcttca tgttgttgca gatgaagcgc gcaagaccgt ctgaagatac cttcaacccc    31080
gtgtatccat atgacacgga aaccggtcct ccaactgtgc cttttcttac tcctcccttt    31140
gtatccccca atgggtttca agagagtccc cctggggtac tctctttgcg cctatccgaa    31200
cctctagtta cctccaatgg catgcttgcg ctcaaaatgg gcaacggcct ctctctggac    31260
gaggccggca accttacctc ccaaaatgta accactgtga gcccacctct caaaaaaacc    31320
aagtcaaaca taaacctgga aatatctgca ccccctcacag ttacctcaga agccctaact    31380
gtggctgccg ccgcacctct aatggtcgcg ggcaacacac tcaccatgca atcacaggcc    31440
ccgctaaccg tgcacgactc caaacttagc attgccaccc aaggacccct cacagtgtca    31500
gaaggaaagc tagccctgca aacatcaggc cccctcacca ccaccgatag cagtacccctt    31560 actatcactg cctcaccccc tctaactact gccactggta gcttgggcat tgacttgaaa    31620
gagcccattt atacacaaaa tggaaaacta ggactaaagt acggggctcc tttgcatgta    31680
acagacgacc taaacacttt gaccgtagca actggtccag gtgtgactat taataatact    31740
tccttgcaaa ctaaagttac tggagccttg ggttttgatt cacaaggcaa tatgcaactt    31800
aatgtagcag gaggactaag gattgattct caaaacagac gccttatact tgatgttagt    31860
tatccgtttg atgctcaaaa ccaactaaat ctaagactag acagggccc tcttttata     31920 aactcagccc acaacttgga tattaactac aacaaaggcc tttacttgtt tacagcttca    31980
aacaattcca aaaagcttga ggttaaccta agcactgcca aggggttgat gtttgacgct    32040
acagccatag ccattaatgc aggagatggg cttgaatttg gttcacctaa tgcaccaaac    32100
acaaatcccc tcaaaacaaa aattggccat ggcctagaat ttgattcaaa caaggctatg    32160
gttcctaaac taggaactgg ccttagtttt gacagcacag gtgccattac agtaggaaac    32220
aaaaataatg ataagctaac tttgtggacc acaccagctc catctcctaa ctgtagacta    32280
aatgcagaga aagatgctaa actcactttg gtcttaacaa aatgtggcag tcaaatactt    32340
gctacagttt cagttttggc tgttaaaggc agtttggctc caatatctgg aacagttcaa    32400
agtgctcatc ttattataag atttgacgaa aatggagtgc tactaaacaa ttccttcctg    32460
gacccagaat attggaactt tagaaatgga gatcttactg aaggcacagc ctatacaaac    32520
gctgttggat ttatgcctaa cctatcagct tatccaaaat ctcacggtaa aactgccaaa    32580
agtaacattg tcagtcaagt ttacttaaac ggagacaaaa ctaaacctgt aacactaacc    32640
attacactaa acggtacaca ggaaacagga gacacaactc caagtgcata ctctatgtca    32700
ttttcatggg actggtctgg ccacaactac attaatgaaa tatttgccac atcctcttac    32760 acttttcat acattgccca agaataaaga atcgtttgtg ttatgtttca acgtgtttat    32820
ttttcaattg cagaaaattt caagtcattt ttcattcagt agtatagccc caccaccaca    32880
tagcttatac agatcaccgt accttaatca aactcacaga accctagtat tcaacctgcc    32940
```

```
acctccctcc caacacacag agtacacagt cctttctccc cggctggcct taaaaagcat  33000
catatcatgg gtaacagaca tattcttagg tgttatattc cacacggttt cctgtcgagc  33060
caaacgctca tcagtgatat taataaactc cccgggcagc tcacttaagt tcatgtcgct  33120
gtccagctgc tgagccacag gctgctgtcc aacttgcggt tgcttaacgg gcggcgaagg  33180
agaagtccac gcctacatgg gggtagagtc ataatcgtgc atcaggatag ggcggtggtg  33240
ctgcagcagc gcgcgaataa actgctgccg ccgccgctcc gtcctgcagg aatcaaacat  33300
ggcagtggtc tcctcagcga tgattcgcac cgcccgcagc ataaggcgcc ttgtcctccg  33360
ggcacagcag cgcaccctga tctcacttaa atcagcacag taactgcagc acagcaccac  33420
aatattgttc aaaatcccac agtgcaaggc gctgtatcca aagctcatgg cggggaccac  33480
agaacccacg tggccatcat accacaagcg caggtagatt aagtggcgac ccctcataaa  33540
cacgctggac ataaacatta cctcttttgg catgttgtaa ttcaccacct cccggtacca  33600
tataaacctc tgattaaaca tggcgccatc caccaccatc ctaaaccagc tggccaaaac  33660
ctgcccgccg gctatacact gcagggaacc gggactggaa caatgacagt ggagagccca  33720
ggactcgtaa ccatggatca tcatgctcgt catgatatca atgttggcac aacacaggca  33780
cacgtgcata cacttcctca ggattacaag ctcctcccgc gttagaacca tatcccaggg  33840
aacaacccat tcctgaatca gcgtaaatcc cacactgcag ggaagacctc gcacgtaact  33900
cacgttgtgc attgtcaaag tgttacattc gggcagcagc ggatgatcct ccagtatggt  33960
agcgcgggtt tctgtctcaa aaggaggtag acgatcccta ctgtacggag tgcgccgaga  34020
caaccgagat cgtgttggtc gtagtgtcat gccaaatgga acgccggacg tagtcatatt  34080
tcctgaagca aaaccaggtg cgggcgtgac aaacagatct gcgtctccgg tctcgccgct  34140
tagatcgctc tgtgtagtag ttgtagtata tccactctct caaagcatcc aggcgccccc  34200
tggcttcggg ttctatgtaa actccttcat gcgccgctgc cctgataaca tccaccaccg  34260
cagaataagc cacacccagc caacctacac attcgttctg cgagtcacac acgggaggag  34320
cgggaagagc tggaagaacc atgttttttt tttattcca aaagattatc caaaacctca  34380
aaatgaagat ctattaagtg aacgcgctcc cctccggtgg cgtggtcaaa ctctacagcc  34440
aaagaacaga taatggcatt tgtaagatgt tgcacaatgg cttccaaaag gcaaacggcc  34500
ctcacgtcca agtggacgta aaggctaaac ccttcagggt gaatctcctc tataaacatt  34560
ccagcacctt caaccatgcc caaataattc tcatctcgcc accttctcaa tatatctcta  34620
agcaaatccc gaatattaag tccggccatt gtaaaaatct gctccagagc gccctccacc  34680
ttcagcctca agcagcgaat catgattgca aaaattcagg ttcctcacag acctgtataa  34740
gattcaaaag cggaacatta acaaaaatac gcgatcccg taggtccctt cgcagggcca  34800
gctgaacata atcgtgcagg tctgcacgga ccagcgcggc cacttccccg ccaggaacct  34860
tgacaaaaga acccacactg attatgacac gcatactcgg agctatgcta accagcgtag  34920
ccccgatgta agctttgttg catgggcggc gatataaaat gcaaggtgct gctcaaaaaa  34980
tcaggcaaag cctcgcgcaa aaaagaaagc acatcgtagt catgctcatg cagatacagg  35040
caggtaagct ccggaaccac cacagaaaaa gacaccattt ttctctcaaa catgtctgcg  35100
ggtttctgca taaacacaaa ataaaataac aaaaaaacat ttaaacatta gaagcctgtc  35160
ttacaacagg aaaaacaacc cttataagca taagacggac tacggccatg ccggcgtgac  35220
cgtaaaaaaa ctggtcaccg tgattaaaaa gcaccaccga cagctcctcg gtcatgtccg  35280
gagtcataat gtaagactcg gtaaacacat caggttgatt catcggtcag tgctaaaaag  35340
```

-continued

| | |
|---|---|
| cgaccgaaat agcccggggg aatacatacc cgcaggcgta gagacaacat tacagccccc | 35400 |
| ataggaggta taacaaaatt aataggagag aaaacacat aaacacctga aaaaccctcc | 35460 |
| tgcctaggca aaatagcacc ctcccgctcc agaacaacat acagcgcttc acagcggcag | 35520 |
| cctaacagtc agccttacca gtaaaaaaga aaacctatta aaaaaacacc actcgacacg | 35580 |
| gcaccagctc aatcagtcac agtgtaaaaa agggccaagt gcagagcgag tatatatagg | 35640 |
| actaaaaaat gacgtaacgg ttaaagtcca caaaaaacac ccagaaaacc gcacgcgaac | 35700 |
| ctacgcccag aaacgaaagc caaaaaaccc acaacttcct caaatcgtca cttccgtttt | 35760 |
| cccacgttac gtaacttccc attttaagaa aactacaatt cccaacacat acaagttact | 35820 |
| ccgccctaaa acctacgtca cccgccccgt tcccacgccc cgcgccacgt cacaaactcc | 35880 |
| accccctcat tatcatattg gcttcaatcc aaaataaggt atattattga tgatg | 35935 |

<210> SEQ ID NO 10
<211> LENGTH: 5965
<212> TYPE: DNA
<213> ORGANISM: Artificial Sequence
<220> FEATURE:
<223> OTHER INFORMATION: NSsuboptmut

<400> SEQUENCE: 10

| | |
|---|---|
| gccaccatgg cccccatcac cgcctacagc cagcagacca ggggcctgct gggctgcatc | 60 |
| atcaccagcc tgaccggacg cgacaagaac caggtggagg gagaggtgca ggtggtgagc | 120 |
| accgctaccc agagcttcct ggccacctgc gtgaacggcg tgtgctggac cgtgtaccac | 180 |
| ggagccggaa gcaagaccct ggccggaccc aagggcccta tcacccagat gtacaccaat | 240 |
| gtggatcagg atctggtggg ctggcaggcc cctcccggag ccaggagcct gacaccctgt | 300 |
| acctgtggaa gcagcgacct gtacctggtg acacgccacg ccgatgtgat ccccgtgagg | 360 |
| cgcaggggcg attctcgcgg aagcctgctg agccctaggc ccgtgagcta cctgaagggc | 420 |
| agcagcggag gacccctgct gtgtccttct ggccatgccg tgggcatttt tcgcgctgcc | 480 |
| gtgtgtacca ggggcgtggc caaagccgtg gattttgtgc ccgtggaaag catggagacc | 540 |
| accatgcgca gccctgtgtt caccgacaac agctctcccc ctgccgtgcc ccaatcattc | 600 |
| caggtggctc acctgcacgc ccctaccgga tctggcaaga gcaccaaggt gcccgctgcc | 660 |
| tacgccgctc agggctacaa ggtgctggtg ctgaacccca gcgtggccgc tacccctggg c | 720 |
| ttcggcgctt acatgagcaa ggcccatggc atcgaccca acatccgcac aggcgtgcgc | 780 |
| accatcacca ccgagctcc cgtgacctac agcacctacg gcaagttcct ggccgatgga | 840 |
| ggctgcagcg gaggagccta cgacatcatc atctgcgacg agtgccacag caccgacagc | 900 |
| accaccatcc tgggcattgg caccgtgctg gatcaggccg aaacagctgg agccaggctg | 960 |
| gtggtgctgg ccacagctac ccctcctggc agcgtgaccg tgccccatcc caatatcgag | 1020 |
| gaggtggccc tgagcaacac aggcgagatc cccttctacg gcaaggccat ccccatcgag | 1080 |
| gccatccgcg aggcaggca cctgatcttc tgccacagca gaagaagtg cgacgagctg | 1140 |
| gctgccaagc tgagcggact gggcatcaac gccgtggcct actacaggg cctggacgtg | 1200 |
| tcagtgatcc ccaccatcgg cgatgtggtg gtggtggcca ccgacgccct gatgacaggc | 1260 |
| tacaccggag acttcgacag cgtgatcgac tgcaacaccc gcgtgaccca gaccgtggac | 1320 |
| ttcagcctgg accccaccct tcaccatcgaa accaccaccg tgcctcagga tgctgtgagc | 1380 |
| aggagccaga ggcgcggacg caccggaagg ggcaggcgcg gaatttatcg ctttgtgacc | 1440 |
| cctggcgaaa ggccctctgg catgttcgac agcagcgtgc tgtgcgagtg ctacgacgct | 1500 |

-continued

```
ggctgcgctt ggtacgagct gacacccgct gaaaccagcg tgcgcctgcg cgcttatctg    1560
aatacccctg gcctgcccgt gtgtcaggac cacctggagt tctgggagag cgtgttcaca    1620
ggactgaccc acatcgacgc ccatttcctg agccagacca agcaggctgg cgacaacttc    1680
ccctatctgg tggcctatca ggccaccgtg tgtgctaggg cccaagctcc acctccttca    1740
tgggaccaga tgtggaagtg cctgatccgc ctgaagccca ccctgcacgg ccctacccct    1800
ctgctgtacc gcctgggagc cgtgcagaac gaggtgaccc tgacccaccc catcaccaag    1860
tacatcatgg cctgcatgag cgctgatctg gaagtggtga ccagcacctg ggtgctggtg    1920
ggaggcgtgc tggccgctct ggctgcctac tgcctgacca ccggaagcgt ggtgatcgtg    1980
ggacgcatca tcctgagcgg aaggcccgct atcgtgcccg atcgcgagtt cctgtaccag    2040
gagttcgacg agatggagga gtgtgccagc cacctgccct acatcgagca gggcatgcag    2100
ctggccgaac agttcaagca gaaggccctg gcctgctgc agacagccac caaacaggcc    2160
gaagctgccg ctcccgtggt ggaaagcaag tggagggccc tggagacctt ctgggctaag    2220
cacatgtgga acttcatctc tggcatccag tacctggccg gactgagcac cctgcctggc    2280
aaccccgcta tcgccagcct gatggccttc accgctagca tcacctctcc cctgaccacc    2340
cagagcaccc tgctgttcaa cattctgggc ggatgggtgg ccgctcagct ggcccctcct    2400
tcagctgctt ctgcctttgt gggcgctggc attgccggag ccgctgtggg cagcattggc    2460
ctgggcaaag tgctggtgga tattctggct ggctatggcg ctggcgtggc cggagccctg    2520
gtggccttca aggtgatgag cggagagatg cccagcaccg aggacctggt gaacctgctg    2580
cctgccattc tgagccctgg agccctggtg gtgggcgtgg tgtgtgctgc cattctgagg    2640
cgccatgtgg gacccggaga gggcgctgtg cagtggatga accgcctgat cgccttcgcc    2700
tctcgcggaa accacgtgag ccctacccac tacgtgcctg agagcgacgc cgctgccagg    2760
gtgacccaga tcctgagcag cctgaccatc acccagctgc tgaagcgcct gcaccagtgg    2820
atcaacgagg actgcagcac accctgcagc ggaagctggc tgagggacgt gtgggactgg    2880
atctgcaccg tgctgaccga cttcaagacc tggctgcaga gcaagctgct gccccaactg    2940
cctggcgtgc ccttcttctc atgccagcgc ggatacaagg gcgtgtggag gggcgatggc    3000
atcatgcaga ccacctgtcc ctgcggagcc cagatcacag gccacgtgaa aacggcagc    3060 atgcgcatcg tgggccctaa gacctgcagc aacacctggc acggcacctt ccccatcaac    3120
gcctacacca ccggaccctg cacacccagc cctgctccca actacagcag ggccctgtgg    3180
agggtggctg ccgaggagta cgtggaggtg accagggtgg gagacttcca ctacgtgacc    3240
ggaatgacca ccgacaacgt gaagtgtccc tgtcaggtgc ccgctcccga atttttacc    3300 gaagtggatg gcgtgcgcct gcatcgctat gcccctgcct gtaggcccct gctgcgcgaa    3360
gaagtgacct tccaggtggg cctgaaccag tacctggtgg gcagccagct gcctgcgag    3420 cctgagcccg atgtggccgt gctgaccagc atgctgaccg accccagcca catcacagcc    3480
gaaaccgcta aaaggcgcct ggccaggggc tctcctccaa gcctggcctc aagcagcgct    3540
agccagctgt ctgctcccag cctgaaggcc acctgcacca cccaccacgt gagccccgac    3600
gccgacctga tcgaggccaa cctgctgtgg cgccaggaga tgggcggcaa catcacccgc    3660
gtggagagca gaacaaggt ggtggtgctg gacagcttcg accccctgcg cgccgaggag    3720
gacgagcgcg aggtgagcgt gccgccgag atcctgcgca agagcaagaa gttccccgct    3780
gccatgccca tctgggctag acctgattac aaccctcccc tgctgagag ctggaaggac    3840 cctgattacg tgcctccagt ggtgcatggc tgtcctctgc ctcccattaa agcccctcct    3900
```

```
attccacctc ctaggcgcaa aaggaccgtg gtgctgacag aaagcagcgt gagctctgct    3960
ctggccgaac tggccaccaa gacctttggc agcagcgaga gctctgccgt ggacagcgga    4020
acagccaccg ctctgcctga ccaggccagc gacgacggcg ataagggcag cgatgtggag    4080
agctatagca gcatgcctcc cctggaaggc gaacctggcg atcccgatct gagcgatggc    4140
agctggagca ccgtgagcga gaggccagc gaggacgtgg tgtgttgcag catgagctac    4200
acctggacag cgctctgat cacaccctgc gctgccgagg agagcaagct gcccatcaac    4260
gccctgagca acagcctgct gaggcaccac aacatggtgt acgccaccac cagcaggtct    4320
gccggactga ggcagaagaa ggtgaccttc gaccgcctgc aggtgctgga cgaccactac    4380
cgcgatgtgc tgaaggagat gaaggccaag gccagcaccg tgaaggccaa gctgctgagc    4440
gtggaggagg cctgcaagct gaccccccc cacagcgcca agagcaagtt cggctacggc    4500
gccaaggacg tgcgcaacct gagcagcaag gccgtgaacc acatccacag cgtgtggaag    4560
gacctgctgg aggacaccgt gacccccatc gacaccacca tcatggccaa gaacgaggtg    4620
ttctgcgtgc agcccgagaa gggcggccgc aagcccgctc gcctgatcgt gttccccgat    4680
ctgggcgtgc gcgtgtgcga gaagatggcc ctgtacgacg tggtgagcac cctgcctcag    4740
gtggtgatgg gctcaagcta cggcttccag tacagccctg ccagcgcgt ggagttcctg    4800
gtgaacacct ggaagagcaa gaagaacccc atgggcttca gctacgacac acgctgcttc    4860
gacagcaccg tgaccgagaa cgacatccgc gtggaggaga gcatctacca gtgctgcgac    4920
ctggcccctg aggccaggca ggccatcaag agcctgaccg agcgcctgta catcggaggc    4980
cctctgacca acagcaaggg acagaactgc ggatacaggc gctgtagggc ctctggcgtg    5040
ctgaccacca gctgtggcaa caccctgacc tgctacctga aggccagcgc tgcctgtcgc    5100
gctgccaagc tgcaggactg caccatgctg gtgaacgccg ctggcctggt ggtgatttgt    5160
gaaagcgctg gcacccagga agatgctgcc agcctgcgcg tgttcaccga ggccatgacc    5220
aggtactctg cccctcccgg agacccccct cagcccgaat acgacctgga gctgatcacc    5280
agctgctcaa gcaacgtgag cgtggctcac gacgccagcg gaaagcgcgt gtactacctg    5340
acacgcgatc ccaccacccc tctggctcgc gctgcctggg aaaccgctcg ccatacacccc    5400
gtgaacagct ggctgggcaa catcatcatg tacgcccta ccctgtgggc tcgcatgatc    5460
ctgatgaccc acttcttcag catcctgctg gctcaggagc agctggagaa ggccctggac    5520
tgccagattt acggcgcttg ctacagcatc gagcccctgg acctgcccca aatcatcgag    5580
cgcctgcacg gccgtctgc cttcagcctg cacagctaca gccctggcga aattaatcgc    5640
gtggccagct gtctgcgcaa actgggcgtg cctcctctgc gcgtgtggag catagggct    5700
aggagcgtga ggctaggct gctgagccag ggaggcaggg ccgctacctg tggaaagtac    5760
ctgttcaact gggccgtgaa gaccaagctg aagctgaccc ctatccctgc cgctagccag    5820
ctggacctga gcgatggtt cgtggctggc tacagcggag gcgacatcta ccacagcctg    5880
tctcgcgctc gccctcgctg gttcatgctg tgcctgctgc tgctgagcgt gggcgtgggc    5940
atctacctgc tgcccaaccg ctaaa                                         5965
```

<210> SEQ ID NO 11
<211> LENGTH: 5965
<212> TYPE: DNA
<213> ORGANISM: Artificial Sequence
<220> FEATURE:
<223> OTHER INFORMATION: Chimeric NSsuboptm

```
gccaccatgg cccccatcac cgcctacagc cagcagaccc gcggcctgct gggctgcatc    60
atcaccagcc tgaccggccg cgacaagaac caggtggagg cgaggtgca ggtggtgagc    120
accgccaccc agagcttcct ggccacctgc gtgaacggcg tgtgctggac cgtgtaccac   180
ggcgccggca gcaagaccct ggccggcccc aagggcccca tcacccagat gtacaccaac   240
gtggaccagg acctggtggg ctggcaggcc ccccccggcg cccgcagcct gacccccctgc  300
acctgcggca gcgcgaccct gtacctggtg acccgccacg ccgacgtgat ccccgtgcgc   360
cgccgcggcg acagccgcgg cagcctgctg agccccgcc ccgtgagcta cctgaagggc    420
agcagcggcg cccccctgct gtgccccagc ggccacgccg tgggcatctt ccgcgccgcc   480
gtgtgcaccc gcggcgtggc caaggccgtg gacttcgtgc ccgtggagag catggagacc   540
accatgcgca ccccgtgtt caccgacaac agcagccccc ccgccgtgcc ccagagcttc    600
caggtggccc acctgcacgc ccccaccggc agcggcaaga gcaccaaggt gcccgccgcc   660
tacgccgccc agggctacaa ggtgctggtg ctgaacccca gcgtggccgc caccctgggc   720
ttcggcgcct acatgagcaa ggcccacggc atcgacccca catccgcac cggcgtgcgc   780
accatcacca ccgccgcccc cgtgacctac agcacctacg caagttcct ggccgacggc    840
ggctgcagcg gcggcgccta cgacatcatc atctgcgacg agtgccacag caccgacagc   900
accaccatcc tgggcatcgg caccgtgctg gaccaggccg agaccgccgg cgcccgcctg   960
gtggtgctgg ccaccgccac cccccccggc agcgtgaccg tgccccaccc caacatcgag  1020
gaggtggccc tgagcaacac cggcgagatc cccttctacg gcaaggccat ccccatcgag  1080
gccatccgcg gcggccgcca cctgatcttc tgccacagca agaagaagtg cgacgagctg  1140
gccgccaagc tgagcggcct gggcatcaac gccgtggcct actaccgcgg cctggacgtg  1200
agcgtgatcc ccaccatcgg cgacgtggtg gtggtggcca ccgacgccct gatgaccggc  1260
tacaccggcg acttcgacag cgtgatcgac tgcaacacct gcgtgaccca gaccgtggac  1320
ttcagcctgg accccaccctt caccatcgag accaccaccg tgccccagga cgccgtgagc 1380
cgcagccagc gccgcggccg caccggccgc ggccgccgcg gcatctaccg cttcgtgacc  1440
cccggcgagc gccccagcgg catgttcgac agcagcgtgc tgtgcgagtg ctacgacgcc  1500
ggctgcgcct ggtacgagct gaccccccgcc gagaccagcg tgcgcctgcg cgcctacctg  1560
aacaccccccg gcctgcccgt gtgccaggac cacctggagt ctgggagag cgtgttcacc  1620
ggcctgaccc acatcgacgc ccacttcctg agccagacca agcaggccgg cgacaacttc  1680
ccctacctgg tggcctacca ggccaccgtg tgcgcccgcg cccaggcccc ccccccagc   1740
tgggaccaga tgtggaagtg cctgatccgc ctgaagccca ccctgcacgg ccccacccc   1800
ctgctgtacc gctgggcgc cgtgcagaac gaggtgaccc tgacccaccc catcaccaag  1860
tacatcatgg cctgcatgag cgccgacctg gaggtggtga ccagcacctg ggtgctggtg  1920
ggcggcgtgc tggccgccct ggccgcctac tgcctgacca ccggcagcgt ggtgatcgtg  1980
ggccgcatca tcctgagcgg ccgccccgcc atcgtgcccg accgcgagtt cctgtaccag  2040
gagttcgacg agatggagga gtgcgccagc cacctgccct acatcgagca gggcatgcag  2100
ctggccgagc agttcaagca gaaggccctg ggcctgctgc agaccgccac caagcaggcc  2160
gaggccgccg ccccccgtggt ggagagcaag tggcgcgccc tggagacctt ctgggccaag  2220
cacatgtgga acttcatcag cggcatccag tacctggccg gcctgagcac cctgcccggc  2280
aaccccgcca tcgccagcct gatggccttc accgccagca tcaccagccc cctgaccacc  2340
cagagcaccc tgctgttcaa catcctgggc ggctgggtgg ccgcccagct ggcccccccc  2400
```

-continued

```
agcgccgcca gcgccttcgt gggcgccggc atcgccggcg ccgccgtggg cagcatcggc    2460
ctgggcaagg tgctggtgga catcctggcc ggctacggcg ccggcgtggc cggcgccctg    2520
gtggccttca aggtgatgag cggcgagatg cccagcaccg aggacctggt gaacctgctg    2580
cccgccatcc tgagccccgg cgccctggtg gtgggcgtgg tgtgcgccgc catcctgcgc    2640
cgccacgtgg gccccggcga gggcgccgtg cagtggatga accgcctgat cgccttcgcc    2700
agccgcggca accacgtgag ccccacccac tacgtgcccg agagcgacgc cgccgcccgc    2760
gtgacccaga tcctgagcag cctgaccatc acccagctgc tgaagcgcct gcaccagtgg    2820
atcaacgagg actgcagcac cccctgcagc ggcagctggc tgcgcgacgt gtgggactgg    2880
atctgcaccg tgctgaccga cttcaagacc tggctgcaga gcaagctgct gccccagctg    2940
cccggcgtgc ccttcttcag ctgccagcgc ggctacaagg gcgtgtggcg cggcgacggc    3000
atcatgcaga ccacctgccc ctgcggcgcc cagatcaccg ccacgtgaa gaacggcagc    3060 atgcgcatcg tggccccaa gacctgcagc aacacctggc acggcacctt ccccatcaac    3120
gcctacacca ccggcccctg cacccccagc cccgccccca actacagccg cgccctgtgg    3180
cgcgtggccg ccgaggagta cgtggaggtg accgcgtgg gcgacttcca ctacgtgacc    3240
ggcatgacca ccgacaacgt gaagtgcccc tgccaggtgc ccgcccccga gttcttcacc    3300
gaggtggacg cgtgcgcct gcaccgctac gccccgcct gccgccccct gctgcgcgag    3360
gaggtgacct tccaggtggg cctgaaccag tacctggtgg gcagccagct gccctgcgag    3420
cccgagcccg acgtggccgt gctgaccagc atgctgaccg accccagcca catcaccgcc    3480
gagaccgcca agcgccgcct ggcccgcggc agccccccca gcctggccag cagcagcgcc    3540
agccagctga cgcccccag cctgaaggcc acctgcacca cccaccacgt gagccccgac    3600
gccgacctga tcgaggccaa cctgctgtgg cgccaggaga tgggcggcaa catcacccgc    3660
gtggagagcg agaacaaggt ggtggtgctg acagcttcg accccctgcg cgccgaggag    3720
gacgagcgcg aggtgagcgt gcccgccgag atcctgcgca agagcaagaa gttccccgct    3780
gccatgccca tctgggctag acctgattac aaccctcccc tgctggagag ctggaaggac    3840
cctgattacg tgcctccagt ggtgcatggc tgtcctctgc ctcccattaa gccccctcct    3900
attccacctc ctaggcgcaa aaggaccgtg gtgctgacag aaagcagcgt gagctctgct    3960
ctggccgaac tggccaccaa gacctttggc agcagcgaga gctctgccgt ggacagcgga    4020
acagccaccg ctctgcctga ccaggccagc gacgacggcg ataagggcag cgatgtggag    4080
agctatagca gcatgcctcc cctggaaggc gaacctggcg atcccgatct gagcgatggc    4140
agctggagca ccgtgagcga agaggccagc gaggacgtgg tgtgttgcag catgagctac    4200
acctggacag gcgctctgat cacaccctgc gctgccgagg agagcaagct gcccatcaac    4260
gccctgagca acagcctgct gaggcaccac aacatggtgt acgccaccac cagcaggtct    4320 gccgactga ggcagaagaa ggtgaccttc accgcctgc aggtgctgga cgaccactac    4380
cgcgatgtgc tgaaggagat gaaggccaag gccagcaccg tgaaggccaa gctgctgagc    4440
gtggaggagg cctgcaagct gaccccccc cacagcgcca agagcaagtt cggctacggc    4500
gccaaggacg tgcgcaacct gagcagcaag gccgtgaacc acatccacag cgtgtggaag    4560
gacctgctgg aggacaccgt gacccccatc gacaccacca tcatggccaa gaacgaggtg    4620
ttctgcgtgc agcccgagaa gggcggccgc aagcccgccc gcctgatcgt gttccccgac    4680
ctgggcgtgc gcgtgtgcga gaagatggcc ctgtacgacg tggtgagcac cctgcccag    4740 gtggtgatgg gcagcagcta cggcttccag tacagccccg ccagcgcgt ggagttcctg    4800
```

```
gtgaacacct ggaagagcaa gaagaacccc atgggcttca gctacgacac ccgctgcttc    4860
gacagcaccg tgaccgagaa cgacatccgc gtggaggaga gcatctacca gtgctgcgac    4920
ctggcccccg aggcccgcca ggccatcaag agcctgaccg agcgcctgta catcggcggc    4980
cccctgacca cagcaaggg ccagaactgc ggctaccgcc gctgccgcgc cagcggcgtg    5040
ctgaccacca gctgcggcaa caccctgacc tgctacctga aggccagcgc cgcctgccgc    5100
gccgccaagc tgcaggactg caccatgctg gtgaacgccg ccggcctggt ggtgatctgc    5160
gagagcgccg gcacccagga ggacgccgcc agcctgcgcg tgttcaccga ggccatgacc    5220
cgctacagcg ccccccccgg cgaccccccc cagcccgagt acgacctgga gctgatcacc    5280
agctgcagca gcaacgtgag cgtggcccac gacgccagcg gcaagcgcgt gtactacctg    5340
acccgcgacc ccaccacccc cctggcccgc gccgcctggg agaccgcccg ccacaccccc    5400
gtgaacagct ggctgggcaa catcatcatg tacgccccca ccctgtgggc ccgcatgatc    5460
ctgatgaccc acttcttcag catcctgctg gccaggagc agctggagaa ggccctggac    5520
tgccagatct acggcgcctg ctacagcatc gagcccctgg acctgcccca gatcatcgag    5580
cgcctgcacg gcctgagcgc cttcagcctg cacagctaca gccccggcga gatcaaccgc    5640
gtggccagct gcctgcgcaa gctgggcgtg ccccccctgc gcgtgtggcg ccaccgcgcc    5700
cgcagcgtgc gcgccccgcct gctgagccag ggcggccgcg ccgccacctg cggcaagtac    5760
ctgttcaact gggccgtgaa gaccaagctg aagctgaccc ccatccccgc cgccagccag    5820
ctggacctga gcggctggtt cgtggccggc tacagcggcg gcgacatcta ccacagcctg    5880
agccgcgccc gccccgctg gttcatgctg tgcctgctgc tgctgagcgt gggcgtgggc    5940
atctacctgc tgcccaaccg ctaaa                                          5965
```

```
<210> SEQ ID NO 12
<211> LENGTH: 10
<212> TYPE: RNA
<213> ORGANISM: Artificial Sequence
<220> FEATURE:
<223> OTHER INFORMATION: Ribosome binding site

<400> SEQUENCE: 12
gccaccaugg                                                             10

<210> SEQ ID NO 13
<211> LENGTH: 49
<212> TYPE: RNA
<213> ORGANISM: Artificial Sequence
<220> FEATURE:
<223> OTHER INFORMATION: Synthetic polyadenylation signal

<400> SEQUENCE: 13
aauaaaagau cuuuauuuuc auuagaucug uguuugguu uuugugug                    49

<210> SEQ ID NO 14
<211> LENGTH: 28
<212> TYPE: DNA
<213> ORGANISM: Artificial Sequence
<220> FEATURE:
<223> OTHER INFORMATION: Additional nucleotides present in pVIJns-NS

<400> SEQUENCE: 14
tctagagcgt ttaaacccctt aattaagg                                        28

<210> SEQ ID NO 15
<211> LENGTH: 15
<212> TYPE: DNA
```

-continued

```
<213> ORGANISM: Artificial Sequence
<220> FEATURE:
<223> OTHER INFORMATION: Additional nucleotides present in
      pV1Jns-NSOPTmut

<400> SEQUENCE: 15
tttaaatgtt taaac                                                      15

<210> SEQ ID NO 16
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 16
tcgaatcgat acgcgaacct acgc                                            24

<210> SEQ ID NO 17
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 17
tcgacgtgtc gacttcgaag cgcacaccaa aaacgtc                              37
```